(12) United States Patent
Throsby et al.

(10) Patent No.: US 11,939,394 B2
(45) Date of Patent: Mar. 26, 2024

(54) BINDING MOLECULES THAT INHIBIT CANCER GROWTH

(71) Applicants: Merus N.V., Utrecht (NL); Fundació Institut de Recerca Biomèdica (IRB Barcelona), Barcelona (ES); Institució Catalana de Recerca I Estudis Avançats, Barcelona (ES)

(72) Inventors: Mark Throsby, Utrecht (NL); Ton Logtenberg, Utrecht (NL); Johannes Carolus Clevers, Utrecht (NL); Robert Gerhardus Jacob Vries, Utrecht (NL); Eduard Batlle, Barcelona (ES); Bram Herpers, Leiden (NL)

(73) Assignees: Merus N.V., Utrecht (NL); Fundacio Institut de Recerca Biomedica, Barcelona (ES); Institució Catalana de Recerca I Estudis Avancats, Barcelona (ES)

( * ) Notice: Subject to any disclaimer, the term of this patent is extended or adjusted under 35 U.S.C. 154(b) by 736 days.

(21) Appl. No.: 15/770,317

(22) PCT Filed: Oct. 21, 2016

(86) PCT No.: PCT/NL2016/050726
§ 371 (c)(1),
(2) Date: Apr. 23, 2018

(87) PCT Pub. No.: WO2017/069628
PCT Pub. Date: Apr. 27, 2017

(65) Prior Publication Data
US 2018/0312604 A1   Nov. 1, 2018

(30) Foreign Application Priority Data

Oct. 23, 2015 (EP) .................................... 15191343
May 6, 2016 (EP) .................................... 16168647

(51) Int. Cl.
*C07K 16/30* (2006.01)
*C07K 16/28* (2006.01)

(52) U.S. Cl.
CPC .......... *C07K 16/3046* (2013.01); *C07K 16/28* (2013.01); *C07K 16/30* (2013.01); *C07K 2317/31* (2013.01); *C07K 2317/34* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,801,687 A | 1/1989 | Ngo |
| 4,816,567 A | 3/1989 | Cabilly et al. |
| 5,151,504 A | 9/1992 | Croze |
| 5,731,168 A | 3/1998 | Carter et al. |
| 7,642,228 B2 | 1/2010 | Carter et al. |
| 7,705,103 B2 | 4/2010 | Sherman et al. |
| 8,349,574 B2 | 1/2013 | Bates et al. |
| 8,592,562 B2 | 11/2013 | Kannan et al. |
| 8,628,774 B2 | 1/2014 | Gurney et al. |
| 9,220,775 B2 | 12/2015 | Chowdhury et al. |
| 9,248,181 B2 | 2/2016 | Kruif et al. |
| 9,248,182 B2 | 2/2016 | De Kruif et al. |
| 9,358,286 B2 | 6/2016 | De Kruif et al. |
| 9,551,208 B2 | 1/2017 | Ma et al. |
| 9,758,805 B2 | 9/2017 | De Kruif et al. |
| 9,914,777 B2 | 3/2018 | Bakker et al. |
| 9,968,676 B2 | 5/2018 | Adler et al. |
| 10,358,492 B2 | 7/2019 | Bakker et al. |
| 10,416,162 B2 | 9/2019 | Huang et al. |
| 10,844,127 B2 | 11/2020 | Logtenberg et al. |
| 2003/0078385 A1 | 4/2003 | Arathoon et al. |
| 2004/0071696 A1 | 4/2004 | Adams et al. |
| 2006/0212956 A1 | 9/2006 | Crocker et al. |
| 2009/0182127 A1 | 7/2009 | Kjaergaard et al. |
| 2009/0191559 A1 | 7/2009 | Huang et al. |
| 2010/0015133 A1 | 1/2010 | Igawa et al. |
| 2010/0183615 A1 | 7/2010 | Kufer et al. |
| 2010/0286374 A1 | 11/2010 | Kannan et al. |
| 2011/0077163 A1 | 3/2011 | Doranz |
| 2011/0195454 A1 | 8/2011 | McWhirter et al. |

(Continued)

FOREIGN PATENT DOCUMENTS

AU   2014/212081 A1   8/2015
EP        0120694 A2   10/1984

(Continued)

OTHER PUBLICATIONS

Brown et al (JI, 156:3285-3291, 1996).*
Adelaide, J., et al., "A Recurrent Chromosome Translocation Breakpoint in Breast and Pancreatic Cancer Cell Lines Targets the Neuregulin/NRG1 Gene," Genes Chromosome Cancer, 37(4), 333-345, Wiley-Liss, Inc, United States (2003).
Agus, D.B., et al., "Targeting ligand-activated ErbB2 signaling inhibits breast and prostate tumor growth," Cancer Cell, 2(2): 127-137, Cell Press, United States (2002).
Alexandra, H., et al., "MM-111, an ErbB2/ErbB3 Bispecific Antibody with Potent Activity in ErbB2-Overexpressing Cells, Positively Combines with Trastuzumab to Inhibit Growth of Breast Cancer Cells Driven by the ErbB2/ErbB3 Oncogenic Unit", American Association for Cancer Research, Proceedings of the Annual Meeting 51:845-846, American Association for Cancer Research, US (Apr. 2010).

(Continued)

*Primary Examiner* — Brad Duffy
(74) *Attorney, Agent, or Firm* — Sterne, Kessler, Goldstein & Fox P.L.L.C.

(57) ABSTRACT

The invention provides means and methods for inhibiting growth of a cancer. The means in some embodiments comprise proteins and antibodies that binds an extracellular part of a membrane associated member of the epidermal growth factor (EGF) receptor family and an extracellular part of a membrane associated member of a WNT signaling pathway. Further provided are various cells and assays that are helpful in the production of the proteins, antibodies and cells.

30 Claims, 54 Drawing Sheets

Specification includes a Sequence Listing.

(56) References Cited

U.S. PATENT DOCUMENTS

| | | | |
|---|---|---|---|
| 2012/0107234 A1 | 5/2012 | Pedersen et al. | |
| 2012/0107306 A1 | 5/2012 | Elis et al. | |
| 2012/0270801 A1 | 10/2012 | Frejd et al. | |
| 2012/0328623 A1 | 12/2012 | Takahashi | |
| 2013/0071859 A1 | 3/2013 | Bates et al. | |
| 2013/0084297 A1 | 4/2013 | Daly et al. | |
| 2013/0095116 A1* | 4/2013 | Gurney | A61K 45/06 424/172.1 |
| 2013/0115208 A1 | 5/2013 | Ho et al. | |
| 2013/0156779 A1 | 6/2013 | Clarke et al. | |
| 2013/0185821 A1 | 7/2013 | Babb et al. | |
| 2013/0251703 A1 | 9/2013 | Elis et al. | |
| 2013/0259867 A1 | 10/2013 | Amler et al. | |
| 2013/0336885 A1 | 12/2013 | Hongo et al. | |
| 2013/0336981 A1 | 12/2013 | De Kruif et al. | |
| 2013/0344093 A1 | 12/2013 | Daly et al. | |
| 2014/0056898 A1 | 2/2014 | Zhang et al. | |
| 2014/0072579 A1 | 3/2014 | De Kruif et al. | |
| 2014/0120096 A1 | 5/2014 | Bakker et al. | |
| 2014/0140999 A1 | 5/2014 | De Kruif et al. | |
| 2014/0141019 A1 | 5/2014 | Kharrat et al. | |
| 2014/0378664 A1 | 12/2014 | Suh et al. | |
| 2015/0013996 A1 | 1/2015 | Davies et al. | |
| 2015/0139996 A1 | 5/2015 | De Kruif et al. | |
| 2015/0196637 A1 | 7/2015 | De Kruif et al. | |
| 2015/0259423 A1* | 9/2015 | Kirshner | A61P 35/00 424/139.1 |
| 2016/0031984 A1 | 2/2016 | Reyes et al. | |
| 2016/0229920 A1 | 8/2016 | Ward et al. | |
| 2017/0037145 A1 | 2/2017 | Geuijen et al. | |
| 2017/0166653 A1 | 6/2017 | Garner et al. | |
| 2020/0102393 A1 | 4/2020 | Throsby et al. | |
| 2020/0247892 A1 | 8/2020 | Geuijen et al. | |
| 2020/0291130 A1 | 9/2020 | Throsby et al. | |
| 2021/0054096 A1 | 5/2021 | David et al. | |
| 2022/0227885 A1* | 7/2022 | Hansen | C07K 16/44 |
| 2022/0249614 A1* | 8/2022 | Chutkow | A61K 38/19 |

FOREIGN PATENT DOCUMENTS

| | | | |
|---|---|---|---|
| EP | 0314161 A1 | 5/1989 | |
| EP | 0481790 A2 | 4/1992 | |
| EP | 0523949 A1 | 1/1993 | |
| EP | 0870459 A2 | 10/1998 | |
| EP | 2604625 A1 | 6/2013 | |
| EP | 3600411 A1 | 2/2020 | |
| EP | 3600413 A1 | 2/2020 | |
| JP | H11500915 A | 1/1999 | |
| JP | 2008531557 A | 8/2008 | |
| JP | 2011508604 A | 3/2011 | |
| JP | 2012509259 A | 4/2012 | |
| WO | WO-9627011 A1 | 9/1996 | |
| WO | WO-9850431 A2 | 11/1998 | |
| WO | WO-0063403 A2 | 10/2000 | |
| WO | WO-0120694 A1 | 3/2001 | |
| WO | WO-03004704 A2 | 1/2003 | |
| WO | WO-03107218 A1 | 12/2003 | |
| WO | WO2004/009618 A2 | 1/2004 | |
| WO | WO-2004061104 A2 | 7/2004 | |
| WO | WO-2005000894 A2 | 1/2005 | |
| WO | WO-2005118635 A2 | 12/2005 | |
| WO | WO-2006028936 A2 | 3/2006 | |
| WO | WO-2006044908 A2 | 4/2006 | |
| WO | WO-2006091209 A2 | 8/2006 | |
| WO | WO-2006106905 A1 | 10/2006 | |
| WO | WO-2007110205 A2 | 10/2007 | |
| WO | WO-2007147901 A1 | 12/2007 | |
| WO | WO2008/027236 A2 | 3/2008 | |
| WO | WO-2008100624 A2 | 8/2008 | |
| WO | WO-2008119353 A1 | 10/2008 | |
| WO | WO-2008140493 A2 | 11/2008 | |
| WO | WO-2009051974 A1 | 4/2009 | |
| WO | WO-2009080251 A1 | 7/2009 | |
| WO | WO-2009080252 A1 | 7/2009 | |
| WO | WO-2009080253 A1 | 7/2009 | |
| WO | WO-2009089004 A1 | 7/2009 | |
| WO | WO-2009098596 A2 | 8/2009 | |
| WO | WO2009/157771 A2 | 12/2009 | |
| WO | WO2010/022736 A2 | 3/2010 | |
| WO | WO-2010059315 A1 | 5/2010 | |
| WO | WO-2010084197 A1 | 7/2010 | |
| WO | WO2010/108127 A1 | 9/2010 | |
| WO | WO-2010129304 A2 | 11/2010 | |
| WO | WO-2010151792 A1 | 12/2010 | |
| WO | WO-2011022727 A2 | 2/2011 | |
| WO | WO-2011028952 A1 | 3/2011 | |
| WO | WO-2011028953 A1 | 3/2011 | |
| WO | WO-2011143545 A1 | 11/2011 | |
| WO | WO-2012023053 A2 | 2/2012 | |
| WO | WO-2012058768 A1 | 5/2012 | |
| WO | WO-2012125864 A2 | 9/2012 | |
| WO | WO-2012131555 A2 | 10/2012 | |
| WO | WO-2012140274 A9 * | 3/2013 | A61K 45/06 |
| WO | WO-2013048883 A2 | 4/2013 | |
| WO | WO-2013084151 A2 | 6/2013 | |
| WO | WO-2013107218 A1 | 7/2013 | |
| WO | WO-2013134686 A1 | 9/2013 | |
| WO | WO2013/149159 A1 | 10/2013 | |
| WO | WO2013/157953 A1 | 10/2013 | |
| WO | WO2013/157954 A1 | 10/2013 | |
| WO | WO-2014051433 A1 | 4/2014 | |
| WO | WO-2014060365 A1 | 4/2014 | |
| WO | WO-2014081954 A1 | 5/2014 | |
| WO | WO2014/159580 A1 | 10/2014 | |
| WO | WO-2014165855 A1 | 10/2014 | |
| WO | WO-2014182970 A1 | 11/2014 | |
| WO | WO2015/130172 A1 | 9/2015 | |
| WO | WO2015/130173 A1 | 9/2015 | |
| WO | WO2016/090024 A2 | 6/2016 | |
| WO | WO-2017069628 A2 | 4/2017 | |
| WO | WO-2018182422 A1 | 10/2018 | |
| WO | WO-2020140084 A1 * | 7/2020 | C07K 16/2818 |

OTHER PUBLICATIONS

Almagro J.C., et al., "Humanization of antibodies," Frontiers in bioscience 13:1619-1633, Frontiers in Bioscience Publications, United states (Jan. 2008).

Appella, E , and IT Weber, F Blasi., "Structure and Function of Epidermal Growth Factor-Like Regions In Proteins, " FEBS Letters 231(1):1-4, John Wiley & Sons Ltd, England (Apr. 1988).

Ardeshirpour, Y., et al., "In vivo assessment of HER2 receptor density in HER2-positive tumors by near-infrared imaging, using repeated injections of the fluorescent probe," Technology In Cancer Research & Treatment, 13(5):427-434, SAGE, United States (Oct. 2014).

Armour, K.L., et al., "Differential Binding to Human FcgammaRIIa and FcgammaRIIb Receptors by Human IgG Wildtype and Mutant Antibodies," Molecular Immunology 40(9):585-593, Pergamon Press, England (2003).

Arteaga, C.L., et al., "Treatment of Her2-positive Breast Cancer: Current Status and Future Perspectives," Nature Reviews Clinical Oncology 9(1):16-32, Nature Publishing Group, England (Nov. 2011).

Atwell, S., et al., "Stable Heterodimers from Remodeling the Domain Interface of a Homodimer Using a Phage Display Library," Journal of Molecular Biology 270(1):26-35, Elsevier, England (1997).

Baeuerle, P.A., et al., "Multiple Myeloma and Monoclonal Gammopathy of Undetermined Significance: Importance of Whole-body Versus Spinal Mr Imaging," Cancer Research 252(2):477-485, Radiology (Aug. 2009).

Bakker, A.B., et al., "C-type Lectin-like Molecule-1: a Novel Myeloid Cell Surface Marker Associated With Acute Myeloid Leukemia," Cancer Research 64(22):8443-8450, American Association for Cancer Research, United States (Nov. 2004).

Balko, J.M., et al., "Profiling of residual breast cancers after neoadjuvant chemotherapy identifies DUSP4 deficiency as a mecha-

(56) References Cited

OTHER PUBLICATIONS nism of drug resistance," Nature Medicine ., 18(7): 1052-1059, Nature Publishing Company, United States (Jul. 2012).

Balko, J.M., et al., "The Receptor Tyrosine Kinase Erbb3 Maintains the Balance Between Luminal and Basal Breast Epithelium," Proceedings of the National Academy of Sciences of the United States of America 109(1):221-226, National Academy of Sciences, United States (Jan. 2012).

Bargou, R., et al., "Tumor Regression in Cancer Patients by Very Low Doses of a T Cell-engaging Antibody," Science 321(5891):974-977, American Association for the Advancement of Science, United States (Aug. 2008).

Barthelemy P.A., et al., "Comprehensive Analysis of the Factors Contributing to the Stability and Solubility of Autonomous Human VH Domains," The Journal of Biological Chemistry283, 3639-3654, American Society for Biochemistry and Molecular Biology (Feb. 2008).

Baselga, J., et al., "Pertuzumab Plus Trastuzumab Plus Docetaxel for Metastatic Breast Cancer," The New England Journal of Medicine 366(2):109-119, Massachusetts Medical Society, United States (Jan. 2012).

Beiboer, S.H., et al., "Guided Selection of a Pan Carcinoma Specific Antibody Reveals Similar Binding Characteristics yet Structural Divergence between the Original Murine Antibody and its Human Equivalent," Journal of Molecular Biology 296(3):833-849, Elsevier, England (Feb. 2000).

Berglund, L., et al., "The Epitope Space of the Human Proteome," Protein Science 17(4):606-613, Cold Spring Harbor Laboratory Press, United States (Apr. 2008).

Bernard et al. (Human Immunol. 1986; 17: 388-405).

Bettler., et al., "Binding site For IgE Of The Human Lymphocyte Low-Affinity Fc Epsilon Receptor (Fc Epsilon RII/CD23) is Confined to the Domain Homologous With Animal Lectins, " Proceedings of the National Academy of Sciences of the United States of America 86(18): 7118-7122, National Academy of Sciences, United States (Sep. 1989).

Blomquist, M.C., et al., Vaccinia Virus 19-Kilodalton Protein: Relationship to Several Mammalian Proteins, Including Two Growth Factors, Proceedings of the National Academy of Sciences of the United States of America 81(23):7363-7367, National Academy of Sciences, United States(Dec. 1984).

Bluemel, C., et al., "Epitope Distance to the Target Cell Membrane and Antigen Size Determine the Potency of T Cell-mediated Lysis by BiTE Antibodies Specific for a Large Melanoma Surface Antigen," Cancer Immunology, Immunotherapy 59(8):1197-1209, Springer Verlag, Germany (Aug. 2010).

Bogan, A., et al., "Anatomy of Hot Spots in Protein Interfaces," Journal of Molecular Biology, vol. 280, pp. 1-9 (1998).

Bostrom, J., et al., "Variants of the Antibody Herceptin that Interact with HER2 and VEGF at the Antigen Binding Site," Science 323(5921): 1610-1614, American Association for the Advancement of Science, United States (Mar. 2009).

Boyer, C.M et al., "Relative Cytotoxic Activity of Immunotoxins Reactive With Different Epitopes on the Extracellular Domain of the C☐Erbb☐2 (Her☐2/Neu) Gene Product P185," International Journal of Cancer, 82(4): 525-531, John Wiley & Sons, Inc, United States (Aug. 1999).

Buday, L. et al., "Epidermal Growth Factor Regulates the Exchange Rate of Guanine Nucleotides on p21ras in Fibroblasts," Molecular and Cellular Biology, vol. 13{3): 1903-1910 {1993).

Caldas, C., et al., "Humanization of the Anti-Cd18 Antibody 6.7: An Unexpected Effect of a Framework Residue in Binding to Antigen," Molecular Immunology 39(15): 941-952, Pergamon Press, England (May 2003).

Capelle, M., et al., "Spectroscopic Characterization of Antibodies Adsorbed to Aluminium Adjuvants: Correlation With Antibody Vaccine Immunogenicity," Vaccine 23(14):1686-1694, Elsevier Science, Netherlands (Feb. 2005).

Carter, P., "Bispecific Human IgG by Design," Journal of Immunological Methods 248(1-2):7-15, Elsevier, Netherlands (2001).

Carter, P., et al., "Toward the Production of Bispecific Antibody Fragments for Clinical Applications," Journal of Hematotherapy, vol. 4, pp. 463-470 (1995).

Casset, F., et al., "A Peptide Mimetic of an Anti-CD4 Monoclonal Antibody By Rational Design," Biochemical and Biophysical Research Communications 307(1):198-205, Academic Press, United States (Jul. 2003).

Chames, P. and Baty, D., "Bispecific Antibodies for Cancer Therapy: The Light at the End of the Tunnel?," MAbs 1(6): 539-547, Taylor & Francis, United States (Nov.-Dec. 2009).

Chandra A., "The Role of ErbB3 Inhibitors as Cancer Therapeutics," Boston University, 1-78 (May 2015).

Chang et al. (Structure. Jan. 7, 2014; 22 (1 ): 9-21).

Chatenoud, L., et al., "In Vivo Cell Activation Following OKT3 Administration. Systemic Cytokine Release and Modulation by Corticosteroids," Transplantation 49(4):697-702, Lippincott Williams & Wilkins, United States (Apr. 1990).

Chen, C.H., et al., "Effect of Duration of Osmotherapy on Bloodbrain Barrier Disruption and Regional Cerebral Edema After Experimental Stroke," Journal of Cerebral Blood Flow and Metabolism 26(7):951-958, SAGE Publications, United States (Jul. 2006).

Chernomordik, V., et al., "Quantitative Analysis of Her2 Receptor Expression in Vivo By Near-Infrared Optical Imaging," Molecular imaging, 9(4): 192-200, SAGE Publications, United States (Aug. 2010).

Chien, N.C., et al., "Significant Structural and Functional Change of an Antigen-Binding Site by a Distant Amino Acid Substitution: Proposal of a Structural Mechanism," Proceedings of the National Academy of Sciences USA 86(14):5532-5536, National Academy of Sciences, United States (1989).

Choi Y, and Deane C.M., "Predicting Antibody Complementarity Determining Region Structures Without Classification," Molecular BioSystems 7:3327-3334, The royal society of chemistry (Sep. 2011).

Chua, Y.L., et al., "The NRG1 gene is frequently silenced by methylation in breast cancers and is a strong candidate for the 8p tumor suppressor gene," Oncogene, 28(46): 4041-4052, Macmillan Publishers Limited, Germany (2009).

Clarke, M.F., et al., "Cancer stem cells—perspectives on current status and future directions: AACR Workshop on cancer stem cells," Cancer Research 66(19):9339-9344, American Association for Cancer Research, United States (2006).

Cochran J.R., et al., "Domain-level Antibody Epitope Mapping Through Yeast Surface Display of Epidermal Growth Factor Receptor Fragments," Journal of Immunology Methods 287(1-2):147-158, Elsevier, Netherland (Apr. 2004).

Conforti F., et al., "Dissecting Breast Cancer Complexity: Specific Biological Features and Vulnerabilities of Triple Positive Breast Cancer Tumors," Clinic of Oncology 2:1288, (May 2017).

Cooke, S.L., et al., High-resolution array CGH clarifies events occurring on 8p in carcinogenesis, BMC Cancer, 8(288): 1-15, BioMed Central Ltd., London (2008).

Corada, M., et al., "Monoclonal Antibodies Directed To Different Regions of Vascular Endothelial Cadherin Extracellular Domain Affect Adhesion and Clustering of the Protein and Modulate Endothelial Permeability," Blood 97(6):1679-1684, American Society of Hematology (Mar. 2001).

Corona S.P., et al., "CDK4/6 Inhibitors in HER2-positive Breast Cancer," Critical reviews in oncology 118:208-214, Hematology (2017).

Cui, H., et al., "Chemically Programmed Bispecific Antibodies That Recruit and Activate T Cells," The Journal of Biological Chemistry 287(34):28206-28214, American Society for Biochemistry and Molecular Biology, United States (Aug. 2012).

Curley M.D., et al., "Seribantumab. An Anti-ERBB3 Antibody. Delays the Onset of Resistance and Restores Sensitivity to Letrozole in an Estrogen Receptor Positive Breast Cancer Model," Molecular cancer Therapeutics 14(11): 2642-2652 (Nov. 2015).

Davies, J. and Riechmann, L., "Antibody VH Domains as Small Recognition Units," Biotechnology 13(5):475-479, Nature Publishing Group, United States (1995).

(56) References Cited

OTHER PUBLICATIONS

Davis, C G., "The Many Faces of Epidermal Growth Factor Repeats, " New biologist 2(5):410-419, W.B. Saunders, United States (May 1990).

Davis, J.H., et al., "SEEDbodies: Fusion Proteins Based on Strand-exchange Engineered Domain (SEED) CH3 Heterodimers in an Fc Analogue Platform for Asymmetric Binders or Immunofusions and Bispecific Antibodies.," Protein Engineering, Design & Selection 23(4):195-202, Oxford University Press, England (2010).

De Kruif, J et al., "Human immunoglobulin repertoires against Tetanus toxoid contain a large and diverse fraction of high-affinity VH genes" J. Mol. Biol., vol. 387 ,(2009) pg.no (548-558).

De Genst, E., et al., "Antibody Repertoire Development in Camelids," Developmental and Comparative Immunology 30(1-2):187-198, Elsevier Science, United States (2006).

De Goeij, B.E., et al., "Efficient Payload Delivery by a Bispecific Antibody-Drug Conjugate Targeting HER2 and CD63," Molecular Cancer Therapeutics 5(11):2688-2697, American Association for Cancer Research, United States (Nov. 2016).

De Kruif, J., et al., "Selection and Application of Human Single Chain Fv Antibody Fragments from a Semi-Synthetic Phage Antibody Display Library with Designed CDR3 Regions," Journal of Molecular Biology 248(1):97-105, Elsevier, England (Apr. 1995).

De Kruif, J., et al., "Generation of Stable Cell Clones Expressing Mixtures of Human Antibodies," Biotechnology and Bioengineering 106(5):741-750, Wiley, United States (Aug. 2010).

De Lau, W., et al., "The R-spondin/Lgr5/Rnf43 module: regulator of Wnt signal strength," Genes Dev, vol. 28:305-316 (2014).

De Lau, W., et al., "Lgr5 Homologues Associate With Wnt Receptors and Mediate R-spondin Signaling," Nature 476: 293-298 (2011).

De Nardis, C., et al., "A new approach for generation bispecific antibodies based on a common light chain format and the stable architecture of human immunoglobulin G1," Journal of Biological Chemistry, 292(35): 14706-14717, The American Society for Biochemistry and Molecular Biology, Inc., United States (2017).

De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).

De Wildt, et al., Analysis of Heavy and Light Chain Pairings Indicates that Receptor Editing Shapes fhe Human Antibody Repertoire, Journal of Molecular Biology, 285(3):895-901, Elsevier,England(1999).

Deisenhofer, J., "Crystallographic refinement and atomic models of a human Fc fragment and its complex with fragment B of protein A from *Staphylococcus aureus* at 2.9- and 2.8-A resolution," Biochemistry 20(9):2361-2370, American Chemical Society, United States (1981).

Demeule, B., et al., "Characterization of Protein Aggregation: the Case of a Therapeutic Immunoglobulin," Biochimica et Biophysica Acta 1774(1):146-153, Elsevier Publisher, Netherlands (Jan. 2007 ).

Demeule, B., et al., "Detection and Characterization of Protein Aggregates by Fluorescence Microscopy," International Journal of Pharmaceutics 329(1-2):37-45, Elsevier/North-Holland Biomedical Press, Netherlands (Feb. 2007 ).

Devash, Y., et al., "Vertical Transmission of Human Immunodeficiency Virus Is Correlated With the Absence of High-affinity/avidity Maternal Antibodies to the Gp120 Principal Neutralizing Domain," Proceedings of the National Academy of Sciences of the United States of America 87(9):3445-3449, National Academy of Sciences, United States (May 1990).

Dhanasekaran SM et al., "Transcriptome meta-analysis of lung cancer reveals recurrent aberrations in NRG1 and Hippo pathway genes," Nat. Commun. Dec. 22, 2014;5:5893.

Dijoseph, J.F., et al., "Antibody-targeted Chemotherapy with CMC-544: A CD22-targeted Immunoconjugate of Calicheamicin for the Treatment of B-lymphoid Malignancies," Blood 103(5):1807-1814, American Society of Hematology, United States (2004).

Doolittle, R.F., et al., "Computer-Based Characterization of Epidermal Growth Factor Precursor," Nature 307(5951):558-560, Nature Publishing Group, England (Feb. 1984).

Dreier, T., et al., "Extremely Potent, Rapid and Costimulation-Independent Cytotoxic T-Cell Response against Lymphoma Cells Catalyzed By a Single-Chain Bispecific Antibody," International Journal of Cancer 100(6):690-697, Wiley-Liss, United States (2002).

Duruisseaux, M., et al., "NRG1 fusion in a French cohort of invasive mucinous lung adenocarcinoma," Cancer Medicine, 5(12): 3579-3585, John Wiley & Sons Ltd., United States (2016).

Edwards, B.M., et al., "The Remarkable Flexibility of the Human Antibody Repertoire; Isolation of Over One Thousand Different Antibodies to a Single Protein, BLyS," Journal of Molecular Biology, 334(1):103-118, Elsevier, England (Nov. 2003).

Ellerson, J.R., et al., "Structure and Function of Immunoglobulin Domains. III. Isolation and Characterization of a Fragment Corresponding to the Cgamma2 Homology Region of Human Immunoglobin G1," Journal of Immunology 116(2):510-517, American Association of Immunologists, United States (Feb. 1976).

Ewer, M.S., et al., "Cardiotoxicity of Anticancer Treatments: What the Cardiologist Needs to Know," Nature Reviews Cardiology 7(10):564-575, Nature Publishing Group, England (Oct. 2010).

Falls, D.L., "Neuregulins: functions, form, and signaling strategies," Exp. Cell Res, 284: 14-30, Elsevier, Netherlands (2003).

Farnan, D. and Moreno, G.T., "Multiproduct High-resolution Monoclonal Antibody Charge Variant Separations by pH Gradient Ion-exchange Chromatography," Analytical Chemistry 81(21):8846-8857, American Chemical Society, United States (2009).

Ferguson, K.M., "Structure-based View of Epidermal Growth Factor Receptor Regulation," Annual Review of Biophysics 37:353-373,AnnualReviews, United States (2008).

Fernandez-Cuesta, L., et al., "CD74-NRG1 Fusions in Lung Adenocarcinoma," Cancer Discovery, 4(4): 415-422, American Association for Cancer Research, United States (2014).

Fernandez-Cuesta, L., et al., "Molecular Pathways: Targeting NRG1 Fusions in Lung Cancer," Clinical Cancer Research, 21 (9): 1989-1994, American Association for Cancer Research, United States (2015).

Freeman D., et al., "Panitumumab and Cetuximab Epitope Mapping and in Vitro Activity," Journal of Clinical Oncology 26(15): 14536-14536, American Society of Clinical Oncology (May 20, 2008).

Fu et al. (MAbs. 2014; 6 (4): 978-90).

Gaborit, N., et al., "Emerging anti-cancer antibodies and combination therapies targeting HER3/ERBB3," Human Vaccines and Immunotherapies, 12(3): 576-592, Taylor & Frances (2015).

Gale, N.W et al. "Grb2 Mediates the Egf-Dependent Activation of Guanine Nucleotide Exchange on Ras," Nature 363:88-92, Springer Nature Limited (May 1993).

Garrett, T.P., et al., "Crystal Structure of a Truncated Epidermal Growth Factor Receptor Extracellular Domain Bound to Transforming Growth Factor alpha," Cell 110(6):763-773, Cell Press, United States (Sep. 2002).

Geginat, J., et al., "Proliferation and Differentiation Potential of Human CD8+ Memory T-cell Subsets in Response to Antigen or Homeostatic Cytokines," Blood 101(11):4260-4266, American Society of Hematology, United States (Jun. 2003).

GenBank Accession No. NP_001005862.1, Receptor Tyrosine-Protein Kinase erbB-2 Isoform b [*Homo sapiens*], 2018.

GenBank Accession No. NP_001005915.1, Receptor Tyrosine-Protein Kinase ErbB-3 isoform s Precursor [*Homo sapiens*], 2018.

GenBank Accession No. NP_001973.2, Receptor Tyrosine-Protein Kinase ErbB-3 isoform 1 precursor [*Homo sapiens*], 2018.

GenBank Accession No. NP_004439.2, Receptor Tyrosine-Protein Kinase ErbB-2 isoform a Precursor [*Homo sapiens*], 2018.

GenBank Accession No. NM_001982.3, 2020, *Homo sapiens* erb-b2 receptor tyrosine kinase 3 (ERBB3), transcript variant 1, mRNA, PRI: Jun. 4, 2019, 8 pages.

GenBank Accession No. NM_004448.2, 2020, *Homo sapiens* v-erb-b2 avian erythroblastic leukemia viral oncogene homolog 2 (ERBB2), transcript variant 1, mRNA, PRI Jan. 19, 2014, 5 pages.

(56) References Cited

OTHER PUBLICATIONS

GenBank XM_002800451.1, 2020, Predicted: Macaca mulatta v-erb-b2 erythroblastic leukemia viral oncogene homolog 2,neuro/glioblastoma derived oncogene homolog (avian) (ERBB2), mRNA, Jun. 1, 2010, 3 pages.
George et al. (Circulation. 1998; 97: 900-906).
Geuijen, C., et al., "Abstract LB-261: Mechanism of action of MCLA-128, a humanized bispecific IgG1 antibody targeting the HER2: HER3 heterodimer," Cancer Research; 1 061h Annual Meeting of The American Association for Cancer Research (AAACR), 75, Suppl. 15, pp. LB-261, Philadelphia (2015).
Giard D.J., et al., "In Vitro Cultivation of Human Tumors: Establishment of Cell Lines Derived From a Series of Solid tumors," Journal of National Cancer Institution 51:1417-1423 (Nov. 1973).
Girlanda, S., et al., "MICA Expressed by Multiple Myeloma and Monoclonal Gammopathy of Undetermined Significance Plasma Cells Costimulates Pamidronate-activated Gammadelta Lymphocytes," Cancer Research, 65(16):7502-7508, American Association for Cancer Research, United States (Aug. 2005).
Giusti, A.M., et al., "Somatic diversification of S107 from an antiphosphocholine to an anti-DNA autoantibody is due to a single base change in its heavy chain variable region," Proceedings of the National Academy of Sciences 84(9):2926-2930, National Academy of Sciences, United States, (1987).
Greco, W.R., et al., "The Search for Synergy: a Critical Review From a Response Surface Perspective," Pharmacological Reviews 47(2):331-385, American Society for Pharmacology and Experimental Therapeutics, United States (Jun. 1995).
Greenspan, N.S. and Di Cera, E., "Defining Epitopes: It's not as Easy as it Seems," Nature Biotechnology 17(10):936-937, Nature Publishing Group, United States (1999).
Griffiths, A.D., et al., "Human Anti-Self Antibodies with High Specificity from Phage Display Libraries," The EMBO Journal 12(2):725-734, Wiley Blackwell, England (Feb. 1993).
Gulli, LF et al., "Epidermal growth factor-induced apoptosis in A431 cells can be reversed by reducing the tyrosine kinase activity," Cell Growth Differentiation 7(2):173-178, The Association, United States(Feb. 1996).
Gussow, D. and Seemann, G., "Humanization of Monoclonal Antibodies," Methods in Enzymology 203:99-121, Elsevier Science, United States (1991).
Haagen, I.A., et al., "The Efficacy of CD3 X CD19 Bispecific Monoclonal Antibody (BsAB) in a Clonogenic Assay: The Effect of Repeated Addition of Bsab and Interleukin-2," Blood 85(11):3208-3212, American Society of Hematology, United States (Jun. 1995).
Hammond M.E.H., et al., "American Society of Clinical Oncology/College Of American Pathologists Guideline Recommendations for Immunohistochemical Testing of Estrogen and Progesterone Receptors in Breast Cancer," Journal of clinical oncology 28(16):2784-2795, Grune & Stratton, United states (Jun. 2010).
Han, Y., et al., "KLRL1, a Novel Killer Cell Lectin like Receptor, Inhibits Natural Killer Cell Cytotoxicity," Blood 104(9):2858-2866, American Society of Hematology, United States (Nov. 2004).
Hao, H.X., et al., "ZNRF3 Promotes Wnt Receptor Turnover in an R-Spondin-Sensitive Manner," Nature 485(7397):195-200, Nature Publishing Group, England (2012).
Harms B., et al., "Understanding the Role of Cross-arm Binding Efficiency in the Activity of Monoclonal and Multispecific Therapeutic Antibodies", Methods 65(1):95-104, Duluth, MN (Jan. 2014).
Hathaway et al. (Breast Cancer Res. Nov. 3, 2011; 13 (5): R 1 08; pp. 1-14).
Hayes, N.V.L., and Gullick, W.J., "The Neuregulin Family of Genes and their Multiple Splice Variants in Breast Cancer," J. Mammary Gland Bioi Neoplasia, 13(205): 214, Springer, New York (2008).
Hendsch, Z.S., et al., "Preferential Heterodimer Formation via Undercompensated Electrostatic Interactions," Journal of the American Chemical Society 123(6):1264-1265, American Chemical Society, United States (Feb. 2001).

Holm, P., et al., "Functional Mapping and Single Chain Construction of the Anti-cytokeratin 8 Monoclonal Antibody TS1," Molecular Immunology 44(6):1075-1084, Pergamon Press, England (Feb. 2007).
Hommel, U., et al., Human Epidermal Growth Factor. High Resolution Solution Structure And Comparison With Human Transforming Growth Factor Alpha, Journal of Molecular Biology 227(1):271-282, Elsevier, England (Sep. 1992).
Huang W, et al., "Comparison of Central HER2 Testing With Quantitative Total HER2 Expression and HER2 Homodimer Measurements Using a Novel Proximity-Based Assay," American journal of clinical pathology 134(2):303-311, Oxford University Press, England (Aug. 2010).
Idusogie, E.E., et al., "Mapping of the C1q Binding Site on Rituxan, A Chimeric Antibody with a Human IgG1 Fc," The Journal of Immunology 164(8):4178-4184, American Association of Immunologists, United States (2000).
Ionescu, R.M., et al., "Contribution of Variable Domains to the Stability of Humanized IgG1 Monoclonal Antibodies," Journal of Pharmaceutical Sciences 97(4): 1414-1426, Elsevier, United States (Apr. 2008 ).
Jackson et al. (Int. J. Cell Bioi. 2013; 2013: 973584; pp. 1-9).
Jain K.K., et al., "A Prospective Randomized Comparison of Epirubicin and Doxorubicin in Patients With Advanced Breast Cancer," Journal of Clinical Oncology 3(6):818-820, American Society of Clinical Oncology, United States (Jun. 1985).
Jelovac, D., et al., "HER2-Directed Therapy for Metastatic Breast Cancer," Oncology (Williston Park) 27(3):166-175, CMP Healthcare Media, United States (Mar. 2013).
Jiang, B., et al., "A Novel Peptide Isolated from a Phage Display Peptide Library with Trastuzumab Can Mimic Antigen Epitope of HER-2," The Journal of Biological Chemistry 280(6):4656-4662, The American Society for Biochemistry and Molecular Biology (2005).
Jorissen, R.N., et al., "Epidermal Growth Factor Receptor: Mechanisms of Activation and Signalling," Experimental Cell Research 284(1):31-53, Academic Press, United States (Mar. 2003).
Jung, Y., et al., "VAMP2-NRG1 Fusion Gene is a Novel Oncogenic Driver of Non-Small-Cell Lung Adenocarcinoma," J Thor Oncol1 0(7): 1107-1111, International Association for the Study of Lung Cancer, Colorado (2015).
Junttila, T.T., et al., "Ligand-Independent HER2/HER3/PI3K Complex Is Disrupted by Trastuzumab and Is Effectively Inhibited by the PI3K Inhibitor GDC-0941," Cancer Cell 15(5):429-440, Cell Press, United States (May 2009).
Kabat, E.A., et al., "Identical V Region Amino Acid Sequences and Segments of Sequences in Antibodies of Different Specificities. Relative Contributions of Vh and Vl Genes, Minigenes, and Complementarity-determining Regions to Binding of Antibody-combining Sites," Journal of Immunology 147(5):1709-1719, American Association of Immunologists, United States (Sep. 1991).
Kang J.C., et al., "Engineering Multivalent Antibodies to Target Heregulin-Induced HER3 Signaling in Breast Cancer Cells," Comparative Study 6(2):340-353, Landes Bioscience, United states (Apr. 2014).
Kipriyanov, S.M., et al., "Bispecific CD3×CD19 Diabody for T Cell-Mediated Lysis of Malignant Human B Cells," International Journal of Cancer 77(5):763-772, Wiley-Liss, United States (1998).
Klein, C., et al., "Progress in Overcoming the Chain Association Issue in Bispecific Heterodimeric IgG Antibodies," MAbs 4(6):653-663, Taylor & Francis, United States (Nov.-Dec. 2012).
Klimka, A., et al., "Human Anti-CD30 Recombinant Antibodies by Guided Phage Antibody Selection Using Cell Panning," British Journal of Cancer 83(2):252-260, Nature Publishing Group, England (Jul. 2000).
Kodack D.P., et al., "Combined Targeting of HER2 and VEGFR2 for Effective Treatment of HER2-amplified Breast Cancer Brain Metastases," Proceedings of the National Academy of Sciences 109(45):E3119-E3127 (Nov. 2012).
Kol, A., et al., "HER3, Serious Partner in Crime: Therapeutic Approaches and Potential Biomarkers for Effect of HER3-targeting," Pharmacology & Therapeutics 143(1):1-11, Pergamon Press, England (Jul. 2014).

(56) References Cited

OTHER PUBLICATIONS

Kontermann, R.E., "Dual Targeting Strategies with Bispecific Antibodies," mAbs 4(2): 182-197, Taylor and Francis, United States (2012).
Krausova,M and Korinek, V., "Wnt Signaling In Adult Intestinal Stem Cells and Cancer," Cell signaling 26(3):570-579, Elsevier Science Ltd, England (Mar. 2014).
Kruif, D.J., et al., "Human Immunoglobulin Repertoires Against Tetanus Toxoid Contain a Large and Diverse Fraction of High-affinity Promiscuous V(H) Genes," Journal of Molecular Biology 387(3):548-558, Elsevier, England (Apr. 2009).
Kubota, T., et al., "Engineered therapeutic antibodies with improved effector functions," Cancer Science 100(9):1566-1572, Wiley Publishing on behalf of the Japanese Cancer Association, England(Sep. 2009).
Kumar, R., et al., "The Second Pdz Domain of Inad Is a Type I Domain Involved in Binding to Eye Protein Kinase C. Mutational Analysis and Naturally Occurring Variants," Journal of Biological Chemistry 276(27):24971-24977, American Society for Biochemistry and Molecular Biology, United States (Jul. 2001).
Landgraf, R., et al., "HER2 Therapy. HER2 (ERBB2): Functional Diversity from Structurally Conserved Building Blocks," Breast Cancer Research 9(1):202, BioMed Central Ltd, England (2007).
Lanzavecchia, A. and Staerz, U.D., "Lysis of Nonnucleated Red Blood Cells by Cytotoxic T Lymphocytes," European Journal of Immunology 17(7):1073-1074, Wiley-VCH, Germany (Jul. 1987).
Lazrek Y., et al."Anti-HER3 Domain 1 and 3Antibodies Reduce TumorGrowth by Hindering HER2/HER3Dimerization and AKT-InducedMDM2. XIAP, and Fox01 Phosphorylation," Neoplasia 15(3):335-347 (Mar. 2013).
Le Clorennec, C., et al., "Neuregulin 1 Allosterically Enhances the Antitumor Effects of the Noncompeting Anti-HER3 Antibody 9 F7-F11 by Increasing Its Binding to HER3," Molecular Cancer Therapeutics, 16(7): 1312-1323, American Association for Cancer Research, United States (2017).
Le Gall, F., et al., "Effect of Linker Sequences Between the Antibody Variable Domains on the Formation, Stability and Biological Activity of a Bispecific Tandem Diabody," Protein Engineering, Design & Selection 17(4):357-366, Oxford University Press, England (Apr. 2004).
Ledon N., et al., "Comparative Analysis of Binding Affinities to Epidermal Growth Factor Receptor of Monoclonal Antibodies Nimotuzumab and Cetuximab Using Different Experimental Animal Models," Placenta 32: 531-534 (2011).
Lee, B., et al., "The Interpretation of Protein Structures: Estimation of Static Accessibility," Journal of Molecular Biology 55(3):379-400, Elsevier, England (Feb. 1971).
Lee H.J., et al., "Gemini Vitamin D Analog Suppresses Erbb2-positive mammary tumor growth via inhibition of ErbB2/AKT/ERK Signaling", Journal of Steroid Biochemistry and Molecular Biology, Elsevier Science LTD., Oxford, DB, 121(1-2):408-412, England (Jul. 2010).
Lee-Hoeflich, S.T., et al., "A Central Role for HER3 in HER2-Amplified Breast Cancer: Implications for Targeted Therapy," Cancer Research, 68(14): 5878-5887, American Association for Cancer Research, United States (2008).
Lichtenberger, B.M., et al., "Epidermal Egfr Controls Cutaneous Host Defense and Prevents Inflammation," Science Translational Medicine 5(199):14, (2013).
Liesveld, J.L., et al., "Expression of IgG Fc Receptors in Myeloid Leukemic Cell Lines. Effect of Colony-stimulating Factors and Cytokines," Journal of Immunology 140(5):1527-1533, American Association of Immunologists, United States (Mar. 1988).
Liu, C and Lee, A., "ADCC Enhancement Technologies for Next Generation Therapeutic Antibody," Trends in Bio/Pharmaceutical Industry, 9 pages, 2009.
Liu, H., et al., "Heterogeneity of Monoclonal Antibodies," Journal of Pharmaceutical Sciences 97(7):2426-2447, Wiley-Liss, United States (Jul. 2008).

Liu, M.A., et al., "Heteroantibody Duplexes Target Cells for Lysis by Cytotoxic T Lymphocytes," Proceedings of the National Academy of Sciences of the United States of America 82(24):8648-8652, National Academy of Sciences, United States (1985).
Loffler, A., et al., "A Recombinant Bispecific Single-chain Antibody, CD19 X CD3, Induces Rapid and High Lymphoma-directed Cytotoxicity by Unstimulated T Lymphocytes," Blood 95(6):2098-2103, American Society of Hematology, United States (Mar. 2000).
Logtenberg, T., "Hub for Organoids", Poster Presentation, www.innovationforhealth.nl/index.php/page/getFileUID/id/82364b177dfed9754d785aafffb21363/cr_usedb/25, 29 pages, Mar. 22, 2016.
Lumachi F., et al., "Endocrine Therapy of Breast Cancer," Current medicinal chemistry 18(4):513-522, Bentham Science Publishers, United Arab Emirates (2011).
Luo, H., et al., "Noninvasive Brain Cancer Imaging With a Bispecific Antibody Fragment, Generated via Click Chemistry," Proceedings of the National Academy of Sciences of the United States of America 112(41):12806-12811, National Academy of Sciences, United States (Oct. 2015).
MacCallum, R.M., et al., "Antibody-antigen Interactions: Contact Analysis and Binding Site Topography," Journal of Molecular Biology 262(5):732-745, Academic Press, England (Oct. 1996).
Malm, M., et al., "Engineering of a Bispecific Affibody Molecule Towards HER2 and HER3 by Addition of an Albumin-Binding Domain Allows for Affinity Purification and in Vivo Half-Life Extension," Biotechnology Journal 9(9):1215-1222, Wiley-VCH Verlag, Germany (Sep. 2014).
Malm, M., et al., "Targeting HER3 Using Mono-and Bispecific Antibodies or Alternative Scaffolds," MABS 8(7):1195-1209, Taylor & Francis, United States (Oct. 2016).
Mariuzza, R.A., et al., "The Structural Basis of Antigen-antibody Recognition," Annual Review of Biophysics and Biomolecular Structure 16:139-159, Annual Reviews, United States (1987).
Marks, J.D., et al., "By-passing Immunization. Human Antibodies from V-gene Libraries Displayed on Phage," Journal of Molecular Biology 222(3):581-597, Academic Press Limited, United States (Dec. 1991).
Marshall, A.S., et al., "Identification and Characterization of a Novel Human Myeloid Inhibitory C-type Lectin-like Receptor (MICL) That Is Predominantly Expressed on Granulocytes and Monocytes," The Journal of Biological Chemistry 279(15):14792-14802, American Society for Biochemistry and Molecular Biology, United States (Apr. 2004).
Marvin, J.S., et al., "Redesigning an Antibody Fragment for Faster Association With Its Antigen," Biochemistry 42(23):7077-7083, American Chemical Society, United States (Jun. 2003).
Maussang ., et al., The Binding Mode of the Bispecific Anti-Her2xHer3 antibody MCLA-128 is Responsible for its Potent Inhibition of HRG-Driven Tumorigenesis, Research Poster Presentation Design, 2001, Apr. 1, 2017, Retrieved from the Internet: (URL: http://www.merus.nl/wordpress/wp-content/uploads/2017/04/MCLA- 128-poster-AACR2017-final-.pdf).
May C., et al., "Advances in Bispecific Biotherapeutics for the Treatment of Cancer," Biochemical Pharmacology 84:1105-1112 (2012).
McDonagh, C.F., et al., "Antitumor Activity of a Novel Bispecific Antibody that Targets the ErbB2/ErbB3 Oncogenic Unit And Inhibits Heregulin-Induced Activation of ErbB3," Molecular Cancer Therapeutics 11(3):582-593, American Association for Cancer Research, United States (Mar. 2012).
McPhee, F., et al., "Engineering Human Immunodeficiency Virus 1 Protease Heterodimers as Macromolecular Inhibitors of Viral Maturation," Proceedings of the National Academy of Sciences of the United States of America 93(21):11477-11481, National Academy of Sciences, United States (Oct. 1996).
Merlino, GT. et al, "Amplification and Enhanced Expression of the Epidermal Growth Factor Receptor Gene in A431Human Carcinoma Cells," Science, vol. 224{4647): 417-419 {1984).
Merten, H., et al., "Antibody-drug Conjugates for Tumor Targeting-novel Conjugation Chemistries and the Promise of Non-IgG Binding Proteins," Bioconjugate Chemistry 26(11):2176-2185, American Chemical Society, United States (Nov. 2015).

(56) References Cited

OTHER PUBLICATIONS

Merus, www.merus.nl, press release, 2 pages, dated Jan. 7, 2013.
Merus, www.merus.nl, press release, 3 pages, dated Jun. 17, 2013.
Meulemans, E.V., et al., "Selection of Phage-displayed Antibodies Specific for a Cytoskeletal Antigen by Competitive Elution With a Monoclonal Antibody," Journal of Molecular Biological 244(4):353-360 (1994).
Miller, S, "Protein-protein Recognition and the Association of Immunoglobulin Constant Domains," Journal of Molecular Biology 216(4):965-973, Elsevier Ltd (Dec. 1990).
Momeny M., et al., "Heregulin-HER3-HER2 signaling promotes matrix metalloproteinase-dependent blood-brain-barrier transendothelial migration of human breast cancer cell lines," Oncotarget 6(6):3932-3946 (Feb. 2015).
Moore, P.A., et al., "Application of Dual Affinity Retargeting Molecules to Achieve Optimal Redirected T-cell killing of B-cell Lymphoma," Blood 117(17):4542-4551, American Society of Hematology, United States (Apr. 2011).
Morrison M.M., et al., "ErbB3 Downregulation Enhances Luminal Breast Tumor Response to Antiestrogens," The Journal of clinical investigation 123(10):4329-4343, American Society for Clinical Investigation, United states (Oct. 2013).
Moshaver, B., et al., "Identification of a Small Subpopulation of Candidate Leukemia-initiating Cells in the Side Population of Patients With Acute Myeloid Leukemia," Stem Cells 26(12):3059-3067, AlphaMed Press, United States (Dec. 2008).
Mullard, A., et al., "Maturing Antibody-drug Conjugate Pipeline Hits 30," Nature Reviews Drug Discovery 12(5):329-332, Nature Publishing Group, England (May 2013).
Nieba, L., et al., "Disrupting the Hydrophobic Patches at the Antibody Variable/constant Domain Interface: Improved in Vivo Folding and Physical Characterization of an Engineered Scfv Fragment," Protein Engineering 10(4):435-444, Oxford University Press, England (Apr. 1997).
Nohaile, M.J., et al., "Altering dimerization specificity by changes in surface electrostatics," Proceedings of the National Academy of Sciences 98(6):3109-3114, National Academy of Sciences, United States (2001).
Norde, W.J., et al., "Myeloid Leukemic Progenitor Cells Can Be Specifically Targeted by Minor Histocompatibility Antigen LRH-1-reactive Cytotoxic T Cells," Blood 113(10):2312-2323, American Society of Hematology, United States (Mar. 2009).
Ocana, A., et al., "HER3 Overexpression and Survival In Solid Tumors: A Meta-Analysis," Journal of the National Cancer Institute 105(4):266-273, Oxford University Press, United States (Feb. 2013).
Offner, S., et al., "Induction of Regular Cytolytic T Cell Synapses by Bispecific Single-chain Antibody Constructs on MHC Class I-negative Tumor Cells," Molecular Immunology 43(6):763-771, Pergamon Press, England (Feb. 2006).
Oganesyan, V., et al., "Structural Characterization of a Human Fc Fragment Engineered for Lack of Effector Functions," Acta Crystallographica. Section D, Biological Crystallography 64(Pt 6):700-704, Wiley-Blackwell, United States (Jun. 2008).
Omenn et al. (J. Proteomics. 2014; 107: 1 03-112; pp. 1-22).
Osborne K.C., et al., "Mechanisms of Endocrine Resistance in Breast Cancer," Annual review of medicine 62:233-247, Annual Reviews Inc, United states (2011).
Padlan, E.A, "X-Ray Crystallography of Antibodies," Advances in Protein Chemistry 49:57-133, Academic Press, United States (1996).
Panke C., et al., "Quantification of Cell Surface Proteins with Bispecific Antibodies", Protein Engineering Design and Selection, Oxford University Press 26(10):645-654, England (Aug. 2013).
Papadea, C., et al., "Human Immunoglobulin G and Immunoglobulin G Subclasses: Biochemical, Genetic, and Clinical Aspects," Critical Reviews in Clinical Laboratory Sciences 27(1):27-58, Informa Healthcare, England (1989).
Pastore, S. et al., "Erk1/2 Regulates Epidermal Chemokine Expression and Skin Inflammation," Journal of Immunology 174:5047-5056 (2005).
Patel, D.K., "Clinical Use of Anti-epidermal Growth Factor Receptor Monoclonal Antibodies in Metastatic Colorectal Cancer," Pharmacotherapy 28(11):31S-41S (2008).
Pedersen M.W., et al., "Targeting Three Distinct HER2 Domains with a Recombinant Antibody Mixture Overcomes Trastuzumab Resistance," Molecular Cancer Therapeutics 14(3):669-680, American Association for cancer Research (Jan. 2015).
Peng, R., et al., "Bleomycin Induces Molecular Changes Directly Relevant to Idiopathic Pulmonary Fibrosis: A Modelor Active," Disease, Pios One, 8{4}: e59348, 15 pages {2013).
Peng, W., et al., "Blockade of the PD-1 Pathway Enhances the Efficacy of Adoptive Cell Therapy against Cancer," Oncoimmunology 2(2):e22691, Taylor & Francis, United States (Feb. 2013).
Petterson, R.D., et al., "CD47 Signals T Cell Death, " Journal of Immunolgy 15; 162 (12): 7031-7040, American Association of Immunologists, United States (Jun. 1999).
Pole, J.C.M., et al., High-resolution analysis of chromosome rearrangements on 8p in breast, colon and pancreatic cancer reveals a complex pattern of loss, gain and translocation, Oncogene, 25: 5693-5706, Nature Publishing Group, United Kingdom (2006).
Press et al. (J. Immunol. Dec. 15, 1988; 141 (12): 4410-4417).
Prigent, S., et al., "Identification of C-erbb-3 Binding Sites for Phosphatidylinositol 3'-kinase and Shc Using an Egf Receptor/c-erbb-3 Chimera," The EMBO Journal 13(12):2831-2841, National Center for Biotechnology Information (Jun. 1994).
Raffen, R., et al., "Reengineering Immunoglobulin Domain Interactions by Introduction of Charged Residues," Protein Engineering 11(4):303-309, Oxford University Press, England (Apr. 1998 ).
Regina, A., et al., "ANG4043, a Novel Brain-Penetrant peptide-mAb Conjugate, Is Efficacious Against HER2-positive Intracranial Tumors in Mice, " Molecular Cancer Therapeutics 14(1):129-140, American Association for Cancer Research, Inc, United States (Jan. 2015).
Reusch, U., et al., "Beyond mAbs with T and Abs," Innovations in Pharmaceutical Technology, 4 pages, (2011).
Richards, D.A., et al., "A Phase 1 Study of Mm-111, a Bispecific HER2/HER3 Antibody Fusion Protein, Combined with Multiple Treatment Regimens in Patients with Advanced HER2-Positive Solid Tumors," Journal of Clinical Oncology 32(15):651 (2014).
Ridgway, J.B., et al., "Knobs-Into-Holes' Engineering of Antibody CH3 Domains for Heavy Chain Heterodimerization," Protein Engineering 9(7):617-621, Oxford University Press, England (1996).
Riemer, A.B., et al., "Matching of Trastuzumab (Herceptin) Epitope Mimics Onto the Surface of Her-2/neu—a New Method of Epitope Definition," Molecular Immunology 42(9):1121-1124, Pergamon Press, England (2005).
Robertson, S.C., et al., "Rtk Mutations and Human Syndromes when Good Receptors Turn Bad," Trends in genetics 16(6):265-271 (Jun. 2000).
Robinson M.K., et al., "Targeting ErbB2 and ErbB3 with a bispecific single-chain FV Enhances targeting selectivity and induces a therapeutic effect in Vitro", British Journal of CA, Nature Publishing Group, GB 99(9):1415-1425, England, London (Oct. 2008).
Rohrer, T., et al. Consideration for the Safe and Effective Manufacturing of Antibody-drug conjugates ADC, Journal of Antibody-drug Conjugates, 30(5):4, Published online 2012, doi: 10.14229/jadc.2013.6.1.003.
Rohrer, T., et al. Consideration for the Safe and Effective Manufacturing of Antibody-drug conjugates ADC, Jun. 2013, Biotechnology+ Chemistry = Antibody drug Conjugates, Retrieved from the Internet https://www.adcreview.com/articles/consideration-safe-effective-manufacturing-antibody-drug-conjugates/, 2020, 10 pages.
Roskoski, R., "The ErbB/HER Family of Protein-Tyrosine Kinases and Cancer," Pharmacological Research 79:34-74, Elsevier, Netherlands (Jan. 2014).
Rudikoff, S., et al., "Single Amino Acid Substitution Altering Antigen-binding Specificity," Proceedings of the National Academy of Sciences of the United States of America 79(6): 1979-1983, National Academy of Sciences, Washington (Mar. 1982).
Sali, A., et al., "Comparative Protein Modelling By Satisfaction of Spatial Restraints, " Journal of Molecular Biology 234(3):779-815, Elsevier, England (Dec. 1993).

(56) References Cited

OTHER PUBLICATIONS

Sal-Man, N. and Shai, Y., "Arginine mutations within a transmembrane domain of Tar, an *Escherichia coli* aspartate receptor, can drive homodimer dissociation and heterodimer association in vivo," Biochemical Journal 385(Pt1):29-36, Portland Press, United Kingdom (2005).

Sanchez-Valdivieso, E.A., et al., "γ-Heregulin has no biological significance in primary breast cancer," British Journal of Cancer, 86(8): 1362-1366, Cancer Research UK, United Kingdom (2002).

Sato, T., et al., "Long-term Expansion of Epithelial Organoids From Human Colon, Adenoma, Adenocarcinoma, and Barrett's Epithelium," Gastroenterology 141:1762-1772, W.B. Saunders, United states (Nov. 2011).

Schaefer, G., et al., "A Two-in-one Antibody Against Her3 and Egfr Has Superior Inhibitory Activity Compared With Monospecific Antibodies," Cancer cell 20(4):472-486, Cell Press, United States (Oct. 2011).

Schiffer, M., et al., "Analysis of Immunoglobulin Domain Interactions. Evidence for a Dominant Role of Salt Bridges," Journal of Molecular Biology 203(3):799-802, Elsevier, England (Oct. 1988).

Schlom, J., et al., "Therapeutic Advantage of High-affinity Anticarcinoma Radioimmunoconjugates," Cancer Research 52(5):1067-1072, American Association for Cancer Research, United States (Mar. 1992).

Schmidt M. et al. "High-resolution insertion-site analysis by linear amplification-mediated PCR (LAM-PCR)," Nature Methods 4, 1051-1057(2007).

Schmitz, K., and Ferguson K.M., "Interaction of Antibodies With Erbb Receptor Extracellular Regions," Experimental Cell Research 315(4):659-670, Academic Press, United states (Feb. 2009).

Schoeberl, B., et al., "An ErbB3 Antibody, MM-121, is Active in Cancers with Ligand-Dependent Activation," Cancer Research 70(6):2485-2494, American Association for Cancer Research, United States (Mar. 2010).

Selzer, T., et al., "Rational Design of Faster Associating and Tighter Binding Protein Complexes," Nature Structural & Molecular Biology 7(7):537-541, Nature Publishing Group, United States (Jul. 2000).

Sergina, N.V., et al., "Escape from HER-Family Tyrosine Kinase Inhibitor Therapy By The Kinase-Inactive HER3," Nature 445(7126):437-441, Nature Publishing Group, England (Jan. 2007).

Shames, D.S., et al., "High Heregulin Expression Is Associated with Activated HER3 and May Define an Actionable Biomarker in Patients with Squamous Cell Carcinomas of the Head and Neck," PLoS One 8(2): e56765, Public Library of Science, United States (2013).

Sheinerman, F.B., et al., "Electrostatic Aspects of Protein-protein Interactions," Current Opinion in Structural Biology 10(2):153-159, Elsevier Science, England (Apr. 2000).

Sheridan, C., "Amgen Swallows Micromet to BiTE Into All Market," Nature Biotechnology 30(4):300-301, Nature America Publishing, United States (Apr. 2012).

Shields, R.L., et al., "High resolution mapping of the binding site on human IgG 1 for Fe gamma RI, F c gamma RII, Fe gamma RiII, and FeRn and design of IgG 1 variants with improved binding to the Fe gamma R," J Bioi Chem., 276(9): 6591-6604, The American Society for Biochemistry and Molecular Biology, Inc., United States (2001).

Shiraiwa H., et al., "Engineering a Bispecific Antibody With a Common Light Chain: Identification and Optimization of an Anti-cd3 Epsilon and Anti-gpc3 Bispecific Antibody, Ery974," Methods 154:10-20, Academic Press (Feb. 2019).

Sinha, N., et al., "Differences in Electrostatic Properties at Antibody-antigen Binding Sites: Implications for Specificity and Cross-reactivity," Biophysical Journal 83(6):2946-2968, Cambridge, United States (Dec. 2002).

Sinha, N., et al., "Electrostatics in Protein Binding and Function," Current Protein and Peptide Science 3(6):601-614, Bentham Science Publishers, Netherlands (Dec. 2002).

Sluijter, B.J., et al., "4-1BB-mediated Expansion Affords Superior Detection of in Vivo Primed Effector Memory CD8+ T Cells from Melanoma Sentinel Lymph Nodes," Clinical Immunology 137(2):221-233, Academic Press, United States (Nov. 2010).

Soltoff, S.P., et al., "ErbB3 is involved in activation of phosphatidylinositol 3-kinase by epidermal growth factor," Molecular and Cellular Biology 14(6):3550-3558, American Society for Microbiology, United States(Jun. 1994).

Sorkin,A., "Internalization of the Epidermal Growth Factor Receptor: Role InSignalling," Biochemical Society Transactions 29(Pt 4):480-484, Portland PressOn The Behalf Of The Biochemical Society, England (Aug. 2001).

Spiess, C., et al., "Alternative Molecular Formats and Therapeutic Applications for Bispecific Antibodies," Molecular Immunology 67(2 Pt A):95-106, Pergamon Press, England (Oct. 2015).

Staerz, U.D., and Bevan, M.J., "Hybrid Hybridoma Producing a Bispecific Monoclonal Antibody that can Focus Effector T-cell Activity," Proceedings of the National Academy of Sciences USA 83(5):1453-1457, National Academy of Sciences, United States (1986).

Stancovski, I., et al., "Mechanistic aspects of the opposing effects of monoclonal antibodies to the ERBB2 receptor on tumor growth," Proceedings of the National Academy of Sciences USA 88(19):8691-8695, National Academy of Sciences, United States (1991).

Strelkauskas, A., et al., "Human Monoclonal Antibody: 2. Simultaneous Expression of IgG and IgM with Similar Binding Specificities by a Human Hybrid Clone," Hybridoma 6(5):479-488, Mary Ann Liebert, United states (Oct. 1987).

Suntharalingam, G., et al., "Cytokine Storm in a Phase 1 Trial of the Anti-CD28 Monoclonal Antibody TGN1412," The New England Journal of Medicine 355(10):1018-1028, Massachusetts Medical Society, United States (Sep. 2006).

Tahallah, N., et al., "The Effect of the Source Pressure on the Abundance of Ions of Noncovalent Protein Assemblies in an Electrospray Ionization Orthogonal Time-of-flight Instrument," Rapid Communications in Mass Spectrometry 15(8):596-601, John Wiley And Sons Ltd, England (2001).

Tanner, M., et al., "Characterization of a Novel Cell Line Established From a Patient With Herceptin-resistant Breast Cancer," Molecular Cancer Therapeutics 3(12):1585-1592, American Association for Cancer Research, United States (Dec. 2004).

Thery, J.C., et al., "Resistance to Human Epidermal Growth Factor Receptor Type 2-targeted Therapies," European Journal of Cancer 50(5):892-901, (Mar. 2014).

Troise, F., et al., "A novel ErbB2 epitope targeted by human antitumor immunoagents," FEBS Journal, 278: 1156-1166, John Wiley & Sons, United States (2011).

Uberall, I. et al., "The status and role of ErbB receptors in human cancer," Exp Mol Pathol., vol. 84:79-89 (2008).

Vajdos, F.F., et al., "Comprehensive Functional Maps of The Antigen-binding Site of an Anti-Erbb2 Antibody Obtained with Shotgun Scanning Mutagenesis," Journal of Molecular Biology 320(2):415-428, Academic Press, England (Jul. 2002).

Van De Wetering, M., et al., "Prospective Derivation of a Living Organoid Biobank of Colorectal Cancer Patients," Cell, vol. 161:933-945, Science direct (Jun. 2015).

Van Rhenen, A., et al., "The Novel AML Stem Cell Associated Antigen CII-1 Aids in Discrimination Between Normal and Leukemic Stem Cells," Blood 110(7):2659-2666, American Society of Hematology, United States (Oct. 2007).

Volpi, CC., et al., The Landscape of D16her2 Splice Variant Expression Across Her2-positive Cancers Sci. Rep. Mar. 5, 2019; 9 (1): 3545; pp. 1-12.

Wadhwa, D., et al., "Trastuzumab Mediated Cardiotoxicity in the Setting of Adjuvant Chemotherapy for Breast Cancer: a Retrospective Study," Breast Cancer Research and Treatment 117(2):357-364, Kluwer Academic, Netherlands (Sep. 2009).

Ward, E.S., et al., "Binding Activities of a Repertoire of Single Immunoglobulin Variable Domains Secreted from *Escherichia coli*," Nature 341(6242):544-546, Nature Publishing Group, England (Oct. 1989).

Wehrman, T.S., et al., "A System for Quantifying Dynamic Protein Interactions Defines a Role for Herceptin in Modulating ErbB2

(56) References Cited

OTHER PUBLICATIONS

Interactions," Proceedings of the National Academy of Sciences of the United States of America 103(50):19063-19068, National Academy of Sciences, United States (Dec. 2006).

Weidle, UH. et al., "The Intriguing Options of Multispecific Antibody Formats for Treatment of Cancer," Cancer3enomics & Proteomics, vol. 10: 1-18 {2013).

Weinstein, E.J., et al., The oncogene heregulin induces apoptosis in breast epithelial cells and tumors, Oncogene, 17: 2107-2113, Stockton Press, United Kingdom (1998).

Wick, M.J., et al., Establishment and Characterization of a HER2-positive, TDM1-Resistant PDX Breast Model. Abstract C74 at AACR-NCI-EORTC International Conference: Molecular Targets and Cancer Therapeutics, Nov. 5-9, 2015, Boston and Drug Resistance and Modifiers, vol. 14, No. 12, Supplement 2, 4 pages.

Wilson, T.R., et al., "Neuregulin-1-Mediated Autocrine Signaling Underlies Sensitivity to HER2 Kinase Inhibitors in a Subset of Human Cancer," Cancer Cells, 20(2): 158-172, Elsevier, Inc., Netherlands (2011).

Wilson, T.R., et al., "Widespread Potential for Growth-factor-driven Resistance to Anticancer Kinase Inhibitors," Nature 487(7408):505-509, Nature Publishing Group, England (Jul. 2012).

Winkler, K., et al., "Changing the Antigen Binding Specificity by Single Point Mutations of an Anti-p24 (HIV-1) Antibody," The Journal of Immunology 165(8):4505-4514, The American Association of Immunologists, United States (2000).

Wolff A.C., et al., "Recommendations for Human Epidermal Growth Factor Receptor 2 Testing in Breast Cancer: American Society of Clinical Oncology/College of American Pathologists Clinical Practice Guideline Update," Journal of clinical oncology 31(31):3997-4013, Grune & Stratton, United states (Nov. 2013).

Woning, S.V.D., et al., "Quantification of ErbB3 Receptor Density on Human Breast Cancer Cells, Using a Stable Radio-Labeled Mutant of Nrg1beta," Biochemical and Biophysical Research Communications, 378(2):285-289, Elsevier, United States (Jan. 2009).

Wu, H., et al., "Humanization of a Murine Monoclonal Antibody by Simultaneous Optimization of Framework and CDR Residues," Journal of Molecular Biology 294(1): 151-162, Elsevier, England (Nov. 1999).

Xu, F., et al., "Antibody-Induced Growth Inhibition is Mediated Through Immunochemically and Functionally Distinct Epitopes on the Extracellular Domain of the c-erb-2 (HER-2/neu) Gene Product p185," International Journal of Cancer 53(3):401-408, Wiley-Liss, United States (1993).

Yano, S., "Molecular Mechanism of EGFR-TK1 Resistance," Japanese Journal of Lung Cancer 49(6): 939-943, The Japan Lung Cancer Society (Oct. 2009).

Yarden, Y. et al., "The EGFR family and its ligands in human cancer: signalling mechanisms and therapeutic opportunities," European Journal of Cancer 37(Supp4): S3-S8,ResearchGate GmbH(Sep. 2001).

Yarden, Y., et al., "The ERBB Network: At Last, Cancer Therapy Meets Systems Biology," Nature Reviews Cancer 12(8):553-563, Nature Publishing Group, England (Jul. 2012).

Yonesaka, K., et al., "Activation of ERBB2 Signaling Causes Resistance to the Egfr-Directed Therapeutic Antibody Cetuximab," Science Translational Medicine 3(99):99ra86, American Association for the Advancement of Science, United States (Sep. 2011).

Yu, H., et al., "Plasma Levels of Insulin-like Growth Factor-I and Lung Cancer Risk: A Case-control Analysis," Journal of the National Cancer Institute 91(2):151-156, Oxford University Press, United States (Jan. 1999).

Zeidler, R., et al., "Simultaneous Activation of T Cells and Accessory Cells by a New Class of Intact Bispecific Antibody Results in Efficient Tumor Cell Killing," Journal of Immunology 163(3):1246-1252, American Association of Immunologists, United States (1999).

Zhang B., et al., "Abstract 655: Combination of Mm-111, an Erbb2/erbb3 Bispecific Antibody, With Endocrine Therapies as an Effective Strategy for Treatment of Er+/her2+ Breast Cancer," Cancer Research 71(8):655-655, ResearchGate (Jul. 2011).

Zhang, H., et al., "ErbB Receptors: From Oncogenes to Targeted Cancer Therapies," Journal of Clinical Investigation 117(8):2051-2058, American Society for Clinical Investigation, United States (Aug. 2007).

Zhao, X., et al., "Targeting C-type Lectin-like Molecule-1 for Antibody-mediated Immunotherapy in Acute Myeloid Leukemia," Haematologica 95(1):71-78, Ferrata Storti Foundation, Italy (Jan. 2010).

Zhu, Z., et al., "Remodeling Domain Interfaces to Enhance Heterodimer Formation," Protein science 6(4):781-788, Cold Spring Harbor Laboratory Press, United States (Apr. 1997).

Zolot, R.S., et al., "Antibody-Drug Conjugates," Nature Reviews Drug Discovery 12(4):259-260, Nature Publishing Group, England (Apr. 2013).

Almagro JC and Fransson J, "Humanization of antibodies." Frontiers in Bioscience 13, 1619-1633 (2008).

Carmon KS et al., "R-spondins function as ligands of the orphan receptors LGR4 and LGR5 to regulate Wnt/beta-catenin signaling." Prot Natl Acad Sci USA 108, 11452-11457 (2011).

Cartron et al., "Therapeutic activity of humanized anti-CD20 monoclonal antibody and polymorphism in IgG Fc receptor FcgammaRIIIa gene," Blood (2002).

Chuan, Weng Peng et al. "A molecular triad governing adult stem cells activation: crystallographic studies of LGR5 R-spondin 1 and E3 ligase ZNRF3" https://dspace.library.uu.nl/bitstream/handle/1874/308080/peng.pdf?sequence=1.

Davidson E and Doranz BJ, "A high-throughput shotgun mutagenesis approach to mapping B-cell antibody epitopes." Immunology. Sep. 2014;143(1):13-20 (2014).

De Haard et al., "A large non-immunized human Fab fragment phage library that permits rapid isolation and kinetic analysis of high affinity antibodies." J Biol Chem. Jun. 25;274(26):18218-30. (1999).

De Lau W et al., "The R-spondin/Lgr5/Rnf43 module: regulator of Wnt signal strength." Genes Dev. Feb. 15, 2014;28(4):305-16. (2014).

De Lau W et al., "Lgr5 homologues associate with Wnt receptors and mediate R-spondin signalling." Nature. Jul. 4, 2011;476(7360):293-7. (2011).

Di et al., "Ultra high content image analysis and phenotype profiling of 3D cultured micro-tissues," PLoS One. Oct. 7, 2014;9(10):e109688 (2011).

GenBank Accession No. XM_005571542, accessed at www.ncbi.nlm.nih.gov, accessed on Oct. 15, 2014.

GenBank Accession No. NM_005228.3, accessed at www.ncbi.nlm.nih.gov, accessed on Oct. 15, 2014.

Genbank Accession No. NM_001206998.1, accessed at www.ncbi.nlm.nih.gov, accessed on Oct. 15, 2014.

Genbank Accession No. NM_001080924.2, accessed at www.ncbi.nlm.nih.gov, accessed on Oct. 15, 2014.

GenBank Accession No. NM_017763, accessed at www.ncbi.nlm.nih.gov, accessed on Oct. 15, 2014.

GenBank Accession No. NM_172448.3, accessed at www.ncbi.nlm.nih.gov, accessed on Oct. 15, 2014.

GenBank Accession No. HM801041.1, accessed at www.ncbi.nlm.nih.gov, accessed on Oct. 15, 2014.

GenBank Accession No. NM_001106784, accessed at www.ncbi.nlm.nih.gov, accessed on Oct. 15, 2014.

GenBank Accession No. NP 005219.2, accessed at www.ncbi.nlm.nih.gov, accessed on Oct. 15, 2014.

GenBank Accession No. AAH96324.1, accessed at www.ncbi.nlm.nih.gov, accessed on Oct. 15, 2014.

Gulli et al., "Epidermal growth factor-induced apoptosis in A431 cells can be reversed by reducing the tyrosine kinase activity." Cell Growth Differ. Feb. 1996;7(2):173-8 (1996).

Gunasekaran et al., "Enhancing antibody Fc heterodimer formation through electrostatic steering effects: applications to bispecific molecules and monovalent IgG." J Biol Chem. Jun. 18, 2010;285(25):19637-46 (2010).

Hao HX et al., "ZNRF3 promotes Wnt receptor turnover in an R-spondin-sensitive manner." Nature. Apr. 29;485(7397): 195-200 (2012).

(56) References Cited

OTHER PUBLICATIONS

International search report and written opinion for International Application No. PCT/NL2016/050726, European Patent Office, Netherlands dated Feb. 6, 2017.

International Preliminary Report on Patentability International Application No. PCT/NL2016/050726, European Patent Office, Netherlands dated Apr. 24, 2018.

Junttila TT et al., "Superior in vivo efficacy of afucosylated trastuzumab in the treatment of HER2-amplified breast cancer." Cancer Res. Jun. 1, 2010;70(11):4481-9.

Kim et al., "Mitogenic influence of human R-spondin1 on the intestinal epithelium." Science. Aug. 19, 2005;309(5738):1256-9.

Koide A, et al., "The fibronectin type III domain as a scaffold for novel binding proteins." J Mol Biol. 1998;284:1141-1151.

Kubota T, et al., "Engineerd therapeutic antibodies with improved effector functions," Cancer Sci. Sep. 2009;100(9):1566-72.

Li et al., "Structural basis for inhibition of the epidermal growth factor receptor by cetuximab.," Cancer Cell. Apr. 2005;7(4):301-11. pdb reference 1YY9.

Lindmo et al., Determination of the immunoreactive fraction of radiolabeled monoclonal antibodies by linear extrapolation to binding at infinite antigen excess. J Immunol Methods. Aug. 3, 1984;72(1):77-89.

Lotenberg, T., "Hub for organoids can we take it beyond the buzz" https://www.innovationforhealth.nl/index.php/page/getFileUID/uid/82364b177dfed9754d785aafffb21363/cr_usedb/25.

Marks et al., "By-passing immunization. Human antibodies from V-gene libraries displayed on phage." J Mol Biol. Dec. 5, 1991;222(3):581-97.

Merchant et al., "An efficient route to human bispecific IgG." Nat Biotechnol. Jul. 1998;16(7):677-81.

Morita H et al. "Neonatal lethality of LGR5 null mice is associated with ankyloglossia and gastrointestinal distension," Molecular and cellular biology 24(22):9736-43 (2004).

Musolino et al., "Immunoglobulin G fragment C receptor polymorphisms and clinical efficacy of trastuzumab-based therapy in patients with HER-2/neu-positive metastatic breast cancer." J Clin Oncol. Apr. 10, 2008;26(11):1789-96.

Nissim et al., "Antibody fragments from a 'single pot' phage display library as immunochemical reagents." EMBO J. Feb. 1, 1994;13(3):692-8.

Ogiso et al, "Crystal structure of the complex of human epidermal growth factor and receptor extracellular domains." Cell. Sep. 20, 2002;110(6):775-87.

Olayioye MA et al., "The ErbB signaling network: receptor heterodimerization in development and cancer." EMBO J. Jul. 3, 2000;19(13):3159-67.

Peng et al., "Structure of stem cell growth factor R-spondin 1 in complex with the ectodomain of its receptor LGR5." Cell Rep. Jun. 27, 2013;3(6):1885-92.

Peng et al., "Structures of Wnt-Antagonist ZNRF3 and Its Complex with R-Spondin 1 and Implications for Signaling," PLoS One. Dec. 12, 2013;8(12):e83110.

Sandercock et al., "Identification of anti-tumour biologics using primary tumour models, 3-D phenotypic screening and image-based multi-parametric profiling." Mol Cancer. Jul. 31, 2015;14:147. PMID 26227951.

Sato et al., "Long-term expansion of epithelial organoids from human colon, adenoma, adenocarcinoma, and Barrett's epithelium," Gastroenterology. Nov. 2011;141(5):1762-72.

Schaefer et al., "A two-in-one antibody against HER3 and EGFR has superior inhibitory activity compared with monospecific antibodies." Cancer Cell. Oct. 18, 2011;20(4):472-86.

Seshagiri et al, "Recurrent R-spondin fusions in colon cancer." Nature. Aug. 30, 2012;488(7413):660-4.

Van de Wetering, "Prospective derivation of a living organoid biobank of colorectal cancer patients." Cell. May 7, 2015;161(4):933-45.

Van Uhm et al., "The ultimate radiochemical nightmare: upon radio-iodination of Botulinum neurotoxin A, the introduced iodine atom itself seems to be fatal for the bioactivity of this macromolecule. " EJNMMI Res. Feb. 19, 2015;5:5.
Von Horsten et al. , "Production of non-fucosylated antibodies by co-expression of heterologous GDP-6-deoxy-D-lyxo-4-hexulose reductase." Glycobiology. Dec. 2010;20(12):1607-18.
Zebisch M and Jones EY, "ZNRF3/RNF43—A direct linkage of extracellular recognition and E3 ligase activity to modulate cell surface signalling." Prog Biophys Mol Biol. Sep. 2015; 118(3):112-8.
Zebisch M and Jones EY, "Crystal structure of R-spondin 2 in complex with the ectodomains of its receptors LGR5 and ZNRF3." J Struct Biol. Aug. 2015;191(2):149-55.
Hu, T., and Li, C., "Convergence between Wnt-ß-catenin and EGFR signaling in cancer," Cancer 2010; 9(236):2-7.
Paul, I., et al., "Current Understanding on EGFR and Wnt/ß-Catenin Signaling in Glioma and Their Possible Crosstalk," Genes & Cancer 2013; 4(11-12):427-446.
125084 Erbitux Pharmacology Review Part 2—FDA, 31 pages.
Castoldi, R., et al., "A Novel Bispecific EGFR/Met Antibody Blocks Tumor-promoting Phenotypic Effects Induced by Resistance to EGFR Inhibition and Has Potent Antitumor Activity," Oncogene 32(50):5593-5601, Nature Publishing Group, United Kingdom (Jul. 2013).
Fong, J.T., et al., "Alternative signaling pathways as potential therapeutic targets for overcoming EGFR and c-Met inhibitor resistance in non-small cell lung cancer," PLoS One 8(11):e78398, Public Library of Science, United States (Nov. 2013).
International Search Report and Written Opinion for International Application No. PCT/NL2018/050537, European Patent Office, Netherlands, dated Jan. 30, 2019, European Patent Office, Rijswijk, Netherlands, 19 pages.
Ji, H., et al., "Epidermal growth factor receptor variant III mutations in lung tumorigenesis and sensitivity to tyrosine kinase inhibitors," PNAS 103(20):7817-7822, United States National Academy of Sciences, United States (May 2006).
Kim, G.P., et al. "Targeting Colorectal Cancer with Human Anti-EGFR Monoclonocal Antibodies: Focus on Panitumumab," Biologics 2(2):223-228, Dove Medical Press, New Zealand (Jun. 2008).
Moores, S.L., et al., "A Novel Bispecific Antibody Targeting EGFR and cMet Is Effective against EGFR Inhibitor-Resistant Lung Tumors," Cancer Research 76(13):3942-3953, American Association for Cancer Research, United States (May 2016).
Morgillo, F., et al., "Mechanisms of resistance to EGFR targeted drugs: lung cancer," ESMO Open 2016 1:e000060, 13 pages, Biomedical Journal, United States (2016).
Nakade, J., et al., "Triple Inhibition of EGFR, MET, and VEGF Suppresses Regrowth of HGF-Triggered, Erlotinib-Resistant Lung Cancer Harboring an EGFR Mutation," Journal of Thoracic Oncology 9(6):775-783, Elsevier, United States (Jun. 2014).
Pan, D.S., et al., "Binding Characteristic of Fully Human Anti-EGFR Monoclonal Antibody to EGFR in Skin Tissues of Different Species of Animals," Chinese Journal of New Drugs Co. Ltd, 21(1):26-30, China (Jan. 2012).
U.S. Appl. No. 61/635,935, inventor Kruif; C.A.D, filed Apr. 20, 2012.
Vecchione, L., et al., "EGFR-targeted therapy," Experimental Cell Research 317(19): 2765-2771, Academic Press, United States (Nov. 2011).
Brown, M., et al., "Tolerance to Single, but Not Multiple, Amino Acid Replacements in Antibody $V_h$ CDR2: A Means of Minimizing B Cell Wastage from Somatic Hypermutation?" Journal of Immunology 156:3285-3291, American Association of Immunologists, United States 1996).

* cited by examiner

Figure 1

| | MF nr: | Specificity: | Germline: | VH Sequence: |
|---|---|---|---|---|
| SEQ ID NO: 17 | 1337 | TT | IGVH1-08 | EVQLVETGAEVKKPGASVKVSCKASDYIFTKYDINWVRQAPGQGLEWMGWMSANTGNTGYAQKFQGRVTMTRDTSINTAYMELSSLTSGDTAVYFCARSSLFKTETAPYYHFALDVWGQGTLVTVSS |
| SEQ ID NO: 27 | 3125 | HER3 | IGVH3-30 | QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCARSSGWPSYSNWGFDYWGQGTLVTVSS |
| SEQ ID NO: 29 | 3176 | HER3 | IGVH3-23 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARDWWYPPYYMGFDYWGQGTLVTVSS |
| SEQ ID NO: 22 | 3178 | HER3 | IGVH1-2 | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARDHGSRHFWSYWGFDYWGQGTLVTVSS |
| SEQ ID NO: 32 | 4863 | HER3 | IGVH7-4-1 | EVQLVQSGSELKKPGASVKVSCKASGYTSIRYALNWVRQAPGQGLEWLGWINTNTGNPTYARGFTGRFVFSLDTSVSTAYLQISSLKAEDTAVYYCARDTYDSTGYLWFDYWGQGTLVTVSS |
| SEQ ID NO: 34 | 3370 | EGFR | IGVH1-18 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCAKDRHWHWLDAFDYWGQGTLVTVSS |
| SEQ ID NO: 20 | 3755 | EGFR | IGVH7-4-1 | QVQLVQSGSELKKPGASVKISCKASGYDFTNYAMNWVRQAPGHGLEWMGWINANTGDPTYAQGFTGRFVFSLDTSVSTAYLQISSLKAEDSAVYYCTRERFLEWLHFDYWGQGTLVTVSS |
| SEQ ID NO: 36 | 4280 | EGFR | IGVH1-24 | QVQLVQSGAEVKKPGASVKVSCKVSGYTLTELSMHWVRQAPGKGLEWMGGFDPEYGKTFFAQNFQGRVTMTEDTSADTAYMELSSLRSEDTAVYYCATEGYYETTTYYYNLFDSWGQGTLVTVSS |
| SEQ ID NO: 38 | 4289 | EGFR | IGVH7-4-1 | QVQLVQSGSELKKPGASVKVSCKTSGYTFTDYAMTWVRQAPGQGLEWMGWITTNTGDPTYAPGFTGRFVFSLDTSVSTAYLQISSLKAEDTAVYYCARVYHWIRGFEFWGQGTLVTVSS |
| SEQ ID NO: 40 | 5777 | LGR4 | IGVH7-4-1 | QVQLVQSGSELKKPGASVKVSCKASGFTFTNYVMNWVRQAPGQGLEWMGWINTNTGNPTYAQGFTGRFVFSLDTSVSTAYLQISSLKAEDTAVYYCARWELLDYWGQGTLVTVSS |
| SEQ ID NO: 42 | 5781 | LGR4 | IGVH3-23 | EVQLVESGGGLVQPGGSLRLSCAASGFTFSSYAMSWVRQAPGKGLEWVSVISGSGGTTYYADSVKGRFTISRDNSKNTLYLQMNSLRAEDTAVYYCAKGAGELDYWGQGTLVTVSS |
| SEQ ID NO: 24 | 5790 | LGR5 | IGVH4-39 | QVQLQESGPGLVKPSETLSLTCTVSGGSFSSSSSSYWGWIRQPPGKGLEWIGSFYYSGNTYYNPSLKSRVTISEDTSKNQFSLKLSSVTAADTAVYYCARQTYSSSWDGVLYFDYWGQGTLVTVSS |
| SEQ ID NO: 44 | 5803 | LGR5 | IGVH4-59 | QVQLQESGPGLVKPSETLSLTCTVSNGSISTYYWSWIRQPPGKGLEWIGYVYYTGRTKYNPSLKSRVTISVDTSKNQFSLNLSSVTAADTAVYYCARGGIVVPAARDYYYMDVWGKGTTLVTVSS |
| SEQ ID NO: 46 | 5805 | LGR5 | IGVH5-51 | EVQLVQSGAEVKKPGESLKIACKGSGFSFTSHWIGWVRQKPGRGLEWMGVIYPGDSDTRYSPSFQGQVTSADKSINTAYLQWNSLKASDTAIYYCARPNSGSPRYFEFWGRGTLVTVSS |
| SEQ ID NO: 48 | 5808 | LGR5 | IGVH4-39 | QVQLQESGPGLVKPSETLSLTCTVSGGSISSSYYWGWIRQPPGKGLEWIGSFYYSGNTYYNPSLKSRVTISVDTSKNQFSLKLSSVTAADTAVYYCARQEYYYGSGSPSYYFDYWGQGTLVTVSS |

Figure 1 (continued)

| | MF nr: | Specificity: | Germline: | FR1 | CDR1 | FR2 | CDR2 |
|---|---|---|---|---|---|---|---|
| SEQ ID NO: 50 | 5809 | LGR5 | IGVH5-51 | EVQLVQSGAEVKKPGESLKISCKGSGDSFISHWIAWVRQMPGKGLEWELLGPFDYWGQGTLVTVSS | LKASDTAMYYCARHEWELLGPFDYWGQGTLVTVSS | WVRQMPGKGLEWMGIVYPGDSDTRYSPSFQGQVTISADKSITTAYLQWSS | |
| SEQ ID NO: 52 | 5814 | LGR5 | IGVH1-69 | EVQLVQSGAEVKKPGSSVKVSCKASGGTSTNDAISWVRQTPGQGLEWMGSIIPILDTTDHAQKFQGRVTITADKSTNTAYMELNSL | RSDDTAVYYCAREHIAARQDYFDYWGQGTLVTVSS | | |
| SEQ ID NO: 26 | 5816 | LGR5 | IGVH7-4-1 | EVQLVQSGSKLKKPGASVKVSCKASGYTFTSYTMNWVRQAPGQGLEWMGWINTDTGDPTYAQGFTGRFVFSLDTSVSTAFLQIN | SLKAEDTAVYYCARGDCDSTSCYRYSGYEDYWGQGTLVTVSS | | |
| SEQ ID NO: 54 | 5817 | LGR5 | IGVH1-69 | QVQLVQSGAEVKKPGSSVKVSCKVSGGTFRSYAISWVRQAPGQGLEWMGGIIPIFDTRNYAQILQGRVTITADLSTSTAYMELNSL | RSEDTAIYYCARGSDEGDWFDPWGQGTLVTVSS | | |
| SEQ ID NO: 56 | 5818 | LGR5 | IGVH1-69 | EVQLVQSGTEVRKPGSSVKVSCKASGGTFSNYAISWVRQAPGQGLEWMGSIIPILGTTDHAQKFQDRVTITADKSSNTTYMELSSL | RSDDTAVYYCAREYIAARLDYFDSWGQGTLVTVSS | | |
| SEQ ID NO: 58 | 5832 | RNF43 | IGVH3-13 | EVQLVESGGGLVQPGGSLRLSCVVSGFTFSYDMHWVRQVTGKGLEWVSAIGTAGATYYPGSVKGRFTISRENAKNSLYLQMNS | LRAGDTAVYYCARDRGYSGYDAYYFDWGQGTMVTVSS | | |
| SEQ ID NO: 60 | 5836 | RNF43 | IGVH4-39 | QVQLQESGPGLVKPSETLSLTCTVSGGSISSSNYYWGWIRQPPGKGLEWIGNIYYRGYTYNPSLKSRVTISVDTSKKQFSLTLSSV | TAADTAMYYCAREGSDYGDYVGAFDIWDQGTMVTVSS | | |
| SEQ ID NO: 62 | 5839 | RNF43 | IGVH3-13 | EVQLVQSGGGLVQPGGSLRLSCAASGFTFSYDMHWVRQVTGKGLEWVSTIGATGDTYYSDSVKGRFTISRQNAKNSLYLQINSL | RAGDTAVYYCVRDRGYIGYDSYYFDNWGQGTLVTVSS | | |
| SEQ ID NO: 64 | 5850 | ZNRF3 | IGVH6-4-1 | QVQLVQSGSELKKPGASVKVSCKASGYTFTRYPMNWVRQAPGQGLEWMGWINTNTGNPTYAQGFTGRFVFSLDTSVSTAFLQIS | SLKAEDTAVYYCARERTNFYDAFDIWGQGTMVTVSS | | |
| SEQ ID NO: 66 | 5853 | ZNRF3 | IGVH7-4-1 | QVQLVQSGSELKKPGASVKVSCKASGYTFNSYAMDWVRQAPGQGLEWMGWINTNTGNPTYAQAFTGRFVFSLDTSVSTAYLEIS | SLKAEDTAVYYCARERHGYFEAFDIWGQGTMVTVSS | | |
| SEQ ID NO: 68 | 5855 | ZNRF3 | IGVH7-4-1 | QVQLVQSGSELKKPGASVKVSCKASGYTFTKYAMNWVRQAPGQGLEWMGWINTNTGNPTYAQGFTGRFVFSLDTSVSTAYLQV | SSLRAEDTALYYCARESNWNYDYFDYWGQGTLVTVSS | | |
| SEQ ID NO: 70 | 5862 | ZNRF3 | IGVH5-51 | QVQLVQSGTEVKKPGESLKISCKGSGYSFTTYWIGWVRQMPGKGLEWMGIIYPGDSDTRYSPSFQGQVTISADKSISTAYLQLSSL | KASDTAMYYCARRGLSMVRLSAFDVWGQGTTVTVSS | | |
| SEQ ID NO: 72 | 5882 | ZNRF3 | IGVH7-4-1 | QVQLVQSGSELKKPGASVKVSCKASGYTFTRYAMNWVRQAPGQGLEWMGWINTKTGNPTYAQGFTGRFVFSLDTSVSTAYLQIS | SLKAEDTAVYYCARDRGSYYDAFDIWGQGTTVTVSS | | |
| SEQ ID NO: 74 | 5884 | ZNRF3 | IGVH7-4-1 | EVQLVQSGSELKKPGASVKVSCKASGYTFTRYAMNWVRQVPGQGLEWMGWINTNTGNPTYAQGFTGRFVFSLDTSVRTAYLQIS | SLKAEDTAVYYCARDKGYNWNYMGAFDIWGQGTTVTVSS | | |
| SEQ ID NO: 76 | 5887 | ZNRF3 | IGVH7-4-1 | QVQLVQSGSELKKPGASVKVSCKASGYTFTRYAMNWVRQAPGQGLEWMGWINTNTGKPTYAQGFTGRFVFSLDTSVSTAYLQIS | SLKAEDTAVYYCARDPGSYYDWFDPWGQGTTVTVSS | | |
| SEQ ID NO: 78 | 5888 | ZNRF3 | IGVH7-4-1 | QVQLVQSGSELKKPGGSMKVSCKASGYTFTRYAMNWLRQAPGQGLEWMGWINTNTGNPTYAQGFTGRFVFSLDTSVSTAYLQIS | SLKAEDTAVYYCARRSGSYDYFDYWGQGTLVTVSS | | |

Figure 1 (continued)

| | MF nr: | Specificity: | Germline: | FR1 | CDR1 | FR2 | CDR2 |
|---|---|---|---|---|---|---|---|
| SEQ ID NO: 17 | 1337 | TT | IGVH1-08 | EVQLVETGAEVKKPGASVKVSCKASDYIFT | KYDIN SEQ ID NO:182 | WVRQAPGQGLEWMG | WMSANTGNTGYAQKFQG SEQ ID NO: 209 |
| SEQ ID NO: 27 | 3125 | HER3 | IGVH3-30 | QVQLVESGGGVVQPGRSLRLSCAASGFTFS | SYGMH SEQ ID NO:183 | WVRQAPGKGLEWVA | VISYDGSNKYYADSVKG SEQ ID NO: 210 |
| SEQ ID NO: 29 | 3176 | HER3 | IGVH3-23 | EVQLLESGGGLVQPGGSLRLSCAASGFTFS | SYAMS SEQ ID NO:184 | WVRQAPGKGLEWVS | AISGSGGSTYYADSVKG SEQ ID NO: 211 |
| SEQ ID NO: 22 | 3178 | HER3 | IGVH1-2 | QVQLVQSGAEVKKPGASVKVSCKASGYTFT | GYYMH SEQ ID NO:185 | WVRQAPGQGLEWMG | WINPNSGGTNYAQKFQG SEQ ID NO: 212 |
| SEQ ID NO: 32 | 4863 | HER3 | IGVH7-4-1 | EVQLVQSGSELKKPGASVKVSCKASGYTSI | RYALN SEQ ID NO:186 | WVRQAPGQGLEWLG | WINTNTGNPTYARGFTG SEQ ID NO: 213 |
| SEQ ID NO: 34 | 3370 | EGFR | IGVH1-18 | QVQLVQSGAEVKKPGASVKVSCKASGYTFT | SYGIS SEQ ID NO:187 | WVRQAPGQGLEWMG | WISAYNGNTNYAQKLQG SEQ ID NO: 214 |
| SEQ ID NO: 20 | 3755 | EGFR | IGVH7-4-1 | QVQLVQSGSELKKPGASVKISCKASGYDFT | NYAMN SEQ ID NO:188 | WVRQAPGHGLEWMG | WINANTGDPTYAQGFTG SEQ ID NO: 215 |
| SEQ ID NO: 36 | 4280 | EGFR | IGVH1-24 | QVQLVQSGAEVKKPGASVKVSCKVSGYTLT | ELSMH SEQ ID NO:189 | WVRQAPGKGLEWMG | GFDPEYGKTFFAQNFQG SEQ ID NO: 216 |
| SEQ ID NO: 38 | 4289 | EGFR | IGVH7-4-1 | QVQLVQSGSELKKPGASVKVSCKTSGYTFT | DYAMT SEQ ID NO:190 | WVRQAPGQGLEWMG | WITTNTGDPTYAPGFTG SEQ ID NO: 217 |
| SEQ ID NO: 40 | 5777 | LGR4 | IGVH7-4-1 | QVQLVQSGSELKKPGASVKVSCKASGYTFT | NYYMN SEQ ID NO:191 | WVRQAPGQGLEWMG | WINTNTGNPTYAQGFTG SEQ ID NO: 218 |
| SEQ ID NO: 42 | 5781 | LGR4 | IGVH3-23 | EVQLVESGGGLVQPGGSLRLSCAASGFTFS | SYAMS SEQ ID NO:192 | WVRQAPGKGLEWVS | VISGSGTTYYADSVKG SEQ ID NO: 219 |
| SEQ ID NO: 24 | 5790 | LGR5 | IGVH4-39 | QVQLQESGPGLVKPSETLSLTCTVSGGSFS | SSSSYWG SEQ ID NO:192 | WIRQPPGKGLEWIG | SFYYSGNTYYNPSLKS SEQ ID NO: 220 |
| SEQ ID NO: 44 | 5803 | LGR5 | IGVH4-59 | QVQLQESGPGLVKPSETLSLTCTVSNGSIS | TYYWS SEQ ID NO:193 | WIRQPPGKGLEWIG | YVYYTGRTKYNPSLKS SEQ ID NO: 221 |
| SEQ ID NO: 46 | 5805 | LGR5 | IGVH5-51 | EVQLVQSGAEVKKPGESLKIACKGSGFSFT | SHWIG SEQ ID NO:194 | WVRQKPGRGLEWMG | VIYPGDSDTRYSPSFQG SEQ ID NO: 222 |
| SEQ ID NO: 48 | 5808 | LGR5 | IGVH4-39 | QVQLQESGPGLVKPSETLSLTCTVSGGSIS | SSSYYWG SEQ ID NO:195 | WIRQPPGKGLEWIG | SFYYSGNTYYNPSLKS SEQ ID NO: 220 |

Figure 1 (continued)

| | MF nr: | Specificity: | Germline: | FR1 | CDR1 | FR2 | CDR2 |
|---|---|---|---|---|---|---|---|
| SEQ ID NO: 50 | 5809 | LGR5 | IGVH5-51 | EVQLVQSGAEVKKPGESLKISCKGSGDSFI | SHWIA SEQ ID NO:196 | WVRQMPGKGLEWMG | IVYPGDSDTRYSPSFQG SEQ ID NO: 224 |
| SEQ ID NO: 52 | 5814 | LGR5 | IGVH1-69 | EVQLVQSGAEVKKPGSSVKVSCKASGGTST | NDAIS SEQ ID NO:197 | WVRQTPGQGLEWMG | SIIPILDTTDHAQKFQG SEQ ID NO: 225 |
| SEQ ID NO: 26 | 5816 | LGR5 | IGVH7-4-1 | EVQLVQSGSKLKKPGASVKVSCKASGYTFT | SYTMN SEQ ID NO:198 | WVRQAPGQGLEWMG | WINDTGDPTYAQGFTG SEQ ID NO: 226 |
| SEQ ID NO: 54 | 5817 | LGR5 | IGVH1-69 | QVQLVQSGAEVKKPGSSVKVSCKVSGGTFR | SYAIS SEQ ID NO:199 | WVRQAPGQGLEWMG | GIIPIFDTRNYAQILQG SEQ ID NO: 227 |
| SEQ ID NO: 56 | 5818 | LGR5 | IGVH1-69 | EVQLVQSGTEVRKPGSSVKVSCKASGGTFS | NYAIS SEQ ID NO:200 | WVRQAPGQGLEWMG | SIIPILGTTDHAQKFQD SEQ ID NO: 228 |
| SEQ ID NO: 58 | 5832 | RNF43 | IGVH3-13 | EVQLVESGGGLVQPGGSLRLSCVVSGFTFS | YYDMH SEQ ID NO:201 | WVRQVTGKGLEWVS | AIGTAGATYYPGSVKG SEQ ID NO: 229 |
| SEQ ID NO: 60 | 5836 | RNF43 | IGVH4-39 | QVQLQESGPGLVKPSETLSLTCTVSGGSIS | SSNYYWG SEQ ID NO:202 | WIRQPPGKGLEWIG | NIYYRGYTYNPSLKS SEQ ID NO: 230 |
| SEQ ID NO: 62 | 5839 | RNF43 | IGVH3-13 | EVQLVQSGGGLVQPGGSLRLSCAASGFTFS | YYDMH SEQ ID NO:203 | WVRQVTGKGLEWVS | TIGATGDTYSDSVKG SEQ ID NO: 231 |
| SEQ ID NO: 64 | 5850 | ZNRF3 | IGVH6-4-1 | QVQLVQSGSELKKPGASVKVSCKASGYTFT | RYPMN SEQ ID NO:204 | WVRQAPGQGLEWMG | WINTNTGNPTYAQGFTG SEQ ID NO: 232 |
| SEQ ID NO: 66 | 5853 | ZNRF3 | IGVH7-4-1 | QVQLVQSGSELKKPGASVKVSCKASGYTFN | SYAMD SEQ ID NO:205 | WVRQAPGQGLEWMG | WINTNTGNPTYAQAFTG SEQ ID NO: 233 |
| SEQ ID NO: 68 | 5855 | ZNRF3 | IGVH7-4-1 | QVQLVQSGSELKKPGASVKVSCKASGYTFT | KYYMN SEQ ID NO:206 | WVRQAPGQGLEWMG | WINTNTGNPTYAQGFTG SEQ ID NO: 234 |
| SEQ ID NO: 70 | 5862 | ZNRF3 | IGVH5-51 | QVQLVQSGTEVKKPGESLKISCKGSGSYSFT | TYWIG SEQ ID NO:207 | WVRQMPGKGLEWMG | IIYPGDSDTRYSPSFQG SEQ ID NO: 233 |
| SEQ ID NO: 72 | 5882 | ZNRF3 | IGVH7-4-1 | QVQLVQSGSELKKPGASVKVSCKASGYTFT | RYAMN SEQ ID NO:208 | WVRQAPGQGLEWMG | WINTKTGNPTYAQGFTG SEQ ID NO: 234 |
| SEQ ID NO: 74 | 5884 | ZNRF3 | IGVH7-4-1 | EVQLVQSGSELKKPGASVKVSCKASGYTFT | KYAMN | WVRQVPGQGLEWMG | WINTNTGNPTYAQGFTG SEQ ID NO: 235 |
| SEQ ID NO: 76 | 5887 | ZNRF3 | IGVH7-4-1 | QVQLVQSGSELKKPGASVKVSCKASGYTFT | RYAMN | WVRQAPGQGLEWMG | WINTNTGKPTYAQGFTG |
| SEQ ID NO: 78 | 5888 | ZNRF3 | IGVH7-4-1 | QVQLVQSGSELKKPGGSMKVSCKASGYTFT | RYAMN | | |

Figure 1 (continued)

| | MF nr: | Specificity: | Germline: | FR3 | CDR3 | FR4 |
|---|---|---|---|---|---|---|
| SEQ ID NO: 17 | 1337 | TT | IGVH1-08 | RVTMTRDTSINTAYMELSSLTSGDTAVYFCAR | SSLFKTETAPYYHFALDV SEQ ID NO: 236 | WGQGTTVTVSS |
| SEQ ID NO: 27 | 3125 | HER3 | IGVH3-30 | RFTISRDNSKNTLYLQMNSLRAEDTAVYYCAK | GSSGWPSYSNWGFDY SEQ ID NO: 237 | WGQGTLVTVSS |
| SEQ ID NO: 29 | 3176 | HER3 | IGVH3-23 | RFTISRDNSKNTLYLQMNSLRAEDTAVYYCAR | DWWYPPYWGFDY SEQ ID NO: 238 | WGQGTLVTVSS |
| SEQ ID NO: 22 | 3178 | HER3 | IGVH1-2 | RVTMTRDTSISTAYMELSRLRSDDTAVYYCA | DHGSRHFWSYWGFDY SEQ ID NO: 239 | WGQGTLVTVSS |
| SEQ ID NO: 32 | 4863 | HER3 | IGVH7-4-1 | RFVFSLDTSVSTAYLQISSLKAEDTAVYYCAR | DTYDSTGYLWFDY SEQ ID NO: 240 | WGQGTLVTVSS |
| SEQ ID NO: 34 | 3370 | EGFR | IGVH1-18 | RVTMTTDTSTSTAYMELRSLRSDDTAVYYCAK | DRHWHWWLDAFDY SEQ ID NO: 241 | WGQGTLVTVSS |
| SEQ ID NO: 20 | 3755 | EGFR | IGVH7-4-1 | RFVFSLDTSVSTAYLQISSLKAEDSAVYYCTR | ERFLEWLHFDY SEQ ID NO: 242 | WGQGTLVTVSS |
| SEQ ID NO: 36 | 4280 | EGFR | IGVH1-24 | RVTMTEDTSADTAYMELSSLRSEDTAVYYCAT | EGYYETTYYYNLFDS SEQ ID NO: 243 | WGQGTLVTVSS |
| SEQ ID NO: 38 | 4289 | EGFR | IGVH7-4-1 | RFVFSLDTSVSTAYLQISSLKAEDTAVYYCAR | VYHWIRGFEF SEQ ID NO: 244 | WGQGTLVTVSS |
| SEQ ID NO: 40 | 5777 | LGR4 | IGVH7-4-1 | RFVFSLDTSVSTAYLQISSLKAEDTAVYYCAR | WELLDY SEQ ID NO: 245 | WGQGTLVTVSS |
| SEQ ID NO: 42 | 5781 | LGR4 | IGVH3-23 | RFTISRDNSKNTLYLQMNSLRAEDTAVYYCAK | GAGELDY SEQ ID NO: 246 | WGQGTLVTVSS |
| SEQ ID NO: 24 | 5790 | LGR5 | IGVH4-39 | RVTISEDTSKNQFSLKLSSVTAADTAVYYCAR | QTYSSSWDGVLYYFDY SEQ ID NO: 247 | WGQGTLVTVSS |
| SEQ ID NO: 44 | 5803 | LGR5 | IGVH4-59 | RVTISVDTSKNQFSLNLSSVTAADTAVYYCAR | GGIVVPAARDYYYYMDV SEQ ID NO: 248 | WGKGTTVTVSS |
| SEQ ID NO: 46 | 5805 | LGR5 | IGVH5-51 | QVTVSADKSINTAYLQWNSLKASDTAIYYCAR | PNSGSPRYFEF SEQ ID NO: 249 | WGRGTLVTVSS |
| SEQ ID NO: 48 | 5808 | LGR5 | IGVH4-39 | RVTISVDTSKNQFSLKLSSVTAADTAVYYCAR | QEYYYGSGSPSYYFDY SEQ ID NO: 250 | WGQGTLVTVSS |

Figure 1 (continued)

| | MF nr: | Specificity: | Germline: | FR3 | CDR3 | FR4 |
|---|---|---|---|---|---|---|
| SEQ ID NO: 50 | 5809 | LGR5 | IGVH5-51 | QVTISADKSITTAYLQWSSLKASDTAMYYCAR | HEWELLGPFDY SEQ ID NO: 251 | WGQGTLVTVSS |
| SEQ ID NO: 52 | 5814 | LGR5 | IGVH1-69 | RVTITADKSTNTAYMELNSLRSDDTAVYYCAR | EHIAARQDYFDY SEQ ID NO: 252 | WGQGTLVTVSS |
| SEQ ID NO: 26 | 5816 | LGR5 | IGVH7-4-1 | RFVFSLDTSVSTAFLQINSLKAEDTAVYYCAR | GDCDSTSCYRYSYGYEDY SEQ ID NO: 253 | WGQGTLVTVSS |
| SEQ ID NO: 54 | 5817 | LGR5 | IGVH1-69 | RVTITADLSTSTAYMELNSLRSEDTAIYYCAR | GSDEGDWFDP SEQ ID NO: 254 | WGQGTLVTVSS |
| SEQ ID NO: 56 | 5818 | LGR5 | IGVH1-69 | RVTITADKSSNTTYMELSSLRSDDTAVYYCAR | EYIAARLDYFDS SEQ ID NO: 255 | WGQGTLVTVSS |
| SEQ ID NO: 58 | 5832 | RNF43 | IGVH3-13 | RFTISRENAKNSLYLQMNSLRAGDTAVYYCAR | DRGYSGYDAYYFDF SEQ ID NO: 256 | WGQGTLVTVSS |
| SEQ ID NO: 60 | 5836 | RNF43 | IGVH4-39 | RVTISVDTSKKQFSLTLSSVTAADTAMYYCAR | EGSDYGDYVGAFDI SEQ ID NO: 257 | WDQGTMVTVSS |
| SEQ ID NO: 62 | 5839 | RNF43 | IGVH3-13 | RFTISRQNAKNSLYLQINSLRAGDTAVYYCVR | DRGYIGYDSYYFDN SEQ ID NO: 258 | WGQGTLVTVSS |
| SEQ ID NO: 64 | 5850 | ZNRF3 | IGVH6-4-1 | RFVFSLDTSVSTAFLQISSLKAEDTAVYYCAR | ERTNFYDAFDI SEQ ID NO: 259 | WGQGTMVTVSS |
| SEQ ID NO: 66 | 5853 | ZNRF3 | IGVH7-4-1 | RFVFSLDTSVSTAYLEISSLKAEDTAVYYCAR | ERHGYFEAFDI SEQ ID NO: 260 | WGQGTLVTVSS |
| SEQ ID NO: 68 | 5855 | ZNRF3 | IGVH7-4-1 | RFVFSLDTSVSTAYLQVSSLRAEDTALYYCAR | ESNWNYDYFDY SEQ ID NO: 261 | WGQGTLVTVSS |
| SEQ ID NO: 70 | 5862 | ZNRF3 | IGVH5-51 | QVTISADKSISTAYLQLSSLKASDTAMYYCAR | RGLSMVRLSAFDV SEQ ID NO: 262 | WGQGTLVTVSS |
| SEQ ID NO: 72 | 5882 | ZNRF3 | IGVH7-4-1 | RFVFSLDTSVSTAYLQISSLKAEDTAVYYCAR | DRGSYDAFDI SEQ ID NO: 263 | WGQGTMVTVSS |
| SEQ ID NO: 74 | 5884 | ZNRF3 | IGVH7-4-1 | RFVFSLDTSVRTAYLQISSLKAEDTAVYYCAR | KGGSYYDWFDP SEQ ID NO: 264 | WGQGTLVTVSS |
| SEQ ID NO: 76 | 5887 | ZNRF3 | IGVH7-4-1 | RFVFSLDTSVSTAYLQISSLKAEDTAVYYCAR | DKGYNWNYMGAFDI SEQ ID NO: 265 | WGQGTTVTVSS |
| SEQ ID NO: 78 | 5888 | ZNRF3 | IGVH7-4-1 | RFVFSLDTSVSTAYLQISSLKAEDTAVYYCAR | RSGSYYDYFDY SEQ ID NO: 266 | WGQGTLVTVSS |

Figure 2

MF1337: SEQ ID NO. 17 gaggtgcagctggtggagactggggctgaggtgaagaagccggggggcctcagtgaaggtctcctgcaagg
cttctgactacatcttcaccaaatatgacatcaactgggtgcgccaggcccctggacaagggcttgaatg
gatgggatggatgagcgctaacactggaaacacgggctatgcacagaagttccagggcagagtcaccatg
accagggacacgtccataaacacagcctacatggagctgagcagcctgacatctggtgacacggccgttt
atttctgtgcgaggagtagtcttttcaagacagagacggcgccctactatcacttcgctctggacgtctg
gggccaagggaccacggtcaccgtctccagt

MF3755: SEQ ID NO. 19 caggtgcagctggtgcagtctgggtctgagttgaagaagcctggggcctcagtgaagatttcctgcaagg
cttctggatacgacttcactaactatgctatgaattgggtgcgacaggcccctggacacgggcttgagtg
gatgggatggatcaacgccaacactggggacccaacgtatgcccagggcttcacaggacggtttgtcttc
tccttggacacctctgtcagcacggcatatctgcagatcagcagtttaaaggctgaggactctgccgtgt
attactgtacgagagagcgattttggagtggttacactttgactactggggccagggaaccctggtcac
cgtctccagt

MF3178: SEQ ID NO. 21 caggtgcagctggtgcagtctggggctgaggtgaagaagccggggcctcagtgaaggtctcctgcaagg
cttctggatacaccttcaccggctactatatgcactgggtgcgacaggcccctggacaagggcttgagtg
gatgggatggatcaaccctaacagtggtggcacaaactatgcacagaagtttcagggcagggtcacgatg
accagggacacgtccatcagcacagcctacatggagctgagcaggctgagatctgacgacacggctgtgt
attactgtcaagagatcatggttctcgtcatttctggtcttactggggctttgattattggggccaagg
taccctggtcaccgtctccagt

MF5790: SEQ ID NO. 23 caggtgcagctgcaggagtcgggcccaggactggtgaagccttcggagaccctgtccctcacctgcactg
tctctggtggctccttcagcagtagtagttcctactggggctggatccgccagcccccagggaaggggct
ggagtggattgggagtttctattatagtgggaacacctactacaacccgtccctcaagagtcgagtcacc
atatccgaagacacgtccaagaaccagttctccctgaagctgagctctgtgaccgccgcagacacggctg
tgtattactgtgcgagacagacgtatagcagcagctgggacggggtcctgtactactttgactactgggg
ccagggaaccctggtcaccgtctccagt

MF5816: SEQ ID NO. 25 gaggtgcagctggtgcagtctgggtctaaattgaagaagcctggggcctcagtgaaggtttcctgcaagg
cttctggatacaccttcactagctatactatgaattgggtgcgacaggcccctggacaagggcttgagtg
gatgggatggatcaacaccgacactggggacccaacgtatgcccagggcttcacaggacggtttgtcttc
tccttggacacctctgtcagcacggcatttctacagatcaacagcctaaaggctgaggacactgccgtat
attactgtgcgagaggagattgtgatagtaccagctgctatagatacagttatggttacgaggactactg
gggccagggaaccctggtcaccgtctccagt

MF3125: SEQ ID NO. 27 caggtgcagctggtggagtctgggggaggcgtggtccagcctggggaggtccctgagactctcctgtgcag
cctctggattcaccttcagtagctatggcatgcactgggtccgccaggctccaggcaaggggctggagtg
ggtggcagttatatcatatgatggaagtaataaatactatgcagactccgtgaagggccgattcaccatc
tccagagacaattccaagaacacgctgtatctgcaaatgaacagcctgagagctgaggacacggccgtgt
attactgtgcaaaaggttcttctggttggccgtcttactctaactggggctttgattattggggccaagg
taccctggtcaccgtctccagt

Figure 2 (continued)

MF3176: SEQ ID NO. 29
gaggtgcagctgttggagtctgggggaggcttggtacagcctgggggtccctgagactctcctgtgcag
cctctggattcacctttagcagctatgccatgagctgggtccgccaggctccagggaaggggctggagtg
ggtctcagctattagtggtagtggtggtagcacatactacgcagactccgtgaagggccggttcaccatc
tccagagacaattccaagaacacgctgtatctgcaaatgaacagcctgagagccgaggacacggctgtgt
attactgtgcaagagattggtggtacccgccgtactactggggctttgattattggggccaaggtaccct
ggtcaccgtctccagt

MF4863: SEQ ID NO. 31
gaggtgcagctggtgcagtctgggtctgagttgaagaagcctggggcctcagtgaaggtttcctgcaagg
cttctggatacacctccattagatatgctttgaactgggtgcgacaggcccctggacaaggccttgagtg
gctgggatggatcaacaccaacactgggaacccaacgtatgcccgggcttcacaggacggtttgtcttc
tccttggacacctctgtcagcacggcatatctgcagatcagcagcctaaaggctgaggacactgccgtgt
attactgtgcgagagatacttatgatagtactggttatctttggtttgactactggggccagggaaccct
ggtcaccgtctccagt

MF3370: SEQ ID NO. 33
caggttcagctggtgcagtctggagctgaggtgaagaagcctggggcctcagtgaaggtctcctgcaagg
cttctggttacacctttaccagctatggtatcagctgggtgcgacaggcccctggacaagggcttgagtg
gatgggatggatcagcgcttacaatggtaacacaaactatgcacagaagctccagggcagagtcaccatg
accacagacacatccacgagcacagcctacatggagctgaggagcctgagatctgacgacacggctgtgt
attactgtgcaaaagatcgtcattggcattggtggctggacgcctttgattattggggccaaggtaccct
ggtcaccgtctccagt

MF4280: SEQ ID NO. 35
caggtgcagctggtgcagtctggggctgaggtgaagaagcctggggcctcagtgaaggtctcctgcaagg
tttccggatacaccctcactgaattatccatgcactgggtgcgacaggctcctggtaaagggcttgaatg
gatgggaggctttgatcctgagtatggtaaaacattcttcgcacagaacttccagggcagagtcaccatg
accgaggacacatctgcagacacagcctacatggagctaagcagcctgagatctgaggacacggccgtgt
attactgtgcaacagagggtattatgagactactacttattactacaacctttttgactcctggggcca
gggaaccctggtcaccgtctccagt

MF4289: SEQ ID NO. 37
caggtgcagctggtgcaatctgggtctgaattgaagaagcctggggcctcagtgaaggtttcctgcaaga
cttctggatacaccttcactgactatgctatgacttgggtgcgacaggcccctggacaagggcttgaatg
gatgggatggatcaccaccaacactgggacccaacgtatgccccgggcttcacaggacggtttgtcttc
tccttggacacctctgtcagcacggcatatctgcagatcagcagcctaaaggccgaggacactgccgtat
attactgtgcgagagtgtatcattggatacggggatttgagttttggggccagggaaccctggtcaccgt
ctccagt

MF5777: SEQ ID NO. 39
caggtgcagctggtgcaatctgggtctgagttgaagaagcctggggcctcagtgaaggtttcctgcaagg
cttctggatacaccttcactaactatgttatgaattgggtgcgacaggcccctggacaagggcttgagtg
gatgggatggatcaacaccaacactgggaacccaacgtatgcccaggcttcacaggacggtttgtcttc
tccttggacacctctgtcagcacggcatatctgcagatcagcagcctaaaggctgaggacactgccgtgt
attactgtgcgaggtgggagctactagactactggggccagggaaccctggtcaccgtctccagt

MF5781: SEQ ID NO. 41
gaggtgcagctggtggagtctgggggaggcttggtacagcctgggggtccctgagactctcctgtgcag
cctctggattcacctttagcagctatgccatgagctgggtccgccaggctccagggaaggggctggagtg
ggtctcagttattagtggtagtggtgggaccacatactacgcagactccgtgaagggccggttcaccatc

Figure 2 (continued)

tccagagacaattccaagaacacgctgtatctgcaaatgaacagcctgagagccgaggacacggccgtat
attactgtgcgaaggggctggggagcttgactactggggccagggaaccctggtcaccgtctccagt

MF5803: SEQ ID NO. 43 caggtgcagctgcaggagtcggggccaggactggtgaagccttcggagaccctgtccctcacctgcactg
tctctaatggctccatcagtacttactactggagctggatccggcagccccagggaagggctggagtg
gattggatatgtctattacactgggcgcaccaagtacaacccctccctcaagagtcgagtcaccatatca
gtagacacgtccaagaaccagttctccctgaacctgagttctgtgaccgctgcggacacggccgtgtatt
actgtgcgagagggggtattgtagtagtcccagctgcgcgggactattactactacatggacgtctgggg
caaagggaccacggtcaccgtctccagt

MF5805: SEQ ID NO. 45 gaggtgcaactggtgcagtctggagcagaggtgaaaaagcccggggagtctctgaagatcgcctgtaagg
gttctggattcagttttaccagccactggatcggctgggtgcgccagaagcccgggagaggcctggagtg
gatgggggtcatctatcctggtgactctgataccagatacagcccgtccttccaaggccaggtcaccgtc
tcagccgacaagtccatcaataccgcctacctgcagtggaacagcctgaaggcctcggacaccgccatat
attactgtgcgagaccgaacagtgggagtccccggtacttcgagttctggggccgtggcaccctggtcac
cgtctccagt

MF5808: SEQ ID NO. 47 caggtgcagctgcaggagtcggggccaggactggtgaagccttcggagaccctgtccctcacctgcactg
tctctggtggctccatcagcagtagtagttactactggggctggatccgccagccccagggaaggggct
ggagtggattgggagtttctattatagtgggaacacctactacaacccgtccctcaagagtcgagtcacc
atatccgtagacacgtccaagaaccagttctccctgaagctgagctctgtgaccgccgcagacacggctg
tgtattactgtgcgagacaggagtattactatggttcggggagtccttcgtactactttgactactgggg
ccagggaaccctggtcaccgtctccagt

MF5809: SEQ ID NO. 49 gaggtgcagctggtgcagtctggagcagaggtgaaaaagcccggggagtctctgaagatctcctgtaagg
gttctggagacagttttatcagccactggatcgcctgggtgcgccagatgcccgggaaaggcctggagtg
gatggggatcgtctatcctggtgactctgataccagatacagcccgtccttccaaggccaggtcaccatc
tcagccgacaagtccatcaccaccgcctacttgcagtggagcagcctgaaggcctcggacaccgccatgt
attactgtgcgagacacgagtgggaactacttggccccctttgactactggggccagggaaccctggtcac
cgtctccagt

MF5814: SEQ ID NO. 51 gaggtgcagctggtgcagtctggggctgaggtgaagaagcctgggtcctcggtgaaggtctcctgcaagg
cttctggaggcacctccactaacgatgctatcagttgggtgcgacagacccctggacaagggcttgagtg
gatgggaagtatcatccctatccttgatacaacagaccacgcacagaagttccaggcagagtcacgatt
accgcggacaaatccacgaacacagcctacatggagctgaacagcctgagatctgatgacacggccgtgt
attactgtgcgagagagcatatagcagctcgtcaggactactttgactattggggccagggaaccctggt
caccgtctccagt

MF5817: SEQ ID NO. 53 caggtgcagctggtgcagtctggggctgaggtgaagaagcctgggtcctcggtgaaggtctcctgcaagg
tttctggaggcaccttcaggagctatgctatcagctgggtgcgacaggcccctggacaagggcttgagtg
gatgggagggatcatccctatctttgataacaagaaactacgcacagattcttcaggcagagtcacgatt
accgcggacttatccacgagcacagcctacatggagctgaacagtctgagatctgaggacacggccattt
attactgtgcgagagggagcgacgaggggggactggttcgaccctggggccaaggaaccctggtcaccgt
ctccagt

Figure 2 (continued)

MF5818: SEQ ID NO. 55 gaggtgcagctggtgcagtctgggactgaggtgaggaagcctgggtcctcggtgaaggtctcctgcaagg
cttctggaggcaccttcagcaactatgctatcagctgggtgcgacaggcccctggacaggggcttgagtg
gatgggaagtatcatccctatccttggaacaacagaccacgcacagaagttccaggacagagtcacgatt
accgcggacaaatcctcgaacacaacctacatggagctgagcagcctgagatctgatgacacggccgtat
attactgtgcgagagagtatatagcagctcgtctggactactttgactcttggggccagggaaccctggt
caccgtctccagt

MF5832: SEQ ID NO. 57 gaggtgcagctggtggagtctgggggaggcttggtacagcctggggggtccctgagactctcctgtgtag
tctctggattcaccttcagttactacgacatgcactgggtccgccaagtcacaggaaaaggtctggagtg
ggtctcagctattggcactgctggtgccacatactatccaggctccgtgaagggccgattcaccatctcc
agagaaaatgccaagaactccttgtatcttcaaatgaatagcctgagagccgggacacggctgtgtatt
actgtgcaagagatcgtggatatagtggctacgatgcgtactactttgacttctggggccagggaaccct
ggtcaccgtctccagt

MF5836: SEQ ID NO. 59 caggtgcagctgcaggagtcgggcccaggactggtgaagccttcggagaccctgtccctcacctgcactg
tctctggtggctccatcagcagtagtaattactactggggctggatccgccagcccccagggaaggggct
ggagtggattgggaatatctattatagagggtacacctattataaccgtccctcaagagtcgagtcacc
atatccgtagacacgtccaagaagcagttctccctgacgctgagctctgtgaccgccgcagacacggcta
tgtattactgtgcgagagagggagtgactacggtgactacgtaggagcttttgatatctgggaccaagg
gacaatggtcaccgtctccagt

MF5839: SEQ ID NO. 61 gaggtgcagctggtgcagtctgggggaggcttggtacagcctggggggtccctgagactctcctgtgcag
cctctggattcaccttcagttactacgacatgcactgggtccgccaagttacaggaaaaggtctggagtg
ggtctcaactattggtgctactggtgacacatactattcagactccgtgaagggccgatttaccatctcc
agacaaaatgccaagaactccttgtatcttcaaataaacagcctgagagccggggacacggctgtatatt
actgtgtaagagatcgtggatatattggctacgattcgtactactttgacaactggggccagggaaccct
ggtcaccgtctccagt

MF5850: SEQ ID NO. 63 caggtgcagctggtgcagtctgggtctgagttgaagaagcctggggcctcagtgaaggtttcctgcaagg
cttctggatacaccttcactaggtatcctatgaattgggtgcgacaggcccctggacaagggcttgagtg
gatgggatggatcaacaccaacactgggaacccaacatatgcccaggcttcacaggacggtttgtcttc
tccttggacacctctgtcagcacggcatttctgcagatcagcagcctaaaggctgaggacactgccgtgt
attactgtgcgagagagaggactaacttttatgatgcttttgatatctggggccaagggacaatggtcac
cgtctccagt

MF5853: SEQ ID NO. 65 caggtgcagctggtgcaatctgggtctgagttgaagaagcctggggcctcagtgaaggtttcctgcaagg
cttctggatataccttcaatagctatgctatggattgggtgcgacaggcccctggacaagggcttgagtg
gatgggatggatcaacaccaatactgggaacccaacgtatgcccaggccttcacaggacggtttgtcttc
tccttggacacctctgtcagcacggcatatctggagatcagcagcctaaaggctgaggacactgccgtgt
attactgtgcgagagagaggcatggatattttgaagcttttgatatctggggccaagggaccacggtcac
cgtctccagt

MF5855: SEQ ID NO. 67 caggtgcagctggtgcaatctgggtctgagttgaagaagcctggggcctcagtgaaggtttcctgcaagg
cttctggatacaccttcactaagtatgttatgaattgggtgcgacaggcccctggacaagggcttgagtg

Figure 2 (continued)

gatgggatggatcaacaccaacactgggaacccaacgtatgcccagggcttcacaggacggtttgtcttc
tccttggacacctctgtcagcacggcatatctgcaggtcagcagtctaagggctgaggacactgccctgt
attactgtgcgagagagtctaactggaactacgactactttgactactggggccagggcaccctggtcac
cgtctccagt

MF5862: SEQ ID NO. 69 caggtgcagctggtgcagtctggaacagaggtgaaaaagcccggggagtctctgaagatctcctgtaagg
gttctggatacagctttaccacctactggatcggctgggtgcgccagatgcccgggaaaggcctggagtg
gatgggaatcatctatcctggtgactctgataccagatacagcccgtccttccaaggccaggtcaccatc
tcagccgacaagtccatcagcaccgcctacctgcagttgagcagcctgaaggcctcggacaccgccatgt
attactgtgcgagacgggtcttagtatggttcggttgagcgcttttgatgtctggggccaaggaaccct
ggtcaccgtctccagt

MF5882: SEQ ID NO. 71 caggtgcagctggtgcaatctgggtctgagttgaagaagcctggggcctcagtgaaggtttcctgcaagg
cttctggatacaccttcactagatatgctatgaattgggtgcgacaggcccctggacaagggcttgagtg
gatgggatggatcaacaccaaaactgggaacccaacgtatgcccagggcttcacaggacggtttgtcttc
tccttggacacctctgtcagcacggcatatctgcagatcagcagcctaaaggctgaggacactgccgtgt
attactgtgcgagagatcgtgggagctactatgatgcttttgatatctggggccaagggacaatggtcac
cgtctccagt

MF5884: SEQ ID NO. 73 gaggtgcagctggtgcagtctgggtctgaattgaagaagcctggggcctcagtgaaggtttcctgcaagg
cttctggatacaccttcactaagtatgctatgaattgggtgcgacaggtccctggacaagggcttgagtg
gatgggatggatcaacaccaacactgggaacccaacgtatgcccagggcttcacaggacggtttgtcttc
tccttggacacctctgtccgcacggcatatctgcagatcagcagcctaaaggctgaggacactgccgtgt
attactgtgcgagaaaaggggggagctactacgactggttcgaccctggggccagggaaccctggtcac
cgtctccagt

MF5887: SEQ ID NO. 75 caggtgcagctggtgcagtctgggtctgagttgaagaagcctggggcctcagtgaaggtttcctgcaagg
cttctggatacaccttcactcgctatgctatgaattgggtgcgacaggcccctggacaagggcttgagtg
gatgggatggatcaacaccaacactgggaaccaacgtatgcccagggcttcacaggacggtttgtcttc
tccttggacacctctgtcagcacggcatatctgcagatcagcagcctgaaggctgaggacactgccgtgt
attactgtgcgagagataagggctataactggaactacatgggtgcttttgatatctggggccaagggac
cacggtcaccgtctccagt

MF5888: SEQ ID NO. 77 caggtgcagctggtgcagtctgggtctgagttgaagaagcccgggggctcaatgaaggtttcctgcaagg
cttctggatacaccttcactagatatgctatgaattggttgcgacaggcccctggacaagggcttgagtg
gatgggatggatcaacaccaacactgggaacccaacgtatgcccagggcttcacaggacggtttgtcttc
tccttggacacctctgtcagcacggcatatctgcagatcagcagcctaaaggctgaggacactgccgtct
attattgtgcgagacggagtgggagctactacgactactttgactactggggccagggaaccctggtcac
cgtctccagt

Figure 3

Common Light Chain amino acid (A.A.) sequence     SEQ ID NO. 80
DIQMTQSPSSLSASVGDRVTITCRASQSISSYLNWYQQKPGKAPKLLIYAASSLQSGVPSRFSGSGSGTDFTLTISSLQ
PEDFATYYCQQSYSTPPTFGQGTKVEIK
RTVAAPSVFIFPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC Annotated sequence:
VL:                                               SEQ ID NO. 79

```
gacatccagatgacccagtctccatcctccctgtctgcatctgtaggagacagagtcacc
 D   I   Q   M   T   Q   S   P   S   S   L   S   A   S   V   G   D   R   V   T
atcacttgccgggcaagtcagagcattagcagctacttaaattggtatcagcagaaacca
 I   T   C   R   A   S   Q   S   I   S   S   Y   L   N   W   Y   Q   Q   K   P
gggaaagcccctaagctcctgatctatgctgcatccagtttgcaaagtggggtcccatca
 G   K   A   P   K   L   L   I   Y   A   A   S   S   L   Q   S   G   V   P   S
aggttcagtggcagtggatctgggacagatttcactctcaccatcagcagtctgcaacct
 R   F   S   G   S   G   S   G   T   D   F   T   L   T   I   S   S   L   Q   P
gaagattttgcaacttactactgtcaacagagttacagtacccctccaacgttcggccaa
 E   D   F   A   T   Y   Y   C   Q   Q   S   Y   S   T   P   P   T   F   G   Q
gggaccaaggtggagatcaaa
 G   T   K   V   E   I   K
```

CL:                                               SEQ ID NO. 81

```
cgaactgtggctgcaccatctgtcttcatcttcccgccatctgatgagcagttgaaatct
 R   T   V   A   A   P   S   V   F   I   F   P   P   S   D   E   Q   L   K   S
ggaactgcctctgttgtgtgcctgctgaataacttctatcccagagaggccaaagtacag
 G   T   A   S   V   V   C   L   L   N   N   F   Y   P   R   E   A   K   V   Q
tggaaggtggataacgccctccaatcgggtaactcccaggagagtgtcacagagcaggac
 W   K   V   D   N   A   L   Q   S   G   N   S   Q   E   S   V   T   E   Q   D
agcaaggacagcacctacagcctcagcagcaccctgacgctgagcaaagcagactacgag
 S   K   D   S   T   Y   S   L   S   S   T   L   T   L   S   K   A   D   Y   E
aaacacaaagtctacgcctgcgaagtcacccatcagggcctgagctcgcccgtcacaaag
 K   H   K   V   Y   A   C   E   V   T   H   Q   G   L   S   S   P   V   T   K
agcttcaacaggggagagtgttag
 S   F   N   R   G   E   C   -
```

Figure 4

VH: dependent on the MF (target): Figures 1 and 2.

CH1:  SEQ ID NO. 83

```
gctagcaccaagggcccatcggtcttcccctggcacctcctccaagagcacctctggg
 A   S   T   K   G   P   S   V   F   P   L   A   P   S   S   K   S   T   S   G
ggcacagcggccctgggctgcctggtcaaggactacttccccgaaccggtgacggtgtcg
 G   T   A   A   L   G   C   L   V   K   D   Y   F   P   E   P   V   T   V   S
tggaactcaggcgccctgaccagcggcgtgcacaccttcccggctgtcctacagtcctca
 W   N   S   G   A   L   T   S   G   V   H   T   F   P   A   V   L   Q   S   S
ggactctactccctcagcagcgtcgtgaccgtgccctccagcagcttgggcacccagacc
 G   L   Y   S   L   S   S   V   V   T   V   P   S   S   S   L   G   T   Q   T
tacatctgcaacgtgaatcacaagcccagcaacaccaaggtggacaagagagtt
 Y   I   C   N   V   N   H   K   P   S   N   T   K   V   D   K   R   V
```

Hinge:  SEQ ID NO. 85

```
gagcccaaatcttgtgacaaaactcacacatgcccaccgtgccca
 E   P   K   S   C   D   K   T   H   T   C   P   P   C   P
```

CH2:  SEQ ID NO. 87

```
gcacctgaactcctggggggaccgtcagtcttcctcttccccccaaaacccaaggacacc
 A   P   E   L   L   G   G   P   S   V   F   L   F   P   P   K   P   K   D   T
ctcatgatctcccggacccctgaggtcacatgcgtggtggtggacgtgagccacgaagac
 L   M   I   S   R   T   P   E   V   T   C   V   V   V   D   V   S   H   E   D
cctgaggtcaagttcaactggtacgtggacggcgtggaggtgcataatgccaagacaaag
 P   E   V   K   F   N   W   Y   V   D   G   V   E   V   H   N   A   K   T   K
ccgcgggaggagcagtacaacagcacgtaccgtgtggtcagcgtcctcaccgtcctgcac
 P   R   E   E   Q   Y   N   S   T   Y   R   V   V   S   V   L   T   V   L   H
caggactggctgaatggcaaggagtacaagtgcaaggtctccaacaaagccctcccagcc
 Q   D   W   L   N   G   K   E   Y   K   C   K   V   S   N   K   A   L   P   A
cccatcgagaaaaccatctccaaagccaaa
 P   I   E   K   T   I   S   K   A   K
```

CH3: KK of DEKK  SEQ ID NO. 89

```
gggcagccccgagaaccacaggtgtacaccaagcccccatcccgggaggagatgaccaag
 G   Q   P   R   E   P   Q   V   Y   T   K   P   P   S   R   E   E   M   T   K
aaccaggtcagcctgaagtgcctggtcaaaggcttctatccagcgacatcgccgtggag
 N   Q   V   S   L   K   C   L   V   K   G   F   Y   P   S   D   I   A   V   E
tgggagagcaatgggcagccggagaacaactacaagaccacgcctcccgtgctggactcc
 W   E   S   N   G   Q   P   E   N   N   Y   K   T   T   P   P   V   L   D   S
gacggctccttcttcctctatagcaagctcaccgtggacaagagcaggtggcagcagggg
 D   G   S   F   F   L   Y   S   K   L   T   V   D   K   S   R   W   Q   Q   G
aacgtcttctcatgctccgtgatgcatgaggctctgcacaaccactacacgcagaagagc
 N   V   F   S   C   S   V   M   H   E   A   L   H   N   H   Y   T   Q   K   S
ctctccctgtctccgggttga
 L   S   L   S   P   G   -
```

Figure 4 (continued)

CH3: DE of DEKK  SEQ ID NO. 91

```
gggcagccccgagaaccacaggtgtacaccgacccccatcccgggaggagatgaccaag
  G   Q   P   R   E   P   Q   V   Y   T   D   P   P   S   R   E   E   M   T   K
aaccaggtcagcctgacctgcgaggtcaaaggcttctatcccagcgacatcgccgtggag
  N   Q   V   S   L   T   C   E   V   K   G   F   Y   P   S   D   I   A   V   E
tgggagagcaatgggcagccggagaacaactacaagaccacgcctcccgtgctggactcc
  W   E   S   N   G   Q   P   E   N   N   Y   K   T   T   P   P   V   L   D   S
gacggctccttcttcctctatagcaagctcaccgtggacaagagcaggtggcagcagggg
  D   G   S   F   F   L   Y   S   K   L   T   V   D   K   S   R   W   Q   Q   G
aacgtcttctcatgctccgtgatgcatgaggctctgcacaaccactacacgcagaagagc
  N   V   F   S   C   S   V   M   H   E   A   L   H   N   H   Y   T   Q   K   S
ctctccctgtctccgggttga
  L   S   L   S   P   G   -
```

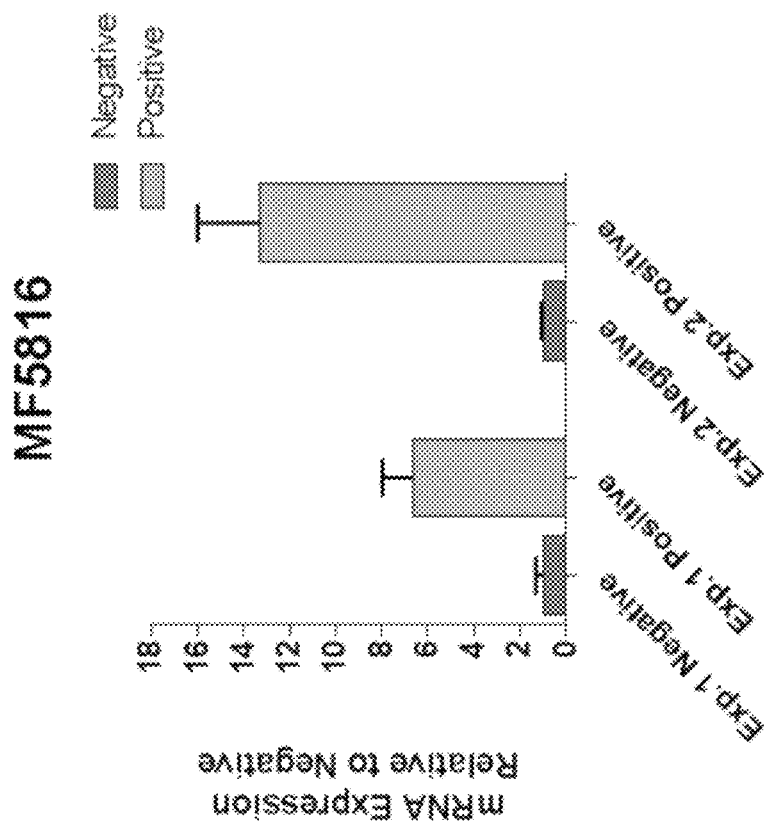
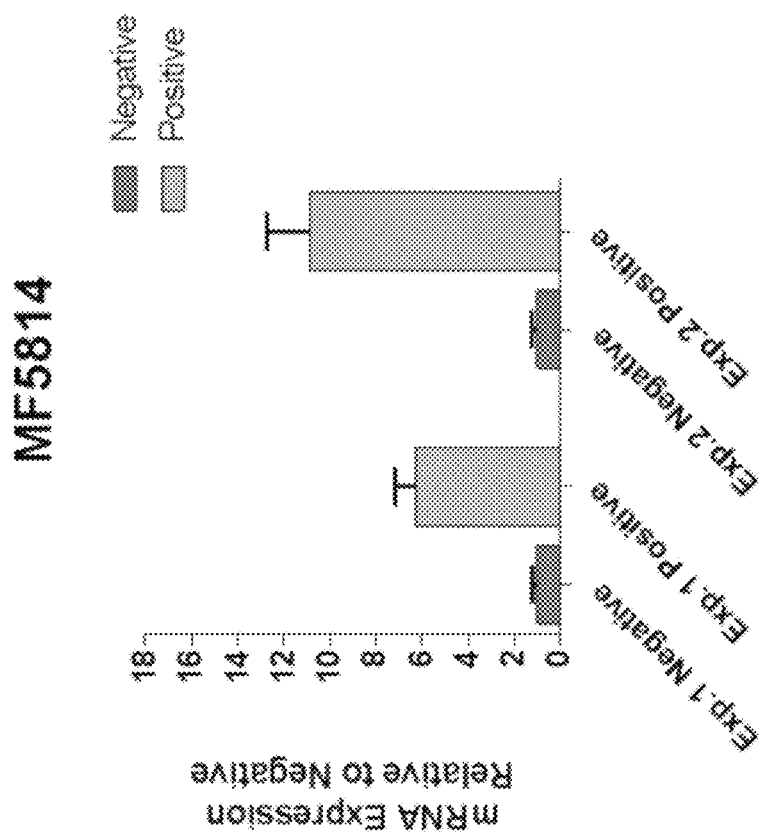
Figure 21

Figure 25A Supercluster 1 (MF5814 and MF5818)

Supercluster 8 (MF5790)

Supercluster 10 (MF5816)

Figure 26
Figure 26A
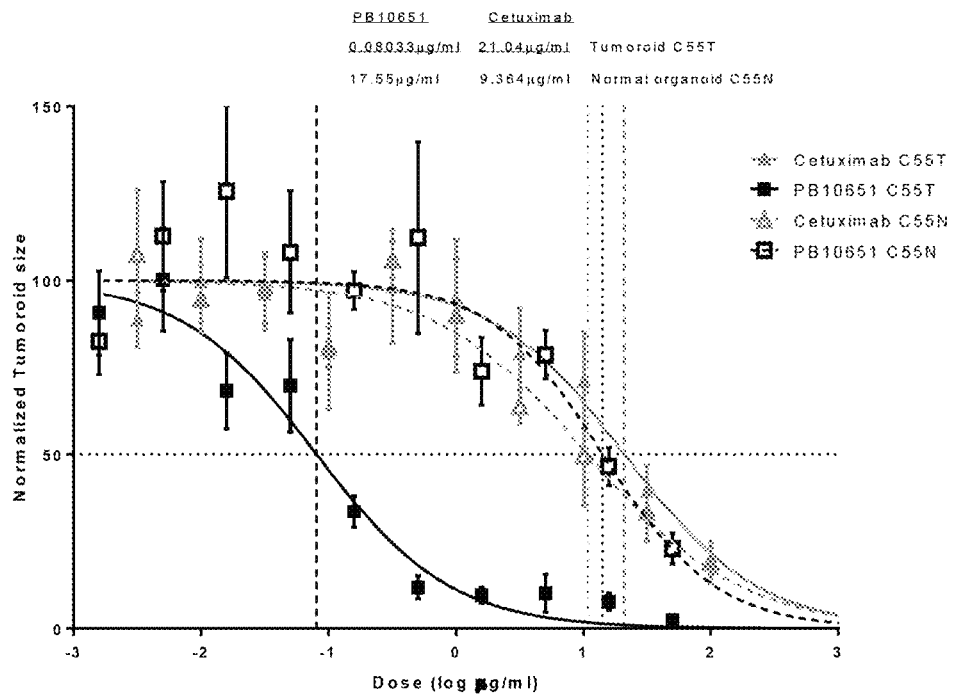
Figure 26B
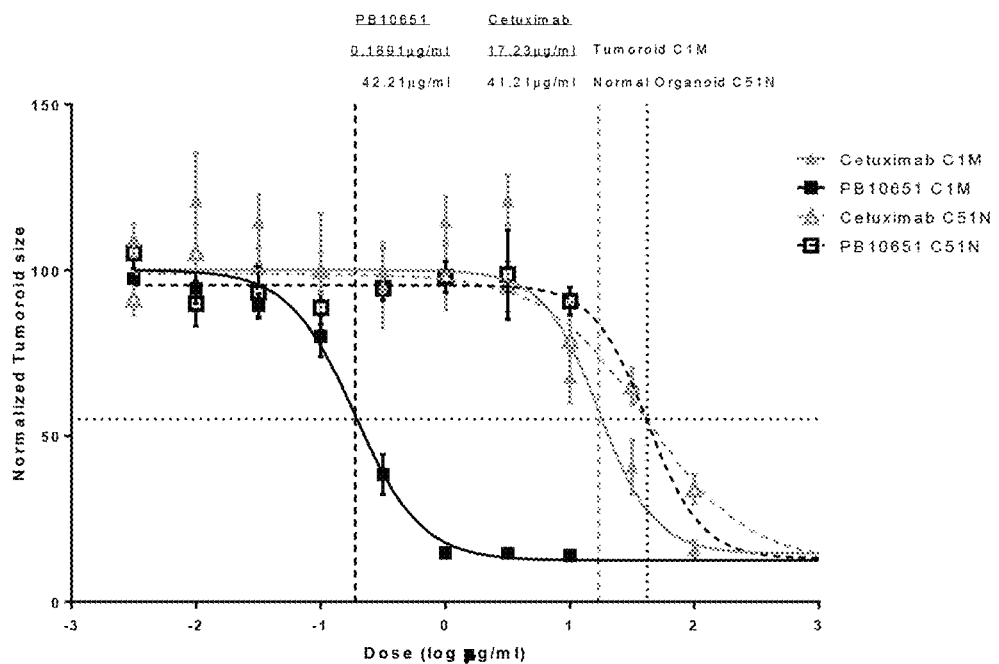

Figure 26C

| Organoid type | Name | IC50 (µg/ml) Cetuximab | PB10651 | Ratio |
|---|---|---|---|---|
| Normal | C7N | 13.43 | 19.05 | 0.7 |
| Normal | C51N | 52 | 67.45 | 0.8 |
| Normal | C71N | 1.37 | 3.09 | 0.4 |
| Normal | C57N | 1.08 | 4.52 | 0.2 |
| Normal | C55N | 11.17 | 14.86 | 0.8 |
| Tumoroid | C55T | 19.63 | 0.08 | 245 |
| Tumoroid | C57T | 22.75 | 1.25 | 18.2 |
| Tumoroid | C0M | 10.12 | 0.39 | 25.9 |
| Tumoroid | C1M | 24.21 | 0.25 | 96.8 |
| Tumoroid | C65M | 18.92 | 0.99 | 19.1 |
| Tumoroid | P18T | 5.17 | 0.25 | 20.7 |

Figure 28B

IC$_{50}$ table
(μg/ml)

| | | Primary tumour | | | Metastasis | | | Normal | | | | |
|---|---|---|---|---|---|---|---|---|---|---|---|---|
| | | P18T | C55T | C57T | C65M | C1M | C0M | C51N | C7N | C71N | C55N | C57N |
| | | IC$_{50}$ | IC$_{50}$ | IC$_{50}$ | IC$_{50}$ | IC$_{50}$ | IC$_{50}$ | IC$_{50}$ | IC$_{50}$ | IC$_{50}$ | IC$_{50}$ | IC$_{50}$ |
| EGFR | Cetuximab | 8.39 | 28.51 | 15.63 | 15.70 | 17.10 | 3.35 | 26.36 | 16.11 | 3.14 | 2.18 | 4.80 |
| EGFRxLGR5 | PB10651 | 0.35 | 0.11 | 1.20 | 3.57 | 0.19 | 0.14 | 53.83 | 17.51 | 4.77 | 6.03 | 8.24 |
| EGFR + LGR5 | PG3755 +PG5816 | 1.59 | 7.87 | 16.94 | 8.89 | 2.58 | 1.36 | 2.17 | 2.39 | 0.32 | 0.47 | 1.32 |

*Average Tumor Volume on Day 0*

|  | Day 0 |
|---|---|
| PBS | 46.9 |
| PB10651 | 47.3 |
| CET | 44.3 |

*N of Xenografts*

| Day | 0 | 2 | 7 | 9 | 13 | 15 | 17 | 20 |
|---|---|---|---|---|---|---|---|---|
| PBS | 29 | 29 | 29 | 28 | 25 | 25 | 6 | 3 |
| PB10651 | 33 | 33 | 33 | 33 | 33 | 33 | 22 | 22 |
| CET | 29 | 29 | 29 | 29 | 26 | 26 | 6 | 4 |

Average Tumor Volume on Day 0

|  | Day 0 |
|---|---|
| PBS | 29.1 |
| PB10651 | 29.6 |
| CET | 31.2 |

N of Xenografts

| Day | 0 | 2 | 5 | 7 | 9 | 12 | 13 | 15 | 19 |
|---|---|---|---|---|---|---|---|---|---|
| PBS | 18 | 18 | 18 | 18 | 18 | 18 | 18 | 18 | 18 |
| PB10651 | 22 | 22 | 22 | 22 | 22 | 22 | 22 | 22 | 22 |
| CET | 21 | 21 | 21 | 21 | 21 | 21 | 21 | 21 | 21 |

Figure 39

SEQ ID NO:1

MDTSRLGVLLSLPVLLQLATGGSSPRSGVLLRGCPTHCHCEPDGRMLLRVDCSDLGLSELPSNLSVFTSYLDL
SMNNISQLLPNPLPSLRFLEELRLAGNALTYIPKGAFTGLYSLKVLMLQNNQLRHVPTEALQNLRSLQSLRLD
ANHISYVPPSCFSGLHSLRHLWLDDNALTEIPVQAFRSLSALQAMTLALNKIHHIPDYAFGNLSSLVVLHLHN
NRIHSLGKKCFDGLHSLETLDLNYNNLDEFPTAIRTLSNLKELGFHSNNIRSIPEKAFVGNPSLITIHFYDNPIQ
FVGRSAFQHLPELRTLTLNGASQITEFPDLTGTANLESLTLTGAQISSLPQTVCNQLPNLQVLDLSYNLLEDLP
SFSVCQKLQKIDLRHNEIYEIKVDTFQQLLSLRSLNLAWNKIAIHPNAFSTLPSLIKLDLSSNLLSSFPITGLHG
LTHLKLTGNHALQSLISSENFPELKVIEMPYAYQCCAFGVCENAYKISNQWNKGDNSSMDDLHKKDAGMFQ
AQDERDLEDFLLDFEEDLKALHSVQCSPSPGPFKPCEHLLDGWLRIGVWTIAVLALTCNALVTSTVFRSPLYI
SPIKLLIGVIAAVNMLTGVSSAVLAGVDAFTFGSFARHGAWWENGVGCHVIGFLSIFASESSVFLLTLAALERG
FSVKYSAKFETKAPFSSLKVIHLCALLALTMAAVPLLGGSKYGASPLCLPLPFGEPSTMGYMVALILLNSLCFL
MMTIAYTKLYCNLDKGDLENIWDCSMVKHIALLLFTNCILNCPVAFLSFSSLINLTFISPEVIKFILLVVVPLPA
CLNPLLYILFNPHFKEDLVSLRKQTYVWTRSKHPSLMSINSDDVEKQSCDSTQALVTFTSSSITYDLPPSSVPSP
AYPVTESCHLSSVAFVPCL

Annotated sequence No1:

Mdtsrlgvllslpvllqlat          Signal peptide

Ggssprsgvllrgcpthchcepdgrmllrvdcsdlglselpsnlsvftsy   N-region

Ldlsmnnisqllpnplpslrflee          LRR1
Lrlagnaltyipkgaftglyslkv          LRR2
Lmlqnnqlrhvptealqnlrslqs          LRR3
Lrldanhisyvppscfsglhslrh          LRR4
Lwlddnalteipvqafrslsalqa          LRR5
mtlalnkihhipdyafgnlsslvv          LRR6
Lhlhnnrihslgkkcfdglhsletl         LRR7
Dlnynnldefptairtlsn               LRR8
Lkelgfhsnnirsipekafvgnpslit       LRR9
Ihfydnpiqfvgrsafqhlpelrt          LRR10
Ltlngasqitefpdltgtanles           LRR11
Ltltgaqisslpqtvcnqlpnlqv          LRR12
Ldlsynlledlpsfsvcqklqk            LRR13
Idlrhneiyeikvdtfqqllslr           LRR14
Slnlawnkiaiihpnafstlpslik         LRR15
Ldlssnllssfpitglhglthlk           LRR16
Ltgnhalqslissenfpelkviem          LRR17 pyayqccafgvcenayki snqwnkgdnssmddlhkkdagmfqaqderd

Figure 39 (continued)

| | |
|---|---|
| *Ledflldfeedlkalhsvqcspspgpfkpcehlldgwlir* | CRL region |
| igvwtiavlaltcnalvtstvf | predicted TM1 |
| rsplyispi | |
| klligviaavnmltgvssavlagvda | predicted TM2 |
| ftfgsfarhgawwengvgchv | |
| igflsifasessvflltlaaler | predicted TM3 |
| gfsvkysakfetkapfss | |
| lkviillcallaltmaavpllggsk | predicted TM4 |
| ygasplclplpfgepstm | |
| gymvalillnslcflmmtiaytkly | predicted TM5 |
| cnldkgdleniwdcsmvk | |
| hialllftncilncpvaflsfssl | predicted TM6 |
| inltfispevi | |
| kfillvvvplpaclnpllyilfnp | predicted TM7 |
| | |
| *hfkedlvslrkqtyvwtrskhpslmsinsddvekqscdstqalvtft* | |
| *sssitydlppssvpspaypvteschlssvafvpcl* | C-terminal tail |

Figure 40

SEQ ID NO: 2
MRPSGTAGAALLALLAALCPASRALEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSGQKTKIISNRGENSCK
ATGQVCHALCSPEGCWGPEPRDCVSCRNVSRGRECVDKCNLLEGEPREFV
ENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIATGM
VGALLLLLVVALGIGLFMRRRHIVRKRTLRRLLQERELVEPLTPSGEAPN
QALLRILKETEFKKIKVLGSGAFGTVYKGLWIPEGEKVKIPVAIKELREA
TSPKANKEILDEAYVMASVDNPHVCRLLGICLTSTVQLITQLMPFGCLLD
YVREHKDNIGSQYLLNWCVQIAKGMNYLEDRRLVHRDLAARNVLVKTPQH
VKITDFGLAKLLGAEEKEYHAEGGKVPIKWMALESILHRIYTHQSDVWSY
GVTVWELMTFGSKPYDGIPASEISSILEKGERLPQPPICTIDVYMIMVKC
WMIDADSRPKFRELIIEFSKMARDPQRYLVIQGDERMHLPSPTDSNFYRA
LMDEEDMDDVVDADEYLIPQQGFFSSPSTSRTPLLSSLSATSNNSTVACI
DRNGLQSCPIKEDSFLQRYSSDPTGALTEDSIDDTFLPVPEYINQSVPKR
PAGSVQNPVYHNQPLNPAPSRDPHYQDPHSTAVGNPEYLNTVQPTCVNST
FDSPAHWAQKGSHQISLDNPDYQQDFFPKEAKPNGIFKGSTAENAEYLRV
APQSSEFIGA

Annotated seq. No: 2

MRPSGTAGAALLALLAALCPASRA  signal peptide

LEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSGQKTKIISNRGENSCK
ATGQVCHALCSPEGCWGPEPRDCVSCRNVSRGRECVDKCNLLEGEPREFV
ENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIAT
Extra-cellular domain GMVGALLLLLVVALGI  predicted transmembrane domain

GLFMRRRHIVRKRTLRRLLQERELVEPLTPSGEAPN

Figure 40 (continued)

```
QALLRILKETEFKKIKVLGSGAFGTVYKGLWIPEGEKVKIPVAIKELREA
TSPKANKEILDEAYVMASVDNPHVCRLLGICLTSTVQLITQLMPFGCLLD
YVREHKDNIGSQYLLNWCVQIAKGMNYLEDRRLVHRDLAARNVLVKTPQH
VKITDFGLAKLLGAEEKEYHAEGGKVPIKWMALESILHRIYTHQSDVWSY
GVTVWELMTFGSKPYDGIPASEISSILEKGERLPQPPICTIDVYMIMVKC
WMIDADSRPKFRELIIEFSKMARDPQRYLVIQGDERMHLPSPTDSNFYRA
LMDEEDMDDVVDADEYLIPQQGFFSSPSTSRTPLLSSLSATSNNSTVACI
DRNGLQSCPIKEDSFLQRYSSDPTGALTEDSIDDTFLPVPEYINQSVPKR
PAGSVQNPVYHNQPLNPAPSRDPHYQDPHSTAVGNPEYLNTVQPTCVNST
FDSPAHWAQKGSHQISLDNPDYQQDFFPKEAKPNGIFKGSTAENAEYLRV
APQSSEFIGA
```

Intra-cellular tyrosine kinase and C-terminal tail

BINDING MOLECULES THAT INHIBIT CANCER GROWTH

The content of the electronically submitted sequence listing (Name: 4096_0110002_Seqlisting_ST25.txt"; Size: 367,932 bytes; and Date of Creation: Aug. 4, 2023) is herein incorporated by reference in its entirety.

The invention relates to the field of binding molecules. In particular it relates to the field of therapeutic binding molecules for the treatment of diseases involving aberrant cells. More in particular it relates to binding molecules that bind an extracellular part of a membrane associated member of the epidermal growth factor (EGF) receptor family and an extra-cellular part of a membrane associated member of a WNT signaling pathway.

Cancer is still a major cause of death in the world, in spite of the many advances that have been made in the treatment of the disease and the increased knowledge of the molecular events that lead to cancer. Colorectal cancer (CRC), for instance, is the third most common cancer worldwide. In 2008, 1.23 million people were diagnosed with the disease. It is the second most common cancer in Europe, with around 447,000 new cases diagnosed in 2012 (13% of the total). Colorectal cancer is the fourth most common cause of cancer death, estimated to be responsible for 608,000 (EU 148,000) deaths per annum. While some new treatments have been advanced in CRC many have failed clinical testing; metastatic CRC is still largely incurable.

Traditionally, most cancer drug discovery has focused on agents that block essential cell functions and kill dividing cells. However, in cases of advanced cancer, no matter how aggressively applied, even to the point where patients suffer life-threatening side-effects from the treatment, chemotherapy rarely results in a complete cure. In most cases, the tumors in the patients stop growing or temporarily shrink (referred to as remission) only to start proliferating again, some times more rapidly (referred to as relapse), and become increasingly more difficult to treat. More recently the focus of cancer drug development has moved away from broadly cytotoxic chemotherapy to targeted cytostatic therapies with less toxicity. Treatment of advanced cancer with targeted therapy that specifically inhibits signaling pathway components has been validated clinically in leukemia. However, in a majority of carcinomas, targeted approaches are still proving ineffective. In colorectal cancer, over 80% of patients overexpress the receptor tyrosine kinase EGFR, but treatment with EGFR blocking therapies results in response rates of ~10% and, as with chemotherapy, these responses are not durable. While in some patients the poor response rate can be linked to activating mutations downstream of the blocking agent, there is accumulating scientific evidence that a special type of self-renewing cancer cell may explain the limited activity of cancer drugs in many situations.

Cancer stem cells are tumor cells that share characteristics with normal stem cells, most importantly the ability to self-renew over long periods of time and give rise to many of the cell types within a given cancer. Recent evidence suggests that while conventional chemotherapy and current targeted therapies kill differentiated and differentiating cells that form the bulk of tumors, the self-renewing cancer stem cell is less sensitive to these therapeutic approaches. Therefore, Cancer stem cells, which typically form a small subpopulation of cells within the tumor, may be responsible for the regeneration of the disease after therapy and the formation of metastases. Cancer stem cells are thought to arise from adult stem cells that have accumulated one or more mutations that initiate cancer development. In normal stem cells, proliferation is strictly controlled both spatially and temporally through signals transmitted in their immediate environment. In contrast, cancer stem cells proliferate and differentiate in a less controlled manner outside of the normal stem cell compartment where they are dependent on mutations in oncogenes and tumor suppressor genes.

Without being bound by theory it is thought that means and methods have been developed that target cancer stem cells and shut down important growth and differentiation pathways in these cells. Targeting is achieved by using proteins that have a binding arm specific for a stem cell target and another binding arm that specifically blocks a growth factor receptor pathway.

SUMMARY OF THE INVENTION

In one aspect the invention provides a protein that binds an extracellular part of a membrane associated member of the epidermal growth factor (EGF) receptor family and an extracellular part of a membrane associated member of a WNT signaling pathway. The protein is preferably an antibody, preferably a bispecific antibody or a functional part, derivative and/or analogue thereof.

The invention also provides a bispecific antibody or a functional part, derivative and/or analogue thereof that binds an extracellular part of a membrane associated member of the epidermal growth factor (EGF) receptor family and an extra-cellular part of a membrane associated member of a WNT-signaling pathway.

Also provided is a method for the treatment of an individual that has a cancer, the method comprising administering a protein of the invention or a bispecific antibody of the invention to the individual in need thereof.

The invention further provides a protein of the invention or a bispecific antibody of the invention, for use in the treatment of an individual that has cancer.

In one embodiment the cancer is an EGF-receptor ligand responsive cancer that expresses a membrane associated member of the WNT pathway.

Further provided is a cell system comprising a protein of the invention or a bispecific antibody of the invention, and a cell that expresses a membrane associated member of the epidermal growth factor (EGF) receptor family and that expresses a membrane associated member of the WNT pathway. The cell is preferably an EGF-receptor ligand responsive cell that expresses a membrane associated member of the WNT pathway.

Also provided is a method for inhibiting growth of a cell that expresses a membrane associated member of the epidermal growth factor (EGF) receptor family and that expresses a membrane associated member of the WNT pathway in a system permissive for growth of the cell, the method providing the system with a protein of the invention or a bispecific antibody of the invention. The cell is preferably an EGF-receptor ligand responsive cell that expresses a membrane associated member of the WNT pathway.

The invention provides an antibody that comprises a variable domain that can bind an epitope on an extracellular part of LGR5 which epitope is located within amino acid residues 21-118 of SEQ ID NO: 1 depicted in FIG. 39 of which amino acid residues D43; G44, M46, F67, G90, and F91 are involved in binding of the antibody to the epitope.

The antibody is preferably an antibody wherein one or more of the amino acid residue substitutions of D43A; G44A, M46A, F67A, G90A, and F91A reduces the binding of the antibody of LGR5.

The invention further provides an antibody that comprises a variable domain that can bind an epitope on an extracellular part of LGR5 which epitope is located within amino acid residues 21-118 of SEQ ID NO: 1 depicted in FIG. 39, and wherein the binding of the antibody to LGR5 reduced by one or more of the following amino acid residue substitutions D43A; G44A, M46A, F67A, G90A, and F91A.

The antibody is preferably an antibody wherein interaction of the antibody with LGR5 on an LGR5-expressing cell does not inhibit the binding of Rspondin 1 (RSPO 1) to LGR5 by more than 20%. The inhibition of binding of the antibody to LGR5 is preferably measured when the antibody and the RSPO are present in a molar ratio of 0.1 or less; preferably in a molar ratio of between 0.1 to 0.001, (inclusive), preferably 0.1 to 0.01 (inclusive).

The invention further provides an antibody that comprises a variable domain that can bind an epitope on LGR5 that is located within amino acid residues 21-118 of SEQ ID NO: 1 depicted in FIG. 39, and wherein interaction of the antibody with LGR5 on an LGR5-expressing cell does not inhibit the binding of an RSPO to LGR5 by more than 20% when the antibody and the RSPO are present in a molar ratio of 0.1 or less; preferably in a molar ratio of between 0.1 to 0.001, (inclusive), preferably 0.1 to 0.01 (inclusive).

The epitope is preferably a conformational epitope. The epitope is preferably located within amino acid residues 40-95 of SEQ ID NO: 1 depicted in FIG. 39. The binding of the antibody to LGR5 is preferably reduced with one or more of the following amino acid residue substitutions D43A; G44A, M46A, F67A, G90A, and F91A. The antibody preferably further comprises a further variable domain that can bind a further protein. The further protein is preferably a membrane protein comprising an extracellular part. The further protein is preferably a membrane associated member of the epidermal growth factor (EGF) receptor family or cMET.

In a particularly preferred embodiment the antibody is a bispecific antibody.

The bispecific antibody preferably comprises a variable domain that can bind said epitope on an extracellular part of LGR5 and a variable domain that can bind a further protein. As mentioned herein the further protein is preferably a membrane associated member of the EGFR receptor family or cMET. The variable domain that binds this further protein preferably binds an extracellular part of said further protein.

The invention further provides a bispecific antibody comprising a variable domain that can bind an epitope on an extracellular part of LGR5 and a variable domain that can bind a further protein, wherein the LGR5 epitope is located within amino acid residues 21-118 of SEQ ID NO: 1 depicted in FIG. 39 of which amino acid residues D43; G44, M46, F67, G90, and F91 are involved in binding of the antibody. The binding of the variable domain to LGR5 is preferably reduced with one or more of the following amino acid residue substitutions D43A; G44A, M46A, F67A, G90A, and F91A. The further protein is preferably a membrane protein comprising an extracellular part. The further protein is preferably a membrane associated member of the EGF receptor family or cMET.

The binding of the (bi)specific antibody to the membrane associated member of the EGF receptor family or cMET preferably reduces ligand-induced signaling in a cell that comprises said membrane associated member of the EGF receptor family or cMET.

The invention further provides an antibody that comprises a variable domain that can bind an epitope on an extracellular part of LGR5 which epitope is located within amino acid residues 21-118 of SEQ ID NO: 1 depicted in FIG. 39 and wherein the binding of the protein to LGR5 is reduced with one or more of the following amino acid residue substitutions D43A; G44A, M46A, F67A, G90A, and F91A.

Without being bound by theory it is believed that M46, F67, G90, and F91 of LGR5 as depicted in FIG. 39, are contact residues for the variable domain, i.e. the antigen-binding site of the variable domain that can bind the LGR epitope. That amino acid residue substitution D43A and G44A reduces the binding of the antibody can be due to the fact that these are contact residues, however, it is also possible that these amino acid residue substitution induce a (slight) modification of the conformation of the part of LGR that has one or more of the other contact residues (i.e. at positions 46, 67, 90 or 91) and that conformation change is such that antibody binding is reduced. The epitope is characterized by the mentioned amino acid substitutions. Whether an antibody binds the same epitope can be determined in various ways. In the examples a preferred method is described. The method utilizes a CHO cells. The CHO cells express LGR5 on the cell membrane, or on alanine substitution mutant, preferably a mutant comprising one or more of the substitutions M46A, F67A, G90A, or F91A. The test antibody is contacted with the CHO cells and binding of the antibody to the cells compared. A test antibody binds the epitope if it binds to LGR5 and to a lesser extent to an LGR5 with a M46A, F67A, G90A, or F91A substitution. Comparing binding with a panel of mutants each comprising one alanine residue substitution is preferred. Such binding studies are well known in the art. Often the panel comprises single alanine substitution mutants covering essentially all amino acid residues. For LGR5 the panel only needs to cover the extracellular part of the protein. Expression of a particular mutant can be compromised but this is easily detected by one or more LGR5 antibodies that bind to different region(s). If expression is also reduced for these control antibodies the level or folding of the protein on the membrane is compromised for this particular mutant. Binding characteristics of the test antibody to the panel readily identifies whether the test antibodies exhibits reduced binding to mutants with a M46A, F67A, G90A, or F91A substitution and thus whether the test antibody is an antibody of the invention. Reduced binding to mutants with a M46A, F67A, G90A, or F91A substitution also identifies the epitope to be located within amino acid residues 21-118 of SEQ ID NO: 1 depicted in FIG. 39, the same applies to the location within amino acid residues 40-95 of SEQ ID NO: 1 depicted in FIG. 39. In a preferred embodiment the panel includes a D43A substitution mutant; a G44A substitution mutant of both. The antibody with the VH sequence of the VH of MF5816 exhibits reduced binding to these substitution mutants.

In a preferred embodiment the interaction of RSPO 1 with LGR5 on an LGR5-expressing cell does not inhibit the binding of the antibody to LGR5 by more than 20%. Inhibition of binding of the antibody to LGR5 is preferably measured under conditions wherein the antibody and the RSPO 1 are present in a molar ratio from of 0.1 or less; preferably in a molar ratio of between 0.1 to 0.001, (inclusive), preferably 0.1 to 0.01 (inclusive).

Inhibition of binding is preferably measured when the antibody and the RSPO 1 are present in a molar ratio from of 0.1 or less, preferably in a molar ratio of between 0.1 to 0.01 (inclusive). It was found that molar ratio's of antibody to RSPO of less than 0.001 can sometimes reduce the binding of the antibody to LGR5.

When herein molar ratio's of antibody to RSPO are mentioned it is preferred that the antibody is present in amounts that result in 40%-80% of the binding achieved when saturating amounts of the antibody are present.

The invention further provides an antibody that comprises a variable domain that can bind an epitope on an extracellular part of human EGFR of which amino acid residues I462; G465; K489; I491; N493; and C499 are involved in binding of the antibody to the epitope. The antibody is preferably an antibody characterized in that the binding of the antibody to EGFR is reduced with an EGFR wherein one or more of the amino acid residue substitutions selected from I462A; G465A; K489A; I491A; N493A; and C499A have been introduced.

The invention further provides an antibody that comprises a variable domain that can bind an epitope on an extracellular part of human EGFR which epitope is located within amino acid residues 420-480 of SEQ ID NO: 2 depicted in FIG. 40, and wherein the binding of the antibody to LGR5 is reduced by one or more of the following amino acid residue substitutions I462A; G465A; K489A; I491A; N493A; and C499A. The binding of the antibody to human EGFR interferes with the binding of EGF to the receptor. The epitope on EGFR is a conformational epitope.

The epitope is located within amino acid residues 420-480 of SEQ ID NO: 2 depicted in FIG. 40, preferably within 430-480 of SEQ ID NO: 2 depicted in FIG. 40; preferably within 438-469 of SEQ ID NO: 2 depicted in FIG. 40.

The antibody preferably comprises a further variable domain which further variable domain can bind a further protein. The further protein is preferably a membrane protein comprising an extracellular part. The further protein is preferably a membrane associated member WNT-pathway.

The antibody is typically a bispecific antibody.

The variable domain that binds human EGFR, is preferably a variable domain with a heavy chain variable region that comprises at least the CDR3 sequence of the VH of MF3755 as depicted in FIG. 1 or a CDR3 sequence that differs in at most three, preferably in at most two, preferably in no more than one amino acid from a CDR3 sequence of the VH of MF3755 as depicted in FIG. 1.

The variable domain that binds human EGFR, is preferably a variable domain with a heavy chain variable region that comprises at least the CDR1. CDR2 and CDR3 sequences of the VH of MF3755 as depicted in FIG. 1; or the CDR1, CDR2 and CDR3 sequences of the VH of MF3755 as depicted in FIG. 1 with at most three, preferably at most two, preferably at most one amino acid substitutions.

The variable domain that binds human EGFR, is preferably a variable domain with a heavy chain variable region that comprises the sequence of the VH chain of MF3755 as depicted in FIG. 1; or the amino acid sequence of the VH chain of MF3755 depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain of MF3755.

The further protein is preferably LGR4; LGR5; LGR6; RNF43 or ZNRF3, preferably LGR5.

The invention further provides a bispecific antibody comprising a variable domain that can bind an epitope on an extracellular part of EGFR and a variable domain that can bind a further protein, wherein the EGFR epitope is located within amino acid residues 420-480 of SEQ ID NO: 2 depicted in FIG. 40, which amino acid residues I462; G465; K489; I491; N493; and C499 are involved in binding of the antibody to the epitope. The binding of the variable domain to EGFR is preferably reduced with one or more of the following amino acid residue substitutions I462A; G465A; K489A; I491A; N493A; and C499A. The further protein is preferably a membrane protein comprising an extracellular part, preferably a membrane associated member of the WNT-pathway, preferably LGR5.

Without being bound by theory it is believed that the contact residues of the epitope, i.e. where the variable domain contacts the human EGFR are likely I462; K489; I491; and N493. The amino acid residues G465 and C499 are likely indirectly involved in the binding of the antibody to EGFR, probably because mutation by substitution into an alanine induces a (slight) conformational alteration of the epitope resulting in a reduced binding to the epitope.

It has been shown that antibodies comprising one or more variable domains that bind EGFR with the mentioned epitope have a better effectivity when used to inhibit growth of an EGFR ligand responsive cancer or cell. In the context of bispecific antibodies, an arm of the antibody comprising an EGFR binding variable domain with the mentioned epitope combines better with a variety of other arms comprising variable domains that bind extra-cellular parts of other cell surface proteins.

DETAILED DESCRIPTION OF THE INVENTION

The invention discloses a protein that binds an extracellular part of a membrane associated member of the epidermal growth factor (EGF) receptor family and an extracellular part of a membrane associated member of a WNT signaling pathway. Such a protein is further also referred to as "a protein of the invention".

In a preferred embodiment the protein of the invention is an antibody (or antibody part, derivative, or analogue, as described elsewhere in the application), an antibody mimetic, a polypeptide, an aptamer or a combination thereof. These proteins or aptamers typically bind to one target. The protein of the invention binds to two targets. It is to be understood that any combination of these antibodies, antibody mimetics, polypeptides and aptamers can be linked together by methods known in the art. For example, in some embodiments the protein of the invention is a conjugate or a fusion protein. For antibodies the technology of making multi-specific antibodies has progressed to also include bispecific antibodies that have the same overall structure as a normal mono-specific antibody but wherein the two arms of the antibody each bind a different target.

An antibody mimetic is a polypeptide that, like antibodies, can specifically bind an antigen, but that is not structurally related to antibodies. Antibody mimetics are usually artificial peptides or proteins with a molar mass of about 3 to 20 kDa. Common advantages over antibodies are better solubility, tissue penetration, stability towards heat and enzymes, and comparatively low production costs. Non-limiting examples of antibody mimetics are affibody molecules (typically based on the Z domain of Protein A); affilins (typically based on Gamma-B crystalline or Ubiquitin); affimers (typically based on Cystatin); affitins (typically based on Sac7d from *Sulfolobus acidocaldarius*); alphabodies (typically based on Triple helix coiled coil); anticalins (typically based on Lipocalins); avimers (typically based on A domains of various membrane receptors); DARPins (typically based on ankyrin repeat motif); fynomers (typically based on SH3 domain of Fyn 7); kunitz domain peptides (typically based on Kunitz domains of various protease inhibitors); and monobodies (typically based on type III domain of fibronectin).

Monobodies are synthetic binding proteins that are constructed using a fibronectin type III domain (FN3) as a molecular scaffold. Monobodies are simple and robust alternative to antibodies for creating target-binding proteins. The term "monobody" was coined in 1998 by the Koide group who published the first paper demonstrating the monobody concept using the tenth FN3 domain of human fibronectin.

Monobodies and other antibody mimetics are typically generated from combinatorial libraries in which portions of the scaffold are diversified using molecular display and directed evolution technologies such as phage display, mRNA display and yeast surface display. A large number of antibody mimetics have high affinity and high specificity to their respective targets.

Aptamers are oligonucleotide or peptide molecules that bind to a specific target molecule. Aptamers are usually created by selecting them from a large random sequence pool, but natural aptamers also exist in riboswitches. Aptamers can be used for both basic research and clinical purposes as macromolecules.

As used herein, the term "conjugate" refers to two or more molecules that have been covalently joined, optionally by a linking region. For example, in some embodiments, a conjugate is a first protein or non-protein moiety joined to a second protein or non-protein moiety by a linking region. For example, in some embodiments of a protein of the invention it comprises or consists of two or more antibodies that have been covalently joined. A conjugate is not limited to a first and second moiety but in some embodiments may also have a third, fourth or more moieties joined by further linking regions. As described elsewhere in this application, examples of protein moieties include, but are not limited to: a polypeptide, a peptidomimetic or an antibody (or antibody part, derivative, or analogue, as described elsewhere in the application). Examples of non-protein moieties include, but are not limited to aptamers. Numerous types of linker can be used, and the linker will be selected to be appropriate according to the molecule types in the conjugate and on the desired properties of the linker (length, flexibility, resistance to protease activity and other similar characteristics). Such linkers may comprise nucleotides, polypeptides, or a suitable synthetic material. For example, a linker may be a flexible peptide linker. In certain embodiments, the linker may be a cleavable linker, allowing the parts of the conjugate to be separated from each other. In other embodiments, a peptide linker might be a helical linker. Various examples and kits for linking proteins and other molecules are well known in the art. As used herein, the term "fusion protein" refers to a protein that comprises two or more polypeptides or proteins that have been joined at the DNA level by recombination and are expressed together as a single polypeptide. A fusion protein may also comprise a peptide linking region also encoded by the DNA and expressed together with the fusion protein. A peptide linker that is part of a fusion protein, may be designed to have particular characteristics such as flexibility, hydrophilicity, protease-resistance, cleavability etc. All these properties can be designed within the DNA sequence and methods for designing linkers are well known in the art. For example, antibodies can be linked together by methods well-known in the art, and as described herein, to form bispecific or multi-targeting antibodies. Furthermore, bispecific antibodies can be constructed by various methods known in the art, for example, by using technology such as BiClonics®. A bispecific monoclonal antibody (BsMAb, BsAb) typically comprises binding domains of two different monoclonal antibodies and consequently binds to two different epitopes. Biclonics® molecules, but also other full length IgG bispecific antibodies have two different antigen binding specificities encoded by two different variable regions of a full length IgG molecule of a Fab of a scFv. Biclonics® can be produced by co-transfection of individual cells with genetic constructs encoding two different common light chain (cLC) antibodies as detailed elsewhere herein. CH3 engineering ensures efficient hetero-dimerization and formation of essentially pure bispecific antibodies. In some embodiments, a protein of the invention suppresses signaling in a cell, group of cells, tissue or tumor by an amount that is useful for the intended purpose of the protein of the invention, for example, may reduce induction of any one or more of these responses by at least 5%, 10%, 15%, 20%, 25%, 30%, 35%, preferably 40%, 45%, 50%, 55%, 60%, more preferably 70%, 80%, 85%, and most preferably 90%, 95%, 99%, or 100% compared to the signaling induced by a neutral substance or negative control as measured in an assay known in the art.

A protein of the invention preferably comprises an antibody or a part, derivative or analogue thereof. A protein of the invention is preferably a bispecific antibody.

Antibodies typically bind their target via the so-called antigen binding site. An unmodified antigen-binding site is typically formed by and present in the variable domain of the antibody. The variable domain contains said antigen-binding site. A variable domain that binds an antigen is a variable domain comprising an antigen-binding site that binds the antigen.

In one embodiment an antibody variable domain comprises a heavy chain variable region (VH) and a light chain variable region (VL). The antigen-binding site can be present in the combined VH/VL variable domain, or in only the VH region or only the VL region. When the antigen-binding site is present in only one of the two regions of the variable domain, the counterpart variable region can contribute to the folding and/or stability of the binding variable region, but does not significantly contribute to the binding of the antigen itself.

As used herein, antigen-binding refers to the typical binding capacity of an antibody to its antigen. Binding of an antibody to an antigen can be assessed in various ways. One way is to incubate the antibody with the antigen (preferably cells expressing the antigen), removing unbound antibody (preferably by a wash step) and detecting bound antibody by means of a labeled antibody that binds to the bound antibody.

Antigen binding by an antibody is typically mediated through the complementarity determining regions (CDR) of the antibody and the specific three-dimensional structure of both the antigen and the variable domain allowing these two structures to bind together with precision (an interaction similar to a lock and key), as opposed to random, non-specific sticking of proteins. As an antibody typically recognizes part of an antigen called the epitope of an antigen, and as such epitope may be present in other compounds as well, antibodies according to the present invention may recognize other proteins as well, if such other compounds contain the same epitope. Hence, the term "binding" does not exclude binding of the antibodies to another protein or protein(s) that contain the same epitope. Such other protein(s) is preferably not a human protein.

A protein of the invention such as an antibody typically does not bind to other proteins than the specified target protein on the membrane of cells in a post-natal, preferably adult human.

An antibody of the invention comprising an antigen-binding site that binds to an extracellular part of one membrane associated member of the epidermal growth factor (EGF) receptor family binds to the specified member and, under otherwise identical conditions, at least 100-fold lower to the extracellular part of another member of the EGF receptor family of the same species. For instance, an antibody comprising an antigen-binding site that binds to ErbB-1, binds to ErbB-1 and, under otherwise identical conditions, at least a 100-fold lower to the homologous receptors ErbB-2 (HER2), ErbB-3 (HER3) and ErbB-4 (HER) of the same species. An antibody comprising an antigen-binding site that binds to ErbB-2, binds to ErbB-2 and, under otherwise identical conditions, at least a 100-fold lower to the homologous receptors ErbB-1, ErbB-3 and ErbB-4 of the same species. An antibody comprising an antigen-binding site that binds to ErbB-3, binds to ErbB-3 and, under otherwise identical conditions, at least a 100-fold lower to the homologous receptors ErbB-1, ErbB-2 and ErbB-4 of the same species. An antibody comprising an antigen-binding site that binds to ErbB-4, binds to ErbB-4 and, under otherwise identical conditions, at least a 100-fold lower to the homologous receptors ErbB-1, ErbB-2 and ErbB-3 of the same species. Of course, when an antibody is designed to bind to two or more members of the family, the binding to the two or more members can be essentially the same. In the present invention it is preferred that respective antibodies each bind to only one member of a family. Considering that the ErbB-family is a family of cell surface receptors, the binding is typically assessed on cells that express the receptor(s) on their cell surface.

An antibody of the invention preferably interferes with the binding of a ligand for the member of the EGF receptor family. The term "interferes with binding" as used herein means that binding of the antibody to the member of the EGF receptor family competes with ligand for binding to the member of the EGF receptor family. The antibody may diminish ligand binding, displace ligand when this is already bound to the member of the EGF receptor family or it may, for instance through steric hindrance, at least partially prevent that ligand can bind to the member of the EGF receptor family.

An EGFR (ErbB1) or HER3 (ErbB3) binding protein of the invention, preferably antibody of the invention preferably inhibits respectively EGFR ligand or HER3 ligand-induced signaling, measured as ligand-induced growth of BxPC3 cells (ATCC CRL-1687) or BxPC3-luc2 cells (Perkin Elmer 125058) or ligand-induced cell death of A431 cells (ATCC CRL-1555). The mentioned EGFR or HER3 binding protein can reduce ligand induced signaling by at least 5%, 10%, 15%, 20%, 25%, 30%, 35%, preferably 40%, 45%, 50%, 55%, 60%, more preferably 70%, 80%, 85%, and most preferably 90%, 95%, 99%, or 100% compared to the ligand induced effect in the presence of a neutral substance or negative control as measured in an assay known in the art. EGFR and ErbB-3 each can bind a number of ligands and stimulate growth of the mentioned BxPC3 cells or BxPC3-luc2 cells. In the presence of a ligand for one or both receptors the growth of BxPC3 or BxPC3-luc2 cells is stimulated. EGFR and/or ErbB-3 ligand-induced growth of BxPC3 cells can be measured by comparing the growth of the cells in the absence and presence of the ligand. The preferred EGFR ligand for measuring EGFR ligand-induced growth of BxPC3 or BxPC3-luc2 cells is EGF. The preferred ErbB-3 ligand for measuring ErbB-3 ligand-induced growth of BxPC3 or BxPC3-luc2 cells is NRG1. The ligand-induced growth is preferably measured using saturating amounts of ligand. In a preferred embodiment EGF is used in an amount of 100 ng/ml of culture medium. NRG1 is preferably used in 10 ng/ml of culture medium. EGF and NRG1 are preferably the EGF and NRG1 of R&D systems, cat. nr. 396-HB and 236-EG as described in the examples. Determination of whether a protein or antibody of the invention inhibits signaling in bivalent format, it is preferred that the method as described herein above is performed with a monospecific monovalent or bivalent version of the protein or antibody. In other words a protein or antibody that only has binding sites for the receptor of which signaling is to be determined. For an antibody it would be a bivalent monospecific antibody wherein the antigen binding variable domains consist of variable domains that bind the EGF-receptor family member.

An EGFR or HER3 binding protein of the invention, preferably antibody of the invention preferably inhibits respectively EGFR ligand or HER3 ligand, induced growth of BxPC3 cells (ATCC CRL-1687) or BxPC3-luc2 cells (Perkin Elmer 125058). The mentioned EGFR or HER3 binding protein can reduce ligand induced growth signaling by at least 5%, 10%, 15%, 20%, 25%, 30%, 35%, preferably 40%, 45%, 50%, 55%, 60%, more preferably 70%, 80%, 85%, and most preferably 90%, 95%, 99%, or 100% compared to the ligand induced growth induced by a neutral substance or negative control as measured in an assay known in the art. EGFR and ErbB-3 each can bind a number of ligands and stimulate growth of the mentioned BxPC3 cells or BxPC3-luc2 cells. In the presence of a ligand for one or both receptors the growth of BxPC3 or BxPC3-luc2 cells is stimulated. EGFR and/or ErbB-3 ligand-induced growth of BxPC3 cells can be measured by comparing the growth of the cells in the absence and presence of the ligand. The preferred EGFR ligand for measuring EGFR ligand-induced growth of BxPC3 or BxPC3-luc2 cells is EGF. The preferred ErbB-3 ligand for measuring ErbB-3 ligand-induced growth of BxPC3 or BxPC3-luc2 cells is NRG1. The ligand-induced growth is preferably measured using saturating amounts of ligand. In a preferred embodiment EGF is used in an amount of 100 ng/ml of culture medium. NRG1 is preferably used in 10 ng/ml of culture medium. EGF and NRG1 are preferably the EGF and NRG1 of R&D systems, cat. nr. 396-HB and 236-EG as described in the examples.

An EGF-receptor family ligand is preferably an EGFR or HER3 receptor ligand. "HER3 or ErbB-3 ligand" as used herein refers to polypeptides which bind and activate ErbB-3. Examples of ErbB-3 ligands include, but are not limited to neuregulin 1 (NRG1) and neuregulin 2 (NRG2) (for review Olayioye M A et al.; EMBO J (2000) Vol 19: pp 3159-3167). The term preferably includes biologically active fragments and/or variants of a naturally occurring polypeptide. "EGFR or ErbB-1 ligand" as used herein refers to polypeptides which bind and activate EGFR. Examples of EGFR ligands include, but are not limited to EGF, TGF-α, HB-EGF, amphiregulin, betacellulin and epiregulin (for review Olayioye M A et al.; EMBO J (2000) Vol 19: pp 3159-3167). The term preferably includes biologically active fragments and/or variants of a naturally occurring polypeptide.

An antibody of the invention comprising an antigen-binding site that binds to extracellular part of a membrane associated member of a WNT signaling pathway binds to the specified member and, under otherwise identical conditions, at least 100-fold lower to the extracellular part of another membrane associated protein that is not a member of a WNT-signaling pathway of the same species such as insulin-like growth factor 1 (IGF-1) receptor. An antibody comprising an antigen-binding site that binds to LGR5, binds to LGR5 and, under otherwise identical conditions, at least a 100-fold lower to an extracellular part of an IGF-1 receptor of the same species. An antibody comprising an antigen-binding site that binds to LGR4, binds to LGR4 and, under otherwise identical conditions, at least a 100-fold lower to IGF-1 receptor of the same species. An antibody comprising an antigen-binding site that binds to RNF43, binds to RNF43 and, under otherwise identical conditions, at least a 100-fold lower to IGF-1 receptor, LGR4 or LGR5 of the same species. An antibody comprising an antigen-binding site that binds to ZNRF3, binds to ZNRF3 and, under otherwise identical conditions, at least a 100-fold lower to IGF-1 receptor or RNF43 of the same species. Of course, when an antibody is designed to bind to two or more members of the family, the binding to the two or more members can be essentially the same. For instance, some of the antibodies that bind LGR5 can bind LGR4 of the same species and vice versa. In a preferred embodiment an antibody of the invention that comprises an antigen-binding site that binds to extracellular part of a membrane associated member of a WNT signaling pathway binds to the specified member and, under otherwise identical conditions, at least 100-fold lower to the extracellular part of another membrane associated of the family of the same species. An antibody comprising an antigen-binding site that binds to LGR5, binds to LGR5 and, under otherwise identical conditions, at least 10-fold and preferably at least 100-fold lower to LGR4 of the same species. An antibody comprising an antigen-binding site that binds to LGR4, binds to LGR4 and, under otherwise identical conditions, at least a 10-fold and preferably at least 100-fold lower to LGR5 of the same species In the present invention it is preferred that respective antibodies each bind to only one member of a family. Preferred members of the WNT signaling pathway in the context of the present invention are LRP5, LRP6, LGR4, LGR5, LGR6, FRZ1, FRZ2, FRZ3, FRZ4, FRZ5, FRZ6, FRZ7, FRZ8, FRZ9 FRZ10, ZNRF3, RNF43, N-Cadherin, Kremen1 and Kremen2, ROR2/RYK). Considering that the members of this list are cell surface receptors, the binding is typically assessed on cells that express the receptor(s) on their cell surface.

The term "antibody" as used herein means a proteinaceous molecule, preferably belonging to the immunoglobulin class of proteins, containing one or more variable domains that bind an epitope on an antigen, where such domains are derived from or share sequence homology with the variable domain of an antibody. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. The affinity is a measure for the strength of binding to a particular antigen or epitope. Specific binding, is defined as binding with affinities (KD) of at least $1 \times 10e-6$ M, more preferably $1 \times 10e-7$ M, more preferably with affinities higher than $1 \times 10e-9$ M. Typically, antibodies for therapeutic applications have affinities of up to $1 \times 10e-10$ M or higher. Antibodies such as the bispecific antibodies of the present invention typically comprise the constant domains (Fc part) of a natural antibody. An antibody of the invention is typically a bispecific full length antibody, preferably of the human IgG subclass. An antibody of the present invention is preferably of the human IgG1 subclass. Such antibodies of the invention have good ADCC properties which can, if desired, be enhanced by techniques known in the art, have favorable half-life upon in vivo administration to humans and CH3 engineering technology exists that can provide for modified heavy chains that preferentially form heterodimers over homodimers upon co-expression in clonal cells.

An antibody of the invention is preferably a "full length" antibody. The term 'full length' according to the invention is defined as comprising an essentially complete antibody, which however does not necessarily have all functions of an intact antibody. For the avoidance of doubt, a full length antibody contains two heavy and two light chains. Each chain contains constant (C) and variable (V) regions, which can be broken down into domains designated CH1, CH2, CH3, VH for the heavy chain, and CL, VL for the light chain. An antibody binds to antigen via the variable domains contained in the Fab fragment portion. The antibody can interact with molecules and cells of the immune system through the constant domains, mostly through the Fc portion.

The terms 'variable domain', 'VH/VL pair', 'VH/VL' are used herein interchangeably. Full length antibodies according to the invention encompass antibodies wherein mutations may be present that provide desired characteristics or are just alternatives to the ones in the original chain. Such mutations should not be deletions of substantial portions of any of the regions. However, antibodies wherein one or several amino acid residues are deleted, without essentially altering the binding characteristics of the resulting antibody are embraced within the term "full length antibody". For instance, an IgG antibody can have 1-20 amino acid residue insertions, deletions or a combination thereof in the constant region. For instance, ADCC activity of an antibody can be improved when the antibody itself has a low ADCC activity, by slightly modifying the constant region of the antibody (Junttila, T. T., K. et al. (2010). Cancer Research 70: 4481-4489). Changes are sometimes also made to improve storage or production or to remove C-terminal lysines (Engineered therapeutic antibodies with improved effector functions. Kubota T. Niwa R. Satoh M. Akinaga S, Shitara K, Hanai N). Another way to improve ADCC activity of an antibody is by enzymatically interfering with the glycosylation pathway resulting in a reduced fucose (von Horsten et al. (2010); Glycobiology 20:1607-1618). Several in vitro methods exist for determining the efficacy of antibodies or effector cells in eliciting ADCC. Among these are chromium-51 [Cr51] release assays, europium [Eu] release assays, and sulfur-35 [S35] release assays. Usually, a labeled target cell line expressing a certain surface-exposed antigen is incubated with antibody specific for that antigen. After washing, effector cells expressing Fc receptor CD16 are co-incubated with the antibody-labeled target cells. Target cell lysis is subsequently measured by release of intracellular label by a scintillation counter or spectrophotometry.

A bispecific antibody of the invention can in one embodiment be afucosylated. A bispecific antibody of the invention preferably comprises a reduced amount of fucosylation of the N-linked carbohydrate structure in the Fc region, when compared to the same antibody produced in a normal CH cell.

Full length IgG antibodies are preferred because of their favorable half-life and the need to stay as close to fully autologous (human) molecules for reasons of immunogenicity. An antibody of the invention is preferably a bispecific IgG antibody, preferably a bispecific full length IgG1 antibody. IgG1 is favored based on its long circulatory half-life in man. In order to prevent any immunogenicity in humans it is preferred that the bispecific IgG antibody according to the invention is a human IgG1.

The term 'bispecific' (bs) means that one part of the antibody (as defined above) binds to one epitope on an antigen whereas a second part binds to a different epitope on either the same antigen, or a different antigen. The different epitopes are typically present on different antigens. The different epitopes can, however, also be present on the same antigen. According to the present invention, said first and second antigens are in fact two different proteins. A preferred bispecific antibody is an antibody that comprises parts of two different monoclonal antibodies and consequently can bind to two different types of antigen. Dependent on the expression level, (sub-)cellular localization and stoichiometry of the two antigens recognized by a bispecific antibody, both Fab arms of the antibody may or may not simultaneously bind their epitope. One arm of the bispecific antibody typically contains the variable domain of one antibody and the other arm contains the variable domain of another antibody (i.e. one arm of the bispecific antibody is formed by one heavy chain paired with one light chain whereas the other arm is formed by a different heavy chain paired with a light chain). The heavy chain variable regions of the bispecific antibody of the invention are typically different from each other, whereas the light chain variable regions are preferably the same in the bispecific antibodies of the invention. A bispecific antibody wherein the different heavy chain variable regions are associated with the same or a common, light chain is also referred to as a bispecific antibody with a common light chain (cLC). Further provided is therefore a bispecific antibody according to the invention, wherein both arms comprise a common light chain.

Preferred bispecific antibodies can be obtained by co-expression of two different heavy chains and a common light chain in a single cell. When wildtype CH3 domains are used, co-expression of two different heavy chains (A and B) and a common light chain will result in three different antibody species, AA, ALB and BB. AA and BB are designations for the two mono-specific, bivalent antibodies, and AB is a designation for the bispecific antibody. To increase the percentage of the desired bispecific product (AB) CH3 engineering can be employed, or in other words, one can use heavy chains with compatible hetero-dimerization domains, as defined hereunder.

The term 'compatible hetero-dimerization domains' as used herein refers to protein domains that are engineered such that engineered domain A' will preferentially form heterodimers with engineered domain B' and vice versa, whereas homo-dimerization between A'-A' and B'-B' is diminished.

Bispecific antibodies as described herein preferably comprise a common light chain. The term 'common light chain' according to the invention refers to light chains which may be identical or have some amino acid sequence differences while the binding specificity of the full length antibody is not affected. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain', 'common VL'. 'single light chain', 'single VL', with or without the addition of the term 'rearranged' are all used herein interchangeably. It is an aspect of the present invention to use as common light chain a human light chain that can combine with different heavy chains to form antibodies with functional antigen binding domains (WO2004/009618, WO2009/157771, Merchant et al. 1998 and Nissim et al. 1994). Preferably, the common light chain has a germline sequence. A preferred germline sequence is a light chain variable region that is frequently used in the human repertoire and has good thermodynamic stability, yield and solubility. A preferred germline light chain is O12, preferably the rearranged germline human kappa light chain IgVκ1-39*01/IGJκ1*01 (FIG. 3) or a fragment or a functional equivalent (i.e. same IgVκ1-39 gene segment but different IGJκ gene segment) thereof (nomenclature according to the IMGT database worldwide web at imgt.org). However, the same principle also works with a lambda light chain and this is therefore also provided in the context of the invention. Further provided is therefore a bispecific antibody according to the invention, wherein said common light chain is a germline light chain, preferably a rearranged germline human kappa light chain comprising the IgVκ1-39 gene segment, most preferably the rearranged germline human kappa light chain IgVκ1-39*01/IGJ$_K$1*01 (FIG. 3).

The terms rearranged germline human kappa light chain IgVκ1-39*01/IGJκ1*01. IGKV1-39/IGκJ1, huVκ1-39 light chain or in short huVκ1-39, or simply 1-39 are used interchangeably throughout the application. Obviously, those of skill in the art will recognize that "common" also refers to functional equivalents of the light chain of which the amino acid sequence is not identical. Many variants of said light chain exist wherein mutations (deletions, substitutions, additions) are present that do not materially influence the formation of functional binding regions. The light chain of the present invention can also be a light chain as specified herein above, having 1-20, preferably 1-5 amino acid insertions, deletions, substitutions or a combination thereof.

Also contemplated are antibodies wherein a VH is capable of specifically recognizing a first antigen and the VL, paired with the VH in an immunoglobulin variable domain, is capable of specifically recognizing a second antigen. The resulting VH/VL pair will bind either antigen 1 or antigen 2. Such so called "two-in-one antibodies", described in for instance WO2008/027236, WO2010/108127 and Schaefer et al (2011 Cancer Cell 20, 472-486), are different from bispecific antibodies of the invention and are further referred to as "two-in-one" antibodies.

A part of an antibody is an antigen binding part and typically contains the variable domains of the antibody. A part can also be a so-called single domain antibody fragment. A single-domain antibody fragment (sdAb, called Nanobody by Ablynx, the developer) is an antibody fragment with a single monomeric variable antibody domain. Like a whole antibody, it is able to bind selectively to a specific antigen. With a molecular weight of only 12-15 kDa, single-domain antibody fragments are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain). Single-domain antibodies by themselves are not much smaller than normal antibodies (being typically 90-100 kDa). Single-domain antibody fragments are mostly engineered from heavy-chain antibodies found in camelids; these are called VHH fragments (Nanobodies®). Some fishes also have heavy-chain only antibodies (IgNAR. 'immunoglobulin new antigen receptor'), from which single-domain antibody fragments called VNAR fragments can be obtained. An alternative approach is to split the dimeric variable domains from common immunoglobulin G (IgG) from humans or mice into monomers. Although most research into single-domain antibodies is currently based on heavy chain variable domains, nanobodies derived from light chains have also been shown to bind specifically to target epitopes. A non-limiting example of an antibody part contains a variable domain of a heavy chain and/or a light chain of an antibody or an equivalent thereof. Non-limiting examples of such parts are VHH, Human Domain Antibodies (dAbs) and Unibodies. Preferred antibody parts or derivatives have at least a variable domain of a heavy chain and a light chain of an antibody or equivalents thereof. Non-limiting examples of such binding molecules are F(ab)-fragments and Single chain Fv fragments. A functional part of a bispecific antibody comprises the antigen binding parts of the bispecific antibody, or a derivative and/or analogue of the binding parts. As mentioned herein above, the binding part of an antibody is encompassed in the variable domain.

A derivative of an antibody is a protein that but for the CDR regions deviates from the amino acid sequence of a natural antibody in at most 20 amino acids. A derivative of an antibody as disclosed herein is an antibody that deviates from said amino acid sequence in at most 20 amino acids.

Preferred membrane associated member of the WNT pathway that a protein of the invention binds to is LRP5, LRP6, LGR4, LGR5, LGR6, FRZ1, FRZ2, FRZ3, FRZ4, FRZ5, FRZ6, FRZ7, FRZ8, FRZ9, FRZ10, ZNRF3, RNF43, N-Cadherin, Kremen1 and Kremen2, ROR2, RYK. From this list the membrane associated members of the LGR family that are active in the WNT pathway are preferred, in particular LGR4, LGR5 and LGR6. In a preferred embodiment the membrane associated member of the LGR family is LGR4 or LGR 5, in particular LGR5. Other preferred membrane associated members of the canonical WNT pathway are ZNRF3 and RNF43.

Mouse Lgr4, Lgr5, and Lgr6 have been demonstrated to be high affinity receptors for R-spondins (R-spondin 1-4) leading to increased phosphorylation of Wnt receptors Lrp5/6 and stabilization of b-catenin without the involvement of G-protein signaling (Carmon, K. S., et al. (2011). Proc Natl Acad Sci USA 108, 11452-11457; de Lau, W., et al. (2011) Nature 476' 293-297.). The R-spondins are members of a much larger family of proteins characterized by the presence of thrombospondin repeats (TSRs). R-spondins also contain N-terminal cysteine-rich Furin repeats which are required to exert the Wnt-enhancing activity as measured by b-catenin stabilization and phosphorylation of the Wnt/Frizzled coreceptor Lrp6 (Kim et al. (2005)). Gene fusions that increase expression levels of functional R-spondins have been reported in a subset of human colon cancers (Seshagiri, S., et al. (2012). Nature 488, 660-664.). While the perceived role of the Lgr-R-spondin complex is to modulate signaling through the Lrp-Frizzed-wnt receptor complex, current models suggest that the Lgr-R-spondin complex is itself subject to modulation through the highly homologous E3 ligases Rnf43 and Znrf3. Specifically, Lgr4, Lgr5, and Lgr6 receptors serve to efficiently recruit R-spondin ligands and bring these into position for interaction with Rnf43/Znrf3, which also contain R-spondin binding sites (de Lau, W., et al (2014). Genes Dev 28, 305-316). This interaction leads to membrane clearance of the Rnf43 or Znrf3, resulting in persistence of surface Frizzled receptors, and the boosting of wnt signal strength (de Lau, et al (2014). Genes Dev 28, 305-316) and enriched in colon cancer (Hao, H.-X., et al. (2012) Nature 485, 195-200).

A membrane associated member of the WNT pathway that is active in the canonical pathway, it can also be active, depending on the particular member, in the non-canonical pathway and vice versa.

The human epidermal growth factor (EGF) receptor family (HER) has four members; ErbB (Erythroblastoma)-1, ErbB-2, ErbB-3 and ErbB-4. Epidermal growth factor (EGF) receptor (EGFR, ErbB1, or HER1) is a member of a family of four receptor tyrosine kinases (RTKs), named Her- or cErbB-1, -2, -3 and -4. ErbB-1 is also known under various synonyms, the most common of which is EGFR. EGFR has an extracellular domain (ECD) that is composed of four sub-domains, two of which are involved in ligand binding and two of which are involved in homo-dimerisation and hetero-dimerisation. EGFR integrates extracellular signals from a variety of ligands to yield diverse intracellular responses. The major signal transduction pathway activated by EGFR is composed of the Ras-mitogen-activated protein kinase (MAPK) mitogenic signalling cascade. Activation of this pathway is initiated by the recruitment of Grb2 to tyrosine phosphorylated EGFR. This leads to activation of Ras through the Grb2-bound Ras-guanine nucleotide exchange factor Son of Sevenless (SOS). In addition, the PI3-kinase-Akt signal transduction pathway is also activated by EGFR, although this activation is much stronger in case there is co-expression of ErbB-3 (HER3). The EGFR is implicated in several human epithelial malignancies, notably cancers of the breast, bladder, non-small cell lung cancer lung, colon, ovarian head and neck and brain. Activating mutations in the gene have been found, as well as overexpression of the receptor and of its ligands, giving rise to autocrine activation loops. This RTK has therefore been extensively used as target for cancer therapy. Both small-molecule inhibitors targeting the RTK and monoclonal antibodies (mAbs) directed to the extracellular ligand-binding domains have been developed and have shown hitherto several clinical successes, albeit mostly for a select group of patients. The database accession number for the human EGFR protein and the gene encoding it is (GenBank NM_005228.3). This accession number is primarily given to provide a further method of identification of EGFR protein as a target, the actual sequence of the EGFR protein bound by an antibody may vary, for instance because of a mutation in the encoding gene such as those occurring in some cancers or the like. The words cancer and tumor are used herein and typically both refer to cancer, unless otherwise specifically stated.

Where reference herein is made to EGFR, the reference refers to human EGFR unless otherwise stated. The antigen-binding site that binds EGFR, binds EGFR and a variety of variants thereof such as those expressed on some EGFR positive tumors.

The term 'ErbB-3' as used herein refers to the protein that in humans is encoded by the ERB33 gene. Alternative names for the gene or protein are HER3; LCCS2; MDA-BF-1; c-ErbB-3; c-ErbB3; ErbB3-S; p180-ErbB3; p45-sErbB3; and p85-sErbB3. Where reference is made herein to ErbB-3, the reference refers to human ErbB-3. An antibody comprising an antigen-binding site that binds ErbB-3, binds human ErbB-3. The ErbB-3 antigen-binding site may, due to sequence and tertiary structure similarity between human and other mammalian orthologs, also bind such an ortholog but not necessarily so. Database accession numbers for the human ErbB-3 protein and the gene encoding it are (NP_001005915.1, NP_001973.2, NC_000012.11, NC_018923.2, NT_029419.12). The accession numbers are primarily given to provide a further method of identification of ErbB-3 as a target, the actual sequence of the ErbB-3 protein bound by an antibody may vary, for instance because of a mutation in the encoding gene such as those occurring in some cancers or the like. The ErbB-3 antigen binding site binds ErbB-3 and a variety of variants thereof, such as those expressed by some ErbB-3 positive tumor cells. The antigen-binding site that binds ErbB-3 preferably binds domain III of ErbB-3. The EGF receptor family member as mentioned herein as a target for the protein of the invention or the bispecific antibody of the invention is preferably epidermal growth factor receptor Erbb-1 (EGFR), ErbB-3 or ErbB-4. In a preferred embodiment the EGF receptor family member is ErbB-1 or ErbB-3.

The term "LGR" refers to the family of proteins known as Leucine-rich repeat-containing G-protein coupled receptors. Several members of the family are known to be involved in the WNT signaling pathway, of note LGR4; LGR5 and LGR6.

LGR4 is Leucine-Rich Repeat Containing G Protein-Coupled Receptor 4 Alternative names for the gene or protein are; GPR48; G Protein-Coupled Receptor 48; BNMD17; Leucine-Rich Repeat-Containing G Protein-Coupled Receptor 4; Leucine-Rich Repeat-Containing G-Protein Coupled Receptor 4; G-Protein Coupled Receptor 48;

A protein or antibody of the invention that binds LGR4, binds human LGR4. The LGR4 binding protein or antibody of the invention may, due to sequence and tertiary structure similarity between human and other mammalian orthologs, also bind such an ortholog but not necessarily so. Database accession numbers for the human LGR4 protein and the gene encoding it are (NC_000011.10; NC_018922.2; NT_009237.19; NP_060960.2). The accession numbers are primarily given to provide a further method of identification of LGR4 as a target, the actual sequence of the LGR4 protein bound may vary, for instance because of a mutation in the encoding gene such as those occurring in some cancers or the like. The LGR4 antigen binding site binds LGR4 and a variety of variants thereof, such as those expressed by some LGR4 positive tumor cells.

LGR5 is Leucine-Rich Repeat Containing G Protein-Coupled Receptor 5 Alternative names for the gene or protein are Leucine-Rich Repeat Containing (G Protein-Coupled Receptor 5; Leucine-Rich Repeat-Containing G Protein-Coupled Receptor 5; G-Protein Coupled Receptor HG38; G-Protein Coupled Receptor 49; G-Protein Coupled Receptor 67; GPR67; GPR49; Orphan G Protein-Coupled Receptor HG38; G Protein-Coupled Receptor 49; GPR49; HG38 and FEX. A protein or antibody of the invention that binds LGR5, binds human LGR5. The LGR5 binding protein or antibody of the invention may, due to sequence and tertiary structure similarity between human and other mammalian orthologs, also bind such an ortholog but not necessarily so. Database accession numbers for the human LGR5 protein and the gene encoding it are (NC_000012.12; NT_029419.13; NC_018923.2; NP_001264155.1; NP_001264156.1; NP_003658.1). The accession numbers are primarily given to provide a further method of identification of LGR5 as a target, the actual sequence of the LGR5 protein bound may vary, for instance because of a mutation in the encoding gene such as those occurring in some cancers or the like. The LGR5 antigen binding site binds LGR5 and a variety of variants thereof, such as those expressed by some LGR5 positive tumor cells.

ZNRF3 is Zinc And Ring Finger 3. Alternative names for the gene or protein are Zinc And Ring Finger 3; Zinc/RING Finger Protein 3; RING Finger Protein 203; KIAA1133; RNF203; Novel C3HC4 Type Zinc Finger (Ring Finger); E3 Ubiquitin-Protein Ligase ZNRF3; (CTA-292E10.6; EC 6.3.2; and BK747E2.3 3.

A protein or antibody of the invention that binds ZNRF3, binds human ZNRF3. The ZNRF3 binding protein or antibody of the invention may, due to sequence and tertiary structure similarity between human and other mammalian orthologs, also bind such an ortholog but not necessarily so. Database accession numbers for the human ZNRF3 protein and the gene encoding it are (NC_000022.11; NT_011520.13; NC_018933.2; NP_001193927.1; NP_115549.2). The accession numbers are primarily given to provide a further method of identification of ZNRF3 as a target, the actual sequence of the ZNRF3 protein bound may vary, for instance because of a mutation in the encoding gene such as those occurring in some cancers or the like. The ZNRF3 antigen binding site binds ZNRF3 and a variety of variants thereof, such as those expressed by some ZNRF3 positive tumor cells.

RNF43 is Ring Finger Protein 43. Alternative names for the gene or protein are Ring Finger Protein 43; RNF124; E3 Ubiquitin-Protein Ligase RNF43; RING Finger Protein 43; EC 6.3.2; URCC.

A protein or antibody of the invention that binds RNF43, binds human RNF43. The RNF43 binding protein or antibody of the invention may, due to sequence and tertiary structure similarity between human and other mammalian orthologs, also bind such an ortholog but not necessarily so. Database accession numbers for the human RNF43 protein and the gene encoding it are (NC_000017.11; NT_010783.16; NC_018928.2; NP_001292473.1; NP_001292474.1; NP_060233.3). The accession numbers are primarily given to provide a further method of identification of RNF43 as a target, the actual sequence of the RNF43 protein bound may vary, for instance because of a mutation in the encoding gene such as those occurring in some cancers or the like. The RNF43 antigen binding site binds RNF43 and a variety of variants thereof, such as those expressed by some RNF43 positive tumor cells.

Insulin-like growth factor 1 (IGF-1) receptor binds insulin-like growth factor with a high affinity. The receptor has tyrosine kinase activity. The insulin-like growth factor 1 receptor plays a critical role in transformation events. Cleavage of the precursor generates alpha and beta subunits. It is overexpressed in most malignant tissues where it functions as an anti-apoptotic agent by enhancing cell survival. The protein is known under a number of different names such as IGF-I Receptor; EC 2.7.10.1; Insulin-Like Growth Factor I Receptor; Soluble IGF1R; Variant 1; Soluble IGF1R Variant 2; CD221 Antigen; EC 2.7.10; CD221; IGF1R; JTK13; and IGFR. External Ids for IGF1R are HGNC: 5465; Entrez Gene: 3480; Ensembl: ENSG00000140443; OMIM: 147370 and UniprotKB: P08069.

The invention further provides a method for inhibiting growth of a cell that expresses a membrane associated member of the epidermal growth factor (EGF) receptor family and that expresses a membrane associated member of the WNT pathway in a system permissive for growth of the cell, the method comprising providing the system with a protein of the invention or a bispecific antibody of the invention. The cell is preferably an EGF-receptor ligand responsive cell that expresses a membrane associated member of the WNT pathway. The system is preferably a culture system. The method preferably comprises culturing said cell in said system.

In the context of the present invention cell is said to express a membrane associated member of the WNT pathway if the cell comprises detectable RNA that codes for the membrane associated member of the WNT pathway. Expression can often also be detected by incubating the cell with an antibody that binds to the membrane associated member of the WNT pathway. However, some members are not expressed high enough for such an antibody test or for some members, there are no specific antibodies available. In such cases mRNA detection is preferred.

Where herein accession numbers or alternative names of proteins/genes are given, they are primarily given to provide a further method of identification of the mentioned protein as a target, the actual sequence of the target protein bound by an antibody of the invention may vary, for instance because of a mutation and/or alternative splicing in the encoding gene such as those occurring in some cancers or the like.

The invention also provides a method for the treatment of an individual that has a cancer, the method comprising administering a protein of the invention or a bispecific antibody of the invention to the individual in need thereof. The individual is preferably an individual that has cancer. The cancer is preferably an adenocarcinoma. Preferred cancers are Colorectal cancer; Pancreatic cancer; Lung cancer; Breast cancer; Liver cancer; Prostate cancer; Ovarian cancer; Cervical cancer; Endometrial cancer; Head and Neck cancer; Melanoma; Testis cancer; Urothelial cancer; Renal cancer; Stomach cancer; or Carcinoid cancer. In a preferred embodiment the cancer is Colorectal cancer; Pancreatic cancer; Lung cancer; Breast cancer; Liver cancer; Prostate cancer; Ovarian cancer; Cervical cancer; Endometrial cancer; Head and Neck cancer; or Melanoma. In a particularly preferred embodiment the cancer is Colorectal cancer; Pancreatic cancer; Lung cancer; Breast cancer; or Liver cancer. In a particularly preferred embodiment the cancer is a gastrointestinal cancer. In a preferred embodiment the cancer is Colorectal cancer.

The cancer is preferably, but not limited to, a cancer that exhibits a growth response when provided with an EGF receptor family member ligand. The protein of the invention is preferably a protein that binds to a EGF receptor family member for which the cancer exhibits a growth response. In a preferred embodiment the cancer exhibits a growth response in vitro in response to EGF family members in the culture medium. The in vitro is preferably a culture as detailed for organoids in the experimental section. The cancer is preferably a cancer that expresses the membrane associated member of the WNT pathway that the protein of the invention binds to.

Further provided is a cell system comprising a protein of the invention or a bispecific antibody of the invention, and a cell that expresses a membrane associated member of the epidermal growth factor (EGF) receptor family and that expresses a membrane associated member of the WNT pathway. The cell is preferably an EGF-receptor ligand responsive cell that expresses a membrane associated member of the WNT pathway.

The system or cell system as described herein is preferably an in vitro culture system. The system can be used to detect growth responses of the cell. In a preferred embodiment the EGF-receptor ligand is a ligand for a preferred member of the EGF receptor family as defined elsewhere herein. In a preferred embodiment the membrane associated member of the WNT pathway is a preferred membrane associated member of the WNT pathway as defined elsewhere herein.

A cancer or a cell that is EGF-receptor ligand responsive exhibits a growth (proliferation) response to an EGF receptor ligand. A preferred method for determining whether a cell or a cancer is EGF-receptor ligand responsive is to determine growth factor responsiveness of the cell in an organoid culture assay as described in the examples. One method is to seed the cell or cells of the cancer in the organoid cell system in the presence or absence of growth factors such as (EGF (5 ng/ml), or NRG (5 ng/ml)) and then culture for 5 days. The number of viable cells can subsequently be determined using the Cell Titer Glo cell viability assay (Promega, cat. nr. G7571). The luminescence readout using growth factor-stimulated cells can then be compared to that obtained using non-stimulated cells (absence of the growth factor(s).

The invention further provides a method for inhibiting growth of a cell that expresses a membrane associated member of the EGF receptor family and that expresses a membrane associated member of the WNT pathway in a system permissive for growth of the cell, the method comprising providing the system with a protein of the invention or a bispecific antibody of the invention. The cell is preferably an EGF-receptor ligand responsive cell that expresses a membrane associated member of the WNT pathway. The inhibition is preferably a decrease of at least 10% in cell number or a derivative measure for the number of cells such as tumor size, when compared to the number of cells resulting under otherwise similar conditions but for the presence of the protein or the bispecific antibody of the invention. The inhibition is preferably a decrease of at least 20%, 30%, 40%, 50%, 60%, 70%, 80% or 90% in the number of cells. The inhibition may also be a decrease of at least 10% in other parameters associated with tumour malignancy or dysplasia, such as the number of lumens per organoid, when compared to the number of lumens resulting under otherwise similar conditions but for the presence of the protein or the bispecific antibody of the invention. The inhibition is preferably a decrease of at least 20%, 30%, 40%, 50%, 60%, 70%, 80% or 90% in the number of lumens per organoid.

For the avoidance of doubt the reference to the growth of a cell as used herein refers to a change in the number of cells. Inhibition of growth refers to a reduction in the number of cells that would otherwise have been obtained. Increase in growth refers to an increase in the number of cells that would otherwise have been obtained. The growth of a cell typically refers to the proliferation of the cell.

The binding of the protein or bispecific antibody of the invention to a cell comprising said membrane associated member of the epidermal growth factor (EGF) receptor family or cMET; and/or said membrane associated member of a WNT signaling pathway on the membrane reduces the growth/proliferation of said cell in the presence of a growth factor for said epidermal growth factor (EGF) receptor family or cMET and/or Rspondin. The reduction is compared to the growth/proliferation of the same cell under otherwise identical conditions in the absence of the protein or bispecific antibody of the invention.

The protein or bispecific antibody of the invention, or functional part, derivative and/or analogue thereof is preferably selected from a protein or bispecific antibody of the invention, or functional part, derivative and/or analogue thereof that binds ErbB-1 and LGR4; ErbB-1 and LGR5; ErbB-1 and LGR6; ErbB-1 and ZNRF3; ErbB-1 and RNF43; ErbB-2 and LGR4; ErbB-2 and LGR5; ErbB-2 and LGR6; ErbB-2 and ZNRF3; ErbB-2 and RNF43; ErbB-3 and LGR4; ErbB-3 and LGR5; ErbB-3 and LGR6; ErbB-3 and ZNRF3; ErbB-3 and RNF43; ErbB-4 and LGR4; ErbB-4 and LGR5; ErbB-4 and LGR6; ErbB-4 and ZNRF3; and ErbB-4 and RNF43.

In a preferred embodiment it is selected from ErbB-1 and LGR4; ErbB-1 and LGR5; ErbB-1 and ZNRF3; ErbB-1 and RNF43; ErbB-3 and LGR4; ErbB-3 and LGR5; ErbB-3 and ZNRF3; ErbB-3 and RNF43; ErbB-4 and LGR4; ErbB-4 and LGR5; ErbB-4 and ZNRF3; and ErbB-4 and RNF43. In a preferred embodiment it is selected from ErbB-1 and LGR4; ErbB-1 and LGR5; ErbB-1 and ZNRF3; ErbB-1 and RNF43; ErbB-3 and LGR4; ErbB-3 and LGR5; ErbB-3 and ZNRF3; ErbB-3 and RNF43. Preferably it is selected from ErbB-1 and LGR5; ErbB-1 and ZNRF3; ErbB-1 and RNF43; ErbB-3 and LGR5; ErbB-3 and ZNRF3; and ErbB-3 and RNF43. In a particularly preferred embodiment the protein or bispecific antibody of the invention, or functional part, derivative and/or analogue thereof is selected from a protein or bispecific antibody of the invention, or functional part, derivative and/or analogue thereof that binds ErbB-1 and LGR5; and ErbB-3 and LGR5.

The antibody or bispecific antibody preferably comprises two variable domains wherein one variable domain binds an extracellular part of one protein and the other variable domain binds an extracellular part of the other protein.

In one embodiment the invention provides a bispecific antibody comprising a variable domain that binds ErbB-1, wherein a heavy chain variable region of said variable domain comprises at least the CDR3 sequence of an ErbB-1 specific heavy chain variable region selected from the group consisting of MF3370; MF3755; MF4280 or MF4289 as depicted in FIG. 1 or wherein a heavy chain variable region of said variable domain comprises a heavy chain CDR3 sequence that differs in at most three, preferably in at most two, preferably in no more than one amino acid from a CDR3 sequence of a VH selected from the group consisting of MF3370; MF3755; MF4280 or MF4289 as depicted in FIG. 1. Said variable domain preferably comprises a heavy chain variable region comprising at least the CDR3 sequence of MF3370; MF3755; MF4280 or MF4289 as depicted in FIG. 1.

Said variable domain preferably comprises a heavy chain variable region comprising at least the CDR1, CDR2 and CDR3 sequences of an ErbB-1 specific heavy chain variable region selected from the group consisting of MF3370; MF3755; MF4280 or MF4289 as depicted in FIG. 1, or heavy chain CDR1, CDR2 and CDR3 sequences that differ in at most three, preferably in at most two, preferably in at most one amino acid from the CDR1, CDR2 and CDR3 sequences of ErbB-1 specific heavy chain variable region selected from the group consisting of MF3370; MF3755; MF4280 or MF4289 as depicted in FIG. 1. Said variable domain preferably comprises a heavy chain variable region comprising at least the CDR1, CDR2 and CDR3 sequences of MF3370; MF3755; MF4280 or MF4289 as depicted in FIG. 1. A preferred heavy chain variable region is MF3755. Another preferred heavy chain variable region is MF4280.

It has been shown that the antibodies comprising one or more variable domains with a heavy chain variable region MF3755 have a better effectivity when used to inhibit growth of an EGFR ligand responsive cancer or cell. In the context of bispecific antibodies, an arm of the antibody comprising a variable domain with a heavy chain variable region MF3755 combines better with a variety of other arms comprising variable domains that bind extra-cellular parts of other cell surface proteins. Antibodies comprising a variable domain with heavy chain variable region MF4280 also work well with a variable domain that binds LGR4, LGR5, LGR6, ZNRF3 or RNF43.

In one embodiment the invention provides a bispecific antibody comprising a variable domain that binds ErbB-3, wherein a heavy chain variable region of said variable domain comprises at least the CDR3 sequence of an ErbB-3 specific heavy chain variable region selected from the group consisting of MF3125; MF3176; MF3178; or MF4863 as depicted in FIG. 1 or wherein a heavy chain variable region of said variable domain comprises a heavy chain CDR3 sequence that differs in at most three, preferably in at most two, preferably in no more than one amino acid from a CDR3 sequence of a VH selected from the group consisting of MF3125; MF3176; MF3178; or MF4863 as depicted in FIG. 1. Said variable domain preferably comprises a heavy chain variable region comprising at least the CDR3 sequence of MF3125; MF3176; MF3178; or MF4863 as depicted in FIG. 1.

Said variable domain preferably comprises a heavy chain variable region comprising at least the CDR1, CDR2 and CDR3 sequences of an ErbB-3 specific heavy chain variable region selected from the group consisting of MF3125; MF3176; MF3178; or MF4863 as depicted in FIG. 1, or heavy chain CDR1, CDR2 and CDR3 sequences that differ in at most three, preferably in at most two, preferably in at most one amino acid from the CDR1, CDR2 and CDR3 sequences of ErbB-3 specific heavy chain variable region selected from the group consisting of MF3125; MF3176; MF3178; or MF4863 as depicted in FIG. 1. Variable domain preferably comprises a heavy chain variable region comprising at least the CDR1. CDR2 and CDR3 sequences of MF3125; MF3176; MF3178; or MF4863 as depicted in FIG. 1. A preferred heavy chain variable region is MF3178.

In one embodiment the invention provides a bispecific antibody comprising a variable domain that binds LGR4, wherein a heavy chain variable region of said variable domain comprises at least the CDR3 sequence of an LGR4 specific heavy chain variable region selected from the group consisting of MF5777; or MF5781 as depicted in FIG. 1 or wherein a heavy chain variable region of said variable domain comprises a heavy chain CDR3 sequence that differs in at most three, preferably in at most two, preferably in no more than one amino acid from a CDR3 sequence of a VH selected from the group consisting of MF5777; or MF5781 as depicted in FIG. 1. Said variable domain preferably comprises a heavy chain variable region comprising at least the CDR3 sequence of MF5777; or MF5781 as depicted in FIG. 1.

Said variable domain preferably comprises a heavy chain variable region comprising at least the CDR1, CDR2 and CDR3 sequences of an LGR4 specific heavy chain variable region selected from the group consisting of MF5777; or MF5781 as depicted in FIG. 1, or heavy chain CDR1, CDR2 and CDR3 sequences that differ in at most three, preferably in at most two, preferably in at most one amino acid from the CDR1, CDR2 and CDR3 sequences of LGR4 specific heavy chain variable region selected from the group consisting of MF5777; or MF5781 as depicted in FIG. 1. Said variable domain preferably comprises a heavy chain variable region comprising at least the CDR1, CDR2 and CDR3 sequences of MF5777; or MF5781 as depicted in FIG. 1. A preferred heavy chain variable region is MF5781.

In one embodiment the invention provides a bispecific antibody comprising a variable domain that binds LGR5, wherein a heavy chain variable region of said bispecific antibody comprises at least the CDR3 sequence of an LGR5 specific heavy chain variable region selected from the group consisting of MF5790; MF5803; MF5805; MF5808; MF5809; MF5814; MF5816; MF5817; or MF5818 as depicted in FIG. 1 or wherein a heavy chain variable region of variable domain comprises a heavy chain CDR3 sequence that differs in at most three, preferably in at most two, preferably in no more than one amino acid from a CDR3 sequence of a VH selected from the group consisting of MF5790; MF5803; MF5805; MF5808; MF5809; MF5814; MF5816; MF5817; or MF5818 as depicted in FIG. 1. Said variable domain preferably comprises a heavy chain variable region comprising at least the CDR3 sequence of MF5790; MF5803; MF 5805; MF5808; MF5809; MF5814; MF5816; MF5817; or MF5818 as depicted in FIG. 1.

Said variable domain preferably comprises a heavy chain variable region comprising at least the CDR1, CDR2 and CDR3 sequences of an LGR5 specific heavy chain variable region selected from the group consisting of MF5790; MF5803; MF5805; MF5808; MF5809; MF5814; MF5816; MF5817; or MF5818 as depicted in FIG. 1, or heavy chain CDR, CDR2 and CDR3 sequences that differ in at most three, preferably in at most two, preferably in at most one amino acid from the CDR1, CDR2 and CDR3 sequences of LGR5 specific heavy chain variable region selected from the group consisting of MF5790; MF5803; MF5805; N5808; MF5809; MF5814; MF5816; MF5817; or MF5818 as depicted in FIG. 1. Said variable domain preferably comprises a heavy chain variable region comprising at least the CDR1, CDR2 and CDR3 sequences of MF5790; MF5803; MF5805; MF5808; MF5809; MF5814; MF5816; MF5817; or MF5818 as depicted in FIG. 1. Preferred heavy chain variable regions are MF5790; MF5803; MF5814; MF5816; MF5817; or MF5818. Particularly preferred heavy chain variable regions are MF5790; MF5814; MF5816; and MF5818; preferably MF5814, MF5818 and MF5816, heavy chain variable region MF5816 is particularly preferred. Another preferred heavy chain variable region is MF5818.

In one embodiment the invention provides a bispecific antibody comprising a variable domain that binds RNF43, wherein a heavy chain variable region of said variable domain comprises at least the CDR3 sequence of an RNF43 specific heavy chain variable region selected from the group consisting of MF5832; MF5836; or MF5839 as depicted in FIG. 1 or wherein a heavy chain variable region of said variable domain comprises a heavy chain variable region comprising a heavy chain CDR3 sequence that differs in at most three, preferably in at most two, preferably in no more than one amino acid from a CDR3 sequence of a VH selected from the group consisting of MF5832; MF5836; or MF5839 as depicted in FIG. 1. Said variable domain preferably comprises a heavy chain variable region comprising at least the CDR3 sequence of MF5832; MF5836; or MF5839 as depicted in FIG. 1.

Said variable domain preferably comprises a heavy chain variable region comprising at least the CDR1, CDR2 and CDR3 sequences of an RNF43 specific heavy chain variable region selected from the group consisting of MF5832; MF5836; or MF5839 as depicted in FIG. 1, or heavy chain CDR1, CDR2 and CDR3 sequences that differ in at most three, preferably in at most two, preferably in at most one amino acid from the CDR1, CDR2 and CDR3 sequences of RNF43 specific heavy chain variable region selected from the group consisting of MF5832; MF5836; or MF5839 as depicted in FIG. 1. Said variable domain preferably comprises a heavy chain variable region comprising at least the CDR1, CDR2 and CDR3 sequences of MF5832; MF5836; or MF5839 as depicted in FIG. 1. Preferred heavy chains are MF5832; or MF5836. A preferred heavy chain variable region is MF5836.

In one embodiment the invention provides a bispecific antibody comprising a variable domain that binds ZNRF3, wherein a heavy chain variable region of said variable domain comprises at least the CDR3 sequence of an ZNRF3 specific heavy chain variable region selected from the group consisting of MF5850; MF5853; MF5855; MF5862; MF5882; MF5884; MF5887; or MF5888 as depicted in FIG. 1 or wherein a heavy chain variable region of said variable domain comprises a heavy chain CDR3 sequence that differs in at most three, preferably in at most two, preferably in no more than one amino acid from a CDR3 sequence of a VH selected from the group consisting of MF5850; MF5853; MF5855; MF5862; MF5882; MF5884; MF5887; or MF5888 as depicted in FIG. 1. Said variable domain preferably comprises a heavy chain variable region comprising at least the CDR3 sequence of MF5850; MF5853; MF5855; MF5862; MF5882; MF5884; MF5887; or MF5888 as depicted in FIG. 1.

Said variable domain preferably comprises a heavy chain variable region comprising at least the CDR1, CDR2 and CDR3 sequences of an ZNRF3 specific heavy chain variable region selected from the group consisting of MF5850; MF5853; MF5855; MF5862; MF5882; MF5884; MF5887; or MF5888 as depicted in FIG. 1, or heavy chain CDR1, CDR2 and CDR3 sequences that differ in at most three, preferably in at most two, preferably in at most one amino acid from the CDR1, CDR2 and CDR3 sequences of ZNRF3 specific heavy chain variable region selected from the group consisting of MF5850; MF5853; MF5855; MF5862; MF5882; MF5884; MF5887; or MF5888 as depicted in FIG. 1. Said variable domain preferably comprises a heavy chain variable region comprising at least the CDR1, CDR2 and CDR3 sequences of MF5850; MF5853; MF5855; MF5862; MF5882; MF5884; MF5887; or MF5888 as depicted in FIG. 1. Preferred heavy chain variable regions are MF5850; MF5853; MF5855; MF5884; or MF5888. Preferred heavy chain variable regions are MF5888 and MF5850, preferably MF5850.

CDR sequences are for instance varied for optimization purposes, preferably in order to improve binding strength or the stability of the antibody. Optimization is for instance performed by mutagenesis procedures where after the stability and/or binding affinity of the resulting antibodies are preferably tested and an improved EGFR or ErbB 3-specific CDR sequence is preferably selected. A skilled person is well capable of generating antibody variants comprising at least one altered CDR sequence according to the invention. For instance, conservative amino acid substitution may be applied. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine.

The bispecific antibody of the invention that comprises a variable domain that binds EGFR, preferably comprises the VH chain of said variable domain comprises the amino acid sequence of VH chain MF3370; MF3755; MF4280 or MF4289 as depicted in FIG. 1; or the amino acid sequence of VH chain MF3370; MF3755; MF4280 or MF4289 depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 1. The bispecific antibody of the invention that comprises a variable domain that binds EGFR, preferably comprises the VH chain of said variable domain and preferably comprises the amino acid sequence of VH chain MF3755. In a preferred embodiment this bispecific antibody comprises a variable domain that binds a membrane associated member of the WNT pathway as defined elsewhere herein. In a preferred embodiment the membrane associated member of the WNT pathway is LGR4, LGR5, RNF43 or ZNRF3.

The bispecific antibody of the invention that comprises a variable domain that binds HER3, preferably comprises the VH chain of said variable domain comprises the amino acid sequence of VH chain MF3125; MF3176; MF3178; or MF4863 as depicted in FIG. 1; or the amino acid sequence of VH chain MF3125; MF3176; MF3178; or MF4863 depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 1. A preferred heavy chain is MF3178. In a preferred embodiment this bispecific antibody comprises a variable domain that binds a membrane associated member of the WNT pathway as defined elsewhere herein. In a preferred embodiment the membrane associated member of the WNT pathway is LGR4, LGR5, RNF43 or ZNRF3.

The bispecific antibody of the invention that comprises a variable domain that binds LGR4, preferably comprises the VH chain of said variable domain comprises the amino acid sequence of VH chain MF5777; or MF5781 as depicted in FIG. 1; or the amino acid sequence of VH chain MF5777; or MF5781 depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 1. In a preferred embodiment this bispecific antibody comprises a variable domain that binds an extracellular part of membrane associated member of the EGFR family as defined elsewhere herein. In a preferred embodiment the membrane associated member of the EGFR family is EGFR or HER3, preferably EGFR. A preferred heavy chain is MF3755.

The bispecific antibody of the invention that comprises a variable domain that binds LGR5, preferably comprises the VH chain of said variable domain comprises the amino acid sequence of VH chain MF5790; MF5803; MF5805; MF5808; MF5809; MF5814; MF5816; MF5817; or MF5818 as depicted in FIG. 1; or the amino acid sequence of VH chain MF5790; MF5803; MF5805; MF5808; MF5809; MF5814; MF5816; MF5817 or MF5818 depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 1. In a preferred embodiment this bispecific antibody comprises a variable domain that binds an extracellular part of membrane associated member of the EGFR family as defined elsewhere herein. In a preferred embodiment the membrane associated member of the EGFR family is EGFR or HER3, preferably EGFR. A preferred heavy chain is MF3755.

The bispecific antibody of the invention that comprises a variable domain that binds RNF43, preferably comprises the VH chain of said variable domain comprises the amino acid sequence of VH chain MF5832; MF5836; or MF5839 as depicted in FIG. 1; or the amino acid sequence of VH chain MF5832; MF5836; or MF5839 depicted in FIG. 1 having at most 15, preferably 1, 2, 3, 4, 5, 6, 7, 8, 9 or and preferably having 1, 2, 3, 4 or 5 amino acid insertions, deletions, substitutions or a combination thereof with respect to the VH chain sequence of FIG. 1. In a preferred embodiment the bispecific antibody comprises a variable domain that binds an extracellular part of membrane associated member of the EGFR family as defined elsewhere herein. In a preferred embodiment the membrane associated member of the EGFR family is EGFR or HER3, preferably EGFR. A preferred heavy chain is MF3755.

The bispecific antibody of the invention that comprises a variable domain that binds ZNRF3, preferably comprises the VH chain of said variable domain comprises the amino acid sequence of VH chain MF5850; MF5853; MF5855; MF5862; MF5882; MF5884; MF5887; or MF5888 as depicted in FIG. 1; or the amino acid sequence of VH chain MF5850; MF5853; MF5855; MF5862; MF5882; MF5884; MF5887; or MF5888 depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 1. In a preferred embodiment the bispecific antibody comprises a variable domain that binds an extracellular part of membrane associated member of the EGFR family as defined elsewhere herein. In a preferred embodiment the membrane associated member of the EGFR family is EGFR or HER3, Preferably EGFR. A preferred heavy chain is MF3755.

Preferably, the mentioned amino acid insertions, deletions and substitutions in a VH or VL as specified herein are not present in the CDR3 region. The mentioned amino acid insertions, deletions and substitutions are also preferably not present in the CDR1 and CDR2 regions. The mentioned amino acid insertions, deletions and substitutions are also preferably not present in the FR4 region.

The invention also provides an antibody comprising a variable domain that binds EGFR and a variable domain that binds LGR4 wherein the VH chain of the variable domain that binds EGFR comprises
  the amino acid sequence of VH chain MF3755 as depicted in FIG. 1; or
  the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and
wherein the VH chain of the variable domain that binds LGR4 comprises
  the amino acid sequence of VH chain MF5777 as depicted in FIG. 1; or
  the amino acid sequence of VH chain MF5777 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds LGR4 wherein the VH chain of the variable domain that binds EGFR comprises
  the amino acid sequence of VH chain MF3755 as depicted in FIG. 1; or
  the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and
wherein the VH chain of the variable domain that binds LGR4 comprises
  the amino acid sequence of VH chain MF5781 as depicted in FIG. 1; or
  the amino acid sequence of VH chain MF5781 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds LGR5 wherein the VH chain of the variable domain that binds EGFR comprises the amino acid sequence of Vi chain MF3755 as depicted in FIG. 1; or the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds LGR5 comprises the amino acid sequence of VH chain MF5790 as depicted in FIG. 1; or the amino acid sequence of VH chain MF5790 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds LGR5 wherein the VH chain of the variable domain that binds EGFR comprises the amino acid sequence of VH chain MF3755 as depicted in FIG. 1; or the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds LGR5 comprises the amino acid sequence of VH chain MF5803 as depicted in FIG. 1; or the amino acid sequence of VH chain MF5803 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds LGR5 wherein the VH chain of the variable domain that binds EGFR comprises the amino acid sequence of VH chain MF3755 as depicted in FIG. 1; or the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds LGR5 comprises the amino acid sequence of VH chain MF5814 as depicted in FIG. 1 or the amino acid sequence of VH chain MF5814 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds LGR5 wherein the VH chain of the variable domain that binds EGFR comprises the amino acid sequence of VH chain MF3755 as depicted in FIG. 1; or the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds LGR5 comprises the amino acid sequence of VH chain MF5816 as depicted in FIG. 1; or the amino acid sequence of VH chain MF5816 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds LGR5 wherein the VH chain of the variable domain that binds EGFR comprises the amino acid sequence of VH chain MF3755 as depicted in FIG. 1; or the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds LGR5 comprises the amino acid sequence of VH chain MF5817 as depicted in FIG. 1; or the amino acid sequence of VH chain MF5817 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds LGR5 wherein the VH chain of the variable domain that binds EGFR comprises the amino acid sequence of VH chain MF3755 as depicted in FIG. 1 or the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds LGR5 comprises the amino acid sequence of VH chain MF5818 as depicted in FIG. 1; or the amino acid sequence of VH chain MF5818 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds RNF43 wherein the VH chain of the variable domain that binds EGFR comprises the amino acid sequence of VH chain MF3755 as depicted in FIG. 1; or the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds RNF43 comprises the amino acid sequence of VH chain MF5832 as depicted in FIG. 1; or the amino acid sequence of VH chain MF5832 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds RNF43 wherein the VH chain of the variable domain that binds EGFR comprises the amino acid sequence of VH chain MF3755 as depicted in FIG. 1 or the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds RNF43 comprises the amino acid sequence of VH chain MF5836 as depicted in FIG. 1; or the amino acid sequence of VH chain MF5836 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds ZNRF3 wherein the VH chain of the variable domain that binds EGFR comprises the amino acid sequence of VH chain MF3755 as depicted in FIG. 1 or the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ZNRF3 comprises the amino acid sequence of VH chain MF5850 as depicted in FIG. 1; or the amino acid sequence of VH chain MF5850 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds ZNRF3 wherein the VH chain of the variable domain that binds EGFR comprises the amino acid sequence of VH chain MF3755 as depicted in FIG. 1; or the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ZNRF3 comprises the amino acid sequence of VH chain MF5853 as depicted in FIG. 1; or the amino acid sequence of VH chain MF5853 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds ZNRF3 wherein the VH chain of the variable domain that binds EGFR comprises the amino acid sequence of VH chain MF3755 as depicted in FIG. 1; or the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ZNRF3 comprises the amino acid sequence of VH chain MF5855 as depicted in FIG. 1; or the amino acid sequence of VH chain MF5855 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds ZNRF3 wherein the VH chain of the variable domain that binds EGFR comprises the amino acid sequence of VH chain MF3755 as depicted in FIG. 1; or the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ZNRF3 comprises the amino acid sequence of VH chain MF5884 as depicted in FIG. 1; or the amino acid sequence of VH chain MF5884 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds EGFR and a variable domain that binds ZNRF3 wherein the VH chain of the variable domain that binds EGFR comprises the amino acid sequence of VH chain MF3755 as depicted in FIG. 1; or the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ZNRF3 comprises the amino acid sequence of VH chain MF5888 as depicted in FIG. 1; or the amino acid sequence of VH chain MF5888 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds LGR4 wherein the VH chain of the variable domain that binds HER3 comprises the amino acid sequence of VH chain MF3178 as depicted in FIG. 1; or the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds LGR4 comprises the amino acid sequence of VH chain MF5777 as depicted in FIG. 1; or the amino acid sequence of VH chain MF5777 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds LGR4 wherein the VH chain of the variable domain that binds HER3 comprises the amino acid sequence of VH chain MF3178 as depicted in FIG. 1; or the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds LGR4 comprises the amino acid sequence of VH chain MF5781 as depicted in FIG. 1; or the amino acid sequence of VH chain MF5781 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds LGR5 wherein the VH chain of the variable domain that binds HER3 comprises the amino acid sequence of VH chain MF3178 as depicted in FIG. 1; or the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds LGR5 comprises the amino acid sequence of VH chain MF5790 as depicted in FIG. 1; or the amino acid sequence of VH chain MF5790 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds LGR5 wherein the VH chain of the variable domain that binds HER3 comprises the amino acid sequence of VH chain MF3178 as depicted in FIG. 1; or the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds LGR5 comprises the amino acid sequence of VH chain MF5803 as depicted in FIG. 1; or the amino acid sequence of VH chain MF5803 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds LGR5 wherein the VH chain of the variable domain that binds HER3 comprises the amino acid sequence of VH chain MF3178 as depicted in FIG. 1; or the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds LGR5 comprises the amino acid sequence of VH chain MF5814 as depicted in FIG. 1; or the amino acid sequence of VH chain MF5814 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds LGR5 wherein the VH chain of the variable domain that binds HER3 comprises the amino acid sequence of VH chain MF3178 as depicted in FIG. 1; or the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds LGR5 comprises the amino acid sequence of VH chain MF5816 as depicted in FIG. 1; or the amino acid sequence of VH chain MF5816 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds LGR5 wherein the VH chain of the variable domain that binds HER3 comprises the amino acid sequence of VH chain MF3178 as depicted in FIG. 1; or the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds LGR5 comprises the amino acid sequence of VH chain MF5817 as depicted in FIG. 1; or the amino acid sequence of VH chain MF5817 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds LGR5 wherein the VH chain of the variable domain that binds HER3 comprises
the amino acid sequence of VH chain MF3178 as depicted in FIG. 1; or
the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and
wherein the VH chain of the variable domain that binds LGR5 comprises
the amino acid sequence of VH chain MF5818 as depicted in FIG. 1; or
the amino acid sequence of VH chain MF5818 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds RNF43 wherein the VH chain of the variable domain that binds HER3 comprises
the amino acid sequence of VH chain MF3178 as depicted in FIG. 1; or
the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and
wherein the VH chain of the variable domain that binds RNF43 comprises
the amino acid sequence of VH chain MF5836 as depicted in FIG. 1; or
the amino acid sequence of VH chain MF5836 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds ZNRF3 wherein the VH chain of the variable domain that binds HER3 comprises
the amino acid sequence of VH chain MF3178 as depicted in FIG. 1; or
the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and
wherein the VH chain of the variable domain that binds ZNRF3 comprises
the amino acid sequence of VH chain MF5850 as depicted in FIG. 1; or
the amino acid sequence of VH chain MF5850 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds ZNRF3 wherein the VH chain of the variable domain that binds HER3 comprises
the amino acid sequence of VH chain MF3178 as depicted in FIG. 1; or
the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and
wherein the VH chain of the variable domain that binds ZNRF3 comprises
the amino acid sequence of VH chain MF5853 as depicted in FIG. 1; or
the amino acid sequence of VH chain MF5853 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds ZNRF3 wherein the VH chain of the variable domain that binds HER3 comprises
the amino acid sequence of VH chain MF3178 as depicted in FIG. 1 or
the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and
wherein the VH chain of the variable domain that binds ZNRF3 comprises
the amino acid sequence of VH chain MF5855 as depicted in FIG. 1; or
the amino acid sequence of VH chain MF5855 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds ZNRF3 wherein the VH chain of the variable domain that binds HER3 comprises
the amino acid sequence of VH chain MF3178 as depicted in FIG. 1; or
the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and
wherein the VH chain of the variable domain that binds ZNRF3 comprises
the amino acid sequence of VH chain MF5884 as depicted in FIG. 1; or
the amino acid sequence of VH chain MF5884 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides an antibody comprising a variable domain that binds HER3 and a variable domain that binds ZNRF3 wherein the VH chain of the variable domain that binds HER3 comprises
the amino acid sequence of VH chain MF3178 as depicted in FIG. 1; or
the amino acid sequence of VH chain MF3178 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ZNRF3 comprises the amino acid sequence of VH chain MF5888 as depicted in FIG. 1; or the amino acid sequence of VH chain MF5888 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

A protein or bispecific antibody of the present invention is preferably used in humans. To this end an antibody of the invention is preferably a human or humanized antibody. Tolerance of a human to a polypeptide is governed by many different aspects. Immunity, be it T-cell mediated, B-cell mediated or other is one of the variables that are encompassed in tolerance of the human for a polypeptide. The constant region of a bispecific antibody of the present invention is preferably a human constant region (FIG. 4). The constant region may contain one or more, preferably not more than 10, preferably not more than 5 amino-acid differences with the constant region of a naturally occurring human antibody. It is preferred that the constant part is entirely derived from a naturally occurring human antibody. Various antibodies produced herein are derived from common light chain mice immunized with the respective target as described in WO2009/157771. Various antibodies produced herein are derived from a human antibody variable domain library. As such these variable domains are human. The unique CDR regions may be derived from humans, be synthetic or derived from another organism. The variable region is considered a human variable region when it has an amino acid sequence that is identical to an amino acid sequence of the variable region of a naturally occurring human antibody, but for the CDR regions. The variable region of a VH of antibody that binds a EGFR-family member or membrane associated member of the WNT pathway, or a light chain in an antibody of the invention may contain one or more, preferably not more than 10, preferably not more than 5 amino-acid differences with the variable region of a naturally occurring human antibody, not counting possible differences in the amino acid sequence of the CDR regions. Such mutations also occur in nature in the context of somatic hypermutation.

Antibodies may be derived from various animal species, at least with regard to the heavy chain variable region. It is common practice to humanize such e.g. murine heavy chain variable regions. There are various ways in which this can be achieved among which there are CDR-grafting into a human heavy chain variable region with a 3D-structure that matches the 3-D structure of the murine heavy chain variable region; de-immunization of the murine heavy chain variable region, preferably done by removing known or suspected T- or B-cell epitopes from the murine heavy chain variable region. The removal is typically by substituting one or more of the amino acids in the epitope for another (typically conservative) amino acid, such that the sequence of the epitope is modified such that it is no longer a T- or B-cell epitope.

De-immunized murine heavy chain variable regions are less immunogenic in humans than the original murine heavy chain variable region. Preferably a variable region or domain of the invention is further humanized, such as for instance veneered. By using veneering techniques, exterior residues which are readily encountered by the immune system are selectively replaced with human residues to provide a hybrid molecule that comprises either a weakly immunogenic or substantially non-immunogenic veneered surface. An animal as used in the invention is preferably a mammal, more preferably a primate, most preferably a human.

A protein or bispecific antibody according to the invention preferably comprises a constant region of a human antibody. According to differences in their heavy chain constant domains, antibodies are grouped into five classes, or isotypes: IgG, IgA, IgM, IgD, and IgE. These classes or isotypes comprise at least one of said heavy chains that is named with a corresponding Greek letter. In a preferred embodiment the invention provides an antibody according to the invention wherein said constant region is selected from the group of IgC, IgA, IgM, IgD, and IgE constant regions, more preferably said constant region comprises an IgG constant region, more preferably an IgG1 constant region (FIG. 4), preferably a mutated IgG1 constant region. Some variation in the constant region of IgG1 occurs in nature and/or is allowed without changing the immunological properties of the resulting antibody. Typically between about 1-10 amino acid insertions, deletions, substitutions or a combination thereof are allowed in the constant region.

Rational methods have evolved toward minimizing the content of non-human residues in the human context. Various methods are available to successfully graft the antigen-binding property of an antibody onto another antibody. The binding properties of antibodies rest predominantly in the exact sequence of the CDR3 region, often supported by the sequence of the CDR1 and CDR2 regions in the variable domain combined with the appropriate structure of the variable domain as a whole. Various methods are presently available to graft CDR regions onto a suitable variable domain of another antibody. Some of these methods are reviewed in J. C. Almagrol and J. Fransson (2008) Frontiers in Bioscience 13, 1619-1633, which is included by reference herein.

The mentioned at most 15, preferably 1, 2, 3, 4, 5, 6, 7, 8, 9 or 10 and preferably 1, 2, 3, 4 or 5 amino acid substitutions are preferably conservative amino acid substitutions, the insertions, deletions, substitutions or a combination thereof are preferably not in the CDR3 region of the VH chain, preferably not in the CDR1, CDR2 or CDR3 region of the VH chain and preferably not in the FR4 region.

The light chain of a variable domain comprising a variable heavy chain sequence as depicted in FIG. 3, is preferably a germline light chain of or based on O12, preferably the rearranged germline human kappa light chain IgVκ1-39*01/IGJκ1*01 or a fragment or a functional derivative thereof (nomenclature according to the IMGT database worldwide web at imgt.org). The terms rearranged germline human kappa light chain IgVκ1-39*01/IGJκ1*01, IGKV1-39/IGKJ1, huVκ1-39 light chain or in short huVκ1-39 are used. The light chain can have 1, 2, 3, 4 or 5 amino acid insertions, deletions, substitutions or combination thereof. The mentioned 1, 2, 3, 4 or 5 amino acid substitutions are preferably conservative amino acid substitutions, the insertions, deletions, substitutions or combination thereof are preferably not in the CDR3 region of the VL chain, preferably not in the CDR1, CDR2 or CDR3 region or FR4 region of the VL chain.

Various methods are available to produce bispecific antibodies. One method involves the expression of two different heavy chains and two different light chains in a cell and collecting antibody that is produced by the cell. Antibody produced in this way will typically contain a collection of antibodies with different combinations of heavy and light chains, some of which are the desired bispecific antibody. The bispecific antibody can subsequently be purified from the collection. The ratio of bispecific to other antibodies that are produced by the cell can be increased in various ways. In a preferred embodiment of the invention, the ratio is increased by expressing not two different light chains but two essentially identical light chains in the cell. This concept is in the art also referred to as the "common light chain" method. When the essentially identical light chains work together with the two different heavy chains allowing the formation of variable domains with different antigen-binding sites and concomitant different binding properties, the ratio of bispecific antibody to other antibody that is produced by the cell is significantly improved over the expression of two different light chains. The ratio of bispecific antibody that is produced by the cell can be further improved by stimulating the pairing of two different heavy chains with each other over the pairing of two identical heavy chains. The art describes various ways in which such heterodimerization of heavy chains can be achieved. One way is to generate 'knob into hole' bispecific antibodies. See US Patent Application 200:30078:385 (Arathoon et al.—Genentech). Another method is by using charge engineering as described in Gunasekaran (JBC 2010, vol 285, pp 19637-19646). Another and preferred method is described in U.S. provisional application 61/635,935, which has been followed up by U.S. regular application Ser. No. 13/866,747 and PCT application No. PCT/NL2013/050294 (WO 2013/157954 A1), which are incorporated herein by reference. Methods and means are disclosed for producing bispecific antibodies (from a single cell), whereby means are provided that favor the formation of bispecific antibodies over the formation of monospecific antibodies. These methods can also be favorably employed in the present invention. Thus the invention provides a method for producing a bispecific antibody according to the invention (from a single cell), wherein said bispecific antibody comprises two CH3 domains that are capable of forming an interface, said method comprising providing in said cell a) a first nucleic acid molecule encoding a 1st CH3 domain comprising heavy chain, b) a second nucleic acid molecule encoding a 2nd CH3 domain comprising heavy chain, wherein said nucleic acid molecules are provided with means for preferential pairing of said 1st and 2nd CH3 domain comprising heavy chains, said method further comprising the step of culturing said host cell and allowing for expression of said two nucleic acid molecules and harvesting said bispecific antibody from the culture. Said first and second nucleic acid molecules may be part of the same nucleic acid molecule, vector or gene delivery vehicle and may be integrated at the same site of the host cell's genome. Alternatively, said first and second nucleic acid molecules are separately provided to said cell.

A preferred embodiment provides a method for producing a bispecific antibody according to the invention from a single cell, wherein said bispecific antibody comprises two CH3 domains that are capable of forming an interface, said method comprising providing:

a cell having a) a first nucleic acid molecule encoding a heavy chain comprising an antigen binding site that binds an extra-cellular part of a membrane associated member of the EGFR family and that contains a 1st CH3 domain, and b) a second nucleic acid molecule encoding a heavy chain comprising an antigen-binding site that binds an extra-cellular part of a membrane associated member of a WNT signaling pathway and that contains a 2nd CH3 domain, wherein said nucleic acid molecules are provided with means for preferential pairing of said 1st and 2nd CH3 domains, said method further comprising the step of culturing said cell and allowing for expression of the proteins encoded by said two nucleic acid molecules and harvesting said bispecific IgG antibody from the culture. In a particularly preferred embodiment, said cell also has a third nucleic acid molecule encoding a common light chain. Said first, second and third nucleic acid molecule may be part of the same nucleic acid molecule, vector or gene delivery vehicle and may be integrated at the same site of the host cell's genome. Alternatively, said first, second and third nucleic acid molecules are separately provided to said cell. A preferred common light chain is based on 012, preferably it is the rearranged germline human kappa light chain IgVκ1 39*01/IGJκ1*01, as described above. Means for preferential pairing of said 1st and said 2nd CH3 domain are preferably the corresponding mutations in the CH3 domain of the heavy chain coding regions. The preferred mutations to produce essentially only bispecific antibodies are the amino acid substitutions L351K and T366K (numbering according to EU numbering) in the first CH3 domain and the amino acid substitutions L351D and L368E in the second CH13 domain, or vice versa. Further provided is therefore a method according to the invention for producing a bispecific antibody, wherein said first CH3 domain comprises the amino acid substitutions L351K and T366K (numbering according to EU numbering) and wherein said second C13 domain comprises the amino acid substitutions L351D and L368E, said method further comprising the step of culturing said cell and allowing for expression of proteins encoded by said nucleic acid molecules and harvesting said bispecific antibody from the culture. Also provided is a method according to the invention for producing a bispecific antibody, wherein said first CH3 domain comprises the amino acid substitutions L351D and L368E (numbering according to EU numbering) and wherein said second CH3 domain comprises the amino acid substitutions L351K and T366K, said method further comprising the step of culturing said cell and allowing for expression of said nucleic acid molecules and harvesting said bispecific antibody from the culture. Antibodies that can be produced by these methods are also part of the present invention. The CH3 hetero-dimerization domains are preferably IgG1 hetero-dimerization domains. The heavy chain constant regions comprising the CH3 hetero-dimerization domains are preferably IgG1 constant regions.

In one embodiment the invention provides a nucleic acid molecule encoding an antibody heavy chain variable region according to the invention. The nucleic acid molecule (typically an in vitro, isolated or recombinant nucleic acid molecule) preferably encodes a heavy chain variable region as depicted in FIG. 1 or a heavy chain variable region as depicted in FIG. 1 having 1, 2, 3, 4 or 5 amino acid insertions, deletions, substitutions or combination thereof. In a preferred embodiment the nucleic acid molecule comprises a sequence as depicted in FIG. 2. In another preferred embodiment the nucleic acid molecule encodes the same amino acid sequence as the nucleic acid depicted in FIG. 2 but has a different sequence because it encodes one or more different codons. The invention further provides a nucleic acid sequence encoding a heavy chain of FIG. 1.

A nucleic acid molecule as used in the invention is typically but not exclusively a ribonucleic acid (RNA) or a deoxyribonucleic acid (DNA). Alternative nucleic acids are available for a person skilled in the art. A nucleic acid according to the invention is for instance comprised in a cell. When said nucleic acid is expressed in said cell, said cell can produce an antibody according to the invention. Therefore, the invention in one embodiment provides a cell comprising an antibody according to the invention and/or a nucleic acid according to the invention. Said cell is preferably an animal cell, more preferably a mammal cell, more preferably a primate cell, most preferably a human cell. For the purposes of the invention a suitable cell is any cell capable of comprising and preferably of producing an antibody according to the invention and/or a nucleic acid according to the invention.

The invention further provides a cell comprising an antibody according to the invention. Preferably said cell (typically an in vitro, isolated or recombinant cell) produces said antibody. In a preferred embodiment said cell is a hybridoma cell, a Chinese hamster ovary (CHO) cell, an NS0 cell or a PER-C6TM cell. In a particularly preferred embodiment said cell is a CHO cell. Further provided is a cell culture comprising a cell according to the invention. Various institutions and companies have developed cell lines for the large scale production of antibodies, for instance for clinical use. Non-limiting examples of such cell lines are CHO cells, NS0 cells or PER.C6 cells. These cells are also used for other purposes such as the production of proteins. Cell lines developed for industrial scale production of proteins and antibodies are herein further referred to as industrial cell lines. Thus in a preferred embodiment the invention provides the use of a cell line developed for the large scale production of antibody for the production of an antibody of the invention. The invention further provides a cell for producing an antibody comprising a nucleic acid molecule that codes for a VH, a VL, and/or a heavy chain as depicted in FIG. 1. Preferably said nucleic acid molecule comprises a sequence as depicted in FIG. 2.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

A cell of the invention is for instance a hybridoma cell line, a CHO cell, a 293F cell, an NS0 cell or another cell type known for its suitability for antibody production for clinical purposes. In a particularly preferred embodiment said cell is a human cell. Preferably a cell that is transformed by an adenovirus E1 region or a functional equivalent thereof. A preferred example of such a cell line is the PER.C6 cell line or equivalent thereof. In a particularly preferred embodiment said cell is a CHO cell or a variant thereof. Preferably a variant that makes use of a Glutamine synthetase (GS) vector system for expression of an antibody.

The invention further provides a pharmaceutical composition comprising an antibody according to the invention. The pharmaceutical composition preferably comprises a preferably pharmaceutically acceptable excipient or carrier. In a preferred embodiment the pharmaceutical composition comprises 5-50 mM Histidine, 100-300 mM Trehalose, 0.1-03 g/L PolySorbate20 or a combination thereof. The pH is preferably set at pH=5.5-6.5. In a preferred embodiment the pharmaceutical composition comprises 25 mM Histidine, 220 mM Trehalose, 0.2 g/L PolySorbate20 or a combination thereof. The pH is preferably set at pH=5.5-6.5, most preferably at pH=6.

An antibody of the invention preferably further comprises a label, preferably a label for in vivo imaging. Such a label is typically not necessary for therapeutic applications. In for instance a diagnostic setting, a label can be helpful. For instance in visualizing target cells in the body. Various labels are suited and many are well known in the art. In a preferred embodiment the label is a radioactive label for detection. In another preferred embodiment, the label is an infrared label. Preferably the infrared label is suited for in vivo imaging. Various infrared labels are available to the person skilled in the art. Preferred infrared labels are for instance, IRDye 800; IRDye 680RD; IRDye 680LT; IRDye 750; IRDye 700DX; IRDye 800RS IRDye 650; IRDye 700 phosphoramidite; IRDye 800 phosphoramidite (LI-COR USA; 4647 Superior Street; Lincoln, Nebraska).

To establish whether a cancer exhibits a growth response when provided with an EGF receptor family member ligand, the skilled person can for instance determine the EGFR amplification and/or staining immune-histochemistry (for an EGF-response). At least 10% of the tumor cells in a tumor sample should be positive. The tumor sample can also contain 20%, 30% 40% 50% 60% 70% or more positive cells. To establish whether a cancer exhibits a growth response to a HER3 ligand the skilled person can for instance determine the HER3 amplification and/or staining in immunohistochemistry. At least 10% tumor cells in a tumor sample should be positive. The sample can also contain 20%, 30% 40% 50% 60% 70% or more positive cells. To establish whether a cancer will be sensitive to Wnt (LGR5, LGR4, ZNRF3, RNF43) receptor targeting the skilled person can for instance determine the Wnt target amplification and/or staining in immunohistochemistry. At least 1% tumor cells in a tumor sample should be positive. The sample can also contain 5%, 10% 20% 30% 40% 50% or more positive cells.

The amount of antibody according to the invention to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to the invention exerting sufficient therapeutic effects at low dosage is, therefore, preferred. The dosage can be in range of the dosing regimen of cetuximab. The dosage can also be lower.

A bispecific antibody according to the invention preferably induces less skin toxicity as compared to cetuximab under otherwise similar conditions of course. A bispecific antibody according to the invention preferably produces less proinflammatory chemokines, preferably of CXCL14 as compared to cetuximab under otherwise similar conditions of course. A bispecific antibody according to the invention preferably induces less impairment of antimicrobial RNAses, preferably Rnase 7, as compared to cetuximab under otherwise similar conditions of course.

The present invention describes among others antibodies that target the an extra-cellular part of a membrane associated member of the EGF receptor family and an extra-cellular part of a membrane associated member of the WNT signaling pathway and result in potent proliferation inhibition of cancer cell lines in vitro and tumor growth inhibition in vivo. The antibodies were produced as bispecific antibodies by cloning them into complementary expression vectors that contain mutations in the CH3 region that drives hetero-dimerization of heavy chains. Many bispecific antibodies were produced at small scale and tested in binding and functional assays on cancer cell lines. An antibody of the invention, particularly a bispecific antibody of the invention can combine low toxicity profiles with high efficacy. An antibody of the invention can be useful in various types and lines of ECFR family member targeted therapies. An antibody of the invention can have an increased therapeutic window when compared to an antibody that binds the same antigen(s) with both arms. A bispecific antibody of the invention can exhibit better growth inhibitory effects in vitro, in vivo or a combination thereof when compared to the MEHD7945A antibody.

Also provided is a method for counteracting the formation of a metastasis in a subject having a cancer that expresses a member of the EGF-receptor family and that expresses a membrane associated member of the WNT pathway. The cancer is preferably an EGF-receptor ligand responsive cancer. High Her ligand (e.g. EGF, Heregulin) levels are typically present during the formation of metastases (i.e. the migration, invasion, growth and/or differentiation of tumor cells or tumor initiating cells). Typically, tumor initiating cells are identified based on stem cell markers such as CD44. These processes can therefore barely be counteracted with currently known therapies like trastuzumab and pertuzumab. Since an antibody according to the invention is capable of counteracting growth and/or differentiation of tumor cells or tumor initiating cells such as cancer stem cells, such antibody according to the invention is also particularly suitable for counteracting the formation of metastases. Further provided is therefore a method for counteracting the formation of a metastasis in a subject having a EGFR, ErbB-3 or EGFR/ErbB-3 positive tumor, wherein said EGFR, ErbB-3 or EGFR/ErbB-3 positive tumor cell and/or surrounding stromal tissue cells (e.g. fibroblasts, Leukocytes such as macrophages and monocytes, endothelium, etc.) has a Her ligand expression level that is at least 60%, preferably at least 70%, more preferably at least 80%, more preferably at least 85%, more preferably at least 90% or 95% of the her ligand expression level of BXPC3 or MCF7 cells, comprising administering to the subject a bispecific antibody or a functional part, derivative and/or analogue thereof that binds an extra-cellular part of EGFR or HER3, an extra-cellular part of a membrane associated member of the WNT signaling pathway. Also provided is a bispecific antibody or a functional part, derivative and/or analogue thereof that binds an extra-cellular part of EGFR or HER3, and an extracellular part of a membrane associated member of the WNT signaling pathway, for use in the treatment or prevention of the formation of metastases. The tumor from which said metastases originate is preferably an ErbB-3 or EGFR/ErbB-3 positive tumor. The tumor and/or surrounding stromal tissue cells preferably has a her ligand expression level that is at least 60%, preferably at least 70%, more preferably at least 80%, more preferably at least 85%, more preferably at least 90% or 95% of the heregulin expression level of BXPC3 or MCF7 cells.

Further provided is a use of a bispecific antibody according to the invention or a functional part, derivative and/or analogue thereof, for the preparation of a medicament for the treatment or prevention of the formation of metastases. The tumor from which said metastases originate is preferably an ErbB-3 or EGFR/ErbB-3 positive tumor. The tumor and/or surrounding stromal tissue cells preferably has a her ligand expression level that is at least 60%, preferably at least 70%, more preferably at least 80%, more preferably at least 85%, more preferably at least 90% or 95% of the heregulin expression level of BXPC3 or MCF7 cells.

Antibodies of the invention can be produced at levels >50 mg/L after transient transfection in suspension 293F cells. The bispecific antibodies can be purified to greater than 98% purity with yields >70%. Analytical characterization studies show bispecific IgG1 antibody profiles that are comparable to bivalent monospecific IgG1.

For the purpose of clarity and a concise description features are described herein as part of the same or separate embodiments, however, it will be appreciated that the scope of the invention may include embodiments having combinations of all or some of the features described.

In mathematics, the Euclidean distance or Euclidean metric is the "ordinary" (i.e. straight-line) distance between two points in Euclidean space. With this distance. Euclidean space becomes a metric space. The associated norm is called the Euclidean norm.

Receptor tyrosine kinases (RTK)s are the high-affinity cell surface receptors for many polypeptide growth factors, cytokines, and hormones. Of the presently known 90 unique tyrosine kinase genes identified in the human genome, 58 encode receptor tyrosine kinase proteins. Receptor tyrosine kinases have been shown to be relevant for normal cellular processes but also to have a role in the development and progression of cancer. Receptor tyrosine kinases contain at least one extracellular domain.

In one aspect the invention provides a protein that binds an extracellular part of a membrane associated member of the RTK receptor family and an extracellular part of a membrane associated member of a WNT signaling pathway. The protein is preferably an antibody, preferably a bispecific antibody or a functional part, derivative and/or analogue thereof.

The invention also provides a bispecific antibody or a functional part, derivative and/or analogue thereof that binds an extracellular part of a membrane associated member of the RTK receptor family and an extra-cellular part of a membrane associated member of a WNT-signaling pathway.

Also provided is a method for the treatment of an individual that has a cancer, the method comprising administering a protein of the invention or a bispecific antibody of the invention to the individual in need thereof.

The invention further provides a protein of the invention or a bispecific antibody of the invention, for use in the treatment of an individual that has cancer.

In one embodiment the cancer is a cancer that is responsive to the ligand of the respective member of the RTK receptor family and a cancer that expresses a membrane associated member of the WNT pathway.

Further provided is a cell system comprising a protein of the invention or a bispecific antibody of the invention, and a cell that expresses a membrane associated member of the RTK receptor family and that expresses a membrane associated member of the WNT pathway. The cell system is preferably is a cell system comprising a protein of the invention or a bispecific antibody of the invention, and a cell that expresses a membrane associated member of the RTK receptor family and that expresses a membrane associated member of the WNT pathway.

Also provided is a system permissive for inhibiting growth/proliferation of the cell, the method comprising providing the system with a protein of the invention or a bispecific antibody of the invention. The cell is preferably is an RTK-receptor ligand responsive cell that expresses a membrane associated member of the WNT pathway in a system permissive for growth/proliferation of the cell, the method comprising providing the system with a protein of the invention or a bispecific antibody of the invention. The cell is preferably is an RTK-receptor ligand responsive cell that expresses a membrane associated member of the WNT pathway.

Preferred members of the RTK receptor family are the mentioned EGF-receptor family and c-MET: Axl and MST1R.

MET or C-MET is a single pass tyrosine kinase receptor relevant for embryonic development, organogenesis and wound healing. Hepatocyte growth factor/Scatter Factor (HGF/SF) and its splicing isoform (NK1, NK2) are the presently known ligands of the MET receptor. MET is normally expressed by cells of epithelial origin, while expression of HGF/SF is observed in cells of mesenchymal origin. When HGF/SF binds its cognate receptor MET it induces activation. Met is also known as MET Proto-Oncogene. Receptor Tyrosine Kinase; Hepatocyte Growth Factor Receptor; Tyrosine-Protein Kinase Met; Scatter Factor Receptor; Proto-Oncogene C-Met; HGF/SF Receptor; HGF Receptor; SF Receptor; EC 2.7.10.1; Met Proto-Oncogene Tyrosine Kinase; Met Proto-Oncogene; EC 2.7.10; AUTS9; RCCP2; C-Met; and HGFR 3. Accession numbers for the gene and protein are NC_000007.14; NT_007933.16; NC_018918.2; NP_000236.2; NP_001120972.1. The accession numbers are primarily given to provide a further method of identification of C-MET as a target, the actual sequence of the C-MET protein bound by an antibody may vary, for instance because of a mutation in the encoding gene such as those occurring in some cancers or the like. The C-MET antigen binding site binds C-MET and a variety of variants thereof, such as those expressed by some C-MET positive tumor cells.

AXL or AXL Receptor Tyrosine Kinase codes for Tyrosine-protein kinase receptor UFO which is an enzyme that in humans is encoded by the AXL gene. Other names for AXL are AXL Receptor Tyrosine Kinase; AXL Oncogene; EC 2.7.10.1; UFO; Tyrosine-Protein Kinase Receptor UFO; AXL Transforming Sequence/Gene; EC 2.7.10; JTK11; Tyro7; and ARK 3. Accession numbers for the gene and protein are NC_000019.10; NC_0189:30.2; NT_011109.17; NP_001265528.1; NP_001690.2; NP_068713.2). The accession numbers are primarily given to provide a further method of identification of AXL as a target, the actual sequence of the AXL protein bound by an antibody may vary, for instance because of a mutation in the encoding gene such as those occurring in some cancers or the like. The AXL antigen binding site binds AXL and a variety of variants thereof, such as those expressed by some AXL positive tumor cells.

MST1R or Macrophage stimulating 1 receptor or RON. Other names for MST1R are Macrophage Stimulating 1 Receptor; RON; PTK8 Protein Tyrosine Kinase 8; C-Met-Related Tyrosine Kinase; MSP Receptor; EC 2.7.10.1; P185-Ron; CDw136; PTK8; Macrophage Stimulating 1 Receptor (C-Met-Related Tyrosine Kinase) 3; Macrophage-Stimulating Protein Receptor; Protein-Tyrosine Kinase 8; MST1R Variant RON30; MST1R Variant RON62; RON Variant E2E3; RON Variant 21; CD136 Antigen; EC 2.7.10; CD136, all in membrane bound form. Accession numbers for the gene and protein are NC_000003.12; NT_022517.19; NC_018914.2; NP_001231866.1; NP_002438.2. The accession numbers are primarily given to provide a further method of identification of MST1R as a target, the actual sequence of the MST1R protein bound by an antibody may vary, for instance because of a mutation in the encoding gene such as those occurring in some cancers or the like. The MST1R antigen binding site binds MST1R and a variety of variants thereof, such as those expressed by some MST1R positive tumor cells.

The invention also provides a monospecific antibody comprising variable domains that bind LGR4 wherein the VH chain of the variable domains comprises
the amino acid sequence of VH chain MF5777 as depicted in FIG. 1; or
the amino acid sequence of VH chain MF5777 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind LGR4 wherein the VH chain of the variable domains comprises
the amino acid sequence of VH chain MF5781 as depicted in FIG. 1; or
the amino acid sequence of VH chain MF5781 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind LGR5 wherein the VH chain of the variable domains comprises
the amino acid sequence of VH chain MF5790 as depicted in FIG. 1; or
the amino acid sequence of VH chain MF5790 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind LGR5 wherein the VH chain of the variable domains comprises
the amino acid sequence of VH chain MF5803 as depicted in FIG. 1; or
the amino acid sequence of VH chain MF5803 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind LGR5 wherein the VH chain of the variable domains comprises
the amino acid sequence of VH chain MF5814 as depicted in FIG. 1; or
the amino acid sequence of VH chain MF5814 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind LGR5 wherein the VH chain of the variable domains comprises
the amino acid sequence of VH chain MF5816 as depicted in FIG. 1; or
the amino acid sequence of VH chain MF5816 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind LGR5 wherein the VH chain of the variable domains comprises
the amino acid sequence of VH chain MF5817 as depicted in FIG. 1; or
the amino acid sequence of VH chain MF5817 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind LGR5 wherein the VH chain of the variable domains comprises
the amino acid sequence of VH chain MF5818 as depicted in FIG. 1; or
the amino acid sequence of VH chain MF5818 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind RNF43 wherein the VH chain of the variable domains comprises
the amino acid sequence of VH chain MF5832 as depicted in FIG. 1; or
the amino acid sequence of VH chain MF5832 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind RNF43 wherein the VH chain of the variable domains comprises
the amino acid sequence of VH chain MF5836 as depicted in FIG. 1; or
the amino acid sequence of VH chain MF5836 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind ZNRF3 wherein the VH chain of the variable domains comprises
the amino acid sequence of VH chain MF5850 as depicted in FIG. 1; or
the amino acid sequence of VH chain MF5850 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind ZNRF3 wherein the VH chain of the variable domains comprises
the amino acid sequence of VH chain MF585:3 as depicted in FIG. 1; or
the amino acid sequence of VH chain MF5853 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind ZNRF3 wherein the VH chain of the variable domains comprises
the amino acid sequence of VH chain MF5855 as depicted in FIG. 1; or
the amino acid sequence of VH chain MF5855 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind ZNRF3 wherein the VH chain of the variable domains comprises
the amino acid sequence of VH chain MF5884 as depicted in FIG. 1; or
the amino acid sequence of VH chain MF5884 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention also provides a monospecific antibody comprising variable domains that bind ZNRF3 wherein the VH chain of the variable domains comprises
the amino acid sequence of VH chain MF5888 as depicted in FIG. 1; or
the amino acid sequence of VH chain MF5888 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

In one embodiment the invention a monospecific antibody comprising variable domains that bind EGFR wherein the VH chain of the variable domains comprises
the amino acid sequence of VH chain MF3755 as depicted in FIG. 1; or
the amino acid sequence of VH chain MF3755 as depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention relates to an antibody that comprises a variable domain that can bind an epitope on an extracellular part of LGR5 which epitope is located within amino acid residues 21-118 of SEQ ID NO: 1 depicted in FIG. 39. It was shown that amino acid residues D43; G44, M46, F67, G90, and F91 are involved in binding of the antibody. Involved in does not necessarily mean that all residues are indeed contacted by the antibody. Without being bound by theory it is believed that the substitution D43A or G44A results in a (slight) conformational change in the epitope and that the conformation change results in reduced binding of the antibody to the epitope.

The interaction of the antibody with LGR5 does not inhibit the binding of RSPO 1 to LGR5 expressed on the membrane of an LGR5-expressing cell. The interaction of the antibody with RSPO 1 does not inhibit the binding of the antibody to LGR5 expressed on the membrane of an LGR5-expressing cell. This means that the antibody and RSPO1 do not compete with each other for binding to LGR5. At least not in the range of molar ratio's indicated herein. The molar ratio of antibody to RSPO 1 it typically from 0.1 to 0.001 (inclusive) preferably in a molar ratio of between 0.1 to 0.01 (inclusive). In this range the binding of the antibody to LGR5 does not inhibit (block) the binding of RSPO 1 to LGR5.

When herein molar ratio's of antibody to RSPO are mentioned it is preferred that the antibody is present in amounts that result in 40%-80% of the binding achieved when saturating amounts of the antibody are present.

Various antibodies that bind to LGR5 have been described. Binding of an antibody to LGR5 can block the binding of an Rspondin to LGR5 or not. It has been found that antibodies that block the binding of Rspondin 1 ligand to LGR5 bind to a region encompassing the N-terminal region. Leucine-rich repeat (LRR) region 1 and LRR2 of the protein (Lau et al 2011; Nature vol 476; pp 293-297 and supplemental information described therein). The elements are contained in amino acids 21-118 (inclusive) of an LGR5 protein sequence as depicted in SEQ ID NO: 1 depicted in FIG. 39; wherein amino acids 21-70 constitute the N-terminal region, amino acids 71-94 (inclusive) constitute LRR1 and 95-118 constitute LRR2. Only few antibodies that do not block the interaction of LGR5 with Rspondin 1 have been reported in the art and to the best of the inventor's knowledge none of these bind to the N-terminal region of LGR5.

The invention now provides a protein that binds to an epitope within amino acid residues 21-118 of an LGR5 sequence of SEQ ID NO: 1 depicted in FIG. 39 and which protein does not block the binding of Rspondin 1 to LGR5.

The test for determining whether an antibody blocks or does not block the binding of an Rspondin to LGR5 preferably incudes CHO cells that express LGR5 on the cell membrane. The antibody and the Rspondin to be analyzed are mixed together and added to the cells whereupon the binding of the antibody to the cells is determined. The amount of binding of the antibody to the LGR5 expressing cells in the presence of an excess of Rspondin indicates that the antibody does not block the binding of Rspondin to LGR5. The test preferably further includes a control antibody that binds LGR5 and that blocks the binding of the Rspondin to LGR5. The control antibody is preferably antibody PB10261 or OMP88R20 as described in as described in the examples A protein does not block the binding of Rspondin 1 to LGR5 if, under otherwise the same conditions, more protein when compared to control antibody can bind to LGR5 expressing cells. This is preferably assessed under conditions wherein the molar ratio of protein or control antibody to Rspondin is 1:10 or less, i.e. 0.1 or less; preferably in a molar ratio of between 0.1 to 0.001, (inclusive), preferably 0.1 to 0.01 (inclusive). The protein preferably also binds an extracellular part of another membrane associated protein. In a preferred embodiment the other membrane associated protein is a membrane associated member of the EGF-receptor family or eMET.

The invention also provides a protein that can bind an epitope on an extracellular part of LGR5 which epitope is located within amino acid residues 21-118 of SEQ ID NO: 1 depicted in FIG. 39 and wherein the binding of the protein to LGR5 is reduced with one or more of the following amino acid residue substitutions D43A; G44A, M46A, F67A, G90A, and F91A. In a preferred embodiment the interaction of Rspondin (RSPO) 1 with LGR5 on an LGR5-expressing cell does not inhibit the binding of the protein to LGR5 by more than 20%. The inhibition of binding of the protein to LGR5 is preferably measured when the protein and the RSPO 1, 2, 3 or 4 are present in a molar ratio of 0.1 or less; preferably in a molar ratio of between 0.1 to 0.001, (inclusive), preferably 0.1 to 0.01 (inclusive) (protein:RSPO).

The invention further provides a protein that can bind an epitope on LGR5 that is located within amino acid residues 21-118 of SEQ ID NO: 1 depicted in FIG. 39, and wherein interaction of RSPO 1 with LGR5 on an LGR5-expressing cell does not inhibit the binding of the protein to LGR5 by more than 20% when the protein and the RSPO 1 are present in a molar ratio from 0.1 or less; preferably in a molar ratio of between 0.1 to 0.001, (inclusive), preferably 0.1 to 0.01 (inclusive). The epitope is preferably located within amino acid residues 40-95 of SEQ ID NO: 1 depicted in FIG. 39. The binding of the protein to LGR5 is preferably reduced with one or more of the following amino acid residue substitutions D43A; G44A, M46A, F67A, G90A, and F91A, This typically indicates that the protein interacts with these mentioned amino acids. Changing these amino acids these alters the binding of the protein to LGR5. These amino acids are therefore likely to be the contact residues in LGR5 for the binding protein. In the present case the inventors consider residues M46; F67, G90A and F91 to be contact residues. D43 and G44 can also be contact residues but can also be residues that alter the specific conformation of other residues such that they are no longer able to be bound by the protein. The protein preferably can bind a further protein. The further protein is preferably a membrane protein comprising an extracellular part. The further protein is preferably a membrane associated member of the epidermal growth factor (EGF) receptor family or cMET. The LGR5 binding protein as discussed herein is preferably an antibody preferably a bispecific antibody.

The invention further provides a bispecific antibody comprising a variable domain that can bind an epitope on an extracellular part of LGR5 which epitope is located within amino acid residues 21-118 of SEQ ID NO: 1 depicted in FIG. 39 and wherein the binding of the variable domain to LGR5 is reduced with one or more of the following amino acid residue substitutions D43A; G44A, M46A, F67A, G90A, and F91A; the bispecific antibody further comprises a variable domain that can bind a further protein. The further protein is preferably a membrane protein comprising an extracellular part. The further protein is a membrane associated member of the EGF receptor family or cMET.

The binding of the protein or bispecific antibody as mentioned herein to the membrane associated member of the EGF receptor family or cMET preferably reduces ligand-induced signaling in a cell that comprises said membrane associated member of the EGF receptor family or eMET.

The invention provides an antibody that comprises a variable domain that can bind an epitope on an extracellular part of LGR5 which epitope is located within amino acid residues 21-118 of SEQ ID NO: 1 depicted in FIG. 39.

The invention further provides an antibody that binds an epitope on an extracellular part of LGR5, wherein amino acid residues D43; G44, M46, F67, G90, and F91 are involved in binding of the antibody to the epitope.

The invention further provides an antibody that binds an epitope on an extracellular part of LGR5, wherein one or more of the amino acid residue substitutions of D43A G44A, M46A, F67A, G90A, and F91A reduces the binding of the antibody to the epitope.

The invention further provides an antibody that comprises a variable domain that can bind an epitope on an extracellular part of LGR5 which epitope is located within amino acid residues 21-118 of SEQ ID NO: 1 depicted in FIG. 39, and wherein the binding of the antibody to the epitope is reduced by one or more of the following amino acid residue substitutions D43A; G44A, M46A, F67A, G90A, and F91A.

A membrane protein as used herein is a cell membrane protein, i.e. a protein that is in the outer membrane of a cell, the membrane that separates the cell from the outside world. The membrane protein has an extracellular part. A membrane protein is at least on a cell if it contains a transmembrane region that is in the cell membrane of the cell.

The antibody preferably further comprises a further variable domain can bind a further protein. The further protein is preferably a membrane protein comprising an extracellular part. The further protein is preferably a membrane associated member of the epidermal growth factor (EGF) receptor family or cMET. The antibody is a bispecific antibody.

For the purpose of clarity and a concise description features are described herein as part of the same or separate embodiments, however, it will be appreciated that the scope of the invention may include embodiments having combinations of all or some of the features described.

BRIEF DESCRIPTION OF THE DRAWINGS

FIG. 1: amino acid sequences of VH fragments described in the current application, CDR1, CDR2 and CDR3 regions, as well as FR1, FR2, FR3 and FR4 regions are indicated.

FIG. 2: nucleotide sequences of selected VH-encoding cDNA's described in the current application.

FIG. 3: Annotated sequence of the common light chain (cLC).

FIG. 4: Annotated Fc (CH1-CH3) region amino acid sequence of antibodies tested in the present application.

Example of the effect of growth factors EGF and HRG on the tumoroid morphology in tumoroids P14T and P18T. Growth factors induce a simultaneous change in tumoroid size, the lumen size and the distribution of the lumen. The combination of these three morphological parameters locates the observed organoids in a unique feature space. The Euclidian distance can be calculated based on the combination of these three features with the no growth factor (no GF) as a reference point. The Euclidian distance is then the change in X, Y and Z direction induced by the treatments.

Figure 6:
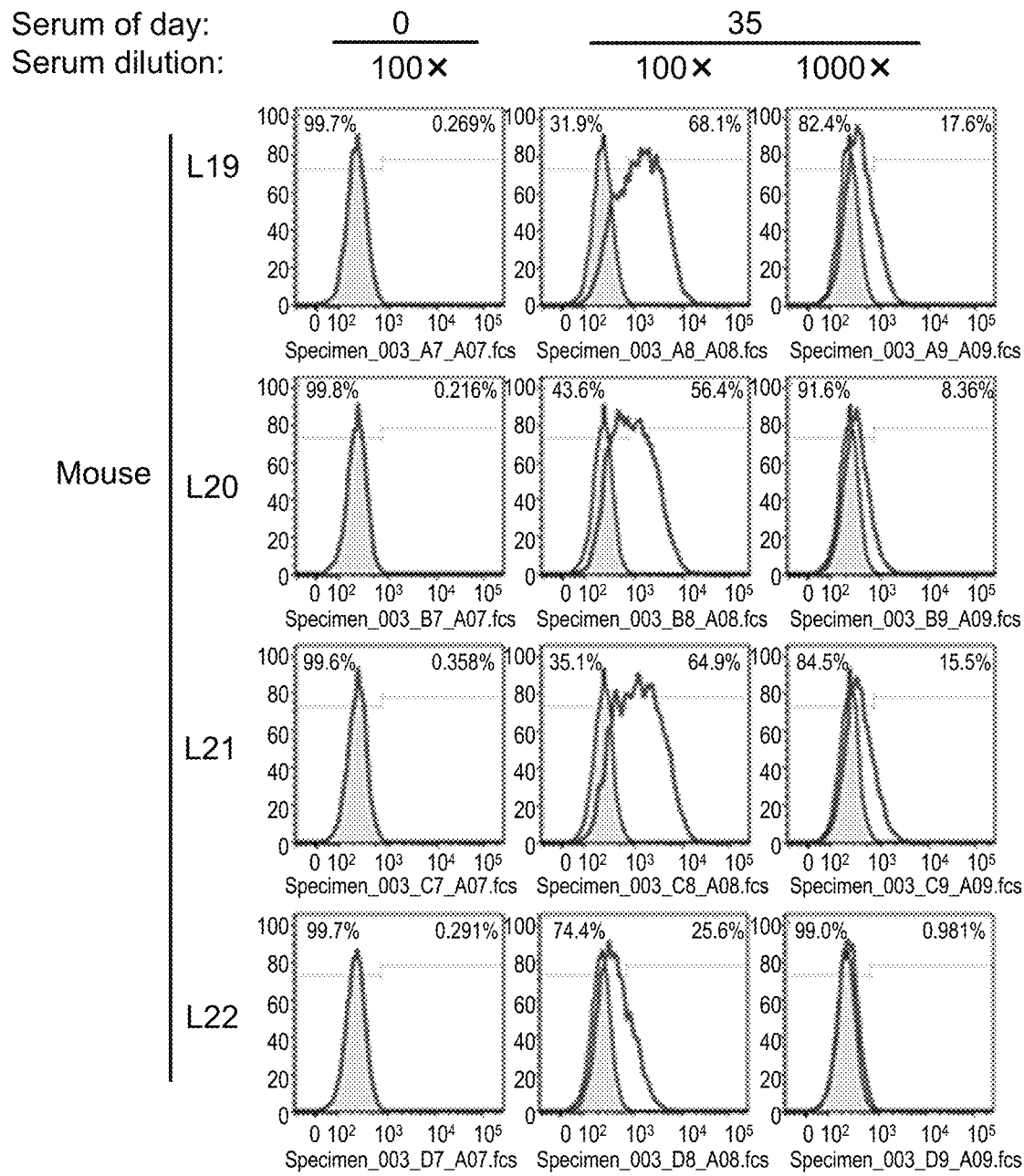
Figure 6:
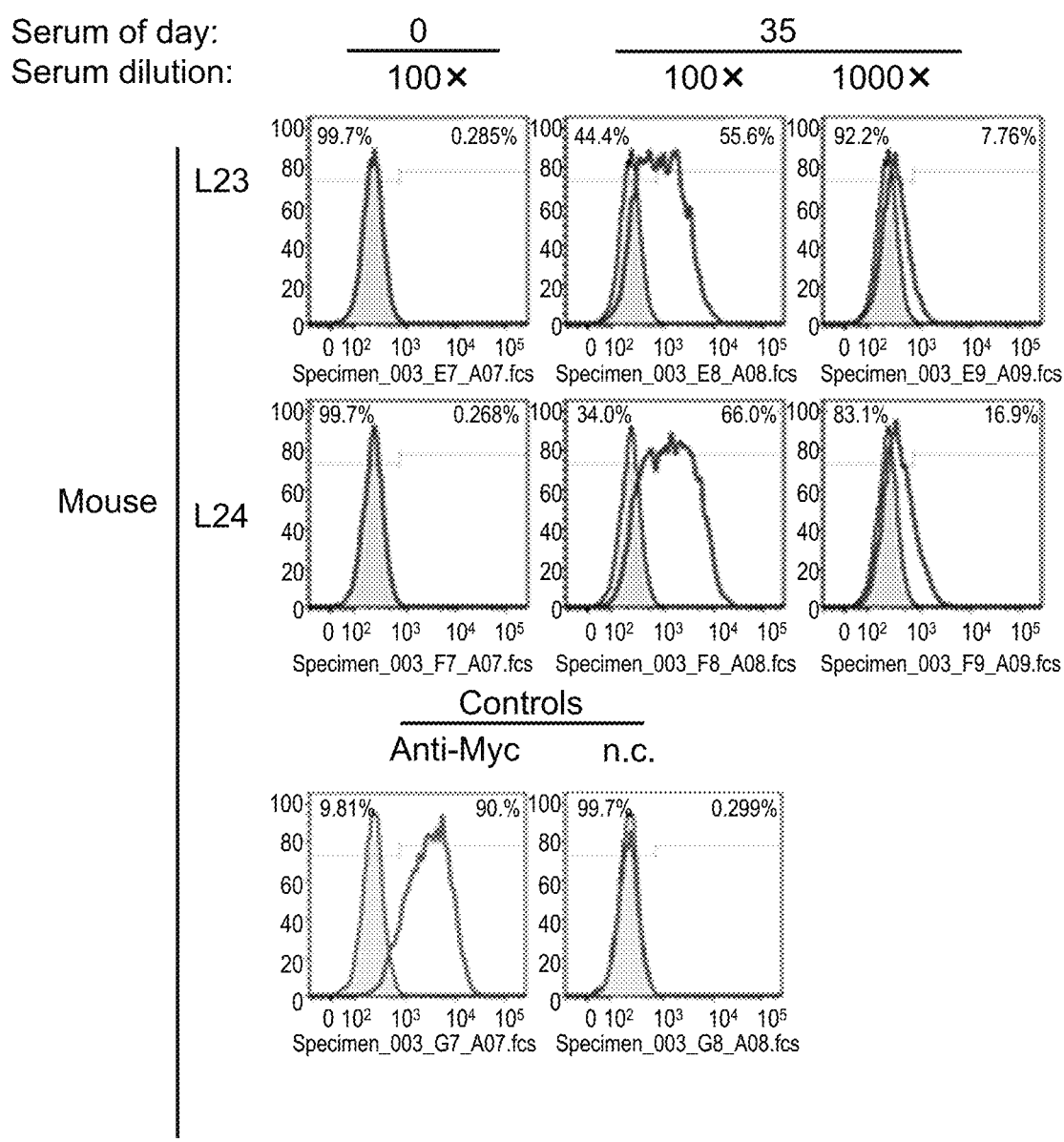

FIG. 6: FACS analysis of sera of ZNRF3-immunised animals binding to Freestyle 293F cells that stably over-expressed the antigen, taken at day 35.

Sera were tested compared to the day 0 (pre-immune) sera for binding to the 293F Freestyle cell line stably expressing the ECD of ZNRF3. Every panel shows an overlay of control (non-stained) cells (filled grey) and the cells stained with the respective sera (no fill). Mice are numbered L19-L24: control stainings are indicated on the right side of the figure n.c.: negative control.

Figure 7:
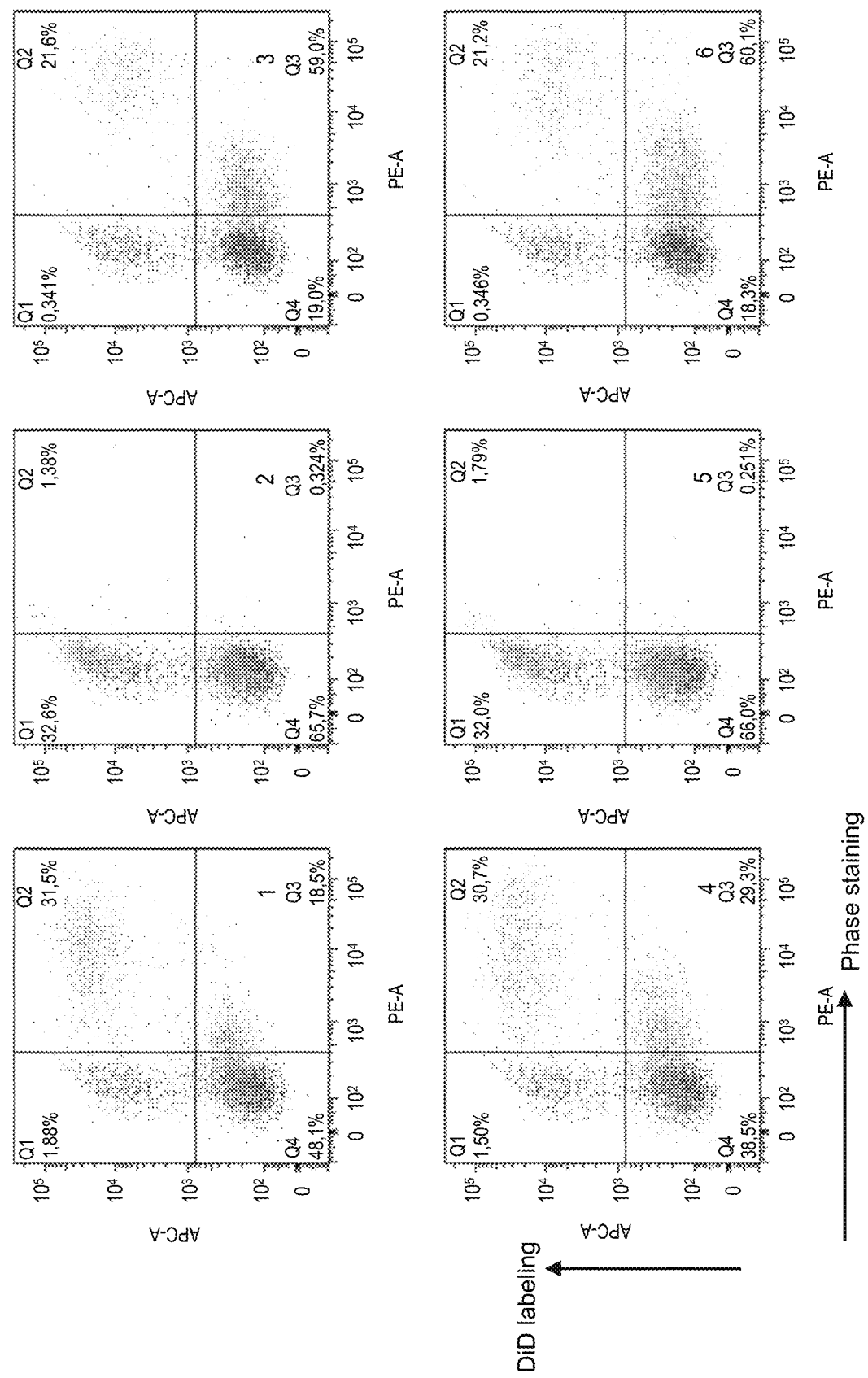
Figure 7:
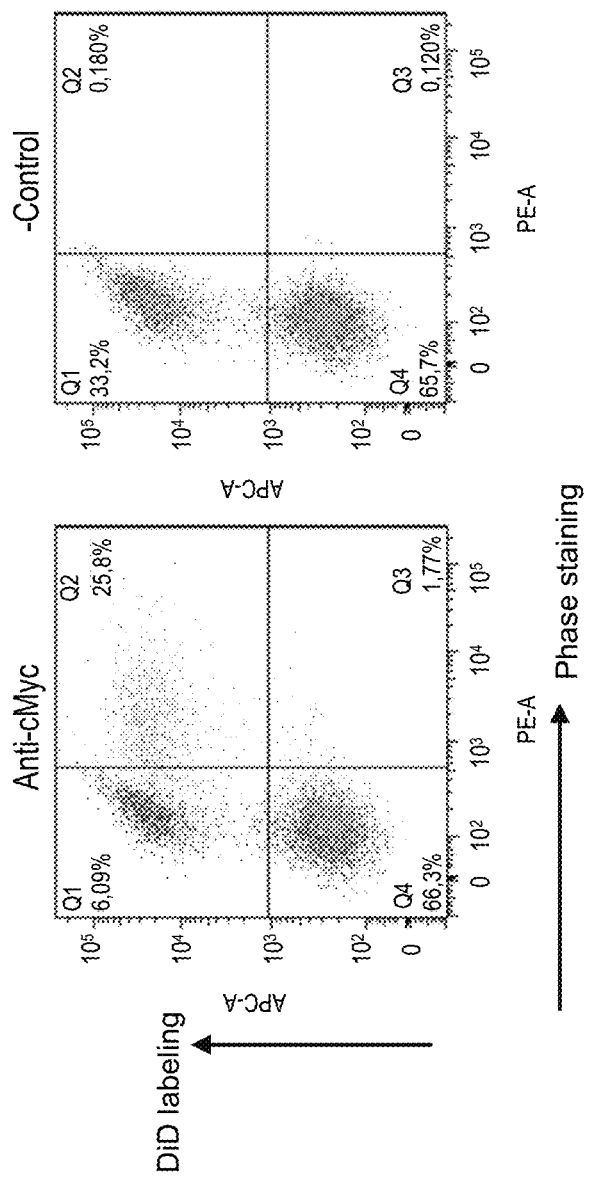

FIG. 7: Example of FACS staining of a mix of DiD-labelled ZNRF3 over-expressing cells and non-labelled (parental) 293F freestyle cells using preparations of selected monoclonal phage clones.

Every dot-plot is an overlay of non-stained cells and cells stained with a selected Fab expressed on phage. The upper half of every panel shows the DiD-labelled antigen-positive cells and the lower half of the panel the non-labelled antigen-negative 293F freestyle cells. Of the six clones shown in the figure (labelled 1-6), four are antigen-specific (1, 3, 4 and 6) and two (2 and 5) are non-reactive. Control for expression of the protein was staining with the antibody directed to the eMyc-derived epitope tag and negative control was staining with the secondary antibodies (anti-M13 and Strep-PE) only.

Figure 8:
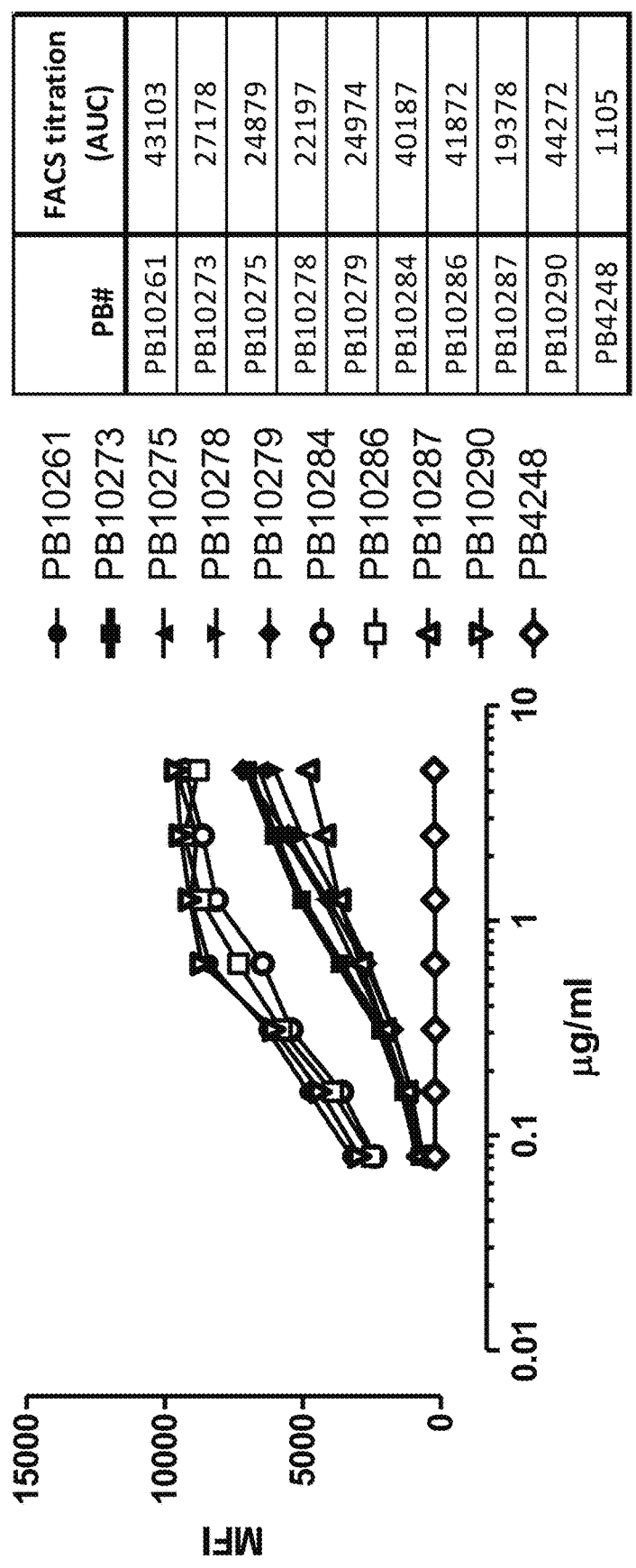

FIG. 8: Affinity ranking of monovalent IgG directed to hLGR5 (all combined with the Tetanus toxoid Fab Fragment) on the cellular surface of Freestyle 293F cells over-expressing hLGR5.

A representative example of the entire panel is shown. A two-fold dilution series of IgG (5 µg/ml-0.08 µg/ml) was tested on a fixed number of cells (5×105 cells/well) stable expressing hLGR5. The mean fluorescence intensity (MF) was measured for each data point and was plotted against the increasing amount of IgG used for staining. From each IgG the area under the curve (AUC) was calculated based on the individual curves and used for ranking. The table (right panel) shows the AUC values of bispecific IgG shown in the graph (left panel). Based on the AUC values the IgG were ranked for binding affinity to their respective target.

Figure 9:
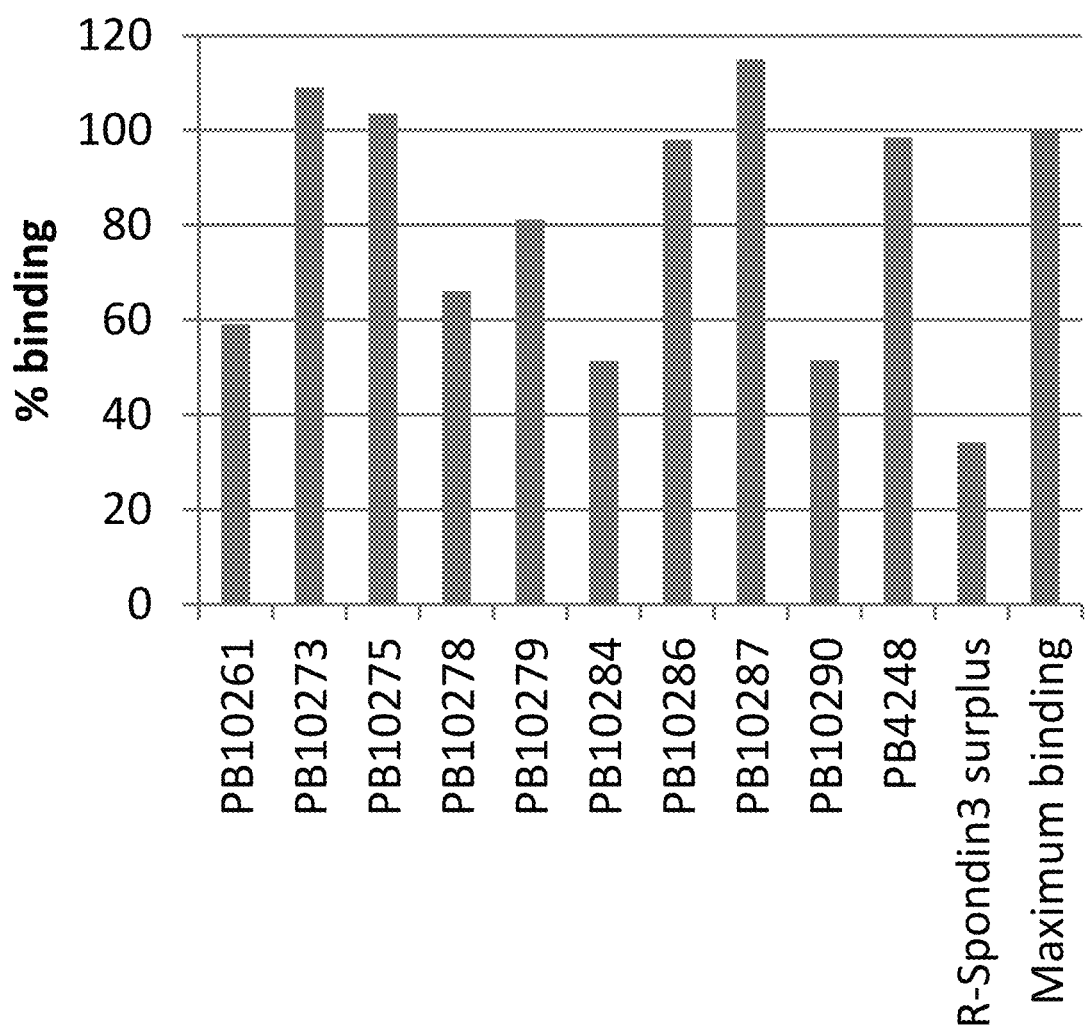

FIG. 9: rhR-Spondin3 blocking capacity of hLGR5 monovalent binding IgG (all combined with a TT Fab fragment) was tested in an R-Spondin blocking ELISA.

A representative example is shown of the LGR5 panel. Maximum binding (normalized to 0%) was established by uninhibited binding to 2 µg/ml coated rhR-Spondin3 using 0.031 µg/ml rhLGR5-Fc, and detection with an anti-Fc antibody. The OD450 nm value for maximum binding was set at 100%. R-Spondin3 surplus indicates the addition of excess R-Spondin3 (05 µg/ml) to serve as a positive control for competition. The bispecific IgG, tested at 15 µg/ml, the OD450 nm values were normalized based on the maximum signal and are indicated by the blue bars. Clones were considered partially blocking when the percentage was below 80% and considered blocking when the percentage was below 50%. This example shows a representative panel of LGR5 targeting LGR5/TT IgG fragments.

Figure 10:
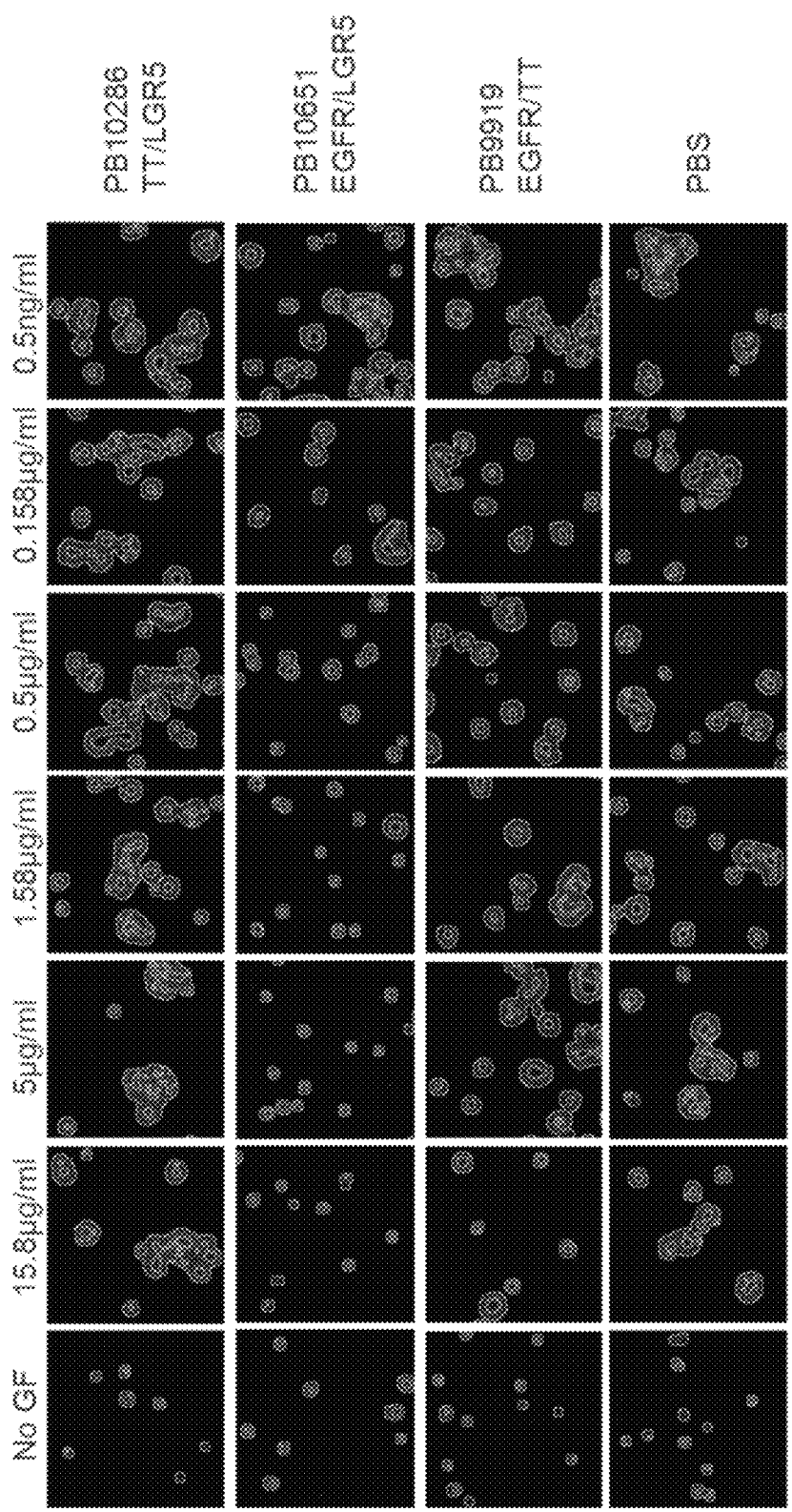

FIG. 10: Growth inhibiting effects of the reference antibody PG3755 (EGFR bivalent, mono-specific) and PB10651 (EGFR/LGR5 bispecific) on the tumoroid line P18T in the presence of 5 ng/ml EGF in the culture medium.

The antibodies revert the EGF-induced tumoroid phenotype to a no growth factor stimulated phenotype (first column). PB10651 is active as a growth inhibitor at lower doses than the EGFR bispecific reference antibody PG3755.

Figure 11:
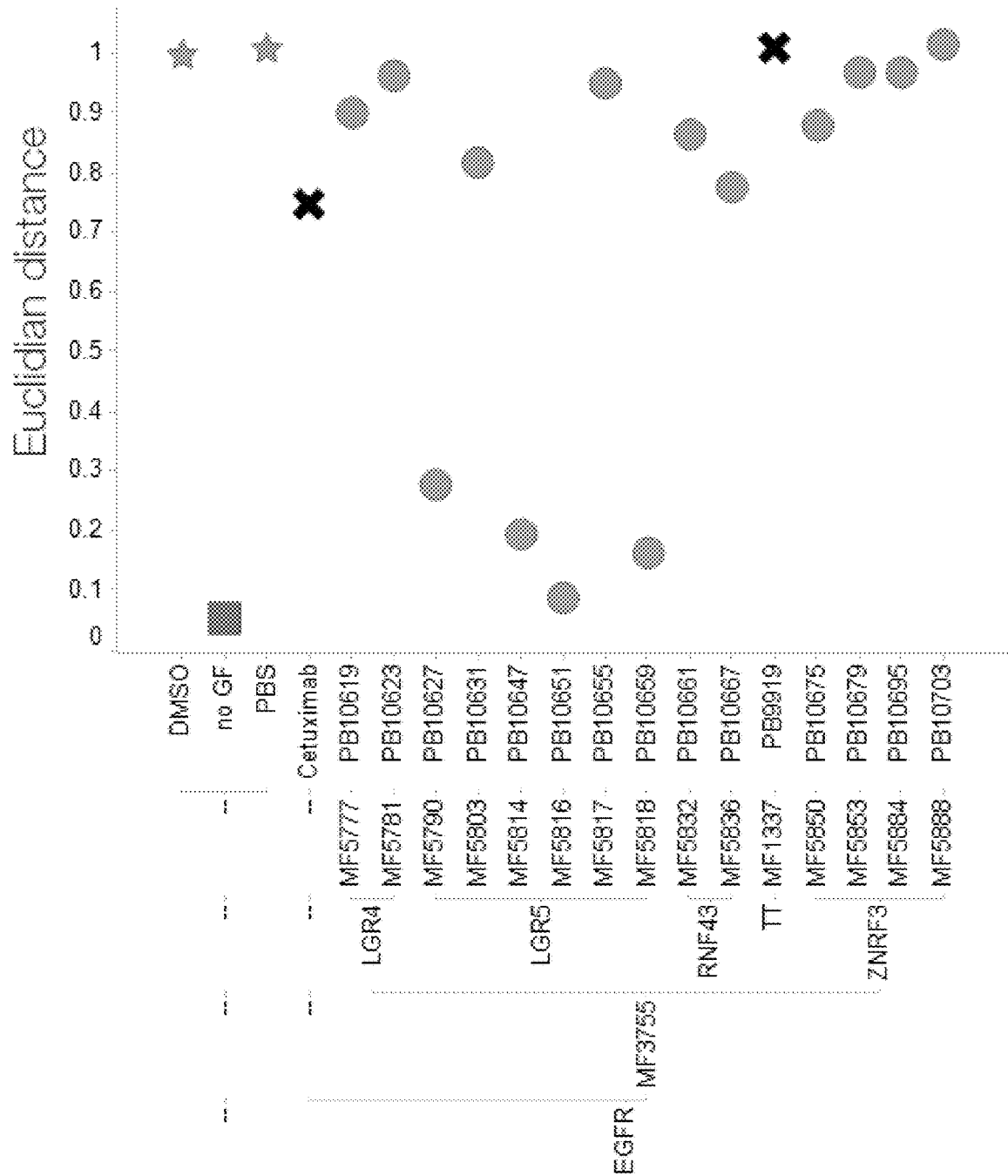

FIG. 11: Example of the validation screen results for one colon tumoroid exposed to EGFR/WNT targeting bispecific antibodies and control treatments.

The lower the Euclidian distance, the more potent the treatment effect; 1 equals normal growth. PB10651 (EGFR/LGR5 antibody with MF3755×MF5816) shows complete growth inhibition at the dose tested (2 µg/ml) and outperforms Cetuximab.

Figure 12:
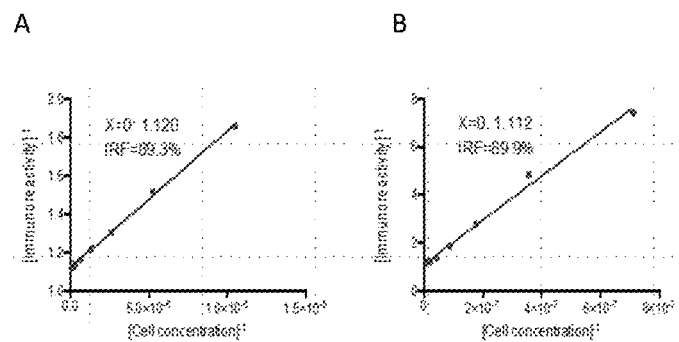

FIG. 12: PB10651 retains immune-reactivity after labelling with $^{125}$I. Immuno-reactivity of radio-active labelled protein. A: Lindmo assay for the anti-EGFR Fab arm in PB10651; B: Lindmo assay for the anti-LGR5 Fab arm of PB10651. There was very little loss of immune-reactivity after labelling of the protein with $^{125}$I.

Figure 13:
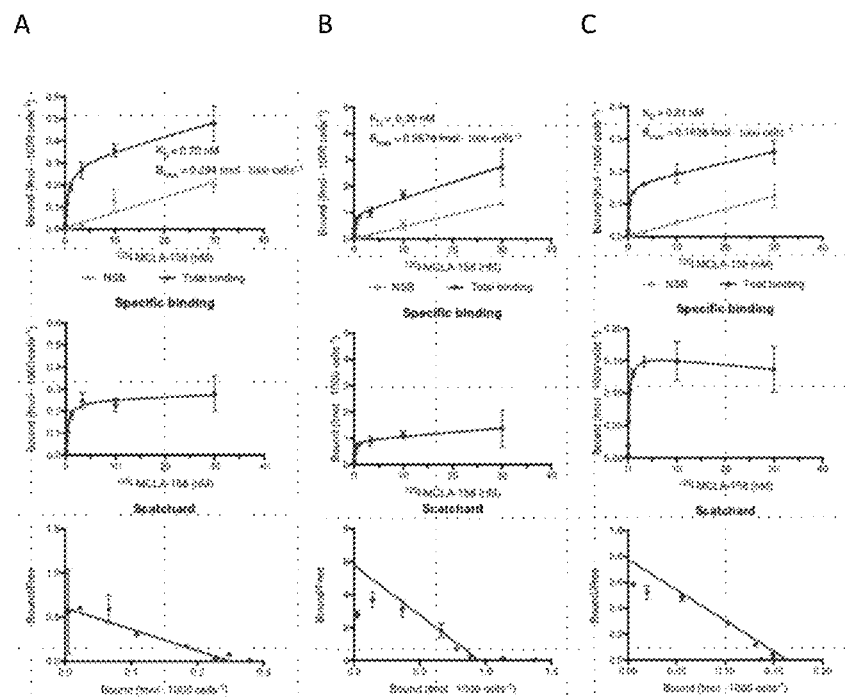

FIG. 13: PB10651 binds with sub-nanomolar affinity to both EGFR and LGR5. Affinity analysis of PB110651 binding to LGR5 and EGFR. A: analysis of PB10651 binding to CHO-LGR5 cells: B: analysis of PB10651 binding to CHO-EGFR cells and C: affinity analysis of PB10651 binding to DLD-1 cells.

Figure 14:
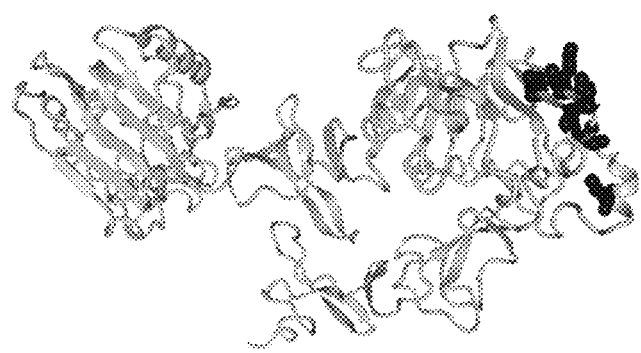

FIG. 14: The anti-EGFR Fab arm in PB10651 binds to residues in domain III of EGFR as determined by shotgun mutagenesis analysis.

The epitope on EGFR recognised by the anti-EGFR Fab arm present in PB10651 is depicted, modelled onto the structure of EGFR (Li et al., 2005: pdb reference 1YY9). Residues that were found to be relevant for the binding of PB10651 are highlighted in the structure.

Figure 15:
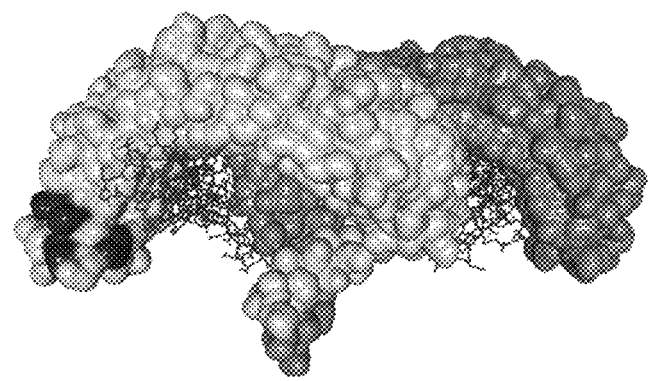

FIG. 15: The anti-LGR5 Fab arm in PB10651 binds to residues present in the N-CAP domain and first leucine-rich repeat of LGR5, as determined by shotgun mutagenesis analysis.

The figure shows the epitope on LGR5 recognised by PB10651, modelled onto the structure of LGR5 in complex with RSPO1 (Peng et al., 2013: pdb reference 4BSR). The residues that are recognised are indicated in black in the left (light grey) LGR5 molecule of the dimer. RSPO1 is indicated in ball and stick.

Figure 16:
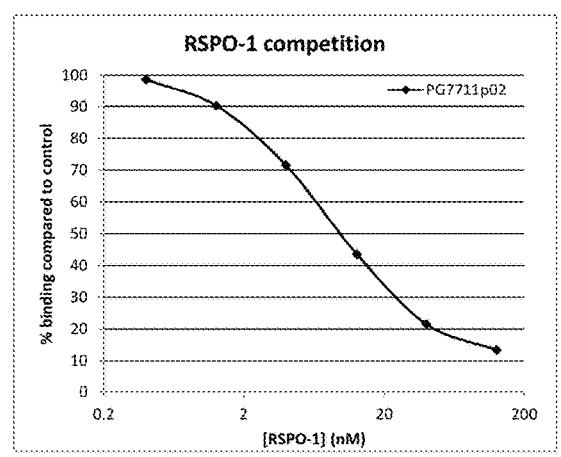

FIG. 16: The copied version of the OMP88R20 anti-LGR5 antibody is dose-dependently inhibited for binding LGR5 by the ligand R-spondin1.

The copied version of OMP88R20 (PG7711) was tested for binding at the EC50 (50 ng/ml) for binding to LGR5 over-expressing cells in the presence of increasing amounts of R-spondin1. The MFI value obtained was normalised to the control (no R-spondin1) value.

Figure 17:
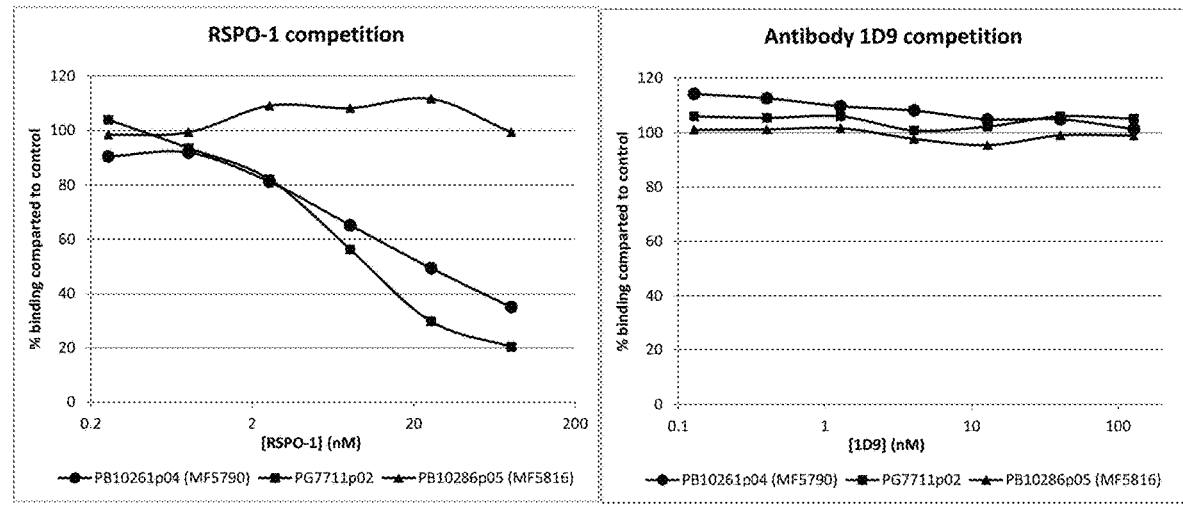

FIG. 17: The anti-11R5 Fab MF5816 present in PB10651 is not inhibited for binding LGR5 in a large molar excess of the ligand R-spondin1.

The copied version of OMP88R20 (PG7711) was tested for binding at 50 ng/ml and bispecifics were tested at 100 ng/ml for binding to LGR5 over-expressing cells in the presence of increasing concentrations of R-spondin1, or of the rat antibody 1D9. Binding of the indicated antibodies was detected with a PE-labeled anti-human IgG secondary antibody. For every point in the curve, the MFI value obtained was normalised to (divided by) the value found in the control (no R-spondin1) situation.

Figure 18:
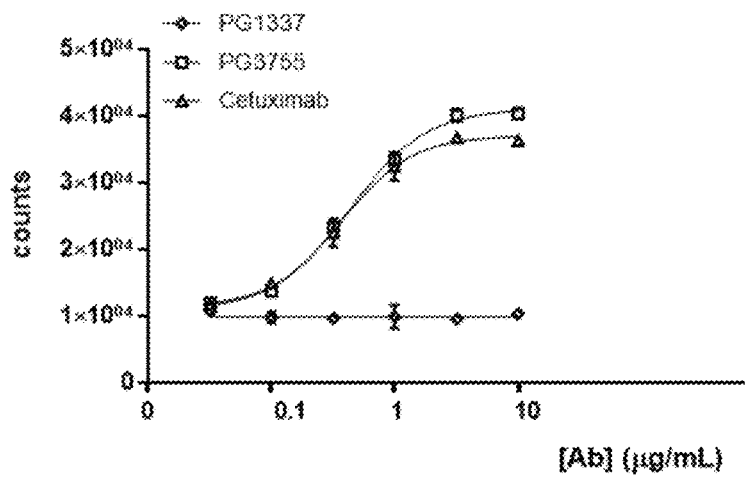

FIG. 18: Bivalent, mono-specific PG3755 potently inhibits EGFR-mediated signalling.

The proliferation (measured as fluorescence counts after alamar blue addition to the cells: Y-axis) of A431 cells was measured in the presence of 62.5 ng/ml of human EGF and increasing amounts of the indicated anti-EGFR antibodies. PG1337 served as non-binding (negative) control. An increasing number of counts is indicative of an increased number of cells and thereby of blocking EGFR-mediated signalling.

Figure 19:
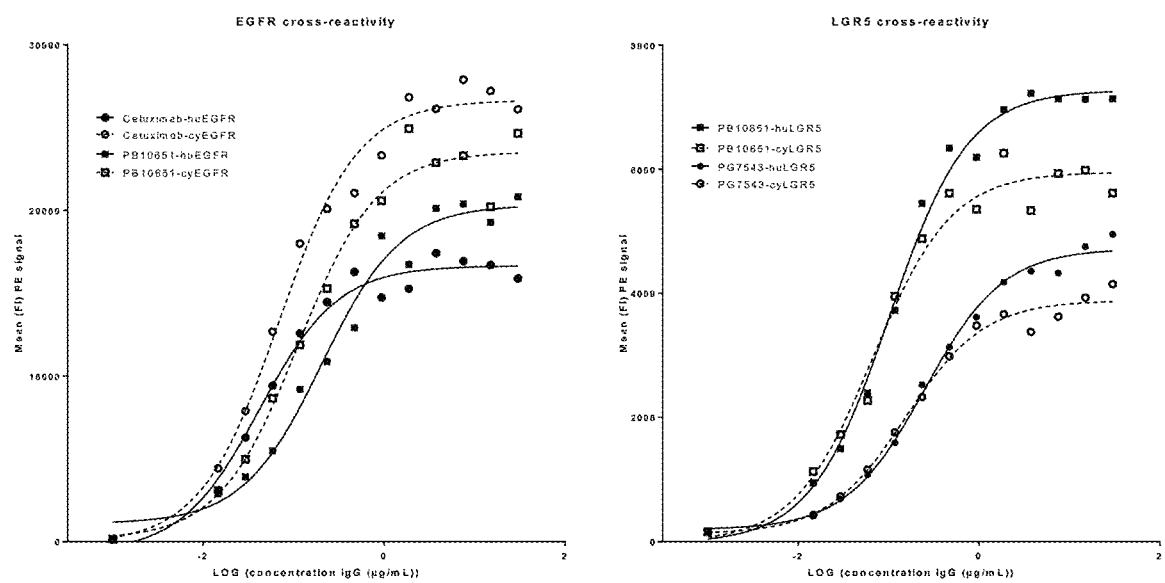

FIG. 19: Afucosylated PB10651 binds with comparable affinity to the cynomolgus orthologues of both EGFR and LGR5.

MFI values obtained after staining with the indicated antibody at the indicated concentration in FACS are depicted as a function of the concentration of antibody used. For EGFR, cetuximab was used as positive control for cynomolgus EGFR binding. For LGR5, the copied version of hu8E11v2 (PC7543) from Genentech was used as positive control for cynomolgus LGR5 binding.

Figure 20:
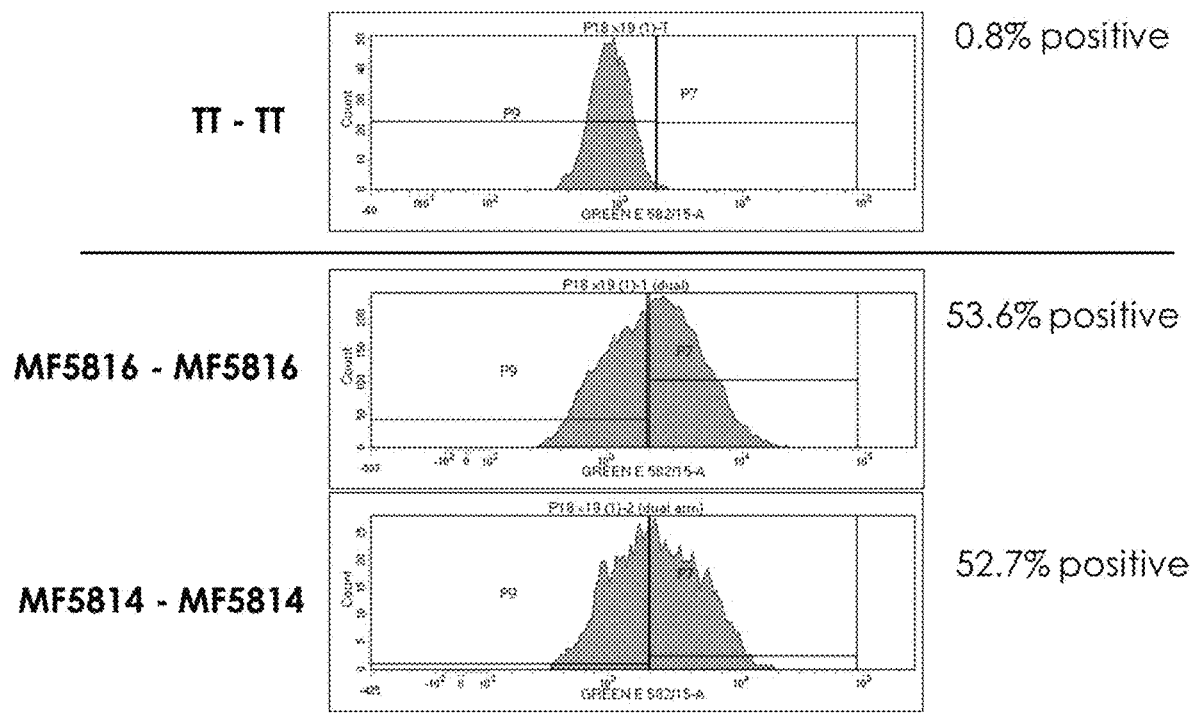

FIG. 20: Staining of patient-derived organoids in FACS using lead anti-LGR5/EGFR bispecific antibodies visualises LGR5 expression.

An organoid sample derived from a colorectal cancer patient (P18) was stained using two different anti-LGR5 antibodies (MF5816 and MF5814) and a negative control that recognizes Tetanus Toxin (TT). The staining of the TT antibody was used to set the threshold for the staining of the two anti-LGR5 antibodies. With the TT staining set at 0.8%, the MF5816 and MF5814 antibodies showed comparable staining levels with 53.6% and 52.7% of the cells scored positive for LGR5 expression.

FIG. 21: Staining and sorting of patient-derived organoids using lead bispecific anti-LGR5/EGFR bispecific antibodies enriches for LGR5-expressing (cancer stem) cells.

A colorectal cancer organoid line (P18T) was used for FACS staining and sorting of the top (positive) and bottom (negative) 15% of stained cells identified by the anti-LGR5 antibodies MF5814 and MF5816. 2000 single cells were sorted for each population and used to generate cDNA for quantitative PCR. The expression of B2M was used as an endogenous control, and the expression of the LGR5 mRNA in the positive fraction was represented relative to the negative fraction using the 2-ΔΔCT method and the StepOne 2.2 plus software. The experiment was ran on two separate occasions (Exp. 1 and Exp. 2), with each antibody, and experimental repeats, displaying an increase in LGR5 mRNA in the positive fraction relative to the negative. Error bars represent the relative quantification max, which was produced as part of the analysis using the StepOne 2.2 plus software.

Figure 22:
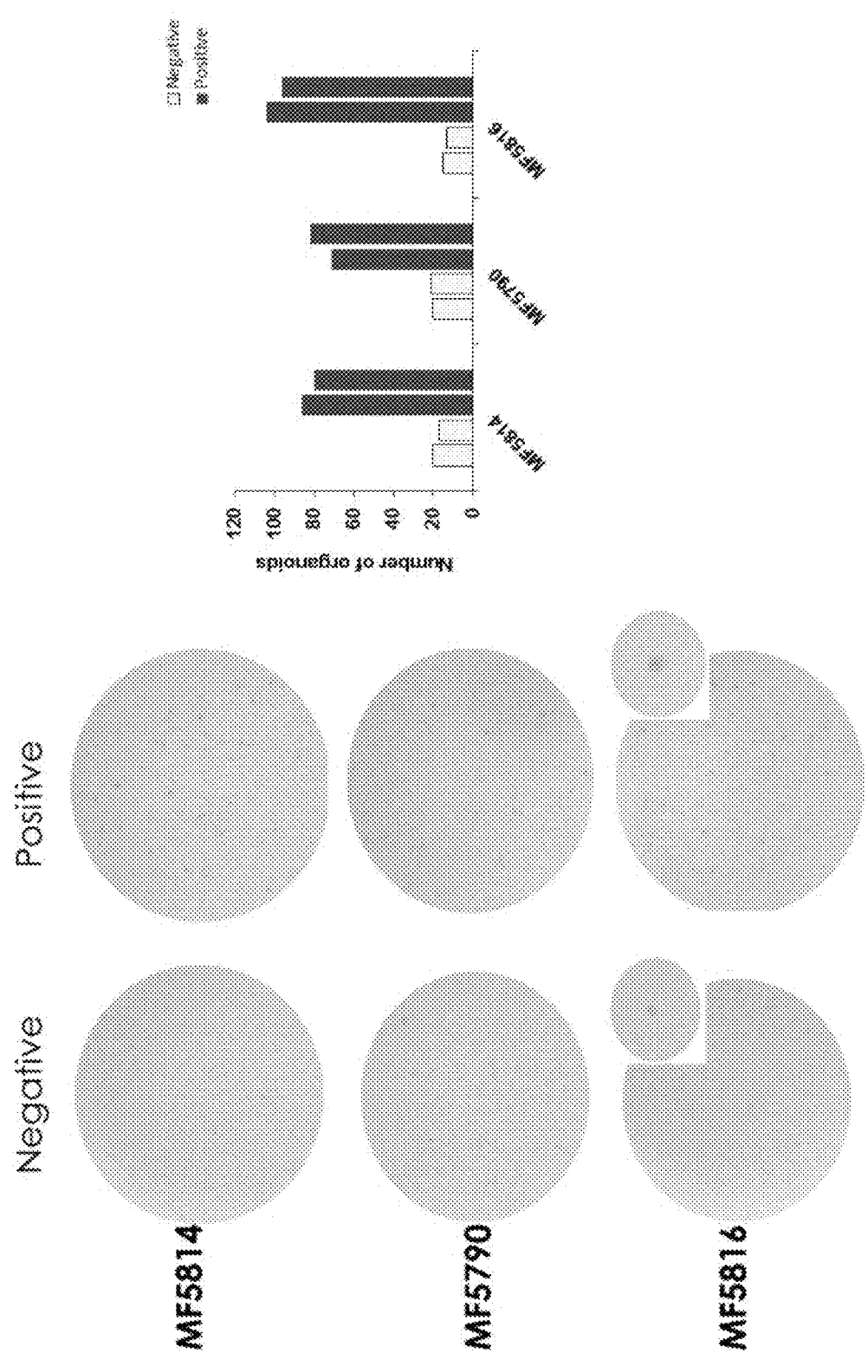

FIG. 22: Sorting of patient-derived organoid for LGR5-expressing cells using lead anti-LGR5/EGFR bispecific antibody enriches for tumour-initiating cells.

Left: pictures of the organoids depict one of the BME drops and were captured using an Olympus MVX10 MacroView microscope. The inset on the MF5816 picture displays a closer view of one of the organoids in the drop. Right: bar graph depicting the number of organoids counted after two weeks of growth found in the LGR5-positive and -negative cell population.

Figure 23:
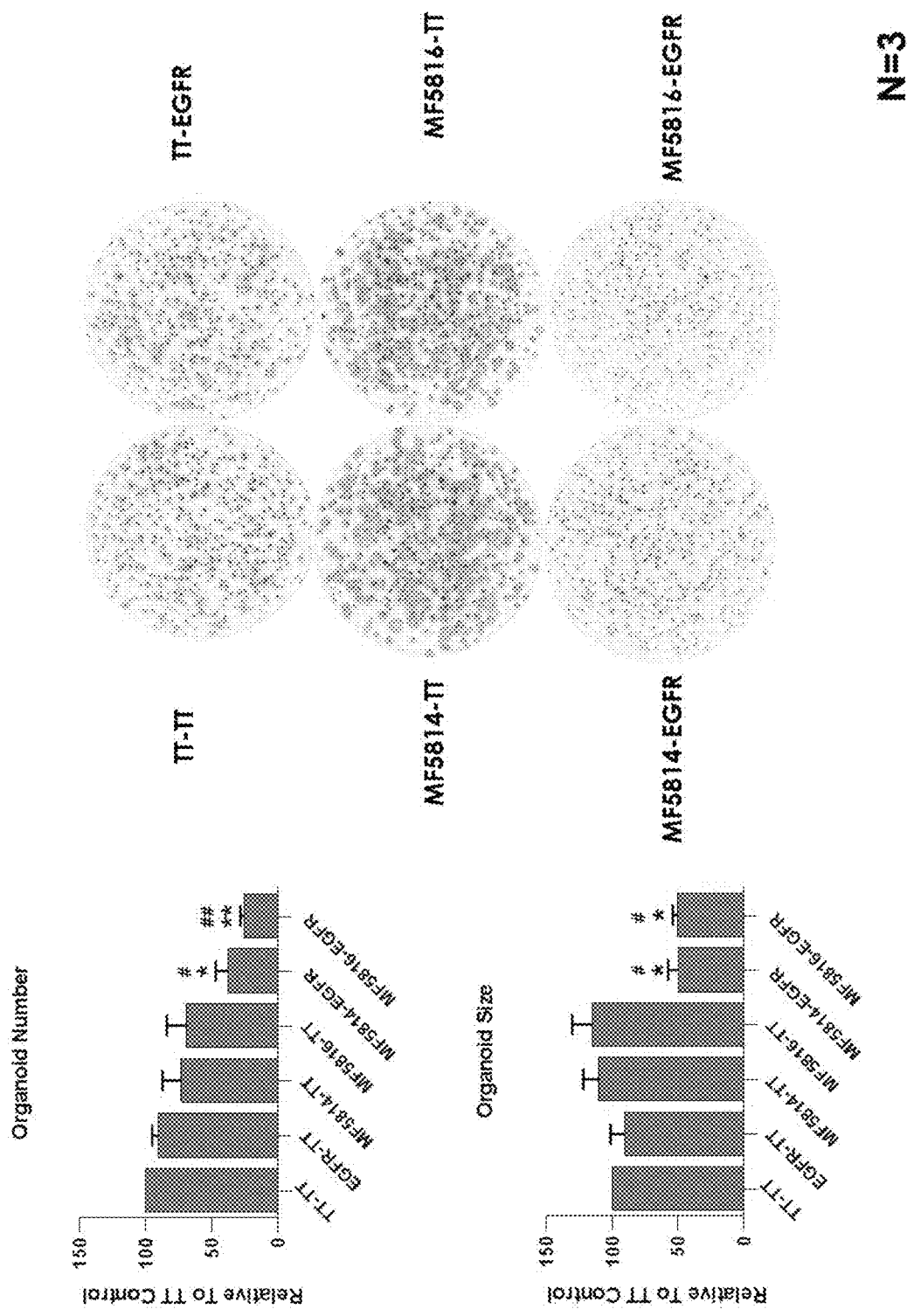

FIG. 23: Treatment of patient-derived organoids with lead anti-LGR5/EGFR bispecific antibody potently inhibits organoid outgrowth.

Left: bar graphs depicting the average organoid number (top) and organoid size (bottom) found after the different treatments with the indicated antibodies (indicated below the graphs). Right: representative examples of images obtained from the organoids after the different treatments. Single cells were seeded and left to establish organoids for three days. On day three the media was removed and replaced with media containing the antibodies at a concentration of 2 µg/mL. The organoids were further cultured for another 7 days. On day 7 the organoids were scanned using an Olympus ScanR using the ×4 light objective, and the number of organoids quantified using ImageJ running an in-house designed macro. The data is presented relative to the TT control, and a two-tailed, paired sample T-Test was run to assess for significant differences between treatments. Error bars represent standard deviation. *=p≤0.05 relative to TT. **=p≤0.001 relative to TT. #=p≤0.05 relative to EGFR-TT. ##=p≤0.001 relative to EGFR-TT.

Figure 24:
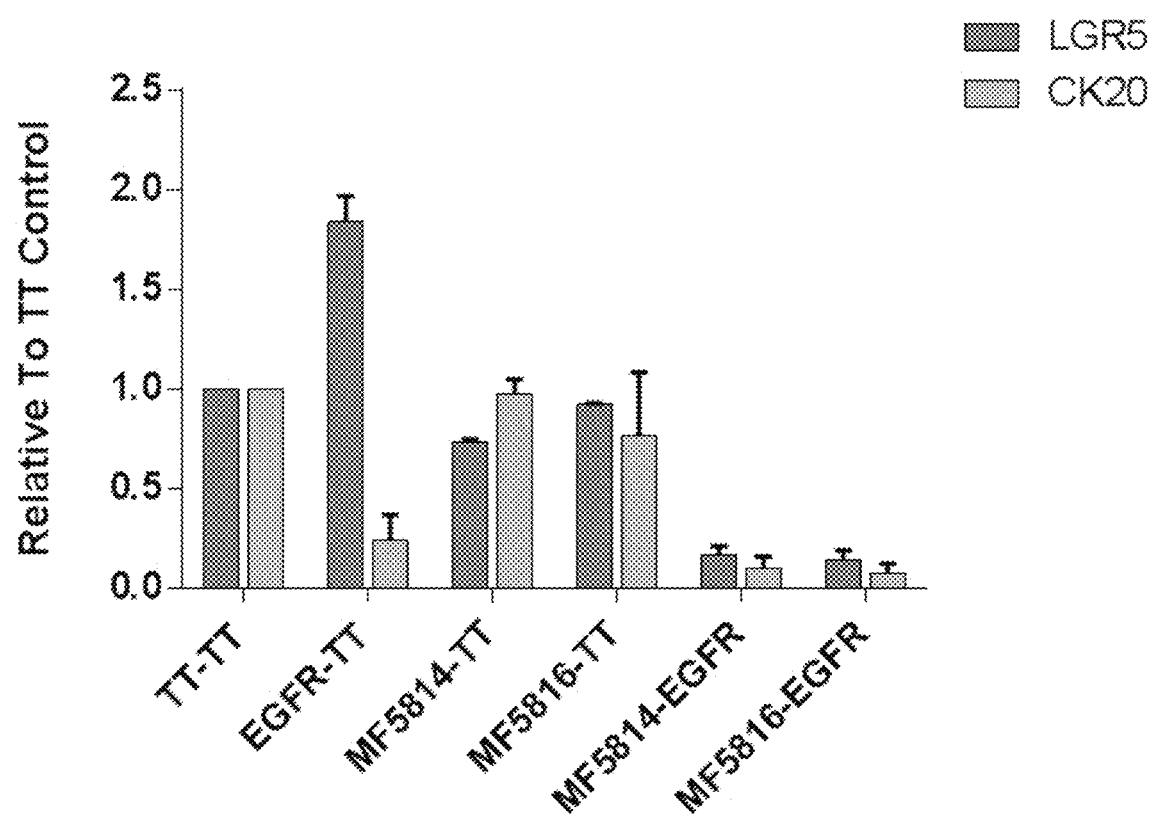

FIG. 24: LGR5×EGFR bispecifics potentiate the reduction of the non-differentiated cell population Single cells were seeded and grown for three days before being treated with the antibodies. After seven days, total RNA was extracted and used for quantitative real-time PCR analysis to detect the mRNA levels of LGR5 and CK20 (a marker of differentiation). Differences in expression were detected using the 2-ΔΔCT method. The data is presented relative to the negative control (TT-TT). The experiment was carried out on two separate occasions, and the average of the two experiments shown. Error bars represent the standard deviation of the two experiments.

Figure 25:
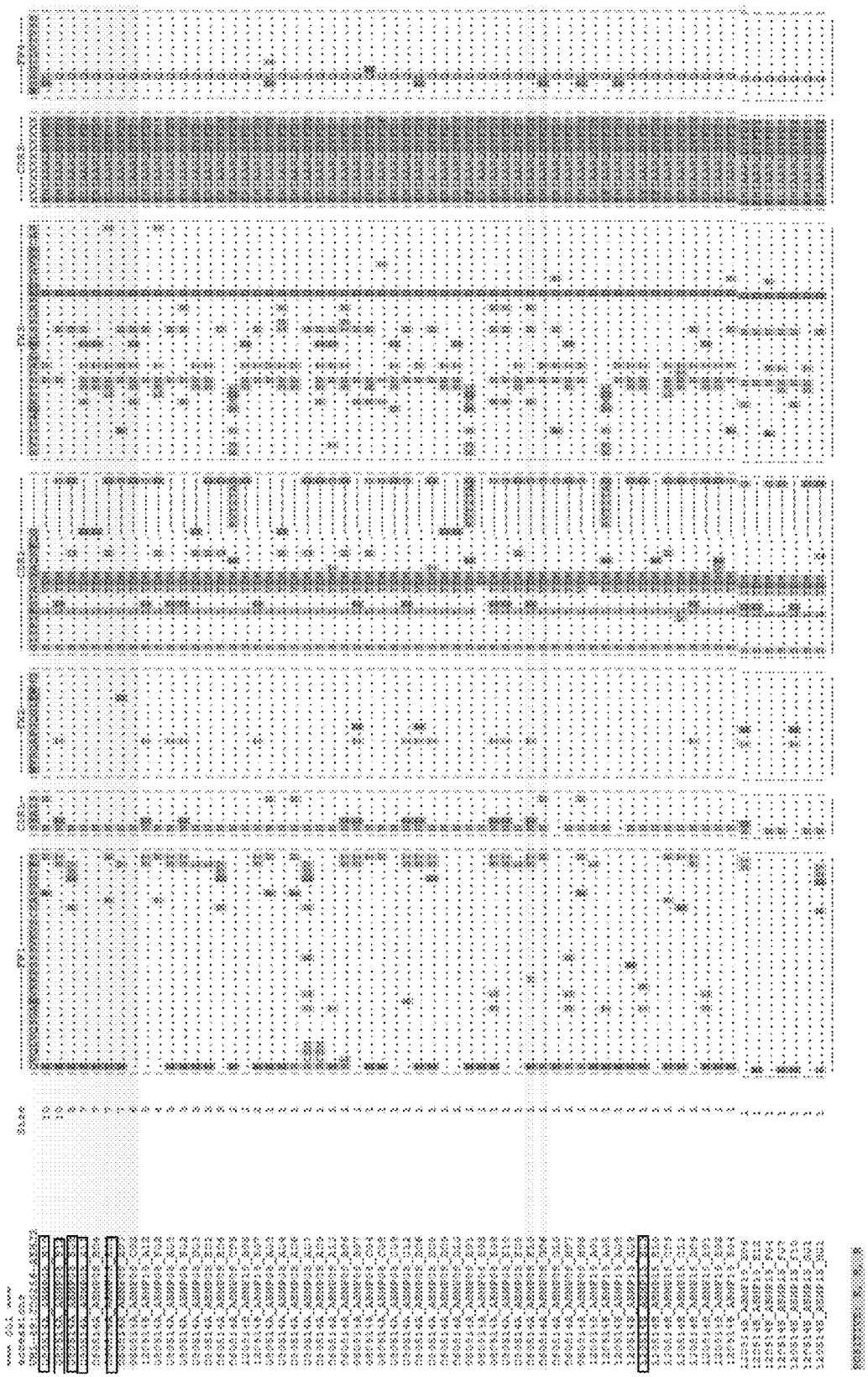
Figure 25B:
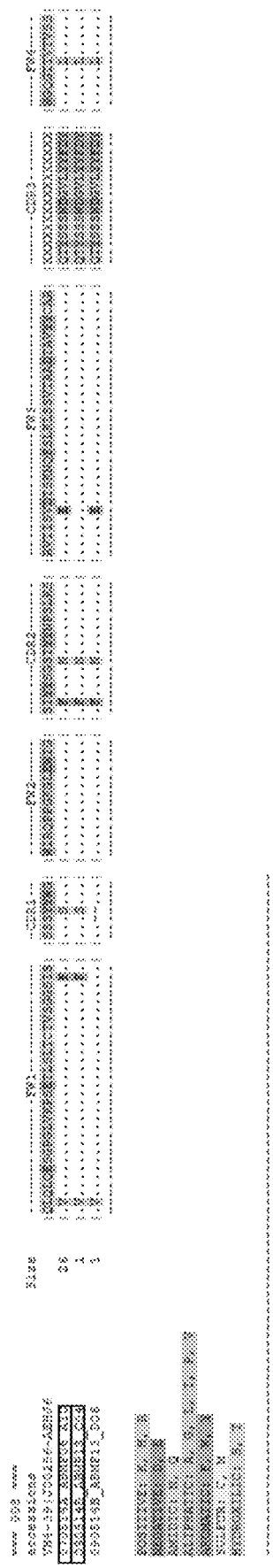
Figure 25C:
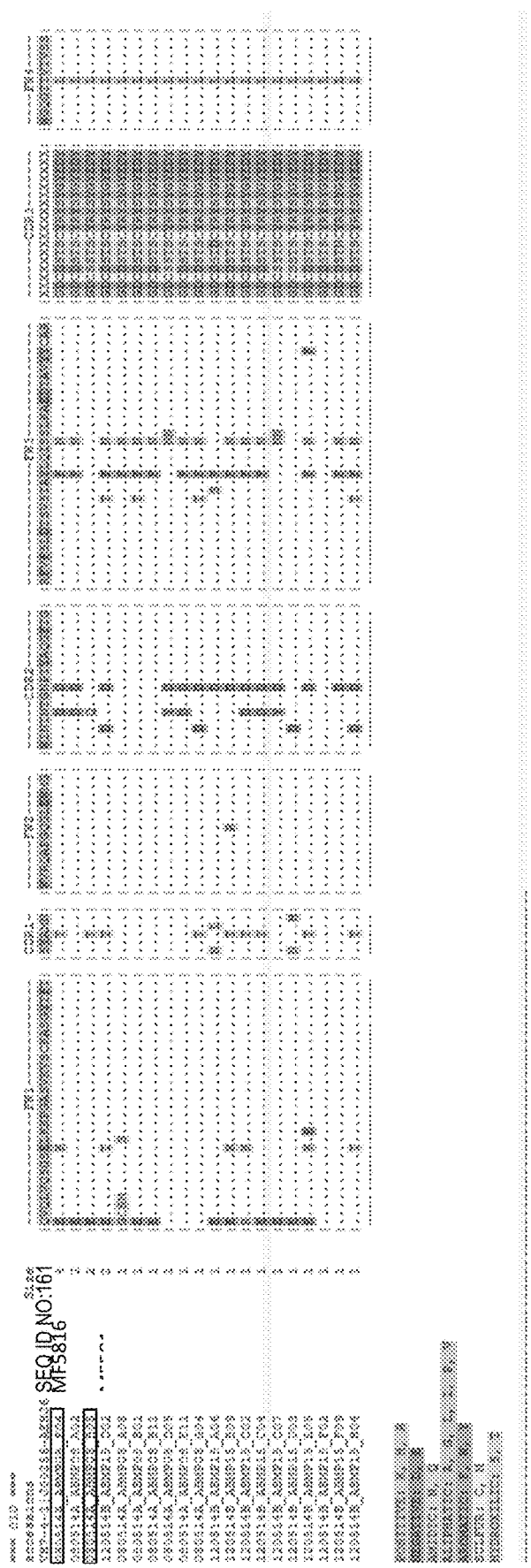

FIG. 25: Examples of superclusters indicating amino acid changes that are tolerated in a VH; and/or CDR therein of the present invention without losing binding specificity.

FIG. 26: Comparison of the potency of PB10651 versus Cetuximab in inhibiting growth of patient-derived tumoroids and organoids derived from normal tissue in vitro Examples of the effects of treatments with concentrations ranges of PB10651 and Cetuximab on organoid cultures from organoids derived from normal tissue and from cancerous tissue (A and B). FIG. 26C: IC50 values for growth inhibition obtained using patient-derived tumoroids and organoids derived from normal tissue. The ratio in the third column depicts the ratio IC50(Cetuximab)/IC50(PB10651).

Figure 27:
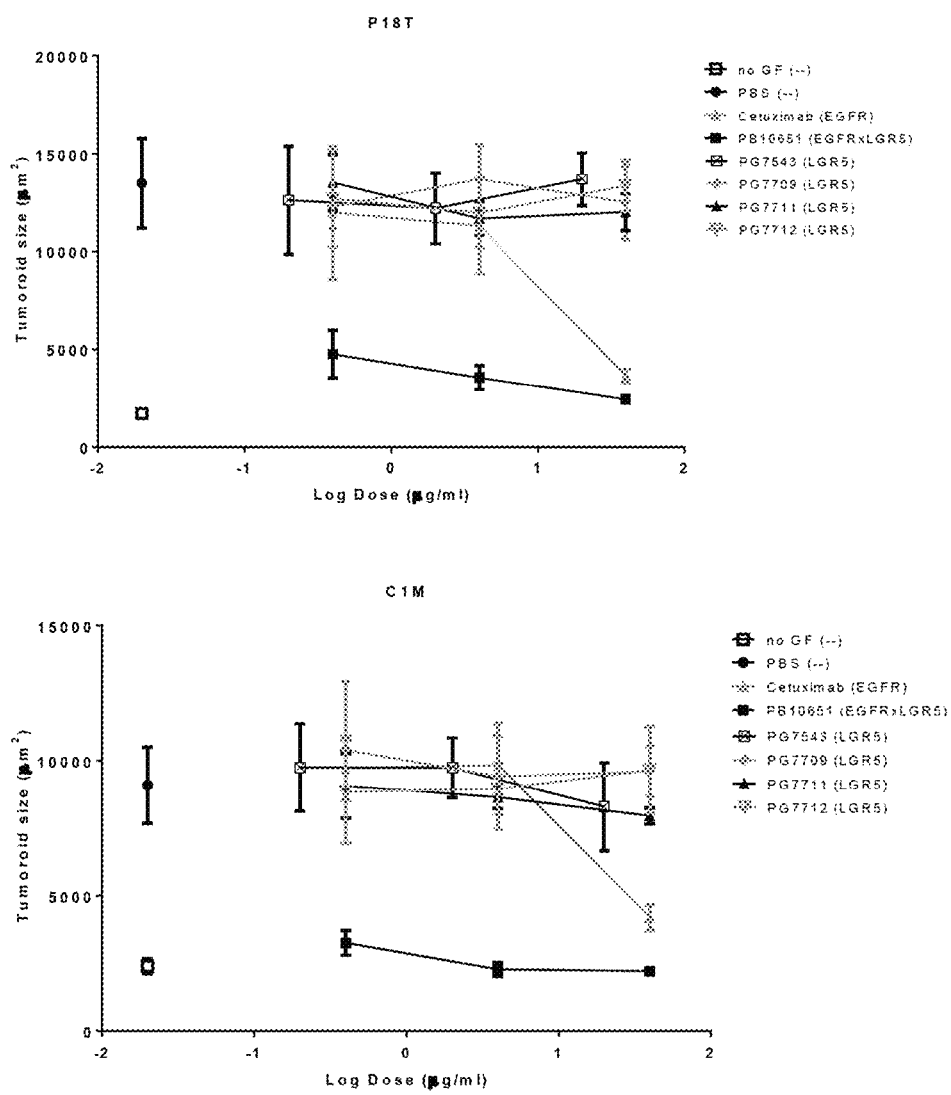

FIG. 27: PB10651 is significantly more potent than monospecific anti-EGFR and anti-LGR5 antibodies in inhibiting organoid growth in vitro.

Figures 28, 28A:
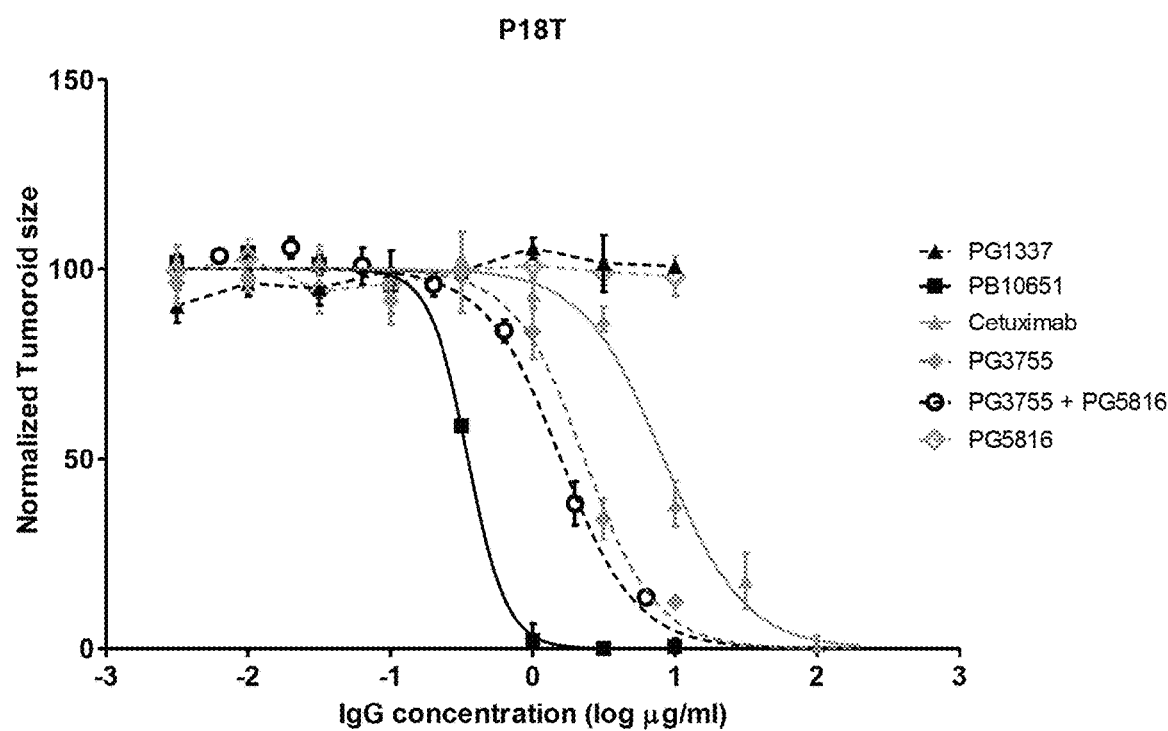

In vitro treatment of p18T (A) and C1M (B) organoid cultures in 3D with the indicated antibodies. Organoid size is plotted as a function of the concentration of antibody used. Anti-LGR5 antibodies do not show any effects on organoid growth:

FIG. 28: PB110651 is more potent in reducing organoid growth in vitro than a mix of the parental bivalent, monospecific antibodies.

The figure shows growth inhibiting effects of the reference antibodies PG3755 (EGFR bivalent, mono-specific). PG5816 (LGR5 bivalent, mono-specific) or an equimolar combination thereof and P310651 (EGFR/LGR5 bispecific) on the tumoroid line P18T in the presence of EGF. A. P18T organoid size is depicted as a function of antibody concentration used for treatment. Organoids treated with PG5816 showed no growth inhibition; PG3755 significantly reduced growth, but not to the same extent as PB10651. The combination of PG3755 and PG5816 was also significantly less potent than PB10651 in inhibiting growth of P18T tumoroids. B. A comparison of the IC50 values for growth inhibition found for treatment of the indicated organoids (top) with the indicated antibodies (left panel). The IC50 values found for PB10651 are always lower than those found for the mix of the parental antibodies.

Figure 29:
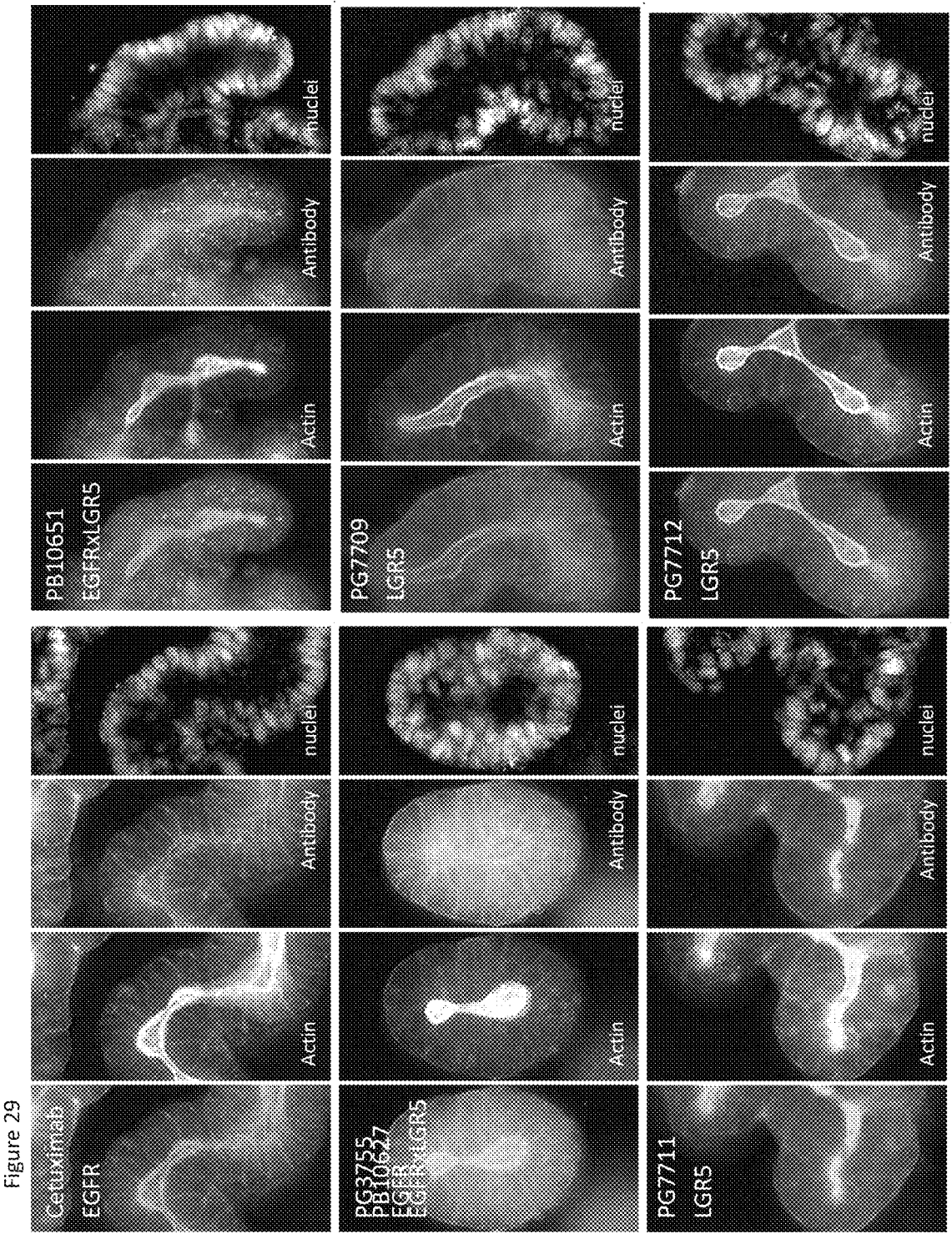

FIG. 29: In vitro organoid treatment with PB10651 causes intra-cellular localisation of antibody that is not observed with monospecific, bivalent antibodies directed to LGR5 or EGFR.

After 24 hours of antibody treatment, organoids were fixed, permeabilised and stained for human IgG to reveal (sub-) cellular localisation of antibody. Only in the case of PB10651, a punctate intra-cellular staining was observed that was absent in the organoids treated with bivalent, mono-specific antibodies. In the latter case, antibody was concentrated and localised onto the cell membrane.

Figure 30:
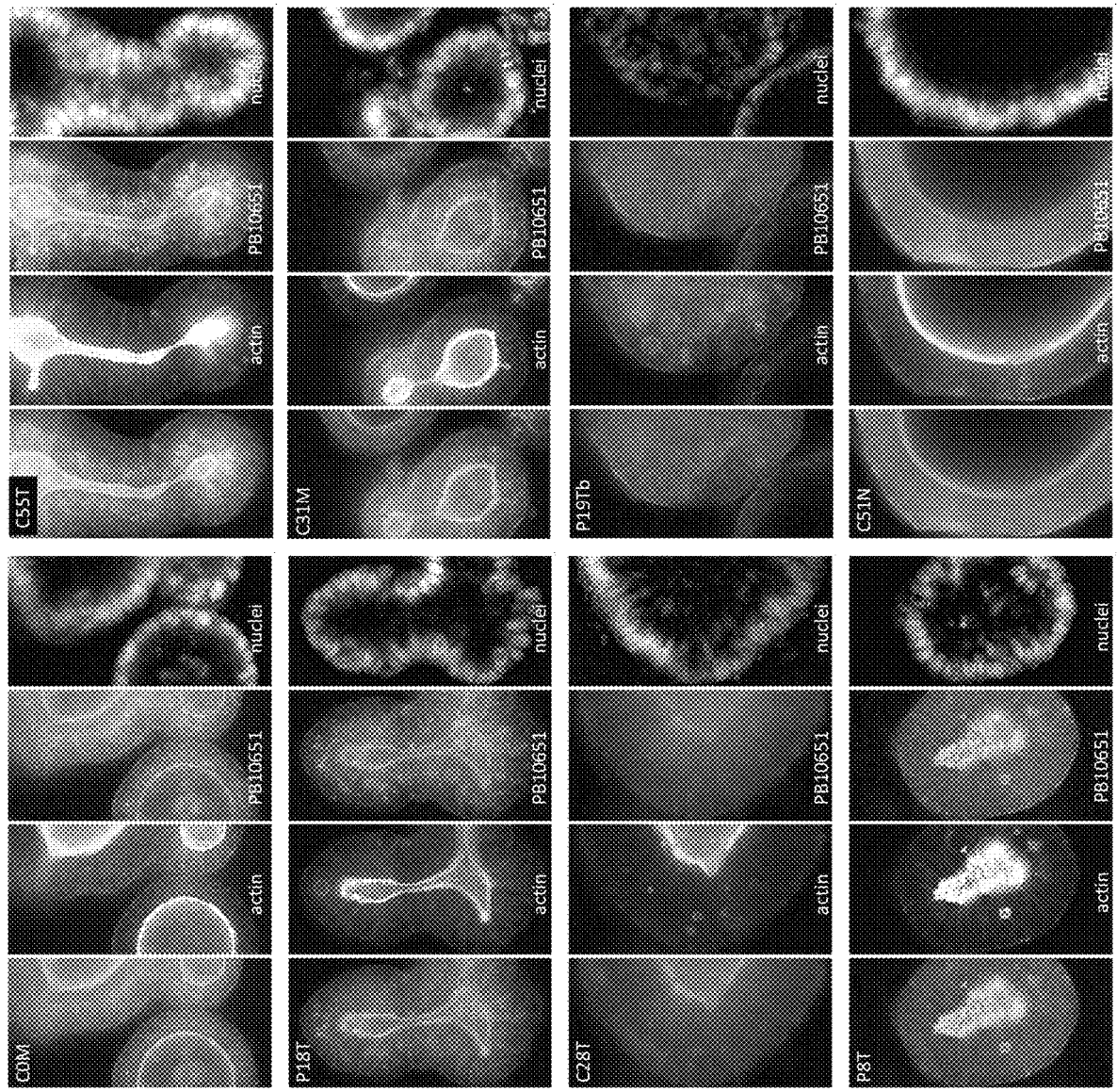

FIG. 30: Organoids that are responsive to treatment with PB0651 show intra-cellular localisation of antibody that is not observed after treatment of organoids that are not responsive to the treatment.

After 24 hours of antibody treatment, organoids were fixed, permeabilised and stained for human IgG to reveal (sub-) cellular localisation of antibody. The different organoids that were responsive to treatment with PB10651 (C0M, C55T, P18T, C31M) showed intra-cellular staining of antibody, whereas the organoids that were non-responsive showed cell surface localisation of PB0651 (C28T, P19Tb, P8T, C51N).

Figure 31:
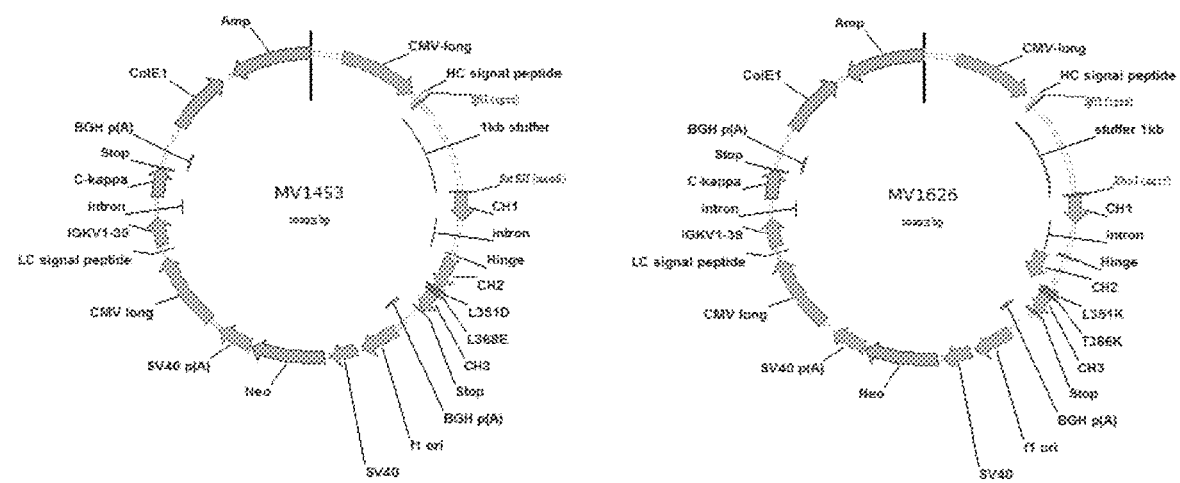

FIG. 31: Vector maps of MV1453 and MV1626 plasmids.

Figure 32:
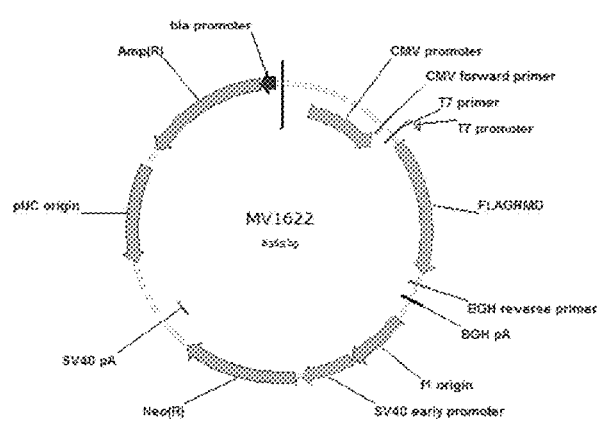

FIG. 32: Vector map of MV1622 (RMD expression vector).

Figure 33:
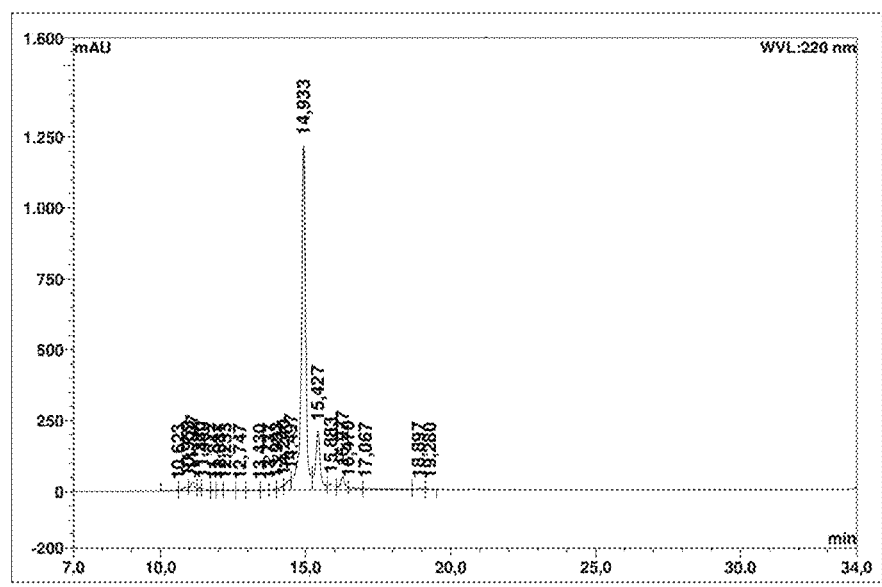

FIG. 33: CEX-HPLC profile of afucosylated PB10651.

Figure 34:
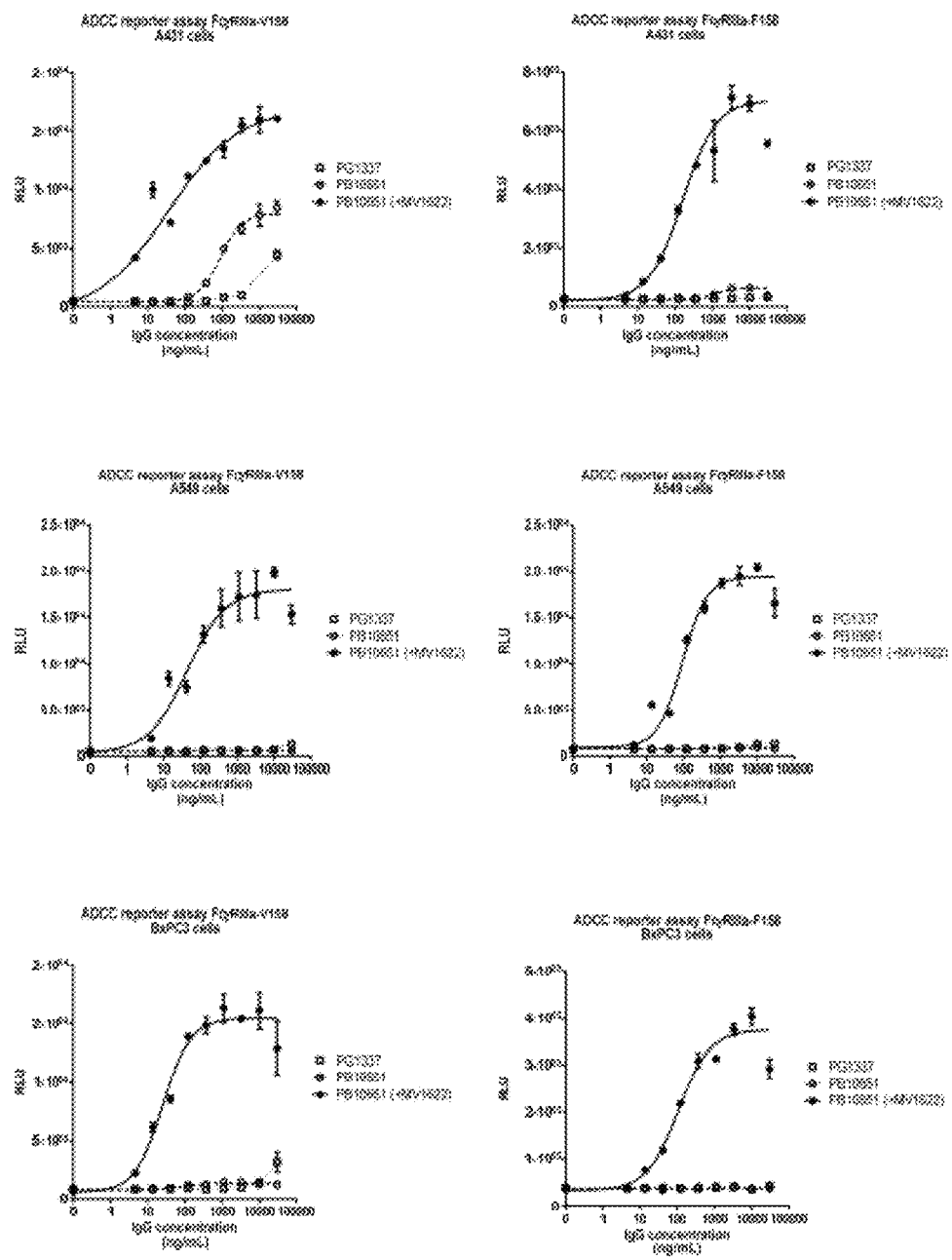

FIG. 34: Results of the ADCC reporter assay of PB10651 (ADCC-enhanced) compared to PB10651(non-enhanced) and PG11337 (control).

Figure 35:
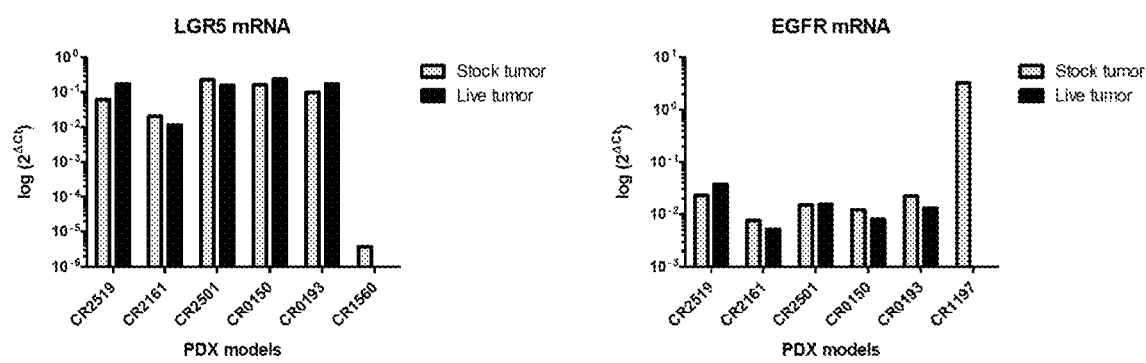

FIG. 35: Expression of EGFR and LGR5 in patient-derived xenograft (PDX) models.

Expression of EGFR and LGR5 genes in live study and frozen stock tumors was measured by TaqMan real time PCR. Expression is represented as the log-transformed value obtained with the 2-ΔΔCT method, using GAPDH as housekeeping gene. Tumors extracted from live animals presented gene expression values similar to the reference stock tumors.

Figure 36:
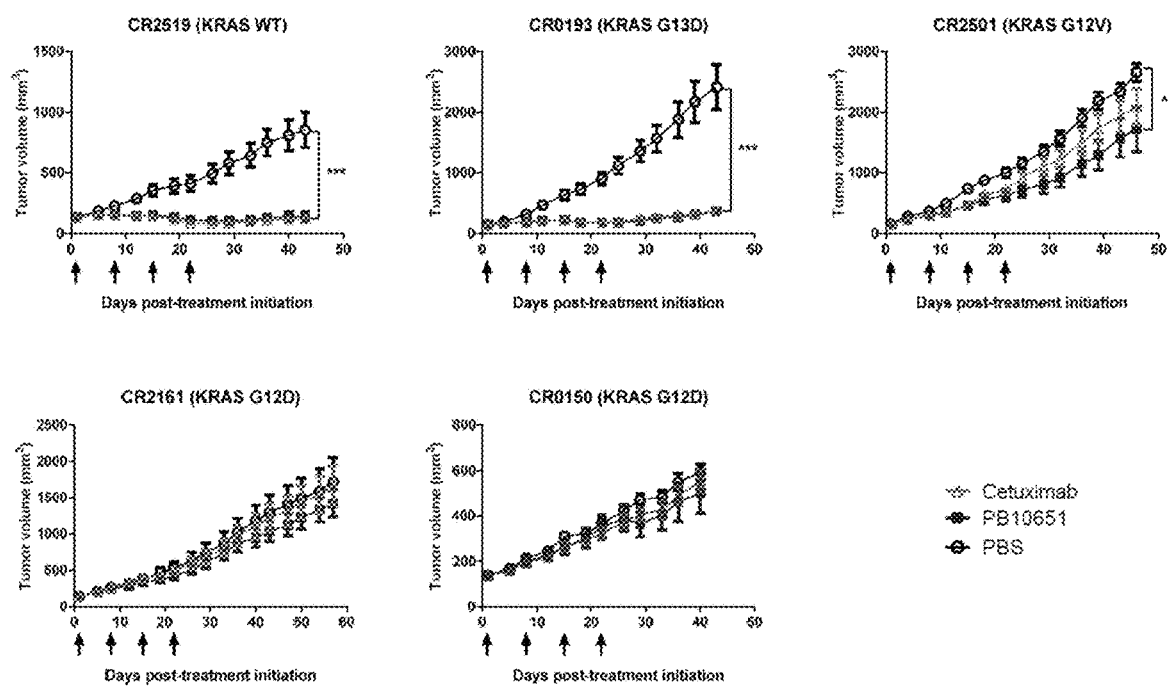

FIG. 36: PB10651 inhibits the in vivo growth of PDX.

The colorectal PDX models were treated weekly (arrows) with PB10651 or Cetuximab or PBS. Tumor growth (indicated in mm3) was followed during and after cessation of the treatment. Models responsive to cetuximab (one WT and one KRAS G13D mutant) also responded to PB10651. One out of three KRAS G12V/D mutant models that did not respond to Cetuximab displayed significant tumor growth inhibition with PB10651.

Figure 37:
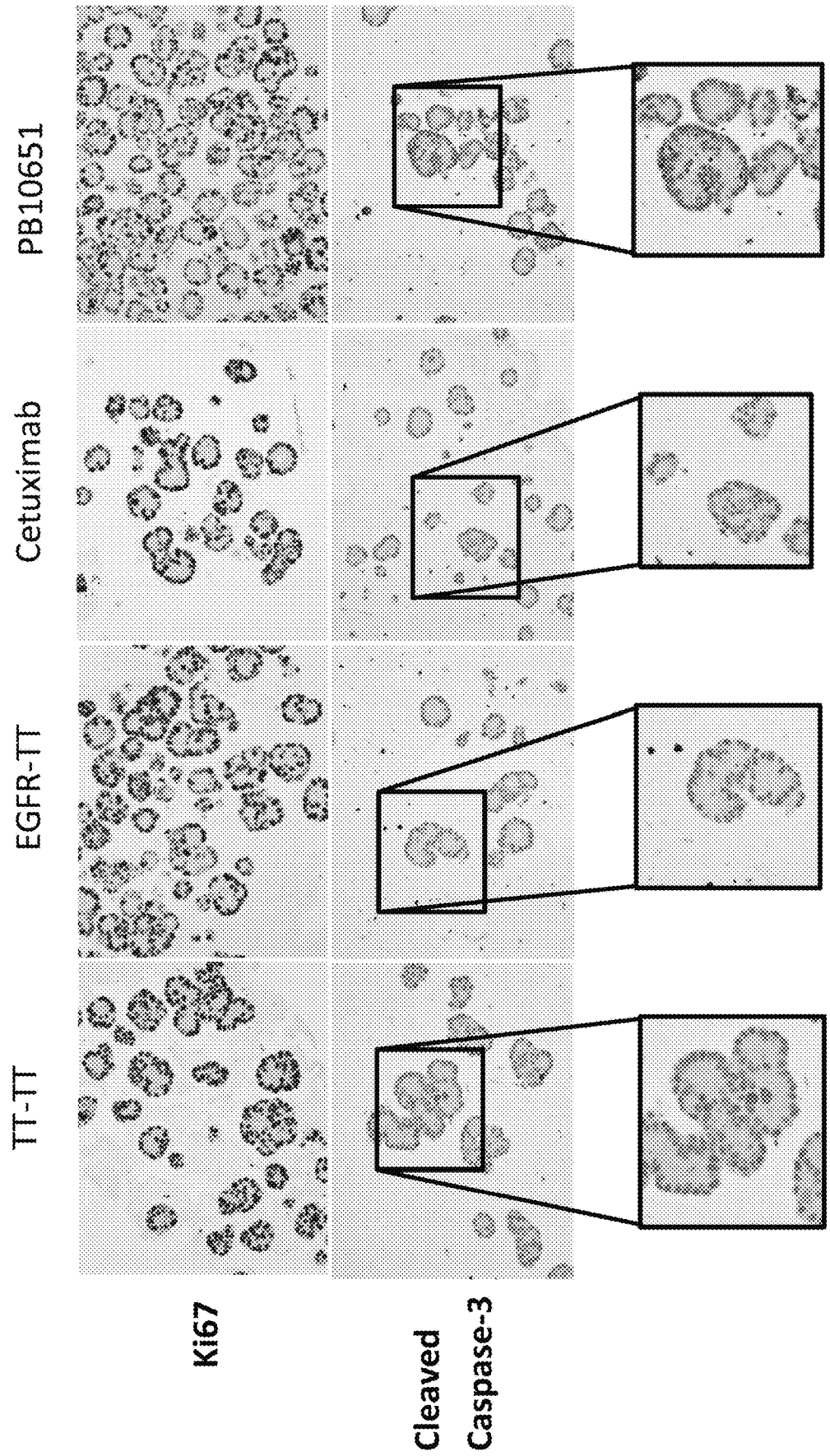

FIG. 37: Treatment with PB10651 causes a significant reduction in the number of proliferating cells in the tumour.

Immunohistochemical Staining of P18 Tumoroids After 48 Hours of Treatment (2 μg/ml). The top panel depicts a marker of proliferation (ki67), and the lower panel a marker of apoptosis (cleaved caspase-3). Images were taken using a ×20 objective, brown staining indicates expression, with nuclei counter stained using haematoxylin FIG. 38: PB10651 is significantly more potent than cetuximab in inhibiting organoid growth in vivo.

A The Effect of Weekly Antibody Dosing on P18 Xenograft Growth.

Once tumours reached an average size of 50 mm$^3$ antibody treatments began (day 0) and the relative change in volume is plotted. Mice were treated once a week (indicated by arrows). All tumour volumes within a treatment group were averaged and plotted; the number of xenografts at each time point is represented in the table. Error bars represent the standard error of the mean. *=P<0.01 compared to PBS. #=P<0.01 compared to cetuximab as determined by paired t-test analysis.

B. The Effect of Weekly Antibody Dosing on C31M Xenograft Growth.

Once tumours reached an average size of 30 mm$^3$ antibody treatments began (day 0) and the relative change in volume is plotted. Mice were treated once a week (indicated by arrows). All tumour volumes within a treatment group were averaged and plotted; the number of xenografts at each time point is represented in the table. Error bars represent the standard error of the mean. *=P<0.01 compared to PBS, #=P<0.05 compared to cetuximab as determined by paired t-test analysis FIG. 39: Annotated amino acid sequence of human LGR5.

Leader indicates the amino acid sequence that is cut from the mature protein, the N-region spans amino acids 21-70 inclusive; LRR stands for leucine-rich repeat region, LLR1 is leucine-rich repeat region 1; LRR2 is leucine-rich repeat region 2 etc. LLR1 starts at amino acid 71 and ends at amino acid 94 (inclusive); LLR2 starts at 95 and ends at 118 inclusive. CRL is the cysteine rich linker region. TM indicates the various transmembrane regions and C-TERM the c-terminal end of the protein. The annotated parts together form one consecutive sequence designated SEQ ID NO: 1. This complete sequence is SEQ ID NO: 1 this numbering prevails even if for some reason another sequence is also listed as SEQ ID NO: 1.

FIG. 40: Annotated amino acid sequence of wild type, human EGFR (GenBank NM_005228).

The signal peptide, extra-cellular part, predicted transmembrane helix and intracellular tyrosine kinase including the C-terminal tail are all indicated. The annotated parts together form one consecutive sequence designated SEQ ID NO: 2. This complete sequence is SEQ ID NO: 2 this numbering prevails even if for some reason another sequence is also listed as SEQ ID NO: 2.

EXAMPLES

As used herein "MFXXXX" wherein X is independently a numeral 0-9, refers to a Fab comprising a variable domain wherein the VH has the amino acid sequence identified by the 4 digits. Unless otherwise indicated the light chain variable region of the variable domain typically has a sequence of FIG. 3. The light chain has a sequence as depicted in FIG. 3. "MFXXXX VH" refers to the amino acid sequence of the VH identified by the 4 digits. The MF further comprises a constant region of a light chain and a constant region of a heavy chain that normally interacts with a constant region of a light chain. PG refers to a monospecific antibody comprising identical heavy and light chains. PB refers to a bispecific antibody with two different heavy chains. The VH/variable region of the heavy chains differs and typically also the CH3 region, wherein one of the heavy chains has a KK mutation of its CH3 domain and the other has the complementing DE mutation of its CH3 domain (see for reference PCT/NL2013/050294 (published as WO2013/157954). In PB, PG and other codes the numerical indication is sometimes followed by an indication of the production batch. For instance PB10651p06 refers to PB10651 batch 6.

Example: 1

Methods, Materials and Screening of Antibodies
Cell Lines:

Freestyle 293F cells (cat. nr. p/n51-0029) were obtained from Invitrogen and routinely maintained in 293 FreeStyle medium. HEK293T (ATCC-CRL-11268) and CHO-K1 (DSMZ ACC110) cell lines were purchased from ATCC and routinely maintained in DMEM/F12 (Gibco) supplemented with L-Glutamine (Gibco) and FBS (Lonza).

Generation of Recombinant Human and Mouse LGR4, LGR5, ZNRF3 and RNF43 Expression Vectors Human LGR4 Full length human (h)LGR4 was present in vector pEF1_Myc/His (Invitrogen), containing 2 FLAG tags and 2 HA tags (pEF1_hLGR4-FLAG-HA), and was cloned into pVax1 (Invitrogen), resulting in pVax1_hLGR4-FLAG-HA. The insert sequence was verified by comparison with the NCBI Reference sequence NM_018490. The sequence contained the following deviations on amino acid level: P2A in the signal peptide. The insert from construct pEF1_hLGR4-FLAG-HA was recloned into pVax1. Alternative the full length hLGR4 in pVax1 was replaced with a truncated version of hLGR4; hLGR4(ECD)-GPA33(TM)-FLAG resulting in pVax1_hLGR4(ECD)-GPA33(TM)-FLAG.
Amino Acid Sequence Full Length hLGR4-FLAG-HA Insert (Both in pEF1_Myc/his and pVax1) for Expression on Cell Surface SEQ ID NO: 3

MAGPLGLLCFLALGLLGSAGPSGAAPPLCAAPCSCDGDRRVDCSGKGL

TAVPEGLSAFTQALDISMNNITQLPEDAFKNFPFLEELQLAGNDLSFI

HPKALSGLKELKVLTLQNNQLKTVPSEAIRGLSALQSLRLDANHITSV

PEDSFEGLVQLRHLWLDDNSLTEVPVHPLSNLPTLQALTLALNKISSI

PDFAFTNLSSLVVLHLHNNKIRSLSQHCFDGLDNLETLDLNYNNLGEF

PQAIKALPSLKELGFHSNSISVIPDGAFDGNPLLRTIHLYDNPLSFVG

NSAFHNLSDLHSLVIRGASMVQQFPNLTGTVHLESLTLTGTKISSIPN

NLCQEQKMLRTLDLSYNNIRDLPSFNGCHALEEISLQRNQIYQIKEGT

FQGLISLRILDLSRNLIHEIHSRAFATLGPITNLDVSFNELTSFPTEG

LNGLNQLKLVGNFKLKEALAAKDFVNLRSLSVPYAYQCCAFWGCDSVA

NLNTEDNSLQDHSVAQEKGTADAANVTSTLENEEHSQIIIHCTPSTGA

FKPCEYLLGSWMIRLTVWFIFLVALFFNLLVILTTFASCTSLPSSKLF

IGLISVSNLFMGIYTGILTFLDAVSWGRFAEFGIWWETGSGCKVAGFL

AVFSSESAIFLLMLATVERSLSAKDIMKNGKSNHLKQFRVAALLAFLG

ATVAGCFPLFHRGEYSASPLCLPFPTGETPSLGFTVTLVLLNSLAFLL

MAVIYTKLYCNLEKEDLSENSQSSMIKHVAWLIFTNCIFFCPVAFFSF

APLITAISISPEIMKSVTLIFFPLPACLNPVLYVFFNPKFKEDWKLLK

RRVTKKSGSVSVSISSQGGCLEQDFYYDCGMYSHLQGNLTVCDCCESF

LLTKPVSCKHLIKSHSCPALAVASCQRPEGYAVSDCGTQSAHSDYADE

EDSFVSDSSDQVQACGRACFYQSRGFPLVRYAYNLPRVKDSRDYKDDD

DKAGADYKDDDDKLDGGYPYDVPDYAAGAYPYDVPDYA

Of which:

MAGPLGLLCFLALGLLGSAGPSGA: signal peptide SEQ ID NO: 267

APPLCAAPCSCDGDRRVDCSGKGLTAVPEGLSAFTQALDISMNNITQLP
EDAFKNEPFLEELQLAGNDLSFIHPKALSGLKELKVLTLQNNQLKTVPS
EAIRGLSALQSLRLDANHITSVPEDSFEGLVQLRHLWLDDNSLTEVPVH
PLSNLPTLQALTLALNKISSIPDFAFTNLSSLVVLHLHNNKIRSLSQHC
FDGLDNLETLDLNYNNLGEFPQAIKALPSLKELGFHSNSISVIPDGAFD
GNPLLRTIHLYDNPLSFVGNSAFHNLSDLHSLVIRGASMVQQFPNLTGT
VHLESLTLTGTKISSIPNNLCQEQKMLRTLDLSYNNIRDLPSENGCHAL
EEISLQRNQIYQIKEGTFQGLISLRILDLSRNLIHEIHSRAFATLGPIT
NLDVSFNELTSFPTEGLNGLNQLKLVGNFKLKEALAAKDFVNLRSLSVP
YAYQCCAFWGCDSYANLNTEDNSLQDHSVAQEKGTADAANVISTLENEE
HSQIIIHCTPSTGAFKPCEYLLGSWMIRLTVWFIFLVALFFNLLVILTT
FASCTSLPSSKLFIGLISVSNLFMGIYTGILTFLDAVSWGRFAEFGIWW
ETGSGCKVAGFLAVFSSESAIFLLMLATVERSLSAKDIMKNGKSNHLKQ
FRVAALLAFLGATVAGCFPLFHRGEYSASPLCLPFPTGETPSLGFTVTL
VLLNSLAFLLMAVIYTKLYCNLEKEDLSENSQSSMIKHVAWLIFTNCIF
FCPVAFFSFAPLITAISISPEIMKSVTLIFFPLPACLNPVLYVFFNPKF
KEDWKLLKRRVTKKSGSVSVSISSQGGCLEQDFYYDCGMYSHLQGNLTV
CDCCESFLLTKPVSCKHLIKSHSCPALAVASCQRPEGYWSDCGTQSAHS
DYADEEDSFVSDSSDQVQACGRACFYQSRGFPLVRYAYNLPRVKD:
hLGR4 (FL) SEQ ID NO: 268

SR: linker region

DYKDDDDK: FLAG tag SEQ ID NO: 269

AGA: linker region

DYKDDDDK: FLAG tag SEQ ID NO: 269

LDGG: Linker region SEQ ID NO: 270

YPYDVPDYA: HA tag SEQ ID NO: 271

AGA: Linker region

YPYDVPDYA HA tag SEQ ID NO: 271

Amino Acid Sequence hLGR4(ECD)-GPA33-FLAG Insert in pVax1 for Expression on Cell Surface: SEQ ID NO: 4

MPGPLGLLCFLALGLLGSAGPSGAAPPLCAAPCSCDGDRRVDCSGKGL

TAVPEGLSAFTQALDISMNNITQLPEDAFKNFPFLEELQLAGNDLSFI

HPKALSGLKELKVLTLQNNQLKTVPSEAIRGLSALQSLRLDANHITSV

PEDSFEGLVQLRHLWLDDNSLTEVPVHPLSNLPTLQALTLALNKISSI

PDFAFTNLSSLVVLHLHNNKIRSLSQHCFDGLDNLETLDLNYNNLGEF

PQAIKALPSLKELGFHSNSISVIPDGAFDGNPLLRTIHLYDNPLSFVG

NSAFHNLSDLHSLVIRGASMVQQFPNLTGTVHLESLTLTGTKISSIPN

NLCQEQKMLRTLDLSYNNIRDLPSFNGCHALEEISLQRNQIYQIKEGT

FQGLISLRILDLSRNLIHEIHSRAFATLGPITNLDVSFNELTSFPTEG

LNGLNQLKLVGNFKLKEALAAKDFVNLRSLSVPYAYQCCAFWGCDSYA

-continued

```
NLNTEDNSLQDHSVAQEKGTADAANVTSTLENEEHSQIIIHCTPSTGA

FKPCEYLLGSWMIRVALYVGIAVGVVAALIIIGIIIYCCCCRGKDDNT

EDKEDARPNREAYEEPPEQLRELSREREEEDDYRQEEQRSTGRESPDH

LDQDYKDDDDK
```

Of which:

```
MPGPLGLLCFLALGLLGSAGPSGA: signal peptide SEQ ID
NO: 272

APPLCAAPCSCDGDRRVDCSGKGLTAVPEGLSAFTQALDISMNNITQLP
EDAFKNEPFLEELQLAGNDLSFIHPKALSGLKELKVLTLQNNQLKTVPS
EAIRGLSALQSLRLDANHITSVPEDSFEGLVQLRHLWLDDNSLTEVPVH
PLSNLPTLQALTLALNKISSIPDFAFTNLSSLVVLHLHNNKIRSLSQHC
FDGLDNLETLDLNYNNLGEFPQAIKALPSLKELGFHSNSISVIPDGAFD
GNPLLRTIHLYDNPLSFVGNSAFHNLSDLHSLVIRGASMVQQFPNLTGT
VHLESLTLTGTKISSIPNNLCQEQKMLRTLDLSYNNIRDLPSFNGCHAL
EEISLQRNQIYQIKEGTFQGLISLRILDLSRNLIHEIHSRAFATLGPIT
NLDVSFNELTSFPTEGLNGLNQLKLVGNFKLKEALAAKDFVNLRSLSVP
YAYQCCAFWGCDSYANLNTEDNSLQDHSVAQEKGTADAANVTSTLENEE
HSQIIIHCTPSTGAFKPCEYLLGSWMIR: hLGRA(ECD) SEQ ID
NO: 273

VALYVGIAVGVVAALIIIGIIIYCCCCRGKDDNTEDKEDARPNREAYEE
PPEQLRELSREREEEDDYRQEEQRSTGRESPDHLDQ: GPA88
sequence containing the TM SEQ ID NO: 274

DYKDDDDK: FLAG SEQ ID NO: 269
```

Human LGR5

Full length human (h)LGR5 was present in vector pEF1_Myc/His (pEF1_hLGR5-FLAG-HA), containing 2 FLAG tags and 2 HA tags, and was cloned into pVax1 (Invitrogen), resulting in pVax1_hLGR5-FLAG-HA. The sequence was verified by comparison with the NCBI Reference sequence NM_00:3667.3. The insert from construct pEF1_hLGR5-FLAG-HA was recloned into pVax1, resulting in pVax1_hLGR5-FLAG-HA. Alternative the full length hLGR5 in pVax1 was replaced with a truncated version of hLGR5; hLGR5(ECD)-GPA33(TM)-FLAG resulting in pVax1_hLGR5(ECD)-GPA33(TM)-FLAG.

Amino Acid Sequence Full Length hLGR5-FLAG-HA Insert (Both in pEF1_Myc/his and pVax1) for Expression on Cell Surface SEQ ID NO: 5

```
MDTSRLGVLLSLPVLLQLATGGSSPRSGVLLRGCPTHCHCEPDGRMLL

RVDCSDLGLSELPSNLSVFTSYLDLSMNNISQLLPNPLPSLRFLEELR

LAGNALTYIPKGAFTGLYSLKVLMLQNNQLRHVPTEALQNLRSLQSLR

LDANHISYVPPSCFSGLHSLRHLWLDDNALTEIPVQAFRSLSALQAMT

LALNKIHHIPDYAFGNLSSLVVLHLHNNRIHSLGKKCEDGLHSLETLD

LNYNNLDEEPTAIRTLSNLKELGFHSNNIRSIPEKAFVGNPSLITIHF

YDNPIQFVGRSAFQHLPELRTLTLNGASQITEFPDLTGTANLESLTLT

GAQISSLPQTVCNQLPNLQVLDLSYNLLEDLPSFSVCQKLQKIDLRHN

EIYEIKVDTFQQLLSLRSLNLAWNKIAIIHPNAFSTLPSLIKDLSSN

LLSSFPITGLHGLTHLKLTGNHALQSLISSENFPELKVIEMPYAYQCC

AFGVCENAYKISNQWNKGDNSSMDDLHKKDAGMFQAQDERDLEDFLLD

FEEDLKALHSVQCSPSPGPFKPCEHLLDGWLIRIGVWTIAVLALTCNA

LVTSTVFRSPLYISPIKLLIGVIAAVNMLTGVSSAVLAGVDAFTFGSF

ARHGAWWENGVGCHVIGFLSIFASESSVFLLTLAALERGFSAKYSAKF

ETKAPFSSLKVIILLCALLALTMAAVPLLGGSKYGASPLCLPLPFGEP

STMGYMVALILLNSLCFLMMTIAYTKLYCNLDKGDLENIWDCSMVKHI

ALLLFTNCILNCPVAFLSFSSLINLTFISPEVIKFILLVVVPLPACLN

PLLYILFNPHFKEDLVSLRKQTYVWTRSKHPSLMSINSDDVEKQSCDS

TQALVTFTSSSITYDLPPSSVPSPAYPVTESCHLSSVAFVPCLARDYK

DDDDKAGADYKDDDDKLDGGYPYDVPDYAAGAYPYDVPDYA
```

Of which:

```
MDTSRLGVLLSLPVLLQLATG: signal peptide SEQ ID
NO: 275

GSSPRSGVLLRGCPTHCHCEPDGRMLLRVDCSDLGLSELPSNLSVFTSY
LDLSMNNISQLLPNPLPSLRFLEELRLAGNALTYIPKGAFTGLYSLKVL
MLQNNQLRHVPTEALQNLRSLQSLRLDANHISYVPPSCFSGLHSLRHLW
LDDNALTEIPVQAFRSLSALQAMTLALNKIHHIPDYAFGNLSSLVVLHL
HNNRIHSLGKKCFDGLHSLETLDLNYNNLDEFPTAIRTLSNLKELGFHS
NNIRSIPEKAFVGNPSLITIHFYDNPIQFVGRSAFQHLPELRTLTLNGA
SQITEFPDLTGTANLESLTLTGAQISSLPQTVCNQLPNLQVLDLSYNLL
EDLPSFSVCQKLQKIDLRHNEIYEIKVDTFQQLLSLRSLNLAWNKIAII
HPNAFSTLPSLIKDLSSNLLSSFPITGLHGLTHLKLTGNHALQSLISS
ENFPELKVIEMPYAYQCCAFGVCENAYKISNQWNKGDNSSMDDLHKKDA
GMFQAQDERDLEDFLLDFEEDLKALHSVQCSPSPGPFKPCEHLLDGWLI
RIGVWTIAVLALTCNALVTSTVFRSPLYISPIKLLIGVIAAVNMLTGVS
SAVLAGVDAFTFGSFARHGAWWENGVGCHVIGFLSIFASESSVFLLTLA
ALERGFSAKYSAKFETKAPFSSLKVIILLCALLALTMAAVPLLGGSKYG
ASPLCLPLPFGEPSTMGYMVALILLNSLCFLMMTIAYTKLYCNLDKGDL
ENIWDCSMVKHIALLLFTNCILNCPVAFLSFSSLINLTFISPEVIKFIL
LVVVPLPACLNPLLYILFNPHFKEDLVSLRKQTYVWTRSKHPSLMSINS
DDVEKQSCDSTQALVTFTSSSITYDLPPSSVPSPAYPVTESCHLSSVAF
VPCL: hLGR5 SEQ ID NO: 276

AR: linker region

DYKDDDDK: FLAG tag SEQ ID NO: 269

AGA: linker region

DYKDDDDK: FLAG tag SEQ ID NO: 269

LDGG linker region SEQ ID NO: 270

YPYDVPDYA: HA tag SEQ ID NO: 271

AGA linker region

YPYDVPDYA: HA tag SEQ ID NO: 271
```

Amino Acid Sequence hLGR5(ECD)-GPA33(TM)-FLAG Insert in pVax1 for Expression on Cell Surface: SEQ ID NO: 6

```
MDTSRLGVLLSLPVLLQLATGGSSPRSGVLLRGCPTHCHCEPDGRMLL

RVDCSDLGLSELPSNLSVFTSYLDLSMNNISQLLPNPLPSLRFLEELR

LAGNALTYIPKGAFTGLYSLKVLMLQNNQLRHVPTEALQNLRSLQSLR

LDANHISYVPPSCFSGLHSLRHLWLDDNALTEIPVQAFRSLSALQAMT

LALNKIHHIPDYAFGNLSSLVVLHLHNNRIHSLGKKCFDGLHSLETLD

LNYNNLDEFPTAIRTLSNLKELGFHSNNIRSIPEKAFVGNPSLITIHF

YDNPIQFVGRSAFQHLPELRTLTLNGASQITEFPDLTGTANLESLTLT

GAQISSLPQTVCNQLPNLQVLDLSYNLLEDLPSFSVCQKLQKIDLRHN

EIYEIKVDTFQQLLSLRSLNLAWNKIAIIHPNAFSTLPSLIKDLSSN
```

-continued

LLSSFPITGLHGLTHLKLTGNHALQSLISSENFPELKVIEMPYAYQCC

AFGVCENAYKISNQWNKGDNSSMDDLHKKDAGMFQAQDERDLEDFLLD

FEEDLKALHSVQCSPSPGPFKPCEHLLDGWLIRVALYVGIAVGVVAAL

IIIGIIIYCCCCRGKDDNTEDKEDARPNREAYEEPPEQLRELSREREE

EDDYRQEEQRSTGRESPDHLDQDYKDDDDK

Of which:

MDTSRLGVLLSLPVLLQLATG: signal peptide SEQ ID NO: 275

GSSPRSGVLLRGCPTHCHCEPDGRMLLRVDCSDLGLSELPSNLSVFTSY
LDLSMNNISQLLPNPLPSLRFLEELRLAGNALTYIPKGAFTGLYSLKVL
MLQNNQLRHVPTEALQNLRSLQSLRLDANHISYVPPSCFSGLHSLRHLW
LDDNALTEIPVQAFRSLSALQAMTLALNKIHHIPDYAFGNLSSLVVLHL
HNNRIHSLGKKCFDGLHSLETLDLNYNNLDEFPTAIRTLSNLKELGFHS
NNIRSIPEKAFVGNPSLITIHFYDNPIQFVGRSAFQHLPELRTLTLNGA
SQITEFPDLTGTANLESLTLTGAQISSLPQTVCNQLPNLQVLDLSYNLL
EDLPSFSVCQKLQKIDLRHNEIYEIKVDTFQQLLSLRSLNLAWNKIAII
HPNAFSTLPSLIKLDLSSNLLSSFPITGLHGLTHLKLTGNHALQSLISS
ENFPELKVIEMPYAYQCCAFGVCENAYKISNQWNKGDNSSMDDLHKKDA
GMFQAQDERDLEDFLLDFEEDLKALHSVQCSPSPGPFKPCEHLLDGWLI
R: hLGR5 (ECD) SEQ ID NO: 276

VALYVGIAVGVVAALIIIGIIIYCCCCRGKDDNTEDKEDARPNREAYEE
PPEQLRELSREREEEDDYRQEEQRSTGRESPDHLDQ: GPA33
sequence containing the TM region SEQ ID NO: 277

DYKDDDDK: FLAG SEQ ID NO: 269

Mouse LGR5

The cDNA encoding full length (FL) mouse (m)LGR5 was present in pEF1_Myc/His (Invitrogen), containing a cMyc and a HIS tag (pEF1_mLgr5-Myc-HIS). The mLgr5 cDNA sequence was verified by sequencing and comparison with the NCBI Reference sequence NM_010195.2.

Amino Acid Sequence Full Length Mouse (m)Lgr5-Myc-HIS Insert in pEF1_Myc/his for Expression on Cell Surface SEQ ID NO: 7

MDTSCVHMLLSLLALLQLVAAGSSPGPDAIPRGCPSHCHCELDGRMLL

RVDCSDLGLSELPSNLSVFTSYLDLSMNNISQLPASLLHRLCFLEELR

LAGNALTHIPKGAFTGLHSLKVLMLQNNQLRQVPEEALQNLRSLQSLR

LDANHISYVPPSCFSGLHSLRHLWLDDNALTDVPVQAFRSLSALQAMT

LALNKIHHIADYAFGNLSSLVVLHLHNNRIHSLGKKCFDGLHSLETLD

LNYNNLDEFPTAIKTLSNLKELGFHSNNIRSIPERAFVGNPSLITIHF

YDNPIQFVGVSAFQHLPELRTLTLNGASHITEFPHLTGTATLESLTLT

GAKISSLPQAVCDQLPNLQVLDLSYNLLEDLPSLSGCQKLQKIDLRHN

EIYEIKGSTFQQLFNLRSLNLAWNKIAIIHPNAFSTLPSLIKLDLSSN

LLSSFPVTGLHGLTHLKLTGNRALQSLIPSANFPELKIIEMPSAYQCC

AFGGCENVYKISNQWNKDDGNSVDDLHKKDAGLFQVQDERDLEDFLLD

FEEDLKALHSVQCSPSPGPFKPCEHLFGSWLIRIGVWTTAVLALSCNA

LVALTVFRTPLYISSIKLLIGVIAVVDILMGVSSAVLAAVDAFTFGRF

AQHGAWWEDGIGCQIVGFLSIFASESSIFLLTLAALERGFSVKCSSKF

EVKAPLFSLRAIVLLCVLLALTIATIPLLGGSKYNASPLCLPLPFGEP

STTGYMVALVLLNSLCFLIMTIAYTKLYCSLEKGELENLWDCSMVKHI

ALLLFANCILYCPVAFLSFSSLLNLTFISPDVIKFILLVIVPLSCLN

PLLYIVFNPHFKEDMGSLGKHTRFWMRSKHASLLSINSDDVEKRSCES

TQALVSFTHASIAYDLPSTSGASPAYPMTESCHLSSVAFVPCLAAARG

HPFEQKLISEEDLNMHTGHHHHHH

Of which:

MDTSCVHMLLSLLALLQLVAA signal peptide SEQ ID NO: 278

GSSPGPDAIPRGCPSHCHCELDGRMLLRVDCSDLGLSELPSNLSVFTSY
LDLSMNNISQLPASLLHRLCFLEELRLAGNALTHIPKGAFTGLHSLKVL
MLQNNQLRQVPEEALQNLRSLQSLRLDANHISYVPPSCFSGLASLRHLW
LDDNALTDVPVQAFRSLSALQAMTLALNKIHHIADYAFGNLSSLVVLHL
HNNRIHSLGKKCFDGLHSLETLDLNYNNLDEFPTAIKTLSNLKELGFHS
NNIRSIPERAFVGNPSLITIHEYDNPIQFVGVSAFQHLPELRTLTLNGA
SHITEFPHLTGTATLESLTLTGAKISSLPQAVCDQLPNLQVLDLSYNLL
EDLPSLSGCQKLQKIDLRHNEIYEIKGSTFQQLFNLRSLNLAWNKIAII
HPNAFSTLPSLIKLDLSSNLLSSFPVTGLHGLTHLKLTGNRALQSLIPS
ANFPELKHIEMPSAYQCCAFGGCENVYKISNQWNKDDGNSVDDLHKKDA
GLFQVQDERDLEDFLLDFEEDLKALHSVQCSPSPGPFKPCEHLFGSWLI
RIGVWTTAVLALSCNALVALTVFRTPLYISSIKLLIGVIAVVDILMGVS
SAVLAAVDAFTFGRFAQHGAWWEDGIGCQIVGFLSIFASESSIFLLTLA
ALERGFSVKCSSKFEVKAPLFSLRAIVLLCVLLALTIATIPLLGGSKYN
ASPLCLPLPFGEPSTTGYMVALVLLNSLCFLIMTIAYTKLYCSLEKGEL
ENLWDCSMVKHIALLLFANCILYCPVAFLSESSLLNLTFISPDVIKFIL
LVIVPLPSCLNPLLYIVFNPHFKEDMGSLGKHTRFWMRSKHASLLSINS
DDVEKRSCESTQALVSFTHASIAYDLPSTSGASPAYPMTESCHLSSVAF
VPCL mLGR5 (FL) SEQ ID NO: 279

AAARGHPF: linker SEQ ID NO: 280

EQKLISEEDL cMyc-derived epitope tag SEQ ID NO: 281

NMHTG: linker SEQ ID NO: 282

HHHHHH: Hexa His lag SEQ ID NO: 283

Cloning of the cDNA Encoding Human ZNRF3 cDNA encoding human (h)ZNRF3 (Genbank NM_001206998.1) was used as template to amplify specific parts of the cDNA (the extra-cellular domain (ECD): amino acids 1-219, or the ECD-TM part (truncation mutant): amino acids 1-256). To be able to express the target protein on the surface of antigen-negative cells and to be able to generate stable cell clones, the cDNA encoding the ECD of hZNRF3 was cloned into pDisplay (pDisplay_hZNRF3(ECD)-cMyc-PDGFR(TM)) and a truncation mutant (ECD with the autologous TM region) was cloned in pcDNA3.1 (pcDNA3.1_hZNRF3(ECD-TM)). The pDisplay construct allows confirmation of protein surface expression via an extra-cellular cMyc-derived epitope tag. Specific primers were designed, synthesized and used to amplify the specific parts of hZNRF3. These were then cloned in pDisplay (only the ECD), resulting in pDisplay_hZNRF3(ECD)-cMyc-PDGFR(TM) and in pcDNA3.1 (ECD with TM region), resulting in pcDNA3.1_hZNRF3(ECD-TM) for expression in (antigen-negative) cells.

Cloning of the cDNA Encoding Mouse ZNRF3 ECD and Human RNF43 ECD and Production of Recombinant Protein The cDNAs encoding the ECD of mouse (m)ZNRF3 (Genbank NM_001080924.2, amino acid 53-205, the signal peptide used was derived from cystatin) and the ECD of human RNF43 (GenBank NM_017763, amino acid 24-109, containing the cystatin leader sequence) were used to generate recombinant purified, his-tagged proteins consisting of the ECDs of the targets, in vector pUPE (U-Protein Express BV). In brief: the constructs (Peng et al. 2013 Plos ONE 8:2-10) were transfected in Hek293E cells (293 c18 ATCC, CRL-10852) and after a week of production, the protein-containing supernatant was harvested. The hexa HIS-tagged proteins were purified by means of IMAC (immobilized metal-ion affinity chromatography) and gelfiltration. Another cDNA encoding the (codon-optimized) ECD of mouse ZNRF3 was made synthetically and cloned in frame with a cMyc-derived epitope tag and the transmembrane region of the Platelet-derived growth factor receptor (PDGFR) in pDisplay for expression on the cell surface (pDisplay_mZnrf3-cMyc-PDGFR(TM)).

Cloning of the cDNA encoding human RNF43

The cDNA encoding human (h)RNF43 (GenBank NM_017763) was used as template to amplify specific parts of the cDNA (the extra-cellular domain (ECD): amino acid 1-199, or the ECD-TM part (truncation mutant): amino acid 1-222). To be able to express the target protein on the surface of antigen-negative cells and to be able to generate stable cell clones, the cDNA encoding the ECD of hRNF43 was cloned into pDisplay (pDisplay_hRNF43(ECD)-cMyc-PDGFR(TM)) and a truncation mutant of hRNF43 (ECD with the autologous TM region) was cloned in pcDNA3.1 (pcDNA3.1_hRNF43(ECD-TM)). The pDisplay construct allows confirmation of protein surface expression via an extra-cellular cMyc-derived epitope tag. Specific primers were designed, synthesized and used to amplify the specific parts of hZNRF3. These were then cloned in pDisplay (only the ECD, for the purpose of immunization) and in pCDNA3.1 (ECD with TM region) for expression in (antigen-negative) cells and the generation of cell clones stably expressing the target.

Cloning of the cDNA Encoding Mouse RNF43

The cDNA encoding the ECD of mouse (m)RNF43 (Genbank NM_172448.3, amino acid 1-199) was ordered as a synthetic gene and was cloned in frame with a cMyc-derived epitope tag and the transmembrane region of the Platelet-derived growth factor receptor (PDGFR) in pDisplay for expression on the cell surface pDisplay_mRnf43-cMyc-PDGFR(TM).

Human ZNRF3(ECD) in pDisplay Amino Acid Sequence for Expression on Cell Surface: SEQ ID NO: 8

MRPRSGGRPGATGRRRRRLRRRPRGLRCSRLPPPPPLPLLLGLLLAAA

GPGAARAKETAFVEVVLFESSPSGDYTTYTTGLTGRFSRAGATLSAEG

EIVQMHPLGLCNNNDEEDLYEYGWVGVVKLEQPELDPKPCLTVLGKAK

RAVQRGATAVIFDVSENPEAIDQLNQGSEDPLKRPVVYVKGADAIKLM

NIVNKQKVARARIQHRPPRQPTEYFDMVDEQKLISEEDLNAVGQDTQE

VIVVPHSLPFKVVVISAILALVVLTIISLIILIMLWQKKPR

Of which:

MRPRSGGRPGATGRRRRRLRRRPRGLRCSRLPPPPPLPLLLGLLLAAAG
PGAARA: signal peptide SEQ ID NO: 284

KETAFVEVVLFESSPSGDYTTYTTGLTGRFSRAGATLSAEGEIVQMHPL
GLCNNNDEEDLYEYGWVGVVKLEQPELDPKPCLTVLGKAKRAVQRGATA
VIFDVSENPEAIDQLNQGSEDPLKRPVVYVKGADAIKLMNIVNKQKVAR
ARIQHRPPRQPTEYFDM:
the ECD of human ZNRF3 VD: amino acids that are encoded by cloning sites SEQ ID NO: 285

EQKLISEEDL: cMyc-derived epitope tag SEQ ID NO: 281

NAVGQDTQEVIVVPHSLPFKVVVISAILALVVLTHISLIILIMLWQKKP
R: PDGER sequence containing the TM region SEQ ID NO: 286

Human ZNRF3 Truncation Mutant Amino Acid Sequence for Expression on Cell Surface: SEQ ID NO: 9

MRPRSGGRPGATGRRRRRLRRRPRGLRCSRLPPPPPLPLLLGLLLAAA

GPGAARAKETAFVEVVLFESSPSGDYTTYTTGLTGRFSRAGATLSAEG

EIVQMHPLGLCNNNDEEDLYEYGWVGVVKLEQPELDPKPCLTVLGKAK

RAVQRGATAVIFDVSENPEAIDQLNQGSEDPLKRPVVYVKGADAIKLM

NIVNKQKVARARIQHRPPRQPTEYFDMGIFLAFFVVVSLVCLILLVKI

KLKQRRSQNSMNRPAV

Of which:

MRPRSGGRPGATGRRRRRLRRRPRGLRCSRLPPPPPLPLLLGLLLAAAG
PGAARA: signal peptide SEQ ID NO: 284

KETAFVEVVLFESSPSGDYTTYTTGLTGRFSRAGATLSAEGEIVQMHPL
GLCNNNDEEDLYEYGWVGVVKLEQPELDPKPCLTVLGKAKRAVQRGATA
VIFDVSENPEAIDQLNQGSEDPLKRPVVYVKGADAIKLMNIVNKQKVAR
ARIQHRPPRQPTEYFD: ECD of human ZNRF3: SEQ ID NO: 288

MGIFLAFFVVVSLV : Predicted TM region SEQ ID NO: 289

CLILLVKIKLKQRRSQNSMNRPAV: Intra-cellular tail SEQ ID NO: 290

Mouse ZNRF3 ECD-his in pUPE Soluble Amino Acid Sequence for Expression Soluble Protein:

GSKETAFVEVVLFESSPSGDYTTHTTGLTGRFSRAGAMLSAEGEIVQMH
PLGLCNNNDEEDLYEYGWVGVVKLEQPELDPKPCLTVLGKAKRAVQRGA
TAVIFDVSENPEAIDQLNQGSEDPLKRPVVYVKGADAIKLMNIVNKQKV
ARARIQHLAAAHHHHHH SEQ ID NO: 10

Of which:

GS : amino acids encoded by cloning sites

KETAFVEVVLFESSPSGDYTTHTTGLTGRFSRAGAMLSAEGEIVQMHPL
GLCNNNDEEDLYEYGWVGVVKLEQPELDPKPCLTVLGKAKRAVQRGATA
VIFDVSENPEAIDQLNQGSEDPLKRPVVYVKGADAIKLMNIVNKQKVAR
ARIQHL: ECD of mouse ZNRF3 SEQ ID NO: 291

AAA : amino acids encoded by cloning sites

HHHHHH : Hexa His tag SEQ ID NO: 283

Mouse (m)ZNRF3 Sequence in pDisplay Amino Acid Sequence Expressed on Cell Surface:

SEQ ID NO: 11
MRPRSGGRPGAPGRRRRRLRRGPRGRRLPPPPPLPLLLGLLLAAAGPG

AARAKETAFVEVVLFESSPSGDYTTHTTGLTGRFSRAGAMLSAEGEIV

QMHPLGLCNNNDEEDLYEYGWVGVVKLEQPELDPKPCLTVLGKAKRAV

QRGATAVIFDVSENPEAIDQLNQGSEDPLKRPVVYVKGADAIKLMNIV

NKQKVARARIQHLPPRQPTEYFDMVDEQKLISEEDLNAVGQDTQEVIV

VPHSLPFKVVVISAILALVVLTIISLIILIMLWQKKPR

Of which:

MRPRSGGRPGAPGRRRRRLRRGPRGRRLPPPPPLPLLLGLLLAAAGPGA
ARA: signal peptide SEQ ID NO: 292

KETAFVEVVLFESSPSGDYTTHTTGLTGRFSRAGAMLSAEGEIVQMHPL
GLCNNNDEEDLYEYGWVGVVKLEQPELDPKPCLTVLGKAKRAVQRGATA
VIFDVSENPEAIDQLNQGSEDPLKRPVVYVKGADAIKLMNIVNKQKVAR
ARIQHLPPRQPTEYFDM: ECD mZNRF3 SEQ ID NO: 293

VD: amino acids that are encoded by cloning sites

EQKLISEEDL: cMyc-derived epitope tay SEQ ID NO: 281

NAVGQDTQEVIVVPHSLPFKVVVISAILALVVLTHISLIILIMLWQKKP
R: PDGFR sequence containing the TM region SEQ ID NO: 287

Human RNF43 in pDisplay Amino Acid Sequence for Expression on Cell Surface:

SEQ ID NO: 12
MSGGHQLQLAALWPWLLMATLQAGFGRTGLVLAAAVESERSAEQKAII

RVIPLKMDPTGKLNLTLEGVFAGVAEITPAEGKLMQSHPLYLCNASDD

DNLEPGFISIVKLESPRRAPRPCLSLASKARMAGERGASAVLFDITED

RAAAEQLQQPLGLTWPVVLIWGNDAEKLMEFVYKNQKAHVRIELKEPP

AWPDYDVVDEQKLISEEDLNAVGQDTQEVIVVPHSLPFKVVVISAILA

LVVLTIISLIILIMLWQKKPR

Of which:

MSGGHQLQLAALWPWLLMATLQAGFGRTGLVLAAAVESERSA: signal peptide SEQ ID NO: 294

EQKAIIRVIPLKMDPTGKLNLTLEGVFAGVAEITPAEGKLMQSHPLYLC
NASDDDNLEPGFISIVKLESPRRAPRPCLSLASKARMAGERGASAVLFD
ITEDRAAAEQLQQPLGLTWPVVLIWGNDAEKLMEFVYKNQKAHVRIELK
EPPAWPDYDV: ECD of human RNF43 SEQ ID NO: 295

VD: amino acids encoded by cloning sites

EQKLISEEDL: Myc-derived epitope lag SEQ ID NO: 281

NAVGQDTQEVIVVPHSLPFKVVVISAILALVVLTHISLIILIMLWQKKP
R: PDGFR sequence containing the TM region SEQ ID NO: 287

Mouse RNF43 in pDisplay Amino Acid Sequence for Expression on Cell Surface

SEQ ID NO: 13
MSGGHQLQLAVLWPWLLMATLHAGFGHTGRVLAAAVESERSAEQKAVI

RVIPLKMDPTGKLNLTLEGVFAGVAEVTPAEGKLMQSHPLYLCNASDD

DNLEPGFISIVKLESPRRAPRPCLSLASKARMAGERGANAVLFDITED

RSAAEQLQQPLGLTKPVVLIWGSDAAKLMEFVYKNRKAYVWIELKEPP

AGANYDVVDEQKLISEEDLNAVGQDTQEVIVVPHSLPFKVVVISAILA

LVVLTIISLIILIMLWQKKPR

Of which:

MSGGHQLQLAVLWPWLLMATLHAGFGHTGRVLAAAVESERSA: signal peptide SEQ ID NO: 296

EQKAVIRVIPLKMDPTGKLNLTLEGVFAGVAEVTPAEGKLMQSHPLYLC
NASDDDNLEPGFISIVKLESPRRAPRPCLSLASKARMAGERGANAVLFD
ITEDRSAAEQLQQPLGLTKPVVLIWGSDAAKLMEFVYKNRKAYVWIELK
EPPAGANYDV: ECD of mouse RNF43 SEQ ID NO: 297

VD: amino acids encoded by cloning site

EQKLISEEDL: Myc-derived epitope tag SEQ ID NO: 281

NAVGQDTQEVIVVPHSLPFKVVVISAILALVVLTIISLIILIMLWQKKP
R: PDGFR sequence containing TM region SEQ ID NO: 287

Cloning of the Cynomolgus and Rat Orthologues of LGR5 and EGFR

The cDNA encoding cynomolgus LGR5 was amplified from cynomolgus colon- and from liver cDNA using human-specific primers (Cyno-LGR5-FOR: 5'-CCAGCAG-GATCCGCCGCCAC-CATGGACACCTCCCGGCTCGGTG-3' SEQ ID NO: 14 and Cyno-LGR5-REV: 5'-CCAGCAGCGGCCGCTTAGA-GACATGGACAAATGCCAC-3' SEQ ID NO: 15). DMSO was added to the reaction to possibly improve the yield and specificity of the PCR reactions. Both liver and colon cDNA allowed for the amplification of the expected 2.7 kb band and the PCR product obtained from colon cDNA was then used for cloning. The obtained cDNA was cloned into pcDNA3.1 (BamH1-Not1) and sequenced. The sequence encoding a chimeric EGF receptor composed of the cynomolgus extra-cellular domain (also described in WO2010/022736-A2) coupled to the human trans-membrane and intra-cellular part was obtained from patent US2010/0183615-A1 (page 79) and the encoding cDNA was codon-optimised for expression in human cells, ordered and cloned by GeneArt. This cDNA was then re-cloned into pcDNA3.1 using NheI and NotI. The cDNA's encoding rat EGFR and rat LGR5 are available through Sino Biological (cDNA encoding rat EGFR: cat. nr. RG80100-UT; GenBank reference HM801041.1) and Origene (cDNA encoding rat LGR5: cat. Nr. RN202738; GenBank reference NM_001106784). Both cDNA's were re-cloned into pcDNA3.1 using Kpn1 and Not1. All cDNA's were, sequenced and shown to be correct.

Full Length Wt Cynomolgus LGR5 Amino Acid Sequence SEQ ID NO: 16

MDTSRLGVLLSLPVLLQLAAGSSSPRSGALLRGCPTHCHCEPDGRMLL

RVDCSDLGLSELPSNLSVFTSYLDLSMNNISQLLPNPLPSLRFLEELR

LAGNALTYIPKGAFTGLYSLKVLMLQNNQLRQVPTEALQNLRSLQSLR

LDANHISYVPPSCFSGLHSLRHLWLDDNALTEIPVQAFRSLSALQAMT

LALNKIHHIPDYAFGNLSSLVVLHLHNNRIHSLGKKCFDGLHSLETLD

LNYNNLDEFPTAIRTLSNLKELGFHSNNIRSIPEKAFVGNPSLITIHF

YDNPIQFVGRSAFQHLPELRTLTLNGASQITEFPDLTGTANLESLTLT

GAQISSLPQTVCNQLPNLQVLDLSYNLLEDLPSFSVCQKLQKIDLRHN

EIYEIKVDTFQQLLSLRSLNLAWNKIAIIHPNAFSTLPSLIKDLSSN

LLSSFPVTGLHGLTHLKLTGNHALQSLISSENFPELKIIEMPYAYQCC

-continued

```
AFGVCENAYKISNQWNKGDNSSMDDLHKKDAGMFQVQDERDLEDFLLD

FEEDLKALHSVQCSPSPGPFKPCEHLLDGWLIRIGVWTIAVLALTCNA

LVTSTVFRSPLYISPIKLLIGVIAVVNMLTGVSSAVLAGVDAFTFGSF

ARHGAWWENGVGCQVIGFLSIFASESSVFLLTLAALERGFSVKCSAKF

ETKAPFSSLKVIILLCALLALTMAAVPLLGGSEYGASPLCLPLPFGEP

STTGYMVALILLNSLCFLMMTIAYTKLYCNLDKGDLENIWDCSMVKHI

ALLLFTNCILYCPVAFLSFSSLLNLTFISPEVIKFILLVIVPLPACLN

PLLYILFNPHFKEDLVSLGKQTYFWTRSKHPSLMSINSDDVEKQSCDS

TQALVTFTSSSIAYDLPPSSVPSPAYPVTESCHLSSVAFVPCL
```

Of which

```
MDTSRLGVLLSLPVLLQLAAG Signal peptide SEQ ID NO:
298

SSSPRSGALLRGCPTHCHCEPDGRMLLRVDCSDLGLSELPSNLSVFTSY
LDLSMNNISQLLPNPLPSLRFLEELRLAGNALTYIPKGAFTGLYSLKVL
MLQNNQLRQVPTEALQNLRSLQSLRLDANHISYVPPSCFSGLHSLRHLW
LDDNALTEIPVQAFRSLSALQAMTLALNKIHHIPDYAFGNLSSLVVLHL
HNNRIHSLGKKCFDGLHSLETLDLNYNNLDEFPTAIRTLSNLKELGFHS
NNIRSIPEKAFVGNPSLITIHFYDNPIQFVGRSAFQHLPELRTLTLNGA
SQITEFPDLTGTANLESLTLTGAQISSLPQTVCNCLPNLQVLDLSYNLL
EDLPSFSVCQKLQKIDLRHNEIYEIKVDTFQQLLSLRSLNLAWNKIAII
HPNAFSTLPSLIKLDLSSNLLSSFPVTGLHGLTHLKLTGNHALQSLISS
ENFPELKIIEMPYAYQCCAFGVCENAYKISNQWNKGDNSSMDDLHKKDA
GMFQVQDERDLEDFLLDFEEDLKALHSVQCSPSPGPFKPCEHLLDGWLI
RIGVWTIAVLALTCNALVTSTVFRSPLYISPIKLLIGVIAVVNMLTGVS
SAVLAGVDAFTFGSFARHGAWWENGVGCQVIGFLSIFASESSVFLLTLA
ALERGFSVKCSAKFETKAPFSSLKVIILLCALLALTMAAVPLLGGSEYG
ASPLCLPLPFGEPSTTGYMVALILLNSLCFLMMTIAYTKLYCNLDKGDL
ENIWDCSMVKHIALLLFTNCILYCPVAFLSFSSLLNLTFISPEVIKFIL
LVIVPLPACLNPLLYILFNPHFKEDLVSLGKQTYFWTRSKHPSLMSINS
DDVEKQSCDSTQALVTFTSSSIAYDLPPSSVPSPAYPVTESCHLSSVAF
VPCL Cynomolgus LGR5 SEQ ID NO: 286
```

Generation of LGR4, LGR5, ZNRF3 and RNF43 Over-Expressing Cell Lines

Constructs expressing hLGR4 (pEF1_hLGR4-FLAG-HA), hLGR5 (pEF1_hLGR5-FLAG-HA), hZNRF3(ECD) (pcDNA3.1_hZNRF3(ECD) and pDisplay_hZNRF3(ECD)-Myc-PDGFR(TM)) and hRNF43(ECD) (pDisplay_hRNF43-(ECD)-Myc-PDGFR(TM)) were used to generate Freestyle 293F and CHO-K1 clones stably expressing the respective proteins. Constructs were transiently transfected in Freestyle 293F and CHO-K1 cells using PEI (Freestyle 293F cells) or lipofectamine (CHO cells) transfection and screened by FACS using antibodies reacting with the respective targets. After successful transfection both Freestyle 293F and CHO-K1 cells were seeded in limiting dilution and cultured under 0.5 mg/ml G418 selection pressure to obtain stable cell clones. After 2-3 weeks of selection, clones were screened by FACS. The selected clones were expanded by serial passage, retested in FACS and frozen to −150° C.

Mice Used for Immunization

For generation of human antibodies binding to LGR4, LGR5, ZNRF3 and RNF43 mice transgenic for the human VK1-39 light chain (common light chain mice, see WO2009/157771) and for a human heavy chain (HC) minilocus (comprising a selection of human V gene segments, all human Ds and all human Js) were immunized with either DNA encoding the proteins or recombinant DNA as briefly described below. These mice are referred to as 'MeMo®' mice.

Immunizations hLGR4/hLGR5 DNA Immunizations 18 mice were immunized with 20 µg plasmid DNA (pVax1_hLGR4-FLAG-HA and pVax1_hLGR5-FLAG-HA) expressing full length hLGR4 and hLGR5 each. Additionally 12 mice were immunized with 20 µg plasmid DNA of the extracellular domain of hLGR4 and hLGR5 fused to the transmembrane domain of GPA33 and a Flag tag (pVax1_hLGR4(ECD)-GPA33-FLAG and pVax1_hLGR5 (ECD)-GPA33-FLAG). Mice were vaccinated at day 0, 3, 6, 14, 17, 28, 31, 49, 63, 70, 84 and 91.

LGR4, LGR5, ZNRF3, RNF43 Protein Immunizations

Six mice were immunized with 40 µg recombinant human (rh)LGR4-Fc (RND systems Cat. Nr. 7750-GP), rhLGR5-Fc (RND systems Cat. Nr. 8078-GP), rhZNRF3-Fc (RND systems Cat. Nr. 7994-RF) or rhRNF43-Fc (RND systems Cat. nr. 7964-RN) protein dissolved in PBS, and supplemented with 40 µl Gerbu adjuvant MM (Gerbu Biotechnik). Subsequently mice were boosted with 20 µg recombinant protein (+20 µl (Gerbu adjuvant MM) on day 14 and day 28 followed by further boosts of 20 µg recombinant protein until a serum titer was observed or the immunization period was greater than three months.

Determination of Antibody Titers

Anti-hbGR4, hLGR5, hZNRF3 or hRNF43 titers in the serum from immunized mice were determined by FACS on Freestyle 293F cells over-expressing the respective target.

Recovery of Lymphoid Tissue

Spleen and draining lymph nodes were removed from all mice that were successfully immunized (see table 1). Single cell suspensions were generated from both spleen and inguinal lymph nodes and subsequently these tissues were lysed in Trizol reagent and stored at −80° C. until use.

Generation of 'Immune' Phage Antibody Repertoires by RT-PCR Cloning of VH Genes

From successfully immunized mice, the inguinal lymph nodes were used for the construction of 'immune' phage antibody repertoires. RNA was extracted from the lymphoid tissue using Trizol and 1 µg of total RNA was used in a RT reaction using an IgG-CH1 specific primer. The resulting cDNA was then used to amplify the polyclonal pool of VH-encoding cDNA using in-house developed VH-specific primers essentially as described in Marks et al. (J Mol Biol. 1991 Dec. 5; 222(3):581-97). The resulting PCR product was then cloned in a phagemid vector for the display of Fab fragments on phage, as described in de Haard et al. (J Biol Chem. 1999 Jun. 25; 274(26):18218-30) with the exception that the light chain was the same for every antibody and was encoded by the vector. After ligation, the phagemids were used to transform E. coli TG1 bacteria and transformed bacteria were plated onto LB-agar plates containing ampicillin and glucose. All phage libraries contained >10$^6$ transformants and had an insert frequency of >80%. Bacteria were harvested after overnight growth and used to prepare phage according to established protocols (de Haard et al., J Biol Chem. 1999 Jun. 25:274(26):18218-30).

Selection of Phage Carrying Fab Fragments Specifically Binding to LGR4, LGR5, ZNRF3 and RNF43 from Synthetic or 'Immune' Phage Antibody Repertoires Phage libraries were rescued according to standardized procedures (J Mol Biol. 1991 Dec. 5; 222(3):581-97; J Biol Chem. 1999 Jun. 25; 274(26):18218-30) and phage were selected for two rounds of selection in case of in-house generated synthetic repertoires and a single round in case of the immune phage antibody repertoires. In the first round, recombinant protein was coated onto the wells of a MAX-ISORP™ ELISA plate or to a NUNC immuno-tube, whereas in the second round, either recombinant protein or cells over-expressing the target were used. The MAXISORP™ ELISA plates or immuno-tubes were blocked with 4% ELK. Phage antibody libraries were also blocked with 4% ELK and excess of human IgG to deplete for Fc region binders prior to the addition of the phage library to the coated antigen.

Incubation with the phage library with the coated protein was performed for 2 hrs at room temperature under shaking conditions. Plates or tubes were then washed five to ten times with 0.05% Tween-20 in PBS followed by 5 to 10 times washing with PBS. Bound phage were eluted using 50 mM glycine (pH 2.2) and added to E. coli TG-1 and incubated at 37° C. for phage infection. Subsequently infected bacteria were plated on agar plates containing Ampicillin, and glucose and incubated at 37° C. overnight. After the first round of selection, colonies were scraped off the plates and combined and thereafter rescued and amplified to prepare an enriched first round phage pool for the synthetic repertoires. For the 'immune' repertoires, single clones were screened for target binding after the first round of phage selection.

For the synthetic repertoires, the enriched library was then selected on either the recombinant human (rh) protein (rhLGR4-Fc, rmLgr4-Fc, rhLGR5-Fc, rhZNRF3-Fc or rhRNF43-Fc, RND systems, soluble rhRNF-43-HIS, rmZnrf3-HIS (produced in-house)) using the protocol described above or on Freestyle 293F cells stably over-expressing hLGR4(FL), hLGR5(FL), hZNRF3(ECD) or hRNF43(ECD). For the cell selections, rescued phage and cells were blocked with 4% ELK. After blocking the rescued phage were incubated with $5^{\wedge}10^6$ parental Freestyle 293F cells for subtraction for 1 hr. After subtraction, cells were spun down and the phage supernatant was transferred to Freestyle 293F cells expressing hLGR4, hLGR5, hZNRF3 or hRNF43. Cells plus phage were incubated for 2 hrs at 2-8° C. Washing the cells (5-10 times) was performed using 5 ml of 0.5% BSA in PBS. Bound phage were eluted using 200 mM TEA, the eluate was neutralized with Tris (pH8) and added to E. coli TG-1 and incubated at 37° C. for phage infection. Subsequently, phage-infected bacteria were plated on agar plates containing ampicillin, and glucose and incubated at 30° C. or 37° C. overnight.

After the second round selection, individual clones were picked and tested for target-reactivity. Positive phage clones binding hLGR4, hLGR5, hZNRF3, or hRNF43 were then identified in FACS for binding to the Freestyle 293F stable over-expressing the respective target (see below).

DiD Labeling of Cells and FACS Staining of a Mix of DiD-Positive and -Negative Cells Freestyle 293F cell clones stably over-expressing the respective targets were generated in house. These cells were cultured and harvested using standardized procedures. Approximately 20 million antigen-expressing cells were then labeled with 1 μl of DiD (Invitrogen, cat. nr. V22889) in a volume of 1 ml of cell culture medium, for 20 minutes at 37° C. DiD labeling was checked on a small aliquot of cells in FACS and consistently found to be more than 90%. Cells were then washed twice with 20 ml of cell culture medium and used subsequently for FACS staining. To this aim, a 1:1 mix of antigen-negative (parental) Freestyle 293F cells and DiD-labeled antigen-positive cells was made and aliquoted at 200,000 cells per well into round bottom 96 wells FACS microtiter plates. Staining using monoclonal phage was performed as described below.

FACS Staining of a Mix of Target-Positive and -Negative Wells Using Monoclonal Phage Monoclonal phage of single clones selected for binding the respective targets were prepared as described (J Mol Biol. 1991 Dec. 5; 222(3):581-97; J Biol Chem. 1999 June 25:274(26):18218-30). These were tested for binding in FACS to a mix of (DiD-labeled) antigen-positive and (non-labeled)-negative cell lines by incubation with phage (30 μl) in a total of 100 μl FACS buffer (PBS, containing 0.5% BSA and 0.5 mM EDTA) containing 4% milk. After three washes, bound phage were detected by staining with a biotinylated anti-M13 antibody (Fitzgerald, cat. nr. 61R-M101ABTB62-FEZ, 1:125 in FACS buffer, 30 minutes on ice) and PE-labeled streptavidin (Invitrogen, cat. nr. SA1004-4; 1:400 in FACS buffer for 15 minutes on ice). Stained cells were analysed using a FACS Canto (Becton and Dickinson).

RTK-Targeting Antibodies

EGFR- and HER3-targeting cLC antibodies were obtained using previously described methods (J Mol Biol. 1991 Dec. 5; 222(3):581-97; J Biol Chem. 1999 Jun. 25; 274(26):18218-30) from in-house generated large synthetic phage antibody repertoires (HER3), or from phage antibody repertoires generated from successfully target-immunised MeMo mice (EGFR). Methods to generate antibodies to EGFR and HER3 and antibody variable domain VH chains for the respective EGFR and HER3 antibodies have been described in pending applications that are incorporated herein by reference: WO 2015/130173 A1 and WO 2015/130172 A1.

Re-Cloning of VH-Encoding cDNA's from the Phagemid Vector to IgG-Expression Vectors The VH-encoding cDNA's of all target-specific clones were sequenced. A selection of unique clones based on sequence identity and cluster analysis (FIG. 25) was then re-cloned to different IgG expression vectors using SfiI-BstEII or a SfiI/XhoI digestion and ligation of the pool of digested cDNA's into the IgG expression plasmid according to standardised molecular biological techniques.

Generation of Bispecific Antibodies

Bispecific antibodies were generated by transient co-transfection of two plasmids encoding IgG with different VH domains, using a proprietary CH3 engineering technology to ensure efficient hetero-dimerisation and formation of bispecific antibodies. The common light chain is also co-transfected in the same cell, either on the same plasmid or on another plasmid. In our co-pending applications (e.g. WO2013/157954 and WO2013/157953; incorporated herein by reference) we have disclosed methods and means for producing bispecific antibodies from a single cell, whereby means are provided that favor the formation of bispecific antibodies over the formation of monospecific antibodies. These methods can also be favorably employed in the present invention. Specifically, preferred mutations to produce essentially only bispecific full length IgG molecules are amino acid substitutions substitutions at positions 351 and 366, e.g. L351K and T366K (numbering according to EU numbering) in the first CH3 domain (the 'KK-variant' heavy chain) and amino acid substitutions at positions 351 and 368, e.g. L351D and L368E in the second CH3 domain (the 'DE-variant' heavy chain), or vice versa. It was previously demonstrated in our co-pending applications that the negatively charged DE-variant heavy chain and positively charged KK-variant heavy chain preferentially pair to form heterodimers (so-called 'DEKK' bispecific molecules). Homodimerization of DE-variant heavy chains (DE-DE homodimers) or KK-variant heavy chains (KK-KK homodimers) hardly occurs due to strong repulsion between the charged residues in the CH3-C13 interface between identical heavy chains.

VH genes encoding the antibodies binding LGR4, LGR5, ZNRF3 and RNF43 described above were cloned into the vector encoding the positively charged CH3 domain and RTK (EGFR- or HER3-) targeting antibodies as previously obtained and disclosed in WO 2015/130172 (incorporated herein by reference) were cloned into vector encoding the negatively charged CH3 domain. Suspension growth-adapted 293F Freestyle cells were cultivated in T125 flasks on a shaker plateau until a density of $3.0 \times 10^6$ cells/ml. Cells were seeded at a density of $0.3$-$0.5 \times 10^6$ viable cells/ml in each well of a 24-deep well plate. The cells were transiently transfected with a mix of two plasmids encoding different antibodies, cloned into the proprietary vector system. Seven days after transfection, the cellular supernatant was harvested and filtered through a 0.22 µM filter (Sartorius). The sterile supernatant was stored at 4° C. until purification of the antibodies.

Generation of Monoclonal Antibodies

A selection of VH sequences were also re-cloned into an IgG1 expression vector encoding mono-specific, bivalent IgG. Suspension adapted 293F Freestyle cells were cultivated in T125 flasks at a shaker plateau until a density of $3.0 \times 10^6$ cells/ml. Cells were seeded at a density of $0.3$-$0.5 \times 10^6$ viable cells/ml in each well of a 24-deep well plate. The cells were transiently transfected with individual sterile DNA: PEI mixtures according to standardized procedures and further cultivated. Seven days after transfection, supernatant was harvested and filtered through a 0.22 µM (Sartorius) filter. The sterile supernatant was stored at 4° C. until antibody was purified by means of protein-A affinity chromatography.

Cloning and Expression of Comparator Antibodies Targeting LGR5, FZD7 and R-Spondin3.

Antibodies that specifically recognise EGFR, FZD, RSPO3 or LGR5 are known in the art. Comparator antibodies were constructed according to published information: cDNA sequences encoding the VH- and VL were derived from published patents and cloned into an expression vector encoding a full length human IgG1 molecule. Antibodies were subsequently expressed in 293F Freestyle cells by transient transfection and purified from the culture supernatant using protein-A affinity chromatography according to standard procedures. The hu8E11v2 (anti-LGR5) antibody was copied from patent US 2013/0336885 A1 (Genentech). Sequence information for the BNC101 antibody (anti-LGR5) was obtained from patent US2016/0031984 A1 (Bionomics Inc.). The sequence encoding the OMP18R5 antibody (anti-FZD) was copied from patent AU2014/212081 A1 (Oncomed Pharmaceuticals Inc.). The OMP18R20 and OMP18R21 antibody sequences (anti-LGR5) were found in and copied from U.S. Pat. No. 8,628,774 B2 (Oncomed Pharmaceuticals Inc.). The sequence encoding OMP131R10 (anti-RSPO3) was copied from patent WO 2016/090024 A2 (Oncomed Pharmaceuticals Inc.). A clinical batch of cetuximab (Erbitux®) was used. A list of the copied antibodies and the internal number given to these versions is given in Table 7.

IgG Purification for Functional Screening

Purification of IgG was performed on a small scale (<500 µg), medium scale (<10 mg) and large scale (>10 mg) using protein-A affinity chromatography. Small scale purifications were performed under sterile conditions in 24 well filter plates using filtration. First, the pH of the medium was adjusted to pH 8.0 and subsequently, IgG-containing supernatants were incubated with protein A Sepharose CL-4B beads (50% v/v) (Pierce) for 2 hrs at 25° C. on a shaking platform at 600 rpm. Next, the beads were harvested by filtration. Beads were washed twice with PBS pH 7.4. Bound IgG was then eluted at pH 3.0 with 0.1 M citrate buffer and the eluate was immediately neutralized using Tris pH 8.0. Buffer exchange was performed by centrifugation using multiscreen Ultracel 10 multiplates (Millipore). The samples were finally harvested in PBS pH7.4. The IgG concentration was measured using Octet. Protein samples were stored at 4° C.

IgG Quantification Using Octet

To determine the amount of IgG purified, the concentration of antibody was determined by means of Octet analysis using protein-A biosensors (Forte-Bio, according to the suppliers recommendations) using total human IgG (Sigma Aldrich, cat. nr. 14506) as standard.

(Characterization of Binding of LGR4/LGR5/ZNRF3/RNF43 Specific IgG

Antibodies targeting LGR4, LGR5, ZNRF3 or RNF43 were first expressed as bispecific common light chain antibodies with a second Fab arm recognizing a non-relevant (control) antigen: Tetanus Toxoid. The antibodies were tested for binding in FACS to Freestyle 293F cells overexpressing hLGR4, hLGR5, hZNR3 or hRNF43. Therefore cells were harvested and diluted to $10^6$ ells/ml in FACS buffer (PBS/0.5% BSA/0.5 mM EDTA). $1$-$2 \times 10^6$ cells were added to each well in a U-bottom 96 well plate. Cells were centrifuged for 2 minutes at 300 g at 4° C. Supernatant was discarded by inverting the plate(s). 50 µl of each IgG sample was added (for screening diluted to a concentration of 5 µg/ml in FACS buffer) and incubated for 1H on ice. Cells were centrifuged once, supernatant was removed and cells were washed twice with 150 µl of FACS buffer. 50 µl diluted 1:400 goat anti human IgG PE (Invitrogen) was added and incubated for 30 minutes on ice in the dark. After adding FACS buffer, cells were centrifuged once, supernatant was removed and cells were washed twice with FACS buffer. Cells were analyzed on a FACSCanto Flow cytometer (Becton and Dickinson) in a HTS setting. Binding of the antibodies to cells was assessed by measuring the mean fluorescence intensity (MFI) of the stained cell population. Antibodies were considered to bind their target when the MFI was at least five-fold that of the same cell population stained with a (negative control) non-binding antibody (directed to tetanus toxoid).

To test for binding reactivity, ELISA assays were also used, LGR4 and LGR5 targeting bispecific IgG were tested for reactivity against the antigens rhLR4-Fc, rhLGR5-Fc and Tetanus Toxoid, ZNRF3 and RNF43 antibodies were tested for reactivity against the antigens rhZNRF3-Fc, rhRNF43-Fc and Tetanus Toxoid. Antigens were coated overnight to MAXISORP™ ELISA plates. Wells of the ELISA plates were blocked with PBS (pH 7.2) containing 5% BSA for 1 hour. Selected antibodies were tested at a concentration of 5 µg/ml diluted in PBS-5% BSA and allowed to bind for 1 hour at 25° C. Alternatively when titrating the bispecific IgG, a seven step two-fold dilution series was prepared starting at 5 µg/ml or 8 µg/ml. As a control, the procedure was performed simultaneously with a commercially-available antibody specific for the coated antigens and an anti-Tetanus Toxoid control antibody. The ELISA plates were washed 3 times with PBS-T (PBS-0.05% v/v Tween 20). Bound IgG was detected with 1:2000 diluted HRP-conjugate (Goat anti-human IgG Becton Dickinson) and was allowed to bind for 1 hour at 25° C. The ELISA plates were washed 3 times with PBS-T (PBS-0.05% Tween 20) and bound IgG was visualized by TMB/H2O2 staining and staining was quantified by means of OD450 nm measurement.

Affinity Ranking of LGR4/LGR5/ZNRF3/RNF43 Specific IgG in FACS

Cells were harvested and diluted to $10^6$ cells/ml in FACS buffer (PBS/0.5% BSA/0.5 mM EDTA). 1-2×$10^5$ cells were added to each well in a U-bottom 96 well FACS plate. Cells were centrifuged for 2 minutes at 300 g at 4° C. Supernatant was discarded by inverting plate(s). 50 µl of each IgG sample was added in a seven step two-fold serial dilution starting at 5 µg/ml and incubated for 1 hr on ice. Cells were centrifuged once, supernatant was removed and cells were washed twice with 150 µl of FACS buffer. 50 µl 1:400 diluted mouse anti human IgG PE (Invitrogen) was added and incubated for 30 minutes on ice in the dark. After adding FACS buffer, cells were centrifuged once, supernatant was removed and cells were washed twice with FACS buffer. Cells were analyzed on a FACSCanto Flow cytometer in a HTS setting. Binding of the antibodies to cells was quantified by measuring the mean fluorescence intensity (MFI) and calculating the area under the curve (AUC) resulting from the resulting plots of the MFI as a function of the antibody concentration used for staining.

IgG Purification for Functional Studies

Medium scale purifications were performed on an ÄKTA-explorer 100 system using HiTrap MabSelect Sure columns and HiTrap desalting columns. Samples were loaded at 5 ml/min. The column was washed with 2 column volumes of PBS. IgG was eluted at pH 3.0 with 0.1 M citrate buffer. Next the sample was desalted and ended up in a final buffer of PBS pH 7.4. IgG were filtered through a 0.45 µM filter (Sartorius). The IgG concentration was measured using OD280. Protein samples were stored at −80° C.

Testing Antibodies for their Reactivity with the Mouse Orthologue of the Target

To test for mLgr4 binding reactivity, an ELISA assay was used. Both LGR4- and LGR5-targeting antibodies were tested for reactivity against the recombinant mLgr4-Fc (RND systems. Cat. nr. 8077-GP) protein, mLgr4-Fc was coated overnight to MAXISORP™ ELISA plates. Wells of the ELISA plates were blocked with PBS (pH 7.2) containing 5% BSA for 1 hour. Selected antibodies were tested at a single concentration of 5 µg/ml diluted in PBS-5% BSA and allowed to bind for 1 hour at 25° C. As a control, the procedure was performed simultaneously with a commercially-available antibody specific for the coated antigens and a control (anti-TT cLC) antibody. The ELISA plates were washed 3 times with PBS-T (PBS-0.05% v/v Tween 20). Bound IgG was detected with 1:2000 diluted HRP-conjugate (Goat, anti-human IgG: Becton Dickinson) and was allowed to bind for 1 hour at 25° C. The ELISA plates were washed 3 times with PBS-T (PBS-0.05% Tween 20) and bound IgG was visualized by TMB/$H_2O_2$ staining; staining was quantified by means of OD450 nm measurement.

Bispecific IgG were also tested for binding in FACS to Freestyle 293F cells transiently expressing mLgr5, mZnr3 or mRnf43. Therefore cells were transiently transfected with mLgr5, mZnrf3 or mRnf43-encoding constructs (pEF1_mLgr5-Myc-HIS, pDisplay_mZnrf3-Myc-PDCFR™, pDisplay_mRnf4:3-Myc-PDGFR(TM)) using lipofectamine and were harvested and diluted to $10^6$ cells/ml in FACS buffer (PBS/0.5% BSA/0.5 mM EDTA). 1-2×$10^5$ cells were added to each well in a U-bottom 96 well plate. Cells were centrifuged for 2 minutes at 300 g at 4° C. Supernatant was discarded by inverting plate(s). 50 µl of each IgG sample was added at a concentration of 5 µg/ml and incubated for 1 hour on ice. Cells were centrifuged once, supernatant was removed and cells were washed twice with FACS buffer. 50 µl diluted 1:400 mouse anti human IgG PE (Invitrogen) was added and incubated for 30-60 minutes on ice in the dark. After adding FACS buffer, cells were centrifuged once, supernatant was removed and cells were washed twice with FACS buffer. Cells were analyzed on a FACSCanto Flow cytometer in a HTS setting. Binding of the antibodies to cells was quantified by measuring the mean fluorescence intensity (MFI) of the transfected cell population.

R-Spondin3 Blocking ELISA Assay

All four WNT targets have R-Spondin as their ligand (Prog Biophys Mol Biol. 2015 September:118(3):112-8: J Struct Biol. 2015 August; 191(2):149-55). For each target, a ligand-blocking assay was developed to test the ability of target (LGR4. LGR5, ZNRF3 or RNF43) specific antibodies to interfere with R-Spondin3 binding to the target. Binding of the Fc fusion proteins of the ECD of the respective target to coated R-Spondin3 was tested in the presence of an excess of cLC IgG directed to LGR4, LGR5, ZNRF3 or RNF43. In case the cLC IgG binds to the R-Spondin3 binding site, the Fc fusion protein would no longer be able to bind to the coating and the ELISA signal would be lost. Recombinant R-Spondin3 (RND systems) was coated onto the wells of a MAXISORP™ ELISA plate. Wells of the ELISA plates were blocked with PBS (pH 7.2) containing 5% BSA for 1 hour. Selected antibodies were tested for blocking at a concentration of 15 µg/ml diluted in PBS-5% BSA in the presence of recombinant human target protein (rhLGR4-Fc, rhLGR5-Fc, rhZNRF3-Fc or rhRNF43-Fc). The IgG/recombinant human target protein complex was pre-incubated for 10 minutes before addition to the R-Spondin3 coated plate for 10 minutes-2 hours. As a control for blocking, the procedure was performed simultaneously by addition of a surplus (15 µg/ml) of rhR-Spondin3 instead of IgG. The ELISA plates were washed 3 times with PBS-T (PBS-0.05% v/v Tween 20). Bound Fc-protein was detected with 1:2000 diluted anti-human IgG HRP-conjugate (Goat anti-human IgG Bethyl labs) and was allowed to bind for 1 hour at 25° C. The ELISA plates were washed 3 times with PBS-T (PBS-0.05% Tween 20) and bound complex was detected by staining with TMB/$H_2O_2$; staining was quantified by means of OD450 nm measurement.

Affinity Measurement of Bispecific Antibody Binding to Cell-Surface Expressed Antigen.

Afucosylated PB10651 was radio-labelled with $^{125}$I using IODO-GEN according to the protocol described by van Uhm et al. The immuno-reactivity of the antibody after radiolabeling was investigated with the method described by Lindmo et al. Steady state cell affinity measurements of $^{125}$I-PB10651 were performed with CHO cells expressing either EGFR or LRG5 to investigate the affinity towards EGFR and LGR5 respectively. In addition, the affinity towards the DLD-1 cell line endogenously expressing EGFR but no detectable LGR5 was also determined. The assay used a constant concentration of target (cells) and the amount of radio ligand was titrated without violating the assumptions behind affinity measurements at steady state conditions. Non-specific binding (NSB) was assessed by the presence of 100-fold molar excess unlabeled PB10651 in a parallel series. The assay was repeated twice and the estimated $K_D$ value is reported as the mean of three independent experiments. Estimation of the $K_D$ values were performed using GraphPad Prism v. 6.0 h non-linear regression. One-Site—Total and Non-specific binding with the constraint that $K_D$ values must be greater than 0.

REFERENCES

Lindmo T, Boven E. Cuttitta F. Fedorko J, Bunn P A. Determination of the immunoreactive fraction of radiolabeled monoclonal antibodies by linear extrapolation to binding at infinite antigen excess. J Immunol Methods. 1984: 72: 77-89.

van Uhm J B, Visser G W, van der Schans M J, Geldof A A, Meuleman E J, Nieuwenhuijzen J A. The ultimate radio-chemical nightmare: upon radio-iodination of Botulinum neurotoxin A, the introduced iodine atom itself seems to be fatal for the bioactivity of this macromolecule. EJNMMI Res. 2015: 5: 5.

Epitope Mapping Through Shotgun Mutagenesis Analysis

The epitopes on EGFR and LGR5 recognised by PB10651 were determined by shotgun mutagenesis analysis according to the method described by Davidson et al., (2014). Two mutation libraries were made from the two antigens: one library encompassed a.a. 300-520 (ligand binding domain L2 or domain 111) of human EGFR (GenBank reference sequence NP_005219.2) and the other a.a. 22-560 (being the N-terminal domain until the first transmembrane helix) of human LGR5 (GenBank reference sequence AAH96324.1). The LGR5 expression construct was truncated at a.a. 834 to increase cell surface expression of the receptor. In-house developed antibodies targeting a different epitope were used as control antibodies for the expression of the mutants.

REFERENCE

Davidson, E, and Doranz, B. J. (2014) A high-throughput shotgun mutagenesis approach to mapping B-cell antibody epitope. Immunology 143. 13-20.

Competition for LGR5 Binding Between the LGR5 Fab Arm in PB10651 and the Ligand R-Spondin1 Using a Cell-Based Assay The literature-copied version of antibody OMP88R20 (called PG7711) described in U.S. Pat. No. 8,628,774B2) was used as a ligand-blocking control to set up an assay to demonstrate ligand-blocking capacity of the anti-LGR5 Fab arms. A CHO-K1-derived cell clone was generated that over-expressed human LGR5 by transient transfection of CHO-K1 cells with the expression construct encoding LGR5, followed by selection of antibiotic (G418) resistant clones by limiting dilution. The binding of the copied version of OMP88R20 to this cell line was then tested in a dilution series of antibody and the EC50 for binding was determined. Next, binding of the antibody to the LGR5 expressing CHO cell clone at the EC50 concentration was measured in FACS in the presence of increasing amounts of the ligand R-spondin1 (R&D Systems, cat. nr. 4645-RF/CF). To test whether the binding of the anti-LGR5 Fab (MF5816) of PB10651 to LGR5 could be inhibited by binding of the ligand, the antibody was tested for LGR5 binding at 100 ng/ml in the presence of increasing amounts of the ligand R-spondin1. A similar assay was performed using the rat anti-LGR5 antibody 1D9 that has been reported to bind to the juxta-membrane region of LGR5 (de Lau et al., 2011) to show the specificity of the interaction.

Ligand Blocking Capacity of the Anti-EGFR Fab Arm in PB10651.

To test anti-EGFR IgG for their effects on EGF-induced signalling, they were tested for their ability to prevent the EGF-induced apoptotic cell death of A431 cells. In brief, high (10 nM) concentrations of EGF induce (apoptotic) cell death in A431 cells (Gulli et al., 1996). This effect can be dose-dependently reverted by the addition of ligand-blocking anti-EGFR antibodies, such as cetuximab (the murine 225 antibody is the mouse equivalent of cetuximab). A431 cells were plated at 1500 cells/well in 96 wells tissue culture plates and grown overnight. The next day, antibody was added at the indicated concentrations together with 62.5 ng/ml (10 nM) of recombinant, human EGF (R&D Systems, cat. nr. 236-EG) and cells were grown for three days. After three days, the number of metabolically active cells was determined by alamar blue (Invitrogen, cat. nr. DAL1100) addition and measurement of the fluorescence at 590 nm emission with 560 nm excitation. All anti-EGFR IgG were tested for their EGF blocking effects in this assay compared with cetuximab.

REFERENCE

Gulli. L. F., et al., *Epidermal growth factor-induced apoptosis in A431 cells can be reversed by reducing the tyrosine kinase activity*. Cell Growth Differ, 1996. 7(2); p. 173-178.

Heat Stability Assay

In order to get an indication on the stability of the bispecific IgG, all IgG were incubated at 40° C. for a week in serum containing medium (DMEM, high glucose (Gibco, cat. nr. 41966-029), supplemented with 9% Fetal bovine serum (Thermo Scientific Cat. nr. SV30180)) and were then tested for binding in a binding ELISA (essentially as described above). This ELISA consisted of coating 2 μg/ml antigen (rhLGR4-Fc, rhLGR5-Fc, rhZNRF3-Fc or rhRNF43-Fc), using 100 μl at 5 μg/ml IgG and blocking in 5% BSA in PBS. In this assay the binding of the same IgG (in serum containing medium) kept at 2-8° C. (refrigerator) to antigen was compared to that of IgG kept at 40° C. The percentage loss of binding after 1 week incubation at 40° C. was calculated.

Colorectal Cancer (CRC) Organoid Cultures

CRC organoids were produced as described (Van de Wetering et al. 2015 Cell 161:933-45) as working cell banks and shipped for screening assays on dry ice as frozen vials at a density of 1,500,000 cells per 1 ml freezing medium (Fetal Bovine Serum containing 10% DMSO as a cryoprotectant). The cryo-tubes are stored at −80° C. for use within 3 months or at −150° C. for long-term storage.

Culture Media

Tumoroid Expansion Medium was produced by enriching 500 ml Advanced DMEM (Thermo Fisher 12491-023) with 5 ml 100× Penicillin-Streptomycin (Thermo Fisher 15140-122), 5 ml 100× Glutamax (Thermo Fisher 35050-038) and 5 ml 1M Hepes (Thermo Fisher 15630-056). To 70 ml of the enriched Advanced DMEM, 20 ml R-spondin 1 conditioned medium and 10 ml of Noggin-conditioned medium (Van de Wetering et al. 2015 Cell 161:933-45) was added to prepare 100 ml Tumoroid Expansion Medium which was additionally supplemented with 2 ml 50×B27 supplement (Thermo Fisher 17504-G44), 1 ml 1M Nicotinamide (Sigma-Aldrich N0636), 250 μl 500 mM N-Acetyl Cysteine (Sigma-Aldrich A9165), 10 μl 5 mM A83-01 (TGFβ inhibitor, Tocris 2939) and 33 μl 30 mM SB202190 (p38 inhibitor. Sigma Aldrich S7067). The Tumoroid Expansion Medium was further supplemented with 100 μl 10 mM Y27632 (Rho kinase inhibitor, Abmole Y-27632 dihydrochloride) upon fresh seeding of colon tumoroids in the presence of human EGF (Peprotech AF-100-15) or human NRG-1/HRG (ImmunoTools 11343047). EGF and HRG are growth factors that stimulate the organoid expansion and their dose determines the sensitivity of the screening assay. EGF was added at doses of 2.5 ng/ml, 5 ng/ml or 10 ng/ml during screening or 10 ng/ml or 50 ng/ml during expansion. HRG was used solely at 5 ng/ml.

Wild type organoid Expansion Medium is equal to the Tumoroid Expansion Medium, with one replacement: the 70 ml enriched Advanced DMEM was replaced by a combination of 20 ml enriched Advanced DMEM and 50 ml WNT3A-conditioned medium (Van de Wetering et al. 2015 Cell 161:933-45). Normal tissue-derived colon organoids and colon tumoroids with wild type APC are WNT-dependent and therefore require the presence of WNT for expansion.

Gel Composition

Frozen colon tumoroids were thawed rapidly in a water bath at 37° C. and collected in 5 ml enriched Advanced DMEM. The organoids were pelleted by 5 minute centrifugation at 1000 rpm at 4° C. The supernatant was removed and the organoids taken up in Tumoroid Expansion Medium without growth factors. This organoid suspension was mixed with Cultrex Reduced Growth Factor Basement Membrane Extract. Type 2. PathClear (Amsbio 3533-010-02). The final Cultrex gel percentage was 60% and the number of cells per ml was 100,000.

Determination of Growth Factor Responsiveness of Patient-Derived Organoids

In order to determine whether patient-derived organoids were responsive to growth factor treatment, they were seeded as described above in the presence or absence of growth factors (EGF (5 ng/ml), or NRG (5 ng/ml)) and then cultured for 5 days. The number of viable cells was then determined using the Cell Titer Glo cell viability assay (Promega, cat. nr. (7571). The luminescence readout using growth factor-stimulated cells was then compared to that obtained using non-stimulated cells.

Preparation of Culture Plates

The gelation was more rapid in pre-warmed culture plates. Therefore all culture plates were placed at 37° C. in a humidified $CO_2$ incubator (Eppendorf) the day before cell seeding.

To expand colon tumoroids, 24-wells or 6-wells plates (Greiner Bio-One) were used and per well, either 3 or 10 drops of 1:5 µl gel/organoid suspension was spotted at regular distances. Tumoroid Expansion Medium (0.5 ml or 2 ml) containing between 10 ng/ml to 50 ng/ml EGF was added after a 30 minute gelation period at 37° C. At day 1 of seeding the Tumoroid Expansion Medium contained 10 µM Y27632. Medium replacements during expansion were with EGF-containing Tumoroid Expansion Medium devoid of Y27632.

To perform a screen, 384-wells µclear plates (Greiner Bio-One 781091) were used. Per well, 15 µl of the gel/organoid mix was dispensed using automated liquid handling. Upon 30 minutes gelation at 37° C., 45 µl Tumoroid Expansion Medium (or Organoid Expansion Medium where applicable) was added on top of the gel in each well. The media were supplemented with or without growth factors and (reference) antibodies and compounds were mixed with the medium in v-bottom 96-wells plates before applying to the 384-wells plates with solidified gel.

Preparation of Antibody Master Plates

Reference antibodies (Cetuximab (4C), negative control antibodies, single arm HER3 or EGFR targeting antibodies and HER3/EGFR antibodies (on dry ice)) were shipped and stored at 4° C. for screening. Bispecific and monospecific antibodies were delivered in deep-well 96-wells plates that were sealed and shipped at 4° C. In general, the notation to monospecific cLC antibodies throughout the examples is recognized by the prefix 'PG' whereas the notation to bispecific cLC antibodies is recognized by the prefix 'PB'. For the avoidance of doubt, the notation to Fab fragments of cLC antibodies are recognized by the prefix 'MF'. The antibodies were manually transferred to four v-bottom 96-wells plates (Greiner Bio-One 736-0118) in randomized locations ranging from well B02 to well G11 (inner 60 wells). Reference antibodies were added to the plates at random locations as well, at equal concentration. These antibody master plates were used to prepare 1:10 dilution plates in PBS. The master plates and dilution plates were stored sealed at 4° C. For validation of screening results a lead panel of bispecific IgG (46 antibodies at a concentration of 0.5 mg/ml) were shipped in screw-capped microvials, to allow easy randomization of the antibodies in screening plates and to prevent cross-contamination and evaporation. Prior to each experimental run, the bispecific IgG were placed in one v-bottom 96-wells plate (inner 60 wells) along with reference antibodies at 0.1 mg/ml by diluting them in PBS. This plate was diluted once more 1:5 in PBS to achieve a second master plate containing antibodies at 20 µg/ml. Dilutions and plate exposures were performed using the Felix liquid handler.

Exposure Regimes

The high dose and low dose v-bottom 96-well antibody master plates were diluted 1:10 in culture medium before exposure. The antibody concentrations applied in primary screen were 10 µg/ml and 1 µg/ml or 40 µg/ml and 4 µg/ml; and in the validation screen the antibody doses were 10 µg/ml and 2 µg/ml. The antibodies were added to the organoids 30 minutes after seeding. The antibody exposure before plate fixation was minimally 7 days and maximally 9 days.

Fixation and Imaging

To prepare the exposed tumoroid plates for imaging, the organoids were fixed and stained to visualize the nuclei and the actin cytoskeleton respectively as previously described (Di et al PlosOne 2014, PMID 25289886). Imaging of the plates was performed using a Molecular Devices ImageXpress Micro XLS connected to a Twister II robotic arm as previously described (Sandercock et al. Molecular Cancer 2015, PMID 26227951). Briefly, z-stacks of each well in a 384-wells plate was captured using a 4× lens, with a z-step size of 50 µm. The number of sections per well ranged from 20 sections to 24 sections, to cover the entire depth range of the gel in each well.

Image Analysis

Figure 5:
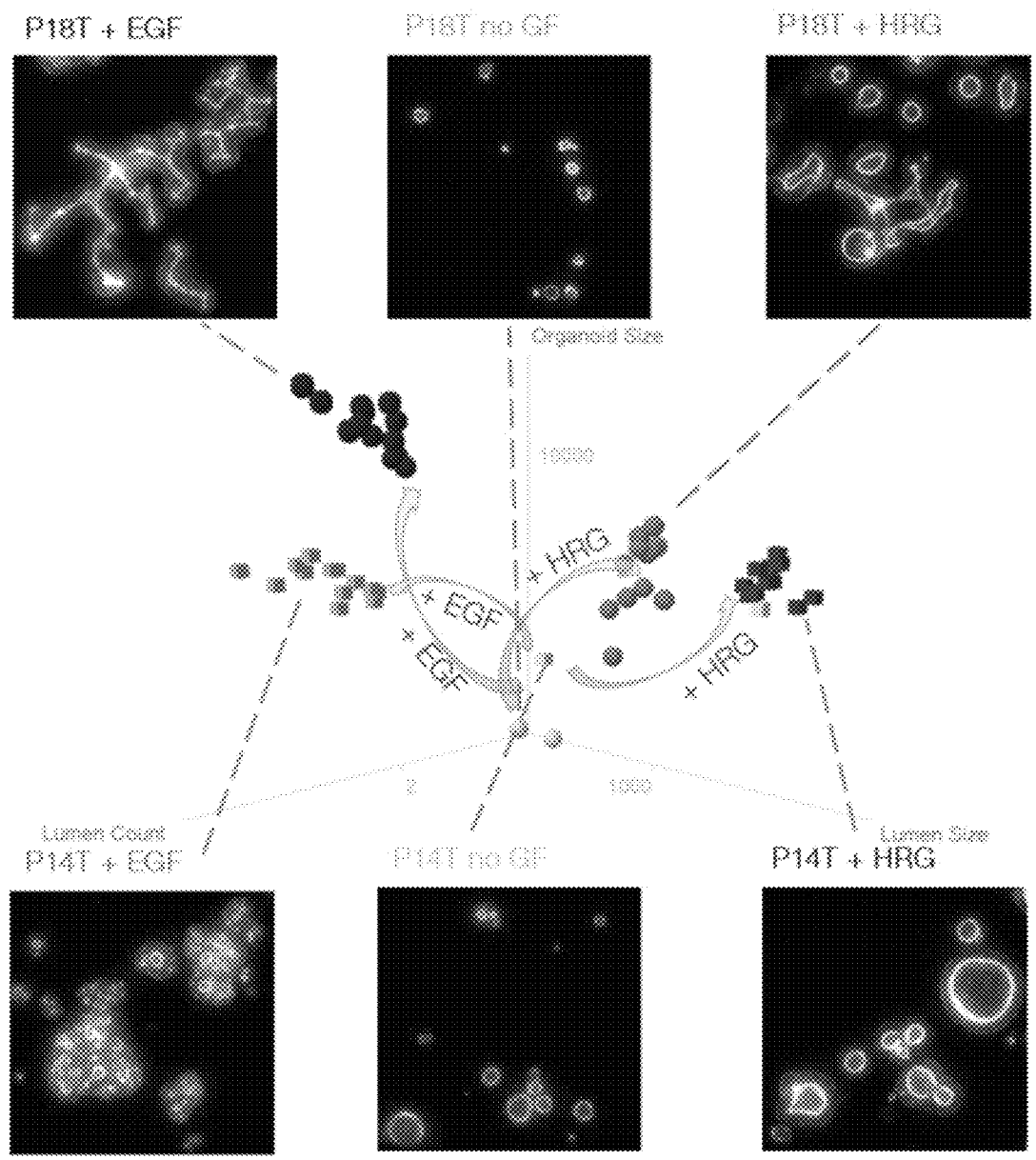
FIG. 5: The effect of growth factors EGF and HRG on the tumoroid morphology in tumoroids P14T and P18T.

Captured images were stored on a central data server, accessible by the OcellO Ominer™ 3D image analysis platform which allows direct parallel analysis of the 3D image stacks by its distributed computational design. The software analyses the structure of the objects (nuclei and cytoskeleton) detected in each well, and their relative positions. Upon analysis, the output was checked to detect the quality of the raw images and the analysis method. The per object measurements the software produced (for the nuclei, the organoids, nuclei within organoids, the lumens, the relative positioning of lumens within organoids and the entire structure (organoids, nuclei and lumens)) were subsequently aggregated per well and the data coupled to the plate layout information (cell line, growth factor condition, treatment, etc.). Upon data aggregation, the data were checked for consistency within control treatments, absence of edge effects, consistency between replicates and the z'-factor between positive and negative controls. Next, the data were z-score normalized and inspected through loading the data into TIBCO Spotfire® to purge additional outliers. 500 different morphological features were collected; The data was then run through a series of statistics that made a sub-selection of 3 to 20 of the ~500 features gathered from the z-stack images, based on the ability of this set of features to distinguish the reference treatment effect from the negative control morphology. The distance between the reference and the negative controls was calculated as a Euclidian distance measurement (FIG. 5) and scaled between zero and one. This unified score of morphology change was used to discriminate hits in the compound screens. The individual selected feature measurements, together with corroboration with the images was used to substantiate and verify the effects of the hit compound treatments on the organoids.

Z'-factor: The Z'-factor is a statistical measure for quality of a high throughput screening assay and indicates the separation window between positive and negative controls. The Z'-factor is defined as 1 minus 3 times the sum of the standard deviations of the positive and negative controls divided by the absolute difference between the means of the positive and negative controls. Z'-values smaller than 0 indicate that there is too much overlap between negative and positive controls, values between 0 and 0.5 indicate a useful but marginal screening window and values between 0.5 and 1.0 indicate an excellent assay with a strong separation between positive and negative controls.

FACS Staining of Cells Obtained from Organoid P18T Using Selected Anti-LGR5 cLC Antibodies Organoids derived from a colorectal cancer sample were cultured in 100% Basement Membrane Extracts (BME, Amsbio), at 37° C. and 5% CO2, with media composed of Advanced DMEM/F12 (Invitrogen) supplemented with: 2 mM GlutaMax (Invitrogen), 10 mM HEPES (Invitrogen), 1×B27 retinoic acid free (Invitrogen), 50 ng/mL EGF (Peprotech), 0.1 µg/mL Noggin (Peprotech), Rock-inhibitor Y-27632 (Sigma-Aldrich), 10 nM PGE2 (Sigma-Aldrich), 3 µm SB202190 (Sigma-Aldrich), 10 nM Gastrin (Tocris), 1 µg/ml R-SPO1 (home-made), 10 mM Nicotinomide (Sigma-Aldrich), 1.25 mM N-Acetyl-cysteine (Sigma-Aldrich), 0.5 µM A83-01 (Tocris). The day prior to analysis, the organoids were disaggregated into single cells. To this aim, the organoids were first liberated from the BME by removing the culturing media, and re-suspending the BME in cell recovery solution (BD Biosciences), and incubating for 1 hour on ice. Subsequently, the organoids were centrifuged (all centrifuge steps were for 5 minutes, 200 g at 4° C.). The pellet was re-suspended in 1 mL of 50% Trypsin/EDTA Solution (TE); 50% PBS, and pipetted up and down, and regularly visually assessed until a single cell suspension was achieved. The TE was diluted in 10 mL of PBS and centrifuged. The cells were washed twice in 10 mL of PBS before re-suspending in BME and aliquoting into 50 µL drops on to pre-warmed plates (37° C.). The BME drops were left to set for 15 minutes before 500 µL of media were added per drop. After 12 hours the cells were isolated from the BME using cell recovery solution. After 1 hour on ice, the cells were centrifuged, and washed once in 10 mL of PBS containing 0.5% BSA and 0.5 mM EDTA (staining buffer). The pellet was then re-suspended in staining buffer and counted. A maximum of 100,000 cells/100 µL of antibody was used. After counting the appropriate number of cells, they were centrifuged and re-suspended in 100 µL of the staining buffer containing the primary antibody (monoclonal and bispecific IgG) diluted to 10 µg/mL. The cells were incubated on ice for 45 minutes, with regular inversion of the tubes to ensure homogeneous staining. After the incubation the cells were washed in 1 mL of staining buffer and centrifuged. The cells were washed again in 1 mL of staining buffer before incubating with 100 µL staining buffer containing an anti-human IgG antibody conjugated to R-PE (Invitrogen, H10104) diluted 1:400. The cells were incubated for 20 minutes on ice, protected from light. After incubating, the cells were washed twice in 1 mL of staining buffer before re-suspending them in staining buffer containing 0.1 µM DAPI (Sigma-Aldrich). The cells were maintained on ice, protected from light, and analyzed immediately. Doublets were excluded using SSC-W vs SSC-A, and DAPI was used to exclude dead cells. Gating of the LGR5 antibodies was set based upon the staining of negative control antibody which was raised against Tetanus Toxin (MF1337). Fluorescence was detected using a BD FACS Aria Fusion using the UV laser and 450/50 filter set for DAPI, and the green laser with the 582/15 filter to detect the R-PE fluorescence.

LGR5 mRNA Enrichment after Sorting

To assess whether the LGR5 FACS staining enriched for cells expressing LR5, the cells were sorted with the sorting gate set so that the highest and lowest 15% of stained cells were isolated. A total of 2000 cells were sorted into picroprofiling buffer (provided by the IRB genomics facility), and the sorted cells were then processed by the IRB genomics facility for RNA extraction and cDNA synthesis. LGR5 expression was assessed using quantitative PCR using TaqMan probes and TaqMan Universal PCR Master Mix (both from Applied Biosystems). The StepOnePlus real-time PCR machine (Applied Biosystems) was used to run the reactions in a clear optical 96-well reaction plates with optical covers, following the manufacturer's instructions. Expression between the negative and positive LGR5 fractions were assessed using an LGR5 probe (Hs00173664_m1) and normalized using the expression of the endogenous control gene B2M (Hs99999907_m1). Differences in target gene expression were determined using the StepOne 2.2 plus software.

P18 Staining for LGR5 and Sorting of LGR5 Positive and Negative Population and the Differences in Growth Between Those Two Cells were stained as described previously and the sorting gates were set so that the highest and lowest 15% of stained cells were sorted into 200 µL of culture media containing Primocin (Invitrogen). The number of sorted cells was determined based upon the number of FACS sorted events. After sorting, the cells were centrifuged and plated at a density of 2000 cells/25 µL of BME. The number of organoids formed after two weeks was manually counted using an inverted light microscope.

Treatment of P18T Organoid with EGFR×LGR5 Bispecifics

For the antibody treatment experiments the culture media was modified, and did not contain Gastrin or PGE2, and had a reduced concentration of EGF (2.5 ng/mL). After disaggregation of organoids. Tryphan Blue staining (Sigma-Aldrich) was used to determine the number of live cells, and 5000 cells were plated/25 µL of BME in a 48-well tissue culture plate. Each treatment had 8 technical replicates, and was cultured in 250 µL of media/well. Three days after seeding single cells, the media was removed and replaced with media containing the antibody treatments (2 µg/mL). After 7 days from the addition of the antibodies, the plate was scanned using an Olympus ScanR using the ×4 light objective, and the number of organoids quantified using ImageJ running a macro designed by the IRB microscopy facility. The experiment was repeated on three separate occasions and a two-tailed, paired sample T-Test was run to assess for significant differences between treatments.

RNA Isolation and Q-PCR Analysis of LGR5 and CK20 mRNA Levels

After the tissue culture plates of treated tumoroids were scanned for enumeration, the tumoroids were isolated using cell recovery solution and incubated on ice for 1 hour. Tumoroids were then centrifuged and re-suspended in 1 mL, of TRIzol® Plus RNA Purification Kit (Life Technologies), and total RNA was extracted. After phase separation with chloroform, the upper aqueous phase was mixed with 70% ethanol and washed through RNA columns (PureLink™ RNA Mini kit, Life Technologies) according to the protocol provided by the manufacturer. RNA was quantified using a Nanodrop spectrophotometer. RNA was then reverse transcribed into cDNA using the High Capacity cDNA Kit (Applied Biosystems). Quantitative real-time PCR using TaqMan probes and TaqMan Universal PCR Master Mix (both from Applied Biosystems) was used to quantify LGR5 (Hs00173664_m1) and CK20 (Hs00300643_m1) levels of mRNA. Differences in expression were detected using the 2-ΔΔCT method and the StepOne 2.2 plus software.

Ex Vivo Measurement of mRNA and Protein Levels of LGR5 and EGFR in PDX Models of Different Indications mRNA extracted from in vivo grown PDX tumours was used to analyse the expression levels of LGR5 and EGFR genes by RNA sequencing (RNAseq). Data from Crown Bioscience database (http://hubase2.crownbio.com) are expressed as log 2 conversion of fragments per kilobase million (FKPM): Table 9. In addition, tumour cells extracted from in vivo grown different PDX tumours were stained with 15 μg/ml of PG5816 (anti-LGR5), PG3755 (anti-EGFR) and (control) PG1337 and bound antibody was then subsequently detected with PE-labeled anti-human IgG. Table 10 shows mean fluorescence intensities for all antibody staining in several cancer indications.

Example 2: Generation of Antibody Panels Directed to WNT Pathway Targets Using Phage Antibody Selections Immunization of MeMo® Mice with the Four Different WNT Targets.

MeMo® mice were immunized with either expression constructs encoding full length human LGR4 and LGR5 (pVax1_hLGR4-FLAG-HA and pVax1_hLGR5-FLAG-HA), with the extracellular domain of LGR4 or LGR5 (pVax1_hLGR4(ECD)-GPA33-FLAG and pVax1_hLGR5(ECD)-GPA33-FLAG) or with recombinant proteins rhLGR4-Fc, rhLGR5-Fc, rhZNRF3-Fc or rhRNF43-Fc (RND systems). Mouse sera were screened for the evidence of a humoral immune response directed towards the target a FACS based assay using in-house generated Freestyle 293F cell lines that stably over-expressed the respective antigen. FIG. 6 shows an example of the data. The serum IgG titers (defined as the highest serum dilution giving a staining of the Freestyle 293F cell line stably expressing the target of at least three times the MFI of serum collected before immunization) of mice successfully immunized with the four WNT targets are depicted in Table 1. Mice that were shown to have mounted a significant and specific immune response towards the respective antigen were then taken out of the study and lymphoid tissues of these mice (inguinal lymph nodes and spleens) were harvested. From the obtained lymph nodes, 'immune' phage antibody repertoires were generated by RT-PCR using IgG- and VH-specific primer pairs and cloning of the polyclonal pool of VH-encoding cDNA's in a phagemid for the expression of Fab fragments on the surface of non-lytic phage. All libraries generated had a size of more than 10^6 clones (individual transformants) and an insert frequency of more than 80%.

Phage Selections to Generate Target-Specific cLC Antibodies

In order to generate cLC antibody panels directed to the targets hLGR4, hLGR5, hZNRF3 and hRNF43, the rhLGR4-Fc, rhLGR5-Fc, rhZNRF3-Fc, rhRNF43-Fc (RND systems) or the soluble ECD of hRNF43 or mZNRF3 (prepared in house) were coated to a solid support and in-house generated synthetic cLC phage antibody repertoires were panned for binding to the coated antigens in the presence of an excess of human IgG (to prevent the selection of Fc-binding phage) essentially as described by Marks et al. (J. Mol. Biol. 1991 Dec. 5; 222(3):581-97). In parallel. 'immune' phage antibody repertoires made from successfully target-immunized animals were also used for selections. Selections on coated protein were performed in microtiter plates (NUNC, maxisorp) and selections on Freestyle 293F cells that over-expressed the respective target were performed in solution; elution of bound phage was performed by a p1 shock using 100 mM glycine (p12) or 100 mM TEA (pH12). After a first round of selection using synthetic phage antibody libraries, the polyclonal pool of selected clones was used to prepare phage again and phage were either panned for binding to the same antigen, or were selected on in-house generated Freestyle 293F cells stably over-expressing the respective antigen. After a single round (immune libraries), or two rounds (synthetic libraries) of selection, single clones were picked and used to prepare monoclonal phage that were tested for binding their respective targets in FACS using a mix of two cell lines: the parental (antigen-negative) Freestyle 293F cell line and DiD-labelled 293F Freestyle cells that stably over-expressed the WNT target. Phage clones that recognized the (DiD-labelled) antigen-positive cell population and not the antigen-negative cells were considered antigen-specific and therefore characterized further. FIG. 7 shows an experiment to test selected clones for antigen specific binding to target expressing cells by FACS.

Clones that were shown to be target-specific were then sequenced and grouped on the basis of their sequence identity: a 'cluster' of antibody clones was defined as a group of antibodies sharing the same VH V-gene usage and having an identical HCDR3 sequence and HCDR3 length (FIG. 17). These clones are all derived from a single ancestral clone that diversified during the in vivo immune response in the MeMo mice. A 'super-cluster' was defined as a group of clones sharing the same VH V-gene usage and having at least 70% sequence identity in HCDR3 and the same HCDR3 length. Although this definition is arbitrary, it is probable (but not proven) that these clones also arose from a single B-cell precursor that was selected, activated and diversified during the in vivo humoral immune response. Practically, the clones in a supercluster are expected to bind the same epitope though with different affinities and/or different location on the epitope. Per super-cluster (defined as described above), at least two clones were then selected to be entered into the clone validation process, during which specific binding to the target was confirmed and the sequence of the clone was verified. These numbers are based on Fab clones of which the VH has a different germline gene usage and/or HCDR3 sequence. Clones that passed the clone validation process (i.e. of which the binding to- and specificity for the target was confirmed and for which the sequence was validated) were then used to re-clone the VH gene into an expression vector to produce and characterize the corresponding IgG. In total, 667 different antibodies were identified that specifically recognized one of the four targets LGR4, LGR5, ZNRF3 or RNF43, of which 288 were characterized further (Table 2). All these clones were then subsequently re-cloned into bispecific cLC IgG format with a 'dummy' (i.e. non-relevant, anti-TT) Fab arm to be able to characterize the mon-valent interaction of the Fab arm directed to the WNT target with its target.

Example 3: Antibody Panel Characterization

The selected Fab fragments (designated with the code MFnnnn) isolated from phage display were re-cloned into an IgG1 expression vector containing DEKK mutations. To this aim, the VH-encoding cDNA was excised from the phagemid vector that was used to select the antibody fragment and re-cloned into the IgG expression vector containing (KK) DEKK mutations. By co-transfection with an expression construct containing the complementary (DE) DEKK mutations and encoding a Fab fragment directed at the non-binding control antigen Tetanus Toxoid (TT: MF1337), bispecific anti-WNT×TT IgG were obtained (WNT referring to LGR4, LGR5, ZNRF3 or RNF43). The bispecific IgG1 panel with monovalent binding activity to the WNT targets was then produced, purified and characterized with regard to their productivity and specificity.

Bispecific IgG were produced on a small scale by transient co-transfection of the plasmids encoding both Fab fragments in Freestyle 293F cells by combining different Fab fragments binding the WNT targeting arm (hLGR4, hLGR5, hZNRF3 or hRNF43) in the positively charged KK vector with the control Fab fragment directed to Tetanus Toxoid in the negatively charged DE bispecific vector. After production, bispecific IgG were purified by protein-A affinity chromatography and the buffer was exchanged to PBS. Successful productions resulted in an IgG1 full length antibody, with a minimal concentration of 0.1 mg/ml, which were assigned a unique code (PBnnnnn: where nnnnn represents a randomly generated number) to identify the specific combination of 2 different target binding Fab fragments.

Successfully produced bispecific IgG were tested for binding to their respective targets in both ELISA and FACS. The ELISA was performed using rhLTR4-Fc, rhLGR5-Fc, rhZNRF3-Fc or rhRNF43-Fc at 2 µg/ml or Tetanus Toxoid at 2.5 µg/ml as coating. IgG were tested at a single concentration of 5 µg/ml. IgG were considered binding to rhLGR4-Fc, rhLGFR5-Fc, rhZNRF3-Fc or rhRNF43-Fc when the $OD_{450\ nm}$ signal observed is five times above background ($OD_{450\ nm}$ signal of negative control antibody). Additionally, a FACS analysis of the bispecific IgG directed to TT and one of the four WNT targets (hLGR4, hLGR5, hZNRF3 or hRNF43) was performed to determine specific binding to their respective WNT target. FACS analysis was performed by using a DiD staining, mixing unlabeled Freestyle 239F cells (DiD-) with labeled antigen positive (hLGR4, hLGR5, hZNRF3 or hRNF43 expressing) Freestyle 293F cells (DiD+). Bispecific IgG were always tested in parallel on two mixes of cells for specificity. The bispecific IgG containing a Fab fragment directed to LGR4 or LGR5 were tested on both hLGR4 and hLGR5 overexpressing Freestyle 293F cells (mixed with antigen-negative Freestyle 293F cells), and the ZNRF3 and RNF43 binding antibodies were tested on both hZNRF3 and hRNF43 overexpressing Freestyle 293F cells (mixed with antigen-negative Freestyle 293F cells). Bispecific IgG were considered binding specifically to hLGR4, hLGFR5, hZNRF3 or hRNF43 when the MFI of the antigen positive population (Freestyle 293F cells stable expressing hLGR4, hLGR5, hZNRF3 or hRNF43) is five times higher than the MFI of the antigen negative population (Freestyle 293F cells).

41 out of 66 LGR4 Fab fragments, 69 out of 84 LGR5 Fab fragments, 92 out of 105 ZNRF3 Fab fragments and 29 out of 33 RNF43 Fab fragments were found to bind specifically to their respective targets (hLGR4, hLGR5, hZNRF3 or hRNF43) in bispecific (Biclonics®) format in both FACS and ELISA, or in a few cases FACS only (hLGR4 binding Fab fragments).

Characterization of the Bispecific Antibody Panel

Bispecific monovalent IgG confirmed to bind specifically to human LGR4, LGR5, ZNRF3 or RNF43 were further characterized for affinity, stability, R-Spondin3 blocking capacity and mouse orthologue cross-reactivity after which a further sub-selection was made.

Affinity Titration FACS Analysis

The binding antibodies were titrated in a limited antibody FACS, to rank them with regard to their affinity. Monovalent IgG directed to hLGR4, hLGR5, hZNRF3 or hRNF43 (all combined with the Tetanus toxoid Fab fragment) on the cellular surface of Freestyle 293F cells overexpressing hLGR4, hLGR5, hZNRF3 or hRNF43. Each IgG was tested on its corresponding overexpressing Freestyle 293F cell line. A two-fold dilution series of IgG (5 µg/ml-0.08 µg/ml) was tested on a fixed number of cells ($5 \times 10^5$ cells/well) stable expressing the WNT targets. The mean fluorescence intensity (MFI) from each individual measurement was determined by FlowJo (FACS analysis software B3D). For each IgG the MFI values were plotted against the concentration of antibody, and from these curves the area under the curves (AUC) were calculated. Based on the AUC values a ranking of the bispecific IgG was made per target. An example of the data used for affinity ranking is given in FIG. 8.

Mouse Orthologue Cross Reactivity of Selected Antibodies

In order to define further the binding characteristics of the bispecific IgG, mouse orthologue cross reactivity was determined. Constructs expressing the mouse orthologues of mLgr5, mZNRF3 and mRNF43 (pEF1_mLgr5-Myc-HIS, pDisplay_mZnrf3-Myc-PDGFR(TM), pDisplay_mRnf43-Myc-PDGFR(TM)) were transiently transfected in HEK293T cells. Mono-valent IgG at a concentration of 5 µg/ml were used for staining and binding of IgG was analyzed by FACS. Bispecific IgG were considered mouse cross-reactive if the mean fluorescent intensity (MFI) increased two-fold compared to the non-transfected Freestyle 293F cells. 92 out of 92 anti-ZNRF3 IgG were cross reactive with mZnrf3; 9 out of 29 anti-RNF43 IgG were cross reactive with mRnf43 and 18 out of 69 anti-LGR5 IgG were cross reactive with the mouse Lgr5 orthologue. mLgr4 cross reactivity was tested in a ELISA on rmLgr4-Fc (RND systems) protein. Bispecific IgG were considered mLgr4 cross reactive in case the $OD_{450\ nm}$ was 5× above background ($OD_{450\ nm}$ signal of negative control antibody). IgG were tested for binding at a single concentration of 5 µg/ml to rmLgr4-Fc and checked for cross reactivity. 36 out of 41 anti-LGR4 IgG tested positive for mLgr4 cross reactivity.

R-Spondin Blocking

All bispecific IgG were tested in a ligand blocking ELISA to be able to test whether LGR4, LGR5, ZNRF3 or RNF43 targeting antibodies can interfere with R-Spondin3 binding. Binding of the Fc fusion proteins of the extracellular domain of the four WNT targets to coated R-Spondin3 was tested in the presence of an excess of bispecific IgG directed to LGR4, LGR5, ZNRF3 or RNF43. To test bispecific IgG directed to the different targets for their ability to block the interaction of the respective Fc fusion protein with rhR-Spondin3, they were tested in a blocking ELISA. IgG were tested using a single IgG concentration of 15 µg/ml.

Clones were considered blocking when in two independent assays at least 50% of the $OD_{450\ nm}$ signal was reduced. When only 20-50% of the $OD_{450\ nm}$ signal was reduced these clones were considered partially blocking. A subset of IgG targeting ZNRF3 (48) and RNF43 (10) and the complete LGR4 (41) and Lgr5 (69) panel, were tested for R-Spondin blocking capacity. For LGR4 3 were blocking and 5 partially blocking. For ZNRF3, 1 blocker and 1 partial blocker was identified. For RNF43 3 blockers and 2 partial blockers were identified, all belonging to 2 different superclusters. For the LGR5 panel 10 IgG that partially blocked binding of R-Spondin3 were identified. An example of the data generated in the R-Spondin3 blocking assay is given in FIG. 9.

Measuring Antibody Stability at 40° C.

In order to gain an indication of the stability of the bispecific IgG, all IgG were incubated in serum-containing medium at 40° C. for 1 week and their binding in ELISA was then compared to that of bispecifics incubated in the same medium at 4° C. After 1 week, the IgG were used in an ELISA screening to determine whether they retained binding to their target. Binding was determined by the percentage of $OD_{450\ nm}$ signal left after one week incubation at 40° C. compared to one week incubation at 4° C. Most IgG were tested twice; when an IgG retained at least 50% of its binding in two independent assays, it was considered stable. When in the two experiments the stability varied; these IgG were considered to be partially stable, and when IgG retained two times less than 50% binding, these were considered unstable. For LGR4 12 out of 41 IgG retained binding (7 partially stable, 2 undetermined; did not bind in ELISA), for LGR5 38 out of 69 IgG retained binding (7 partially stable), for ZNRF3 28 out of 92 IgG retained binding (10 partially stable) and for RNF43 10 out of 29 IgG retained binding (9 partially stable).

Ranking and Selection of Bispecific IgG

After characterization was finished, the data were collected and a ranking was made based on all data obtained. Selection of Wnt targeting Fab fragments for follow up functional screening was performed in the following way: Bispecific IgG which retained binding of at least 50% at 40° C. were selected. The highest affinity binders were then selected. This selection contained binders with different characteristics e.g. mouse orthologue cross reactivity or R-Spondin blocking capacity. In total, 54 bispecific Fab fragments directed at the four different WNT targets were selected for functional screening; for LGR4 10 out of 41 Fab fragments, for LGR5 17 out of 69 Fab fragments, for ZNRF3 18 out of 92 Fab fragments and for RNF43 9 out of 29 Fab fragments were selected (Table 3).

Panel Generation for Functional Screening

The selected WNT targeting Fab fragments against hLGR4, hLGR5, hZNRF3 or hRNF43 were used for the generation of a large panel of bispecific antibodies (>500 bispecifics). The selected WNT-targeting Fab fragments were combined with receptor tyrosine kinase (RTK) binding Fab fragments into a panel of bispecific IgG and produced and purified. The Fab fragments specific for EGFR and HER3 that were selected block receptor activation in cell-based assays do not interfere with functionality of other Fab fragment when combined in bispecific format. Four EGFR Fab fragments MF3755, MF4280, MF3370 and MF4289 as well as four HER3 Fab fragments MF3178, MF3176, MF3125 and MF4863 were used in combination with the selected WNT-targeting Fab fragments (see Table 5 for a subselection of the produced panel).

Bispecifics were produced by coexpression of IgG vectors in which the WNT arm was expressed on the heavy chain containing the positively charged KK mutation and the RTK arm was expressed on the heavy chain containing the negatively charged DE mutation, purified and validated for their target binding, specificity and stability. The panels of bispecifics that passed binding and stability quality control (QC) were used for functional screening (53 out of 54 WNT targeting Fab fragments passed QC). The panel of >500 purified and validated bispecific antibodies targeting one of the four WNT targets (hLGR4, hLGR5, hZNRF3 or hRNF43) and an EGFR or HER3 Fab fragment or Tetanus Toxoid as a mock negative control Fab fragment control were screened for their activity towards patient-derived organoids in the functional screening assays described below.

Example 4: Functional Screening of Bispecific Antibodies in Colon Organoids

Colon organoids are derived from LGR5-positive (cancer) stem cells grown in growth factor-containing expansion medium that allows the formation of epithelial colon structures that form a functional lumen (Sato et al. 2011 Gastroenterology 141:1762-1772). The organoid growth, development and lumen formation depends on the genetic background of the colorectal cancer cells and on the response to growth-stimulating growth factors, epidermal growth factor (EGF) or Neuregulin-1 (NRG)/Heregulin (HRG). Although the morphology of CRC tumoroids from different patients differs widely, the morphological profile is consistent between the tumoroids of the same origin and they are genetically almost identical to the original tumour they were derived from. High content quantitative analysis of images of cultured CRC organoids can therefore discriminate CRC organoids from different patients and can also be used to measure the morphological changes associated with activation of signaling pathways—e.g. driven by the ligands for HER receptors e.g. EGF and HRG. Similarly, inhibition of these responses by function blocking antibodies or other therapeutic molecules can be measured. Image-based analysis allows changes in morphology to be measured that may be independent of cell proliferation, providing additional information on compound activity to that which is obtained from conventional proliferation assays. Compound-induced phenotypic changes therefore form the basis for the functional screening of antibodies in CRC organoids.

The bispecific antibodies that have been developed target either EGFR or HER3 in combination with targeting the WNT-signaling related cell surface expressed proteins LGR4, LGR5, RNF43 or ZNRF3. The screening system is designed to monitor the inhibition of tumoroid outgrowth due to the activity of bispecific antibodies. This can be used for both the selection of organoids (and associated molecular profile) that are sensitive to targeted inhibition of specific pathways and also for the selection of novel molecules that are active in the organoids.

Selection of Colon Tumoroid Models

Colon tumoroid models used for the screens were selected based on the demonstration of morphological changes in response to EGF, HRG or WNT3A. Morphological responses to these factors were investigated in a panel of 20 tumoroids of different patient origin (Van de Wetering et al. 2015 Cell 161:933-45). First, the tumoroids were expanded, split and re-seeded in 384-wells plates to analyze and document the basic morphology after 1 week of growth. Next, the same tumoroids were tested for their responsiveness to growth factors, being EGF or HRG, or no growth factor present in the expansion medium. To do this, all 500 morphological features were analyzed and the changes induced by the soluble factors were measured. A set of robust features was selected for each organoid that enabled measurement of the growth factor response and discrimination between growth-factor dependent tumoroid cultures and growth-factor independent tumoroid cultures (see Table 4). This demonstrated that no single feature was sufficient to optimally quantify responses in different CRC organoids. Based on these data the following tumoroid lines were selected: P18T ($APC^{mut}$) which is heavily EGFR signaling dependent for growth and the formation of branched lumen structures inside the tumoroids; P14T ($APC^{mut}$, $SMAD4^{mut}$) that shows clear morphology altering effects upon EGFR and HER3 signaling and inhibition; P19Tb ($APC^{wt}$, but PIK3CA, TP53, BRAF, ARID1A, ARID2, ERBB3, POLE and RNF43 mutant) as a tumoroid model that lacks APC mutations and hence depends on WNT3A for expansion: finally, P26T ($APC^{mut}$, $KRAS^{mut}$, $TP53^{mut}$ and $CTNNB^{mut}$) as a model that exhibits no dependency on the presence of growth factors for expansion. In the initial screening of bispecific antibodies P26T did not show any growth factor dependency and no sensitivity towards growth factor receptor targeting antibodies, and was dropped from further antibody screening.

Identification of Functional Fab Fragments in Bispecific Antibodies

To identify functional bispecific antibodies capable of altering the morphological characteristics of colon tumoroids, they were compared to growth conditions without EGF stimulation and to the effect of EGFR/MAPK signaling inhibiting compounds (e.g. Cetuximab and Trametinib) in EGF growth conditions. Functional bispecific antibodies were defined by their ability to limit tumoroid expansion in EGF conditions in the direction of the morphological profile obtained by EGFR/MAPK signaling inhibitors and/or omitting EGF from the culture medium. WNT-targeting Fab fragments that potentiated the effect of the EGFR-targeting arm are those that showed significantly enhanced growth inhibiting capacity compared to the equivalent monovalent (bispecific EGFR×TT)-targeting Fab fragment.

Bispecific antibodies that only targeted LGR4, LGR5, ZNRF3 or RNF43 (in combination with the non-targeting Tetanus Toxoid (TT)-Fab fragment) were compared to the negative control morphology in either no growth factor containing medium (P19Tb) or EGF or HRG containing medium (P18T and P14T) to seek potential effects of targeting WNT-signaling receptors alone.

Bispecific antibodies carrying HER3-targeting Fab fragments were functionally compared to growth conditions without HRG stimulation or the effect of HER3 targeting antibodies and the PI3K inhibitor in HRG conditions; Functional HER3-inhibiting bispecific antibodies were defined as those that inhibited the HRG-stimulated growth response into the same direction in Euclidean space as the MEK kinase inhibitor, Trametinib, no HRG culture conditions and/or HER3 targeting reference antibodies. WNT-targeting Fab fragments that potentiated the HER3-targeting arm effect in terms of growth inhibiting effect compared to the equivalent monovalent HER3 bispecific were considered as candidate targeting Fab fragments.

Selection of Bispecific Antibody Candidates in the Primary-Screen

Bispecific antibodies that, in the presence of EGF, induced a change in the morphology of P14T and P18T colon tumoroids approaching, matching or exceeding the phenotype in the absence of growth factors or presence of reference EGFR/MAPK inhibitors, these antibodies were identified as potential candidates. Similarly to the EGF conditions, the antibodies tested in HRG culture conditions were marked for follow-up if the effect approached, matched or exceeded the negative control distance of the no growth factor conditions and/or reference HER3/PI3K inhibitors. For P19Th, which was relatively insensitive to growth factor treatment, the functional antibody selection was based on calculating the distance from the negative controls marked by the morphological profile induced by Trametinib and the PI3K-inhibitor CH-5132799.

The bispecific panels were screened in 3 different colon tumoroids (P18T, P14T and P19Tb). The screened antibody panel tested the combinations of four different EGFR-targeting Fab fragments, four different HER3-targeting Fab fragments and one anti-Tetanus Toxoid (negative control) Fab fragment with 53 different WNT-targeting Fab fragments and one TT targeting Fab fragment. Each bispecific antibody was scored for its capacity to inhibit tumoroid outgrowth. None of the TT/WNT fragment combinations inhibited tumoroid outgrowth (0/53). Within the EGFR-targeting Fab fragment group, the MF3755 Fab fragment was most potent: 22/53 bispecific MF3755/WNT Fab fragment combinations inhibited tumoroid development. The runner up EGFR-targeting fragment was MF4280 with 4/53 active inhibitory EGFR/WNT Fab fragment combinations. One (1/53) EGFR-targeting bispecific MF3370/WNT Fab fragment combination showed inhibitory activity and none (0/53) of the EGFR-targeting bispecific MF4289/WNT Fab fragment combinations significantly limited the tumoroid outgrowth. Within the HER3-targeting Fab fragment containing bispecific antibody group, the MF3178 Fab fragment in combination with the WNT-targeting Fab fragments was most potent: 19/52 MF3178/WNT combinations inhibited tumoroid outgrowth. Runner up HER3 targeting Fab fragment was MF4863 with 6/53 active MF4863/WNT bispecific antibodies. Bispecific antibodies containing the HER3 targeting Fab fragments MF3125 (0/53) and MF3176 (0/52) showed no significant tumoroid outgrowth inhibition.

In ranking, the RTK-targeting Fab fragments that most potently combined in the bispecific IgG format with the WNT targeting Fab fragments were MF3755 as the EGFR targeting Fab fragment and MF3178 as the HER3 targeting Fab fragment. The LGR4 targeting Fab fragments MF5777 and MF5781, the LGR5 targeting Fab fragments MF5790, MF5803, MF5814, MF5816, MF5817 and MF5818, the RNF43 Fab fragments MF5832 and MF5836 and the ZNRF3 targeting Fab fragments MF5850, MF5853, MF5855, MF5884 and MF5888 were identified as potential candidates to progress to the validation screen based on their functional effect on P18T, P14T and P19Tb tumoroid morphology when combined with RTK targeting Fab fragments in the bispecific IgG format. The LGR4, LGR5, RNF43 and ZNRF3-targeting Fab fragments were combined with either the EGFR targeting Fab fragments MF3755, the HER3 targeting Fab fragments MF3178 or the non-targeting TT Fab fragments MF1337 and produced in new batches to confirm their activity in the follow-up validation screen.

Bispecific RTK/WNT Antibody Validation Screen

Because the RTK/WNT bispecific antibody candidates had shown potentially therapeutically relevant activity in both EGF and in HRG culture conditions, the validation screen of the bispecific candidate antibodies was also performed in two growth factor conditions: 5 ng/ml EGF or 5 ng/ml HRG. Controls included wells that received culture medium without either EGF or HRG. Other controls used in growth factor conditions: Cetuximab (EGFR), PG3755 (EGFR/EGFR), Trametinib (MEK), CH5132799 (PI3K), PG3178 (HER3/HER3), PG2863 (HER3/HER3), PG3794 (HER3/EGFR) and PB4522 (HER3/EGFR). PG1337 (TT/TT) served as a negative control antibody, and was referred to as negative control, along with wells receiving equal volumes of DMSO or PBS as the compound- or antibody-treated wells respectively.

The antibody validation screen of 46 bispecifics was performed in 24 colon tumoroids of different patient origin, in duplicate or in quadruplicate. The set of tested colon tumoroid lines consisted of 3 growth factor-dependent patient samples described in Van de Wetering et al. (2015 Cell 161:933-45); P18T, P14T and P8T and 2 growth factor independent patient samples, P19Tb and P28N. A novel set of 19 colon tumoroids were screened: 10 growth factor dependent primary colon tumoroid lines, 5 growth factor independent primary colon tumoroid lines and 4 (growth factor dependent) metastatic colon tumoroid lines. The screening of the bispecific antibody candidates in the panel of 24 different patient-derived colon tumoroid lines revealed that growth-factor dependency for tumoroid outgrowth is able to identify RTK-targeting Fab fragment mediated tumor inhibition.

The cut-off to identify functional colon tumor inhibitory antibodies in the bispecific antibody validation screen was calculated by normalizing the morphological profile on a scale of 0 (phenotype equal to a fully growth inhibited profile) and 1 (phenotype similar to the negative controls). Every time a single antibody, at a certain dose, in a certain tumoroid line scored less than 0.5, this antibody treatment was marked as showing inhibition of tumor development. The number of times an antibody, at a certain dose in either EGF or HRG culture conditions showed inhibition was scored and expressed as a percentage of the number of treated wells for that condition. This percentage was calculated in all 24 screened colon tumoroid lines.

The validation screen in 24 colon tumoroids identified four LGR5 targeting Fab fragments and 2 RNF43 targeting Fab fragments that potentiated the RTK-Fab fragments mediated tumor development inhibition: MF5816, MF5814, MF5818 and MF5790 as LGR5 targeting antibody Fab fragments and MF5832 and MF5836 as RNF43 targeting Fab fragments. The top ranking antibody was the EGFR/LGR5 bispecific antibody PB10651 composed of the targeting Fab fragments MF3755 and MF5816: FIG. 10. In HRG conditions, the top ranking antibody was the HER3/LGR5 bispecific antibody PB10748 composed of the targeting Fab fragments MF3178 and MF5816. This showed, in two independent growth factor conditions and in combination with two different RTK targeting Fab fragments, that the LGR5-targeting Fab fragments MF5816 is the most potent WNT-targeting Fab fragments that enhances RTK targeting, MF5816 combined with MF3755 in PB10651 adds another level of tumor inhibition by potently reducing tumoroid growth and development, observable by further loss of lumen formation, cell shrinkage and rounding up of the nuclei. These morphological findings indicate that the EGFR/LGR5 antibody PB10651 actively blocks epidermal growth factor signaling and induces a cell death response in the growth-impaired tumoroid cells: FIG. 11. This morphological phenotype was not observed with EGFR targeting antibody Cetuximab nor when MF3755 was formatted as a conventional IgG.

Selection of the Lead Candidate Antibody

PB10651 (EGFR/LGR5 bispecific antibody (composed of the Fab fragments MF3755 and MF5816)) was selected as the primary lead candidate antibody in 5 ng/ml EGF conditions for the following characteristics: PB10651 showed potent inhibitory effects at 10 µg/ml test dose in 75% of the 24 different colon tumoroid models: 2) 67% of the wells treated with PB10651 at 10 µg/ml (40/60) showed more than 50% growth reduction: 3) 52% (31 out of 59 wells) showed more than 50% growth reduction upon PB10651 treatment at 2 µg/ml; 4) PB10651 outperformed Cetuximab (47% (56/119) at 10 µg/ml and 29% (35/119) at 2 µg/ml) and the EGFR/IT reference antibody PB9919 (27% (16/60) at 10 µg/ml and 5% (3/60) at 2 µg/ml).

PB10647 (EGFR/LGR5 MF3755×MF5814) is the second candidate antibody that inhibited 54% of the 24 different tumoroid models (13/24) at 10 µg/ml, and more than 50% growth reduction was found in 52% of the exposed wells (31/60) at 10 µg/ml and in 37% (22/60) at 2 µg/ml.

Other EGFR/LGR5 antibodies are PB10659 (MF3755×MF5818), effective in 50% of the 24 tumoroid models (12/24), 50% of the wells exposed with PB10659 at 10 µg/ml showed inhibition (30/60) and 32% (19/60) at 2 µg/ml. PB10627 (MF3755×MF5790) was active in 42% of the tumoroids (10/24) and showed reduction at 10 µg/ml in 39% of the wells (23/59) and at 2 µg/ml in 33% of the wells (20/60). PB10631 (MF3755×MF5803) was active in 33% of the tumoroids (8/24) and inhibitory at 10 µg/ml in 34% of the wells (20/59) and in 12% (7/59) at 2 µg/ml. PB10655 (MF3755×MF5817) was active in 20% (5) of the 24 tumoroid models and showed inhibition in 25% of the wells (15/60) at 10 µg/ml and 6/60 (10%) at 2 µg/ml.

EGFR/LGR4 antibody PB10619 (MF3755×MF5777) was active in 29% (7/24) tumoroid models and led to tumoroid inhibition in 28% (17/60) wells at 10 µg/ml and 15% (9/60) at 2 µg/ml. EGFR/LGR4 antibody PB10623 (MF3755×MF5781) was active in 8 of the 24 tumoroid models (33%) and inhibited at 10 µg/ml in 30% of the wells (18/60) and 10% of the wells at 2 µg/ml (6/60).

EGFR/RNF43 antibody PB10661 (MF3755×MF5832) was active in 13 of the 24 tumoroid models (54%) and showed inhibition in 42% of the wells (25/60) at 10 µg/ml and 22% (13/60) at 2 µg/ml test dose. EGFR/RNF43 antibody PB10667 (MF3755×MF5836) was active in 13/24 tumoroid models (54%) and showed inhibition at 10 µg/ml in 35% of the wells (21/60) and at 2 µg/ml in 20% of the wells (12/60).

EGFR/ZNRF3 antibodies are: PB10675 (MF3755×MF5850), active in 8/24 tumoroid models (33%) with 35% of the tested wells (21/60) showing more than 50% inhibition at 10 µg/ml and 15% (9/60) at 2 µg/ml; PB10695 (MF3755×MF5884) was active in 37% of the tumoroid models (9/24) and showed inhibition in 34% (20/59) at 10 µg/ml and 12% (7/59) at 2 µg/ml; PB10679 (MF3755×MF5853) inhibited the tumoroid development in 21% of the tumoroid models (5/24), 20% of the wells at 10 µg/ml (12/60); PB10703 (MF3755×MF5888) was active in 5 of the 24 tumoroid models (21%) and inhibited at 10 µg/ml in 22% of the wells (13/60) and at 2 µg/ml in 12% of the wells (7/59).

PB10748, the HER3/LGR5 antibody composed of the Fab fragments MF3178 and MF5816, is active as a HRG-stimulated tumoroid inhibiting antibody in 62% of the tested colon tumoroid models (15/24), showing inhibition in 56% of the exposed wells (67/120). PB10748 outperformed the HER3/IT reference antibody PB9215 (MF3178×MF1337) which inhibited more than 50% of the HRG-stimulated tumoroid development in 34% (41/120) exposed wells.

Other HER3/LGR5 antibodies are: PB10735 (MF3178×MF5814), active in 11/24 tumoroid models (46%) and inhibitory in 43% of the exposed wells (51/118); PB10756 (MF3178×MF5818) was active in 8/24 (33%) of the tumoroid models and inhibitory in 37% of the exposed wells (44/119); PB110715 (MF3178×MF5790) was active in 12/24 (50%) of the tumoroid models and inhibitory in 42% of the wells (49/117); PB10719 (MF3178×MF5803) was active in 7/24 (29%) of the tumoroid models and inhibitory in 34% of the exposed wells (40/119); PB10752 (MF3178× MF5817) was active in 12/24 (50%) of the tumoroid models and inhibitory in 28% of the wells (33/120).

Two HER3/RNF43 antibodies are: PB10764 (MF3178× MF5836), active in 17/24 tumoroid models (71%) and inhibitory in 38% of the exposed wells (46/120) and PB12336 (MF3178×MF5832), active in 11/24 tumoroid models (46%) and inhibitory in 41% of the exposed wells (49/120).

Two HER3/LGR4 antibodies are: PB10711 (MF3178× MF5781, active in 62% of the tumoroid models (15/24) and inhibitory in 50% of the exposed wells (59/119) and PB10707 (MF3178×MF5777), active in 13 of the 24 tested tumoroid models (54%) and inhibitory in 41 of the 120 exposed wells (34%).

Bispecific antibodies targeting both HER3 and ZNRF3 are: PB10776 (MF3178×MF5853), active in 11/24 (46%) of the tumoroid models exposed to HRG and inhibitory in 40% of the exposed wells (48/120); PB10772 (MF3178× MF5850), active in 12/24 models (50%) and inhibitory in 39% of the exposed wells (46/119); PB10780 (MF3178× MF5855), active in 8/24 (33%) colon tumoroid models and 31% of the exposed wells (37/119); PB10800 (MF3178× MF5888) was active in 12/24 tumoroid models (50%) and inhibitory in 29% (34/119) of the exposed wells.

Example 5: Characterization of the Lead Candidate Antibody

Affinity Measurement of Bispecific Antibody Binding Using a Cell Based Assay.

After optimization of the iodination protocol, a labelled PB10651 protein with a specific radioactivity of 40 GBq/μmol was obtained. The radiochemical purity was >99% as analyzed by protein precipitation. In the Lindmo assay, only a minor reduction of the immunoreactivity was observed. The immunoreactivity of $^{125}$I-PB10651 towards EGFR and LGR5 was estimated to be >89% using CHO cells expressing either EGFR or LRG5. Results of the Lindmo assay are depicted in FIG. 12. Using steady-state affinity measurements, the $K_D$ of $^{125}$I-PB10651 towards CHO-LGR5 cells was measured to be 0.86±0.13 nM, and the $K_D$ of $^{125}$I-PB10651 towards CHO-EGFR cells was found to be 0.22±0.086 nM. The $K_D$ of $^{125}$I-PB10651 towards DLD-1 cells was estimated to 0.18±0.024 nM. An example of the data is depicted in FIG. 13.

Epitope Mapping of PB10651 Through Shotgun Mutagenesis Analysis

To map the epitopes on EGFR and LGR5 respectively recognised by both Fab arms present in PB10651, the shotgun mutagenesis approach was used. Residues that were relevant for the binding of both Fab arms to their respective antigens could unequivocally be determined. Mutations that abrogated the binding of PB10651 to either EGFR or LGR5 and that did not inhibit the binding of the control antibodies (identifying relevant residues) are depicted in Table 8. These data show the anti-EGFR Fab arm to recognise domain III on a region that partially overlaps with the site that normally contacts the ligand EGF (Ogiso et al., 2002). This indicates that PB10651 may directly block the ligand-EGFR interaction. The epitope is indicated in the structure of EGFR (pdb reference 1YY9) in FIG. 14. The Fab arm recognising LGR5 was shown to recognise residues that are located in the N-CAP domain and first Leucine Rich Repeat (LRR). The residues are indicated in FIG. in the structure of LGR5 in complex with RSPO1 (pdb reference 4BSR, Peng et al., 2013).

REFERENCES

Li S, Schmitz K R, el al., (2005) *Structural basis for inhibition of the epidermal growth factor receptor by cetuximab*. Cancer Cell. April; 7(4): 301-11.
Ogiso, H. Ishitani, R. et al., (2002) *Crystal structure of the complex of human epidermal growth factor and receptor extracellular domains*. Cell, Vol. 110, 775-787.
Peng. W. C. de Lau W. el al., (2013) *Structure of Stem Cell Growth Factor R-spondin 1 in Complex with the Ectodomain of Its Receptor LGR5*. Cell Rep 27; 3(6): 1885-1892.

Competition for Binding of the Anti-LGR Fab Arm in PB10651 by the Ligand R-Spondin1 Using a Cell Based Assay To be able to determine the ability of the anti-LGR5 Fab arm present in PB10651 to bind LGR5 in the presence of the ligand R-spondin1, a cell-based assay was set up. The EC50 for binding of the ligand-blocking anti-LGR5 antibody OMP88R20 (PG7711) to the LGR5-expressing cell clone was determined to be 50 ng/ml (333 pM) and this concentration was then used to determine the competition with the ligand R-spondin1 for binding to LGR5. FIG. 16 shows the MFI signal (normalised to the MFI signal obtained in the absence of R-spondin1) of OMP88R20 binding to LGR5-expressing CHO-K1 cells measured in FACS as a function of the concentration of added R-spondin1. Bispecific anti-(TT×LGR5) antibodies were then tested for their ability to bind the LR5 expressing CHO cell clone in the presence of increasing concentrations of R-spondin1. PC7711 was included as positive control at 50 ng/ml. The bispecifics were first tested for binding to the CHO cell clone expressing LGR5 in a concentration range to determine the EC50 for binding in FACS. The EC50 was found to be 156 ng/ml for PB10286 containing the lead Fab MF5816 and 200 ng/ml for PB10261 containing MF5790. However, bispecifics were tested at 100 ng/ml to compare the same concentrations of antigen-specific Fabs in the assay as used or PG7711 and to possibly even increase the sensitivity of the assay. FIG. 17 shows that the lead anti-LGR5 Fab MF5816 was not inhibited from binding LGR5, even in the presence of a large (120-fold) molar excess of the ligand, whereas in the same assay, binding of the copied version of OMP88R20 was fully inhibited. In addition, reduced binding of PB10261 (containing the LGR5 targeting arm MF5790) was observed, demonstrating that, the assay is able to discriminate between ligand-blocking, as well as ligand non-blocking anti-LGR5 Fabs. No differences and no competition were observed when using the 1D9 rat anti-LGR5 antibody in the blocking assay (FIG. 17), demonstrating specificity of the interaction.

REFERENCE de Lau W. Barker N, et al., *Lgr5 homologues associate with Wnt receptors and mediate R-spondin signalling*. Nature. 2011 Jul. 4; 476 (7360): 293-7.

Ligand-Blocking Capacity of the Anti-EGFR Fab Arm of PB10651 Using a Cell Based Assay.

In order to test the capacity of the anti-EGFR Fab of PB10651 to block EGF-mediated signalling, a cell-based assay was used. FIG. 18 shows the potency of PG3755 to block the EGF-mediated cell death in A431 cells (tested according to the method described by Gulli et al.) compared to that of cetuximab. The antibody blocks EGF-mediated signalling with a potency that is at least equal to that of cetuximab.

REFERENCE

Gulli, L. F., et al., *Epidermal growth factor-induced apoptosis in A431 cells can be reversed by reducing the tyrosine kinase activity*. Cell Growth Differ, 1996. 7(2): p. 173-178.

Species Cross-Reactivity of PB10651.

PB10651 was tested for its cross-reactivity with the rat- and cynomolgus orthologues of both targets: EGFR and LGR5. The cDNA sequence of cynomolgus LGR5 that was obtained by RT-PCR from cynomolgus cDNA matched the predicted sequence from GenBank (reference XM_005571542). Both the human—as well as the rat—and cynomolgus-encoding constructs were used for a transient transfection of CHO-K1 cells. Antibody binding to cells transiently expressing either the human—rat—or cynomolgus orthologue was then tested in FACS. FIG. 19 shows the graphs of the mean fluorescence intensity (MFI) obtained in FACS after staining as a function of the antibody concentration used for staining. Both the Fab arm recognising EGFR, as well as the Fab arm recognising LGR5 were found to be fully cross-reactive to the cynomolgus orthologue of the target: the EC50 values for binding were not significantly different for binding to the human or cynomolgus orthologue. In a similar experiment, the cross-reactivity of both arms with the rat orthologue was assessed. PB10651 was found to bind well to the rat orthologue of LGR5, although the EC50 was shifted with about a log compared to the value found for binding human LGR5. However, the anti-EGFR Fab arm was hardly cross-reactive (two log difference in EC50) to the rat orthologue of EGFR, making the antibody unsuited for rat in vivo models or toxicity studies in rats. As positive control for cynomolgus LGR5 cross-reactivity, the copied version of hu8E11v2 (PG7543) was used. Cetuximab was used as control for cynomolgus EGFR cross-reactivity.

Specific LGR5 Targeting on a Patient-Derived Organoid

In order to demonstrate that Fab fragments MF5816 and MF5814 bind to LGR5 expressed on the surface of patient-derived organoids, PG5816 and PG5814 (bivalent, monoclonal IgG) containing Fab fragments MF5816 or MF5814 were used to stain the individual cells derived from the organoid P18T. Using PG5816 resulted in staining of 53.6% of the P18T tumoroid derived cells and PG5814 resulted in staining 52.5% of the P18T tumoroid derived cells, compared to staining using the negative control antibody directed to TT (FIG. 20).

LGR5-Sorting Enriches for LGR5-Expressing Cells and for Tumour-Initiating Cells

In addition, to show that the LGR5 targeting Fab fragments in a bispecific format actually bind LGR5 on the P18T tumoroid cells, cells were stained with bispecific antibodies PB10284 and PB10286 containing Fab fragments MF5814 or MF5816 combined with the anti-TT Fab fragment. After staining, cells were sorted using FACS, and the stained and non-stained cell populations were analyzed by Q-PCR for LGR5 mRNA levels. Staining P18T derived tumoroid cells using the bispecifics containing LGR5 Fab arm MF5816 or MF5814 resulted in a 6-14 fold enrichment of LGR5 mRNA expression levels in the sorted LGR5-positive cell fraction compared to the LGR5-negative cell fraction: FIG. 21.

Furthermore these enriched LGR5 expressing P18T tumoroid cell populations allowed for a 4-fold increase in colony forming capabilities: P18T was used for FACS staining and sorting of the top (positive) and bottom (negative) 15% of stained cells identified by the anti-LGR5 antibodies; MF5814-TT, MF5816-TT and MF5790-TT. 2000 cells were plated in 25 μL of BME in duplicate (technical replicates). After two weeks of growth, the organoids were manually counted using an inverted light microscope. The results demonstrate that on average the MF5814-TT, MF5790-TT and MF5816-TT antibodies enrich for organoid growth, with the positive fractions forming 4.5, 3.7 and 7.1 times more organoids than the negative fractions, respectively: FIG. 22. These data demonstrate a clear enrichment for tumour initiating cells after sorting for LAR5-positive cells from a patient-derived organoid.

LGR5×EGFR Bispecifics Inhibit Patient-Derived Organoid Outgrowth

As an independent way of measuring the therapeutic efficacy of the lead bispecific anti-LGR5×EGFR antibodies, identified in the 3-D screening, organoids were treated with the different bispecifics and organoid growth was assessed in a standard colony formation assay after 7 days: FIG. 23. The images shown on the right of the figure are an example of the images produced by the macro's analysis, and depicts one drop containing organoids (black circles). The experiment was repeated on three separate occasions and the number and size of organoids was averaged between the experiments. These data corroborate the data obtained using the antibody validation screen and show that lead bispecific LGR5×EGFR antibodies are potent inhibitors of patient-derived organoid growth.

Treatment of Patient-Derived Organoids with LGR5×EGFR Bispecific Antibodies Strongly Reduces the Non-Differentiated Cell Population.

After tumoroids were treated for seven days with the lead bispecific LGR5/EGFR bispecific, quantitative real-time PCR analysis was used to assess the antibodies effects upon expression of LGR5 and CK20 (a marker of differentiation) (FIG. 24). The results demonstrate that treatment with the EGFR×TT (MF3755×MF1337; PB999) antibody causes a 0.5-fold increase in LGR5 mRNA levels whilst reducing the levels of CK20 4-fold relative to TT×TT. The LGR5 antibodies MF5814×TT (MF5814×MF1337; PB10284) and MF5816-TT (MF5816×MF1337; PB310286) show little effects. However, when the EGFR arm is substituted for the TT arm, the LGR5 levels are reduced by 5.9 and 7.2-fold after treatment with the MF5814×EGFR (MF5814× MF3755; LGR5×EGFR; 1PB10647) and MF5816-EGFR (MF5816×MF3755; LGR5×EGFR; PB10651) antibodies respectively. The CK20 expression is also reduced by both the PB10647 (EGFR/LGR5, MF5814×MF3755) and PB10651 (EGFR/LGR5, MF5816×MF3755) antibodies by 10.4- and 13.7-fold. These data suggest that in this tumoroid line, through addition of an LGR5 targeting arm, the relative increase in LGR5 mRNA levels caused by EGFR inhibition can be abrogated, whilst also enhancing the original effects of the EGFR inhibition (decrease in CK20 mRNA).

Treatment of Organoids from Tumours (Tumoroids) and Organoids from Normal Tissue with PB10651.

In order to demonstrate that PB10651 is selectively targeting colon cancer-derived tumoroids and not normal colon tissue-derived organoids, organoid cultures were incubated with afucosylated PB10651 or Cetuximab. FIG. 26 shows the organoid (tumoroid) size at the respective dosage of the indicated antibody. (C51N is an organoid from normal colon tissue. C1M is an organoid (tumoroid) from cancerous tissue (FIG. 26B). FIG. 26A depicts the results on an organoid from normal tissue (C55N) and cancerous tissue (C55T)

from the same patient. FIG. 26C shows the $IC_{50}$ table for Cetuximab and PB10651 in 5 normal tissue organoids, 3 primary colon cancer tumoroids and 3 metastatic colon cancer tumoroids. The Cetuximab $IC_{50}$:PB10651 $IC_{50}$ ratio is given in the last column of FIG. 26C. This shows that PB10651 is 20-200× more potent than Cetuximab in tumoroids, while the effect of PB10651 in normal organoids is weaker than Cetuximab. Additional tests demonstrated that the presence of WNT or R-Spondin in the culture medium had no influence on the efficacy of Cetuximab or PB10651 in inhibiting outgrowth of the tumoroids (not shown).

LGR5 Targeting Antibodies do not Inhibit Colon Tumoroid Outgrowth

To verify that the bispecific aspect of PB130651 is required to achieve the tumour-inhibiting capacity, PB10651 was compared to other WNT-targeting antibodies in production by Genentech. Bionomics or OncoMed (Table 7). In FIG. 27, the effects of LGR5 targeting antibodies (PG7709, PG7711, PG7712 and PG7543) on organoid growth are compared to those mediated by PB10651 and Cetuximab in the tumoroid models P18T and C1M. The results show that none of the comparator antibodies inhibit colon tumoroid outgrowth.

Bispecific PB10651 is More Potent than the Mix of the Bivalent, Mono-Specific Antibodies in Inhibiting Tumoroid Growth The bispecific antibody PB10651 is composed of an EGFR targeting arm (MF3755) and an LGR5-targeting arm (MF5816). To show that the actual physical interaction between both Fab arms is required to achieve the potent inhibition effect on colon tumoroids, these were incubated with increasing doses of PB10651 (MF3755×MF5816; EGFR×LGR5), Cetuximab, PG3755 (MF3755×MF3755; EGFR×EGFR), PG5816 (MF5816×MF5816; LGR5× LGR5), PG1337 (MF1337×MF1337; TT×TT) and a 1:1 mix of PG3755 with PG5816. FIG. 28A shows that treatment with a mixture of anti-LGR5 and anti-EGFR antibodies results in a less potent growth inhibition of tumoroids compared to treatment with the bispecific antibody PB10651. Interestingly, the growth of normal organoids was more potently inhibited by the mixture of anti-EGFR and anti-LTR5 antibodies than by the bispecific antibody. These effects are summarized in the $IC_{50}$ table for other tumoroid and normal organoid models in FIG. 28B.

Localization Studies of PB10651 in Colon Tumoroids Reveal a Specific Intracellular Staining Pattern In order to show that the antibodies reach the tumoroids while seeded in the BME2 RGF hydrogel, 7-day old P18T tumoroids were treated for 24 hours with the indicated antibodies (2 μg/ml) and then fixed (15 minutes, 4% paraformaldehyde) and permeabilised (0.1% Triton-X100 and 0.5% BSA in PBS). Organoids were subsequently counter-stained with goat-anti-human-FITC (Thermo Scientific, 1:3000). Nuclei and actin were stained as described in (Di et al PlosOne 2014, PMID 25289886). FIG. 29 show that all antibodies are able to penetrate the gel and bind all the cells in a tumoroid. The EGFR-targeting antibodies Cetuximab and PG3755 localize to the plasma membrane, while PB10651 shows an intracellular speckled staining pattern, which is not observed for any of the comparator LGR5 antibodies (PG7709, PG7711 or PG7712).

Localization Studies of PB10651 in Colon Tumoroids Reveal a Juxtanuclear Intracellular Punctate Staining Pattern that Correlates with Tumoroid Sensitivity More colon tumoroid and organoid models were included in the PB10651 counterstaining and imaging assay (see above). FIG. 30 shows that the intracellular staining pattern of PB10651 is observed in P18T, C0M, C55T (highly sensitive to PB110651, $IC_{50}$<1 μg/ml), in some tumoroids of C31M (moderately sensitive to PB10651), but not in the PB10651 insensitive ($IC_{51}$>10 μg/ml) C28T, P8T or P19Tb tumoroids or C51N normal colon organoids. The appearance of juxtanuclear intracellular speckles with PB10651 is consistently found, independent of the antibody incubation-time (24 hours or 7 days), at low antibody concentrations (50 ng/ml PB10651) and in Alexa-488-conjugated form.

Example 6: Production and Biochemical Characterization of PB10651

Plasmid Generation

The plasmids for transfection were generated from plasmids MV1453 and MV1626, see FIG. 31. These plasmids were digested with SfiI and BstEII restriction enzymes (MV1453) and SfiI and XhoI restriction enzymes (MV1626) after which the VHs MF3755 (digested SfiI and BstEII) and MF5816 (digested SfiI and XhoI), were ligated to form constructs MG3755C453 and MG5816C626. MV1622 encodes the Flag-tagged RMD enzyme (FIG. 32).

Antibody Production

Protein production was performed by transient transfection of Freestyle 293-F suspension cells (Invitrogen cat. no. R79007) cultured in FreeStyle 293 Expression Medium (Gibco, cat. no. 12338-018) supplemented with 2 mM L-Glutamine (Gibco, cat. no. 25030-024) that were inhibited in attaching fucose residues to the tail of the antibodies [Henning von Horsten et. al., Glycobiology, vol. 20, no. 12, pp. 1607-1618, 2010]. One day before transfection, cells were seeded at a density of $5.0\times10^5$ cells/mL and incubated o/n at 37° C. 8% $CO_2$ at an orbital shaking speed of 155 rpm. For transfection, a mixture of plasmid DNA and polyethyleneimine (PEI, MW 25,000 Da. Polysciences Inc., cat. no. 23966) in culture medium was prepared. For a 25 mL transfection volume, 25 μg endotoxin-free plasmid DNA was mixed with 62.5 μg PEI and 2.5 mL culture medium. The mixture was then vortexed, incubated for 20 minutes at RT and added to the cells. The cells were incubated at 37° C. 8% $CO_2$ at an orbital shaking speed of 155 rpm for 6 days. The cell suspension was collected, centrifuged at 1000 g for 10 min and the supernatant was collected and centrifuged at 4000 g for 10 min.

Antibody Purification

Antibody purification is performed by binding the antibodies batch-wise to MabSelectSure LX (GE Healthcare) for several hours at room temperature. The MabSelectSure LX sepharose containing bound antibody was then transferred to a gravity flow column. The column was washed with PBS, antibodies were eluted using 100 mM citrate buffer pH 3.0 and pH was neutralized to 7.0 using 1M Tris pH 8.0. Samples were concentrated using Vivaspin20 (Sartorius) 10 kDa spin filters and further purified by gel filtration using a Superdex200 26/600 column (GE Healthcare) pre-equilibrated with PBS buffer.

Cation Exchange HPLC

Cation exchange chromatography (CEX-HPLC) was used to address the charge heterogeneity of the antibody samples as well as to determine the presence and amount of product-related impurities (homodimers and halfbodies). The experiments were performed at ambient temperature on a Dionex HPLC system equipped with an SP STAT 7 μm column (Tosoh Biosciences) and a UV-vis detector. 10 μg of sample was injected in each run. A gradient of 25 mM phosphate buffer pH 6.0 with NaCl concentrations increasing from 0 to 1 M was applied to separate the antibodies. The data were analyzed using Chromeleon software.

ADCC Reporter Assay

The activity of the afucosylated antibody PB10651 (MV1622) was tested on ADCC reporter cells containing either the V158 (high affinity) FcγRIIIa receptor variant or the F158 (low affinity) FcγRIIIa receptor variant (Promega). A serial titration of antibody, i.e. afucosylated PB10651 (PB10651-MV1622), non-afucosylated PB10651 and a non-targeting IgG1 (PC1337) was added in combination with ADCC reporter cells harboring high and low affinity FcγRIIIa variants [Cartron et. al., Blood, vol. 99, no. 3, pp. 754-758, 2002;] Musolino et. al., Journal of Clinical Oncology, vol. 26, no. 11, pp. 1789-1796] to A431 cells, A549 cells and BxPC3 cells. ADCC activity was detected by measuring luciferase activity.

Experimental

Freestyle 293-F cells were transfected with MG3755C453, MG5816C626 and MV1622, resulting in IgG PB10651p10. After purification, the yield of PB10651 (MV1622) was determined to be 29 mg per liter production volume by OD280 measurement. CEX-HPLC analysis was performed on the purified protein (FIG. 33), showing a main peak with some acidic charge variants at a retention time of 15 minutes representing the bispecific PB10651(MV1622) molecule. A small peak (<5%) representing MF3755× MF3755 DEDE homodimers is visible at ca. 11 minutes.

Additionally, an ADCC reporter assay was performed. The data show that afucosylated PB10651(MV1622) displays significantly increased ADCC activity for all cell lines in combination with the high (V158) and low (F158) FcγRIIIa receptor variant. The control, non-afucosylated PB10651 showed some ADCC activity in A431 cells combined with high affinity FcγRIIIa receptor variant effector cells, but the signal was significantly lower than the PB10651(MV1622) signal. For the other cell line/effector cell combinations the PB10651 was negative while PB10651(MV1622) showed strong ADCC activity. PG1337 (anti-tetanus toxoid) is a non-binding control IgG which was negative in all experiments (FIG. 34).

Example 7 In Vivo Effectivity of the Lead Antibody

Animal Model Selection

Therapeutic efficacy of afucosylated PB10651(MV1622) was assessed in immunocompromised mice bearing tumors from colorectal patients—known as patient-derived xenograft (PDX) models. PDX models CR2519, CR2161, CR2501, CR0150 and CR0193 (Crown Bioscience database, http://hubase2.crownbio.com) were selected based on the expression of both LGR5 and EGFR genes as analyzed by RNA sequencing (RNAseq). The models presented different status of KRAS gene. Namely, CR2519 and CR2161 were wild type for KRAS while CR2501, CR0150 were KRAS G12V and CR0193 were KRAS were G13D mutants. CR0231 and CR2501 were sensitive to Cetuximab, while CR0150 was low responsive to Cetuximab.

Gene Expression Analysis

To verify that the PDX models had retained the indicated LGR5 and EGFR mRNA expression levels in animals used in the efficacy study, expression in live tumors was compared to that in PDX stock tumors. RNA was extracted from stock tumors (frozen material) and live tumors (study animals), homogenized with TRIzol (Ambiom 15596-018) and Tissue Lyser II (Qiagen 85300). RNA was then purified with RNeasy Mini Kit (Qiagen 74106) and RNase-Free DNase Set (Qiagen 76254). RNA quality was confirmed by Nano-Drop™ spectrophotometer. cDNA was prepared by reverse transcription (ABI 4374966). Expression of LGR5 and EGFR was measured by real time RT-PCR reaction using TaqMan probes Hs00969422_m1 and Hs01076090_m1, respectively, and normalized against glyceraldehyde-3-phosphate dehydrogenase (GAPDH) expression using TaqMan probe Hs02758991_g1. Data were analyzed by calculating the difference in Ct value between the gene of interest and GAPDH, and converting it to the power of 2. FIG. 35 shows that all six PDX models used in the efficacy study presented an expression of both EGFR and LGR5 comparable to the original frozen PDX tumor stocks, LGR5 expression in these six models was over a thousand-fold higher than in the PDX model presenting the lowest LGR5 expression (CR01560) from the available collection of 137 colorectal cancer PDX models. EGFR mRNA expression in the selected six models was lower than CR1197, which presented the highest. EGFR expression in the whole CRC PDX collection.

Efficacy Study in PDX

BALB/c nude mice were inoculated subcutaneously at the right flank with a PDX tumor fragment (2-3 mm in diameter) originating from one of the five colorectal cancer PDX tumor models (CR2519, CR2161, CR2501, CR0150 and CR0193). Tumors were allowed to grow to a volume of 100-200 mm$^3$. Mice were then treated with four weekly intraperitoneal (i.p.) doses of PBS (200 µl) or afucosylated PB10651 (0.5 mg per animal in PBS). Tumors were measured biweekly by caliper and tumor volume (TV) was calculated using the formula TV=0.5×a×b$^2$ where a and b were the long and short diameters of the tumor, respectively. Afucosylated PB10651 presented strong tumoristatic activity in CR2519 and CR0193 PDX models, and this activity was similar to that of Cetuximab (FIG. 36). Afucosylated PB10651 presented limited but significant anti-tumor activity in CR2501 PDX model, while Cetuximab failed to significantly reduce tumor growth. PDX models CR2161 and CR0150 did not strongly respond to Cetuximab or afucosylated PB10651 and only showed a trend in anti-tumor activity for afucosylated PB10651 (FIG. 36).

Example 8 P18T and C31M Xenograft Studies

Materials and Methods

Immunohistochemistry of P18 Tumoroids

After 48 hours from the addition of the antibodies, culture media was removed, and BME drops on a 48-well plate fixed in 300 µL of formalin for 2 hours at room temperature. BME drops were then manually broken using a pipette, pelleted, and placed in fresh formalin without disrupting the pellet. Pellets were left at room temperature overnight before washing in PBS three times. The pellet was then gently re-suspended in PBS and placed into a microcassette for processing by the IRB (Institute for Research in Biomedicine) histology facility for generation of paraffin embedded sections.

Ki67 and cleaved caspase-3 staining were performed by the IRB histology facility using an Autostainer Plus (Dako—Agilent). Prior to staining, sections were dewaxed as part of the antigen retrieval process using the low pH EnVision™ FLEX Target Retrieval Solutions (Dako, Burlington) for 20 mins at 97TC using a PT Link (Dako—Agilent). Endogenous peroxidase was quenched for 10 mins using peroxidase-blocking solution (Dako REAL S2023). Rabbit polyclonal anti-Ki67 (ab15580, Abeam) and rabbit polyclonal anti-caspase 3 (Cell signaling, 9661S) were diluted 1:1000 and 1:500 and incubated for 60 and 120 min at room temperature respectively. BrightVision Poly-HRP-Anti Rabbit IgG Biotin-free was used for the secondary antibody (Immunologic, DPVR-110HRP), and was incubated for 30 mins at room temperature. Staining was revealed using 3-3'-diaminobenzidine (K3468, Dako), for 5 mins. Sections were counterstained with hematoxylin (Dako, S202084) and mounted with toluene-free mounting medium (CS705, Dako) using a Dako CoverStainer. Specificity of staining was confirmed by omission of the primary antibody. Images were captured using a Nikon Eclipse E600 attached to a Nikon DS-Ri1 camera.

Treatment of P18T and C31M Organoid Xenografts

All mouse experiments were approved by the Animal Care and Use Committee of Barcelona Science Park (CEEA-PCB) and the Catalan government under protocol number DAAM7329. Tumoroids were grown for seven days before disaggregating into a single cells suspension for injection. Culture conditions and the method of creating single cells are described in section "FACS staining of cells obtained from organoid P18T using selected 5 anti-LGR5 cLC Antibodies". For all mouse studies female NOD.CB17/AlhnRj-Prkdescid/Rj mice (Janvier Labs) aged between 6-8 weeks were used. Xenografts were initiated by subcutaneously injecting 100 µL of BME:PBS (50:50) solution containing 200,000 P18T cells or 1,000,000 C31M cells. Once the tumor volume reached 300 mm3 mice were sacrificed and tumors harvested. One tumor was manually cut in to small pieces approximately 0.5 mm×0.5 mm×0.5 mm (width×length×height). The pieces were then placed into four flanks of recipient NOD-SCID mice, using one piece/flank. A tracker was used to implant the pieces into the mice, a device which pushes a tumour piece underneath the skin. A total of 30 mice were used for engraftment. Once the tumour volume on a mouse reached an average of 50 mm3 the mice were randomly assigned to a treatment group. Mice were injected once a week for four weeks with 200 µL of PBS (pH 7.4 Gibco Ref 10010-015), Cetuximab (clinical batch, 5 mg/ml), or afucosylated PB10651 (2.5 mg/ml). Cetuximab and afucosylated PB10651 were injected at a dose of 0.5 mg/mouse, regardless of mouse weight. Tumor volume was calculated using manual callipers with measurements taken thrice a week, and using the formula: (length×width×height)/2. Mice were sacrificed when either the tumor volume exceeded 300 mm3, the tumor ulcerated, or the end point of the study had been reached; 28 days since the first antibody injection. If only a single tumor on a mouse needed to be taken due to size constraints/ulceration then it was resected leaving the remaining in place for further study. If an additional resections or multiple tumors needed to be harvested then the mouse was culled and all the samples taken simultaneously. The data is expressed relative to day 0 (the first day of treatment) and a paired sample t-tests analysis was performed between each treatment group using GraphPad Prism.

Results

Ki67 staining is an indicator of cellular proliferation, and was used to determine whether the effects on growth caused by the antibody treatments were due to a reduction in proliferation. Tumoroids were treated in vitro for 48 hours (2 µg/mL) before fixation. Treatment of tumoroids with afucosylated PB10651 caused a reduction in the number of positive cells, and in the intensity of staining, compared to the other treatment groups (FIG. 37). Cetuximab and the EGFR-TT antibodies caused a small, modest, reduction in the number of positive cells relative to the TT-TT control treatment. Cleaved caspase-3 staining was also performed to assess whether the antibodies promoted apoptosis. Low levels of apoptosis were observed in the TT control, EGFR-T and cetuximab treatment groups, with comparable staining's seen between the three groups. The number of positive cells increased in the afucosylated PB10651-treated group. These results suggest the afucosylated PB10651 bispecific antibody is superior at reducing proliferation, and inducing apoptosis than cetuximab and the single anti-EGFR arm.

Figures 38, 38A:
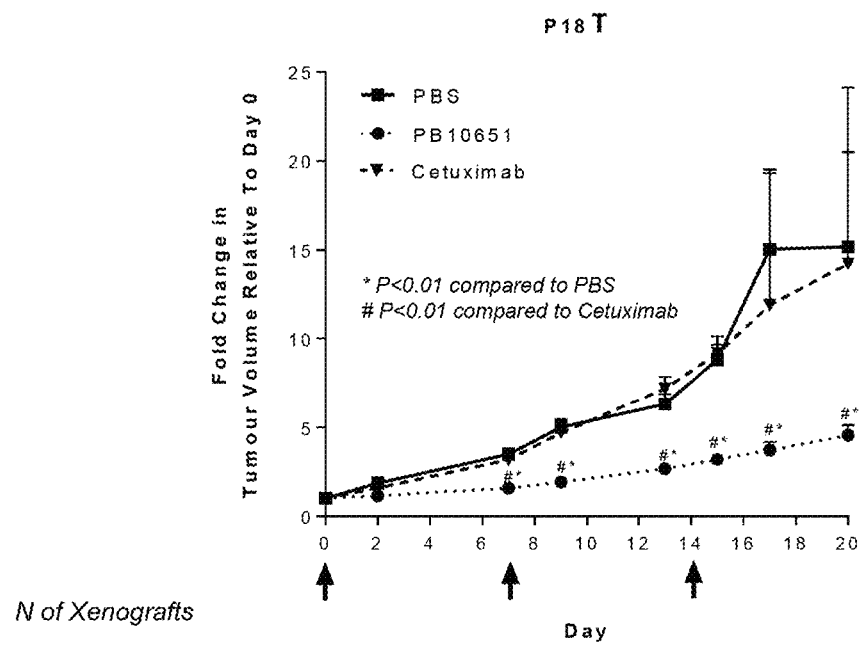
Figure 38B:
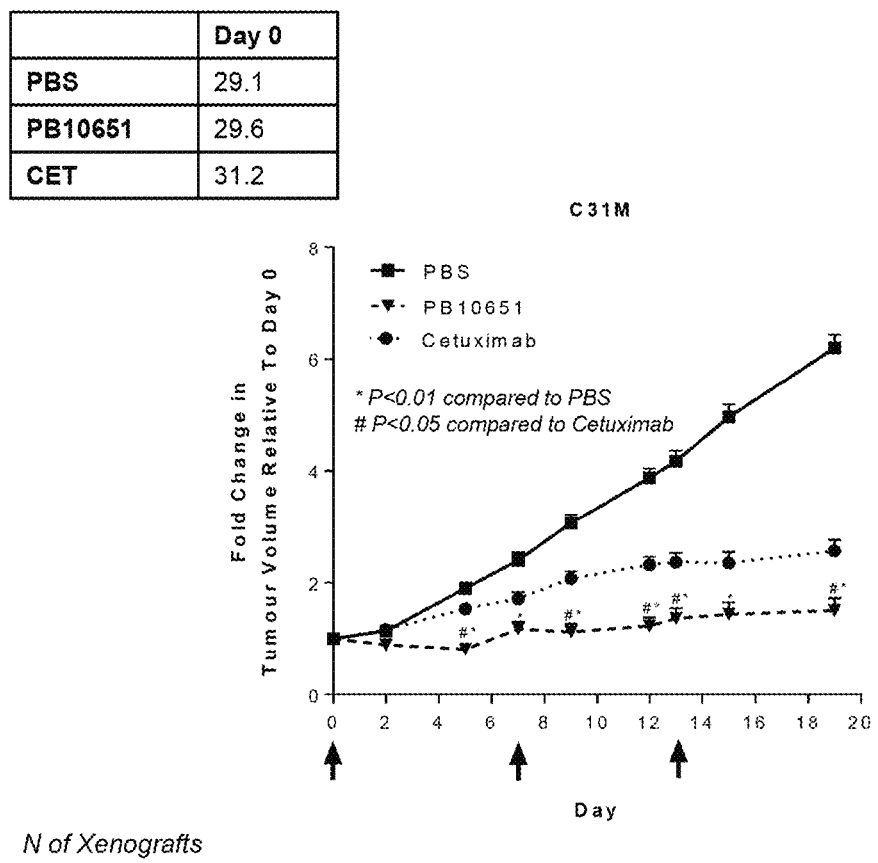

Xenografts were established in NOD-SICD mice and treated once a week for four weeks with afucosylated PB10651 (0.5 mg/mouse/week), Cetuximab (0.5 mg/mouse/week) or PBS. To assess antibody responses the tumour volumes were tracked and compared between groups. Treatment with afucosylated PB10651 caused a significant reduction in the average tumour volume increase compared to both PBS and cetuximab for both the P18T and C31M xenograft models from day 2 onwards (P=<0.01 for all time points, FIG. 38). In the P18T xenograft model, Cetuximab treated mice showed similar growth kinetics to the PBS treated mice and due to large tumour volumes the majority of the mice in the PBS and cetuximab group needed to be removed from the study on day 16. By day 20 the average fold change in tumour volume was 15.2 (±5.3) and 14.2 (±9.9) for PBS and cetuximab respectively, whereas for the afucosylated PB10651 group the value was 4.5 (±0.59). The tumour doubling times, determined by nonlinear curve fitting of an exponential growth equation, were calculated as 9 days for the PBS and cetuximab groups, and 6 days for the afucosylated PB10651 treatment group, a 30% reduction in tumour doubling time. Similarly, in the C31M xenograft model, PB1065 significantly reduced tumor growth compared to both PBS and cetuximab treatment arms (FIG. 38).

Example 8: Non-GLP Cynomolgus Toxicity Study Using Repeated Doses of PB10651

To gauge the possible toxicity of PB10651, a non-GLP repeated dose toxicity study in cynomolgus monkey was performed. In view of the EGFR Fab arm present in PB10651, skin and gastro-intestinal (GI) tract toxicity may be expected. In the case of the anti-EGFR antibody Cetuximab (Erbitux), deaths were observed in monkeys at a weekly dose of 75 mg/kg due to severe skin toxicity, with a dose of 24 mg/kg/week being the highest tolerated dose in chronic monkey toxicity studies. In the case of Panitumumab (Vectibix), mortality was seen in monkeys at a dose of 30 mg/kg/week after only three weeks of treatment in a 4 week study, with occasional deaths at lower dosages (7.5 and 15 mg/kg/week) in a 13 week IV toxicity study. Based on this information, a dose level of 25 mg/kg was selected for PB10651 as the highest dose in the present study. One male and one female animal were used per group and four groups were designated: control (vehicle only), 2.5 mg/kg/week, 7.5 mg/kg/week and 25 mg/kg/week and four weekly doses were given to each group. Antibody was administered via intravenous infusion over an hour to the animals.

Results

Toxicity studies in cynomolgus monkeys with Cetuximab and Panitumumab revealed dermal toxicity (erythema, dry/flaking skin/hair loss) and gastro-intestinal (GI) tract effects (soft faeces/diarrhoea, dehydration) as the dose-limiting toxicities (EMA-EPAR 2004 cetuximab, EMA-EPAR 2007 panitumumab), consistent with the anti-EGFR activity of the test items. For PB10651, however, even at the highest dose administered in this study, neither skin toxicity nor GI tract toxicity was observed after repeated administration. Clinical signs, such as fur thinning, bruising and incidence of loose faeces were equally observed in active and control groups and these clinical signs were therefore not considered to be drug-related. There were no organ weight and/or organ weight ratio changes considered to be related to administration of PB10651. In addition, there were no macroscopic or microscopic findings considered to be related to administration of PB10651. In conclusion, once weekly intravenous (infusion) administration of PB10651 to the cynomolgus monkey for 4 weeks did not result in organ weight or organ weight ratio changes, macroscopic or microscopic findings considered to be related to administration of PB10651.

The work leading to this invention has received funding from the [European Union] [European Atomic Energy Community] Seventh Framework Programme ([FP7/2007-2013] [FP7/2007-2011]) under grant agreement n° [601876].14

TABLE 1

Titers of successfully immunized MeMo ® mice.

| Mouse # | Immunized antigen | Reciprocal serum titer FACS | Library | Library size |
|---|---|---|---|---|
| L1 | pVax1 hLGR4-2xFLAG-2xHA | hLGR4 100 | ML1246 | $2.8 \times 10^7$ |
|  | pVax1 hLGR5-2xFLAG-2xHA | hLGR5 0 |  |  |
| H1 | rhLGR5-Fc | hLGR5 < 100 | ML1247 | $2.5 \times 10^7$ |
| H2 | rhLGR5-Fc | hLGR5 < 100 | ML1248 | $2.2 \times 10^7$ |
| H3 | rhLGR5-Fc | hLGR5 100 | ML1249 | $2.6 \times 10^6$ |

TABLE 1-continued

Titers of successfully immunized MeMo ® mice.

| Mouse # | Immunized antigen | Reciprocal serum titer FACS | Library | Library size |
|---|---|---|---|---|
| H4 | rhLGR5-Fc | hLGR5 100 | ML1250 | $7.7 \times 10^6$ |
| H5 | rhLGR5-Fc | hLGR5 100 |  |  |
| H6 | rhLGR5-Fc | hLGR5 100 | ML1251 | $1.6 \times 10^7$ |
| L19 | rhZNRF3-Fc | hZNRF3 100 | ML1223 | $1.0 \times 10^7$ |
| L20 | rhZNRF3-Fc | hZNRF3 100 | ML1224 | $7.8 \times 10^6$ |
| L21 | rhZNRF3-Fc | hZNRF3 100 | ML1225 | $1.2 \times 10^7$ |
| L22 | rhZNRF3-Fc | hZNRF3 100 | ML1226 | $8.1 \times 10^6$ |
| L23 | rhZNRF3-Fc | hZNRF3 100 | ML1227 | $6.1 \times 10^6$ |
| L24 | rhZNRF3-Fc | hZNRF3 100 | ML1228 | $5.0 \times 10^6$ |
| K14 | rhRNF43-Fc | hRNF43 100 | ML1229 | $9.1 \times 10^6$ |
| K15 | rhRNF43-Fc | hRNF43 100 | ML1230 | $2.0 \times 10^6$ |
| K17 | rhRNF43-Fc | hRNF43 100 | ML1231 | $5.4 \times 10^6$ |

TABLE 2

Overview of the antibody panels generated from phage antibody repertoires against the different WNT targets.

| Target | Final antibody panel size (number of different clones characterized) |
|---|---|
| LGR4 | 66 |
| LGR5 | 84 |
| ZNRF3 | 105 |
| RNF43 | 33 |

TABLE 3

Characteristics of bispecific IgG containing a selected panel of Wnt targeting Fab fragments against LGR4, LGR5, ZNRF3 and RNF43 combined with the Tetanus toxoid Fab Fragment.

| PB# | Target Fab fragment | FACS titration AUC | R-spondin blocking % binding | Blocking | $OD_{450}$ 4° C. | $OD_{450}$ 40° C. | % ($OD_{450}$ 40° C./ $OD_{450}$ 4° C.) | Stable at 40° C. |
|---|---|---|---|---|---|---|---|---|
| PB10251 | LGR4 | 28154 | 102 | No | 0.452 | 0.248 | 55 | Yes |
| PB10252 | LGR4 | 12888 | 103 | No | 0.099 | 0.064 | 65 | NA |
| PB10261 | LGR5 | 43103 | 59 | Partial | 1.005 | 0.876 | 87 | Yes |
| PB10273 | LGR5 | 27178 | 92 | No | 1.793 | 1.819 | 101 | Yes |
| PB10275 | LGR5 | 24879 | 94 | No | 1.677 | 1.664 | 99 | Yes |
| PB10278 | LGR5 | 22197 | 80 | Partial | 0.655 | 0.401 | 61 | Yes |
| PB10279 | LGR5 | 24974 | 82 | No | 0.839 | 0.597 | 71 | Yes |
| PB10284 | LGR5 | 40187 | 59 | Partial | 0.985 | 0.867 | 88 | Yes |
| PB10286 | LGR5 | 41872 | 95 | No | 1.050 | 0.964 | 92 | Yes |
| PB10287 | LGR5 | 19378 | 107 | No | 0.810 | 0.609 | 75 | Yes |
| PB10290 | LGR5 | 44272 | 67 | Partial | 1.059 | 1.043 | 98 | Yes |
| PB10300 | ZNRF3 | 32012 | 90 | No | 1.693 | 1.264 | 75 | Partial |
| PB10302 | ZNRF3 | 29235 | 102 | No | 1.783 | 1.722 | 97 | Yes |
| PB10304 | ZNRF3 | 38321 | 75 | Partial | 1.747 | 1.336 | 76 | Partial |
| PB10309 | ZNRF3 | 19446 | 93 | No | 1.688 | 1.087 | 64 | Yes |
| PB10328 | ZNRF3 | 26933 | 86 | No | 1.714 | 1.776 | 104 | Yes |
| PB10330 | ZNRF3 | 46341 | 50 | Yes | 1.793 | 1.357 | 76 | Yes |
| PB10332 | ZNRF3 | 24318 | 93 | No | 1.602 | 1.415 | 88 | Yes |
| PB10333 | ZNRF3 | 36923 | 82 | No | 1.434 | 1.137 | 79 | Yes |
| PB10346 | RNF43 | 82605 | 29 | Yes | 1.397 | 1.377 | 99 | Yes |
| PB10349 | RNF43 | 92972 | 71 | Partial | 1.523 | 1.529 | 100 | Yes |
| PB10350 | RNF43 | 93258 | 33 | Yes | 1.430 | 1.325 | 93 | Yes |

Shown are the FACS affinity titration, the R-Spondin3 blocking ELISA and the 40° C. stability ELISA. For the FACS affinity titration the area under the curve (AUC) values are indicated. For the R-Spondin blocking ELISA the percentage binding remaining per IgG compared to the maximum binding value (set at 100% binding) was indicated, as well as the final conclusion from 2 independent experiments. The 40° C. stability ELISA is shown. $OD_{450\ nm}$ values after one week at 4° C. and at 40° C. are indicated in the table. The ratios (in percentage) of the $OD_{450\ nm}$ from 4° C. versus 40° C. are indicated in the table. The final conclusion is inserted in the right column, whether an IgG is considered stable, partially stable or NA when OD signals were below 0.1

TABLE 4

Z' factor scores for different features and a multi-parametric score in different organoids, comparing growth with and without EGF in EGF dependent tumoroids.
The multi-parametric Z' factor score was either similar or higher than individual feature scores, demonstrating that using such a score is both sensitive and can be applied across multiple different organoids which undergo different phenotypic responses after growth factor treatment.

| Z'-factor | P18T | P14T | P8T |
|---|---|---|---|
| Nucleus count | 0.58 | −0.34 | −0.68 |
| Tumoroid size | −0.01 | 0.18 | 0.05 |

TABLE 4-continued

Z' factor scores for different features and a multi-parametric score in different organoids, comparing growth with and without EGF in EGF dependent tumoroids.
The multi-parametric Z' factor score was either similar or higher than individual feature scores, demonstrating that using such a score is both sensitive and can be applied across multiple different organoids which undergo different phenotypic responses after growth factor treatment.

| Z'-factor | P18T | P14T | P8T |
|---|---|---|---|
| Lumen count | −0.56 | 0.56 | 0.27 |
| Lumen roundness | 0.22 | 0.13 | 0.30 |
| Multiparametric | 0.80 | 0.53 | 0.50 |

TABLE 5

Preferred heavy chain combinations for bispecific antibodies that bind LGR4/EGFR; LGR4/HER3; LGR5/EGFR; LGR5/HER3; RNF43/EGFR; RNF43/HER3; and ZNRF3/EGFR; ZNRF3/HER3. TT is a heavy chain for tetanus toxoid and for reference only.

| | | TT | EGFR | | | |
|---|---|---|---|---|---|---|
| | | MF1337 | MF3755 | MF4280 | MF3370 | MF4289 |
| TT | MF1337 | PB4248 | PB9919 | PB9647 | PB9920 | PB10104 |
| LGR4 | MF5777 | PB10251 | PB10619 | PB10620 | PB10621 | PB10622 |
| | MF5781 | PB10252 | PB10623 | PB10624 | PB10625 | PB10626 |
| LGR5 | MF5790 | PB10261 | PB10627 | PB10628 | PB10629 | PB10630 |
| | MF5803 | PB10273 | PB10631 | PB10632 | PB10633 | PB10634 |
| | MF5805 | PB10275 | PB10635 | PB10636 | PB10637 | PB10638 |
| | MF5808 | PB10278 | PB10639 | PB10640 | PB10641 | PB10642 |
| | MF5809 | PB10279 | PB10643 | PB10644 | PB10645 | PB10646 |
| | MF5814 | PB10284 | PB10647 | PB10648 | PB10649 | PB10650 |
| | MF5816 | PB10286 | PB10651 | PB10652 | PB10653 | PB10654 |
| | MF5817 | PB10287 | PB10655 | PB10656 | PB10657 | PB10658 |
| | MF5818 | PB10290 | PB10659 | PB10660 | PB10663 | PB10664 |
| RNF43 | MF5832 | PB10346 | PB10661 | PB10662 | PB10665 | PB10666 |
| | MF5836 | PB10349 | PB10667 | PB10668 | PB10669 | PB10670 |
| | MF5839 | PB10350 | PB10671 | PB10672 | PB10673 | PB10674 |
| ZNRF3 | MF5850 | PB10300 | PB10675 | PB10676 | PB10677 | PB10678 |
| | MF5853 | PB10302 | PB10679 | PB10680 | PB10681 | PB10682 |
| | MF5855 | PB10304 | PB10683 | PB10684 | PB10685 | PB10686 |
| | MF5862 | PB10309 | PB10687 | PB10688 | PB10689 | PB10690 |
| | MF5882 | PB10328 | PB10691 | PB10692 | PB10693 | PB10694 |
| | MF5884 | PB10330 | PB10695 | PB10696 | PB10697 | PB10698 |
| | MF5887 | PB10332 | PB10699 | PB10700 | PB10701 | PB10702 |
| | MF5888 | PB10333 | PB10703 | PB10704 | PB10705 | PB10706 |

| | | TT | HER3 | | | |
|---|---|---|---|---|---|---|
| | | MF1337 | MF3178 | MF3176 | MF3125 | MF4863 |
| TT | MF1337 | PB4248 | PB9215 | PB9921 | PB9918 | PB10111 |
| LGR4 | MF5777 | PB10251 | PB10707 | PB10708 | PB10709 | PB10710 |
| | MF5781 | PB10252 | PB10711 | PB10712 | PB10713 | PB10714 |
| LGR5 | MF5790 | PB10261 | PB10715 | PB10716 | PB10717 | PB10718 |
| | MF5803 | PB10273 | PB10719 | PB10720 | PB10721 | PB10722 |
| | MF5805 | PB10275 | PB10723 | PB10724 | PB10725 | PB10726 |
| | MF5808 | PB10278 | PB10727 | PB10728 | PB10729 | PB10730 |
| | MF5809 | PB10279 | PB10731 | PB10732 | PB10733 | PB10734 |
| | MF5814 | PB10284 | PB10735 | PB10736 | PB10737 | PB10738 |
| | MF5816 | PB10286 | PB10748 | PB10749 | PB10750 | PB10751 |

TABLE 5-continued

Preferred heavy chain combinations for bispecific antibodies that bind LGR4/EGFR; LGR4/HER3; LGR5/EGFR; LGR5/HER3; RNF43/EGFR; RNF43/HER3; and ZNRF3/EGFR; ZNRF3/HER3. TT is a heavy chain for tetanus toxoid and for reference only.

|       |        |         |         |         |          |          |
|-------|--------|---------|---------|---------|----------|----------|
|       | MF5817 | PB10287 | PB10752 | PB10753 | PB10754  | PB10755  |
|       | MF5818 | PB10290 | PB10756 | PB10757 | Not made | Not made |
| RNF43 | MF5832 | PB10346 | Not made| Not made| PB10758  | PB10759  |
|       | MF5836 | PB10349 | PB10764 | PB10765 | PB10766  | PB10767  |
|       | MF5839 | PB10350 | PB10768 | PB10769 | PB10770  | PB10771  |
| ZNRF3 | MF5850 | PB10300 | PB10772 | PB10773 | PB10774  | PB10775  |
|       | MF5853 | PB10302 | PB10776 | PB10777 | PB10778  | PB10779  |
|       | MF5855 | PB10304 | PB10780 | PB10781 | PB10782  | PB10783  |
|       | MF5862 | PB10309 | PB10784 | PB10785 | PB10786  | PB10787  |
|       | MF5882 | PB10328 | PB10788 | PB10789 | PB10790  | PB10791  |
|       | MF5884 | PB10330 | PB10792 | PB10793 | PB10794  | PB10795  |
|       | MF5887 | PB10332 | PB10796 | PB10797 | PB10798  | PB10799  |
|       | MF5888 | PB10333 | PB10800 | PB10801 | PB10802  | PB10803  |

TABLE 6

Preferred heavy chain combinations for bispecific antibodies that bind LGR4/EGFR; LGR4/HER3; LGR5/EGFR; LGR5/HER3; RNF43/EGFR; RNF43/HER3; and ZNRF3/EGFR; ZNRF3/HER3. TT is a heavy chain for tetanus toxoid and for reference only.

|       |        | TT<br>MF1337 | EGFR<br>MF3755 | HER3<br>MF3178 |
|-------|--------|--------|---------|----------|
| TT    | MF1337 | PB4248 | PB9919  | PB9215   |
| LGR4  | MF5777 | PB10251| PB10619 | PB10707  |
|       | MF5781 | PB10252| PB10623 | PB10711  |
| LGR5  | MF5790 | PB10261| PB10627 | PB10715  |
|       | MF5803 | PB10273| PB10631 | PB10719  |
|       | MF5814 | PB10284| PB10647 | PB10735  |
|       | MF5816 | PB10286| PB10651 | PB10748  |
|       | MF5817 | PB10287| PB10655 | PB10752  |
|       | MF5818 | PB10290| PB10659 | PB10756  |
| RNF43 | MF5832 | PB10346| PB10661 | PB12336  |
|       | MF5836 | PB10349| PB10667 | PB10764  |
| ZNRF3 | MF5850 | PB10300| PB10675 | PB10772  |
|       | MF5853 | PB10302| PB10679 | PB10776  |
|       | MF5855 | PB10304| Not made| PB10780  |
|       | MF5884 | PB10330| PB10695 | Not made |
|       | MF5888 | PB10333| PB10703 | PB10800  |

TABLE 7

List of comparator antibodies copied from literature with their internal number.
Antibody VH- and VL- sequences were copied from patents, made as synthetic cDNA's and then cloned into an expression vector for the expression of human IgG1. Antibodies were expressed and purified using standardised procedures.

| Antibody  | Target | Firm      | Species   | Internal number |
|-----------|--------|-----------|-----------|-----------------|
| hu8E11v2  | LGR5   | Genentech | Humanised | PG7543          |
| BNC101    | LGR5   | Bionomics | Humanised | PG7709          |
| OMP18R5   | FZD7   | OncoMed   | Human     | PG7710          |
| OMP88R20  | LGR5   | OncoMed   | Human     | PG7711          |
| OMP88R21  | LGR5   | OncoMed   | Human     | PG7712          |
| OMP131R10 | RSPO3  | OncoMed   | Humanised | PG7713          |

TABLE 8

Residues in EGFR and LGR5 found to be relevant for the binding of PB10651 to the respective target in shotgun mutagenesis analysis.

| LGR5 relevant residues | EGFR relevant residues |
|------------------------|------------------------|
| D43A                   | I462A                  |
| G44A                   | G465A                  |
| M46A                   | K489A                  |
| F67A                   | I491A                  |
| G90A                   | N493A                  |
| F91A                   | C499A                  |

TABLE 9

EGFR and LGR5 mRNA expression levels in PDX tumors used for ex vivo FACS staining

| Cell name  | Cancer type         | EGFR log2(FPKM) | LGR5 log2(FPKM) |
|------------|---------------------|-----------------|-----------------|
| EX-CR2394  | Colorectal Cancer   | Not done yet    | Not done yet    |
| EX-OV3077  | Ovarian Cancer      | 2.178           | 6.1989          |
| EX-GA6239  | Gastric Cancer      | 2.4679          | 5.3676          |
| EX-HN2195  | Head and Neck Cancer| 8.9258          | 5.3171          |
| EX-LI0574  | Liver Cancer        | 3.6252          | 5.0135          |
| EX-GA6210  | Gastric Cancer      | 1.0841          | 4.6505          |
| EX-OV1286  | Ovarian Cancer      | 2.3905          | 4.6434          |
| EX-CC6638  | Cholangiocarcinoma  | 3.3147          | 3.5631          |
| EX-LU2529  | Lung Cancer         | 4.0328          | 3.2662          |
| EX-OV0273  | Ovarian Cancer      | -2              | 3.0802          |
| EX-LU6429  | Lung Cancer         | 4.0896          | 2.897           |
| EX-ES0201  | Esophageal Cancer   | 5.6923          | 1.8035          |

TABLE 10

Mean fluorescence intensity (MFI) values obtained after ex vivo staining of patient-derived xenografts of different indications.

| Cancer type         | Crown model | PG5816 (anti-LGR5) | PG3755 (anti-EGFR) | PG1337 (anti-TT control) |
|---------------------|-------------|--------------------|---------------------|--------------------------|
| Ovarian Cancer      | OV1286      | 7482               | 2120                | 1575                     |
| Ovarian Cancer      | OV0273      | 5960               | 2152                | 1728                     |
| Esophageal Cancer   | ES0201      | 5772               | 5967                | 1642                     |
| Colorectal Cancer   | CR2394      | 3661               | 2602                | 1879                     |
| Gastric Cancer      | GA6210      | 3240               | 1003                | 1105                     |
| Liver Cancer        | LI0574      | 2543               | 6110                | 1070                     |
| Gastric Cancer      | GA6239      | 2265               | 2104                | 1731                     |
| Head and Neck Cancer| HN2195      | 1846               | 11814               | 1134                     |

TABLE 10-continued

Mean fluorescence intensity (MFI) values obtained after ex vivo staining of patient-derived xenografts of different indications.

| Cancer type | Crown model | Mean fluorescence intensity (MFI) value | | |
|---|---|---|---|---|
| | | PG5816 (anti-LGR5) | PG3755 (anti-EGFR) | PG1337 (anti-TT control) |
| Lung Cancer | LU2529 | 1705 | 6863 | 1685 |
| Lung Cancer | LU6429 | 1532 | 6081 | 1006 |
| Cholangiocarcinoma | CC6638 | 1370 | 9366 | 1104 |

The invention provides the following aspects (among others).

Aspect 1. An antibody that comprises a variable domain that can bind an epitope on an extracellular part of human EGFR of which amino acid residues I462; G465; K489; I491; N493; and C499 are involved in binding of the antibody to the epitope.

Aspect 2. The antibody of aspect 1, wherein one or more of the amino acid residue substitutions selected from I462A; G465A; K489A; I491A; N493A; and C499A reduce the binding of the antibody to human EGFR.

Aspect 3. An antibody that comprises a variable domain that can bind an epitope on an extracellular part of human EGFR which epitope is located within amino acid residues 420-480 of SEQ ID NO: 2 depicted in FIG. 40, and wherein the binding of the antibody to LGR5 is reduced by one or more of the following amino acid residue substitutions I462A; G465A; K489A; I491A; N493A; and C499A.

Aspect 4. The antibody of any one of aspects 1-3, wherein the binding of the antibody to human EGFR interferes with the binding of EGF to the receptor.

Aspect 5. The antibody of any one of aspects 1-4, wherein the epitope is a conformational epitope.

Aspect 6. The antibody of any one of aspects 1-5, wherein the epitope is located within amino acid residues 420-480 of SEQ ID NO: 2 depicted in FIG. 40, preferably within 430-480 of SEQ ID NO: 2 depicted in FIG. 40; preferably within 438-469 of SEQ ID NO: 2 depicted in FIG. 40.

Aspect 7. The antibody of any one of aspects 1-6, wherein the antibody comprises a further variable domain which further variable domain can bind a further protein.

Aspect 8. The antibody of aspect 7, wherein the further protein is a membrane protein comprising an extracellular part.

Aspect 9. The antibody of aspect 7 or aspect 8, wherein the further protein is a membrane associated member WNT-pathway.

Aspect 10. The antibody of any one of aspects 1-9, wherein the antibody is a bispecific antibody comprising a variable domain that binds human EGFR and a variable domain that binds a further protein.

Aspect 11. The antibody of any one of aspects 1-10, wherein the variable domain that binds human EGFR, wherein a heavy chain variable region of said variable domain comprises at least the CDR3 sequence of the VH of MF3755 as depicted in FIG. 1 or wherein a heavy chain variable region of said variable domain comprises a heavy chain CDR3 sequence that differs in at most three, preferably in at most two, preferably in no more than one amino acid from a CDR3 sequence of the VH of MF3755 as depicted in FIG. 1.

Aspect 12. The antibody of aspect 10 or aspect 11, wherein said variable domain comprises a heavy chain variable region comprising at least the CDR1, CDR2 and CDR3 sequences of the VH of MF3755 as depicted in FIG. 1; or the CDR1, CDR2 and CDR3 sequences of the VH of MF3755 as depicted in FIG. 1 with at most three, preferably at most two, preferably at most one amino acid substitutions.

Aspect 13. The antibody of aspect 11 or aspect 12, wherein the variable domain that binds EGFR, comprises the sequence of the VH chain of MF3755 as depicted in FIG. 1; or the amino acid sequence of the VH chain of MF3755 depicted in FIG. 1 having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain of MF3755.

Aspect 14. The antibody of any one of aspects 7-13, wherein the further protein is LGR4; LGR5; LGR6; RNF43 or ZNRF3.

Aspect 15. The antibody of aspect 14, wherein the further protein is LGR5.

Aspect 16. A bispecific antibody comprising a variable domain that can bind an epitope on an extracellular part of EGFR and a variable domain that can bind a further protein, wherein the EGFR epitope is located within amino acid residues 420-480 of SEQ ID NO: 2 depicted in FIG. 40, which amino acid residues I462; G465; K489; I491; N493; and C499 are involved in binding of the antibody to the epitope.

Aspect 17. The bispecific antibody of aspect 16, wherein the binding of the variable domain to EGFR is reduced with one or more of the following amino acid residue substitutions I462A; G465A; K489A; I491A; N493A; and C499A.

Aspect 18. The bispecific antibody of aspect 16 or aspect 17, wherein the further protein is membrane protein comprising an extracellular part.

Aspect 19. The bispecific antibody of any one of aspects 16-18, wherein the further protein is a membrane associated member of the WNT-pathway, preferably LGR5.

It has been shown that antibodies comprising one or more variable domains that bind EGFR with the mentioned epitope have a better effectivity when used to inhibit growth of an EGFR ligand responsive cancer or cell. In the context of bispecific antibodies, an arm of the antibody comprising an EGFR binding variable domain with the mentioned epitope combines better with a variety of other arms comprising variable domains that bind extra-cellular parts of other cell surface proteins.

The invention claimed is:

1. A bispecific antibody that comprises a variable domain that binds an extracellular part of EGFR and a variable domain that binds an extracellular part of LGR5, wherein the VH chain of the variable domain that binds EGFR comprises the CDR1, CDR2 and CDR3 amino acid sequences NYAMN (SEQ ID NO:188), WINANTGDPTYAQGFTG (SEQ ID NO: 215), and ERFLEWLHFDY (SEQ ID NO: 242); and the VH chain of the variable domain that binds LGR5 comprises the CDR1, CDR2 and CDR3 amino acid sequences SSSSYWG (SEQ ID NO: 192), SFYYSGNTYYNPSLKS (SEQ ID NO: 220), and TYSSSWDGVLYYFDY (SEQ ID NO:247);

the VH chain of the variable domain that binds EGFR comprises the CDR1, CDR2 and CDR3 amino acid sequences NYAMN (SEQ ID NO: 188), WINANTGDPTYAQGFTG (SEQ ID NO: 215) and ERFLEWLHFDY (SEQ ID NO: 242); and the VH chain of the variable domain that binds LGR5 comprises the CDR1, CDR2 and CDR3 amino acid sequences TYYWS (SEQ ID NO: 193), YVYYTGRTKYNPSLKS (SEQ ID NO: 221) and GGIVVVPAARDYYYYMDV (SEQ ID NO: 248);

the VH chain of the variable domain that binds EGFR comprises the CDR1, CDR2 and CDR3 amino acid sequences NYAMN (SEQ ID NO: 188), WINANTGDPTYAQGFTG (SEQ ID NO: 215) and ERFLEWLHFDY (SEQ ID NO: 242), and the VH chain of the variable domain that binds LGR5 comprises the CDR1, CDR2 and CDR3 amino acid sequences SHWIG (SEQ ID NO: 194), VIYPGDSDTRYSPSFQG (SEQ ID NO: 222) and PNSGSPRYFEF (SEQ ID NO:249);

the VH chain of the variable domain that binds EGFR comprises the CDR1, CDR2 and CDR3 amino acid sequences NYAMN (SEQ ID NO: 188), WINANTGDPTYAQGFTG (SEQ ID NO: 215), and ERFLEWLHFDY (SEQ ID NO: 242), and the VH chain of the variable domain that binds LGR5 comprises the CDR1, CDR2 and CDR3 amino acid sequences SHWIA (SEQ ID NO: 196), IVYPGDSDTRYSPSFQG (SEQ ID NO: 224), and HEWELLGPFDY (SEQ ID NO: 251);

the VH chain of the variable domain that binds EGFR comprises the CDR1, CDR2 and CDR3 amino acid sequences NYAMN (SEQ ID NO: 188), WINANTGDPTYAQGFTG (SEQ ID NO: 215), and ERFLEWLHFDY (SEQ ID NO: 242) and the VH chain of the variable domain that binds LGR5 comprises the CDR1, CDR2 and CDR3 amino acid sequences NDAIS (SEQ ID NO: 197), SIIPILDTTDHAQKFQG (SEQ ID NO: 225), and EHIAARQDYFDY (SEQ ID NO: 252);

the VH chain of the variable domain that binds EGFR comprises the CDR1, CDR2 and CDR3 amino acid sequences NYAMN (SEQ ID NO: 188), WINANTGDPTYAQGFTG (SEQ ID NO: 215), and ERFLEWLHFDY (SEQ ID NO: 242); and the VH chain of the variable domain that binds LGR5 comprises the CDR1, CDR2 and CDR3 amino acid sequences SYTMN (SEQ ID NO: 198), WINTDTGDPTYAQGFTG (SEQ ID NO: 226), and GDCDSTSCYRYSYGYEDY (SEQ ID NO: 253);

the VH chain of the variable domain that binds EGFR comprises the CDR1, CDR2 and CDR3 amino acid sequences NYAMN (SEQ ID NO:188), WINANTGDPTYAQGFTG (SEQ ID NO: 215), and ERFLEWLHFDY (SEQ ID NO: 242); and the VH chain of the variable domain that binds LGR5 comprises the CDR1, CDR2 and CDR3 amino acid sequences SYAIS (SEQ ID NO: 199), GIIPIFDTRNYAQILQG (SEQ ID NO: 227), and GSDEGDWFDP (SEQ ID NO: 254);

the VH chain of the variable domain that binds EGFR comprises the CDR1, CDR2 and CDR3 amino acid sequences NYAMN (SEQ ID NO:188), WINANTGDPTYAQGFTG (SEQ ID NO: 215), and ERFLEWLHFDY (SEQ ID NO: 242); and the VH chain of the variable domain that binds LGR5 comprises the CDR1, CDR2 and CDR3 amino acid sequences NYAIS (SEQ ID NO: 200), SIIPILGTTDHAQKFQD (SEQ ID NO: 228), and EYIAARLDYFDS (SEQ ID NO: 255);

the VH chain of the variable domain that binds EGFR comprises the CDR1, CDR2 and CDR3 amino acid sequences ELSMH (SEQ ID NO: 189), GFDPEYGKTFFAQNFQG (SEQ ID NO: 216), and EGYYETTTYYYNLFDS (SEQ ID NO: 243); and the VH chain of the variable domain that binds LGR5 comprises the CDR1, CDR2 and CDR3 amino acid sequences SHWIG (SEQ ID NO: 194), VIYPGDSDTRYSPSFQG (SEQ ID NO: 222) and PNSGSPRYFEF (SEQ ID NO: 249);

wherein the VH chain of the variable domain that binds EGFR comprises the CDR1, CDR2 and CDR3 amino acid sequences ELSMH (SEQ ID NO: 189), GFDPEYGKTFFAQNFQG (SEQ ID NO: 216), and EGYYETTTYYYNLFDS (SEQ ID NO: 243); and the VH chain of the variable domain that binds LGR5 comprises the CDR1, CDR2 and CDR3 amino acid sequences SYTMN (SEQ ID NO: 198), WINTDTGDPTYAQGFTG (SEQ ID NO:226), and GDCDSTSCYRYSYGYEDY (SEQ ID NO: 253), the VH chain of the variable domain that binds EGFR comprises the CDR1, CDR2 and CDR3 amino acid sequences SYGIS (SEQ ID NO: 187), WISAYNGNTNYAQKLQG (SEQ ID NO: 214), and DRHWHWWLDAFDY (SEQ ID NO: 241); and the VH chain of the variable domain that binds LGR5 comprises the CDR1, CDR2 and CDR3 amino acid sequences SHWIG (SEQ ID NO: 194), VIYPGDSDTRYSPSFQG (SEQ ID NO: 222) and PNSGSPRYFEF (SEQ ID NO: 249); or the VH chain of the variable domain that binds EGFR comprises the CDR1, CDR2 and CDR3 amino acid sequences SYGIS (SEQ ID NO: 187), WISAYN-GNTNYAQKLQG (SEQ ID NO: 214), and DRHWHWWLDAFDY (SEQ ID NO: 241); and the VH chain of the variable domain that binds LGR5 comprises the CDR1, CDR2 and CDR3 amino acid sequences SYTMN (SEQ ID NO: 198), WIN-TDTGDPTYAQGFTG (SEQ ID NO: 226), and GDCDSTSCYRYSYGYEDY (SEQ ID NO: 253);

and wherein the first and second variable domains further comprise the light chain variable domain comprising a CDR1 sequence QSISSY (SEQ ID NO: 299), a CDR2 sequence AAS, and a CDR3 sequence QQSYSTPPT (SEQ ID NO: 300).

2. The bispecific antibody of claim 1, wherein the light chain variable domain comprises the amino acid sequence

```
                                           (SEQ ID NO: 80)
DIQMTQSPSSLSASVGDRVTITCRASQSISSYLNWYQQKPGKAPKLLIY

AASSLQSGVPSRFSGSGSGTDFTLTISSLQPEDFATYYCQQSYSTPPTF

GQGTKVEIK
```

3. A cell comprising the bispecific antibody according to claim 1.

4. The cell according to claim 3, wherein said cell produces said antibody.

5. The cell according to claim 3, wherein said cell is a hybridoma cell, a Chinese hamster ovary (CHO) cell, an NS0 cell or a PER-C6TM cell.

6. A pharmaceutical composition comprising an antibody of claim 1.

7. The bispecific antibody of claim 1, wherein the VH chain of the variable domain that binds EGFR comprises the amino acid sequence of SED ID NO: 20 having at most 15 amino acid insertions, deletions, substitutions or a combination thereof which are not in the CDR1, CDR2 or CDR3 region, and the VH chain of the variable domain that binds LGR5 comprises the amino acid sequence of SEQ ID NO:24 having at most 15 amino acid insertions, deletions, substitutions or a combination thereof which are not in the CDR1, CDR2 or CDR3 region.

8. The bispecific antibody of claim 1, wherein the VH chain of the variable domain that binds EGFR comprises the amino acid sequence of SEQ ID NO: 20 having at most 15 amino acid insertions, deletions, substitutions or a combination thereof which are not in the CDR1, CDR2 or CDR3 region, and the VH chain of the variable domain that binds LGR5 comprises the amino acid sequence of SEQ ID NO: 44 having at most 15 amino acid insertions, deletions, substitutions or a combination thereof which are not in the CDR1, CDR2 or CDR3 region.

9. The bispecific antibody of claim 1, wherein the VH chain of the variable domain that binds EGFR comprises the amino acid sequence of SEQ ID NO: 20, having at most 15 amino acid insertions, deletions, substitutions or a combination thereof which are not in the CDR1, CDR2 or CDR3 region and the VH chain of the variable domain that binds LGR5 comprises the amino acid sequence of SEQ ID NO: 46 having at most 15 amino acid insertions, deletions, substitutions or a combination thereof which are not in the CDR1, CDR2 or CDR3 region.

10. The bispecific antibody of claim 1, wherein the VH chain of the variable domain that binds EGFR comprises the amino acid sequence of SEQ ID NO: 20, having at most 15 amino acid insertions, deletions, substitutions or a combination thereof which are not in the CDR1, CDR2 or CDR3 region and the VH chain of the variable domain that binds LGR5 comprises the amino acid sequence of SEQ ID NO: 50 having at most 15 amino acid insertions, deletions, substitutions or a combination thereof which are not in the CDR1, CDR2 or CDR3 region.

11. The bispecific antibody of claim 1, wherein the VH chain of the variable domain that binds EGFR comprises the amino acid sequence of SEQ ID NO: 20, having at most 15 amino acid insertions, deletions, substitutions or a combination thereof which are not in the CDR1, CDR2 or CDR3 region and the VH chain of the variable domain that binds LGR5 comprises the amino acid sequence of SEQ ID NO: 52 having at most 15 amino acid insertions, deletions, substitutions or a combination thereof which are not in the CDR1, CDR2 or CDR3 region.

12. The bispecific antibody of claim 1, wherein the VH chain of the variable domain that binds EGFR comprises the amino acid sequence of SEQ ID NO: 20, having at most 15 amino acid insertions, deletions, substitutions or a combination thereof which are not in the CDR1, CDR2 or CDR3 region and the VH chain of the variable domain that binds LGR5 comprises the amino acid sequence of SEQ ID NO: 26 having at most 15 amino acid insertions, deletions, substitutions or a combination thereof which are not in the CDR1, CDR2 or CDR3 region.

13. The bispecific antibody of claim 1, wherein the VH chain of the variable domain that binds EGFR comprises the amino acid sequence of SEQ ID NO: 20 having at most 15 amino acid insertions, deletions, substitutions or a combination thereof which are not in the CDR1, CDR2 or CDR3 region, and the VH chain of the variable domain that binds LGR5 comprises the amino acid sequence of SEQ ID NO: 54 having at most 15 amino acid insertions, deletions, substitutions or a combination thereof which are not in the CDR1, CDR2 or CDR3 region.

14. The bispecific antibody of claim 1, wherein the VH chain of the variable domain that binds EGFR comprises the amino acid sequence of SEQ ID NO: 20 having at most 15 amino acid insertions, deletions, substitutions or a combination thereof which are not in the CDR1, CDR2 or CDR3 region, and the VH chain of the variable domain that binds LGR5 comprises the amino acid sequence of SEQ ID NO: 56 having at most 15 amino acid insertions, deletions, substitutions or a combination thereof which are not in the CDR1, CDR2 or CDR3 region.

15. The bispecific antibody of claim 1, wherein the VH chain of the variable domain that binds EGFR comprises the amino acid sequence of SEQ ID NO: 36 having at most 15 amino acid insertions, deletions, substitutions or a combination thereof which are not in the CDR1, CDR2 or CDR3 region, and the VH chain of the variable domain that binds LGR5 comprises the amino acid sequence of SEQ ID NO: 46 having at most 15 amino acid insertions, deletions, substitutions or a combination thereof which are not in the CDR1, CDR2 or CDR3 region.

16. The bispecific antibody of claim 1, wherein the VH chain of the variable domain that binds EGFR comprises the amino acid sequence of SEQ ID NO: 36 having at most 15 amino acid insertions, deletions, substitutions or a combination thereof which are not in the CDR1, CDR2 or CDR3 region, and the VH chain of the variable domain that binds LGR5 comprises the amino acid sequence of SEQ ID NO: 26 having at most 15 amino acid insertions, deletions, substitutions or a combination thereof which are not in the CDR1, CDR2 or CDR3 region.

17. The bispecific antibody of claim 1, wherein the VH chain of the variable domain that binds EGFR comprises the amino acid sequence of SEQ ID NO: 34 having at most 15 amino acid insertions, deletions, substitutions or a combination thereof which are not in the CDR1, CDR2 or CDR3 region, and the VH chain of the variable domain that binds LGR5 comprises the amino acid sequence of SEQ ID NO: 46 having at most 15 amino acid insertions, deletions, substitutions or a combination thereof which are not in the CDR1, CDR2 or CDR3 region.

18. The bispecific antibody of claim 1, wherein the VH chain of the variable domain that binds EGFR comprises the amino acid sequence SEQ ID NO: 34 having at most 15 amino acid insertions, deletions, substitutions or a combination thereof which are not in the CDR1, CDR2 or CDR3 region and the VH chain of the variable domain that binds LGR5 comprises the amino acid sequence of SEQ ID NO: 26 having at most 15 amino acid insertions, deletions, substitutions or a combination thereof which are not in the CDR1, CDR2 or CDR3 region.

19. The bispecific antibody of claim 1, wherein the VH chain of the variable domain that binds EGFR comprises the amino acid sequence of SED ID NO: 20 and the VH chain of the variable domain that binds LGR5 comprises the amino acid sequence of SEQ ID NO:24.

20. The bispecific antibody of claim 1, wherein the VH chain of the variable domain that binds EGFR comprises the amino acid sequence of SEQ ID NO: 20 and the VH chain of the variable domain that binds LGR5 comprises the amino acid sequence of SEQ ID NO: 44.

21. The bispecific antibody of claim 1, wherein the VH chain of the variable domain that binds EGFR comprises the amino acid sequence of SEQ ID NO: 20 and the VH chain of the variable domain that binds LGR5 comprises the amino acid sequence of SEQ ID NO: 46.

22. The bispecific antibody of claim 1, wherein the VH chain of the variable domain that binds EGFR comprises the amino acid sequence of SEQ ID NO: 20 and the VH chain of the variable domain that binds LGR5 comprises the amino acid sequence of SEQ ID NO: 50.

23. The bispecific antibody of claim 1, wherein the VH chain of the variable domain that binds EGFR comprises the amino acid sequence of SEQ ID NO: 20 and the VH chain of the variable domain that binds LGR5 comprises the amino acid sequence of SEQ ID NO: 52.

24. The bispecific antibody of claim 1, wherein the VH chain of the variable domain that binds EGFR comprises the amino acid sequence of SEQ ID NO: 20 and the VH chain of the variable domain that binds LGR5 comprises the amino acid sequence of SEQ ID NO: 26.

25. The bispecific antibody of claim 1, wherein the VH chain of the variable domain that binds EGFR comprises the amino acid sequence of SEQ ID NO: 20 and the VH chain of the variable domain that binds LGR5 comprises the amino acid sequence of SEQ ID NO: 54.

26. The bispecific antibody of claim 1, wherein the VH chain of the variable domain that binds EGFR comprises the amino acid sequence of SEQ ID NO:20 and the VH chain of the variable domain that binds LGR5 comprises the amino acid sequence of SEQ ID NO: 56.

27. The bispecific antibody of claim 1, wherein the VH chain of the variable domain that binds EGFR comprises the amino acid sequence of SEQ ID NO: 36 and the VH chain of the variable domain that binds LGR5 comprises the amino acid sequence of SEQ ID NO: 46.

28. The bispecific antibody of claim 1, wherein the VH chain of the variable domain that binds EGFR comprises the amino acid sequence of SEQ ID NO: 36 and the VH chain of the variable domain that binds LGR5 comprises the amino acid sequence of SEQ ID NO: 26.

29. The bispecific antibody of claim 1, wherein the VH chain of the variable domain that binds EGFR comprises the amino acid sequence of SEQ ID NO: 34 and the VH chain of the variable domain that binds LGR5 comprises the amino acid sequence of SEQ ID NO: 46.

30. The bispecific antibody of claim 1, wherein the VH chain of the variable domain that binds EGFR comprises the amino acid sequence SEQ ID NO: 34 and the VH chain of the variable domain that binds LGR5 comprises the amino acid sequence of SEQ ID NO: 26.

* * * * *

SEQUENCE LISTING

<160> NUMBER OF SEQ ID NOS: 300

<210> SEQ ID NO 1
<211> LENGTH: 907
<212> TYPE: PRT
<213> ORGANISM: Homo sapiens

```
<220> FEATURE:
<221> NAME/KEY: SIGNAL
<222> LOCATION: (1)..(20)
<220> FEATURE:
<221> NAME/KEY: DOMAIN
<222> LOCATION: (21)..(69)
<223> OTHER INFORMATION: N-region
<220> FEATURE:
<221> NAME/KEY: DOMAIN
<222> LOCATION: (70)..(93)
<223> OTHER INFORMATION: LRR1
<220> FEATURE:
<221> NAME/KEY: DOMAIN
<222> LOCATION: (94)..(117)
<223> OTHER INFORMATION: LRR2
<220> FEATURE:
<221> NAME/KEY: DOMAIN
<222> LOCATION: (118)..(141)
<223> OTHER INFORMATION: LRR3
<220> FEATURE:
<221> NAME/KEY: DOMAIN
<222> LOCATION: (142)..(165)
<223> OTHER INFORMATION: LRR4
<220> FEATURE:
<221> NAME/KEY: DOMAIN
<222> LOCATION: (166)..(189)
<223> OTHER INFORMATION: LRR5
<220> FEATURE:
<221> NAME/KEY: DOMAIN
<222> LOCATION: (190)..(213)
<223> OTHER INFORMATION: LRR6
<220> FEATURE:
<221> NAME/KEY: DOMAIN
<222> LOCATION: (214)..(238)
<223> OTHER INFORMATION: LRR7
<220> FEATURE:
<221> NAME/KEY: DOMAIN
<222> LOCATION: (239)..(257)
<223> OTHER INFORMATION: LRR8
<220> FEATURE:
<221> NAME/KEY: DOMAIN
<222> LOCATION: (258)..(284)
<223> OTHER INFORMATION: LRR9
<220> FEATURE:
<221> NAME/KEY: DOMAIN
<222> LOCATION: (285)..(308)
<223> OTHER INFORMATION: LRR10
<220> FEATURE:
<221> NAME/KEY: DOMAIN
<222> LOCATION: (309)..(331)
<223> OTHER INFORMATION: LRR11
<220> FEATURE:
<221> NAME/KEY: DOMAIN
<222> LOCATION: (332)..(355)
<223> OTHER INFORMATION: LRR12
<220> FEATURE:
<221> NAME/KEY: DOMAIN
<222> LOCATION: (356)..(377)
<223> OTHER INFORMATION: LRR13
<220> FEATURE:
<221> NAME/KEY: DOMAIN
<222> LOCATION: (378)..(400)
<223> OTHER INFORMATION: LRR14
<220> FEATURE:
<221> NAME/KEY: DOMAIN
<222> LOCATION: (401)..(425)
<223> OTHER INFORMATION: LRR15
<220> FEATURE:
<221> NAME/KEY: DOMAIN
<222> LOCATION: (426)..(448)
<223> OTHER INFORMATION: LRR16
<220> FEATURE:
<221> NAME/KEY: DOMAIN
<222> LOCATION: (449)..(472)
<223> OTHER INFORMATION: LRR17
<220> FEATURE:
<221> NAME/KEY: DOMAIN
<222> LOCATION: (473)..(560)
<223> OTHER INFORMATION: CRL region
```

-continued

```
<220> FEATURE:
<221> NAME/KEY: DOMAIN
<222> LOCATION: (561)..(582)
<223> OTHER INFORMATION: predicted TM1
<220> FEATURE:
<221> NAME/KEY: DOMAIN
<222> LOCATION: (592)..(617)
<223> OTHER INFORMATION: predicted TM2
<220> FEATURE:
<221> NAME/KEY: DOMAIN
<222> LOCATION: (639)..(661)
<223> OTHER INFORMATION: predicted TM3
<220> FEATURE:
<221> NAME/KEY: DOMAIN
<222> LOCATION: (680)..(704)
<223> OTHER INFORMATION: predicted TM4
<220> FEATURE:
<221> NAME/KEY: DOMAIN
<222> LOCATION: (723)..(747)
<223> OTHER INFORMATION: predicted TM5
<220> FEATURE:
<221> NAME/KEY: DOMAIN
<222> LOCATION: (766)..(789)
<223> OTHER INFORMATION: predicted TM6
<220> FEATURE:
<221> NAME/KEY: DOMAIN
<222> LOCATION: (801)..(824)
<223> OTHER INFORMATION: predicted TM7
<220> FEATURE:
<221> NAME/KEY: DOMAIN
<222> LOCATION: (825)..(907)
<223> OTHER INFORMATION: C-terminal tail

<400> SEQUENCE: 1

Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240
```

```
Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
            275                 280                 285

Tyr Asp Asn Pro Ile Gln Phe Val Gly Arg Ser Ala Phe Gln His Leu
            290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
                340                 345                 350

Asn Leu Gln Val Leu Asp Leu Ser Tyr Asn Leu Leu Glu Asp Leu Pro
                355                 360                 365

Ser Phe Ser Val Cys Gln Lys Leu Gln Lys Ile Asp Leu Arg His Asn
                370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile His Pro Asn
                405                 410                 415

Ala Phe Ser Thr Leu Pro Ser Leu Ile Lys Leu Asp Leu Ser Ser Asn
                420                 425                 430

Leu Leu Ser Ser Phe Pro Ile Thr Gly Leu His Gly Leu Thr His Leu
                435                 440                 445

Lys Leu Thr Gly Asn His Ala Leu Gln Ser Leu Ile Ser Ser Glu Asn
                450                 455                 460

Phe Pro Glu Leu Lys Val Ile Glu Met Pro Tyr Ala Tyr Gln Cys Cys
465                 470                 475                 480

Ala Phe Gly Val Cys Glu Asn Ala Tyr Lys Ile Ser Asn Gln Trp Asn
                485                 490                 495

Lys Gly Asp Asn Ser Ser Met Asp Asp Leu His Lys Lys Asp Ala Gly
                500                 505                 510

Met Phe Gln Ala Gln Asp Glu Arg Asp Leu Glu Asp Phe Leu Leu Asp
                515                 520                 525

Phe Glu Glu Asp Leu Lys Ala Leu His Ser Val Gln Cys Ser Pro Ser
530                 535                 540

Pro Gly Pro Phe Lys Pro Cys Glu His Leu Leu Asp Gly Trp Leu Ile
545                 550                 555                 560

Arg Ile Gly Val Trp Thr Ile Ala Val Leu Ala Leu Thr Cys Asn Ala
                565                 570                 575

Leu Val Thr Ser Thr Val Phe Arg Ser Pro Leu Tyr Ile Ser Pro Ile
                580                 585                 590

Lys Leu Leu Ile Gly Val Ile Ala Ala Val Asn Met Leu Thr Gly Val
                595                 600                 605

Ser Ser Ala Val Leu Ala Gly Val Asp Ala Phe Thr Phe Gly Ser Phe
                610                 615                 620

Ala Arg His Gly Ala Trp Trp Glu Asn Gly Val Gly Cys His Val Ile
625                 630                 635                 640

Gly Phe Leu Ser Ile Phe Ala Ser Glu Ser Ser Val Phe Leu Leu Thr
                645                 650                 655
```

```
Leu Ala Ala Leu Glu Arg Gly Phe Ser Val Lys Tyr Ser Ala Lys Phe
                660                 665                 670

Glu Thr Lys Ala Pro Phe Ser Ser Leu Lys Val Ile Leu Leu Cys
            675                 680                 685

Ala Leu Leu Ala Leu Thr Met Ala Ala Val Pro Leu Leu Gly Gly Ser
690                 695                 700

Lys Tyr Gly Ala Ser Pro Leu Cys Leu Pro Leu Pro Phe Gly Glu Pro
705                 710                 715                 720

Ser Thr Met Gly Tyr Met Val Ala Leu Ile Leu Leu Asn Ser Leu Cys
                725                 730                 735

Phe Leu Met Met Thr Ile Ala Tyr Thr Lys Leu Tyr Cys Asn Leu Asp
                740                 745                 750

Lys Gly Asp Leu Glu Asn Ile Trp Asp Cys Ser Met Val Lys His Ile
            755                 760                 765

Ala Leu Leu Leu Phe Thr Asn Cys Ile Leu Asn Cys Pro Val Ala Phe
770                 775                 780

Leu Ser Phe Ser Ser Leu Ile Asn Leu Thr Phe Ile Ser Pro Glu Val
785                 790                 795                 800

Ile Lys Phe Ile Leu Leu Val Val Val Pro Leu Pro Ala Cys Leu Asn
                805                 810                 815

Pro Leu Leu Tyr Ile Leu Phe Asn Pro His Phe Lys Glu Asp Leu Val
            820                 825                 830

Ser Leu Arg Lys Gln Thr Tyr Val Trp Thr Arg Ser Lys His Pro Ser
            835                 840                 845

Leu Met Ser Ile Asn Ser Asp Asp Val Glu Lys Gln Ser Cys Asp Ser
850                 855                 860

Thr Gln Ala Leu Val Thr Phe Thr Ser Ser Ile Thr Tyr Asp Leu
865                 870                 875                 880

Pro Pro Ser Ser Val Pro Ser Pro Ala Tyr Pro Val Thr Glu Ser Cys
            885                 890                 895

His Leu Ser Ser Val Ala Phe Val Pro Cys Leu
            900                 905
```

<210> SEQ ID NO 2
<211> LENGTH: 1210
<212> TYPE: PRT
<213> ORGANISM: Homo sapiens
<220> FEATURE:
<221> NAME/KEY: SIGNAL
<222> LOCATION: (1)..(24)
<220> FEATURE:
<221> NAME/KEY: DOMAIN
<222> LOCATION: (25)..(660)
<223> OTHER INFORMATION: Extracellular domain
<220> FEATURE:
<221> NAME/KEY: DOMAIN
<222> LOCATION: (661)..(676)
<223> OTHER INFORMATION: predicted transmembrane domain
<220> FEATURE:
<221> NAME/KEY: DOMAIN
<222> LOCATION: (677)..(1210)
<223> OTHER INFORMATION: intracellular tyrosine kinase and C-terminal
      tail

<400> SEQUENCE: 2

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
```

```
                35                  40                  45
Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
                115                 120                 125

Lys Thr Gly Leu Lys Glu Leu Pro Met Arg Asn Leu Gln Glu Ile Leu
                130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Asn Cys Gln
                195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
                275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
                355                 360                 365

Leu His Ile Leu Pro Val Ala Phe Arg Gly Asp Ser Phe Thr His Thr
                370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
                435                 440                 445

Gly Leu Arg Ser Leu Lys Glu Ile Ser Asp Gly Asp Val Ile Ile Ser
450                 455                 460
```

```
Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
        500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
        580                 585                 590

Lys Thr Cys Pro Ala Gly Val Met Gly Glu Asn Asn Thr Leu Val Trp
    595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
            645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
            725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
            805                 810                 815

Trp Cys Val Gln Ile Ala Lys Gly Met Asn Tyr Leu Glu Asp Arg Arg
        820                 825                 830

Leu Val His Arg Asp Leu Ala Ala Arg Asn Val Leu Val Lys Thr Pro
    835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880
```

```
Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
        900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
        930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
                995                1000               1005

Asp Val Val Asp Ala Asp Glu Tyr Leu Ile Pro Gln Gln Gly Phe
        1010               1015               1020

Phe Ser Ser Pro Ser Thr Ser Arg Thr Pro Leu Leu Ser Ser Leu
        1025               1030               1035

Ser Ala Thr Ser Asn Asn Ser Thr Val Ala Cys Ile Asp Arg Asn
        1040               1045               1050

Gly Leu Gln Ser Cys Pro Ile Lys Glu Asp Ser Phe Leu Gln Arg
        1055               1060               1065

Tyr Ser Ser Asp Pro Thr Gly Ala Leu Thr Glu Asp Ser Ile Asp
        1070               1075               1080

Asp Thr Phe Leu Pro Val Pro Glu Tyr Ile Asn Gln Ser Val Pro
        1085               1090               1095

Lys Arg Pro Ala Gly Ser Val Gln Asn Pro Val Tyr His Asn Gln
        1100               1105               1110

Pro Leu Asn Pro Ala Pro Ser Arg Asp Pro His Tyr Gln Asp Pro
        1115               1120               1125

His Ser Thr Ala Val Gly Asn Pro Glu Tyr Leu Asn Thr Val Gln
        1130               1135               1140

Pro Thr Cys Val Asn Ser Thr Phe Asp Ser Pro Ala His Trp Ala
        1145               1150               1155

Gln Lys Gly Ser His Gln Ile Ser Leu Asp Asn Pro Asp Tyr Gln
        1160               1165               1170

Gln Asp Phe Phe Pro Lys Glu Ala Lys Pro Asn Gly Ile Phe Lys
        1175               1180               1185

Gly Ser Thr Ala Glu Asn Ala Glu Tyr Leu Arg Val Ala Pro Gln
        1190               1195               1200

Ser Ser Glu Phe Ile Gly Ala
        1205               1210

<210> SEQ ID NO 3
<211> LENGTH: 997
<212> TYPE: PRT
<213> ORGANISM: Artificial Sequence
<220> FEATURE:
<223> OTHER INFORMATION: Amino acid sequence full length hLGR4-FLAG-HA
      insert
<220> FEATURE:
<221> NAME/KEY: SIGNAL
<222> LOCATION: (1)..(24)
<220> FEATURE:
<221> NAME/KEY: MISC_FEATURE
```

```
<222> LOCATION: (952)..(953)
<223> OTHER INFORMATION: linker
<220> FEATURE:
<221> NAME/KEY: MISC_FEATURE
<222> LOCATION: (954)..(961)
<223> OTHER INFORMATION: FLG tag
<220> FEATURE:
<221> NAME/KEY: MISC_FEATURE
<222> LOCATION: (962)..(964)
<223> OTHER INFORMATION: linker
<220> FEATURE:
<221> NAME/KEY: MISC_FEATURE
<222> LOCATION: (965)..(972)
<223> OTHER INFORMATION: FLAG tag
<220> FEATURE:
<221> NAME/KEY: MISC_FEATURE
<222> LOCATION: (973)..(976)
<223> OTHER INFORMATION: linker
<220> FEATURE:
<221> NAME/KEY: MISC_FEATURE
<222> LOCATION: (977)..(985)
<223> OTHER INFORMATION: HA tag
<220> FEATURE:
<221> NAME/KEY: MISC_FEATURE
<222> LOCATION: (986)..(988)
<223> OTHER INFORMATION: linker
<220> FEATURE:
<221> NAME/KEY: MISC_FEATURE
<222> LOCATION: (989)..(997)
<223> OTHER INFORMATION: HA tag

<400> SEQUENCE: 3

Met Ala Gly Pro Leu Gly Leu Leu Cys Phe Leu Ala Leu Gly Leu Leu
1               5                   10                  15

Gly Ser Ala Gly Pro Ser Gly Ala Ala Pro Pro Leu Cys Ala Ala Pro
            20                  25                  30

Cys Ser Cys Asp Gly Asp Arg Arg Val Asp Cys Ser Gly Lys Gly Leu
        35                  40                  45

Thr Ala Val Pro Glu Gly Leu Ser Ala Phe Thr Gln Ala Leu Asp Ile
    50                  55                  60

Ser Met Asn Asn Ile Thr Gln Leu Pro Glu Asp Ala Phe Lys Asn Phe
65                  70                  75                  80

Pro Phe Leu Glu Glu Leu Gln Leu Ala Gly Asn Asp Leu Ser Phe Ile
                85                  90                  95

His Pro Lys Ala Leu Ser Gly Leu Lys Glu Leu Lys Val Leu Thr Leu
            100                 105                 110

Gln Asn Asn Gln Leu Lys Thr Val Pro Ser Glu Ala Ile Arg Gly Leu
        115                 120                 125

Ser Ala Leu Gln Ser Leu Arg Leu Asp Ala Asn His Ile Thr Ser Val
    130                 135                 140

Pro Glu Asp Ser Phe Glu Gly Leu Val Gln Leu Arg His Leu Trp Leu
145                 150                 155                 160

Asp Asp Asn Ser Leu Thr Glu Val Pro Val His Pro Leu Ser Asn Leu
                165                 170                 175

Pro Thr Leu Gln Ala Leu Thr Leu Ala Leu Asn Lys Ile Ser Ser Ile
            180                 185                 190

Pro Asp Phe Ala Phe Thr Asn Leu Ser Ser Leu Val Val Leu His Leu
        195                 200                 205

His Asn Asn Lys Ile Arg Ser Leu Ser Gln His Cys Phe Asp Gly Leu
    210                 215                 220

Asp Asn Leu Glu Thr Leu Asp Leu Asn Tyr Asn Asn Leu Gly Glu Phe
225                 230                 235                 240

Pro Gln Ala Ile Lys Ala Leu Pro Ser Leu Lys Glu Leu Gly Phe His
```

245                 250                 255
    Ser Asn Ser Ile Ser Val Ile Pro Asp Gly Ala Phe Asp Gly Asn Pro
                    260                 265                 270

Leu Leu Arg Thr Ile His Leu Tyr Asp Asn Pro Leu Ser Phe Val Gly
                275                 280                 285

Asn Ser Ala Phe His Asn Leu Ser Asp Leu His Ser Leu Val Ile Arg
            290                 295                 300

Gly Ala Ser Met Val Gln Gln Phe Pro Asn Leu Thr Gly Thr Val His
    305                 310                 315                 320

Leu Glu Ser Leu Thr Leu Thr Gly Thr Lys Ile Ser Ile Pro Asn
                    325                 330                 335

Asn Leu Cys Gln Glu Gln Lys Met Leu Arg Thr Leu Asp Leu Ser Tyr
                340                 345                 350

Asn Asn Ile Arg Asp Leu Pro Ser Phe Asn Gly Cys His Ala Leu Glu
                355                 360                 365

Glu Ile Ser Leu Gln Arg Asn Gln Ile Tyr Gln Ile Lys Glu Gly Thr
                370                 375                 380

Phe Gln Gly Leu Ile Ser Leu Arg Ile Leu Asp Leu Ser Arg Asn Leu
    385                 390                 395                 400

Ile His Glu Ile His Ser Arg Ala Phe Ala Thr Leu Gly Pro Ile Thr
                    405                 410                 415

Asn Leu Asp Val Ser Phe Asn Glu Leu Thr Ser Phe Pro Thr Glu Gly
                420                 425                 430

Leu Asn Gly Leu Asn Gln Leu Lys Leu Val Gly Asn Phe Lys Leu Lys
                435                 440                 445

Glu Ala Leu Ala Ala Lys Asp Phe Val Asn Leu Arg Ser Leu Ser Val
    450                 455                 460

Pro Tyr Ala Tyr Gln Cys Cys Ala Phe Trp Gly Cys Asp Ser Tyr Ala
    465                 470                 475                 480

Asn Leu Asn Thr Glu Asp Asn Ser Leu Gln Asp His Ser Val Ala Gln
                    485                 490                 495

Glu Lys Gly Thr Ala Asp Ala Ala Asn Val Thr Ser Thr Leu Glu Asn
                500                 505                 510

Glu Glu His Ser Gln Ile Ile Ile His Cys Thr Pro Ser Thr Gly Ala
                515                 520                 525

Phe Lys Pro Cys Glu Tyr Leu Leu Gly Ser Trp Met Ile Arg Leu Thr
                530                 535                 540

Val Trp Phe Ile Phe Leu Val Ala Leu Phe Phe Asn Leu Leu Val Ile
    545                 550                 555                 560

Leu Thr Thr Phe Ala Ser Cys Thr Ser Leu Pro Ser Ser Lys Leu Phe
                    565                 570                 575

Ile Gly Leu Ile Ser Val Ser Asn Leu Phe Met Gly Ile Tyr Thr Gly
                580                 585                 590

Ile Leu Thr Phe Leu Asp Ala Val Ser Trp Gly Arg Phe Ala Glu Phe
                595                 600                 605

Gly Ile Trp Trp Glu Thr Gly Ser Gly Cys Lys Val Ala Gly Phe Leu
    610                 615                 620

Ala Val Phe Ser Ser Glu Ser Ala Ile Phe Leu Leu Met Leu Ala Thr
    625                 630                 635                 640

Val Glu Arg Ser Leu Ser Ala Lys Asp Ile Met Lys Asn Gly Lys Ser
                    645                 650                 655

Asn His Leu Lys Gln Phe Arg Val Ala Ala Leu Leu Ala Phe Leu Gly
                660                 665                 670

```
Ala Thr Val Ala Gly Cys Phe Pro Leu Phe His Arg Gly Glu Tyr Ser
            675                 680                 685

Ala Ser Pro Leu Cys Leu Pro Phe Pro Thr Gly Glu Thr Pro Ser Leu
    690                 695                 700

Gly Phe Thr Val Thr Leu Val Leu Leu Asn Ser Leu Ala Phe Leu Leu
705                 710                 715                 720

Met Ala Val Ile Tyr Thr Lys Leu Tyr Cys Asn Leu Glu Lys Glu Asp
                725                 730                 735

Leu Ser Glu Asn Ser Gln Ser Ser Met Ile Lys His Val Ala Trp Leu
            740                 745                 750

Ile Phe Thr Asn Cys Ile Phe Phe Cys Pro Val Ala Phe Phe Ser Phe
        755                 760                 765

Ala Pro Leu Ile Thr Ala Ile Ser Ile Ser Pro Glu Ile Met Lys Ser
    770                 775                 780

Val Thr Leu Ile Phe Phe Pro Leu Pro Ala Cys Leu Asn Pro Val Leu
785                 790                 795                 800

Tyr Val Phe Phe Asn Pro Lys Phe Lys Glu Asp Trp Lys Leu Leu Lys
                805                 810                 815

Arg Arg Val Thr Lys Lys Ser Gly Ser Val Ser Val Ser Ile Ser Ser
            820                 825                 830

Gln Gly Gly Cys Leu Glu Gln Asp Phe Tyr Tyr Asp Cys Gly Met Tyr
        835                 840                 845

Ser His Leu Gln Gly Asn Leu Thr Val Cys Asp Cys Cys Glu Ser Phe
    850                 855                 860

Leu Leu Thr Lys Pro Val Ser Cys Lys His Leu Ile Lys Ser His Ser
865                 870                 875                 880

Cys Pro Ala Leu Ala Val Ala Ser Cys Gln Arg Pro Glu Gly Tyr Trp
                885                 890                 895

Ser Asp Cys Gly Thr Gln Ser Ala His Ser Asp Tyr Ala Asp Glu Glu
            900                 905                 910

Asp Ser Phe Val Ser Asp Ser Ser Asp Gln Val Gln Ala Cys Gly Arg
        915                 920                 925

Ala Cys Phe Tyr Gln Ser Arg Gly Phe Pro Leu Val Arg Tyr Ala Tyr
    930                 935                 940

Asn Leu Pro Arg Val Lys Asp Ser Arg Asp Tyr Lys Asp Asp Asp Asp
945                 950                 955                 960

Lys Ala Gly Ala Asp Tyr Lys Asp Asp Asp Lys Leu Asp Gly Gly
                965                 970                 975

Tyr Pro Tyr Asp Val Pro Asp Tyr Ala Ala Gly Ala Tyr Pro Tyr Asp
            980                 985                 990

Val Pro Asp Tyr Ala
        995

<210> SEQ ID NO 4
<211> LENGTH: 635
<212> TYPE: PRT
<213> ORGANISM: Artificial Sequence
<220> FEATURE:
<223> OTHER INFORMATION: Amino acid sequence hLGR4(ECD)-GPA33-FLAG
      insert in pVax1
<220> FEATURE:
<221> NAME/KEY: SIGNAL
<222> LOCATION: (1)..(24)
<220> FEATURE:
<221> NAME/KEY: MISC_FEATURE
<222> LOCATION: (543)..(627)
<223> OTHER INFORMATION: GPA33
```

```
<220> FEATURE:
<221> NAME/KEY: MISC_FEATURE
<222> LOCATION: (628)..(635)
<223> OTHER INFORMATION: FLAG tag

<400> SEQUENCE: 4
```

| Met | Pro | Gly | Pro | Leu | Gly | Leu | Leu | Cys | Phe | Leu | Ala | Leu | Gly | Leu | Leu |
|---|---|---|---|---|---|---|---|---|---|---|---|---|---|---|---|
| 1 | | | | 5 | | | | | 10 | | | | | 15 | |

| Gly | Ser | Ala | Gly | Pro | Ser | Gly | Ala | Ala | Pro | Leu | Cys | Ala | Ala | Pro |
|---|---|---|---|---|---|---|---|---|---|---|---|---|---|---|
| | | | 20 | | | | | 25 | | | | | 30 | |

Cys Ser Cys Asp Gly Asp Arg Arg Val Asp Cys Ser Gly Lys Gly Leu
            35                  40                  45

Thr Ala Val Pro Glu Gly Leu Ser Ala Phe Thr Gln Ala Leu Asp Ile
 50                      55                  60

Ser Met Asn Asn Ile Thr Gln Leu Pro Glu Asp Ala Phe Lys Asn Phe
 65                  70                      75                  80

Pro Phe Leu Glu Glu Leu Gln Leu Ala Gly Asn Asp Leu Ser Phe Ile
                85                  90                  95

His Pro Lys Ala Leu Ser Gly Leu Lys Glu Leu Lys Val Leu Thr Leu
            100                 105                 110

Gln Asn Asn Gln Leu Lys Thr Val Pro Ser Glu Ala Ile Arg Gly Leu
            115                 120                 125

Ser Ala Leu Gln Ser Leu Arg Leu Asp Ala Asn His Ile Thr Ser Val
130                 135                 140

Pro Glu Asp Ser Phe Glu Gly Leu Val Gln Leu Arg His Leu Trp Leu
145                 150                 155                 160

Asp Asp Asn Ser Leu Thr Glu Val Pro Val His Pro Leu Ser Asn Leu
                165                 170                 175

Pro Thr Leu Gln Ala Leu Thr Leu Ala Leu Asn Lys Ile Ser Ser Ile
            180                 185                 190

Pro Asp Phe Ala Phe Thr Asn Leu Ser Ser Leu Val Val Leu His Leu
            195                 200                 205

His Asn Asn Lys Ile Arg Ser Leu Ser Gln His Cys Phe Asp Gly Leu
210                 215                 220

Asp Asn Leu Glu Thr Leu Asp Leu Asn Tyr Asn Asn Leu Gly Glu Phe
225                 230                 235                 240

Pro Gln Ala Ile Lys Ala Leu Pro Ser Leu Lys Glu Leu Gly Phe His
                245                 250                 255

Ser Asn Ser Ile Ser Val Ile Pro Asp Gly Ala Phe Asp Gly Asn Pro
                260                 265                 270

Leu Leu Arg Thr Ile His Leu Tyr Asp Asn Pro Leu Ser Phe Val Gly
            275                 280                 285

Asn Ser Ala Phe His Asn Leu Ser Asp Leu His Ser Leu Val Ile Arg
290                 295                 300

Gly Ala Ser Met Val Gln Gln Phe Pro Asn Leu Thr Gly Thr Val His
305                 310                 315                 320

Leu Glu Ser Leu Thr Leu Thr Gly Thr Lys Ile Ser Ser Ile Pro Asn
                325                 330                 335

Asn Leu Cys Gln Glu Gln Lys Met Leu Arg Thr Leu Asp Leu Ser Tyr
                340                 345                 350

Asn Asn Ile Arg Asp Leu Pro Ser Phe Asn Gly Cys His Ala Leu Glu
            355                 360                 365

Glu Ile Ser Leu Gln Arg Asn Gln Ile Tyr Gln Ile Lys Glu Gly Thr
370                 375                 380

```
Phe Gln Gly Leu Ile Ser Leu Arg Ile Leu Asp Leu Ser Arg Asn Leu
385                 390                 395                 400

Ile His Glu Ile His Ser Arg Ala Phe Ala Thr Leu Gly Pro Ile Thr
                405                 410                 415

Asn Leu Asp Val Ser Phe Asn Glu Leu Thr Ser Phe Pro Thr Glu Gly
            420                 425                 430

Leu Asn Gly Leu Asn Gln Leu Lys Leu Val Gly Asn Phe Lys Leu Lys
        435                 440                 445

Glu Ala Leu Ala Ala Lys Asp Phe Val Asn Leu Arg Ser Leu Ser Val
450                 455                 460

Pro Tyr Ala Tyr Gln Cys Cys Ala Phe Trp Gly Cys Asp Ser Tyr Ala
465                 470                 475                 480

Asn Leu Asn Thr Glu Asp Asn Ser Leu Gln Asp His Ser Val Ala Gln
                485                 490                 495

Glu Lys Gly Thr Ala Asp Ala Ala Asn Val Thr Ser Thr Leu Glu Asn
            500                 505                 510

Glu Glu His Ser Gln Ile Ile His Cys Thr Pro Ser Thr Gly Ala
        515                 520                 525

Phe Lys Pro Cys Glu Tyr Leu Leu Gly Ser Trp Met Ile Arg Val Ala
530                 535                 540

Leu Tyr Val Gly Ile Ala Val Gly Val Val Ala Ala Leu Ile Ile Ile
545                 550                 555                 560

Gly Ile Ile Ile Tyr Cys Cys Cys Cys Arg Gly Lys Asp Asp Asn Thr
                565                 570                 575

Glu Asp Lys Glu Asp Ala Arg Pro Asn Arg Glu Ala Tyr Glu Glu Pro
            580                 585                 590

Pro Glu Gln Leu Arg Glu Leu Ser Arg Glu Arg Glu Glu Asp Asp
        595                 600                 605

Tyr Arg Gln Glu Glu Gln Arg Ser Thr Gly Arg Glu Ser Pro Asp His
610                 615                 620

Leu Asp Gln Asp Tyr Lys Asp Asp Asp Lys
625                 630                 635
```

<210> SEQ ID NO 5
<211> LENGTH: 953
<212> TYPE: PRT
<213> ORGANISM: Artificial Sequence
<220> FEATURE:
<223> OTHER INFORMATION: Amino acid sequence full length hLGR5-FLAG-HA
      insert (
<220> FEATURE:
<221> NAME/KEY: SIGNAL
<222> LOCATION: (1)..(21)
<220> FEATURE:
<221> NAME/KEY: MISC_FEATURE
<222> LOCATION: (908)..(909)
<223> OTHER INFORMATION: linker
<220> FEATURE:
<221> NAME/KEY: MISC_FEATURE
<222> LOCATION: (910)..(918)
<223> OTHER INFORMATION: FLAG tag
<220> FEATURE:
<221> NAME/KEY: MISC_FEATURE
<222> LOCATION: (919)..(921)
<223> OTHER INFORMATION: linker
<220> FEATURE:
<221> NAME/KEY: MISC_FEATURE
<222> LOCATION: (922)..(929)
<223> OTHER INFORMATION: FLAG tag
<220> FEATURE:
<221> NAME/KEY: MISC_FEATURE
<222> LOCATION: (930)..(933)
<223> OTHER INFORMATION: linker

```
<220> FEATURE:
<221> NAME/KEY: MISC_FEATURE
<222> LOCATION: (934)..(942)
<223> OTHER INFORMATION: HA tag
<220> FEATURE:
<221> NAME/KEY: MISC_FEATURE
<222> LOCATION: (943)..(945)
<223> OTHER INFORMATION: linker
<220> FEATURE:
<221> NAME/KEY: MISC_FEATURE
<222> LOCATION: (946)..(953)
<223> OTHER INFORMATION: HA tag

<400> SEQUENCE: 5
```

Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
        275                 280                 285

Tyr Asp Asn Pro Ile Gln Phe Val Gly Arg Ser Ala Phe Gln His Leu
290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro

```
              340             345             350
Asn Leu Gln Val Leu Asp Leu Ser Tyr Asn Leu Leu Glu Asp Leu Pro
            355                 360                 365
Ser Phe Ser Val Cys Gln Lys Leu Gln Lys Ile Asp Leu Arg His Asn
        370                 375                 380
Glu Ile Tyr Glu Ile Lys Val Asp Thr Phe Gln Gln Leu Leu Ser Leu
385                 390                 395                 400
Arg Ser Leu Asn Leu Ala Trp Asn Lys Ile Ala Ile His Pro Asn
                405                 410                 415
Ala Phe Ser Thr Leu Pro Ser Leu Ile Lys Leu Asp Leu Ser Ser Asn
            420                 425                 430
Leu Leu Ser Ser Phe Pro Ile Thr Gly Leu His Gly Leu Thr His Leu
            435                 440                 445
Lys Leu Thr Gly Asn His Ala Leu Gln Ser Leu Ile Ser Ser Glu Asn
            450                 455                 460
Phe Pro Glu Leu Lys Val Ile Glu Met Pro Tyr Ala Tyr Gln Cys Cys
465                 470                 475                 480
Ala Phe Gly Val Cys Glu Asn Ala Tyr Lys Ile Ser Asn Gln Trp Asn
                485                 490                 495
Lys Gly Asp Asn Ser Ser Met Asp Asp Leu His Lys Lys Asp Ala Gly
                500                 505                 510
Met Phe Gln Ala Gln Asp Glu Arg Asp Leu Glu Asp Phe Leu Leu Asp
            515                 520                 525
Phe Glu Glu Asp Leu Lys Ala Leu His Ser Val Gln Cys Ser Pro Ser
530                 535                 540
Pro Gly Pro Phe Lys Pro Cys Glu His Leu Leu Asp Gly Trp Leu Ile
545                 550                 555                 560
Arg Ile Gly Val Trp Thr Ile Ala Val Leu Ala Leu Thr Cys Asn Ala
                565                 570                 575
Leu Val Thr Ser Thr Val Phe Arg Ser Pro Leu Tyr Ile Ser Pro Ile
            580                 585                 590
Lys Leu Leu Ile Gly Val Ile Ala Ala Val Asn Met Leu Thr Gly Val
            595                 600                 605
Ser Ser Ala Val Leu Ala Gly Val Asp Ala Phe Thr Phe Gly Ser Phe
            610                 615                 620
Ala Arg His Gly Ala Trp Trp Glu Asn Gly Val Gly Cys His Val Ile
625                 630                 635                 640
Gly Phe Leu Ser Ile Phe Ala Ser Glu Ser Ser Val Phe Leu Leu Thr
                645                 650                 655
Leu Ala Ala Leu Glu Arg Gly Phe Ser Ala Lys Tyr Ser Ala Lys Phe
                660                 665                 670
Glu Thr Lys Ala Pro Phe Ser Ser Leu Lys Val Ile Ile Leu Leu Cys
            675                 680                 685
Ala Leu Leu Ala Leu Thr Met Ala Ala Val Pro Leu Leu Gly Gly Ser
            690                 695                 700
Lys Tyr Gly Ala Ser Pro Leu Cys Leu Pro Leu Pro Phe Gly Glu Pro
705                 710                 715                 720
Ser Thr Met Gly Tyr Met Val Ala Leu Ile Leu Leu Asn Ser Leu Cys
                725                 730                 735
Phe Leu Met Met Thr Ile Ala Tyr Thr Lys Leu Tyr Cys Asn Leu Asp
            740                 745                 750
Lys Gly Asp Leu Glu Asn Ile Trp Asp Cys Ser Met Val Lys His Ile
            755                 760                 765
```

```
Ala Leu Leu Leu Phe Thr Asn Cys Ile Leu Asn Cys Pro Val Ala Phe
            770                 775                 780

Leu Ser Phe Ser Ser Leu Ile Asn Leu Thr Phe Ile Ser Pro Glu Val
785                 790                 795                 800

Ile Lys Phe Ile Leu Leu Val Val Val Pro Leu Pro Ala Cys Leu Asn
                805                 810                 815

Pro Leu Leu Tyr Ile Leu Phe Asn Pro His Phe Lys Glu Asp Leu Val
                820                 825                 830

Ser Leu Arg Lys Gln Thr Tyr Val Trp Thr Arg Ser Lys His Pro Ser
                835                 840                 845

Leu Met Ser Ile Asn Ser Asp Asp Val Glu Lys Gln Ser Cys Asp Ser
            850                 855                 860

Thr Gln Ala Leu Val Thr Phe Thr Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu Ala Arg Asp Tyr Lys
            900                 905                 910

Asp Asp Asp Asp Lys Ala Gly Ala Asp Tyr Lys Asp Asp Asp Asp Lys
            915                 920                 925

Leu Asp Gly Gly Tyr Pro Tyr Asp Val Pro Asp Tyr Ala Ala Gly Ala
            930                 935                 940

Tyr Pro Tyr Asp Val Pro Asp Tyr Ala
945                 950

<210> SEQ ID NO 6
<211> LENGTH: 654
<212> TYPE: PRT
<213> ORGANISM: Artificial Sequence
<220> FEATURE:
<223> OTHER INFORMATION: Amino acid sequence hLGR5(ECD)-GPA33(TM)-FLAG
      insert in pVax1
<220> FEATURE:
<221> NAME/KEY: SIGNAL
<222> LOCATION: (1)..(21)
<220> FEATURE:
<221> NAME/KEY: MISC_FEATURE
<222> LOCATION: (563)..(646)
<223> OTHER INFORMATION: GPA33
<220> FEATURE:
<221> NAME/KEY: MISC_FEATURE
<222> LOCATION: (647)..(654)
<223> OTHER INFORMATION: FLAG tag

<400> SEQUENCE: 6

Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
                20                  25                  30

Gly Cys Pro Thr His Cys His Cys Glu Pro Asp Gly Arg Met Leu Leu
            35                  40                  45

Arg Val Asp Cys Ser Asp Leu Gly Leu Ser Glu Leu Pro Ser Asn Leu
        50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110
```

```
Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
                180                 185                 190

Leu Ala Leu Asn Lys Ile His His Ile Pro Asp Tyr Ala Phe Gly Asn
            195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
                260                 265                 270

Pro Glu Lys Ala Phe Val Gly Asn Pro Ser Leu Ile Thr Ile His Phe
            275                 280                 285

Tyr Asp Asn Pro Ile Gln Phe Val Gly Arg Ser Ala Phe Gln His Leu
    290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
                340                 345                 350

Asn Leu Gln Val Leu Asp Leu Ser Tyr Asn Leu Leu Glu Asp Leu Pro
            355                 360                 365

Ser Phe Ser Val Cys Gln Lys Leu Gln Lys Ile Asp Leu Arg His Asn
    370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile His Pro Asn
                405                 410                 415

Ala Phe Ser Thr Leu Pro Ser Leu Ile Lys Leu Asp Leu Ser Ser Asn
            420                 425                 430

Leu Leu Ser Ser Phe Pro Ile Thr Gly Leu His Gly Leu Thr His Leu
    435                 440                 445

Lys Leu Thr Gly Asn His Ala Leu Gln Ser Leu Ile Ser Ser Glu Asn
450                 455                 460

Phe Pro Glu Leu Lys Val Ile Glu Met Pro Tyr Ala Tyr Gln Cys Cys
465                 470                 475                 480

Ala Phe Gly Val Cys Glu Asn Ala Tyr Lys Ile Ser Asn Gln Trp Asn
                485                 490                 495

Lys Gly Asp Asn Ser Ser Met Asp Asp Leu His Lys Lys Asp Ala Gly
                500                 505                 510

Met Phe Gln Ala Gln Asp Glu Arg Asp Leu Glu Asp Phe Leu Leu Asp
            515                 520                 525
```

```
Phe Glu Glu Asp Leu Lys Ala Leu His Ser Val Gln Cys Ser Pro Ser
            530                 535                 540

Pro Gly Pro Phe Lys Pro Cys Glu His Leu Leu Asp Gly Trp Leu Ile
545                 550                 555                 560

Arg Val Ala Leu Tyr Val Gly Ile Ala Val Gly Val Val Ala Ala Leu
                565                 570                 575

Ile Ile Ile Gly Ile Ile Ile Tyr Cys Cys Cys Arg Gly Lys Asp
                580                 585                 590

Asp Asn Thr Glu Asp Lys Glu Asp Ala Arg Pro Asn Arg Glu Ala Tyr
                595                 600                 605

Glu Glu Pro Pro Glu Gln Leu Arg Glu Leu Ser Arg Glu Arg Glu Glu
            610                 615                 620

Glu Asp Asp Tyr Arg Gln Glu Glu Gln Arg Ser Thr Gly Arg Glu Ser
625                 630                 635                 640

Pro Asp His Leu Asp Gln Asp Tyr Lys Asp Asp Asp Lys
                645                 650
```

```
<210> SEQ ID NO 7
<211> LENGTH: 936
<212> TYPE: PRT
<213> ORGANISM: Artificial Sequence
<220> FEATURE:
<223> OTHER INFORMATION: Amino acid sequence full length mouse
      (m)Lgr5-Myc-HIS insert in pEF1_Myc/His
<220> FEATURE:
<221> NAME/KEY: SIGNAL
<222> LOCATION: (1)..(21)
<220> FEATURE:
<221> NAME/KEY: MISC_FEATURE
<222> LOCATION: (908)..(915)
<223> OTHER INFORMATION: linker
<220> FEATURE:
<221> NAME/KEY: MISC_FEATURE
<222> LOCATION: (916)..(925)
<223> OTHER INFORMATION: cMyc-tag
<220> FEATURE:
<221> NAME/KEY: MISC_FEATURE
<222> LOCATION: (926)..(930)
<223> OTHER INFORMATION: linker
<220> FEATURE:
<221> NAME/KEY: MISC_FEATURE
<222> LOCATION: (931)..(936)
<223> OTHER INFORMATION: His tag

<400> SEQUENCE: 7

Met Asp Thr Ser Cys Val His Met Leu Leu Ser Leu Leu Ala Leu Leu
1               5                   10                  15

Gln Leu Val Ala Ala Gly Ser Ser Pro Gly Pro Asp Ala Ile Pro Arg
                20                  25                  30

Gly Cys Pro Ser His Cys His Cys Glu Leu Asp Gly Arg Met Leu Leu
                35                  40                  45

Arg Val Asp Cys Ser Asp Leu Gly Leu Ser Glu Leu Pro Ser Asn Leu
            50                  55                  60

Ser Val Phe Thr Ser Tyr Leu Asp Leu Ser Met Asn Asn Ile Ser Gln
65              70                  75                  80

Leu Pro Ala Ser Leu Leu His Arg Leu Cys Phe Leu Glu Glu Leu Arg
                85                  90                  95

Leu Ala Gly Asn Ala Leu Thr His Ile Pro Lys Gly Ala Phe Thr Gly
                100                 105                 110

Leu His Ser Leu Lys Val Leu Met Leu Gln Asn Asn Gln Leu Arg Gln
                115                 120                 125

Val Pro Glu Glu Ala Leu Gln Asn Leu Arg Ser Leu Gln Ser Leu Arg
```

-continued

```
            130                 135                 140
Leu Asp Ala Asn His Ile Ser Tyr Val Pro Ser Cys Phe Ser Gly
145                 150                 155                 160

Leu His Ser Leu Arg His Leu Trp Leu Asp Asn Ala Leu Thr Asp
                165                 170                 175

Val Pro Val Gln Ala Phe Arg Ser Leu Ser Ala Leu Gln Ala Met Thr
                180                 185                 190

Leu Ala Leu Asn Lys Ile His His Ile Ala Asp Tyr Ala Phe Gly Asn
                195                 200                 205

Leu Ser Ser Leu Val Val Leu His Leu His Asn Asn Arg Ile His Ser
                210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Lys Thr Leu
                    245                 250                 255

Ser Asn Leu Lys Glu Leu Gly Phe His Ser Asn Asn Ile Arg Ser Ile
                260                 265                 270

Pro Glu Arg Ala Phe Val Gly Asn Pro Ser Leu Ile Thr Ile His Phe
            275                 280                 285

Tyr Asp Asn Pro Ile Gln Phe Val Gly Val Ser Ala Phe Gln His Leu
            290                 295                 300

Pro Glu Leu Arg Thr Leu Thr Leu Asn Gly Ala Ser His Ile Thr Glu
305                 310                 315                 320

Phe Pro His Leu Thr Gly Thr Ala Thr Leu Glu Ser Leu Thr Leu Thr
                325                 330                 335

Gly Ala Lys Ile Ser Ser Leu Pro Gln Ala Val Cys Asp Gln Leu Pro
                340                 345                 350

Asn Leu Gln Val Leu Asp Leu Ser Tyr Asn Leu Leu Glu Asp Leu Pro
                355                 360                 365

Ser Leu Ser Gly Cys Gln Lys Leu Gln Lys Ile Asp Leu Arg His Asn
                370                 375                 380

Glu Ile Tyr Glu Ile Lys Gly Ser Thr Phe Gln Gln Leu Phe Asn Leu
385                 390                 395                 400

Arg Ser Leu Asn Leu Ala Trp Asn Lys Ile Ala Ile His Pro Asn
                405                 410                 415

Ala Phe Ser Thr Leu Pro Ser Leu Ile Lys Leu Asp Leu Ser Ser Asn
                420                 425                 430

Leu Leu Ser Ser Phe Pro Val Thr Gly Leu His Gly Leu Thr His Leu
                435                 440                 445

Lys Leu Thr Gly Asn Arg Ala Leu Gln Ser Leu Ile Pro Ser Ala Asn
450                 455                 460

Phe Pro Glu Leu Lys Ile Glu Met Pro Ser Ala Tyr Gln Cys Cys
465                 470                 475                 480

Ala Phe Gly Gly Cys Glu Asn Val Tyr Lys Ile Ser Asn Gln Trp Asn
                485                 490                 495

Lys Asp Asp Gly Asn Ser Val Asp Leu His Lys Lys Asp Ala Gly
                500                 505                 510

Leu Phe Gln Val Gln Asp Glu Arg Asp Leu Glu Asp Phe Leu Leu Asp
                515                 520                 525

Phe Glu Glu Asp Leu Lys Ala Leu His Ser Val Gln Cys Ser Pro Ser
530                 535                 540

Pro Gly Pro Phe Lys Pro Cys Glu His Leu Phe Gly Ser Trp Leu Ile
545                 550                 555                 560
```

```
Arg Ile Gly Val Trp Thr Thr Ala Val Leu Ala Leu Ser Cys Asn Ala
            565                 570                 575

Leu Val Ala Leu Thr Val Phe Arg Thr Pro Leu Tyr Ile Ser Ser Ile
            580                 585                 590

Lys Leu Leu Ile Gly Val Ile Ala Val Val Asp Ile Leu Met Gly Val
            595                 600                 605

Ser Ser Ala Val Leu Ala Ala Val Asp Ala Phe Thr Phe Gly Arg Phe
            610                 615                 620

Ala Gln His Gly Ala Trp Trp Glu Asp Gly Ile Gly Cys Gln Ile Val
625                 630                 635                 640

Gly Phe Leu Ser Ile Phe Ala Ser Glu Ser Ile Phe Leu Leu Thr
            645                 650                 655

Leu Ala Ala Leu Glu Arg Gly Phe Ser Val Lys Cys Ser Ser Lys Phe
            660                 665                 670

Glu Val Lys Ala Pro Leu Phe Ser Leu Arg Ala Ile Val Leu Leu Cys
            675                 680                 685

Val Leu Leu Ala Leu Thr Ile Ala Thr Ile Pro Leu Leu Gly Gly Ser
            690                 695                 700

Lys Tyr Asn Ala Ser Pro Leu Cys Leu Pro Leu Pro Phe Gly Glu Pro
705                 710                 715                 720

Ser Thr Thr Gly Tyr Met Val Ala Leu Val Leu Asn Ser Leu Cys
            725                 730                 735

Phe Leu Ile Met Thr Ile Ala Tyr Thr Lys Leu Tyr Cys Ser Leu Glu
            740                 745                 750

Lys Gly Glu Leu Glu Asn Leu Trp Asp Cys Ser Met Val Lys His Ile
            755                 760                 765

Ala Leu Leu Leu Phe Ala Asn Cys Ile Leu Tyr Cys Pro Val Ala Phe
            770                 775                 780

Leu Ser Phe Ser Ser Leu Leu Asn Leu Thr Phe Ile Ser Pro Asp Val
785                 790                 795                 800

Ile Lys Phe Ile Leu Leu Val Ile Val Pro Leu Pro Ser Cys Leu Asn
            805                 810                 815

Pro Leu Leu Tyr Ile Val Phe Asn Pro His Phe Lys Glu Asp Met Gly
            820                 825                 830

Ser Leu Gly Lys His Thr Arg Phe Trp Met Arg Ser Lys His Ala Ser
            835                 840                 845

Leu Leu Ser Ile Asn Ser Asp Asp Val Glu Lys Arg Ser Cys Glu Ser
            850                 855                 860

Thr Gln Ala Leu Val Ser Phe Thr His Ala Ser Ile Ala Tyr Asp Leu
865                 870                 875                 880

Pro Ser Thr Ser Gly Ala Ser Pro Ala Tyr Pro Met Thr Glu Ser Cys
            885                 890                 895

His Leu Ser Ser Val Ala Phe Val Pro Cys Leu Ala Ala Ala Arg Gly
            900                 905                 910

His Pro Phe Glu Gln Lys Leu Ile Ser Glu Glu Asp Leu Asn Met His
            915                 920                 925

Thr Gly His His His His His His
    930                 935

<210> SEQ ID NO 8
<211> LENGTH: 281
<212> TYPE: PRT
<213> ORGANISM: Artificial Sequence
<220> FEATURE:
```

<223> OTHER INFORMATION: Human ZNRF3(ECD) in pDisplay
<220> FEATURE:
<221> NAME/KEY: SIGNAL
<222> LOCATION: (1)..(55)
<220> FEATURE:
<221> NAME/KEY: MISC_FEATURE
<222> LOCATION: (222)..(231)
<223> OTHER INFORMATION: cMyc-tag
<220> FEATURE:
<221> NAME/KEY: MISC_FEATURE
<222> LOCATION: (232)..(281)
<223> OTHER INFORMATION: PDGFR

<400> SEQUENCE: 8

```
Met Arg Pro Arg Ser Gly Gly Arg Pro Gly Ala Thr Gly Arg Arg
 1               5                  10                  15

Arg Arg Leu Arg Arg Arg Pro Arg Gly Leu Arg Cys Ser Arg Leu Pro
                20                  25                  30

Pro Pro Pro Pro Leu Pro Leu Leu Gly Leu Leu Leu Ala Ala Ala
                35                  40                  45

Gly Pro Gly Ala Ala Arg Ala Lys Glu Thr Ala Phe Val Glu Val Val
        50                  55                  60

Leu Phe Glu Ser Ser Pro Ser Gly Asp Tyr Thr Thr Tyr Thr Gly
 65                  70                  75                  80

Leu Thr Gly Arg Phe Ser Arg Ala Gly Ala Thr Leu Ser Ala Glu Gly
                85                  90                  95

Glu Ile Val Gln Met His Pro Leu Gly Leu Cys Asn Asn Asn Asp Glu
                100                 105                 110

Glu Asp Leu Tyr Glu Tyr Gly Trp Val Gly Val Val Lys Leu Glu Gln
                115                 120                 125

Pro Glu Leu Asp Pro Lys Pro Cys Leu Thr Val Leu Gly Lys Ala Lys
        130                 135                 140

Arg Ala Val Gln Arg Gly Ala Thr Ala Val Ile Phe Asp Val Ser Glu
145                 150                 155                 160

Asn Pro Glu Ala Ile Asp Gln Leu Asn Gln Gly Ser Glu Asp Pro Leu
                165                 170                 175

Lys Arg Pro Val Val Tyr Val Lys Gly Ala Asp Ala Ile Lys Leu Met
                180                 185                 190

Asn Ile Val Asn Lys Gln Lys Val Ala Arg Ala Arg Ile Gln His Arg
                195                 200                 205

Pro Pro Arg Gln Pro Thr Glu Tyr Phe Asp Met Val Asp Glu Gln Lys
        210                 215                 220

Leu Ile Ser Glu Glu Asp Leu Asn Ala Val Gly Gln Asp Thr Gln Glu
225                 230                 235                 240

Val Ile Val Val Pro His Ser Leu Pro Phe Lys Val Val Val Ile Ser
                245                 250                 255

Ala Ile Leu Ala Leu Val Val Leu Thr Ile Ile Ser Leu Ile Ile Leu
                260                 265                 270

Ile Met Leu Trp Gln Lys Lys Pro Arg
        275                 280
```

<210> SEQ ID NO 9
<211> LENGTH: 256
<212> TYPE: PRT
<213> ORGANISM: Artificial Sequence
<220> FEATURE:
<223> OTHER INFORMATION: Human ZNRF3 truncation mutant
<220> FEATURE:
<221> NAME/KEY: SIGNAL
<222> LOCATION: (1)..(55)

```
<220> FEATURE:
<221> NAME/KEY: MISC_FEATURE
<222> LOCATION: (218)..(232)
<223> OTHER INFORMATION: predicted TM region
<220> FEATURE:
<221> NAME/KEY: MISC_FEATURE
<222> LOCATION: (233)..(256)
<223> OTHER INFORMATION: intracellular tail

<400> SEQUENCE: 9

Met Arg Pro Arg Ser Gly Gly Arg Pro Gly Ala Thr Gly Arg Arg
1               5                   10                  15

Arg Arg Leu Arg Arg Arg Pro Arg Gly Leu Arg Cys Ser Arg Leu Pro
            20                  25                  30

Pro Pro Pro Pro Leu Pro Leu Leu Gly Leu Leu Leu Ala Ala Ala
            35                  40                  45

Gly Pro Gly Ala Ala Arg Ala Lys Glu Thr Ala Phe Val Glu Val Val
50                  55                  60

Leu Phe Glu Ser Ser Pro Ser Gly Asp Tyr Thr Thr Tyr Thr Thr Gly
65                  70                  75                  80

Leu Thr Gly Arg Phe Ser Arg Ala Gly Ala Thr Leu Ser Ala Glu Gly
                85                  90                  95

Glu Ile Val Gln Met His Pro Leu Gly Leu Cys Asn Asn Asn Asp Glu
            100                 105                 110

Glu Asp Leu Tyr Glu Tyr Gly Trp Val Gly Val Val Lys Leu Glu Gln
            115                 120                 125

Pro Glu Leu Asp Pro Lys Pro Cys Leu Thr Val Leu Gly Lys Ala Lys
    130                 135                 140

Arg Ala Val Gln Arg Gly Ala Thr Ala Val Ile Phe Asp Val Ser Glu
145                 150                 155                 160

Asn Pro Glu Ala Ile Asp Gln Leu Asn Gln Gly Ser Glu Asp Pro Leu
                165                 170                 175

Lys Arg Pro Val Val Tyr Val Lys Gly Ala Asp Ala Ile Lys Leu Met
            180                 185                 190

Asn Ile Val Asn Lys Gln Lys Val Ala Arg Ala Arg Ile Gln His Arg
        195                 200                 205

Pro Pro Arg Gln Pro Thr Glu Tyr Phe Asp Met Gly Ile Phe Leu Ala
    210                 215                 220

Phe Phe Val Val Val Ser Leu Val Cys Leu Ile Leu Leu Val Lys Ile
225                 230                 235                 240

Lys Leu Lys Gln Arg Arg Ser Gln Asn Ser Met Asn Arg Pro Ala Val
                245                 250                 255

<210> SEQ ID NO 10
<211> LENGTH: 164
<212> TYPE: PRT
<213> ORGANISM: Artificial Sequence
<220> FEATURE:
<223> OTHER INFORMATION: Mouse ZNRF3 ECD-His in pUPE
<220> FEATURE:
<221> NAME/KEY: MISC_FEATURE
<222> LOCATION: (1)..(2)
<223> OTHER INFORMATION: amino acids encoded by cloning sites
<220> FEATURE:
<221> NAME/KEY: MISC_FEATURE
<222> LOCATION: (155)..(157)
<223> OTHER INFORMATION: amino acids encoded by cloning sites
<220> FEATURE:
<221> NAME/KEY: MISC_FEATURE
<222> LOCATION: (158)..(164)
<223> OTHER INFORMATION: His tag
```

-continued

<400> SEQUENCE: 10

```
Gly Ser Lys Glu Thr Ala Phe Val Glu Val Val Leu Phe Glu Ser Ser
1               5                   10                  15

Pro Ser Gly Asp Tyr Thr Thr His Thr Thr Gly Leu Thr Gly Arg Phe
            20                  25                  30

Ser Arg Ala Gly Ala Met Leu Ser Ala Glu Gly Glu Ile Val Gln Met
        35                  40                  45

His Pro Leu Gly Leu Cys Asn Asn Asp Glu Glu Asp Leu Tyr Glu
    50                  55                  60

Tyr Gly Trp Val Gly Val Val Lys Leu Glu Gln Pro Glu Leu Asp Pro
65                  70                  75                  80

Lys Pro Cys Leu Thr Val Leu Gly Lys Ala Lys Arg Ala Val Gln Arg
                85                  90                  95

Gly Ala Thr Ala Val Ile Phe Asp Val Ser Glu Asn Pro Glu Ala Ile
            100                 105                 110

Asp Gln Leu Asn Gln Gly Ser Glu Asp Pro Leu Lys Arg Pro Val Val
        115                 120                 125

Tyr Val Lys Gly Ala Asp Ala Ile Lys Leu Met Asn Ile Val Asn Lys
    130                 135                 140

Gln Lys Val Ala Arg Ala Arg Ile Gln His Leu Ala Ala Ala His His
145                 150                 155                 160

His His His His
```

<210> SEQ ID NO 11
<211> LENGTH: 278
<212> TYPE: PRT
<213> ORGANISM: Artificial Sequence
<220> FEATURE:
<223> OTHER INFORMATION: Mouse (m)ZNRF3 sequence in pDisplay
<220> FEATURE:
<221> NAME/KEY: SIGNAL
<222> LOCATION: (1)..(52)
<220> FEATURE:
<221> NAME/KEY: MISC_FEATURE
<222> LOCATION: (217)..(218)
<223> OTHER INFORMATION: amino acids that are encoded by cloning sites
<220> FEATURE:
<221> NAME/KEY: MISC_FEATURE
<222> LOCATION: (219)..(228)
<223> OTHER INFORMATION: cMyc-tag
<220> FEATURE:
<221> NAME/KEY: MISC_FEATURE
<222> LOCATION: (229)..(278)
<223> OTHER INFORMATION: PDGFR

<400> SEQUENCE: 11

```
Met Arg Pro Arg Ser Gly Gly Arg Pro Gly Ala Pro Gly Arg Arg Arg
1               5                   10                  15

Arg Arg Leu Arg Arg Gly Pro Arg Gly Arg Arg Leu Pro Pro Pro Pro
            20                  25                  30

Pro Leu Pro Leu Leu Leu Gly Leu Leu Leu Ala Ala Ala Gly Pro Gly
        35                  40                  45

Ala Ala Arg Ala Lys Glu Thr Ala Phe Val Glu Val Val Leu Phe Glu
    50                  55                  60

Ser Ser Pro Ser Gly Asp Tyr Thr Thr His Thr Thr Gly Leu Thr Gly
65                  70                  75                  80

Arg Phe Ser Arg Ala Gly Ala Met Leu Ser Ala Glu Gly Glu Ile Val
                85                  90                  95

Gln Met His Pro Leu Gly Leu Cys Asn Asn Asn Asp Glu Glu Asp Leu
            100                 105                 110
```

```
Tyr Glu Tyr Gly Trp Val Gly Val Lys Leu Glu Gln Pro Glu Leu
        115                 120                 125

Asp Pro Lys Pro Cys Leu Thr Val Leu Gly Lys Ala Lys Arg Ala Val
        130                 135                 140

Gln Arg Gly Ala Thr Ala Val Ile Phe Asp Val Ser Glu Asn Pro Glu
145                 150                 155                 160

Ala Ile Asp Gln Leu Asn Gln Gly Ser Glu Asp Pro Leu Lys Arg Pro
                165                 170                 175

Val Val Tyr Val Lys Gly Ala Asp Ala Ile Lys Leu Met Asn Ile Val
                180                 185                 190

Asn Lys Gln Lys Val Ala Arg Ala Arg Ile Gln His Leu Pro Pro Arg
                195                 200                 205

Gln Pro Thr Glu Tyr Phe Asp Met Val Asp Glu Gln Lys Leu Ile Ser
        210                 215                 220

Glu Glu Asp Leu Asn Ala Val Gly Gln Asp Thr Gln Glu Val Ile Val
225                 230                 235                 240

Val Pro His Ser Leu Pro Phe Lys Val Val Ile Ser Ala Ile Leu
                245                 250                 255

Ala Leu Val Val Leu Thr Ile Ile Ser Leu Ile Ile Leu Ile Met Leu
        260                 265                 270

Trp Gln Lys Lys Pro Arg
        275

<210> SEQ ID NO 12
<211> LENGTH: 261
<212> TYPE: PRT
<213> ORGANISM: Artificial Sequence
<220> FEATURE:
<223> OTHER INFORMATION: Human RNF43 in pDisplay
<220> FEATURE:
<221> NAME/KEY: SIGNAL
<222> LOCATION: (1)..(42)
<220> FEATURE:
<221> NAME/KEY: MISC_FEATURE
<222> LOCATION: (200)..(201)
<223> OTHER INFORMATION: amino acids encoded by cloning sites
<220> FEATURE:
<221> NAME/KEY: MISC_FEATURE
<222> LOCATION: (202)..(211)
<223> OTHER INFORMATION: cMyc-tag
<220> FEATURE:
<221> NAME/KEY: MISC_FEATURE
<222> LOCATION: (212)..(261)
<223> OTHER INFORMATION: PDGFR

<400> SEQUENCE: 12

Met Ser Gly Gly His Gln Leu Gln Leu Ala Ala Leu Trp Pro Trp Leu
1               5                   10                  15

Leu Met Ala Thr Leu Gln Ala Gly Phe Gly Arg Thr Gly Leu Val Leu
                20                  25                  30

Ala Ala Ala Val Glu Ser Glu Arg Ser Ala Glu Gln Lys Ala Ile Ile
            35                  40                  45

Arg Val Ile Pro Leu Lys Met Asp Pro Thr Gly Lys Leu Asn Leu Thr
        50                  55                  60

Leu Glu Gly Val Phe Ala Gly Val Ala Glu Ile Thr Pro Ala Glu Gly
65                  70                  75                  80

Lys Leu Met Gln Ser His Pro Leu Tyr Leu Cys Asn Ala Ser Asp Asp
                85                  90                  95

Asp Asn Leu Glu Pro Gly Phe Ile Ser Ile Val Lys Leu Glu Ser Pro
                100                 105                 110
```

```
Arg Arg Ala Pro Arg Pro Cys Leu Ser Leu Ala Ser Lys Ala Arg Met
        115                 120                 125

Ala Gly Glu Arg Gly Ala Ser Ala Val Leu Phe Asp Ile Thr Glu Asp
    130                 135                 140

Arg Ala Ala Glu Gln Leu Gln Gln Pro Leu Gly Leu Thr Trp Pro
145                 150                 155                 160

Val Val Leu Ile Trp Gly Asn Asp Ala Glu Lys Leu Met Glu Phe Val
                165                 170                 175

Tyr Lys Asn Gln Lys Ala His Val Arg Ile Glu Leu Lys Glu Pro Pro
                180                 185                 190

Ala Trp Pro Asp Tyr Asp Val Val Asp Glu Gln Lys Leu Ile Ser Glu
                195                 200                 205

Glu Asp Leu Asn Ala Val Gly Gln Asp Thr Gln Glu Val Ile Val Val
210                 215                 220

Pro His Ser Leu Pro Phe Lys Val Val Ile Ser Ala Ile Leu Ala
225                 230                 235                 240

Leu Val Val Leu Thr Ile Ile Ser Leu Ile Ile Leu Ile Met Leu Trp
                245                 250                 255

Gln Lys Lys Pro Arg
                260

<210> SEQ ID NO 13
<211> LENGTH: 261
<212> TYPE: PRT
<213> ORGANISM: Artificial Sequence
<220> FEATURE:
<223> OTHER INFORMATION: Mouse RNF43 in pDisplay
<220> FEATURE:
<221> NAME/KEY: MISC_FEATURE
<222> LOCATION: (200)..(201)
<223> OTHER INFORMATION: amino acids  encoded by cloning site
<220> FEATURE:
<221> NAME/KEY: MISC_FEATURE
<222> LOCATION: (202)..(211)
<223> OTHER INFORMATION: cMyc-tag
<220> FEATURE:
<221> NAME/KEY: MISC_FEATURE
<222> LOCATION: (212)..(261)
<223> OTHER INFORMATION: PDGFR

<400> SEQUENCE: 13

Met Ser Gly Gly His Gln Leu Gln Leu Ala Val Leu Trp Pro Trp Leu
1               5                   10                  15

Leu Met Ala Thr Leu His Ala Gly Phe Gly His Thr Gly Arg Val Leu
                20                  25                  30

Ala Ala Ala Val Glu Ser Glu Arg Ser Ala Glu Gln Lys Ala Val Ile
            35                  40                  45

Arg Val Ile Pro Leu Lys Met Asp Pro Thr Gly Lys Leu Asn Leu Thr
    50                  55                  60

Leu Glu Gly Val Phe Ala Gly Val Ala Glu Val Thr Pro Ala Glu Gly
65                  70                  75                  80

Lys Leu Met Gln Ser His Pro Leu Tyr Leu Cys Asn Ala Ser Asp Asp
                85                  90                  95

Asp Asn Leu Glu Pro Gly Phe Ile Ser Ile Val Lys Leu Glu Ser Pro
                100                 105                 110

Arg Arg Ala Pro Arg Pro Cys Leu Ser Leu Ala Ser Lys Ala Arg Met
            115                 120                 125

Ala Gly Glu Arg Gly Ala Asn Ala Val Leu Phe Asp Ile Thr Glu Asp
        130                 135                 140
```

```
Arg Ser Ala Ala Glu Gln Leu Gln Gln Pro Leu Gly Leu Thr Lys Pro
145                 150                 155                 160

Val Val Leu Ile Trp Gly Ser Asp Ala Ala Lys Leu Met Glu Phe Val
                165                 170                 175

Tyr Lys Asn Arg Lys Ala Tyr Val Trp Ile Glu Leu Lys Glu Pro Pro
            180                 185                 190

Ala Gly Ala Asn Tyr Asp Val Val Asp Glu Gln Lys Leu Ile Ser Glu
        195                 200                 205

Glu Asp Leu Asn Ala Val Gly Gln Asp Thr Gln Gln Val Ile Val Val
210                 215                 220

Pro His Ser Leu Pro Phe Lys Val Val Ile Ser Ala Ile Leu Ala
225                 230                 235                 240

Leu Val Val Leu Thr Ile Ile Ser Leu Ile Ile Leu Ile Met Leu Trp
                245                 250                 255

Gln Lys Lys Pro Arg
            260

<210> SEQ ID NO 14
<211> LENGTH: 43
<212> TYPE: DNA
<213> ORGANISM: Artificial Sequence
<220> FEATURE:
<223> OTHER INFORMATION: primer

<400> SEQUENCE: 14
ccagcaggat ccgccgccac catggacacc tcccggctcg gtg                              43

<210> SEQ ID NO 15
<211> LENGTH: 38
<212> TYPE: DNA
<213> ORGANISM: Artificial Sequence
<220> FEATURE:
<223> OTHER INFORMATION: primer

<400> SEQUENCE: 15
ccagcagcgg ccgcttagag acatgggaca aatgccac                                   38

<210> SEQ ID NO 16
<211> LENGTH: 907
<212> TYPE: PRT
<213> ORGANISM: Macaca fascicularis
<220> FEATURE:
<221> NAME/KEY: SIGNAL
<222> LOCATION: (1)..(21)

<400> SEQUENCE: 16

Met Asp Thr Ser Arg Leu Gly Val Leu Leu Ser Leu Pro Val Leu Leu
1               5                   10                  15

Gln Leu Ala Ala Gly Ser Ser Pro Arg Ser Gly Ala Leu Leu Arg
            20                  25                  30

Gly Cys Pro Thr His Cys His Cys Glu Pro Asp Gly Arg Met Leu Leu
            35                  40                  45

Arg Val Asp Cys Ser Asp Leu Gly Leu Ser Glu Leu Pro Ser Asn Leu
        50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
```

```
                100                 105                 110
Leu Tyr Ser Leu Lys Val Leu Met Leu Gln Asn Asn Gln Leu Arg Gln
                115                 120                 125

Val Pro Thr Glu Ala Leu Gln Asn Leu Arg Ser Leu Gln Ser Leu Arg
                130                 135                 140

Leu Asp Ala Asn His Ile Ser Tyr Val Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
                180                 185                 190

Leu Ala Leu Asn Lys Ile His His Ile Pro Asp Tyr Ala Phe Gly Asn
                195                 200                 205

Leu Ser Ser Leu Val Val Leu His Leu His Asn Asn Arg Ile His Ser
                210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
                260                 265                 270

Pro Glu Lys Ala Phe Val Gly Asn Pro Ser Leu Ile Thr Ile His Phe
                275                 280                 285

Tyr Asp Asn Pro Ile Gln Phe Val Gly Arg Ser Ala Phe Gln His Leu
                290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
                340                 345                 350

Asn Leu Gln Val Leu Asp Leu Ser Tyr Asn Leu Leu Glu Asp Leu Pro
                355                 360                 365

Ser Phe Ser Val Cys Gln Lys Leu Gln Lys Ile Asp Leu Arg His Asn
                370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile Ile His Pro Asn
                405                 410                 415

Ala Phe Ser Thr Leu Pro Ser Leu Ile Lys Leu Asp Leu Ser Ser Asn
                420                 425                 430

Leu Leu Ser Ser Phe Pro Val Thr Gly Leu His Gly Leu Thr His Leu
                435                 440                 445

Lys Leu Thr Gly Asn His Ala Leu Gln Ser Leu Ile Ser Ser Glu Asn
                450                 455                 460

Phe Pro Glu Leu Lys Ile Ile Glu Met Pro Tyr Ala Tyr Gln Cys Cys
465                 470                 475                 480

Ala Phe Gly Val Cys Glu Asn Ala Tyr Lys Ile Ser Asn Gln Trp Asn
                485                 490                 495

Lys Gly Asp Asn Ser Ser Met Asp Asp Leu His Lys Lys Asp Ala Gly
                500                 505                 510

Met Phe Gln Val Gln Asp Glu Arg Asp Leu Glu Asp Phe Leu Leu Asp
                515                 520                 525
```

Phe Glu Glu Asp Leu Lys Ala Leu His Ser Val Gln Cys Ser Pro Ser
            530                 535                 540

Pro Gly Pro Phe Lys Pro Cys Glu His Leu Leu Asp Gly Trp Leu Ile
545                 550                 555                 560

Arg Ile Gly Val Trp Thr Ile Ala Val Leu Ala Leu Thr Cys Asn Ala
                565                 570                 575

Leu Val Thr Ser Thr Val Phe Arg Ser Pro Leu Tyr Ile Ser Pro Ile
            580                 585                 590

Lys Leu Leu Ile Gly Val Ile Ala Val Val Asn Met Leu Thr Gly Val
        595                 600                 605

Ser Ser Ala Val Leu Ala Gly Val Asp Ala Phe Thr Phe Gly Ser Phe
    610                 615                 620

Ala Arg His Gly Ala Trp Trp Glu Asn Gly Val Gly Cys Gln Val Ile
625                 630                 635                 640

Gly Phe Leu Ser Ile Phe Ala Ser Glu Ser Ser Val Phe Leu Leu Thr
                645                 650                 655

Leu Ala Ala Leu Glu Arg Gly Phe Ser Val Lys Cys Ser Ala Lys Phe
            660                 665                 670

Glu Thr Lys Ala Pro Phe Ser Ser Leu Lys Val Ile Ile Leu Leu Cys
        675                 680                 685

Ala Leu Leu Ala Leu Thr Met Ala Ala Val Pro Leu Leu Gly Gly Ser
    690                 695                 700

Glu Tyr Gly Ala Ser Pro Leu Cys Leu Pro Leu Pro Phe Gly Glu Pro
705                 710                 715                 720

Ser Thr Thr Gly Tyr Met Val Ala Leu Ile Leu Leu Asn Ser Leu Cys
                725                 730                 735

Phe Leu Met Met Thr Ile Ala Tyr Thr Lys Leu Tyr Cys Asn Leu Asp
            740                 745                 750

Lys Gly Asp Leu Glu Asn Ile Trp Asp Cys Ser Met Val Lys His Ile
        755                 760                 765

Ala Leu Leu Leu Phe Thr Asn Cys Ile Leu Tyr Cys Pro Val Ala Phe
    770                 775                 780

Leu Ser Phe Ser Ser Leu Leu Asn Leu Thr Phe Ile Ser Pro Glu Val
785                 790                 795                 800

Ile Lys Phe Ile Leu Leu Val Ile Val Pro Leu Pro Ala Cys Leu Asn
                805                 810                 815

Pro Leu Leu Tyr Ile Leu Phe Asn Pro His Phe Lys Glu Asp Leu Val
            820                 825                 830

Ser Leu Gly Lys Gln Thr Tyr Phe Trp Thr Arg Ser Lys His Pro Ser
        835                 840                 845

Leu Met Ser Ile Asn Ser Asp Asp Val Glu Lys Gln Ser Cys Asp Ser
    850                 855                 860

Thr Gln Ala Leu Val Thr Phe Thr Ser Ser Ile Ala Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu
            900                 905

<210> SEQ ID NO 17
<211> LENGTH: 381
<212> TYPE: DNA
<213> ORGANISM: Artificial Sequence
<220> FEATURE:

<223> OTHER INFORMATION: MF1337
<220> FEATURE:
<221> NAME/KEY: CDS
<222> LOCATION: (1)..(381)

<400> SEQUENCE: 17

```
gag gtg cag ctg gtg gag act ggg gct gag gtg aag aag ccg ggg gcc      48
Glu Val Gln Leu Val Glu Thr Gly Ala Glu Val Lys Lys Pro Gly Ala
1               5                   10                  15 tca gtg aag gtc tcc tgc aag gct tct gac tac atc ttc acc aaa tat      96
Ser Val Lys Val Ser Cys Lys Ala Ser Asp Tyr Ile Phe Thr Lys Tyr
            20                  25                  30 gac atc aac tgg gtg cgc cag gcc cct gga caa ggg ctt gaa tgg atg     144
Asp Ile Asn Trp Val Arg Gln Ala Pro Gly Gln Gly Leu Glu Trp Met
        35                  40                  45 gga tgg atg agc gct aac act gga aac acg ggc tat gca cag aag ttc     192
Gly Trp Met Ser Ala Asn Thr Gly Asn Thr Gly Tyr Ala Gln Lys Phe
    50                  55                  60 cag ggc aga gtc acc atg acc agg gac acg tcc ata aac aca gcc tac     240
Gln Gly Arg Val Thr Met Thr Arg Asp Thr Ser Ile Asn Thr Ala Tyr
65                  70                  75                  80 atg gag ctg agc agc ctg aca tct ggt gac acg gcc gtt tat ttc tgt     288
Met Glu Leu Ser Ser Leu Thr Ser Gly Asp Thr Ala Val Tyr Phe Cys
                85                  90                  95 gcg agg agt agt ctt ttc aag aca gag acg gcg ccc tac tat cac ttc     336
Ala Arg Ser Ser Leu Phe Lys Thr Glu Thr Ala Pro Tyr Tyr His Phe
            100                 105                 110 gct ctg gac gtc tgg ggc caa ggg acc acg gtc acc gtc tcc agt         381
Ala Leu Asp Val Trp Gly Gln Gly Thr Thr Val Thr Val Ser Ser
        115                 120                 125
```

<210> SEQ ID NO 18
<211> LENGTH: 127
<212> TYPE: PRT
<213> ORGANISM: Artificial Sequence
<220> FEATURE:
<223> OTHER INFORMATION: Synthetic Construct

<400> SEQUENCE: 18

```
Glu Val Gln Leu Val Glu Thr Gly Ala Glu Val Lys Lys Pro Gly Ala
1               5                   10                  15

Ser Val Lys Val Ser Cys Lys Ala Ser Asp Tyr Ile Phe Thr Lys Tyr
            20                  25                  30

Asp Ile Asn Trp Val Arg Gln Ala Pro Gly Gln Gly Leu Glu Trp Met
        35                  40                  45

Gly Trp Met Ser Ala Asn Thr Gly Asn Thr Gly Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Gly Asp Thr Ala Val Tyr Phe Cys
                85                  90                  95

Ala Arg Ser Ser Leu Phe Lys Thr Glu Thr Ala Pro Tyr Tyr His Phe
            100                 105                 110

Ala Leu Asp Val Trp Gly Gln Gly Thr Thr Val Thr Val Ser Ser
        115                 120                 125
```

<210> SEQ ID NO 19
<211> LENGTH: 360
<212> TYPE: DNA
<213> ORGANISM: Artificial Sequence
<220> FEATURE:

<223> OTHER INFORMATION: MF3755
<220> FEATURE:
<221> NAME/KEY: CDS
<222> LOCATION: (1)..(360)

<400> SEQUENCE: 19

```
cag gtg cag ctg gtg cag tct ggg tct gag ttg aag aag cct ggg gcc        48
Gln Val Gln Leu Val Gln Ser Gly Ser Glu Leu Lys Lys Pro Gly Ala
1               5                   10                  15 tca gtg aag att tcc tgc aag gct tct gga tac gac ttc act aac tat        96
Ser Val Lys Ile Ser Cys Lys Ala Ser Gly Tyr Asp Phe Thr Asn Tyr
            20                  25                  30 gct atg aat tgg gtg cga cag gcc cct gga cac ggg ctt gag tgg atg       144
Ala Met Asn Trp Val Arg Gln Ala Pro Gly His Gly Leu Glu Trp Met
        35                  40                  45 gga tgg atc aac gcc aac act ggg gac cca acg tat gcc cag ggc ttc       192
Gly Trp Ile Asn Ala Asn Thr Gly Asp Pro Thr Tyr Ala Gln Gly Phe
    50                  55                  60 aca gga cgg ttt gtc ttc tcc ttg gac acc tct gtc agc acg gca tat       240
Thr Gly Arg Phe Val Phe Ser Leu Asp Thr Ser Val Ser Thr Ala Tyr
65                  70                  75                  80 ctg cag atc agc agt tta aag gct gag gac tct gcc gtg tat tac tgt       288
Leu Gln Ile Ser Ser Leu Lys Ala Glu Asp Ser Ala Val Tyr Tyr Cys
                85                  90                  95 acg aga gag cga ttt ttg gag tgg tta cac ttt gac tac tgg ggc cag       336
Thr Arg Glu Arg Phe Leu Glu Trp Leu His Phe Asp Tyr Trp Gly Gln
            100                 105                 110 gga acc ctg gtc acc gtc tcc agt                                       360
Gly Thr Leu Val Thr Val Ser Ser
        115                 120
```

<210> SEQ ID NO 20
<211> LENGTH: 120
<212> TYPE: PRT
<213> ORGANISM: Artificial Sequence
<220> FEATURE:
<223> OTHER INFORMATION: Synthetic Construct

<400> SEQUENCE: 20

```
Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Asp Phe Thr Asn Tyr
            20                  25                  30

Ala Met Asn Trp Val Arg Gln Ala Pro Gly His Gly Leu Glu Trp Met
        35                  40                  45

Gly Trp Ile Asn Ala Asn Thr Gly Asp Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Ser Ala Val Tyr Tyr Cys
                85                  90                  95

Thr Arg Glu Arg Phe Leu Glu Trp Leu His Phe Asp Tyr Trp Gly Gln
            100                 105                 110

Gly Thr Leu Val Thr Val Ser Ser
        115                 120
```

<210> SEQ ID NO 21
<211> LENGTH: 372
<212> TYPE: DNA
<213> ORGANISM: Artificial Sequence
<220> FEATURE:

<223> OTHER INFORMATION: MF3178
<220> FEATURE:
<221> NAME/KEY: CDS
<222> LOCATION: (1)..(372)

<400> SEQUENCE: 21

```
cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc aac cct aac agt ggt ggc aca aac tat gca cag aag ttt     192
Gly Trp Ile Asn Pro Asn Ser Gly Gly Thr Asn Tyr Ala Gln Lys Phe
    50                  55                  60 cag ggc agg gtc acg atg acc agg gac acg tcc atc agc aca gcc tac     240
Gln Gly Arg Val Thr Met Thr Arg Asp Thr Ser Ile Ser Thr Ala Tyr
65                  70                  75                  80 atg gag ctg agc agg ctg aga tct gac gac acg gct gtg tat tac tgt     288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc gtc tcc agt                     372
Tyr Trp Gly Gln Gly Thr Leu Val Thr Val Ser Ser
        115                 120
```

<210> SEQ ID NO 22
<211> LENGTH: 124
<212> TYPE: PRT
<213> ORGANISM: Artificial Sequence
<220> FEATURE:
<223> OTHER INFORMATION: Synthetic Construct

<400> SEQUENCE: 22

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 23
<211> LENGTH: 378
<212> TYPE: DNA
<213> ORGANISM: Artificial Sequence
<220> FEATURE:

<223> OTHER INFORMATION: MF5790
<220> FEATURE:
<221> NAME/KEY: CDS
<222> LOCATION: (1)..(378)

<400> SEQUENCE: 23

```
cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc ttc agc agt agt      96
Thr Leu Ser Leu Thr Cys Thr Val Ser Gly Gly Ser Phe Ser Ser Ser
            20                  25                  30 agt tcc tac tgg ggc tgg atc cgc cag ccc cca ggg aag ggg ctg gag      144
Ser Ser Tyr Trp Gly Trp Ile Arg Gln Pro Pro Gly Lys Gly Leu Glu
        35                  40                  45 tgg att ggg agt ttc tat tat agt ggg aac acc tac tac aac ccg tcc      192
Trp Ile Gly Ser Phe Tyr Tyr Ser Gly Asn Thr Tyr Tyr Asn Pro Ser
    50                  55                  60 ctc aag agt cga gtc acc ata tcc gaa gac acg tcc aag aac cag ttc      240
Leu Lys Ser Arg Val Thr Ile Ser Glu Asp Thr Ser Lys Asn Gln Phe
65                  70                  75                  80 tcc ctg aag ctg agc tct gtg acc gcc gca gac acg gct gtg tat tac      288
Ser Leu Lys Leu Ser Ser Val Thr Ala Ala Asp Thr Ala Val Tyr Tyr
                85                  90                  95 tgt gcg aga cag acg tat agc agc agc tgg gac ggg gtc ctg tac tac      336
Cys Ala Arg Gln Thr Tyr Ser Ser Ser Trp Asp Gly Val Leu Tyr Tyr
            100                 105                 110 ttt gac tac tgg ggc cag gga acc ctg gtc acc gtc tcc agt              378
Phe Asp Tyr Trp Gly Gln Gly Thr Leu Val Thr Val Ser Ser
        115                 120                 125
```

<210> SEQ ID NO 24
<211> LENGTH: 126
<212> TYPE: PRT
<213> ORGANISM: Artificial Sequence
<220> FEATURE:
<223> OTHER INFORMATION: Synthetic Construct

<400> SEQUENCE: 24

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser Ser
            20                  25                  30

Ser Ser Tyr Trp Gly Trp Ile Arg Gln Pro Pro Gly Lys Gly Leu Glu
        35                  40                  45

Trp Ile Gly Ser Phe Tyr Tyr Ser Gly Asn Thr Tyr Tyr Asn Pro Ser
    50                  55                  60

Leu Lys Ser Arg Val Thr Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Thr Tyr Ser Ser Ser Trp Asp Gly Val Leu Tyr Tyr
            100                 105                 110

Phe Asp Tyr Trp Gly Gln Gly Thr Leu Val Thr Val Ser Ser
        115                 120                 125
```

<210> SEQ ID NO 25
<211> LENGTH: 381
<212> TYPE: DNA
<213> ORGANISM: Artificial Sequence
<220> FEATURE:

<223> OTHER INFORMATION: MF5816
<220> FEATURE:
<221> NAME/KEY: CDS
<222> LOCATION: (1)..(381)

<400> SEQUENCE: 25

```
gag gtg cag ctg gtg cag tct ggg tct aaa ttg aag aag cct ggg gcc      48
Glu Val Gln Leu Val Gln Ser Gly Ser Lys Leu Lys Lys Pro Gly Ala
1               5                   10                  15 tca gtg aag gtt tcc tgc aag gct tct gga tac acc ttc act agc tat      96
Ser Val Lys Val Ser Cys Lys Ala Ser Gly Tyr Thr Phe Thr Ser Tyr
            20                  25                  30 act atg aat tgg gtg cga cag gcc cct gga caa ggg ctt gag tgg atg     144
Thr Met Asn Trp Val Arg Gln Ala Pro Gly Gln Gly Leu Glu Trp Met
        35                  40                  45 gga tgg atc aac acc gac act ggg gac cca acg tat gcc cag ggc ttc     192
Gly Trp Ile Asn Thr Asp Thr Gly Asp Pro Thr Tyr Ala Gln Gly Phe
    50                  55                  60 aca gga cgg ttt gtc ttc tcc ttg gac acc tct gtc agc acg gca ttt     240
Thr Gly Arg Phe Val Phe Ser Leu Asp Thr Ser Val Ser Thr Ala Phe
65                  70                  75                  80 cta cag atc aac agc cta aag gct gag gac act gcc gta tat tac tgt     288
Leu Gln Ile Asn Ser Leu Lys Ala Glu Asp Thr Ala Val Tyr Tyr Cys
                85                  90                  95 gcg aga gga gat tgt gat agt acc agc tgc tat aga tac agt tat ggt     336
Ala Arg Gly Asp Cys Asp Ser Thr Ser Cys Tyr Arg Tyr Ser Tyr Gly
            100                 105                 110 tac gag gac tac tgg ggc cag gga acc ctg gtc acc gtc tcc agt         381
Tyr Glu Asp Tyr Trp Gly Gln Gly Thr Leu Val Thr Val Ser Ser
        115                 120                 125
```

<210> SEQ ID NO 26
<211> LENGTH: 127
<212> TYPE: PRT
<213> ORGANISM: Artificial Sequence
<220> FEATURE:
<223> OTHER INFORMATION: Synthetic Construct

<400> SEQUENCE: 26

```
Glu Val Gln Leu Val Gln Ser Gly Ser Lys Leu Lys Lys Pro Gly Ala
1               5                   10                  15

Ser Val Lys Val Ser Cys Lys Ala Ser Gly Tyr Thr Phe Thr Ser Tyr
            20                  25                  30

Thr Met Asn Trp Val Arg Gln Ala Pro Gly Gln Gly Leu Glu Trp Met
        35                  40                  45

Gly Trp Ile Asn Thr Asp Thr Gly Asp Pro Thr Tyr Ala Gln Gly Phe
    50                  55                  60

Thr Gly Arg Phe Val Phe Ser Leu Asp Thr Ser Val Ser Thr Ala Phe
65                  70                  75                  80

Leu Gln Ile Asn Ser Leu Lys Ala Glu Asp Thr Ala Val Tyr Tyr Cys
                85                  90                  95

Ala Arg Gly Asp Cys Asp Ser Thr Ser Cys Tyr Arg Tyr Ser Tyr Gly
            100                 105                 110

Tyr Glu Asp Tyr Trp Gly Gln Gly Thr Leu Val Thr Val Ser Ser
        115                 120                 125
```

<210> SEQ ID NO 27
<211> LENGTH: 372
<212> TYPE: DNA
<213> ORGANISM: Artificial Sequence
<220> FEATURE:

<223> OTHER INFORMATION: MF3125
<220> FEATURE:
<221> NAME/KEY: CDS
<222> LOCATION: (1)..(372)

<400> SEQUENCE: 27

| | | | | | | | | | | | | | | | | |
|---|---|---|---|---|---|---|---|---|---|---|---|---|---|---|---|---|
| cag | gtg | cag | ctg | gtg | gag | tct | ggg | gga | ggc | gtg | gtc | cag | cct | ggg | agg | 48 |
| Gln | Val | Gln | Leu | Val | Glu | Ser | Gly | Gly | Gly | Val | Val | Gln | Pro | Gly | Arg | |
| 1 | | | | 5 | | | | | 10 | | | | | 15 | | |
| tcc | ctg | aga | ctc | tcc | tgt | gca | gcc | tct | gga | ttc | acc | ttc | agt | agc | tat | 96 |
| Ser | Leu | Arg | Leu | Ser | Cys | Ala | Ala | Ser | Gly | Phe | Thr | Phe | Ser | Ser | Tyr | |
| | | | 20 | | | | | 25 | | | | | 30 | | | |
| ggc | atg | cac | tgg | gtc | cgc | cag | gct | cca | ggc | aag | ggg | ctg | gag | tgg | gtg | 144 |
| Gly | Met | His | Trp | Val | Arg | Gln | Ala | Pro | Gly | Lys | Gly | Leu | Glu | Trp | Val | |
| | | 35 | | | | | 40 | | | | | 45 | | | | |
| gca | gtt | ata | tca | tat | gat | gga | agt | aat | aaa | tac | tat | gca | gac | tcc | gtg | 192 |
| Ala | Val | Ile | Ser | Tyr | Asp | Gly | Ser | Asn | Lys | Tyr | Tyr | Ala | Asp | Ser | Val | |
| 50 | | | | | 55 | | | | | 60 | | | | | | |
| aag | ggc | cga | ttc | acc | atc | tcc | aga | gac | aat | tcc | aag | aac | acg | ctg | tat | 240 |
| Lys | Gly | Arg | Phe | Thr | Ile | Ser | Arg | Asp | Asn | Ser | Lys | Asn | Thr | Leu | Tyr | |
| 65 | | | | 70 | | | | | 75 | | | | | 80 | | |
| ctg | caa | atg | aac | agc | ctg | aga | gct | gag | gac | acg | gcc | gtg | tat | tac | tgt | 288 |
| Leu | Gln | Met | Asn | Ser | Leu | Arg | Ala | Glu | Asp | Thr | Ala | Val | Tyr | Tyr | Cys | |
| | | | 85 | | | | | 90 | | | | | 95 | | | |
| gca | aaa | ggt | tct | tct | ggt | tgg | ccg | tct | tac | tct | aac | tgg | ggc | ttt | gat | 336 |
| Ala | Lys | Gly | Ser | Ser | Gly | Trp | Pro | Ser | Tyr | Ser | Asn | Trp | Gly | Phe | Asp | |
| | | | 100 | | | | | 105 | | | | | 110 | | | |
| tat | tgg | ggc | caa | ggt | acc | ctg | gtc | acc | gtc | tcc | agt | | | | | 372 |
| Tyr | Trp | Gly | Gln | Gly | Thr | Leu | Val | Thr | Val | Ser | Ser | | | | | |
| | | 115 | | | | | 120 | | | | | | | | | |

<210> SEQ ID NO 28
<211> LENGTH: 124
<212> TYPE: PRT
<213> ORGANISM: Artificial Sequence
<220> FEATURE:
<223> OTHER INFORMATION: Synthetic Construct

<400> SEQUENCE: 28

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Ser Ser Gly Trp Pro Ser Tyr Ser Asn Trp Gly Phe Asp
        100                 105                 110

Tyr Trp Gly Gln Gly Thr Leu Val Thr Val Ser Ser
        115                 120

<210> SEQ ID NO 29
<211> LENGTH: 366
<212> TYPE: DNA
<213> ORGANISM: Artificial Sequence
<220> FEATURE:

<223> OTHER INFORMATION: MF3176
<220> FEATURE:
<221> NAME/KEY: CDS
<222> LOCATION: (1)..(366)

<400> SEQUENCE: 29

```
gag gtg cag ctg ttg gag tct ggg gga ggc ttg gta cag cct ggg ggg    48
Glu Val Gln Leu Leu Glu Ser Gly Gly Gly Leu Val Gln Pro Gly Gly
1               5                   10                  15 tcc ctg aga ctc tcc tgt gca gcc tct gga ttc acc ttt agc agc tat    96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc   144
Ala Met Ser Trp Val Arg Gln Ala Pro Gly Lys Gly Leu Glu Trp Val
        35                  40                  45 tca gct att agt ggt agt ggt ggt agc aca tac tac gca gac tcc gtg   192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat   240
Lys Gly Arg Phe Thr Ile Ser Arg Asp Asn Ser Lys Asn Thr Leu Tyr
65                  70                  75                  80 ctg caa atg aac agc ctg aga gcc gag gac acg gct gtg tat tac tgt   288
Leu Gln Met Asn Ser Leu Arg Ala Glu Asp Thr Ala Val Tyr Tyr Cys
                85                  90                  95 gca aga gat tgg tgg tac ccg ccg tac tac tgg ggc ttt gat tat tgg   336
Ala Arg Asp Trp Trp Tyr Pro Pro Tyr Tyr Trp Gly Phe Asp Tyr Trp
            100                 105                 110 ggc caa ggt acc ctg gtc acc gtc tcc agt                            366
Gly Gln Gly Thr Leu Val Thr Val Ser Ser
        115                 120
```

<210> SEQ ID NO 30
<211> LENGTH: 122
<212> TYPE: PRT
<213> ORGANISM: Artificial Sequence
<220> FEATURE:
<223> OTHER INFORMATION: Synthetic Construct

<400> SEQUENCE: 30

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Trp Tyr Pro Pro Tyr Tyr Trp Gly Phe Asp Tyr Trp
            100                 105                 110

Gly Gln Gly Thr Leu Val Thr Val Ser Ser
        115                 120
```

<210> SEQ ID NO 31
<211> LENGTH: 366
<212> TYPE: DNA
<213> ORGANISM: Artificial Sequence
<220> FEATURE:

<223> OTHER INFORMATION: MF4863
<220> FEATURE:
<221> NAME/KEY: CDS
<222> LOCATION: (1)..(366)

<400> SEQUENCE: 31

| gag | gtg | cag | ctg | gtg | cag | tct | ggg | tct | gag | ttg | aag | aag | cct | ggg | gcc | 48 |
|-----|-----|-----|-----|-----|-----|-----|-----|-----|-----|-----|-----|-----|-----|-----|-----|-----|
| Glu | Val | Gln | Leu | Val | Gln | Ser | Gly | Ser | Glu | Leu | Lys | Lys | Pro | Gly | Ala | |
| 1 | | | | 5 | | | | | 10 | | | | | 15 | | |

| tca | gtg | aag | gtt | tcc | tgc | aag | gct | tct | gga | tac | acc | tcc | att | aga | tat | 96 |
| Ser | Val | Lys | Val | Ser | Cys | Lys | Ala | Ser | Gly | Tyr | Thr | Ser | Ile | Arg | Tyr | |
| | | | 20 | | | | | 25 | | | | | 30 | | | |

| gct | ttg | aac | tgg | gtg | cga | cag | gcc | cct | gga | caa | ggc | ctt | gag | tgg | ctg | 144 |
| Ala | Leu | Asn | Trp | Val | Arg | Gln | Ala | Pro | Gly | Gln | Gly | Leu | Glu | Trp | Leu | |
| | | | 35 | | | | | 40 | | | | | 45 | | | |

| gga | tgg | atc | aac | acc | aac | act | ggg | aac | cca | acg | tat | gcc | cgg | ggc | ttc | 192 |
| Gly | Trp | Ile | Asn | Thr | Asn | Thr | Gly | Asn | Pro | Thr | Tyr | Ala | Arg | Gly | Phe | |
| 50 | | | | | 55 | | | | | 60 | | | | | | |

| aca | gga | cgg | ttt | gtc | ttc | tcc | ttg | gac | acc | tct | gtc | agc | acg | gca | tat | 240 |
| Thr | Gly | Arg | Phe | Val | Phe | Ser | Leu | Asp | Thr | Ser | Val | Ser | Thr | Ala | Tyr | |
| 65 | | | | 70 | | | | | 75 | | | | | 80 | | |

| ctg | cag | atc | agc | agc | cta | aag | gct | gag | gac | act | gcc | gtg | tat | tac | tgt | 288 |
| Leu | Gln | Ile | Ser | Ser | Leu | Lys | Ala | Glu | Asp | Thr | Ala | Val | Tyr | Tyr | Cys | |
| | | | | 85 | | | | | 90 | | | | | 95 | | |

| gcg | aga | gat | act | tat | gat | agt | act | ggt | tat | ctt | tgg | ttt | gac | tac | tgg | 336 |
| Ala | Arg | Asp | Thr | Tyr | Asp | Ser | Thr | Gly | Tyr | Leu | Trp | Phe | Asp | Tyr | Trp | |
| | | | 100 | | | | | 105 | | | | | 110 | | | |

| ggc | cag | gga | acc | ctg | gtc | acc | gtc | tcc | agt | | | | | | | 366 |
| Gly | Gln | Gly | Thr | Leu | Val | Thr | Val | Ser | Ser | | | | | | | |
| | | 115 | | | | | 120 | | | | | | | | | |

<210> SEQ ID NO 32
<211> LENGTH: 122
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Ser Ile Arg Tyr
            20                  25                  30

Ala Leu Asn Trp Val Arg Gln Ala Pro Gly Gln Gly Leu Glu Trp Leu
        35                  40                  45

Gly Trp Ile Asn Thr Asn Thr Gly Asn Pro Thr Tyr Ala Arg Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Thr Tyr Asp Ser Thr Gly Tyr Leu Trp Phe Asp Tyr Trp
            100                 105                 110

Gly Gln Gly Thr Leu Val Thr Val Ser Ser
        115                 120

<210> SEQ ID NO 33
<211> LENGTH: 366
<212> TYPE: DNA
<213> ORGANISM: Artificial Sequence
<220> FEATURE:

<223> OTHER INFORMATION: MF3370
<220> FEATURE:
<221> NAME/KEY: CDS
<222> LOCATION: (1)..(366)

<400> SEQUENCE: 33

```
cag gtt cag ctg gtg cag tct gga gct gag gtg aag aag cct ggg gcc    48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc agc tat    96
Ser Val Lys Val Ser Cys Lys Ala Ser Gly Tyr Thr Phe Thr Ser Tyr
            20                  25                  30 ggt atc agc tgg gtg cga cag gcc cct gga caa ggg ctt gag tgg atg   144
Gly Ile Ser Trp Val Arg Gln Ala Pro Gly Gln Gly Leu Glu Trp Met
        35                  40                  45 gga tgg atc agc gct tac aat ggt aac aca aac tat gca cag aag ctc   192
Gly Trp Ile Ser Ala Tyr Asn Gly Asn Thr Asn Tyr Ala Gln Lys Leu
    50                  55                  60 cag ggc aga gtc acc atg acc aca gac aca tcc acg agc aca gcc tac   240
Gln Gly Arg Val Thr Met Thr Thr Asp Thr Ser Thr Ser Thr Ala Tyr
65                  70                  75                  80 atg gag ctg agg agc ctg aga tct gac gac acg gct gtg tat tac tgt   288
Met Glu Leu Arg Ser Leu Arg Ser Asp Asp Thr Ala Val Tyr Tyr Cys
                85                  90                  95 gca aaa gat cgt cat tgg cat tgg tgg ctg gac gcc ttt gat tat tgg   336
Ala Lys Asp Arg His Trp His Trp Trp Leu Asp Ala Phe Asp Tyr Trp
            100                 105                 110 ggc caa ggt acc ctg gtc acc gtc tcc agt                            366
Gly Gln Gly Thr Leu Val Thr Val Ser Ser
        115                 120
```

<210> SEQ ID NO 34
<211> LENGTH: 122
<212> TYPE: PRT
<213> ORGANISM: Artificial Sequence
<220> FEATURE:
<223> OTHER INFORMATION: Synthetic Construct

<400> SEQUENCE: 34

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Asp Arg His Trp His Trp Trp Leu Asp Ala Phe Asp Tyr Trp
            100                 105                 110

Gly Gln Gly Thr Leu Val Thr Val Ser Ser
        115                 120
```

<210> SEQ ID NO 35
<211> LENGTH: 375
<212> TYPE: DNA
<213> ORGANISM: Artificial Sequence
<220> FEATURE:

<223> OTHER INFORMATION: MF4280
<220> FEATURE:
<221> NAME/KEY: CDS
<222> LOCATION: (1)..(375)

<400> SEQUENCE: 35

```
cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gtt tcc gga tac acc ctc act gaa tta      96
Ser Val Lys Val Ser Cys Lys Val Ser Gly Tyr Thr Leu Thr Glu Leu
            20                  25                  30 tcc atg cac tgg gtg cga cag gct cct ggt aaa ggg ctt gaa tgg atg     144
Ser Met His Trp Val Arg Gln Ala Pro Gly Lys Gly Leu Glu Trp Met
        35                  40                  45 gga ggc ttt gat cct gag tat ggt aaa aca ttc ttc gca cag aac ttc     192
Gly Gly Phe Asp Pro Glu Tyr Gly Lys Thr Phe Phe Ala Gln Asn Phe
    50                  55                  60 cag ggc aga gtc acc atg acc gag gac aca tct gca gac aca gcc tac     240
Gln Gly Arg Val Thr Met Thr Glu Asp Thr Ser Ala Asp Thr Ala Tyr
65                  70                  75                  80 atg gag cta agc agc ctg aga tct gag gac acg gcc gtg tat tac tgt     288
Met Glu Leu Ser Ser Leu Arg Ser Glu Asp Thr Ala Val Tyr Tyr Cys
                85                  90                  95 gca aca gag ggg tat tat gag act act act tat tac tac aac ctt ttt     336
Ala Thr Glu Gly Tyr Tyr Glu Thr Thr Thr Tyr Tyr Tyr Asn Leu Phe
            100                 105                 110 gac tcc tgg ggc cag gga acc ctg gtc acc gtc tcc agt                 375
Asp Ser Trp Gly Gln Gly Thr Leu Val Thr Val Ser Ser
        115                 120                 125
```

<210> SEQ ID NO 36
<211> LENGTH: 125
<212> TYPE: PRT
<213> ORGANISM: Artificial Sequence
<220> FEATURE:
<223> OTHER INFORMATION: Synthetic Construct

<400> SEQUENCE: 36

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Tyr Gly Lys Thr Phe Phe Ala Gln Asn Phe
    50                  55                  60

Gln Gly Arg Val Thr Met Thr Glu Asp Thr Ser Ala Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Gly Tyr Tyr Glu Thr Thr Thr Tyr Tyr Tyr Asn Leu Phe
            100                 105                 110

Asp Ser Trp Gly Gln Gly Thr Leu Val Thr Val Ser Ser
        115                 120                 125
```

<210> SEQ ID NO 37
<211> LENGTH: 357
<212> TYPE: DNA
<213> ORGANISM: Artificial Sequence
<220> FEATURE:

<223> OTHER INFORMATION: MF4289
<220> FEATURE:
<221> NAME/KEY: CDS
<222> LOCATION: (1)..(357)

<400> SEQUENCE: 37

```
cag gtg cag ctg gtg caa tct ggg tct gaa ttg aag aag cct ggg gcc        48
Gln Val Gln Leu Val Gln Ser Gly Ser Glu Leu Lys Lys Pro Gly Ala
1               5                   10                  15 tca gtg aag gtt tcc tgc aag act tct gga tac acc ttc act gac tat        96
Ser Val Lys Val Ser Cys Lys Thr Ser Gly Tyr Thr Phe Thr Asp Tyr
            20                  25                  30 gct atg act tgg gtg cga cag gcc cct gga caa ggg ctt gaa tgg atg       144
Ala Met Thr Trp Val Arg Gln Ala Pro Gly Gln Gly Leu Glu Trp Met
        35                  40                  45 gga tgg atc acc acc aac act ggg gac cca acg tat gcc ccg ggc ttc       192
Gly Trp Ile Thr Thr Asn Thr Gly Asp Pro Thr Tyr Ala Pro Gly Phe
    50                  55                  60 aca gga cgg ttt gtc ttc tcc ttg gac acc tct gtc agc acg gca tat       240
Thr Gly Arg Phe Val Phe Ser Leu Asp Thr Ser Val Ser Thr Ala Tyr
65                  70                  75                  80 ctg cag atc agc agc cta aag gcc gag gac act gcc gta tat tac tgt       288
Leu Gln Ile Ser Ser Leu Lys Ala Glu Asp Thr Ala Val Tyr Tyr Cys
                85                  90                  95 gcg aga gtg tat cat tgg ata cgg gga ttt gag ttt tgg ggc cag gga       336
Ala Arg Val Tyr His Trp Ile Arg Gly Phe Glu Phe Trp Gly Gln Gly
            100                 105                 110 acc ctg gtc acc gtc tcc agt                                            357
Thr Leu Val Thr Val Ser Ser
        115
```

<210> SEQ ID NO 38
<211> LENGTH: 119
<212> TYPE: PRT
<213> ORGANISM: Artificial Sequence
<220> FEATURE:
<223> OTHER INFORMATION: Synthetic Construct

<400> SEQUENCE: 38

```
Gln Val Gln Leu Val Gln Ser Gly Ser Glu Leu Lys Lys Pro Gly Ala
1               5                   10                  15

Ser Val Lys Val Ser Cys Lys Thr Ser Gly Tyr Thr Phe Thr Asp Tyr
            20                  25                  30

Ala Met Thr Trp Val Arg Gln Ala Pro Gly Gln Gly Leu Glu Trp Met
        35                  40                  45

Gly Trp Ile Thr Thr Asn Thr Gly Asp Pro Thr Tyr Ala Pro Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Val Tyr His Trp Ile Arg Gly Phe Glu Phe Trp Gly Gln Gly
            100                 105                 110

Thr Leu Val Thr Val Ser Ser
        115
```

<210> SEQ ID NO 39
<211> LENGTH: 345
<212> TYPE: DNA
<213> ORGANISM: Artificial Sequence
<220> FEATURE:

<223> OTHER INFORMATION: MF5777
<220> FEATURE:
<221> NAME/KEY: CDS
<222> LOCATION: (1)..(345)

<400> SEQUENCE: 39

```
cag gtg cag ctg gtg caa tct ggg tct gag ttg aag aag cct ggg gcc    48
Gln Val Gln Leu Val Gln Ser Gly Ser Glu Leu Lys Lys Pro Gly Ala
1               5                   10                  15 tca gtg aag gtt tcc tgc aag gct tct gga tac acc ttc act aac tat    96
Ser Val Lys Val Ser Cys Lys Ala Ser Gly Tyr Thr Phe Thr Asn Tyr
            20                  25                  30 gtt atg aat tgg gtg cga cag gcc cct gga caa ggg ctt gag tgg atg   144
Val Met Asn Trp Val Arg Gln Ala Pro Gly Gln Gly Leu Glu Trp Met
        35                  40                  45 gga tgg atc aac acc aac act ggg aac cca acg tat gcc cag ggc ttc   192
Gly Trp Ile Asn Thr Asn Thr Gly Asn Pro Thr Tyr Ala Gln Gly Phe
    50                  55                  60 aca gga cgg ttt gtc ttc tcc ttg gac acc tct gtc agc acg gca tat   240
Thr Gly Arg Phe Val Phe Ser Leu Asp Thr Ser Val Ser Thr Ala Tyr
65                  70                  75                  80 ctg cag atc agc agc cta aag gct gag gac act gcc gtg tat tac tgt   288
Leu Gln Ile Ser Ser Leu Lys Ala Glu Asp Thr Ala Val Tyr Tyr Cys
                85                  90                  95 gcg agg tgg gag cta cta gac tac tgg ggc cag gga acc ctg gtc acc   336
Ala Arg Trp Glu Leu Leu Asp Tyr Trp Gly Gln Gly Thr Leu Val Thr
            100                 105                 110 gtc tcc agt                                                        345
Val Ser Ser
        115
```

<210> SEQ ID NO 40
<211> LENGTH: 115
<212> TYPE: PRT
<213> ORGANISM: Artificial Sequence
<220> FEATURE:
<223> OTHER INFORMATION: Synthetic Construct

<400> SEQUENCE: 40

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Val Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Glu Leu Leu Asp Tyr Trp Gly Gln Gly Thr Leu Val Thr
            100                 105                 110

Val Ser Ser
        115
```

<210> SEQ ID NO 41
<211> LENGTH: 348
<212> TYPE: DNA
<213> ORGANISM: Artificial Sequence
<220> FEATURE:

<223> OTHER INFORMATION: MF5781
<220> FEATURE:
<221> NAME/KEY: CDS
<222> LOCATION: (1)..(348)

<400> SEQUENCE: 41

```
gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc     144
Ala Met Ser Trp Val Arg Gln Ala Pro Gly Lys Gly Leu Glu Trp Val
        35                  40                  45 tca gtt att agt ggt agt ggt ggg acc aca tac tac gca gac tcc gtg     192
Ser Val Ile Ser Gly Ser Gly Gly Thr Thr Tyr Tyr Ala Asp Ser Val
    50                  55                  60 aag ggc cgg ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt     288
Leu Gln Met Asn Ser Leu Arg Ala Glu Asp Thr Ala Val Tyr Tyr Cys
                85                  90                  95 gcg aaa ggg gct ggg gag ctt gac tac tgg ggc cag gga acc ctg gtc     336
Ala Lys Gly Ala Gly Glu Leu Asp Tyr Trp Gly Gln Gly Thr Leu Val
            100                 105                 110 acc gtc tcc agt                                                     348
Thr Val Ser Ser
        115
```

<210> SEQ ID NO 42
<211> LENGTH: 116
<212> TYPE: PRT
<213> ORGANISM: Artificial Sequence
<220> FEATURE:
<223> OTHER INFORMATION: Synthetic Construct

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Gly Glu Leu Asp Tyr Trp Gly Gln Gly Thr Leu Val
            100                 105                 110

Thr Val Ser Ser
        115
```

<210> SEQ ID NO 43
<211> LENGTH: 378
<212> TYPE: DNA
<213> ORGANISM: Artificial Sequence
<220> FEATURE:

<223> OTHER INFORMATION: MF5803
<220> FEATURE:
<221> NAME/KEY: CDS
<222> LOCATION: (1)..(378)

<400> SEQUENCE: 43

| | | | | | | | | | | | | | | | | |
|---|---|---|---|---|---|---|---|---|---|---|---|---|---|---|---|---|
| cag | gtg | cag | ctg | cag | gag | tcg | ggg | cca | gga | ctg | gtg | aag | cct | tcg | gag | 48 |
| Gln | Val | Gln | Leu | Gln | Glu | Ser | Gly | Pro | Gly | Leu | Val | Lys | Pro | Ser | Glu | |
| 1 | | | | 5 | | | | | 10 | | | | | 15 | | |
| acc | ctg | tcc | ctc | acc | tgc | act | gtc | tct | aat | ggc | tcc | atc | agt | act | tac | 96 |
| Thr | Leu | Ser | Leu | Thr | Cys | Thr | Val | Ser | Asn | Gly | Ser | Ile | Ser | Thr | Tyr | |
| | | | 20 | | | | | 25 | | | | | 30 | | | |
| tac | tgg | agc | tgg | atc | cgg | cag | ccc | cca | ggg | aag | ggg | ctg | gag | tgg | att | 144 |
| Tyr | Trp | Ser | Trp | Ile | Arg | Gln | Pro | Pro | Gly | Lys | Gly | Leu | Glu | Trp | Ile | |
| | | 35 | | | | | 40 | | | | | 45 | | | | |
| gga | tat | gtc | tat | tac | act | ggg | cgc | acc | aag | tac | aac | ccc | tcc | ctc | aag | 192 |
| Gly | Tyr | Val | Tyr | Tyr | Thr | Gly | Arg | Thr | Lys | Tyr | Asn | Pro | Ser | Leu | Lys | |
| 50 | | | | | 55 | | | | | 60 | | | | | | |
| agt | cga | gtc | acc | ata | tca | gta | gac | acg | tcc | aag | aac | cag | ttc | tcc | ctg | 240 |
| Ser | Arg | Val | Thr | Ile | Ser | Val | Asp | Thr | Ser | Lys | Asn | Gln | Phe | Ser | Leu | |
| 65 | | | | | 70 | | | | | 75 | | | | | 80 | |
| aac | ctg | agt | tct | gtg | acc | gct | gcg | gac | acg | gcc | gtg | tat | tac | tgt | gcg | 288 |
| Asn | Leu | Ser | Ser | Val | Thr | Ala | Ala | Asp | Thr | Ala | Val | Tyr | Tyr | Cys | Ala | |
| | | | | 85 | | | | | 90 | | | | | 95 | | |
| aga | ggg | ggt | att | gta | gta | gtc | cca | gct | gcg | cgg | gac | tat | tac | tac | tac | 336 |
| Arg | Gly | Gly | Ile | Val | Val | Val | Pro | Ala | Ala | Arg | Asp | Tyr | Tyr | Tyr | Tyr | |
| | | | 100 | | | | | 105 | | | | | 110 | | | |
| atg | gac | gtc | tgg | ggc | aaa | ggg | acc | acg | gtc | acc | gtc | tcc | agt | | | 378 |
| Met | Asp | Val | Trp | Gly | Lys | Gly | Thr | Thr | Val | Thr | Val | Ser | Ser | | | |
| | | | 115 | | | | | 120 | | | | | 125 | | | |

<210> SEQ ID NO 44
<211> LENGTH: 126
<212> TYPE: PRT
<213> ORGANISM: Artificial Sequence
<220> FEATURE:
<223> OTHER INFORMATION: Synthetic Construct

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Thr Val Ser Asn Gly Ser Ile Ser Thr Tyr
            20                  25                  30

Tyr Trp Ser Trp Ile Arg Gln Pro Pro Gly Lys Gly Leu Glu Trp Ile
        35                  40                  45

Gly Tyr Val Tyr Tyr Thr Gly Arg Thr Lys Tyr Asn Pro Ser Leu Lys
50                  55                  60

Ser Arg Val Thr Ile Ser Val Asp Thr Ser Lys Asn Gln Phe Ser Leu
65                  70                  75                  80

Asn Leu Ser Ser Val Thr Ala Ala Asp Thr Ala Val Tyr Tyr Cys Ala
                85                  90                  95

Arg Gly Gly Ile Val Val Val Pro Ala Ala Arg Asp Tyr Tyr Tyr Tyr
            100                 105                 110

Met Asp Val Trp Gly Lys Gly Thr Thr Val Thr Val Ser Ser
        115                 120                 125

<210> SEQ ID NO 45
<211> LENGTH: 360
<212> TYPE: DNA
<213> ORGANISM: Artificial Sequence
<220> FEATURE:

<223> OTHER INFORMATION: MF5805
<220> FEATURE:
<221> NAME/KEY: CDS
<222> LOCATION: (1)..(360)

<400> SEQUENCE: 45

```
gag gtg caa ctg gtg cag tct gga gca gag gtg aaa aag ccc ggg gag      48
Glu Val Gln Leu Val Gln Ser Gly Ala Glu Val Lys Lys Pro Gly Glu
1               5                   10                  15 tct ctg aag atc gcc tgt aag ggt tct gga ttc agt ttt acc agc cac      96
Ser Leu Lys Ile Ala Cys Lys Gly Ser Gly Phe Ser Phe Thr Ser His
            20                  25                  30 tgg atc ggc tgg gtg cgc cag aag ccc ggg aga ggc ctg gag tgg atg     144
Trp Ile Gly Trp Val Arg Gln Lys Pro Gly Arg Gly Leu Glu Trp Met
        35                  40                  45 ggg gtc atc tat cct ggt gac tct gat acc aga tac agc ccg tcc ttc     192
Gly Val Ile Tyr Pro Gly Asp Ser Asp Thr Arg Tyr Ser Pro Ser Phe
    50                  55                  60 caa ggc cag gtc acc gtc tca gcc gac aag tcc atc aat acc gcc tac     240
Gln Gly Gln Val Thr Val Ser Ala Asp Lys Ser Ile Asn Thr Ala Tyr
65                  70                  75                  80 ctg cag tgg aac agc ctg aag gcc tcg gac acc gcc ata tat tac tgt     288
Leu Gln Trp Asn Ser Leu Lys Ala Ser Asp Thr Ala Ile Tyr Tyr Cys
                85                  90                  95 gcg aga ccg aac agt ggg agt ccc cgg tac ttc gag ttc tgg ggc cgt     336
Ala Arg Pro Asn Ser Gly Ser Pro Arg Tyr Phe Glu Phe Trp Gly Arg
            100                 105                 110 ggc acc ctg gtc acc gtc tcc agt                                      360
Gly Thr Leu Val Thr Val Ser Ser
        115                 120
```

<210> SEQ ID NO 46
<211> LENGTH: 120
<212> TYPE: PRT
<213> ORGANISM: Artificial Sequence
<220> FEATURE:
<223> OTHER INFORMATION: Synthetic Construct

<400> SEQUENCE: 46

```
Glu Val Gln Leu Val Gln Ser Gly Ala Glu Val Lys Lys Pro Gly Glu
1               5                   10                  15

Ser Leu Lys Ile Ala Cys Lys Gly Ser Gly Phe Ser Phe Thr Ser His
            20                  25                  30

Trp Ile Gly Trp Val Arg Gln Lys Pro Gly Arg Gly Leu Glu Trp Met
        35                  40                  45

Gly Val Ile Tyr Pro Gly Asp Ser Asp Thr Arg Tyr Ser Pro Ser Phe
    50                  55                  60

Gln Gly Gln Val Thr Val Ser Ala Asp Lys Ser Ile Asn Thr Ala Tyr
65                  70                  75                  80

Leu Gln Trp Asn Ser Leu Lys Ala Ser Asp Thr Ala Ile Tyr Tyr Cys
                85                  90                  95

Ala Arg Pro Asn Ser Gly Ser Pro Arg Tyr Phe Glu Phe Trp Gly Arg
            100                 105                 110

Gly Thr Leu Val Thr Val Ser Ser
        115                 120
```

<210> SEQ ID NO 47
<211> LENGTH: 378
<212> TYPE: DNA
<213> ORGANISM: Artificial Sequence
<220> FEATURE:

<223> OTHER INFORMATION: MF5808
<220> FEATURE:
<221> NAME/KEY: CDS
<222> LOCATION: (1)..(378)

<400> SEQUENCE: 47

```
cag gtg cag ctg cag gag tcg ggc cca gga ctg gtg aag cct tcg gag         48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc agc agt agt         96
Thr Leu Ser Leu Thr Cys Thr Val Ser Gly Gly Ser Ile Ser Ser Ser
                20                  25                  30 agt tac tac tgg ggc tgg atc cgc cag ccc cca ggg aag ggg ctg gag        144
Ser Tyr Tyr Trp Gly Trp Ile Arg Gln Pro Pro Gly Lys Gly Leu Glu
            35                  40                  45 tgg att ggg agt ttc tat tat agt ggg aac acc tac tac aac ccg tcc        192
Trp Ile Gly Ser Phe Tyr Tyr Ser Gly Asn Thr Tyr Tyr Asn Pro Ser
        50                  55                  60 ctc aag agt cga gtc acc ata tcc gta gac acg tcc aag aac cag ttc        240
Leu Lys Ser Arg Val Thr Ile Ser Val Asp Thr Ser Lys Asn Gln Phe
65                  70                  75                  80 tcc ctg aag ctg agc tct gtg acc gcc gca gac acg gct gtg tat tac        288
Ser Leu Lys Leu Ser Ser Val Thr Ala Ala Asp Thr Ala Val Tyr Tyr
                85                  90                  95 tgt gcg aga cag gag tat tac tat ggt tcg ggg agt cct tcg tac tac        336
Cys Ala Arg Gln Glu Tyr Tyr Tyr Gly Ser Gly Ser Pro Ser Tyr Tyr
            100                 105                 110 ttt gac tac tgg ggc cag gga acc ctg gtc acc gtc tcc agt                378
Phe Asp Tyr Trp Gly Gln Gly Thr Leu Val Thr Val Ser Ser
        115                 120                 125
```

<210> SEQ ID NO 48
<211> LENGTH: 126
<212> TYPE: PRT
<213> ORGANISM: Artificial Sequence
<220> FEATURE:
<223> OTHER INFORMATION: Synthetic Construct

<400> SEQUENCE: 48

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Phe Tyr Tyr Ser Gly Asn Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Glu Tyr Tyr Tyr Gly Ser Gly Ser Pro Ser Tyr Tyr
            100                 105                 110

Phe Asp Tyr Trp Gly Gln Gly Thr Leu Val Thr Val Ser Ser
        115                 120                 125
```

<210> SEQ ID NO 49
<211> LENGTH: 360
<212> TYPE: DNA
<213> ORGANISM: Artificial Sequence
<220> FEATURE:

<223> OTHER INFORMATION: MF5809
<220> FEATURE:
<221> NAME/KEY: CDS
<222> LOCATION: (1)..(360)

<400> SEQUENCE: 49

```
gag gtg cag ctg gtg cag tct gga gca gag gtg aaa aag ccc ggg gag      48
Glu Val Gln Leu Val Gln Ser Gly Ala Glu Val Lys Lys Pro Gly Glu
1               5                   10                  15 tct ctg aag atc tcc tgt aag ggt tct gga gac agt ttt atc agc cac      96
Ser Leu Lys Ile Ser Cys Lys Gly Ser Gly Asp Ser Phe Ile Ser His
            20                  25                  30 tgg atc gcc tgg gtg cgc cag atg ccc ggg aaa ggc ctg gag tgg atg     144
Trp Ile Ala Trp Val Arg Gln Met Pro Gly Lys Gly Leu Glu Trp Met
        35                  40                  45 ggg atc gtc tat cct ggt gac tct gat acc aga tac agc ccg tcc ttc     192
Gly Ile Val Tyr Pro Gly Asp Ser Asp Thr Arg Tyr Ser Pro Ser Phe
    50                  55                  60 caa ggc cag gtc acc atc tca gcc gac aag tcc atc acc acc gcc tac     240
Gln Gly Gln Val Thr Ile Ser Ala Asp Lys Ser Ile Thr Thr Ala Tyr
65                  70                  75                  80 ttg cag tgg agc agc ctg aag gcc tcg gac acc gcc atg tat tac tgt     288
Leu Gln Trp Ser Ser Leu Lys Ala Ser Asp Thr Ala Met Tyr Tyr Cys
                85                  90                  95 gcg aga cac gag tgg gaa cta ctt ggc ccc ttt gac tac tgg ggc cag     336
Ala Arg His Glu Trp Glu Leu Leu Gly Pro Phe Asp Tyr Trp Gly Gln
            100                 105                 110 gga acc ctg gtc acc gtc tcc agt                                     360
Gly Thr Leu Val Thr Val Ser Ser
        115                 120
```

<210> SEQ ID NO 50
<211> LENGTH: 120
<212> TYPE: PRT
<213> ORGANISM: Artificial Sequence
<220> FEATURE:
<223> OTHER INFORMATION: Synthetic Construct

<400> SEQUENCE: 50

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Asp Ser Phe Ile Ser His
            20                  25                  30

Trp Ile Ala Trp Val Arg Gln Met Pro Gly Lys Gly Leu Glu Trp Met
        35                  40                  45

Gly Ile Val Tyr Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Glu Trp Glu Leu Leu Gly Pro Phe Asp Tyr Trp Gly Gln
            100                 105                 110

Gly Thr Leu Val Thr Val Ser Ser
        115                 120
```

<210> SEQ ID NO 51
<211> LENGTH: 363
<212> TYPE: DNA
<213> ORGANISM: Artificial Sequence
<220> FEATURE:

<223> OTHER INFORMATION: MF5814
<220> FEATURE:
<221> NAME/KEY: CDS
<222> LOCATION: (1)..(363)

<400> SEQUENCE: 51

| | | | | | | | | | | | | | | | | |
|---|---|---|---|---|---|---|---|---|---|---|---|---|---|---|---|---|
| gag | gtg | cag | ctg | gtg | cag | tct | ggg | gct | gag | gtg | aag | aag | cct | ggg | tcc | 48 |
| Glu | Val | Gln | Leu | Val | Gln | Ser | Gly | Ala | Glu | Val | Lys | Lys | Pro | Gly | Ser | |
| 1 | | | | 5 | | | | | 10 | | | | | 15 | | |
| tcg | gtg | aag | gtc | tcc | tgc | aag | gct | tct | gga | ggc | acc | tcc | act | aac | gat | 96 |
| Ser | Val | Lys | Val | Ser | Cys | Lys | Ala | Ser | Gly | Gly | Thr | Ser | Thr | Asn | Asp | |
| | | | 20 | | | | | 25 | | | | | 30 | | | |
| gct | atc | agt | tgg | gtg | cga | cag | acc | cct | gga | caa | ggg | ctt | gag | tgg | atg | 144 |
| Ala | Ile | Ser | Trp | Val | Arg | Gln | Thr | Pro | Gly | Gln | Gly | Leu | Glu | Trp | Met | |
| | | 35 | | | | | 40 | | | | | 45 | | | | |
| gga | agt | atc | atc | cct | atc | ctt | gat | aca | aca | gac | cac | gca | cag | aag | ttc | 192 |
| Gly | Ser | Ile | Ile | Pro | Ile | Leu | Asp | Thr | Thr | Asp | His | Ala | Gln | Lys | Phe | |
| | 50 | | | | | 55 | | | | | 60 | | | | | |
| cag | ggc | aga | gtc | acg | att | acc | gcg | gac | aaa | tcc | acg | aac | aca | gcc | tac | 240 |
| Gln | Gly | Arg | Val | Thr | Ile | Thr | Ala | Asp | Lys | Ser | Thr | Asn | Thr | Ala | Tyr | |
| 65 | | | | | 70 | | | | | 75 | | | | | 80 | |
| atg | gag | ctg | aac | agc | ctg | aga | tct | gat | gac | acg | gcc | gtg | tat | tac | tgt | 288 |
| Met | Glu | Leu | Asn | Ser | Leu | Arg | Ser | Asp | Asp | Thr | Ala | Val | Tyr | Tyr | Cys | |
| | | | | 85 | | | | | 90 | | | | | 95 | | |
| gcg | aga | gag | cat | ata | gca | gct | cgt | cag | gac | tac | ttt | gac | tat | tgg | ggc | 336 |
| Ala | Arg | Glu | His | Ile | Ala | Ala | Arg | Gln | Asp | Tyr | Phe | Asp | Tyr | Trp | Gly | |
| | | | 100 | | | | | 105 | | | | | 110 | | | |
| cag | gga | acc | ctg | gtc | acc | gtc | tcc | agt | | | | | | | | 363 |
| Gln | Gly | Thr | Leu | Val | Thr | Val | Ser | Ser | | | | | | | | |
| | | 115 | | | | | 120 | | | | | | | | | |

<210> SEQ ID NO 52
<211> LENGTH: 121
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Ser Thr Asn Asp
            20                  25                  30

Ala Ile Ser Trp Val Arg Gln Thr Pro Gly Gln Gly Leu Glu Trp Met
        35                  40                  45

Gly Ser Ile Ile Pro Ile Leu Asp Thr Thr Asp His Ala Gln Lys Phe
    50                  55                  60

Gln Gly Arg Val Thr Ile Thr Ala Asp Lys Ser Thr Asn Thr Ala Tyr
65                  70                  75                  80

Met Glu Leu Asn Ser Leu Arg Ser Asp Asp Thr Ala Val Tyr Tyr Cys
                85                  90                  95

Ala Arg Glu His Ile Ala Ala Arg Gln Asp Tyr Phe Asp Tyr Trp Gly
            100                 105                 110

Gln Gly Thr Leu Val Thr Val Ser Ser
        115                 120

<210> SEQ ID NO 53
<211> LENGTH: 357
<212> TYPE: DNA
<213> ORGANISM: Artificial Sequence
<220> FEATURE:

<223> OTHER INFORMATION: MF5817
<220> FEATURE:
<221> NAME/KEY: CDS
<222> LOCATION: (1)..(357)

<400> SEQUENCE: 53

```
cag gtg cag ctg gtg cag tct ggg gct gag gtg aag aag cct ggg tcc      48
Gln Val Gln Leu Val Gln Ser Gly Ala Glu Val Lys Lys Pro Gly Ser
1               5                   10                  15 tcg gtg aag gtc tcc tgc aag gtt tct gga ggc acc ttc agg agc tat      96
Ser Val Lys Val Ser Cys Lys Val Ser Gly Gly Thr Phe Arg Ser Tyr
            20                  25                  30 gct atc agc tgg gtg cga cag gcc cct gga caa ggg ctt gag tgg atg     144
Ala Ile Ser Trp Val Arg Gln Ala Pro Gly Gln Gly Leu Glu Trp Met
        35                  40                  45 gga ggg atc atc cct atc ttt gat aca aga aac tac gca cag att ctt     192
Gly Gly Ile Ile Pro Ile Phe Asp Thr Arg Asn Tyr Ala Gln Ile Leu
    50                  55                  60 cag ggc aga gtc acg att acc gcg gac tta tcc acg agc aca gcc tac     240
Gln Gly Arg Val Thr Ile Thr Ala Asp Leu Ser Thr Ser Thr Ala Tyr
65                  70                  75                  80 atg gag ctg aac agt ctg aga tct gag gac acg gcc att tat tac tgt     288
Met Glu Leu Asn Ser Leu Arg Ser Glu Asp Thr Ala Ile Tyr Tyr Cys
                85                  90                  95 gcg aga ggg agc gac gag ggg gac tgg ttc gac ccc tgg ggc caa gga     336
Ala Arg Gly Ser Asp Glu Gly Asp Trp Phe Asp Pro Trp Gly Gln Gly
            100                 105                 110 acc ctg gtc acc gtc tcc agt                                         357
Thr Leu Val Thr Val Ser Ser
        115
```

<210> SEQ ID NO 54
<211> LENGTH: 119
<212> TYPE: PRT
<213> ORGANISM: Artificial Sequence
<220> FEATURE:
<223> OTHER INFORMATION: Synthetic Construct

<400> SEQUENCE: 54

```
Gln Val Gln Leu Val Gln Ser Gly Ala Glu Val Lys Lys Pro Gly Ser
1               5                   10                  15

Ser Val Lys Val Ser Cys Lys Val Ser Gly Gly Thr Phe Arg Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Arg Asn Tyr Ala Gln Ile Leu
    50                  55                  60

Gln Gly Arg Val Thr Ile Thr Ala Asp Leu Ser Thr Ser Thr Ala Tyr
65                  70                  75                  80

Met Glu Leu Asn Ser Leu Arg Ser Glu Asp Thr Ala Ile Tyr Tyr Cys
                85                  90                  95

Ala Arg Gly Ser Asp Glu Gly Asp Trp Phe Asp Pro Trp Gly Gln Gly
            100                 105                 110

Thr Leu Val Thr Val Ser Ser
        115
```

<210> SEQ ID NO 55
<211> LENGTH: 363
<212> TYPE: DNA
<213> ORGANISM: Artificial Sequence
<220> FEATURE:

<223> OTHER INFORMATION: MF5818
<220> FEATURE:
<221> NAME/KEY: CDS
<222> LOCATION: (1)..(363)

<400> SEQUENCE: 55

```
gag gtg cag ctg gtg cag tct ggg act gag gtg agg aag cct ggg tcc      48
Glu Val Gln Leu Val Gln Ser Gly Thr Glu Val Arg Lys Pro Gly Ser
1               5                   10                  15 tcg gtg aag gtc tcc tgc aag gct tct gga ggc acc ttc agc aac tat      96
Ser Val Lys Val Ser Cys Lys Ala Ser Gly Gly Thr Phe Ser Asn Tyr
            20                  25                  30 gct atc agc tgg gtg cga cag gcc cct gga cag ggg ctt gag tgg atg     144
Ala Ile Ser Trp Val Arg Gln Ala Pro Gly Gln Gly Leu Glu Trp Met
        35                  40                  45 gga agt atc atc cct atc ctt gga aca aca gac cac gca cag aag ttc     192
Gly Ser Ile Ile Pro Ile Leu Gly Thr Thr Asp His Ala Gln Lys Phe
    50                  55                  60 cag gac aga gtc acg att acc gcg gac aaa tcc tcg aac aca acc tac     240
Gln Asp Arg Val Thr Ile Thr Ala Asp Lys Ser Ser Asn Thr Thr Tyr
65                  70                  75                  80 atg gag ctg agc agc ctg aga tct gat gac acg gcc gta tat tac tgt     288
Met Glu Leu Ser Ser Leu Arg Ser Asp Asp Thr Ala Val Tyr Tyr Cys
                85                  90                  95 gcg aga gag tat ata gca gct cgt ctg gac tac ttt gac tct tgg ggc     336
Ala Arg Glu Tyr Ile Ala Ala Arg Leu Asp Tyr Phe Asp Ser Trp Gly
            100                 105                 110 cag gga acc ctg gtc acc gtc tcc agt                                  363
Gln Gly Thr Leu Val Thr Val Ser Ser
        115                 120
```

<210> SEQ ID NO 56
<211> LENGTH: 121
<212> TYPE: PRT
<213> ORGANISM: Artificial Sequence
<220> FEATURE:
<223> OTHER INFORMATION: Synthetic Construct

<400> SEQUENCE: 56

```
Glu Val Gln Leu Val Gln Ser Gly Thr Glu Val Arg Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Lys Phe
    50                  55                  60

Gln Asp Arg Val Thr Ile Thr Ala Asp Lys Ser Ser Asn Thr Thr Tyr
65                  70                  75                  80

Met Glu Leu Ser Ser Leu Arg Ser Asp Asp Thr Ala Val Tyr Tyr Cys
                85                  90                  95

Ala Arg Glu Tyr Ile Ala Ala Arg Leu Asp Tyr Phe Asp Ser Trp Gly
            100                 105                 110

Gln Gly Thr Leu Val Thr Val Ser Ser
        115                 120
```

<210> SEQ ID NO 57
<211> LENGTH: 366
<212> TYPE: DNA
<213> ORGANISM: Artificial Sequence
<220> FEATURE:

<223> OTHER INFORMATION: MF5832
<220> FEATURE:
<221> NAME/KEY: CDS
<222> LOCATION: (1)..(366)

<400> SEQUENCE: 57

```
gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gta gtc tct gga ttc acc ttc agt tac tac      96
Ser Leu Arg Leu Ser Cys Val Val Ser Gly Phe Thr Phe Ser Tyr Tyr
            20                  25                  30 gac atg cac tgg gtc cgc caa gtc aca gga aaa ggt ctg gag tgg gtc     144
Asp Met His Trp Val Arg Gln Val Thr Gly Lys Gly Leu Glu Trp Val
        35                  40                  45 tca gct att ggc act gct ggt gcc aca tac tat cca ggc tcc gtg aag     192
Ser Ala Ile Gly Thr Ala Gly Ala Thr Tyr Tyr Pro Gly Ser Val Lys
    50                  55                  60 ggc cga ttc acc atc tcc aga gaa aat gcc aag aac tcc ttg tat ctt     240
Gly Arg Phe Thr Ile Ser Arg Glu Asn Ala Lys Asn Ser Leu Tyr Leu
65                  70                  75                  80 caa atg aat agc ctg aga gcc ggg gac acg gct gtg tat tac tgt gca     288
Gln Met Asn Ser Leu Arg Ala Gly Asp Thr Ala Val Tyr Tyr Cys Ala
                85                  90                  95 aga gat cgt gga tat agt ggc tac gat gcg tac tac ttt gac ttc tgg     336
Arg Asp Arg Gly Tyr Ser Gly Tyr Asp Ala Tyr Tyr Phe Asp Phe Trp
            100                 105                 110 ggc cag gga acc ctg gtc acc gtc tcc agt                             366
Gly Gln Gly Thr Leu Val Thr Val Ser Ser
        115                 120
```

<210> SEQ ID NO 58
<211> LENGTH: 122
<212> TYPE: PRT
<213> ORGANISM: Artificial Sequence
<220> FEATURE:
<223> OTHER INFORMATION: Synthetic Construct

<400> SEQUENCE: 58

```
Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser Tyr Tyr
            20                  25                  30

Asp Met His Trp Val Arg Gln Val Thr Gly Lys Gly Leu Glu Trp Val
        35                  40                  45

Ser Ala Ile Gly Thr Ala Gly Ala Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Gly Tyr Ser Gly Tyr Asp Ala Tyr Tyr Phe Asp Phe Trp
            100                 105                 110

Gly Gln Gly Thr Leu Val Thr Val Ser Ser
        115                 120
```

<210> SEQ ID NO 59
<211> LENGTH: 372
<212> TYPE: DNA
<213> ORGANISM: Artificial Sequence
<220> FEATURE:

<223> OTHER INFORMATION: MF5836
<220> FEATURE:
<221> NAME/KEY: CDS
<222> LOCATION: (1)..(372)

<400> SEQUENCE: 59

```
cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                  10                  15 acc ctg tcc ctc acc tgc act gtc tct ggt ggc tcc atc agc agt agt      96
Thr Leu Ser Leu Thr Cys Thr Val Ser Gly Gly Ser Ile Ser Ser Ser
            20                  25                  30 aat tac tac tgg ggc tgg atc cgc cag ccc cca ggg aag ggg ctg gag     144
Asn Tyr Tyr Trp Gly Trp Ile Arg Gln Pro Pro Gly Lys Gly Leu Glu
        35                  40                  45 tgg att ggg aat atc tat tat aga ggg tac acc tat tat aac ccg tcc     192
Trp Ile Gly Asn Ile Tyr Tyr Arg Gly Tyr Thr Tyr Tyr Asn Pro Ser
    50                  55                  60 ctc aag agt cga gtc acc ata tcc gta gac acg tcc aag aag cag ttc     240
Leu Lys Ser Arg Val Thr Ile Ser Val Asp Thr Ser Lys Lys Gln Phe
65                  70                  75                  80 tcc ctg acg ctg agc tct gtg acc gcc gca gac acg gct atg tat tac     288
Ser Leu Thr Leu Ser Ser Val Thr Ala Ala Asp Thr Ala Met Tyr Tyr
                85                  90                  95 tgt gcg aga gag ggg agt gac tac ggt gac tac gta gga gct ttt gat     336
Cys Ala Arg Glu Gly Ser Asp Tyr Gly Asp Tyr Val Gly Ala Phe Asp
            100                 105                 110 atc tgg gac caa ggg aca atg gtc acc gtc tcc agt                     372
Ile Trp Asp Gln Gly Thr Met Val Thr Val Ser Ser
        115                 120
```

<210> SEQ ID NO 60
<211> LENGTH: 124
<212> TYPE: PRT
<213> ORGANISM: Artificial Sequence
<220> FEATURE:
<223> OTHER INFORMATION: Synthetic Construct

<400> SEQUENCE: 60

```
Gln Val Gln Leu Gln Glu Ser Gly Pro Gly Leu Val Lys Pro Ser Glu
1               5                  10                  15

Thr Leu Ser Leu Thr Cys Thr Val Ser Gly Gly Ser Ile Ser Ser Ser
            20                  25                  30

Asn Tyr Tyr Trp Gly Trp Ile Arg Gln Pro Pro Gly Lys Gly Leu Glu
        35                  40                  45

Trp Ile Gly Asn Ile Tyr Tyr Arg Gly Tyr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Thr Leu Ser Ser Val Thr Ala Ala Asp Thr Ala Met Tyr Tyr
                85                  90                  95

Cys Ala Arg Glu Gly Ser Asp Tyr Gly Asp Tyr Val Gly Ala Phe Asp
            100                 105                 110

Ile Trp Asp Gln Gly Thr Met Val Thr Val Ser Ser
        115                 120
```

<210> SEQ ID NO 61
<211> LENGTH: 366
<212> TYPE: DNA
<213> ORGANISM: Artificial Sequence
<220> FEATURE:

<223> OTHER INFORMATION: MF5839
<220> FEATURE:
<221> NAME/KEY: CDS
<222> LOCATION: (1)..(366)

<400> SEQUENCE: 61

| gag | gtg | cag | ctg | gtg | cag | tct | ggg | gga | ggc | ttg | gta | cag | cct | ggg | ggg | 48 |
| Glu | Val | Gln | Leu | Val | Gln | Ser | Gly | Gly | Gly | Leu | Val | Gln | Pro | Gly | Gly | |
| 1 | | | | 5 | | | | | 10 | | | | | 15 | | |

| tcc | ctg | aga | ctc | tcc | tgt | gca | gcc | tct | gga | ttc | acc | ttc | agt | tac | tac | 96 |
| Ser | Leu | Arg | Leu | Ser | Cys | Ala | Ala | Ser | Gly | Phe | Thr | Phe | Ser | Tyr | Tyr | |
| | | | 20 | | | | | 25 | | | | | 30 | | | |

| gac | atg | cac | tgg | gtc | cgc | caa | gtt | aca | gga | aaa | ggt | ctg | gag | tgg | gtc | 144 |
| Asp | Met | His | Trp | Val | Arg | Gln | Val | Thr | Gly | Lys | Gly | Leu | Glu | Trp | Val | |
| | | 35 | | | | | 40 | | | | | 45 | | | | |

| tca | act | att | ggt | gct | act | ggt | gac | aca | tac | tat | tca | gac | tcc | gtg | aag | 192 |
| Ser | Thr | Ile | Gly | Ala | Thr | Gly | Asp | Thr | Tyr | Tyr | Ser | Asp | Ser | Val | Lys | |
| 50 | | | | | 55 | | | | | 60 | | | | | | |

| ggc | cga | ttt | acc | atc | tcc | aga | caa | aat | gcc | aag | aac | tcc | ttg | tat | ctt | 240 |
| Gly | Arg | Phe | Thr | Ile | Ser | Arg | Gln | Asn | Ala | Lys | Asn | Ser | Leu | Tyr | Leu | |
| 65 | | | | 70 | | | | | 75 | | | | | 80 | | |

| caa | ata | aac | agc | ctg | aga | gcc | ggg | gac | acg | gct | gta | tat | tac | tgt | gta | 288 |
| Gln | Ile | Asn | Ser | Leu | Arg | Ala | Gly | Asp | Thr | Ala | Val | Tyr | Tyr | Cys | Val | |
| | | | 85 | | | | | 90 | | | | | 95 | | | |

| aga | gat | cgt | gga | tat | att | ggc | tac | gat | tcg | tac | tac | ttt | gac | aac | tgg | 336 |
| Arg | Asp | Arg | Gly | Tyr | Ile | Gly | Tyr | Asp | Ser | Tyr | Tyr | Phe | Asp | Asn | Trp | |
| | | | 100 | | | | | 105 | | | | | 110 | | | |

| ggc | cag | gga | acc | ctg | gtc | acc | gtc | tcc | agt | | | | | | | 366 |
| Gly | Gln | Gly | Thr | Leu | Val | Thr | Val | Ser | Ser | | | | | | | |
| | | 115 | | | | | 120 | | | | | | | | | |

<210> SEQ ID NO 62
<211> LENGTH: 122
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Met His Trp Val Arg Gln Val Thr Gly Lys Gly Leu Glu Trp Val
        35                  40                  45

Ser Thr Ile Gly Ala Thr Gly Asp Thr Tyr Tyr Ser Asp Ser Val Lys
    50                  55                  60

Gly Arg Phe Thr Ile Ser Arg Gln Asn Ala Lys Asn Ser Leu Tyr Leu
65                  70                  75                  80

Gln Ile Asn Ser Leu Arg Ala Gly Asp Thr Ala Val Tyr Tyr Cys Val
                85                  90                  95

Arg Asp Arg Gly Tyr Ile Gly Tyr Asp Ser Tyr Tyr Phe Asp Asn Trp
            100                 105                 110

Gly Gln Gly Thr Leu Val Thr Val Ser Ser
        115                 120

<210> SEQ ID NO 63
<211> LENGTH: 360
<212> TYPE: DNA
<213> ORGANISM: Artificial Sequence
<220> FEATURE:

<223> OTHER INFORMATION: M5850
<220> FEATURE:
<221> NAME/KEY: CDS
<222> LOCATION: (1)..(360)

<400> SEQUENCE: 63

```
cag gtg cag ctg gtg cag tct ggg tct gag ttg aag aag cct ggg gcc      48
Gln Val Gln Leu Val Gln Ser Gly Ser Glu Leu Lys Lys Pro Gly Ala
1               5                   10                  15 tca gtg aag gtt tcc tgc aag gct tct gga tac acc ttc act agg tat      96
Ser Val Lys Val Ser Cys Lys Ala Ser Gly Tyr Thr Phe Thr Arg Tyr
            20                  25                  30 cct atg aat tgg gtg cga cag gcc cct gga caa ggg ctt gag tgg atg     144
Pro Met Asn Trp Val Arg Gln Ala Pro Gly Gln Gly Leu Glu Trp Met
        35                  40                  45 gga tgg atc aac acc aac act ggg aac cca aca tat gcc cag ggc ttc     192
Gly Trp Ile Asn Thr Asn Thr Gly Asn Pro Thr Tyr Ala Gln Gly Phe
    50                  55                  60 aca gga cgg ttt gtc ttc tcc ttg gac acc tct gtc agc acg gca ttt     240
Thr Gly Arg Phe Val Phe Ser Leu Asp Thr Ser Val Ser Thr Ala Phe
65                  70                  75                  80 ctg cag atc agc agc cta aag gct gag gac act gcc gtg tat tac tgt     288
Leu Gln Ile Ser Ser Leu Lys Ala Glu Asp Thr Ala Val Tyr Tyr Cys
                85                  90                  95 gcg aga gag agg act aac ttt tat gat gct ttt gat atc tgg ggc caa     336
Ala Arg Glu Arg Thr Asn Phe Tyr Asp Ala Phe Asp Ile Trp Gly Gln
            100                 105                 110 ggg aca atg gtc acc gtc tcc agt                                     360
Gly Thr Met Val Thr Val Ser Ser
        115                 120
```

<210> SEQ ID NO 64
<211> LENGTH: 120
<212> TYPE: PRT
<213> ORGANISM: Artificial Sequence
<220> FEATURE:
<223> OTHER INFORMATION: Synthetic Construct

<400> SEQUENCE: 64

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Arg Tyr
            20                  25                  30

Pro Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Phe
65                  70                  75                  80

Leu Gln Ile Ser Ser Leu Lys Ala Glu Asp Thr Ala Val Tyr Tyr Cys
                85                  90                  95

Ala Arg Glu Arg Thr Asn Phe Tyr Asp Ala Phe Asp Ile Trp Gly Gln
            100                 105                 110

Gly Thr Met Val Thr Val Ser Ser
        115                 120
```

<210> SEQ ID NO 65
<211> LENGTH: 360
<212> TYPE: DNA
<213> ORGANISM: Artificial Sequence
<220> FEATURE:

<223> OTHER INFORMATION: MF5853
<220> FEATURE:
<221> NAME/KEY: CDS
<222> LOCATION: (1)..(360)

<400> SEQUENCE: 65

```
cag gtg cag ctg gtg caa tct ggg tct gag ttg aag aag cct ggg gcc        48
Gln Val Gln Leu Val Gln Ser Gly Ser Glu Leu Lys Lys Pro Gly Ala
1               5                   10                  15 tca gtg aag gtt tcc tgc aag gct tct gga tat acc ttc aat agc tat        96
Ser Val Lys Val Ser Cys Lys Ala Ser Gly Tyr Thr Phe Asn Ser Tyr
            20                  25                  30 gct atg gat tgg gtg cga cag gcc cct gga caa ggg ctt gag tgg atg       144
Ala Met Asp Trp Val Arg Gln Ala Pro Gly Gln Gly Leu Glu Trp Met
        35                  40                  45 gga tgg atc aac acc aat act ggg aac cca acg tat gcc cag gcc ttc       192
Gly Trp Ile Asn Thr Asn Thr Gly Asn Pro Thr Tyr Ala Gln Ala Phe
    50                  55                  60 aca gga cgg ttt gtc ttc tcc ttg gac acc tct gtc agc acg gca tat       240
Thr Gly Arg Phe Val Phe Ser Leu Asp Thr Ser Val Ser Thr Ala Tyr
65                  70                  75                  80 ctg gag atc agc agc cta aag gct gag gac act gcc gtg tat tac tgt       288
Leu Glu Ile Ser Ser Leu Lys Ala Glu Asp Thr Ala Val Tyr Tyr Cys
                85                  90                  95 gcg aga gag agg cat gga tat ttt gaa gct ttt gat atc tgg ggc caa       336
Ala Arg Glu Arg His Gly Tyr Phe Glu Ala Phe Asp Ile Trp Gly Gln
            100                 105                 110 ggg acc acg gtc acc gtc tcc agt                                       360
Gly Thr Thr Val Thr Val Ser Ser
        115                 120
```

<210> SEQ ID NO 66
<211> LENGTH: 120
<212> TYPE: PRT
<213> ORGANISM: Artificial Sequence
<220> FEATURE:
<223> OTHER INFORMATION: Synthetic Construct

<400> SEQUENCE: 66

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Asn Ser Tyr
            20                  25                  30

Ala Met Asp Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Ala Phe
    50                  55                  60

Thr Gly Arg Phe Val Phe Ser Leu Asp Thr Ser Val Ser Thr Ala Tyr
65                  70                  75                  80

Leu Glu Ile Ser Ser Leu Lys Ala Glu Asp Thr Ala Val Tyr Tyr Cys
                85                  90                  95

Ala Arg Glu Arg His Gly Tyr Phe Glu Ala Phe Asp Ile Trp Gly Gln
            100                 105                 110

Gly Thr Thr Val Thr Val Ser Ser
        115                 120
```

<210> SEQ ID NO 67
<211> LENGTH: 360
<212> TYPE: DNA
<213> ORGANISM: Artificial Sequence
<220> FEATURE:

<223> OTHER INFORMATION: MF5855
<220> FEATURE:
<221> NAME/KEY: CDS
<222> LOCATION: (1)..(360)

<400> SEQUENCE: 67

```
cag gtg cag ctg gtg caa tct ggg tct gag ttg aag aag cct ggg gcc        48
Gln Val Gln Leu Val Gln Ser Gly Ser Glu Leu Lys Lys Pro Gly Ala
1               5                   10                  15 tca gtg aag gtt tcc tgc aag gct tct gga tac acc ttc act aag tat        96
Ser Val Lys Val Ser Cys Lys Ala Ser Gly Tyr Thr Phe Thr Lys Tyr
            20                  25                  30 gtt atg aat tgg gtg cga cag gcc cct gga caa ggg ctt gag tgg atg       144
Val Met Asn Trp Val Arg Gln Ala Pro Gly Gln Gly Leu Glu Trp Met
        35                  40                  45 gga tgg atc aac acc aac act ggg aac cca acg tat gcc cag ggc ttc       192
Gly Trp Ile Asn Thr Asn Thr Gly Asn Pro Thr Tyr Ala Gln Gly Phe
    50                  55                  60 aca gga cgg ttt gtc ttc tcc ttg gac acc tct gtc agc acg gca tat       240
Thr Gly Arg Phe Val Phe Ser Leu Asp Thr Ser Val Ser Thr Ala Tyr
65                  70                  75                  80 ctg cag gtc agc agt cta agg gct gag gac act gcc ctg tat tac tgt       288
Leu Gln Val Ser Ser Leu Arg Ala Glu Asp Thr Ala Leu Tyr Tyr Cys
                85                  90                  95 gcg aga gag tct aac tgg aac tac gac tac ttt gac tac tgg ggc cag       336
Ala Arg Glu Ser Asn Trp Asn Tyr Asp Tyr Phe Asp Tyr Trp Gly Gln
            100                 105                 110 ggc acc ctg gtc acc gtc tcc agt                                       360
Gly Thr Leu Val Thr Val Ser Ser
        115                 120
```

<210> SEQ ID NO 68
<211> LENGTH: 120
<212> TYPE: PRT
<213> ORGANISM: Artificial Sequence
<220> FEATURE:
<223> OTHER INFORMATION: Synthetic Construct

<400> SEQUENCE: 68

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Lys Tyr
            20                  25                  30

Val Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Val Ser Ser Leu Arg Ala Glu Asp Thr Ala Leu Tyr Tyr Cys
                85                  90                  95

Ala Arg Glu Ser Asn Trp Asn Tyr Asp Tyr Phe Asp Tyr Trp Gly Gln
            100                 105                 110

Gly Thr Leu Val Thr Val Ser Ser
        115                 120
```

<210> SEQ ID NO 69
<211> LENGTH: 366
<212> TYPE: DNA
<213> ORGANISM: Artificial Sequence
<220> FEATURE:

<223> OTHER INFORMATION: MF5862
<220> FEATURE:
<221> NAME/KEY: CDS
<222> LOCATION: (1)..(366)

<400> SEQUENCE: 69

```
cag gtg cag ctg gtg cag tct gga aca gag gtg aaa aag ccc ggg gag      48
Gln Val Gln Leu Val Gln Ser Gly Thr Glu Val Lys Lys Pro Gly Glu
1               5                   10                  15 tct ctg aag atc tcc tgt aag ggt tct gga tac agc ttt acc acc tac      96
Ser Leu Lys Ile Ser Cys Lys Gly Ser Gly Tyr Ser Phe Thr Thr Tyr
            20                  25                  30 tgg atc ggc tgg gtg cgc cag atg ccc ggg aaa ggc ctg gag tgg atg     144
Trp Ile Gly Trp Val Arg Gln Met Pro Gly Lys Gly Leu Glu Trp Met
        35                  40                  45 gga atc atc tat cct ggt gac tct gat acc aga tac agc ccg tcc ttc     192
Gly Ile Ile Tyr Pro Gly Asp Ser Asp Thr Arg Tyr Ser Pro Ser Phe
    50                  55                  60 caa ggc cag gtc acc atc tca gcc gac aag tcc atc agc acc gcc tac     240
Gln Gly Gln Val Thr Ile Ser Ala Asp Lys Ser Ile Ser Thr Ala Tyr
65                  70                  75                  80 ctg cag ttg agc agc ctg aag gcc tcg gac acc gcc atg tat tac tgt     288
Leu Gln Leu Ser Ser Leu Lys Ala Ser Asp Thr Ala Met Tyr Tyr Cys
                85                  90                  95 gcg aga cgg ggt ctt agt atg gtt cgg ttg agc gct ttt gat gtc tgg     336
Ala Arg Arg Gly Leu Ser Met Val Arg Leu Ser Ala Phe Asp Val Trp
            100                 105                 110 ggc caa gga acc ctg gtc acc gtc tcc agt                              366
Gly Gln Gly Thr Leu Val Thr Val Ser Ser
        115                 120
```

<210> SEQ ID NO 70
<211> LENGTH: 122
<212> TYPE: PRT
<213> ORGANISM: Artificial Sequence
<220> FEATURE:
<223> OTHER INFORMATION: Synthetic Construct

<400> SEQUENCE: 70

```
Gln Val Gln Leu Val Gln Ser Gly Thr Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Ala Arg Arg Gly Leu Ser Met Val Arg Leu Ser Ala Phe Asp Val Trp
            100                 105                 110

Gly Gln Gly Thr Leu Val Thr Val Ser Ser
        115                 120
```

<210> SEQ ID NO 71
<211> LENGTH: 360
<212> TYPE: DNA
<213> ORGANISM: Artificial Sequence
<220> FEATURE:

<223> OTHER INFORMATION: MF5882
<220> FEATURE:
<221> NAME/KEY: CDS
<222> LOCATION: (1)..(360)

<400> SEQUENCE: 71

```
cag gtg cag ctg gtg caa tct ggg tct gag ttg aag aag cct ggg gcc      48
Gln Val Gln Leu Val Gln Ser Gly Ser Glu Leu Lys Lys Pro Gly Ala
1               5                   10                  15 tca gtg aag gtt tcc tgc aag gct tct gga tac acc ttc act aga tat      96
Ser Val Lys Val Ser Cys Lys Ala Ser Gly Tyr Thr Phe Thr Arg Tyr
            20                  25                  30 gct atg aat tgg gtg cga cag gcc cct gga caa ggg ctt gag tgg atg     144
Ala Met Asn Trp Val Arg Gln Ala Pro Gly Gln Gly Leu Glu Trp Met
        35                  40                  45 gga tgg atc aac acc aaa act ggg aac cca acg tat gcc cag ggc ttc     192
Gly Trp Ile Asn Thr Lys Thr Gly Asn Pro Thr Tyr Ala Gln Gly Phe
    50                  55                  60 aca gga cgg ttt gtc ttc tcc ttg gac acc tct gtc agc acg gca tat     240
Thr Gly Arg Phe Val Phe Ser Leu Asp Thr Ser Val Ser Thr Ala Tyr
65                  70                  75                  80 ctg cag atc agc agc cta aag gct gag gac act gcc gtg tat tac tgt     288
Leu Gln Ile Ser Ser Leu Lys Ala Glu Asp Thr Ala Val Tyr Tyr Cys
                85                  90                  95 gcg aga gat cgt ggg agc tac tat gat gct ttt gat atc tgg ggc caa     336
Ala Arg Asp Arg Gly Ser Tyr Tyr Asp Ala Phe Asp Ile Trp Gly Gln
            100                 105                 110 ggg aca atg gtc acc gtc tcc agt                                     360
Gly Thr Met Val Thr Val Ser Ser
        115                 120
```

<210> SEQ ID NO 72
<211> LENGTH: 120
<212> TYPE: PRT
<213> ORGANISM: Artificial Sequence
<220> FEATURE:
<223> OTHER INFORMATION: Synthetic Construct

<400> SEQUENCE: 72

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Arg Tyr
            20                  25                  30

Ala Met Asn Trp Val Arg Gln Ala Pro Gly Gln Gly Leu Glu Trp Met
        35                  40                  45

Gly Trp Ile Asn Thr Lys Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Arg Gly Ser Tyr Tyr Asp Ala Phe Asp Ile Trp Gly Gln
            100                 105                 110

Gly Thr Met Val Thr Val Ser Ser
        115                 120
```

<210> SEQ ID NO 73
<211> LENGTH: 360
<212> TYPE: DNA
<213> ORGANISM: Artificial Sequence
<220> FEATURE:

<223> OTHER INFORMATION: MF5884
<220> FEATURE:
<221> NAME/KEY: CDS
<222> LOCATION: (1)..(360)

<400> SEQUENCE: 73

```
gag gtg cag ctg gtg cag tct ggg tct gaa ttg aag aag cct ggg gcc      48
Glu Val Gln Leu Val Gln Ser Gly Ser Glu Leu Lys Lys Pro Gly Ala
1               5                   10                  15 tca gtg aag gtt tcc tgc aag gct tct gga tac acc ttc act aag tat      96
Ser Val Lys Val Ser Cys Lys Ala Ser Gly Tyr Thr Phe Thr Lys Tyr
            20                  25                  30 gct atg aat tgg gtg cga cag gtc cct gga caa ggg ctt gag tgg atg     144
Ala Met Asn Trp Val Arg Gln Val Pro Gly Gln Gly Leu Glu Trp Met
        35                  40                  45 gga tgg atc aac acc aac act ggg aac cca acg tat gcc cag ggc ttc     192
Gly Trp Ile Asn Thr Asn Thr Gly Asn Pro Thr Tyr Ala Gln Gly Phe
    50                  55                  60 aca gga cgg ttt gtc ttc tcc ttg gac acc tct gtc cgc acg gca tat     240
Thr Gly Arg Phe Val Phe Ser Leu Asp Thr Ser Val Arg Thr Ala Tyr
65                  70                  75                  80 ctg cag atc agc agc cta aag gct gag gac act gcc gtg tat tac tgt     288
Leu Gln Ile Ser Ser Leu Lys Ala Glu Asp Thr Ala Val Tyr Tyr Cys
                85                  90                  95 gcg aga aaa ggg ggg agc tac tac gac tgg ttc gac ccc tgg ggc cag     336
Ala Arg Lys Gly Gly Ser Tyr Tyr Asp Trp Phe Asp Pro Trp Gly Gln
            100                 105                 110 gga acc ctg gtc acc gtc tcc agt                                     360
Gly Thr Leu Val Thr Val Ser Ser
        115                 120
```

<210> SEQ ID NO 74
<211> LENGTH: 120
<212> TYPE: PRT
<213> ORGANISM: Artificial Sequence
<220> FEATURE:
<223> OTHER INFORMATION: Synthetic Construct

<400> SEQUENCE: 74

```
Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Lys Tyr
            20                  25                  30

Ala Met Asn Trp Val Arg Gln Val Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Arg Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Gly Ser Tyr Tyr Asp Trp Phe Asp Pro Trp Gly Gln
            100                 105                 110

Gly Thr Leu Val Thr Val Ser Ser
        115                 120
```

<210> SEQ ID NO 75
<211> LENGTH: 369
<212> TYPE: DNA
<213> ORGANISM: Artificial Sequence
<220> FEATURE:

<223> OTHER INFORMATION: MF5887
<220> FEATURE:
<221> NAME/KEY: CDS
<222> LOCATION: (1)..(369)

<400> SEQUENCE: 75

```
cag gtg cag ctg gtg cag tct ggg tct gag ttg aag aag cct ggg gcc    48
Gln Val Gln Leu Val Gln Ser Gly Ser Glu Leu Lys Lys Pro Gly Ala
1               5                   10                  15 tca gtg aag gtt tcc tgc aag gct tct gga tac acc ttc act cgc tat    96
Ser Val Lys Val Ser Cys Lys Ala Ser Gly Tyr Thr Phe Thr Arg Tyr
            20                  25                  30 gct atg aat tgg gtg cga cag gcc cct gga caa ggg ctt gag tgg atg   144
Ala Met Asn Trp Val Arg Gln Ala Pro Gly Gln Gly Leu Glu Trp Met
        35                  40                  45 gga tgg atc aac acc aac act ggg aaa cca acg tat gcc cag ggc ttc   192
Gly Trp Ile Asn Thr Asn Thr Gly Lys Pro Thr Tyr Ala Gln Gly Phe
    50                  55                  60 aca gga cgg ttt gtc ttc tcc ttg gac acc tct gtc agc acg gca tat   240
Thr Gly Arg Phe Val Phe Ser Leu Asp Thr Ser Val Ser Thr Ala Tyr
65                  70                  75                  80 ctg cag atc agc agc ctg aag gct gag gac act gcc gtg tat tac tgt   288
Leu Gln Ile Ser Ser Leu Lys Ala Glu Asp Thr Ala Val Tyr Tyr Cys
                85                  90                  95 gcg aga gat aag ggc tat aac tgg aac tac atg ggt gct ttt gat atc   336
Ala Arg Asp Lys Gly Tyr Asn Trp Asn Tyr Met Gly Ala Phe Asp Ile
            100                 105                 110 tgg ggc caa ggg acc acg gtc acc gtc tcc agt                       369
Trp Gly Gln Gly Thr Thr Val Thr Val Ser Ser
        115                 120
```

<210> SEQ ID NO 76
<211> LENGTH: 123
<212> TYPE: PRT
<213> ORGANISM: Artificial Sequence
<220> FEATURE:
<223> OTHER INFORMATION: Synthetic Construct

<400> SEQUENCE: 76

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Arg Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Lys Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Lys Gly Tyr Asn Trp Asn Tyr Met Gly Ala Phe Asp Ile
            100                 105                 110

Trp Gly Gln Gly Thr Thr Val Thr Val Ser Ser
        115                 120
```

<210> SEQ ID NO 77
<211> LENGTH: 360
<212> TYPE: DNA
<213> ORGANISM: Artificial Sequence
<220> FEATURE:

<223> OTHER INFORMATION: MF5888
<220> FEATURE:
<221> NAME/KEY: CDS
<222> LOCATION: (1)..(360)

<400> SEQUENCE: 77

```
cag gtg cag ctg gtg cag tct ggg tct gag ttg aag aag ccc ggg ggc        48
Gln Val Gln Leu Val Gln Ser Gly Ser Glu Leu Lys Lys Pro Gly Gly
1               5                   10                  15 tca atg aag gtt tcc tgc aag gct tct gga tac acc ttc act aga tat        96
Ser Met Lys Val Ser Cys Lys Ala Ser Gly Tyr Thr Phe Thr Arg Tyr
                20                  25                  30 gct atg aat tgg ttg cga cag gcc cct gga caa ggg ctt gag tgg atg        144
Ala Met Asn Trp Leu Arg Gln Ala Pro Gly Gln Gly Leu Glu Trp Met
            35                  40                  45 gga tgg atc aac acc aac act ggg aac cca acg tat gcc cag ggc ttc        192
Gly Trp Ile Asn Thr Asn Thr Gly Asn Pro Thr Tyr Ala Gln Gly Phe
        50                  55                  60 aca gga cgg ttt gtc ttc tcc ttg gac acc tct gtc agc acg gca tat        240
Thr Gly Arg Phe Val Phe Ser Leu Asp Thr Ser Val Ser Thr Ala Tyr
65                  70                  75                  80 ctg cag atc agc agc cta aag gct gag gac act gcc gtc tat tat tgt        288
Leu Gln Ile Ser Ser Leu Lys Ala Glu Asp Thr Ala Val Tyr Tyr Cys
                85                  90                  95 gcg aga cgg agt ggg agc tac tac gac tac ttt gac tac tgg ggc cag        336
Ala Arg Arg Ser Gly Ser Tyr Tyr Asp Tyr Phe Asp Tyr Trp Gly Gln
                100                 105                 110 gga acc ctg gtc acc gtc tcc agt                                        360
Gly Thr Leu Val Thr Val Ser Ser
            115                 120
```

<210> SEQ ID NO 78
<211> LENGTH: 120
<212> TYPE: PRT
<213> ORGANISM: Artificial Sequence
<220> FEATURE:
<223> OTHER INFORMATION: Synthetic Construct

<400> SEQUENCE: 78

```
Gln Val Gln Leu Val Gln Ser Gly Ser Glu Leu Lys Lys Pro Gly Gly
1               5                   10                  15

Ser Met Lys Val Ser Cys Lys Ala Ser Gly Tyr Thr Phe Thr Arg Tyr
                20                  25                  30

Ala Met Asn Trp Leu Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg Ser Gly Ser Tyr Tyr Asp Tyr Phe Asp Tyr Trp Gly Gln
                100                 105                 110

Gly Thr Leu Val Thr Val Ser Ser
            115                 120
```

<210> SEQ ID NO 79
<211> LENGTH: 321
<212> TYPE: DNA
<213> ORGANISM: Artificial Sequence
<220> FEATURE:

-continued

```
<223> OTHER INFORMATION: common light chain - 1
<220> FEATURE:
<221> NAME/KEY: CDS
<222> LOCATION: (1)..(321)

<400> SEQUENCE: 79 gac atc cag atg acc cag tct cca tcc tcc ctg tct gca tct gta gga      48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac      96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc     192
Tyr Ala Ala Ser Ser Leu Gln Ser Gly Val Pro Ser Arg Phe Ser Gly
    50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct cca     288
Glu Asp Phe Ala Thr Tyr Tyr Cys Gln Gln Ser Tyr Ser Thr Pro Pro
                85                  90                  95 acg ttc ggc caa ggg acc aag gtg gag atc aaa                         321
Thr Phe Gly Gln Gly Thr Lys Val Glu Ile Lys
            100                 105

<210> SEQ ID NO 80
<211> LENGTH: 107
<212> TYPE: PRT
<213> ORGANISM: Artificial Sequence
<220> FEATURE:
<223> OTHER INFORMATION: Synthetic Construct

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 81
<211> LENGTH: 324
<212> TYPE: DNA
<213> ORGANISM: Artificial Sequence
<220> FEATURE:
<223> OTHER INFORMATION: common light chain - 2
<220> FEATURE:
<221> NAME/KEY: CDS
<222> LOCATION: (1)..(324)

<400> SEQUENCE: 81
```

```
cga act gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg     288
Lys His Lys Val Tyr Ala Cys Glu Val Thr His Gln Gly Leu Ser Ser
                85                  90                  95 ccc gtc aca aag agc ttc aac agg gga gag tgt tag                     324
Pro Val Thr Lys Ser Phe Asn Arg Gly Glu Cys
            100                 105

<210> SEQ ID NO 82
<211> LENGTH: 107
<212> TYPE: PRT
<213> ORGANISM: Artificial Sequence
<220> FEATURE:
<223> OTHER INFORMATION: Synthetic Construct

<400> SEQUENCE: 82

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 83
<211> LENGTH: 294
<212> TYPE: DNA
<213> ORGANISM: Artificial Sequence
<220> FEATURE:
<223> OTHER INFORMATION: VH-CH1
<220> FEATURE:
<221> NAME/KEY: CDS
<222> LOCATION: (1)..(294)

<400> SEQUENCE: 83 gct agc acc aag ggc cca tcg gtc ttc ccc ctg gca ccc tcc tcc aag      48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30
```

```
ttc ccc gaa ccg gtg acg gtg tcg tgg aac tca ggc gcc ctg acc agc    144
Phe Pro Glu Pro Val Thr Val Ser Trp Asn Ser Gly Ala Leu Thr Ser
         35                  40                  45 ggc gtg cac acc ttc ccg gct gtc cta cag tcc tca gga ctc tac tcc    192
Gly Val His Thr Phe Pro Ala Val Leu Gln Ser Ser Gly Leu Tyr Ser
 50                  55                  60 ctc agc agc gtc gtg acc gtg ccc tcc agc agc ttg ggc acc cag acc    240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag    288
Tyr Ile Cys Asn Val Asn His Lys Pro Ser Asn Thr Lys Val Asp Lys
                 85                  90                  95 aga gtt                                                            294
Arg Val
```

```
<210> SEQ ID NO 84
<211> LENGTH: 98
<212> TYPE: PRT
<213> ORGANISM: Artificial Sequence
<220> FEATURE:
<223> OTHER INFORMATION: Synthetic Construct

<400> SEQUENCE: 84

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Arg Val
```

```
<210> SEQ ID NO 85
<211> LENGTH: 45
<212> TYPE: DNA
<213> ORGANISM: Artificial Sequence
<220> FEATURE:
<223> OTHER INFORMATION: VH-hinge
<220> FEATURE:
<221> NAME/KEY: CDS
<222> LOCATION: (1)..(45)

<400> SEQUENCE: 85 gag ccc aaa tct tgt gac aaa act cac aca tgc cca ccg tgc cca        45
Glu Pro Lys Ser Cys Asp Lys Thr His Thr Cys Pro Pro Cys Pro
1               5                   10                  15
```

```
<210> SEQ ID NO 86
<211> LENGTH: 15
<212> TYPE: PRT
<213> ORGANISM: Artificial Sequence
<220> FEATURE:
<223> OTHER INFORMATION: Synthetic Construct

<400> SEQUENCE: 86

Glu Pro Lys Ser Cys Asp Lys Thr His Thr Cys Pro Pro Cys Pro
1               5                   10                  15
```

<210> SEQ ID NO 87
<211> LENGTH: 330
<212> TYPE: DNA
<213> ORGANISM: Artificial Sequence
<220> FEATURE:
<223> OTHER INFORMATION: VH-CH2
<220> FEATURE:
<221> NAME/KEY: CDS
<222> LOCATION: (1)..(330)

<400> SEQUENCE: 87

```
gca cct gaa ctc ctg ggg gga ccg tca gtc ttc ctc ttc ccc cca aaa      48
Ala Pro Glu Leu Leu Gly Gly Pro Ser Val Phe Leu Phe Pro Pro Lys
1               5                   10                  15 ccc aag gac acc ctc atg atc tcc cgg acc cct gag gtc aca tgc gtg      96
Pro Lys Asp Thr Leu Met Ile Ser Arg Thr Pro Glu Val Thr Cys Val
            20                  25                  30 gtg gtg gac gtg agc cac gaa gac cct gag gtc aag ttc aac tgg tac     144
Val Val Asp Val Ser His Glu Asp Pro Glu Val Lys Phe Asn Trp Tyr
        35                  40                  45 gtg gac ggc gtg gag gtg cat aat gcc aag aca aag ccg cgg gag gag     192
Val Asp Gly Val Glu Val His Asn Ala Lys Thr Lys Pro Arg Glu Glu
    50                  55                  60 cag tac aac agc acg tac cgt gtg gtc agc gtc ctc acc gtc ctg cac     240
Gln Tyr Asn Ser Thr Tyr Arg Val Val Ser Val Leu Thr Val Leu His
65                  70                  75                  80 cag gac tgg ctg aat ggc aag gag tac aag tgc aag gtc tcc aac aaa     288
Gln Asp Trp Leu Asn Gly Lys Glu Tyr Lys Cys Lys Val Ser Asn Lys
                85                  90                  95 gcc ctc cca gcc ccc atc gag aaa acc atc tcc aaa gcc aaa             330
Ala Leu Pro Ala Pro Ile Glu Lys Thr Ile Ser Lys Ala Lys
            100                 105                 110
```

<210> SEQ ID NO 88
<211> LENGTH: 110
<212> TYPE: PRT
<213> ORGANISM: Artificial Sequence
<220> FEATURE:
<223> OTHER INFORMATION: Synthetic Construct

<400> SEQUENCE: 88

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 89
<211> LENGTH: 321
<212> TYPE: DNA
<213> ORGANISM: Artificial Sequence
<220> FEATURE:

<223> OTHER INFORMATION: VH-CH3
<220> FEATURE:
<221> NAME/KEY: CDS
<222> LOCATION: (1)..(321)

<400> SEQUENCE: 89

```
ggg cag ccc cga gaa cca cag gtg tac acc aag ccc cca tcc cgg gag      48
Gly Gln Pro Arg Glu Pro Gln Val Tyr Thr Lys Pro Pro Ser Arg Glu
1               5                   10                  15 gag atg acc aag aac cag gtc agc ctg aag tgc ctg gtc aaa ggc ttc      96
Glu Met Thr Lys Asn Gln Val Ser Leu Lys Cys Leu Val Lys Gly Phe
            20                  25                  30 tat ccc agc gac atc gcc gtg gag tgg gag agc aat ggg cag ccg gag     144
Tyr Pro Ser Asp Ile Ala Val Glu Trp Glu Ser Asn Gly Gln Pro Glu
        35                  40                  45 aac aac tac aag acc acg cct ccc gtg ctg gac tcc gac ggc tcc ttc     192
Asn Asn Tyr Lys Thr Thr Pro Pro Val Leu Asp Ser Asp Gly Ser Phe
    50                  55                  60 ttc ctc tat agc aag ctc acc gtg gac aag agc agg tgg cag cag ggg     240
Phe Leu Tyr Ser Lys Leu Thr Val Asp Lys Ser Arg Trp Gln Gln Gly
65                  70                  75                  80 aac gtc ttc tca tgc tcc gtg atg cat gag gct ctg cac aac cac tac     288
Asn Val Phe Ser Cys Ser Val Met His Glu Ala Leu His Asn His Tyr
                85                  90                  95 acg cag aag agc ctc tcc ctg tct ccg ggt tga                         321
Thr Gln Lys Ser Leu Ser Leu Ser Pro Gly
            100                 105
```

<210> SEQ ID NO 90
<211> LENGTH: 106
<212> TYPE: PRT
<213> ORGANISM: Artificial Sequence
<220> FEATURE:
<223> OTHER INFORMATION: Synthetic Construct

<400> SEQUENCE: 90

```
Gly Gln Pro Arg Glu Pro Gln Val Tyr Thr Lys Pro Pro Ser Arg Glu
1               5                   10                  15

Glu Met Thr Lys Asn Gln Val Ser Leu Lys Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 91
<211> LENGTH: 321
<212> TYPE: DNA
<213> ORGANISM: Artificial Sequence
<220> FEATURE:
<223> OTHER INFORMATION: VH-CH3
<220> FEATURE:
<221> NAME/KEY: CDS
<222> LOCATION: (1)..(321)

<400> SEQUENCE: 91

```
ggg cag ccc cga gaa cca cag gtg tac acc gac ccc cca tcc cgg gag      48
Gly Gln Pro Arg Glu Pro Gln Val Tyr Thr Asp Pro Pro Ser Arg Glu
1               5                   10                  15 gag atg acc aag aac cag gtc agc ctg acc tgc gag gtc aaa ggc ttc      96
Glu Met Thr Lys Asn Gln Val Ser Leu Thr Cys Glu Val Lys Gly Phe
            20                  25                  30 tat ccc agc gac atc gcc gtg gag tgg gag agc aat ggg cag ccg gag     144
Tyr Pro Ser Asp Ile Ala Val Glu Trp Glu Ser Asn Gly Gln Pro Glu
        35                  40                  45 aac aac tac aag acc acg cct ccc gtg ctg gac tcc gac ggc tcc ttc     192
Asn Asn Tyr Lys Thr Thr Pro Pro Val Leu Asp Ser Asp Gly Ser Phe
    50                  55                  60 ttc ctc tat agc aag ctc acc gtg gac aag agc agg tgg cag cag ggg     240
Phe Leu Tyr Ser Lys Leu Thr Val Asp Lys Ser Arg Trp Gln Gln Gly
65                  70                  75                  80 aac gtc ttc tca tgc tcc gtg atg cat gag gct ctg cac aac cac tac     288
Asn Val Phe Ser Cys Ser Val Met His Glu Ala Leu His Asn His Tyr
                85                  90                  95 acg cag aag agc ctc tcc ctg tct ccg ggt tga                         321
Thr Gln Lys Ser Leu Ser Leu Ser Pro Gly
                100                 105
```

<210> SEQ ID NO 92
<211> LENGTH: 106
<212> TYPE: PRT
<213> ORGANISM: Artificial Sequence
<220> FEATURE:
<223> OTHER INFORMATION: Synthetic Construct

<400> SEQUENCE: 92

```
Gly Gln Pro Arg Glu Pro Gln Val Tyr Thr Asp Pro Pro Ser Arg Glu
1               5                   10                  15

Glu Met Thr Lys Asn Gln Val Ser Leu Thr Cys Glu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
                100                 105
```

<210> SEQ ID NO 93
<211> LENGTH: 110
<212> TYPE: PRT
<213> ORGANISM: Artificial Sequence
<220> FEATURE:
<223> OTHER INFORMATION: VH1-69 J00256-AEHJ2

<400> SEQUENCE: 93

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Lys
```

```
                 50                  55                  60
Phe Gln Gly Arg Val Thr Ile Thr Ala Asp Lys Ser Thr Ser Thr Ala
 65                  70                  75                  80

Tyr Met Glu Leu Ser Ser Leu Arg Ser Glu Asp Thr Ala Val Tyr Tyr
                 85                  90                  95

Cys Ala Arg Trp Gly Arg Gly Thr Leu Val Thr Val Ser Ser
                100                 105                 110

<210> SEQ ID NO 94
<211> LENGTH: 121
<212> TYPE: PRT
<213> ORGANISM: Artificial Sequence
<220> FEATURE:
<223> OTHER INFORMATION: member of supercluster 1

<400> SEQUENCE: 94

Glu Val Gln Leu Val Gln Ser Gly Ala Glu Val Lys Lys Pro Gly Ser
 1               5                  10                  15

Ser Val Lys Val Ser Cys Lys Ala Phe Gly Thr Phe Asn Asn Tyr
                 20                  25                  30

Ala Ile Asn Trp Val Arg Gln Ala Pro Gly Gln Gly Leu Glu Trp Met
                 35                  40                  45

Gly Ser Ile Ile Pro Ile Leu Gly Thr Val Asp His Ala Gln Lys Phe
 50                  55                  60

Gln Gly Arg Val Thr Ile Thr Ala Asp Lys Ser Thr Asn Thr Val Tyr
 65                  70                  75                  80

Met Glu Leu Ser Ser Leu Arg Ser Asp Asp Thr Ala Val Tyr Tyr Cys
                 85                  90                  95

Ala Arg Glu His Ile Ala Ala Arg Leu Asp Tyr Phe Asp Tyr Trp Asp
                100                 105                 110

Leu Gly Thr Leu Val Thr Val Ser Ser
                115                 120

<210> SEQ ID NO 95
<211> LENGTH: 121
<212> TYPE: PRT
<213> ORGANISM: Artificial Sequence
<220> FEATURE:
<223> OTHER INFORMATION: member of supercluster 1

<400> SEQUENCE: 95

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Ser Thr Asn Asp
                 20                  25                  30

Ala Ile Ser Trp Val Arg Gln Thr Pro Gly Gln Gly Leu Glu Trp Met
                 35                  40                  45

Gly Ser Ile Ile Pro Ile Leu Asp Thr Thr Asp His Ala Gln Lys Phe
 50                  55                  60

Gln Gly Arg Val Thr Ile Thr Ala Asp Lys Ser Thr Asn Thr Ala Tyr
 65                  70                  75                  80

Met Glu Leu Asn Ser Leu Arg Ser Asp Asp Thr Ala Val Tyr Tyr Cys
                 85                  90                  95

Ala Arg Glu His Ile Ala Ala Arg Gln Asp Tyr Phe Asp Tyr Trp Gly
                100                 105                 110

Gln Gly Thr Leu Val Thr Val Ser Ser
                115                 120
```

<210> SEQ ID NO 96
<211> LENGTH: 121
<212> TYPE: PRT
<213> ORGANISM: Artificial Sequence
<220> FEATURE:
<223> OTHER INFORMATION: member of supercluster 1

<400> SEQUENCE: 96

```
Glu Val Gln Leu Val Gln Ser Gly Ala Glu Val Lys Lys Pro Gly Ser
1               5                   10                  15

Ser Val Lys Val Ser Cys Arg Ala Ser Gly Asp Ser Val Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Phe
    50                  55                  60

Gln Asp Arg Val Thr Ile Thr Ala Asp Lys Ser Thr Ser Thr Ala Tyr
65                  70                  75                  80

Met Glu Leu Gly Ser Leu Arg Ser Asp Asp Thr Ala Val Tyr Tyr Cys
                85                  90                  95

Ala Arg Glu Arg Ile Ala Ala Arg Gln Asp Tyr Phe Asp Tyr Trp Gly
            100                 105                 110

Gln Gly Thr Leu Val Thr Val Ser Ser
        115                 120
```

<210> SEQ ID NO 97
<211> LENGTH: 121
<212> TYPE: PRT
<213> ORGANISM: Artificial Sequence
<220> FEATURE:
<223> OTHER INFORMATION: member of supercluster 1

<400> SEQUENCE: 97

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Lys Phe
    50                  55                  60

Gln Asp Arg Val Thr Ile Thr Ala Asp Arg Ser Ser Asn Thr Thr Tyr
65                  70                  75                  80

Met Asp Leu Asn Ser Leu Arg Ser Asp Asp Thr Ala Val Tyr Tyr Cys
                85                  90                  95

Ala Arg Glu Leu Ile Ala Ala Arg Leu Asp Tyr Phe Asp Ser Trp Gly
            100                 105                 110

Gln Gly Thr Leu Val Thr Val Ser Ser
        115                 120
```

<210> SEQ ID NO 98
<211> LENGTH: 121
<212> TYPE: PRT
<213> ORGANISM: Artificial Sequence
<220> FEATURE:
<223> OTHER INFORMATION: member of supercluster 1

<400> SEQUENCE: 98

```
Glu Val Gln Leu Val Gln Ser Gly Ala Glu Val Lys Lys Pro Gly Ser
```

```
            1               5                  10                 15
Ser Val Lys Val Ser Cys Lys Ala Ser Gly Gly Thr Phe Ser Asn Tyr
                20                  25                  30

Ala Ile Ser Trp Val Arg Gln Ala Pro Gly Gln Gly Leu Glu Trp Met
            35                  40                  45

Gly Ser Ile Ile Pro Ile Leu Gly Thr Thr Asp His Ala Gln Lys Phe
        50                  55                  60

Gln Asp Arg Val Thr Ile Thr Ala Asp Lys Ser Ser Asn Thr Thr Tyr
65                  70                  75                  80

Met Asp Leu Ser Ser Leu Arg Ser Asp Asp Thr Ala Val Tyr Tyr Cys
                85                  90                  95

Ala Arg Glu Arg Ile Ala Ala Arg Leu Asp Tyr Phe Asp Ser Trp Gly
                100                 105                 110

Gln Gly Thr Leu Val Thr Val Ser Ser
            115                 120
```

<210> SEQ ID NO 99
<211> LENGTH: 121
<212> TYPE: PRT
<213> ORGANISM: Artificial Sequence
<220> FEATURE:
<223> OTHER INFORMATION: member of supercluster 1

<400> SEQUENCE: 99

```
Glu Val Gln Leu Val Gln Ser Gly Ala Glu Val Lys Lys Pro Gly Ser
1               5                   10                  15

Ser Val Lys Val Ser Cys Lys Ser Gly Gly Thr Phe Lys Asn Tyr
                20                  25                  30

Ala Ile Ser Trp Val Arg Gln Ala Pro Gly Gln Gly Leu Glu Trp Met
            35                  40                  45

Gly Ser Ile Ile Pro Ile Leu Gly Thr Thr Asp His Ala Gln Asn Phe
        50                  55                  60

Gln Asp Arg Val Thr Ile Thr Ala Asp Lys Leu Ser Asn Thr Thr Tyr
65                  70                  75                  80

Met Glu Leu Ser Ser Leu Arg Ser Asp Asp Thr Ala Val Tyr Tyr Cys
                85                  90                  95

Ala Ile Glu Leu Ile Ala Ala Arg Leu Asp Tyr Phe His Ser Trp Gly
                100                 105                 110

Gln Gly Thr Leu Val Thr Val Ser Ser
            115                 120
```

<210> SEQ ID NO 100
<211> LENGTH: 121
<212> TYPE: PRT
<213> ORGANISM: Artificial Sequence
<220> FEATURE:
<223> OTHER INFORMATION: member of supercluster 1

<400> SEQUENCE: 100

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Val Ser Asn Tyr
                20                  25                  30

Ala Ile Ser Trp Val Arg Gln Ala Pro Gly Gln Gly Leu Asp Trp Met
            35                  40                  45

Gly Ser Ile Ile Pro Ile Leu Gly Thr Thr Asp His Ala Gln Lys Phe
        50                  55                  60
```

-continued

Gln Gly Arg Val Thr Phe Thr Ala Asp Lys Ser Thr Asn Thr Ser Tyr
65                  70                  75                  80

Met Glu Leu Asn Ser Leu Arg Ser Asp Asp Thr Ala Val Tyr Tyr Cys
                85                  90                  95

Ala Arg Glu Leu Ile Ala Ala Arg Gln Asp Tyr Phe Asp Tyr Trp Gly
            100                 105                 110

Gln Gly Thr Leu Val Thr Val Ser Ser
            115                 120

<210> SEQ ID NO 101
<211> LENGTH: 121
<212> TYPE: PRT
<213> ORGANISM: Artificial Sequence
<220> FEATURE:
<223> OTHER INFORMATION: member of supercluster 1

<400> SEQUENCE: 101

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Lys Phe
    50                  55                  60

Gln Asp Arg Val Thr Ile Thr Ala Asp Arg Ser Ser Asn Thr Thr Tyr
65                  70                  75                  80

Met Asp Leu Asn Ser Leu Arg Ser Asp Asp Thr Ala Val Tyr Tyr Cys
                85                  90                  95

Ala Arg Glu Leu Ile Ala Ala Arg Leu Asp Tyr Phe Asp Ser Trp Gly
            100                 105                 110

Gln Gly Thr Leu Val Thr Val Ser Ser
            115                 120

<210> SEQ ID NO 102
<211> LENGTH: 121
<212> TYPE: PRT
<213> ORGANISM: Artificial Sequence
<220> FEATURE:
<223> OTHER INFORMATION: member of supercluster 1

<400> SEQUENCE: 102

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ser Thr Asn Asp
            20                  25                  30

Ala Ile Ser Trp Val Arg Gln Thr Pro Gly Gln Gly Leu Glu Trp Met
        35                  40                  45

Gly Ser Ile Ile Pro Ile Leu Asp Thr Thr Asp His Ala Gln Lys Phe
    50                  55                  60

Gln Gly Arg Val Thr Ile Thr Ala Asp Lys Ser Thr Asn Thr Ala Tyr
65                  70                  75                  80

Met Glu Leu Asn Ser Leu Arg Ser Asp Asp Thr Ala Val Tyr Tyr Cys
                85                  90                  95

Ala Arg Glu His Ile Ala Ala Arg Gln Asp Tyr Phe Asp Tyr Trp Gly
            100                 105                 110

Gln Gly Thr Leu Val Thr Val Ser Ser
            115                 120

<210> SEQ ID NO 103
<211> LENGTH: 121
<212> TYPE: PRT
<213> ORGANISM: Artificial Sequence
<220> FEATURE:
<223> OTHER INFORMATION: member of supercluster 1

<400> SEQUENCE: 103

Gln Val Gln Leu Val Gln Ser Gly Ala Glu Val Lys Lys Pro Gly Ser
1               5                   10                  15

Ser Val Lys Val Ser Cys Lys Ser Ser Gly Gly Thr Phe Lys Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Asn Phe
    50                  55                  60

Gln Asp Arg Val Thr Ile Thr Ala Asp Lys Leu Ser Asn Thr Thr Tyr
65                  70                  75                  80

Met Glu Leu Ser Ser Leu Arg Ser Asp Asp Thr Ala Val Tyr Tyr Cys
                85                  90                  95

Ala Ile Glu Leu Ile Ala Ala Arg Leu Asp Tyr Phe His Ser Trp Gly
            100                 105                 110

Gln Gly Thr Leu Val Thr Val Ser Ser
        115                 120

<210> SEQ ID NO 104
<211> LENGTH: 121
<212> TYPE: PRT
<213> ORGANISM: Artificial Sequence
<220> FEATURE:
<223> OTHER INFORMATION: member of supercluster 1

<400> SEQUENCE: 104

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Ser Thr Asn Tyr
            20                  25                  30

Ala Ile Ser Trp Val Arg Gln Thr Pro Gly Gln Gly Leu Glu Trp Met
        35                  40                  45

Gly Ser Ile Ile Pro Ile Leu Asp Thr Thr Asp His Ala Gln Lys Phe
    50                  55                  60

Gln Gly Arg Val Thr Ile Thr Ala Asp Lys Ser Thr Asn Thr Ala Tyr
65                  70                  75                  80

Met Glu Leu Asn Ser Leu Arg Ser Asp Asp Thr Ala Val Tyr Tyr Cys
                85                  90                  95

Ala Arg Glu His Ile Ala Ala Arg Gln Asp Tyr Phe Asp Tyr Trp Gly
            100                 105                 110

Gln Gly Thr Leu Val Thr Val Ser Ser
        115                 120

<210> SEQ ID NO 105
<211> LENGTH: 121
<212> TYPE: PRT
<213> ORGANISM: Artificial Sequence
<220> FEATURE:
<223> OTHER INFORMATION: member of supercluster 1

<400> SEQUENCE: 105

-continued

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Thr Asn Asp
            20                  25                  30

Ala Ile Ser Trp Val Arg Gln Thr Pro Gly Gln Gly Leu Glu Trp Met
        35                  40                  45

Gly Ser Ile Ile Pro Ile Leu Asp Thr Thr Asp His Ala Gln Lys Phe
    50                  55                  60

Gln Gly Arg Val Thr Ile Thr Ala Asp Arg Ser Thr Asn Thr Ala Tyr
65                  70                  75                  80

Met Glu Leu Asn Ser Leu Lys Ser Asp Asp Thr Ala Val Tyr Tyr Cys
                85                  90                  95

Ala Arg Glu His Ile Ala Ala Arg Gln Asp Tyr Phe Asp Tyr Trp Gly
            100                 105                 110

Gln Gly Thr Leu Val Thr Val Ser Ser
            115                 120

<210> SEQ ID NO 106
<211> LENGTH: 121
<212> TYPE: PRT
<213> ORGANISM: Artificial Sequence
<220> FEATURE:
<223> OTHER INFORMATION: member of supercluster 1

<400> SEQUENCE: 106

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Asn Phe
    50                  55                  60

Gln Asp Arg Val Thr Ile Thr Ala Asp Lys Ser Ser Asn Thr Thr Tyr
65                  70                  75                  80

Met Glu Leu Ser Ser Leu Arg Ser Asp Asp Thr Ala Val Tyr Tyr Cys
                85                  90                  95

Ala Arg Glu Arg Ile Ala Ala Arg Leu Asp Tyr Phe Asp Ser Trp Gly
            100                 105                 110

Gln Gly Thr Leu Val Thr Val Ser Ser
            115                 120

<210> SEQ ID NO 107
<211> LENGTH: 121
<212> TYPE: PRT
<213> ORGANISM: Artificial Sequence
<220> FEATURE:
<223> OTHER INFORMATION: member of supercluster 1

<400> SEQUENCE: 107

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Ile Asp His Ala Gln Asn Phe
    50                  55                  60

```
Gln Asp Arg Val Thr Ile Thr Ala Asp Lys Ser Ser Asn Thr Thr Tyr
 65                  70                  75                  80

Met Glu Leu Ser Ser Leu Arg Ser Asp Asp Thr Ala Val Tyr Tyr Cys
                 85                  90                  95

Ala Arg Glu Arg Ile Ala Ala Arg Leu Asp Tyr Phe Asp Ser Trp Gly
            100                 105                 110

Gln Gly Thr Leu Val Thr Val Ser Ser
        115                 120

<210> SEQ ID NO 108
<211> LENGTH: 121
<212> TYPE: PRT
<213> ORGANISM: Artificial Sequence
<220> FEATURE:
<223> OTHER INFORMATION: member of supercluster 1

<400> SEQUENCE: 108

Gln Val Gln Leu Val Gln Ser Gly Ala Glu Val Lys Lys Pro Gly Ser
 1               5                  10                  15

Ser Val Lys Val Ser Cys Arg Ala Ser Gly Asp Ser Val Ser Asn Tyr
             20                  25                  30

Ala Ile Ser Trp Val Arg Gln Ala Pro Gly Gln Gly Leu Glu Trp Met
         35                  40                  45

Gly Ser Ile Ile Pro Ile Leu Gly Thr Thr Asp His Ala Gln Gln Phe
     50                  55                  60

Gln Asp Arg Val Thr Ile Thr Ala Asp Lys Ser Thr Ser Thr Ala Tyr
 65                  70                  75                  80

Met Glu Leu Gly Ser Leu Arg Ser Asp Asp Thr Ala Val Tyr Tyr Cys
                 85                  90                  95

Ala Arg Glu Arg Ile Ala Ala Arg Gln Asp Tyr Phe Asp Tyr Trp Gly
            100                 105                 110

Gln Gly Thr Leu Val Thr Val Ser Ser
        115                 120

<210> SEQ ID NO 109
<211> LENGTH: 128
<212> TYPE: PRT
<213> ORGANISM: Artificial Sequence
<220> FEATURE:
<223> OTHER INFORMATION: member of supercluster 1

<400> SEQUENCE: 109

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
             20                  25                  30

Ala Ile Ser Trp Val Arg Gln Ala Pro Gly Gln Gly Leu Glu Trp Met
         35                  40                  45

Gly Ser Ile Ile Pro Ile Leu Gly Thr Thr Asp His Ala Glu Lys Phe
     50                  55                  60

Gln Gly Arg Val Thr Ile Thr Ala Asp Lys Ser Thr Ser Thr Ala Tyr
 65                  70                  75                  80

Met Asp Leu Ser Thr Ala Tyr Met Glu Leu Ser Ser Leu Arg Ser Asp
                 85                  90                  95

Asp Thr Ala Val Tyr Tyr Cys Ala Arg Glu Phe Ile Ala Ala Arg Gln
            100                 105                 110

Asp Tyr Phe Asp Tyr Trp Gly Gln Gly Thr Leu Val Thr Val Ser Ser
```

115                 120                 125

<210> SEQ ID NO 110
<211> LENGTH: 121
<212> TYPE: PRT
<213> ORGANISM: Artificial Sequence
<220> FEATURE:
<223> OTHER INFORMATION: member of supercluster 1

<400> SEQUENCE: 110

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Lys Phe
    50                  55                  60

Gln Asp Arg Val Thr Ile Thr Ala Asp Lys Ser Ser Asn Thr Thr Tyr
65                  70                  75                  80

Met Asp Leu Ser Ser Leu Arg Ser Asp Asp Thr Ala Val Tyr Tyr Cys
                85                  90                  95

Ala Arg Glu Arg Ile Ala Ala Arg Leu Asp Tyr Phe Asp Ser Trp Gly
            100                 105                 110

Gln Gly Thr Leu Val Thr Val Ser Ser
        115                 120

<210> SEQ ID NO 111
<211> LENGTH: 121
<212> TYPE: PRT
<213> ORGANISM: Artificial Sequence
<220> FEATURE:
<223> OTHER INFORMATION: member of supercluster 1

<400> SEQUENCE: 111

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Thr Asn Tyr
            20                  25                  30

Ala Ile Ser Trp Val Arg Gln Thr Pro Gly Gln Gly Leu Glu Trp Met
        35                  40                  45

Gly Ser Ile Ile Pro Ile Leu Asp Thr Thr Asp His Ala Gln Lys Phe
    50                  55                  60

Gln Gly Arg Val Thr Ile Thr Ala Asp Lys Ser Thr Asn Thr Thr Tyr
65                  70                  75                  80

Met Glu Leu Asn Ser Leu Arg Ser Asp Asp Thr Ala Val Tyr Tyr Cys
                85                  90                  95

Ala Arg Glu His Ile Ala Ala Arg Leu Asp Tyr Phe Asp Tyr Trp Gly
            100                 105                 110

Gln Gly Thr Leu Val Thr Val Ser Ser
        115                 120

<210> SEQ ID NO 112
<211> LENGTH: 121
<212> TYPE: PRT
<213> ORGANISM: Artificial Sequence
<220> FEATURE:
<223> OTHER INFORMATION: member of supercluster 1

<400> SEQUENCE: 112

-continued

Glu Val Gln Leu Val Gln Ser Gly Ala Glu Val Lys Lys Pro Gly Ser
1               5                   10                  15

Ser Val Lys Val Ser Cys Lys Ala Phe Gly Gly Thr Phe Asn Asn Tyr
            20                  25                  30

Ala Ile Asn Trp Val Arg Gln Ala Pro Gly Gln Gly Leu Glu Trp Met
        35                  40                  45

Gly Ser Ile Ile Pro Ile Leu Gly Thr Val Asp His Ala Gln Lys Phe
    50                  55                  60

Gln Gly Arg Val Thr Ile Thr Ala Asp Lys Ser Thr Asn Thr Val Tyr
65                  70                  75                  80

Met Glu Leu Ser Ser Leu Arg Ser Asp Asp Thr Ala Val Tyr Tyr Cys
                85                  90                  95

Ala Arg Glu His Ile Ala Ala Arg Leu Asp Tyr Phe Asp Tyr Trp Asp
                100                 105                 110

Leu Gly Ile Leu Val Thr Val Ser Ser
            115                 120

<210> SEQ ID NO 113
<211> LENGTH: 121
<212> TYPE: PRT
<213> ORGANISM: Artificial Sequence
<220> FEATURE:
<223> OTHER INFORMATION: member of supercluster 1

<400> SEQUENCE: 113

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Asn Phe
    50                  55                  60

Gln Asp Arg Val Thr Ile Thr Ala Asp Lys Ser Ser Asn Thr Thr Tyr
65                  70                  75                  80

Met Glu Leu Ile Gly Leu Lys Ser Asp Asp Thr Ala Val Tyr Tyr Cys
                85                  90                  95

Ala Arg Glu Arg Ile Ala Ala Arg Leu Asp Tyr Phe Asp Ser Trp Gly
                100                 105                 110

Gln Gly Thr Leu Val Thr Val Ser Ser
            115                 120

<210> SEQ ID NO 114
<211> LENGTH: 121
<212> TYPE: PRT
<213> ORGANISM: Artificial Sequence
<220> FEATURE:
<223> OTHER INFORMATION: member of supercluster 1

<400> SEQUENCE: 114

Arg Val Gln Leu Val Gln Ser Gly Ala Glu Val Lys Lys Pro Gly Ser
1               5                   10                  15

Ser Val Lys Val Ser Cys Lys Ala Phe Gly Gly Thr Phe Asn Asn Tyr
            20                  25                  30

Ala Ile Asn Trp Val Arg Gln Ala Pro Gly Gln Gly Leu Glu Trp Met
        35                  40                  45

Gly Ser Ile Ile Pro Ile Leu Gly Thr Val Asp His Ala Gln Lys Phe

```
            50                  55                  60
Gln Gly Arg Val Thr Ile Thr Ala Asp Lys Ser Ser Asn Thr Val Tyr
 65                  70                  75                  80

Met Glu Leu Ser Ser Leu Arg Ser Asp Asp Thr Ala Val Tyr Tyr Cys
                 85                  90                  95

Ala Arg Glu His Ile Ala Ala Arg Leu Asp Tyr Phe Asp Ser Trp Gly
                100                 105                 110

Leu Gly Thr Leu Val Thr Val Ser Ser
            115                 120

<210> SEQ ID NO 115
<211> LENGTH: 121
<212> TYPE: PRT
<213> ORGANISM: Artificial Sequence
<220> FEATURE:
<223> OTHER INFORMATION: member of supercluster 1

<400> SEQUENCE: 115

Arg Cys Ser Met Val Gln Ser Gly Ser Glu Leu Lys Lys Pro Gly Ala
  1               5                  10                  15

Ser Val Lys Val Ser Cys Arg Ala Ser Gly Asp Ser Val Ser Asn Tyr
                 20                  25                  30

Ala Ile Ser Trp Val Arg Gln Ala Pro Gly Gln Gly Leu Glu Trp Met
             35                  40                  45

Gly Ser Ile Ile Pro Ile Leu Gly Thr Thr Asp His Ala Gln Gln Phe
         50                  55                  60

Gln Asp Arg Val Thr Ile Thr Ala Asp Lys Ser Thr Ser Thr Ala Tyr
 65                  70                  75                  80

Met Glu Leu Gly Ser Leu Arg Ser Asp Asp Thr Ala Val Tyr Tyr Cys
                 85                  90                  95

Ala Arg Glu Arg Ile Ala Ala Arg Gln Asp Tyr Phe Asp Tyr Trp Gly
                100                 105                 110

Gln Gly Thr Leu Val Thr Val Ser Ser
            115                 120

<210> SEQ ID NO 116
<211> LENGTH: 121
<212> TYPE: PRT
<213> ORGANISM: Artificial Sequence
<220> FEATURE:
<223> OTHER INFORMATION: member of supercluster 1

<400> SEQUENCE: 116

Arg Cys Ser Met Val Gln Ser Gly Ala Glu Val Lys Lys Pro Gly Ser
  1               5                  10                  15

Ser Val Lys Val Ser Cys Lys Ala Ser Gly Gly Thr Phe Ser Asn Tyr
                 20                  25                  30

Ala Ile Ser Trp Val Arg Gln Ala Pro Gly Gln Gly Leu Glu Trp Met
             35                  40                  45

Gly Ser Ile Ile Pro Ile Leu Gly Thr Thr Asp His Ala Gln Lys Phe
         50                  55                  60

Gln Asp Arg Val Thr Ile Thr Ala Asp Arg Ser Ser Asn Thr Thr Tyr
 65                  70                  75                  80

Met Asp Leu Asn Ser Leu Arg Ser Asp Asp Thr Ala Val Tyr Tyr Cys
                 85                  90                  95

Ala Arg Glu Leu Ile Ala Ala Arg Leu Asp Tyr Phe Asp Ser Trp Gly
                100                 105                 110
```

```
Gln Gly Thr Leu Val Thr Val Ser Ser
        115                 120
```

<210> SEQ ID NO 117
<211> LENGTH: 121
<212> TYPE: PRT
<213> ORGANISM: Artificial Sequence
<220> FEATURE:
<223> OTHER INFORMATION: member of supercluster 1

<400> SEQUENCE: 117

```
Glu Val Gln Leu Val Gln Ser Gly Thr Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Thr Gln Lys Phe
    50                  55                  60

Gln Gly Arg Ile Thr Ile Thr Ala Asp Lys Ser Thr Asn Thr Ser Tyr
65                  70                  75                  80

Met Asp Leu Asn Ser Leu Arg Ser Asp Asp Thr Ala Val Tyr Tyr Cys
                85                  90                  95

Ala Arg Glu Arg Ile Ala Ala Arg Gln Asp Tyr Phe Asp Ser Trp Gly
            100                 105                 110

Gln Gly Thr Leu Val Thr Val Ser Ser
        115                 120
```

<210> SEQ ID NO 118
<211> LENGTH: 121
<212> TYPE: PRT
<213> ORGANISM: Artificial Sequence
<220> FEATURE:
<223> OTHER INFORMATION: member of supercluster 1

<400> SEQUENCE: 118

```
Arg Leu Gln Leu Val Gln Ser Gly Ala Glu Val Lys Lys Pro Gly Ser
1               5                   10                  15

Ser Val Lys Val Ser Cys Lys Ala Ser Gly Gly Thr Ser Thr Asn Asp
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Asn Phe
    50                  55                  60

Gln Asp Arg Val Thr Ile Thr Ala Asp Lys Ser Ser Asn Thr Thr Tyr
65                  70                  75                  80

Met Glu Leu Ile Gly Leu Lys Ser Asp Asp Thr Ala Val Tyr Tyr Cys
                85                  90                  95

Ala Arg Glu Arg Ile Ala Ala Arg Leu Asp Tyr Phe Asp Ser Trp Gly
            100                 105                 110

Gln Gly Thr Leu Val Thr Val Ser Ser
        115                 120
```

<210> SEQ ID NO 119
<211> LENGTH: 121
<212> TYPE: PRT
<213> ORGANISM: Artificial Sequence
<220> FEATURE:
<223> OTHER INFORMATION: member of supercluster 1

```
<400> SEQUENCE: 119

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ser Thr Asn Asp
            20                  25                  30

Ala Ile Ser Trp Val Arg Gln Thr Pro Glu Gln Gly Leu Glu Trp Met
        35                  40                  45

Gly Ser Ile Ile Pro Ile Leu Asp Thr Thr Asp His Ala Gln Lys Phe
    50                  55                  60

Gln Gly Arg Val Thr Ile Thr Ala Asp Arg Ser Thr Asn Thr Ala Tyr
65                  70                  75                  80

Met Glu Leu Asn Ser Leu Arg Ser Asp Asp Thr Ala Val Tyr Tyr Cys
                85                  90                  95

Ala Arg Glu Leu Ile Ala Ala Arg Leu Asp Tyr Phe Asp Ser Trp Gly
            100                 105                 110

Gln Gly Thr Leu Val Thr Val Ser Ser
            115                 120

<210> SEQ ID NO 120
<211> LENGTH: 121
<212> TYPE: PRT
<213> ORGANISM: Artificial Sequence
<220> FEATURE:
<223> OTHER INFORMATION: member of supercluster 1

<400> SEQUENCE: 120

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Asn Phe
    50                  55                  60

Gln Gly Arg Val Thr Ile Thr Ala Asp Arg Ser Ala Asn Thr Ala Tyr
65                  70                  75                  80

Met Glu Leu Asn Ser Leu Arg Ser Asp Asp Thr Ala Val Tyr Tyr Cys
                85                  90                  95

Ala Arg Glu His Ile Ala Ala Arg Gln Asp Tyr Phe Asp Tyr Trp Gly
            100                 105                 110

Gln Glu Thr Leu Val Thr Val Ser Ser
            115                 120

<210> SEQ ID NO 121
<211> LENGTH: 121
<212> TYPE: PRT
<213> ORGANISM: Artificial Sequence
<220> FEATURE:
<223> OTHER INFORMATION: member of supercluster 1

<400> SEQUENCE: 121

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Tyr
            20                  25                  30

Ala Ile Ser Trp Val Arg Gln Ala Pro Gly Gln Gly Leu Glu Trp Met
        35                  40                  45
```

-continued

```
Gly Ser Ile Ile Pro Ile Leu Gly Thr Thr Asp His Ala Gln Lys Phe
        50                  55                  60

Gln Gly Arg Val Thr Ile Thr Ala Asp Ile Ser Thr Ile Thr Ala Tyr
65                  70                  75                  80

Met Glu Leu Ser Ser Leu Arg Ser Asp Asp Thr Ala Ile Tyr Tyr Cys
                85                  90                  95

Ala Arg Glu Arg Ile Ala Ala Arg Gln Asp Tyr Phe Asp Phe Trp Gly
            100                 105                 110

Gln Gly Thr Leu Val Thr Val Ser Ser
            115                 120

<210> SEQ ID NO 122
<211> LENGTH: 121
<212> TYPE: PRT
<213> ORGANISM: Artificial Sequence
<220> FEATURE:
<223> OTHER INFORMATION: member of supercluster 1

<400> SEQUENCE: 122

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Lys Phe
        50                  55                  60

Gln Asp Arg Val Thr Ile Thr Ala Gly Lys Ser Asn Thr Thr Tyr
65                  70                  75                  80

Met Asp Leu Ser Ser Leu Arg Ser Asp Asp Thr Ala Val Tyr Tyr Cys
                85                  90                  95

Ala Arg Glu Arg Ile Ala Ala Arg Leu Asp Tyr Phe Asp Ser Trp Gly
            100                 105                 110

Gln Gly Thr Leu Val Thr Val Ser Ser
            115                 120

<210> SEQ ID NO 123
<211> LENGTH: 121
<212> TYPE: PRT
<213> ORGANISM: Artificial Sequence
<220> FEATURE:
<223> OTHER INFORMATION: member of supercluster 1

<400> SEQUENCE: 123

Gln Val Gln Leu Val Gln Ser Gly Ala Ala Val Lys Lys Pro Gly Ser
1               5                   10                  15

Ser Val Lys Val Ser Cys Lys Ala Ser Gly Gly Thr Ser Thr Asn Asp
            20                  25                  30

Ala Ile Ser Trp Val Arg Gln Thr Pro Gly Gln Gly Leu Glu Trp Met
        35                  40                  45

Gly Ser Ile Ile Pro Ile Leu Asp Thr Thr Asp His Ala Gln Lys Phe
        50                  55                  60

Gln Gly Arg Val Thr Ile Thr Ala Asp Lys Ser Thr Asn Thr Ala Tyr
65                  70                  75                  80

Met Glu Leu Asn Ser Leu Arg Ser Asp Asp Thr Ala Val Tyr Tyr Cys
                85                  90                  95

Ala Arg Glu His Ile Ala Ala Arg Gln Asp Tyr Phe Asp Tyr Trp Gly
            100                 105                 110
```

```
Gln Gly Thr Leu Val Thr Val Ser Ser
        115                 120
```

<210> SEQ ID NO 124
<211> LENGTH: 121
<212> TYPE: PRT
<213> ORGANISM: Artificial Sequence
<220> FEATURE:
<223> OTHER INFORMATION: member of supercluster 1

<400> SEQUENCE: 124

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Ser Thr Asn Asp
            20                  25                  30

Ala Ile Ser Trp Val Arg Gln Thr Pro Glu Gln Gly Leu Glu Trp Met
        35                  40                  45

Gly Ser Ile Ile Pro Ile Leu Gly Thr Val Asp His Ala Gln Lys Phe
    50                  55                  60

Gln Gly Arg Val Thr Ile Thr Ala Asp Lys Ser Thr Asn Thr Val Tyr
65                  70                  75                  80

Met Glu Leu Ser Ser Leu Arg Ser Asp Asp Thr Ala Val Tyr Tyr Cys
                85                  90                  95

Ala Arg Glu His Ile Ala Ala Arg Leu Asp Tyr Phe Asp Tyr Trp Asp
            100                 105                 110

Leu Gly Thr Leu Val Thr Val Ser Ser
        115                 120
```

<210> SEQ ID NO 125
<211> LENGTH: 121
<212> TYPE: PRT
<213> ORGANISM: Artificial Sequence
<220> FEATURE:
<223> OTHER INFORMATION: member of supercluster 1

<400> SEQUENCE: 125

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Ser Thr Asn Tyr
            20                  25                  30

Ala Ile Ser Trp Val Arg Gln Thr Pro Gly Gln Gly Leu Glu Trp Met
        35                  40                  45

Gly Ser Ile Ile Pro Ile Leu Gly Thr Thr Asp His Thr Gln Lys Phe
    50                  55                  60

Gln Asp Arg Val Thr Ile Thr Ala Asp Lys Ser Thr Asn Thr Ala Tyr
65                  70                  75                  80

Met Glu Leu Asn Ser Leu Arg Ser Asp Asp Thr Ala Val Tyr Tyr Cys
                85                  90                  95

Ala Arg Glu His Ile Ala Ser Arg Gln Asp Phe Phe Asp Tyr Trp Gly
            100                 105                 110

Gln Gly Thr Leu Val Thr Val Ser Ser
        115                 120
```

<210> SEQ ID NO 126
<211> LENGTH: 121
<212> TYPE: PRT
<213> ORGANISM: Artificial Sequence
<220> FEATURE:
<223> OTHER INFORMATION: member of supercluster 1

<400> SEQUENCE: 126

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Lys Phe
    50                  55                  60

Gln Asp Arg Val Thr Ile Thr Ala Asp Lys Ser Ser Asn Thr Thr Tyr
65                  70                  75                  80

Met Glu Leu Ser Ser Leu Arg Ser Asp Asp Thr Ala Val Tyr Tyr Cys
                85                  90                  95

Ala Arg Glu Arg Ile Ala Ala Arg Leu Asp Tyr Phe Asp Ser Trp Gly
            100                 105                 110

Gln Gly Thr Leu Val Thr Val Ser Ser
        115                 120

<210> SEQ ID NO 127
<211> LENGTH: 121
<212> TYPE: PRT
<213> ORGANISM: Artificial Sequence
<220> FEATURE:
<223> OTHER INFORMATION: member of supercluster 1

<400> SEQUENCE: 127

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Lys Phe
    50                  55                  60

Gln Asp Arg Val Thr Ile Thr Ala Asp Lys Ser Ser Asn Thr Thr Tyr
65                  70                  75                  80

Met Asp Leu Ser Ser Leu Arg Ser Asp Asp Thr Ala Val Tyr Tyr Cys
                85                  90                  95

Ala Arg Glu Arg Ile Ala Ala Arg Leu Asp Tyr Phe Asp Tyr Trp Gly
            100                 105                 110

Gln Gly Thr Leu Val Thr Val Ser Ser
        115                 120

<210> SEQ ID NO 128
<211> LENGTH: 128
<212> TYPE: PRT
<213> ORGANISM: Artificial Sequence
<220> FEATURE:
<223> OTHER INFORMATION: member of supercluster 1

<400> SEQUENCE: 128

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Glu Lys Phe
        50                  55                  60

Gln Gly Lys Val Thr Ile Thr Ala Asp Lys Ser Thr Ser Thr Ala Tyr
 65                  70                  75                  80

Met Asp Leu Ser Thr Ala Tyr Met Glu Leu Ser Ser Leu Arg Ser Asp
                85                  90                  95

Asp Thr Ala Val Tyr Tyr Cys Ala Arg Glu Phe Ile Ala Ala Arg Gln
            100                 105                 110

Asp Tyr Phe Asp Tyr Trp Gly Gln Gly Thr Leu Val Thr Val Ser Ser
            115                 120                 125

<210> SEQ ID NO 129
<211> LENGTH: 121
<212> TYPE: PRT
<213> ORGANISM: Artificial Sequence
<220> FEATURE:
<223> OTHER INFORMATION: member of supercluster 1

<400> SEQUENCE: 129

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
                20                  25                  30

Ala Ile Ser Trp Val Arg Gln Ala Pro Gly Gln Gly Leu Glu Trp Met
            35                  40                  45

Gly Ser Ile Ile Pro Ile Phe Gly Thr Ala Asp Asn Ala Gln Lys Phe
        50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Asp Asp Thr Ala Val Tyr Tyr Cys
                85                  90                  95

Ala Arg Glu Arg Ile Ala Ala Arg Gln Asp Tyr Phe Asp Tyr Trp Gly
            100                 105                 110

Gln Gly Thr Leu Val Thr Val Ser Ser
        115                 120

<210> SEQ ID NO 130
<211> LENGTH: 121
<212> TYPE: PRT
<213> ORGANISM: Artificial Sequence
<220> FEATURE:
<223> OTHER INFORMATION: member of supercluster 1

<400> SEQUENCE: 130

Glu Val Gln Leu Val Gln Ser Gly Ser Glu Leu Lys Lys Pro Gly Ser
 1               5                  10                  15

Ser Val Lys Val Ser Cys Lys Ala Ser Gly Gly Thr Ser Thr Asn Asp
                20                  25                  30

Ala Ile Ser Trp Val Arg Gln Thr Pro Gly Gln Gly Leu Glu Trp Met
            35                  40                  45

Gly Ser Ile Ile Pro Ile Leu Asp Thr Thr Asp His Ala Gln Lys Phe
        50                  55                  60

Gln Gly Arg Val Thr Ile Thr Ala Asp Arg Ser Thr Asn Thr Ala Tyr
 65                  70                  75                  80

Met Glu Leu Asn Ser Leu Lys Ser Asp Asp Thr Ala Val Tyr Tyr Cys
                85                  90                  95

Ala Arg Glu His Ile Ala Ala Arg Gln Asp Tyr Phe Asp Tyr Trp Gly 100             105             110

Gln Gly Thr Leu Val Thr Val Ser Ser
        115                 120

<210> SEQ ID NO 131
<211> LENGTH: 121
<212> TYPE: PRT
<213> ORGANISM: Artificial Sequence
<220> FEATURE:
<223> OTHER INFORMATION: member of supercluster 1

<400> SEQUENCE: 131

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ser Thr Asn Asp
            20                  25                  30

Ala Ile Ser Trp Val Arg Gln Thr Pro Gly Gln Gly Leu Glu Trp Met
        35                  40                  45

Gly Ser Ile Ile Pro Ile Leu Asp Thr Thr Asp His Ala Gln Lys Phe
    50                  55                  60

Gln Gly Arg Val Thr Ile Thr Ala Asp Arg Ser Thr Asn Thr Ala Tyr
65                  70                  75                  80

Met Glu Leu Asn Ser Leu Lys Ser Asp Asp Thr Ala Val Tyr Tyr Cys
                85                  90                  95

Ala Arg Glu His Ile Ala Ala Arg Gln Asp Tyr Phe Asp Tyr Trp Gly
            100                 105                 110

Gln Gly Thr Leu Val Thr Val Ser Ser
        115                 120

<210> SEQ ID NO 132
<211> LENGTH: 121
<212> TYPE: PRT
<213> ORGANISM: Artificial Sequence
<220> FEATURE:
<223> OTHER INFORMATION: member of supercluster 1

<400> SEQUENCE: 132

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Asn Phe
    50                  55                  60

Gln Asp Arg Val Thr Ile Thr Ala Asp Lys Ser Ser Asn Thr Thr Tyr
65                  70                  75                  80

Met Glu Leu Ser Ser Leu Arg Ser Asp Asp Thr Ala Val Tyr Tyr Cys
                85                  90                  95

Ala Arg Glu Arg Ile Ala Ala Arg Leu Asp Tyr Phe Asp Ser Trp Gly
            100                 105                 110

Gln Gly Thr Leu Val Thr Val Ser Ser
        115                 120

<210> SEQ ID NO 133
<211> LENGTH: 121
<212> TYPE: PRT
<213> ORGANISM: Artificial Sequence
<220> FEATURE:

<223> OTHER INFORMATION: member of supercluster 1

<400> SEQUENCE: 133

Glu Val Gln Leu Val Gln Ser Gly Ala Glu Val Lys Met Pro Gly Ser
1               5                   10                  15

Ser Val Lys Val Ser Cys Lys Ala Ser Gly Gly Thr Ser Thr Asn Asp
            20                  25                  30

Ala Ile Ser Trp Val Arg Gln Thr Pro Gly Gln Gly Leu Glu Trp Met
        35                  40                  45

Gly Ser Ile Ile Pro Ile Leu Asp Thr Thr Asp His Ala Gln Lys Phe
    50                  55                  60

Gln Gly Arg Val Thr Ile Thr Ala Asp Arg Ser Thr Asn Thr Ala Tyr
65                  70                  75                  80

Met Glu Leu Asn Ser Leu Lys Ser Asp Asp Thr Ala Val Tyr Tyr Cys
                85                  90                  95

Ala Arg Glu His Ile Ala Ala Arg Gln Asp Tyr Phe Asp Tyr Trp Gly
            100                 105                 110

Gln Gly Thr Leu Val Thr Val Ser Ser
        115                 120

<210> SEQ ID NO 134
<211> LENGTH: 121
<212> TYPE: PRT
<213> ORGANISM: Artificial Sequence
<220> FEATURE:
<223> OTHER INFORMATION: member of supercluster 1

<400> SEQUENCE: 134

Arg Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Tyr
            20                  25                  30

Ala Ile Asn Trp Val Arg Gln Ala Pro Gly Gln Gly Leu Glu Trp Met
        35                  40                  45

Gly Ser Ile Ile Pro Ile Leu Gly Thr Val Asp His Ala Gln Lys Phe
    50                  55                  60

Gln Gly Arg Val Thr Ile Thr Ala Asp Lys Ser Thr Asn Thr Val Tyr
65                  70                  75                  80

Met Glu Leu Ser Ser Leu Arg Ser Asp Asp Thr Ala Val Tyr Tyr Cys
                85                  90                  95

Ala Arg Glu His Ile Ala Ala Arg Leu Asp Tyr Phe Asp Tyr Trp Asp
            100                 105                 110

Leu Gly Thr Leu Val Thr Val Ser Ser
        115                 120

<210> SEQ ID NO 135
<211> LENGTH: 121
<212> TYPE: PRT
<213> ORGANISM: Artificial Sequence
<220> FEATURE:
<223> OTHER INFORMATION: member of supercluster 1

<400> SEQUENCE: 135

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met

```
              35                  40                  45
Gly Ser Ile Ile Pro Ile Leu Gly Thr Thr Asp His Ala Gln Lys Phe
        50                  55                  60

Gln Gly Arg Val Thr Phe Thr Ala Asp Lys Ser Thr Asn Thr Ser Tyr
 65                  70                  75                  80

Met Glu Leu Asn Ser Leu Arg Ser Asp Ser Ala Val Tyr Tyr Cys
                85                  90                  95

Ala Arg Glu Arg Ile Ala Ala Arg Gln Asp Tyr Phe Asp Ser Trp Gly
                100                 105                 110

Gln Gly Thr Leu Val Thr Val Ser Ser
            115                 120

<210> SEQ ID NO 136
<211> LENGTH: 121
<212> TYPE: PRT
<213> ORGANISM: Artificial Sequence
<220> FEATURE:
<223> OTHER INFORMATION: member of supercluster 1

<400> SEQUENCE: 136

Arg Val Gln Leu Val Gln Ser Gly Ser Glu Leu Lys Lys Pro Gly Ala
 1               5                  10                  15

Ser Val Lys Val Ser Cys Lys Ala Ser Gly Gly Thr Phe Ser Asn Tyr
                20                  25                  30

Ala Ile Ser Trp Val Arg Gln Ala Pro Gly Gln Gly Leu Glu Trp Met
            35                  40                  45

Gly Ser Ile Ile Pro Ile Leu Gly Thr Thr Asp His Ala Gln Lys Phe
        50                  55                  60

Gln Asp Arg Val Thr Ile Thr Ala Asp Lys Ser Ser Asn Thr Thr Tyr
 65                  70                  75                  80

Met Asp Leu Ser Ser Leu Arg Ser Asp Asp Thr Ala Val Tyr Tyr Cys
                85                  90                  95

Ala Arg Glu Arg Ile Ala Ala Arg Leu Asp Tyr Phe Asp Ser Trp Gly
                100                 105                 110

Gln Gly Thr Leu Val Thr Val Ser Ser
            115                 120

<210> SEQ ID NO 137
<211> LENGTH: 121
<212> TYPE: PRT
<213> ORGANISM: Artificial Sequence
<220> FEATURE:
<223> OTHER INFORMATION: member of supercluster 1

<400> SEQUENCE: 137

Arg Val Gln Leu Val Gln Ser Gly Ala Glu Val Lys Lys Pro Gly Ser
 1               5                  10                  15

Ser Val Lys Val Ser Cys Lys Ala Phe Gly Gly Thr Phe Asn Asn Tyr
                20                  25                  30

Ala Ile Asn Trp Val Arg Gln Ala Pro Gly Gln Gly Leu Glu Trp Met
            35                  40                  45

Gly Ser Ile Ile Pro Ile Leu Gly Thr Val Asp His Ala Gln Lys Phe
        50                  55                  60

Gln Gly Arg Val Thr Ile Thr Ala Asp Lys Ser Thr Asn Thr Val Tyr
 65                  70                  75                  80

Met Glu Leu Ser Ser Leu Arg Ser Asp Asp Thr Ala Val Tyr Tyr Cys
                85                  90                  95
```

Ala Arg Glu His Ile Ala Ala Arg Leu Asp Tyr Phe Asp Tyr Trp Asp
            100                 105                 110

Leu Gly Thr Leu Val Thr Val Ser Ser
        115                 120

<210> SEQ ID NO 138
<211> LENGTH: 121
<212> TYPE: PRT
<213> ORGANISM: Artificial Sequence
<220> FEATURE:
<223> OTHER INFORMATION: member of supercluster 1

<400> SEQUENCE: 138

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Ala Asp His Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Glu Arg Ile Ala Ala Arg Gln Asp Tyr Phe Asp Tyr Trp Gly
            100                 105                 110

Gln Gly Thr Leu Val Thr Val Ser Ser
        115                 120

<210> SEQ ID NO 139
<211> LENGTH: 128
<212> TYPE: PRT
<213> ORGANISM: Artificial Sequence
<220> FEATURE:
<223> OTHER INFORMATION: member of supercluster 1

<400> SEQUENCE: 139

Glu Val Gln Leu Val Gln Ser Gly Thr Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Glu Lys Phe
    50                  55                  60

Gln Gly Arg Val Thr Ile Thr Ala Asp Lys Ser Thr Ser Thr Ala Tyr
65                  70                  75                  80

Met Asp Leu Ser Thr Ala Tyr Met Glu Leu Ser Ser Leu Arg Ser Asp
                85                  90                  95

Asp Thr Ala Val Tyr Tyr Cys Ala Arg Glu Phe Ile Ala Ala Arg Gln
            100                 105                 110

Asp Tyr Phe Asp Tyr Trp Gly Gln Gly Thr Leu Val Thr Val Ser Ser
        115                 120                 125

<210> SEQ ID NO 140
<211> LENGTH: 121
<212> TYPE: PRT
<213> ORGANISM: Artificial Sequence

```
<220> FEATURE:
<223> OTHER INFORMATION: member of supercluster 1

<400> SEQUENCE: 140

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Val Asp His Ala Gln Lys Phe
    50                  55                  60

Gln Gly Arg Val Thr Ile Thr Ala Asp Lys Ser Thr Asn Thr Val Tyr
65                  70                  75                  80

Met Glu Leu Ser Ser Leu Arg Ser Asp Asp Thr Ala Val Tyr Tyr Cys
                85                  90                  95

Ala Arg Glu His Ile Ala Ala Arg Leu Asp Tyr Phe Asp Tyr Trp Asp
            100                 105                 110

Leu Gly Thr Leu Val Thr Val Ser Ser
        115                 120

<210> SEQ ID NO 141
<211> LENGTH: 121
<212> TYPE: PRT
<213> ORGANISM: Artificial Sequence
<220> FEATURE:
<223> OTHER INFORMATION: member of supercluster 1

<400> SEQUENCE: 141

Glu Val Gln Leu Val Gln Ser Gly Ala Glu Val Lys Lys Pro Glu Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Lys Phe
    50                  55                  60

Gln Asp Arg Val Thr Ile Thr Ala Asp Lys Ser Ser Asn Thr Thr Tyr
65                  70                  75                  80

Met Glu Leu Ser Ser Leu Arg Ser Asp Asp Thr Ala Val Tyr Tyr Cys
                85                  90                  95

Ala Arg Glu His Ile Ala Ala Arg Leu Asp Tyr Phe Asp Ser Trp Gly
            100                 105                 110

Gln Gly Thr Leu Val Thr Val Ser Ser
        115                 120

<210> SEQ ID NO 142
<211> LENGTH: 121
<212> TYPE: PRT
<213> ORGANISM: Artificial Sequence
<220> FEATURE:
<223> OTHER INFORMATION: member of supercluster 1

<400> SEQUENCE: 142

Glu Val Gln Leu Val Gln Ser Gly Thr Glu Val Arg Lys Pro Gly Ser
1               5                   10                  15

Ser Val Lys Val Ser Cys Lys Ala Ser Gly Gly Thr Phe Ser Asn Tyr
            20                  25                  30
```

```
Ala Ile Ser Trp Val Arg Gln Ala Pro Gly Gln Gly Leu Glu Trp Met
            35                  40                  45

Gly Ser Ile Ile Pro Ile Leu Gly Thr Thr Asp His Ala Gln Lys Phe
 50                  55                  60

Gln Asp Arg Val Thr Ile Thr Ala Asp Lys Ser Ser Asn Thr Thr Tyr
 65                  70                  75                  80

Met Glu Leu Ser Ser Leu Arg Ser Asp Asp Thr Ala Val Tyr Tyr Cys
                 85                  90                  95

Ala Arg Glu Tyr Ile Ala Ala Arg Leu Asp Tyr Phe Asp Ser Trp Gly
                100                 105                 110

Gln Gly Thr Leu Val Thr Val Ser Ser
            115                 120

<210> SEQ ID NO 143
<211> LENGTH: 121
<212> TYPE: PRT
<213> ORGANISM: Artificial Sequence
<220> FEATURE:
<223> OTHER INFORMATION: member of supercluster 1

<400> SEQUENCE: 143

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
                20                  25                  30

Ala Ile Ser Trp Val Arg Gln Ala Pro Gly Gln Gly Leu Glu Trp Met
            35                  40                  45

Gly Ser Ile Ile Pro Ile Leu Gly Thr Thr Asp His Ala Glu Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Glu Phe Ile Ala Ala Arg Gln Asp Tyr Phe Asp Tyr Trp Gly
                100                 105                 110

Gln Gly Thr Leu Val Thr Val Ser Ser
            115                 120

<210> SEQ ID NO 144
<211> LENGTH: 121
<212> TYPE: PRT
<213> ORGANISM: Artificial Sequence
<220> FEATURE:
<223> OTHER INFORMATION: member of supercluster 1

<400> SEQUENCE: 144

Glu Val Gln Leu Val Gln Ser Gly Ala Glu Val Lys Lys Pro Gly Ser
 1               5                  10                  15

Ser Val Lys Val Ser Cys Lys Ser Ser Gly Gly Thr Phe Lys Asn Tyr
                20                  25                  30

Ala Ile Ser Trp Val Arg Gln Ala Pro Gly Gln Gly Leu Glu Trp Met
            35                  40                  45

Gly Ser Ile Ile Pro Ile Leu Gly Thr Thr Asp His Ala Gln Asn Phe
 50                  55                  60

Gln Asp Arg Val Thr Ile Thr Ala Asp Lys Leu Ser Asn Thr Thr Tyr
 65                  70                  75                  80

Met Glu Leu Ser Ser Leu Arg Ser Asp Asp Thr Ala Val Tyr Tyr Cys
                 85                  90                  95
```

Ala Arg Glu Arg Ile Ala Ala Arg Leu Asp Tyr Phe Asp Ser Trp Gly
            100                 105                 110

Gln Gly Thr Leu Val Thr Val Ser Ser
        115                 120

<210> SEQ ID NO 145
<211> LENGTH: 121
<212> TYPE: PRT
<213> ORGANISM: Artificial Sequence
<220> FEATURE:
<223> OTHER INFORMATION: member of supercluster 1

<400> SEQUENCE: 145

Glu Val Gln Leu Val Gln Ser Gly Ala Glu Val Lys Lys Pro Gly Ser
1               5                   10                  15

Ser Val Lys Val Ser Cys Glu Ala Ser Gly Gly Thr Phe Thr Asn Tyr
            20                  25                  30

Ala Ile Ser Trp Val Arg Gln Ala Pro Gly Gln Gly Leu Glu Trp Met
        35                  40                  45

Gly Ser Ile Ile Pro Val Leu Gly Thr Thr Asp His Ala Gln Lys Phe
    50                  55                  60

Gln Asp Arg Val Thr Ile Thr Ala Asp Lys Ser Ser Asn Ile Thr Tyr
65                  70                  75                  80

Met Glu Leu Ser Ser Leu Arg Ser Asp Asp Thr Ala Val Tyr Tyr Cys
                85                  90                  95

Ala Arg Glu Arg Ile Ala Ala Arg Leu Asp Tyr Phe Asp Ser Trp Gly
            100                 105                 110

Gln Gly Thr Leu Val Thr Val Ser Ser
        115                 120

<210> SEQ ID NO 146
<211> LENGTH: 121
<212> TYPE: PRT
<213> ORGANISM: Artificial Sequence
<220> FEATURE:
<223> OTHER INFORMATION: member of supercluster 1

<400> SEQUENCE: 146

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ser Thr Asn Tyr
            20                  25                  30

Ala Ile Ser Trp Val Arg Gln Thr Pro Gly Gln Gly Leu Glu Trp Met
        35                  40                  45

Gly Ser Ile Ile Pro Ile Leu Asp Thr Thr Asp His Ala Gln Lys Phe
    50                  55                  60

Gln Gly Arg Val Thr Ile Thr Ala Asp Lys Ser Thr Asn Thr Thr Tyr
65                  70                  75                  80

Met Glu Leu Asn Ser Leu Arg Ser Asp Asp Thr Ala Val Tyr Tyr Cys
                85                  90                  95

Ala Arg Glu His Ile Ala Ala Arg Leu Asp Tyr Phe Asp Tyr Trp Gly
            100                 105                 110

Gln Gly Thr Leu Val Thr Val Ser Ser
        115                 120

<210> SEQ ID NO 147
<211> LENGTH: 121
<212> TYPE: PRT

<213> ORGANISM: Artificial Sequence
<220> FEATURE:
<223> OTHER INFORMATION: member of supercluster 1

<400> SEQUENCE: 147

Glu Val Gln Leu Val Gln Ser Gly Ser Glu Leu Lys Lys Pro Gly Ser
1               5                   10                  15

Ser Val Lys Val Ser Cys Lys Ala Ser Gly Gly Thr Phe Ser Asn Tyr
                20                  25                  30

Ala Ile Ser Trp Val Arg Gln Ala Pro Gly Gln Gly Leu Glu Trp Met
            35                  40                  45

Gly Ser Ile Ile Pro Ile Leu Gly Thr Thr Asp His Ala Gln Lys Phe
    50                  55                  60

Gln Asp Arg Val Thr Ile Thr Ala Asp Lys Ser Ser Asn Thr Thr Tyr
65                  70                  75                  80

Met Asp Leu Ser Ser Leu Arg Ser Asp Thr Ala Val Tyr Tyr Cys
                85                  90                  95

Ala Arg Glu Arg Ile Ala Ala Arg Leu Asp Tyr Phe Asp Ser Trp Gly
            100                 105                 110

Gln Gly Thr Leu Val Thr Val Ser Ser
        115                 120

<210> SEQ ID NO 148
<211> LENGTH: 121
<212> TYPE: PRT
<213> ORGANISM: Artificial Sequence
<220> FEATURE:
<223> OTHER INFORMATION: member of supercluster 1

<400> SEQUENCE: 148

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
                20                  25                  30

Ala Ile Ser Trp Val Arg Gln Ala Pro Gly Gln Gly Leu Glu Trp Met
            35                  40                  45

Gly Ser Ile Ile Pro Ile Leu Gly Thr Thr Asp His Val Glu Lys Phe
    50                  55                  60

Gln Asp Arg Val Thr Ile Thr Ala Asp Lys Ser Ser Asn Thr Thr Tyr
65                  70                  75                  80

Met Glu Leu Ser Ser Leu Arg Ser Asp Asp Thr Ala Val Tyr Tyr Cys
                85                  90                  95

Ala Arg Glu Leu Ile Ala Ala Arg Leu Asp Tyr Phe Asp Ser Trp Gly
            100                 105                 110

Gln Gly Thr Leu Val Thr Val Ser Ser
        115                 120

<210> SEQ ID NO 149
<211> LENGTH: 121
<212> TYPE: PRT
<213> ORGANISM: Artificial Sequence
<220> FEATURE:
<223> OTHER INFORMATION: member of supercluster 1

<400> SEQUENCE: 149

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
                20                  25                  30

Ala Ile Ser Trp Val Arg Gln Ala Pro Gly Gln Gly Leu Glu Trp Met
             35                  40                  45

Gly Ser Ile Ile Pro Ile Leu Gly Thr Thr Asp His Ala Gln Lys Phe
         50                  55                  60

Gln Gly Arg Val Thr Phe Thr Ala Asp Lys Ser Thr Asn Thr Ser Tyr
65                  70                  75                  80

Met Glu Leu Asn Ser Leu Arg Ser Asp Asp Ser Ala Val Tyr Tyr Cys
                 85                  90                  95

Ala Arg Glu Arg Ile Ala Ala Arg Gln Asp Tyr Phe Asp Ser Trp Gly
            100                 105                 110

Gln Gly Thr Leu Val Thr Val Ser Ser
            115                 120

<210> SEQ ID NO 150
<211> LENGTH: 121
<212> TYPE: PRT
<213> ORGANISM: Artificial Sequence
<220> FEATURE:
<223> OTHER INFORMATION: member of supercluster 1

<400> SEQUENCE: 150

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ser Thr Asn Asp
            20                  25                  30

Ala Ile Ser Trp Val Arg Gln Thr Pro Glu Gln Gly Leu Glu Trp Met
             35                  40                  45

Gly Ser Ile Ile Pro Ile Leu Asp Thr Thr Asp His Ala Gln Lys Phe
         50                  55                  60

Gln Gly Arg Val Thr Ile Thr Ala Asp Arg Ser Thr Asn Thr Ala Tyr
65                  70                  75                  80

Met Glu Leu Asn Ser Leu Arg Ser Asp Asp Thr Ala Val Tyr Tyr Cys
                 85                  90                  95

Ala Arg Glu His Ile Ala Ala Arg Gln Asp Tyr Phe Asp Tyr Trp Gly
            100                 105                 110

Gln Gly Thr Leu Val Thr Val Ser Ser
            115                 120

<210> SEQ ID NO 151
<211> LENGTH: 121
<212> TYPE: PRT
<213> ORGANISM: Artificial Sequence
<220> FEATURE:
<223> OTHER INFORMATION: member of supercluster 1

<400> SEQUENCE: 151

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
             35                  40                  45

Gly Ser Ile Ile Pro Ile Leu Asp Thr Thr Asp His Ala Gln Lys Phe
         50                  55                  60

Gln Gly Arg Val Thr Ile Thr Ala Asp Lys Ser Thr Asn Thr Ala Tyr
65                  70                  75                  80

Met Glu Leu Asn Ser Leu Arg Ser Asp Asp Thr Ala Val Tyr Tyr Cys 85                  90                  95

Ala Arg Glu His Ile Ala Ala Arg Gln Asp Tyr Phe Asp Tyr Trp Gly
                100                 105                 110

Gln Gly Thr Leu Val Thr Val Ser Ser
        115                 120

<210> SEQ ID NO 152
<211> LENGTH: 121
<212> TYPE: PRT
<213> ORGANISM: Artificial Sequence
<220> FEATURE:
<223> OTHER INFORMATION: member of supercluster 1

<400> SEQUENCE: 152

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
                20                  25                  30

Ala Ile Ser Trp Val Arg Gln Ala Pro Gly Gln Gly Leu Glu Trp Met
            35                  40                  45

Gly Ser Ile Ile Pro Ile Leu Gly Thr Thr Asp His Ala Gln Lys Phe
    50                  55                  60

Gln Gly Arg Val Thr Phe Thr Ala Asp Lys Ser Thr Asn Thr Ser Tyr
65                  70                  75                  80

Met Glu Leu Asn Ser Leu Arg Ser Asp Asp Ser Ala Val Tyr Tyr Cys
                85                  90                  95

Ala Arg Glu Arg Ile Ala Ala Arg Gln Asp Tyr Phe Asp Ser Trp Gly
                100                 105                 110

Gln Gly Thr Leu Val Thr Val Ser Ser
        115                 120

<210> SEQ ID NO 153
<211> LENGTH: 121
<212> TYPE: PRT
<213> ORGANISM: Artificial Sequence
<220> FEATURE:
<223> OTHER INFORMATION: member of supercluster 1

<400> SEQUENCE: 153

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
                20                  25                  30

Ala Ile Ser Trp Val Arg Gln Ala Pro Gly Gln Gly Leu Glu Trp Met
            35                  40                  45

Gly Ser Ile Ile Pro Ile Leu Gly Thr Thr Asp His Ala Gln Lys Phe
    50                  55                  60

Gln Asp Arg Val Thr Ile Thr Ala Asp Lys Ser Ser Lys Thr Thr Tyr
65                  70                  75                  80

Met Glu Leu Asn Ser Leu Arg Ser Asp Asp Thr Ala Val Tyr Tyr Cys
                85                  90                  95

Ala Arg Glu Leu Ile Ala Ala Arg Leu Asp Tyr Phe Asp Ser Trp Gly
                100                 105                 110

Gln Gly Thr Leu Val Thr Val Ser Ser
        115                 120

<210> SEQ ID NO 154
<211> LENGTH: 121

<212> TYPE: PRT
<213> ORGANISM: Artificial Sequence
<220> FEATURE:
<223> OTHER INFORMATION: member of supercluster 1

<400> SEQUENCE: 154

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Thr Pro Glu Gln Gly Leu Glu Trp Met
        35                  40                  45

Gly Ser Ile Ile Pro Ile Leu Asp Thr Thr Asp His Ala Gln Lys Phe
    50                  55                  60

Gln Gly Arg Val Thr Ile Thr Ala Asp Arg Ser Thr Asn Thr Ala Tyr
65                  70                  75                  80

Met Glu Leu Asn Ser Leu Arg Ser Asp Asp Thr Ala Val Tyr Tyr Cys
                85                  90                  95

Ala Arg Glu His Ile Ala Ala Arg Gln Asp Tyr Phe Asp Tyr Trp Gly
            100                 105                 110

Gln Gly Thr Leu Val Thr Val Ser Ser
        115                 120

<210> SEQ ID NO 155
<211> LENGTH: 121
<212> TYPE: PRT
<213> ORGANISM: Artificial Sequence
<220> FEATURE:
<223> OTHER INFORMATION: member of supercluster 1

<400> SEQUENCE: 155

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Ser Ile Ile Pro Ile Leu Gly Thr Thr Asp His Ala Gln Lys Phe
    50                  55                  60

Gln Asp Arg Val Thr Ile Thr Ala Asp Lys Ser Ser Asn Thr Thr Tyr
65                  70                  75                  80

Met Glu Leu Ser Ser Leu Arg Ser Asp Asp Thr Ala Val Tyr Tyr Cys
                85                  90                  95

Ala Arg Glu His Ile Ala Ala Arg Leu Asp Tyr Phe Asp Ser Trp Gly
            100                 105                 110

Gln Gly Thr Leu Val Thr Val Ser Ser
        115                 120

<210> SEQ ID NO 156
<211> LENGTH: 121
<212> TYPE: PRT
<213> ORGANISM: Artificial Sequence
<220> FEATURE:
<223> OTHER INFORMATION: member of supercluster 1

<400> SEQUENCE: 156

Arg Val Gln Leu Val Gln Ser Gly Ala Glu Val Lys Lys Pro Gly Ser
1               5                   10                  15

Ser Val Lys Val Ser Cys Arg Ala Ser Gly Asp Ser Val Ser Asn Tyr

```
                20                  25                  30
Ala Ile Ser Trp Val Arg Gln Ala Pro Gly Gln Gly Leu Glu Trp Met
            35                  40                  45

Gly Ser Ile Ile Pro Ile Leu Gly Thr Thr Asp His Ala Gln Gln Phe
        50                  55                  60

Gln Asp Arg Val Thr Ile Thr Ala Asp Lys Ser Thr Ser Thr Ala Tyr
65                  70                  75                  80

Met Glu Leu Gly Ser Leu Arg Ser Asp Asp Thr Ala Val Tyr Tyr Cys
                85                  90                  95

Ala Arg Glu Arg Ile Ala Ala Arg Gln Asp Tyr Phe Asp Tyr Trp Gly
            100                 105                 110

Gln Gly Thr Leu Val Thr Val Ser Ser
            115                 120

<210> SEQ ID NO 157
<211> LENGTH: 99
<212> TYPE: PRT
<213> ORGANISM: Artificial Sequence
<220> FEATURE:
<223> OTHER INFORMATION: VH4-390256-AEHJ6

<400> SEQUENCE: 157

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 158
<211> LENGTH: 126
<212> TYPE: PRT
<213> ORGANISM: Artificial Sequence
<220> FEATURE:
<223> OTHER INFORMATION: member of supercluster 8

<400> SEQUENCE: 158

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser Ser
            20                  25                  30

Ser Ser Tyr Trp Gly Trp Ile Arg Gln Pro Pro Gly Lys Gly Leu Glu
        35                  40                  45

Trp Ile Gly Ser Phe Tyr Tyr Ser Gly Asn Thr Tyr Tyr Asn Pro Ser
    50                  55                  60

Leu Lys Ser Arg Val Thr Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Thr Tyr Ser Ser Ser Trp Asp Gly Val Leu Tyr Tyr
```

100                 105                 110

Phe Asp Tyr Trp Gly Gln Gly Thr Leu Val Thr Val Ser Ser
            115                 120                 125

<210> SEQ ID NO 159
<211> LENGTH: 126
<212> TYPE: PRT
<213> ORGANISM: Artificial Sequence
<220> FEATURE:
<223> OTHER INFORMATION: member of supercluster 8

<400> SEQUENCE: 159

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser Ser
            20                  25                  30

Ser Ser Tyr Trp Gly Trp Ile Arg Gln Pro Pro Gly Lys Gly Leu Glu
        35                  40                  45

Trp Ile Gly Ser Phe Tyr Tyr Ser Gly Asn Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Thr Tyr Ser Ser Ser Trp Asp Gly Val Leu Tyr Tyr
            100                 105                 110

Phe Asp Tyr Trp Gly Gln Gly Thr Leu Val Thr Val Ser Ser
            115                 120                 125

<210> SEQ ID NO 160
<211> LENGTH: 124
<212> TYPE: PRT
<213> ORGANISM: Artificial Sequence
<220> FEATURE:
<223> OTHER INFORMATION: member of supercluster 8

<400> SEQUENCE: 160

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Tyr Trp Gly Trp Ile Arg Gln Pro Pro Gly Lys Gly Leu Glu Trp Ile
        35                  40                  45

Gly Ser Phe Tyr Tyr Ser Gly Asn Thr Tyr Tyr Asn Pro Ser Leu Lys
    50                  55                  60

Ser Arg Val Thr Ile Ser Glu Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gln Thr Tyr Ser Ser Ser Trp Asp Gly Val Leu Tyr Tyr Phe Asp
            100                 105                 110

Tyr Trp Gly Gln Gly Thr Leu Val Thr Val Ser Ser
            115                 120

<210> SEQ ID NO 161
<211> LENGTH: 109
<212> TYPE: PRT
<213> ORGANISM: Artificial Sequence
<220> FEATURE:

-continued

<223> OTHER INFORMATION: member of supercluster10

<400> SEQUENCE: 161

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Gly Gln Gly Thr Thr Val Thr Val Ser Ser
            100                 105

<210> SEQ ID NO 162
<211> LENGTH: 127
<212> TYPE: PRT
<213> ORGANISM: Artificial Sequence
<220> FEATURE:
<223> OTHER INFORMATION: member of supercluster10

<400> SEQUENCE: 162

Glu Val Gln Leu Val Gln Ser Gly Ser Lys Leu Lys Lys Pro Gly Ala
1               5                   10                  15

Ser Val Lys Val Ser Cys Lys Ala Ser Gly Tyr Thr Phe Thr Ser Tyr
            20                  25                  30

Thr Met Asn Trp Val Arg Gln Ala Pro Gly Gln Gly Leu Glu Trp Met
        35                  40                  45

Gly Trp Ile Asn Thr Asp Thr Gly Asp Pro Thr Tyr Ala Gln Gly Phe
    50                  55                  60

Thr Gly Arg Phe Val Phe Ser Leu Asp Thr Ser Val Ser Thr Ala Phe
65                  70                  75                  80

Leu Gln Ile Asn Ser Leu Lys Ala Glu Asp Thr Ala Val Tyr Tyr Cys
                85                  90                  95

Ala Arg Gly Asp Cys Asp Ser Ser Cys Tyr Arg Tyr Ser Tyr Gly
            100                 105                 110

Tyr Glu Asp Tyr Trp Gly Gln Gly Thr Leu Val Thr Val Ser Ser
        115                 120                 125

<210> SEQ ID NO 163
<211> LENGTH: 127
<212> TYPE: PRT
<213> ORGANISM: Artificial Sequence
<220> FEATURE:
<223> OTHER INFORMATION: member of supercluster10

<400> SEQUENCE: 163

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asp Thr Gly Asp Pro Thr Tyr Ala Gln Gly Phe

```
                  50                  55                  60

Thr Gly Arg Phe Val Phe Ser Leu Asp Thr Ser Val Ser Thr Ala Phe
 65                  70                  75                  80

Leu Gln Ile Asn Ser Leu Lys Ala Glu Asp Thr Ala Val Tyr Tyr Cys
                 85                  90                  95

Ala Arg Gly Asp Cys Asp Ser Thr Ser Cys Tyr Arg Tyr Ser Tyr Gly
                100                 105                 110

Tyr Glu Asp Tyr Trp Gly Gln Gly Thr Leu Val Thr Val Ser Ser
            115                 120                 125

<210> SEQ ID NO 164
<211> LENGTH: 127
<212> TYPE: PRT
<213> ORGANISM: Artificial Sequence
<220> FEATURE:
<223> OTHER INFORMATION: member of supercluster10

<400> SEQUENCE: 164

Glu Val Gln Leu Val Gln Ser Gly Ser Ala Leu Lys Lys Pro Gly Ala
 1               5                  10                  15

Ser Val Lys Val Ser Cys Lys Ala Ser Gly Tyr Thr Phe Thr Ser Tyr
                20                  25                  30

Thr Met Asn Trp Val Arg Ala Gln Pro Gly Gln Gly Leu Glu Trp Met
             35                  40                  45

Gly Trp Ile Asn Thr Gln Thr Gly Asn Pro Thr Tyr Ala Gln Gly Phe
         50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Gly Asp Cys Ser Ser Thr Ser Cys Tyr Arg Tyr Ser Tyr Gly
                100                 105                 110

Tyr Glu Asp Tyr Trp Gly Gln Gly Thr Leu Val Thr Val Ser Ser
            115                 120                 125

<210> SEQ ID NO 165
<211> LENGTH: 127
<212> TYPE: PRT
<213> ORGANISM: Artificial Sequence
<220> FEATURE:
<223> OTHER INFORMATION: member of supercluster10

<400> SEQUENCE: 165

Glu Val Gln Leu Val Gln Ser Gly Ser Thr Leu Lys Lys Pro Gly Ala
 1               5                  10                  15

Ser Val Lys Val Ser Cys Lys Ala Ser Gly Tyr Thr Phe Thr Ser Tyr
                20                  25                  30

Thr Met Asn Trp Val Arg Gln Ala Pro Gly Gln Gly Leu Glu Trp Met
             35                  40                  45

Gly Trp Ile Asp Thr Asn Thr Gly Asp Pro Thr Tyr Ala Gln Gly Phe
         50                  55                  60

Thr Gly Arg Phe Val Phe Ser Leu Asp Thr Ser Val Thr Thr Ala Phe
 65                  70                  75                  80

Leu Gln Ile Asn Ser Leu Lys Ala Glu Asp Thr Ala Val Tyr Tyr Cys
                 85                  90                  95

Ala Arg Gly Asp Cys Asp Ser Thr Ser Cys Tyr Arg Tyr Ser Tyr Gly
                100                 105                 110
```

Tyr Glu Asp Tyr Trp Gly Gln Gly Thr Leu Val Thr Val Ser Ser
            115                 120                 125

<210> SEQ ID NO 166
<211> LENGTH: 127
<212> TYPE: PRT
<213> ORGANISM: Artificial Sequence
<220> FEATURE:
<223> OTHER INFORMATION: member of supercluster10

<400> SEQUENCE: 166

Gly Cys Ser Met Val Gln Ser Gly Ser Glu Ser Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Phe
65                  70                  75                  80

Leu Gln Ile Asn Ser Leu Lys Ala Glu Asp Thr Ala Val Tyr Tyr Cys
                85                  90                  95

Ala Arg Gly Asp Cys Asp Ser Thr Ser Cys Tyr Arg Tyr Ser Tyr Gly
            100                 105                 110

Tyr Glu Asp Tyr Trp Gly Gln Gly Thr Leu Val Thr Val Ser Ser
            115                 120                 125

<210> SEQ ID NO 167
<211> LENGTH: 127
<212> TYPE: PRT
<213> ORGANISM: Artificial Sequence
<220> FEATURE:
<223> OTHER INFORMATION: member of supercluster10

<400> SEQUENCE: 167

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Thr Thr Ala Phe
65                  70                  75                  80

Leu Gln Ile Asn Ser Leu Lys Ala Glu Asp Thr Ala Val Tyr Tyr Cys
                85                  90                  95

Ala Arg Gly Asp Cys Asp Ser Thr Ser Cys Tyr Arg Tyr Ser Tyr Gly
            100                 105                 110

Tyr Glu Asp Tyr Trp Gly Gln Gly Thr Leu Val Thr Val Ser Ser
            115                 120                 125

<210> SEQ ID NO 168
<211> LENGTH: 127
<212> TYPE: PRT
<213> ORGANISM: Artificial Sequence
<220> FEATURE:
<223> OTHER INFORMATION: member of supercluster10

<400> SEQUENCE: 168

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Tyr Ala Gln Gly Phe
    50                  55                  60

Thr Gly Arg Phe Val Phe Ser Leu Asp Thr Ser Val Ser Thr Ala Phe
65                  70                  75                  80

Leu Gln Ile Asn Ser Leu Lys Ala Glu Asp Thr Ala Val Tyr Tyr Cys
                85                  90                  95

Ala Arg Gly Asp Cys Asp Ser Ser Cys Tyr Arg Tyr Ser Tyr Gly
            100                 105                 110

Tyr Glu Asp Tyr Trp Gly Gln Gly Thr Leu Val Thr Val Ser Ser
            115                 120                 125

<210> SEQ ID NO 169
<211> LENGTH: 127
<212> TYPE: PRT
<213> ORGANISM: Artificial Sequence
<220> FEATURE:
<223> OTHER INFORMATION: member of supercluster10

<400> SEQUENCE: 169

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Tyr Thr Gly Asp Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Asn Asn Leu Lys Ala Glu Asp Thr Ala Val Tyr Tyr Cys
                85                  90                  95

Ala Arg Gly Asp Cys Ser Ser Thr Ser Cys Tyr Arg Tyr Ser Tyr Gly
            100                 105                 110

Tyr Glu Asp Tyr Trp Gly Gln Gly Thr Leu Val Thr Val Ser Ser
            115                 120                 125

<210> SEQ ID NO 170
<211> LENGTH: 127
<212> TYPE: PRT
<213> ORGANISM: Artificial Sequence
<220> FEATURE:
<223> OTHER INFORMATION: member of supercluster10

<400> SEQUENCE: 170

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asp Thr Gly Asp Pro Thr Tyr Ala Gln Gly Phe
            50                  55                  60

Thr Gly Arg Phe Val Phe Ser Leu Asp Thr Ser Val Ser Thr Ala Phe
 65                  70                  75                  80

Leu Gln Ile Asn Ser Leu Lys Ala Glu Asp Thr Ala Val Tyr Tyr Cys
                85                  90                  95

Ala Arg Gly Asp Cys Asp Ser Thr Ser Cys Tyr Arg Tyr Ser Tyr Gly
            100                 105                 110

Tyr Glu Asp Tyr Trp Gly Gln Gly Thr Leu Val Thr Val Ser Ser
            115                 120                 125

<210> SEQ ID NO 171
<211> LENGTH: 127
<212> TYPE: PRT
<213> ORGANISM: Artificial Sequence
<220> FEATURE:
<223> OTHER INFORMATION: member of supercluster10

<400> SEQUENCE: 171

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Ser Tyr
                20                  25                  30

Thr Met Asn Trp Val Arg Gln Ala Pro Gly Gln Gly Leu Glu Trp Met
            35                  40                  45

Gly Trp Ile Asp Thr Asn Thr Gly Asp Pro Thr Tyr Ala Gln Gly Phe
            50                  55                  60

Thr Gly Arg Phe Val Phe Ser Leu Asp Thr Ser Val Thr Thr Ala Phe
 65                  70                  75                  80

Leu Gln Ile Asn Ser Leu Lys Ala Glu Asp Thr Ala Val Tyr Tyr Cys
                85                  90                  95

Ala Arg Gly Asp Cys Asp Ser Thr Ser Cys Tyr Arg Tyr Ser Tyr Gly
            100                 105                 110

Tyr Glu Asp Tyr Trp Gly Gln Gly Thr Leu Val Thr Val Ser Ser
            115                 120                 125

<210> SEQ ID NO 172
<211> LENGTH: 127
<212> TYPE: PRT
<213> ORGANISM: Artificial Sequence
<220> FEATURE:
<223> OTHER INFORMATION: member of supercluster10

<400> SEQUENCE: 172

Glu Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
                20                  25                  30

Ala Leu Asn Trp Val Arg Gln Ala Pro Gly Gln Gly Leu Glu Trp Met
            35                  40                  45

Gly Trp Ile Asn Thr Asn Thr Gly Asp Pro Thr Tyr Ala Gln Gly Phe
            50                  55                  60

Thr Gly Arg Phe Val Phe Ser Leu Asp Thr Ser Val Ser Ser Ala Phe
 65                  70                  75                  80

Leu Gln Ile Ser Ser Leu Lys Ala Glu Asp Thr Ala Val Tyr Tyr Cys
                85                  90                  95

Ala Arg Gly Asp Cys Asp Ser Thr Asp Cys Tyr Arg Tyr Ser Tyr Gly
            100                 105                 110

```
Tyr Glu Asp Tyr Trp Gly Gln Gly Thr Leu Val Thr Val Ser Ser
        115                 120                 125

<210> SEQ ID NO 173
<211> LENGTH: 127
<212> TYPE: PRT
<213> ORGANISM: Artificial Sequence
<220> FEATURE:
<223> OTHER INFORMATION: member of supercluster10

<400> SEQUENCE: 173

Glu Val Gln Leu Val Gln Ser Gly Ser Lys Leu Lys Lys Pro Gly Ala
1               5                   10                  15

Ser Val Lys Val Ser Cys Lys Ala Ser Gly Tyr Thr Phe Thr Ser Tyr
            20                  25                  30

Thr Met Asn Trp Val Arg Gln Ala Pro Gly Arg Gly Leu Glu Trp Met
        35                  40                  45

Gly Trp Ile Asn Thr Asn Thr Gly Asp Pro Thr Tyr Ala Gln Gly Phe
    50                  55                  60

Thr Gly Arg Phe Val Phe Ser Leu Asp Thr Ser Val Ser Thr Ala Phe
65                  70                  75                  80

Leu Gln Ile Asn Ser Leu Lys Ala Glu Asp Thr Ala Val Tyr Tyr Cys
                85                  90                  95

Ala Arg Gly Asp Cys Asp Ser Thr Ser Cys Tyr Arg Tyr Ser Tyr Gly
            100                 105                 110

Tyr Glu Asp Tyr Trp Gly Gln Gly Thr Leu Val Thr Val Ser Ser
        115                 120                 125

<210> SEQ ID NO 174
<211> LENGTH: 127
<212> TYPE: PRT
<213> ORGANISM: Artificial Sequence
<220> FEATURE:
<223> OTHER INFORMATION: member of supercluster10

<400> SEQUENCE: 174

Glu Val Gln Leu Val Gln Ser Gly Ser Lys Leu Lys Lys Pro Gly Ala
1               5                   10                  15

Ser Val Lys Val Ser Cys Lys Ala Ser Gly Tyr Thr Phe Thr Ser Tyr
            20                  25                  30

Thr Met Asn Trp Val Arg Gln Ala Pro Gly Gln Gly Leu Glu Trp Met
        35                  40                  45

Gly Trp Ile Asn Thr Asp Thr Gly Asp Pro Thr Tyr Ala Gln Gly Phe
    50                  55                  60

Thr Gly Arg Phe Val Phe Ser Leu Asp Thr Ser Val Ser Thr Ala Phe
65                  70                  75                  80

Leu Gln Ile Asn Ser Leu Lys Ala Glu Asp Thr Ala Val Tyr Tyr Cys
                85                  90                  95

Ala Arg Gly Asp Cys Asp Ser Thr Ser Cys Tyr Arg Tyr Ser Tyr Gly
            100                 105                 110

Tyr Glu Asp Tyr Trp Gly Gln Gly Thr Leu Val Thr Val Ser Ser
        115                 120                 125

<210> SEQ ID NO 175
<211> LENGTH: 127
<212> TYPE: PRT
<213> ORGANISM: Artificial Sequence
<220> FEATURE:
<223> OTHER INFORMATION: member of supercluster10
```

<400> SEQUENCE: 175

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Thr Met Asn Trp Val Arg Gln Ala Pro Gly Gln Gly Leu Glu Trp Met
        35                  40                  45

Gly Trp Ile Asn Thr Asp Thr Gly Asp Pro Thr Tyr Ala Gln Gly Phe
    50                  55                  60

Thr Gly Arg Phe Val Phe Ser Leu Asp Thr Ser Val Ser Thr Ala Phe
65                  70                  75                  80

Leu Gln Ile Asn Ser Leu Lys Ala Glu Asp Thr Ala Val Tyr Tyr Cys
                85                  90                  95

Ala Arg Gly Asp Cys Asp Ser Thr Ser Cys Tyr Arg Tyr Ser Tyr Gly
            100                 105                 110

Tyr Glu Asp Tyr Trp Gly Gln Gly Thr Leu Val Thr Val Ser Ser
        115                 120                 125

<210> SEQ ID NO 176
<211> LENGTH: 127
<212> TYPE: PRT
<213> ORGANISM: Artificial Sequence
<220> FEATURE:
<223> OTHER INFORMATION: member of supercluster10

<400> SEQUENCE: 176

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Tyr Thr Gly Asp Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Asn Asn Leu Lys Ala Glu Asp Thr Ala Val Tyr Tyr Cys
                85                  90                  95

Ala Arg Gly Asp Cys Ser Ser Thr Ser Cys Tyr Arg Tyr Ser Tyr Gly
            100                 105                 110

Tyr Glu Asp Tyr Trp Gly Gln Gly Thr Leu Val Thr Val Ser Ser
        115                 120                 125

<210> SEQ ID NO 177
<211> LENGTH: 127
<212> TYPE: PRT
<213> ORGANISM: Artificial Sequence
<220> FEATURE:
<223> OTHER INFORMATION: member of supercluster10

<400> SEQUENCE: 177

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Ala Met His Trp Val Arg Gln Ala Pro Gly Gln Gly Leu Glu Trp Met
        35                  40                  45

```
Gly Trp Ile Asp Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asp Cys Ser Ser Thr Ser Cys Tyr Arg Tyr Ser Tyr Gly
                100                 105                 110

Tyr Glu Asp Tyr Trp Gly Gln Gly Thr Leu Val Thr Val Ser Ser
                115                 120                 125

<210> SEQ ID NO 178
<211> LENGTH: 127
<212> TYPE: PRT
<213> ORGANISM: Artificial Sequence
<220> FEATURE:
<223> OTHER INFORMATION: member of supercluster10

<400> SEQUENCE: 178

Glu Val Gln Leu Val Gln Ser Gly Ser Lys Leu Glu Lys Pro Gly Ala
1               5                   10                  15

Ser Val Lys Val Ser Cys Lys Ala Ser Gly Tyr Thr Phe Thr Ser Tyr
                20                  25                  30

Thr Met Asn Trp Val Arg Gln Ala Pro Gly Gln Gly Leu Glu Trp Met
            35                  40                  45

Gly Trp Ile Asn Thr Asn Thr Gly Asp Pro Thr Tyr Ala Gln Gly Phe
        50                  55                  60

Thr Gly Arg Phe Val Phe Ser Leu Asp Thr Ser Val Ser Thr Ala Phe
65                  70                  75                  80

Leu Gln Ile Asn Ser Leu Lys Ala Glu Asp Thr Ala Val Tyr Phe Cys
                85                  90                  95

Ala Arg Gly Asp Cys Asp Ser Thr Ser Cys Tyr Arg Tyr Ser Tyr Gly
                100                 105                 110

Tyr Glu Asp Tyr Trp Gly Gln Gly Thr Leu Val Thr Val Ser Ser
                115                 120                 125

<210> SEQ ID NO 179
<211> LENGTH: 127
<212> TYPE: PRT
<213> ORGANISM: Artificial Sequence
<220> FEATURE:
<223> OTHER INFORMATION: member of supercluster10

<400> SEQUENCE: 179

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Gly Asp Cys Asp Ser Thr Ser Cys Tyr Arg Tyr Ser Tyr Gly
```

```
                100                 105                 110
Tyr Glu Asp Tyr Trp Gly Gln Gly Thr Leu Val Thr Val Ser Ser
        115                 120                 125

<210> SEQ ID NO 180
<211> LENGTH: 127
<212> TYPE: PRT
<213> ORGANISM: Artificial Sequence
<220> FEATURE:
<223> OTHER INFORMATION: member of supercluster10

<400> SEQUENCE: 180

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asp Pro Thr Tyr Ala Gln Gly Phe
    50                  55                  60

Thr Gly Arg Phe Val Phe Ser Leu Asp Thr Ser Val Ser Thr Ala Phe
65                  70                  75                  80

Leu Gln Ile Asn Ser Leu Lys Ala Glu Asp Thr Ala Val Tyr Phe Cys
                85                  90                  95

Ala Arg Gly Asp Cys Asp Ser Thr Asn Cys Tyr Arg Tyr Ser Tyr Gly
            100                 105                 110

Tyr Glu Asp Tyr Trp Gly Gln Gly Thr Leu Val Thr Val Ser Ser
        115                 120                 125

<210> SEQ ID NO 181
<211> LENGTH: 127
<212> TYPE: PRT
<213> ORGANISM: Artificial Sequence
<220> FEATURE:
<223> OTHER INFORMATION: member of supercluster10

<400> SEQUENCE: 181

Gln Val Gln Leu Val Gln Ser Gly Ser Thr Leu Lys Lys Pro Gly Ala
1               5                   10                  15

Ser Val Lys Val Ser Cys Lys Ala Ser Gly Tyr Thr Phe Thr Ser Tyr
            20                  25                  30

Thr Met Asn Trp Val Arg Gln Ala Pro Gly Gln Gly Leu Glu Trp Met
        35                  40                  45

Gly Trp Ile Asp Thr Asn Thr Gly Asp Pro Thr Tyr Ala Gln Gly Phe
    50                  55                  60

Thr Gly Arg Phe Val Phe Ser Leu Asp Thr Ser Val Thr Thr Ala Phe
65                  70                  75                  80

Leu Gln Ile Asn Ser Leu Lys Ala Glu Asp Thr Ala Val Tyr Phe Cys
                85                  90                  95

Ala Arg Gly Asp Cys Asp Ser Thr Ser Cys Tyr Arg Tyr Ser Tyr Gly
            100                 105                 110

Tyr Glu Asp Tyr Trp Gly Gln Gly Thr Leu Val Thr Val Ser Ser
        115                 120                 125

<210> SEQ ID NO 182
<211> LENGTH: 5
<212> TYPE: PRT
<213> ORGANISM: Artificial Sequence
<220> FEATURE:
```

```
<223> OTHER INFORMATION: Synthetic sequence

<400> SEQUENCE: 182

Lys Tyr Asp Ile Asn
1               5

<210> SEQ ID NO 183
<211> LENGTH: 5
<212> TYPE: PRT
<213> ORGANISM: Artificial Sequence
<220> FEATURE:
<223> OTHER INFORMATION: Synthetic sequence

<400> SEQUENCE: 183

Ser Tyr Gly Met His
1               5

<210> SEQ ID NO 184
<211> LENGTH: 5
<212> TYPE: PRT
<213> ORGANISM: Artificial Sequence
<220> FEATURE:
<223> OTHER INFORMATION: Synthetic sequence

<400> SEQUENCE: 184

Ser Tyr Ala Met Ser
1               5

<210> SEQ ID NO 185
<211> LENGTH: 5
<212> TYPE: PRT
<213> ORGANISM: Artificial Sequence
<220> FEATURE:
<223> OTHER INFORMATION: Synthetic sequence

<400> SEQUENCE: 185

Gly Tyr Tyr Met His
1               5

<210> SEQ ID NO 186
<211> LENGTH: 5
<212> TYPE: PRT
<213> ORGANISM: Artificial Sequence
<220> FEATURE:
<223> OTHER INFORMATION: Synthetic sequence

<400> SEQUENCE: 186

Arg Tyr Ala Leu Asn
1               5

<210> SEQ ID NO 187
<211> LENGTH: 5
<212> TYPE: PRT
<213> ORGANISM: Artificial Sequence
<220> FEATURE:
<223> OTHER INFORMATION: Synthetic sequence

<400> SEQUENCE: 187

Ser Tyr Gly Ile Ser
1               5

<210> SEQ ID NO 188
<211> LENGTH: 5
<212> TYPE: PRT
<213> ORGANISM: Artificial Sequence
<220> FEATURE:
<223> OTHER INFORMATION: Synthetic sequence
```

<400> SEQUENCE: 188

Asn Tyr Ala Met Asn
1               5

<210> SEQ ID NO 189
<211> LENGTH: 5
<212> TYPE: PRT
<213> ORGANISM: Artificial Sequence
<220> FEATURE:
<223> OTHER INFORMATION: Synthetic sequence

<400> SEQUENCE: 189

Glu Leu Ser Met His
1               5

<210> SEQ ID NO 190
<211> LENGTH: 5
<212> TYPE: PRT
<213> ORGANISM: Artificial Sequence
<220> FEATURE:
<223> OTHER INFORMATION: Synthetic sequence

<400> SEQUENCE: 190

Asp Tyr Ala Met Thr
1               5

<210> SEQ ID NO 191
<211> LENGTH: 5
<212> TYPE: PRT
<213> ORGANISM: Artificial Sequence
<220> FEATURE:
<223> OTHER INFORMATION: Synthetic sequence

<400> SEQUENCE: 191

Asn Tyr Val Met Asn
1               5

<210> SEQ ID NO 192
<211> LENGTH: 7
<212> TYPE: PRT
<213> ORGANISM: Artificial Sequence
<220> FEATURE:
<223> OTHER INFORMATION: Synthetic sequence

<400> SEQUENCE: 192

Ser Ser Ser Ser Tyr Trp Gly
1               5

<210> SEQ ID NO 193
<211> LENGTH: 5
<212> TYPE: PRT
<213> ORGANISM: Artificial Sequence
<220> FEATURE:
<223> OTHER INFORMATION: Synthetic sequence

<400> SEQUENCE: 193

Thr Tyr Tyr Trp Ser
1               5

<210> SEQ ID NO 194
<211> LENGTH: 5
<212> TYPE: PRT
<213> ORGANISM: Artificial Sequence
<220> FEATURE:
<223> OTHER INFORMATION: Synthetic sequence

```
<400> SEQUENCE: 194

Ser His Trp Ile Gly
1               5

<210> SEQ ID NO 195
<211> LENGTH: 7
<212> TYPE: PRT
<213> ORGANISM: Artificial Sequence
<220> FEATURE:
<223> OTHER INFORMATION: Synthetic sequence

<400> SEQUENCE: 195

Ser Ser Ser Tyr Tyr Trp Gly
1               5

<210> SEQ ID NO 196
<211> LENGTH: 5
<212> TYPE: PRT
<213> ORGANISM: Artificial Sequence
<220> FEATURE:
<223> OTHER INFORMATION: Synthetic sequence

<400> SEQUENCE: 196

Ser His Trp Ile Ala
1               5

<210> SEQ ID NO 197
<211> LENGTH: 5
<212> TYPE: PRT
<213> ORGANISM: Artificial Sequence
<220> FEATURE:
<223> OTHER INFORMATION: Synthetic sequence

<400> SEQUENCE: 197

Asn Asp Ala Ile Ser
1               5

<210> SEQ ID NO 198
<211> LENGTH: 5
<212> TYPE: PRT
<213> ORGANISM: Artificial Sequence
<220> FEATURE:
<223> OTHER INFORMATION: Synthetic sequence

<400> SEQUENCE: 198

Ser Tyr Thr Met Asn
1               5

<210> SEQ ID NO 199
<211> LENGTH: 5
<212> TYPE: PRT
<213> ORGANISM: Artificial Sequence
<220> FEATURE:
<223> OTHER INFORMATION: Synthetic sequence

<400> SEQUENCE: 199

Ser Tyr Ala Ile Ser
1               5

<210> SEQ ID NO 200
<211> LENGTH: 5
<212> TYPE: PRT
<213> ORGANISM: Artificial Sequence
<220> FEATURE:
<223> OTHER INFORMATION: Synthetic sequence

<400> SEQUENCE: 200
```

Asn Tyr Ala Ile Ser
1               5

<210> SEQ ID NO 201
<211> LENGTH: 5
<212> TYPE: PRT
<213> ORGANISM: Artificial Sequence
<220> FEATURE:
<223> OTHER INFORMATION: Synthetic sequence

<400> SEQUENCE: 201

Tyr Tyr Asp Met His
1               5

<210> SEQ ID NO 202
<211> LENGTH: 7
<212> TYPE: PRT
<213> ORGANISM: Artificial Sequence
<220> FEATURE:
<223> OTHER INFORMATION: Synthetic sequence

<400> SEQUENCE: 202

Ser Ser Asn Tyr Tyr Trp Gly
1               5

<210> SEQ ID NO 203
<211> LENGTH: 5
<212> TYPE: PRT
<213> ORGANISM: Artificial Sequence
<220> FEATURE:
<223> OTHER INFORMATION: Synthetic sequence

<400> SEQUENCE: 203

Arg Tyr Pro Met Asn
1               5

<210> SEQ ID NO 204
<211> LENGTH: 5
<212> TYPE: PRT
<213> ORGANISM: Artificial Sequence
<220> FEATURE:
<223> OTHER INFORMATION: Synthetic sequence

<400> SEQUENCE: 204

Ser Tyr Ala Met Asp
1               5

<210> SEQ ID NO 205
<211> LENGTH: 5
<212> TYPE: PRT
<213> ORGANISM: Artificial Sequence
<220> FEATURE:
<223> OTHER INFORMATION: Synthetic sequence

<400> SEQUENCE: 205

Lys Tyr Val Met Asn
1               5

<210> SEQ ID NO 206
<211> LENGTH: 5
<212> TYPE: PRT
<213> ORGANISM: Artificial Sequence
<220> FEATURE:
<223> OTHER INFORMATION: Synthetic sequence

<400> SEQUENCE: 206

```
Thr Tyr Trp Ile Gly
1               5

<210> SEQ ID NO 207
<211> LENGTH: 5
<212> TYPE: PRT
<213> ORGANISM: Artificial Sequence
<220> FEATURE:
<223> OTHER INFORMATION: Synthetic sequence

<400> SEQUENCE: 207

Arg Tyr Ala Met Asn
1               5

<210> SEQ ID NO 208
<211> LENGTH: 5
<212> TYPE: PRT
<213> ORGANISM: Artificial Sequence
<220> FEATURE:
<223> OTHER INFORMATION: Synthetic sequence

<400> SEQUENCE: 208

Lys Tyr Ala Met Asn
1               5

<210> SEQ ID NO 209
<211> LENGTH: 17
<212> TYPE: PRT
<213> ORGANISM: Artificial Sequence
<220> FEATURE:
<223> OTHER INFORMATION: Synthetic sequence

<400> SEQUENCE: 209

Trp Met Ser Ala Asn Thr Gly Asn Thr Gly Tyr Ala Gln Lys Phe Gln
1               5                   10                  15

Gly

<210> SEQ ID NO 210
<211> LENGTH: 17
<212> TYPE: PRT
<213> ORGANISM: Artificial Sequence
<220> FEATURE:
<223> OTHER INFORMATION: Synthetic sequence

<400> SEQUENCE: 210

Val Ile Ser Tyr Asp Gly Ser Asn Lys Tyr Tyr Ala Asp Ser Val Lys
1               5                   10                  15

Gly

<210> SEQ ID NO 211
<211> LENGTH: 17
<212> TYPE: PRT
<213> ORGANISM: Artificial Sequence
<220> FEATURE:
<223> OTHER INFORMATION: Synthetic sequence

<400> SEQUENCE: 211

Ala Ile Ser Gly Ser Gly Gly Ser Thr Tyr Tyr Ala Asp Ser Val Lys
1               5                   10                  15

Gly

<210> SEQ ID NO 212
<211> LENGTH: 17
<212> TYPE: PRT
<213> ORGANISM: Artificial Sequence
```

<220> FEATURE:
<223> OTHER INFORMATION: Synthetic sequence

<400> SEQUENCE: 212

Trp Ile Asn Pro Asn Ser Gly Gly Thr Asn Tyr Ala Gln Lys Phe Gln
1               5                   10                  15
Gly

<210> SEQ ID NO 213
<211> LENGTH: 17
<212> TYPE: PRT
<213> ORGANISM: Artificial Sequence
<220> FEATURE:
<223> OTHER INFORMATION: Synthetic sequence

<400> SEQUENCE: 213

Trp Ile Asn Thr Asn Thr Gly Asn Pro Thr Tyr Ala Arg Gly Phe Thr
1               5                   10                  15
Gly

<210> SEQ ID NO 214
<211> LENGTH: 17
<212> TYPE: PRT
<213> ORGANISM: Artificial Sequence
<220> FEATURE:
<223> OTHER INFORMATION: Synthetic sequence

<400> SEQUENCE: 214

Trp Ile Ser Ala Tyr Asn Gly Asn Thr Asn Tyr Ala Gln Lys Leu Gln
1               5                   10                  15
Gly

<210> SEQ ID NO 215
<211> LENGTH: 17
<212> TYPE: PRT
<213> ORGANISM: Artificial Sequence
<220> FEATURE:
<223> OTHER INFORMATION: Synthetic sequence

<400> SEQUENCE: 215

Trp Ile Asn Ala Asn Thr Gly Asp Pro Thr Tyr Ala Gln Gly Phe Thr
1               5                   10                  15
Gly

<210> SEQ ID NO 216
<211> LENGTH: 17
<212> TYPE: PRT
<213> ORGANISM: Artificial Sequence
<220> FEATURE:
<223> OTHER INFORMATION: Synthetic sequence

<400> SEQUENCE: 216

Gly Phe Asp Pro Glu Tyr Gly Lys Thr Phe Phe Ala Gln Asn Phe Gln
1               5                   10                  15
Gly

<210> SEQ ID NO 217
<211> LENGTH: 17
<212> TYPE: PRT
<213> ORGANISM: Artificial Sequence
<220> FEATURE:
<223> OTHER INFORMATION: Synthetic sequence

<400> SEQUENCE: 217

```
Trp Ile Thr Thr Asn Thr Gly Asp Pro Thr Tyr Ala Pro Gly Phe Thr
1               5                   10                  15
Gly

<210> SEQ ID NO 218
<211> LENGTH: 17
<212> TYPE: PRT
<213> ORGANISM: Artificial Sequence
<220> FEATURE:
<223> OTHER INFORMATION: Synthetic sequence

<400> SEQUENCE: 218

Trp Ile Asn Thr Asn Thr Gly Asn Pro Thr Tyr Ala Gln Gly Phe Thr
1               5                   10                  15
Gly

<210> SEQ ID NO 219
<211> LENGTH: 17
<212> TYPE: PRT
<213> ORGANISM: Artificial Sequence
<220> FEATURE:
<223> OTHER INFORMATION: Synthetic sequence

<400> SEQUENCE: 219

Val Ile Ser Gly Ser Gly Gly Thr Thr Tyr Tyr Ala Asp Ser Val Lys
1               5                   10                  15
Gly

<210> SEQ ID NO 220
<211> LENGTH: 16
<212> TYPE: PRT
<213> ORGANISM: Artificial Sequence
<220> FEATURE:
<223> OTHER INFORMATION: Synthetic sequence

<400> SEQUENCE: 220

Ser Phe Tyr Tyr Ser Gly Asn Thr Tyr Tyr Asn Pro Ser Leu Lys Ser
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: Synthetic sequence

<400> SEQUENCE: 221

Tyr Val Tyr Tyr Thr Gly Arg Thr Lys Tyr Asn Pro Ser Leu Lys Ser
1               5                   10                  15

<210> SEQ ID NO 222
<211> LENGTH: 17
<212> TYPE: PRT
<213> ORGANISM: Artificial Sequence
<220> FEATURE:
<223> OTHER INFORMATION: Synthetic sequence

<400> SEQUENCE: 222

Val Ile Tyr Pro Gly Asp Ser Asp Thr Arg Tyr Ser Pro Ser Phe Gln
1               5                   10                  15
Gly

<210> SEQ ID NO 223
```

<400> SEQUENCE: 223

000

<210> SEQ ID NO 224
<211> LENGTH: 17
<212> TYPE: PRT
<213> ORGANISM: Artificial Sequence
<220> FEATURE:
<223> OTHER INFORMATION: Synthetic sequence

<400> SEQUENCE: 224

Ile Val Tyr Pro Gly Asp Ser Asp Thr Arg Tyr Ser Pro Ser Phe Gln
1               5                   10                  15

Gly

<210> SEQ ID NO 225
<211> LENGTH: 17
<212> TYPE: PRT
<213> ORGANISM: Artificial Sequence
<220> FEATURE:
<223> OTHER INFORMATION: Synthetic sequence

<400> SEQUENCE: 225

Ser Ile Ile Pro Ile Leu Asp Thr Thr Asp His Ala Gln Lys Phe Gln
1               5                   10                  15

Gly

<210> SEQ ID NO 226
<211> LENGTH: 17
<212> TYPE: PRT
<213> ORGANISM: Artificial Sequence
<220> FEATURE:
<223> OTHER INFORMATION: Synthetic sequence

<400> SEQUENCE: 226

Trp Ile Asn Thr Asp Thr Gly Asp Pro Thr Tyr Ala Gln Gly Phe Thr
1               5                   10                  15

Gly

<210> SEQ ID NO 227
<211> LENGTH: 17
<212> TYPE: PRT
<213> ORGANISM: Artificial Sequence
<220> FEATURE:
<223> OTHER INFORMATION: Synthetic sequence

<400> SEQUENCE: 227

Gly Ile Ile Pro Ile Phe Asp Thr Arg Asn Tyr Ala Gln Ile Leu Gln
1               5                   10                  15

Gly

<210> SEQ ID NO 228
<211> LENGTH: 17
<212> TYPE: PRT
<213> ORGANISM: Artificial Sequence
<220> FEATURE:
<223> OTHER INFORMATION: Synthetic sequence

<400> SEQUENCE: 228

Ser Ile Ile Pro Ile Leu Gly Thr Thr Asp His Ala Gln Lys Phe Gln
1               5                   10                  15

Asp

<210> SEQ ID NO 229
<211> LENGTH: 16
<212> TYPE: PRT
<213> ORGANISM: Artificial Sequence
<220> FEATURE:
<223> OTHER INFORMATION: Synthetic sequence

<400> SEQUENCE: 229

Ala Ile Gly Thr Ala Gly Ala Thr Tyr Tyr Pro Gly Ser Val Lys Gly
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: Synthetic sequence

<400> SEQUENCE: 230

Asn Ile Tyr Tyr Arg Gly Tyr Thr Tyr Tyr Asn Pro Ser Leu Lys Ser
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: Synthetic sequence

<400> SEQUENCE: 231

Thr Ile Gly Ala Thr Gly Asp Thr Tyr Tyr Ser Asp Ser Val Lys Gly
1               5                   10                  15

<210> SEQ ID NO 232
<211> LENGTH: 17
<212> TYPE: PRT
<213> ORGANISM: Artificial Sequence
<220> FEATURE:
<223> OTHER INFORMATION: Synthetic sequence

<400> SEQUENCE: 232

Trp Ile Asn Thr Asn Thr Gly Asn Pro Thr Tyr Ala Gln Ala Phe Thr
1               5                   10                  15

Gly

<210> SEQ ID NO 233
<211> LENGTH: 17
<212> TYPE: PRT
<213> ORGANISM: Artificial Sequence
<220> FEATURE:
<223> OTHER INFORMATION: Synthetic sequence

<400> SEQUENCE: 233

Ile Ile Tyr Pro Gly Asp Ser Asp Thr Arg Tyr Ser Pro Ser Phe Gln
1               5                   10                  15

Gly

<210> SEQ ID NO 234
<211> LENGTH: 17
<212> TYPE: PRT
<213> ORGANISM: Artificial Sequence
<220> FEATURE:
<223> OTHER INFORMATION: Synthetic sequence

<400> SEQUENCE: 234

```
Trp Ile Asn Thr Lys Thr Gly Asn Pro Thr Tyr Ala Gln Gly Phe Thr
1               5                   10                  15
Gly

<210> SEQ ID NO 235
<211> LENGTH: 17
<212> TYPE: PRT
<213> ORGANISM: Artificial Sequence
<220> FEATURE:
<223> OTHER INFORMATION: Synthetic sequence

<400> SEQUENCE: 235

Trp Ile Asn Thr Asn Thr Gly Lys Pro Thr Tyr Ala Gln Gly Phe Thr
1               5                   10                  15
Gly

<210> SEQ ID NO 236
<211> LENGTH: 18
<212> TYPE: PRT
<213> ORGANISM: Artificial Sequence
<220> FEATURE:
<223> OTHER INFORMATION: Synthetic sequence

<400> SEQUENCE: 236

Ser Ser Leu Phe Lys Thr Glu Thr Ala Pro Tyr Tyr His Phe Ala Leu
1               5                   10                  15
Asp Val

<210> SEQ ID NO 237
<211> LENGTH: 15
<212> TYPE: PRT
<213> ORGANISM: Artificial Sequence
<220> FEATURE:
<223> OTHER INFORMATION: Synthetic sequence

<400> SEQUENCE: 237

Gly Ser Ser Gly Trp Pro Ser Tyr Ser Asn Trp Gly Phe Asp Tyr
1               5                   10                  15

<210> SEQ ID NO 238
<211> LENGTH: 13
<212> TYPE: PRT
<213> ORGANISM: Artificial Sequence
<220> FEATURE:
<223> OTHER INFORMATION: Synthetic sequence

<400> SEQUENCE: 238

Asp Trp Trp Tyr Pro Pro Tyr Tyr Trp Gly Phe Asp Tyr
1               5                   10

<210> SEQ ID NO 239
<211> LENGTH: 15
<212> TYPE: PRT
<213> ORGANISM: Artificial Sequence
<220> FEATURE:
<223> OTHER INFORMATION: Synthetic sequence

<400> SEQUENCE: 239

Asp His Gly Ser Arg His Phe Trp Ser Tyr Trp Gly Phe Asp Tyr
1               5                   10                  15

<210> SEQ ID NO 240
<211> LENGTH: 13
<212> TYPE: PRT
```

<213> ORGANISM: Artificial Sequence
<220> FEATURE:
<223> OTHER INFORMATION: Synthetic sequence

<400> SEQUENCE: 240

Asp Thr Tyr Asp Ser Thr Gly Tyr Leu Trp Phe Asp Tyr
1               5                   10

<210> SEQ ID NO 241
<211> LENGTH: 13
<212> TYPE: PRT
<213> ORGANISM: Artificial Sequence
<220> FEATURE:
<223> OTHER INFORMATION: Synthetic sequence

<400> SEQUENCE: 241

Asp Arg His Trp His Trp Trp Leu Asp Ala Phe Asp Tyr
1               5                   10

<210> SEQ ID NO 242
<211> LENGTH: 11
<212> TYPE: PRT
<213> ORGANISM: Artificial Sequence
<220> FEATURE:
<223> OTHER INFORMATION: Synthetic sequence

<400> SEQUENCE: 242

Glu Arg Phe Leu Glu Trp Leu His Phe Asp Tyr
1               5                   10

<210> SEQ ID NO 243
<211> LENGTH: 16
<212> TYPE: PRT
<213> ORGANISM: Artificial Sequence
<220> FEATURE:
<223> OTHER INFORMATION: Synthetic sequence

<400> SEQUENCE: 243

Glu Gly Tyr Tyr Glu Thr Thr Thr Tyr Tyr Tyr Asn Leu Phe Asp Ser
1               5                   10                  15

<210> SEQ ID NO 244
<211> LENGTH: 10
<212> TYPE: PRT
<213> ORGANISM: Artificial Sequence
<220> FEATURE:
<223> OTHER INFORMATION: Synthetic sequence

<400> SEQUENCE: 244

Val Tyr His Trp Ile Arg Gly Phe Glu Phe
1               5                   10

<210> SEQ ID NO 245
<211> LENGTH: 6
<212> TYPE: PRT
<213> ORGANISM: Artificial Sequence
<220> FEATURE:
<223> OTHER INFORMATION: Synthetic sequence

<400> SEQUENCE: 245

Trp Glu Leu Leu Asp Tyr
1               5

<210> SEQ ID NO 246
<211> LENGTH: 7
<212> TYPE: PRT
<213> ORGANISM: Artificial Sequence

```
<220> FEATURE:
<223> OTHER INFORMATION: Synthetic sequence

<400> SEQUENCE: 246

Gly Ala Gly Glu Leu Asp Tyr
1               5

<210> SEQ ID NO 247
<211> LENGTH: 16
<212> TYPE: PRT
<213> ORGANISM: Artificial Sequence
<220> FEATURE:
<223> OTHER INFORMATION: Synthetic sequence

<400> SEQUENCE: 247

Gln Thr Tyr Ser Ser Ser Trp Asp Gly Val Leu Tyr Tyr Phe Asp Tyr
1               5                   10                  15

<210> SEQ ID NO 248
<211> LENGTH: 18
<212> TYPE: PRT
<213> ORGANISM: Artificial Sequence
<220> FEATURE:
<223> OTHER INFORMATION: Synthetic sequence

<400> SEQUENCE: 248

Gly Gly Ile Val Val Pro Ala Ala Arg Asp Tyr Tyr Tyr Tyr Met
1               5                   10                  15

Asp Val

<210> SEQ ID NO 249
<211> LENGTH: 11
<212> TYPE: PRT
<213> ORGANISM: Artificial Sequence
<220> FEATURE:
<223> OTHER INFORMATION: Synthetic sequence

<400> SEQUENCE: 249

Pro Asn Ser Gly Ser Pro Arg Tyr Phe Glu Phe
1               5                   10

<210> SEQ ID NO 250
<211> LENGTH: 16
<212> TYPE: PRT
<213> ORGANISM: Artificial Sequence
<220> FEATURE:
<223> OTHER INFORMATION: Synthetic sequence

<400> SEQUENCE: 250

Gln Glu Tyr Tyr Tyr Gly Ser Gly Ser Pro Ser Tyr Tyr Phe Asp Tyr
1               5                   10                  15

<210> SEQ ID NO 251
<211> LENGTH: 11
<212> TYPE: PRT
<213> ORGANISM: Artificial Sequence
<220> FEATURE:
<223> OTHER INFORMATION: Synthetic sequence

<400> SEQUENCE: 251

His Glu Trp Glu Leu Leu Gly Pro Phe Asp Tyr
1               5                   10

<210> SEQ ID NO 252
<211> LENGTH: 12
<212> TYPE: PRT
```

<213> ORGANISM: Artificial Sequence
<220> FEATURE:
<223> OTHER INFORMATION: Synthetic sequence

<400> SEQUENCE: 252

Glu His Ile Ala Ala Arg Gln Asp Tyr Phe Asp Tyr
1               5                   10

<210> SEQ ID NO 253
<211> LENGTH: 18
<212> TYPE: PRT
<213> ORGANISM: Artificial Sequence
<220> FEATURE:
<223> OTHER INFORMATION: Synthetic sequence

<400> SEQUENCE: 253

Gly Asp Cys Asp Ser Thr Ser Cys Tyr Arg Tyr Ser Tyr Gly Tyr Glu
1               5                   10                  15

Asp Tyr

<210> SEQ ID NO 254
<211> LENGTH: 10
<212> TYPE: PRT
<213> ORGANISM: Artificial Sequence
<220> FEATURE:
<223> OTHER INFORMATION: Synthetic sequence

<400> SEQUENCE: 254

Gly Ser Asp Glu Gly Asp Trp Phe Asp Pro
1               5                   10

<210> SEQ ID NO 255
<211> LENGTH: 12
<212> TYPE: PRT
<213> ORGANISM: Artificial Sequence
<220> FEATURE:
<223> OTHER INFORMATION: Synthetic sequence

<400> SEQUENCE: 255

Glu Tyr Ile Ala Ala Arg Leu Asp Tyr Phe Asp Ser
1               5                   10

<210> SEQ ID NO 256
<211> LENGTH: 14
<212> TYPE: PRT
<213> ORGANISM: Artificial Sequence
<220> FEATURE:
<223> OTHER INFORMATION: Synthetic sequence

<400> SEQUENCE: 256

Asp Arg Gly Tyr Ser Gly Tyr Asp Ala Tyr Tyr Phe Asp Phe
1               5                   10

<210> SEQ ID NO 257
<211> LENGTH: 14
<212> TYPE: PRT
<213> ORGANISM: Artificial Sequence
<220> FEATURE:
<223> OTHER INFORMATION: Synthetic sequence

<400> SEQUENCE: 257

Glu Gly Ser Asp Tyr Gly Asp Tyr Val Gly Ala Phe Asp Ile
1               5                   10

<210> SEQ ID NO 258
<211> LENGTH: 14

```
<212> TYPE: PRT
<213> ORGANISM: Artificial Sequence
<220> FEATURE:
<223> OTHER INFORMATION: Synthetic sequence

<400> SEQUENCE: 258

Asp Arg Gly Tyr Ile Gly Tyr Asp Ser Tyr Tyr Phe Asp Asn
1               5                   10

<210> SEQ ID NO 259
<211> LENGTH: 11
<212> TYPE: PRT
<213> ORGANISM: Artificial Sequence
<220> FEATURE:
<223> OTHER INFORMATION: Synthetic sequence

<400> SEQUENCE: 259

Glu Arg Thr Asn Phe Tyr Asp Ala Phe Asp Ile
1               5                   10

<210> SEQ ID NO 260
<211> LENGTH: 11
<212> TYPE: PRT
<213> ORGANISM: Artificial Sequence
<220> FEATURE:
<223> OTHER INFORMATION: Synthetic sequence

<400> SEQUENCE: 260

Glu Arg His Gly Tyr Phe Glu Ala Phe Asp Ile
1               5                   10

<210> SEQ ID NO 261
<211> LENGTH: 11
<212> TYPE: PRT
<213> ORGANISM: Artificial Sequence
<220> FEATURE:
<223> OTHER INFORMATION: Synthetic sequence

<400> SEQUENCE: 261

Glu Ser Asn Trp Asn Tyr Asp Tyr Phe Asp Tyr
1               5                   10

<210> SEQ ID NO 262
<211> LENGTH: 13
<212> TYPE: PRT
<213> ORGANISM: Artificial Sequence
<220> FEATURE:
<223> OTHER INFORMATION: Synthetic sequence

<400> SEQUENCE: 262

Arg Gly Leu Ser Met Val Arg Leu Ser Ala Phe Asp Val
1               5                   10

<210> SEQ ID NO 263
<211> LENGTH: 11
<212> TYPE: PRT
<213> ORGANISM: Artificial Sequence
<220> FEATURE:
<223> OTHER INFORMATION: Synthetic sequence

<400> SEQUENCE: 263

Asp Arg Gly Ser Tyr Tyr Asp Ala Phe Asp Ile
1               5                   10

<210> SEQ ID NO 264
<211> LENGTH: 11
<212> TYPE: PRT
```

<213> ORGANISM: Artificial Sequence
<220> FEATURE:
<223> OTHER INFORMATION: Synthetic sequence

<400> SEQUENCE: 264

Lys Gly Gly Ser Tyr Tyr Asp Trp Phe Asp Pro
1               5                   10

<210> SEQ ID NO 265
<211> LENGTH: 14
<212> TYPE: PRT
<213> ORGANISM: Artificial Sequence
<220> FEATURE:
<223> OTHER INFORMATION: Synthetic sequence

<400> SEQUENCE: 265

Asp Lys Gly Tyr Asn Trp Asn Tyr Met Gly Ala Phe Asp Ile
1               5                   10

<210> SEQ ID NO 266
<211> LENGTH: 11
<212> TYPE: PRT
<213> ORGANISM: Artificial Sequence
<220> FEATURE:
<223> OTHER INFORMATION: Synthetic sequence

<400> SEQUENCE: 266

Arg Ser Gly Ser Tyr Tyr Asp Tyr Phe Asp Tyr
1               5                   10

<210> SEQ ID NO 267
<211> LENGTH: 24
<212> TYPE: PRT
<213> ORGANISM: Artificial Sequence
<220> FEATURE:
<223> OTHER INFORMATION: Signal Peptide

<400> SEQUENCE: 267

Met Ala Gly Pro Leu Gly Leu Leu Cys Phe Leu Ala Leu Gly Leu Leu
1               5                   10                  15

Gly Ser Ala Gly Pro Ser Gly Ala
            20

<210> SEQ ID NO 268
<211> LENGTH: 927
<212> TYPE: PRT
<213> ORGANISM: Artificial Sequence
<220> FEATURE:
<223> OTHER INFORMATION: hLGR4 (FL)

<400> SEQUENCE: 268

Ala Pro Pro Leu Cys Ala Ala Pro Cys Ser Cys Asp Gly Asp Arg Arg
1               5                   10                  15

Val Asp Cys Ser Gly Lys Gly Leu Thr Ala Val Pro Glu Gly Leu Ser
            20                  25                  30

Ala Phe Thr Gln Ala Leu Asp Ile Ser Met Asn Asn Ile Thr Gln Leu
        35                  40                  45

Pro Glu Asp Ala Phe Lys Asn Phe Pro Phe Leu Glu Glu Leu Gln Leu
    50                  55                  60

Ala Gly Asn Asp Leu Ser Phe Ile His Pro Lys Ala Leu Ser Gly Leu
65                  70                  75                  80

Lys Glu Leu Lys Val Leu Thr Leu Gln Asn Asn Gln Leu Lys Thr Val
                85                  90                  95

-continued

```
Pro Ser Glu Ala Ile Arg Gly Leu Ser Ala Leu Gln Ser Leu Arg Leu
            100                 105                 110
Asp Ala Asn His Ile Thr Ser Val Pro Glu Asp Ser Phe Gly Leu
        115                 120                 125
Val Gln Leu Arg His Leu Trp Leu Asp Asp Asn Ser Leu Thr Glu Val
    130                 135                 140
Pro Val His Pro Leu Ser Asn Leu Pro Thr Leu Gln Ala Leu Thr Leu
145                 150                 155                 160
Ala Leu Asn Lys Ile Ser Ser Ile Pro Asp Phe Ala Phe Thr Asn Leu
                165                 170                 175
Ser Ser Leu Val Val Leu His Leu His Asn Asn Lys Ile Arg Ser Leu
            180                 185                 190
Ser Gln His Cys Phe Asp Gly Leu Asp Asn Leu Glu Thr Leu Asp Leu
        195                 200                 205
Asn Tyr Asn Asn Leu Gly Glu Phe Pro Gln Ala Ile Lys Ala Leu Pro
    210                 215                 220
Ser Leu Lys Glu Leu Gly Phe His Ser Asn Ser Ile Ser Val Ile Pro
225                 230                 235                 240
Asp Gly Ala Phe Asp Gly Asn Pro Leu Leu Arg Thr Ile His Leu Tyr
                245                 250                 255
Asp Asn Pro Leu Ser Phe Val Gly Asn Ser Ala Phe His Asn Leu Ser
            260                 265                 270
Asp Leu His Ser Leu Val Ile Arg Gly Ala Ser Met Val Gln Gln Phe
        275                 280                 285
Pro Asn Leu Thr Gly Thr Val His Leu Glu Ser Leu Thr Leu Thr Gly
    290                 295                 300
Thr Lys Ile Ser Ser Ile Pro Asn Asn Leu Cys Gln Glu Gln Lys Met
305                 310                 315                 320
Leu Arg Thr Leu Asp Leu Ser Tyr Asn Asn Ile Arg Asp Leu Pro Ser
                325                 330                 335
Phe Asn Gly Cys His Ala Leu Glu Glu Ile Ser Leu Gln Arg Asn Gln
            340                 345                 350
Ile Tyr Gln Ile Lys Glu Gly Thr Phe Gln Gly Leu Ile Ser Leu Arg
        355                 360                 365
Ile Leu Asp Leu Ser Arg Asn Leu Ile His Glu Ile His Ser Arg Ala
    370                 375                 380
Phe Ala Thr Leu Gly Pro Ile Thr Asn Leu Asp Val Ser Phe Asn Glu
385                 390                 395                 400
Leu Thr Ser Phe Pro Thr Glu Gly Leu Asn Gly Leu Asn Gln Leu Lys
                405                 410                 415
Leu Val Gly Asn Phe Lys Leu Lys Glu Ala Leu Ala Ala Lys Asp Phe
            420                 425                 430
Val Asn Leu Arg Ser Leu Ser Val Pro Tyr Ala Tyr Gln Cys Cys Ala
        435                 440                 445
Phe Trp Gly Cys Asp Ser Tyr Ala Asn Leu Asn Thr Glu Asp Asn Ser
    450                 455                 460
Leu Gln Asp His Ser Val Ala Gln Glu Lys Gly Thr Ala Asp Ala Ala
465                 470                 475                 480
Asn Val Thr Ser Thr Leu Glu Asn Glu Glu His Ser Gln Ile Ile Ile
                485                 490                 495
His Cys Thr Pro Ser Thr Gly Ala Phe Lys Pro Cys Glu Tyr Leu Leu
            500                 505                 510
Gly Ser Trp Met Ile Arg Leu Thr Val Trp Phe Ile Phe Leu Val Ala
```

```
              515                 520                 525
Leu Phe Phe Asn Leu Leu Val Ile Leu Thr Thr Phe Ala Ser Cys Thr
530                 535                 540

Ser Leu Pro Ser Ser Lys Leu Phe Ile Gly Leu Ile Ser Val Ser Asn
545                 550                 555                 560

Leu Phe Met Gly Ile Tyr Thr Gly Ile Leu Thr Phe Leu Asp Ala Val
                565                 570                 575

Ser Trp Gly Arg Phe Ala Glu Phe Gly Ile Trp Trp Glu Thr Gly Ser
                580                 585                 590

Gly Cys Lys Val Ala Gly Phe Leu Ala Val Phe Ser Ser Glu Ser Ala
            595                 600                 605

Ile Phe Leu Leu Met Leu Ala Thr Val Glu Arg Ser Leu Ser Ala Lys
            610                 615                 620

Asp Ile Met Lys Asn Gly Lys Ser Asn His Leu Lys Gln Phe Arg Val
625                 630                 635                 640

Ala Ala Leu Leu Ala Phe Leu Gly Ala Thr Val Ala Gly Cys Phe Pro
                645                 650                 655

Leu Phe His Arg Gly Glu Tyr Ser Ala Ser Pro Leu Cys Leu Pro Phe
                660                 665                 670

Pro Thr Gly Glu Thr Pro Ser Leu Gly Phe Thr Val Thr Leu Val Leu
            675                 680                 685

Leu Asn Ser Leu Ala Phe Leu Leu Met Ala Val Ile Tyr Thr Lys Leu
690                 695                 700

Tyr Cys Asn Leu Glu Lys Glu Asp Leu Ser Glu Asn Ser Gln Ser Ser
705                 710                 715                 720

Met Ile Lys His Val Ala Trp Leu Ile Phe Thr Asn Cys Ile Phe Phe
                725                 730                 735

Cys Pro Val Ala Phe Phe Ser Phe Ala Pro Leu Ile Thr Ala Ile Ser
                740                 745                 750

Ile Ser Pro Glu Ile Met Lys Ser Val Thr Leu Ile Phe Phe Pro Leu
            755                 760                 765

Pro Ala Cys Leu Asn Pro Val Leu Tyr Val Phe Phe Asn Pro Lys Phe
770                 775                 780

Lys Glu Asp Trp Lys Leu Leu Lys Arg Arg Val Thr Lys Lys Ser Gly
785                 790                 795                 800

Ser Val Ser Val Ser Ile Ser Ser Gln Gly Gly Cys Leu Glu Gln Asp
                805                 810                 815

Phe Tyr Tyr Asp Cys Gly Met Tyr Ser His Leu Gln Gly Asn Leu Thr
                820                 825                 830

Val Cys Asp Cys Cys Glu Ser Phe Leu Leu Thr Lys Pro Val Ser Cys
            835                 840                 845

Lys His Leu Ile Lys Ser His Ser Cys Pro Ala Leu Ala Val Ala Ser
            850                 855                 860

Cys Gln Arg Pro Glu Gly Tyr Trp Ser Asp Cys Gly Thr Gln Ser Ala
865                 870                 875                 880

His Ser Asp Tyr Ala Asp Glu Glu Asp Ser Phe Val Ser Asp Ser Ser
                885                 890                 895

Asp Gln Val Gln Ala Cys Gly Arg Ala Cys Phe Tyr Gln Ser Arg Gly
                900                 905                 910

Phe Pro Leu Val Arg Tyr Ala Tyr Asn Leu Pro Arg Val Lys Asp
            915                 920                 925

<210> SEQ ID NO 269
```

```
<211> LENGTH: 8
<212> TYPE: PRT
<213> ORGANISM: Artificial Sequence
<220> FEATURE:
<223> OTHER INFORMATION: FLAG TAG

<400> SEQUENCE: 269

Asp Tyr Lys Asp Asp Asp Asp Lys
1               5

<210> SEQ ID NO 270
<211> LENGTH: 4
<212> TYPE: PRT
<213> ORGANISM: Artificial Sequence
<220> FEATURE:
<223> OTHER INFORMATION: Linker REgion

<400> SEQUENCE: 270

Leu Asp Gly Gly
1

<210> SEQ ID NO 271
<211> LENGTH: 9
<212> TYPE: PRT
<213> ORGANISM: Artificial Sequence
<220> FEATURE:
<223> OTHER INFORMATION: HA tag

<400> SEQUENCE: 271

Tyr Pro Tyr Asp Val Pro Asp Tyr Ala
1               5

<210> SEQ ID NO 272
<211> LENGTH: 24
<212> TYPE: PRT
<213> ORGANISM: Artificial Sequence
<220> FEATURE:
<223> OTHER INFORMATION: Signal Peptide

<400> SEQUENCE: 272

Met Pro Gly Pro Leu Gly Leu Leu Cys Phe Leu Ala Leu Gly Leu Leu
1               5                   10                  15

Gly Ser Ala Gly Pro Ser Gly Ala
            20

<210> SEQ ID NO 273
<211> LENGTH: 518
<212> TYPE: PRT
<213> ORGANISM: Artificial Sequence
<220> FEATURE:
<223> OTHER INFORMATION: hLGR4 (ECD)

<400> SEQUENCE: 273

Ala Pro Pro Leu Cys Ala Ala Pro Cys Ser Cys Asp Gly Asp Arg Arg
1               5                   10                  15

Val Asp Cys Ser Gly Lys Gly Leu Thr Ala Val Pro Glu Gly Leu Ser
            20                  25                  30

Ala Phe Thr Gln Ala Leu Asp Ile Ser Met Asn Asn Ile Thr Gln Leu
        35                  40                  45

Pro Glu Asp Ala Phe Lys Asn Phe Pro Phe Leu Glu Glu Leu Gln Leu
    50                  55                  60

Ala Gly Asn Asp Leu Ser Phe Ile His Pro Lys Ala Leu Ser Gly Leu
65                  70                  75                  80

Lys Glu Leu Lys Val Leu Thr Leu Gln Asn Asn Gln Leu Lys Thr Val
```

```
                  85                  90                  95
Pro Ser Glu Ala Ile Arg Gly Leu Ser Ala Leu Gln Ser Leu Arg Leu
                100                 105                 110

Asp Ala Asn His Ile Thr Ser Val Pro Glu Asp Ser Phe Glu Gly Leu
                115                 120                 125

Val Gln Leu Arg His Leu Trp Leu Asp Asp Asn Ser Leu Thr Glu Val
130                 135                 140

Pro Val His Pro Leu Ser Asn Leu Pro Thr Leu Gln Ala Leu Thr Leu
145                 150                 155                 160

Ala Leu Asn Lys Ile Ser Ser Ile Pro Asp Phe Ala Phe Thr Asn Leu
                165                 170                 175

Ser Ser Leu Val Val Leu His Leu His Asn Asn Lys Ile Arg Ser Leu
                180                 185                 190

Ser Gln His Cys Phe Asp Gly Leu Asp Asn Leu Glu Thr Leu Asp Leu
                195                 200                 205

Asn Tyr Asn Asn Leu Gly Glu Phe Pro Gln Ala Ile Lys Ala Leu Pro
                210                 215                 220

Ser Leu Lys Glu Leu Gly Phe His Ser Asn Ser Ile Ser Val Ile Pro
225                 230                 235                 240

Asp Gly Ala Phe Asp Gly Asn Pro Leu Leu Arg Thr Ile His Leu Tyr
                245                 250                 255

Asp Asn Pro Leu Ser Phe Val Gly Asn Ser Ala Phe His Asn Leu Ser
                260                 265                 270

Asp Leu His Ser Leu Val Ile Arg Gly Ala Ser Met Val Gln Gln Phe
                275                 280                 285

Pro Asn Leu Thr Gly Thr Val His Leu Glu Ser Leu Thr Leu Thr Gly
                290                 295                 300

Thr Lys Ile Ser Ser Ile Pro Asn Asn Leu Cys Gln Glu Gln Lys Met
305                 310                 315                 320

Leu Arg Thr Leu Asp Leu Ser Tyr Asn Asn Ile Arg Asp Leu Pro Ser
                325                 330                 335

Phe Asn Gly Cys His Ala Leu Glu Glu Ile Ser Leu Gln Arg Asn Gln
                340                 345                 350

Ile Tyr Gln Ile Lys Glu Gly Thr Phe Gln Gly Leu Ile Ser Leu Arg
                355                 360                 365

Ile Leu Asp Leu Ser Arg Asn Leu Ile His Glu Ile His Ser Arg Ala
                370                 375                 380

Phe Ala Thr Leu Gly Pro Ile Thr Asn Leu Asp Val Ser Phe Asn Glu
385                 390                 395                 400

Leu Thr Ser Phe Pro Thr Glu Gly Leu Asn Gly Leu Asn Gln Leu Lys
                405                 410                 415

Leu Val Gly Asn Phe Lys Leu Lys Glu Ala Leu Ala Ala Lys Asp Phe
                420                 425                 430

Val Asn Leu Arg Ser Leu Ser Val Pro Tyr Ala Tyr Gln Cys Cys Ala
                435                 440                 445

Phe Trp Gly Cys Asp Ser Tyr Ala Asn Leu Asn Thr Glu Asp Asn Ser
                450                 455                 460

Leu Gln Asp His Ser Val Ala Gln Glu Lys Gly Thr Ala Asp Ala Ala
465                 470                 475                 480

Asn Val Thr Ser Thr Leu Glu Asn Glu His Ser Gln Ile Ile Ile
                485                 490                 495

His Cys Thr Pro Ser Thr Gly Ala Phe Lys Pro Cys Glu Tyr Leu Leu
                500                 505                 510
```

```
Gly Ser Trp Met Ile Arg
            515

<210> SEQ ID NO 274
<211> LENGTH: 85
<212> TYPE: PRT
<213> ORGANISM: Artificial Sequence
<220> FEATURE:
<223> OTHER INFORMATION: GPA33 Sequence containing the TM Region

<400> SEQUENCE: 274

Val Ala Leu Tyr Val Gly Ile Ala Val Gly Val Val Ala Ala Leu Ile
1               5                   10                  15

Ile Ile Gly Ile Ile Ile Tyr Cys Cys Cys Arg Gly Lys Asp Asp
            20                  25                  30

Asn Thr Glu Asp Lys Glu Asp Ala Arg Pro Asn Arg Glu Ala Tyr Glu
        35                  40                  45

Glu Pro Pro Glu Gln Leu Arg Glu Leu Ser Arg Glu Arg Glu Glu
    50                  55                  60

Asp Asp Tyr Arg Gln Glu Glu Gln Arg Ser Thr Gly Arg Glu Ser Pro
65                  70                  75                  80

Asp His Leu Asp Gln
                85

<210> SEQ ID NO 275
<211> LENGTH: 21
<212> TYPE: PRT
<213> ORGANISM: Artificial Sequence
<220> FEATURE:
<223> OTHER INFORMATION: Signal Peptide

<400> SEQUENCE: 275

Met Asp Thr Ser Arg Leu Gly Val Leu Leu Ser Leu Pro Val Leu Leu
1               5                   10                  15

Gln Leu Ala Thr Gly
            20

<210> SEQ ID NO 276
<211> LENGTH: 541
<212> TYPE: PRT
<213> ORGANISM: Artificial Sequence
<220> FEATURE:
<223> OTHER INFORMATION: hLGR5 (ECD)

<400> SEQUENCE: 276

Gly Gly Ser Ser Pro Arg Ser Gly Val Leu Leu Arg Gly Cys Pro Thr
1               5                   10                  15

His Cys His Cys Glu Pro Asp Gly Arg Met Leu Leu Arg Val Asp Cys
            20                  25                  30

Ser Asp Leu Gly Leu Ser Glu Leu Pro Ser Asn Leu Ser Val Phe Thr
        35                  40                  45

Ser Tyr Leu Asp Leu Ser Met Asn Asn Ile Ser Gln Leu Leu Pro Asn
    50                  55                  60

Pro Leu Pro Ser Leu Arg Phe Leu Glu Glu Leu Arg Leu Ala Gly Asn
65                  70                  75                  80

Ala Leu Thr Tyr Ile Pro Lys Gly Ala Phe Thr Gly Leu Tyr Ser Leu
                85                  90                  95

Lys Val Leu Met Leu Gln Asn Asn Gln Leu Arg His Val Pro Thr Glu
            100                 105                 110
```

```
Ala Leu Gln Asn Leu Arg Ser Leu Gln Ser Leu Arg Leu Asp Ala Asn
            115                 120                 125
His Ile Ser Tyr Val Pro Pro Ser Cys Phe Ser Gly Leu His Ser Leu
    130                 135                 140
Arg His Leu Trp Leu Asp Asp Asn Ala Leu Thr Glu Ile Pro Val Gln
145                 150                 155                 160
Ala Phe Arg Ser Leu Ser Ala Leu Gln Ala Met Thr Leu Ala Leu Asn
                165                 170                 175
Lys Ile His His Ile Pro Asp Tyr Ala Phe Gly Asn Leu Ser Ser Leu
            180                 185                 190
Val Val Leu His Leu His Asn Asn Arg Ile His Ser Leu Gly Lys Lys
        195                 200                 205
Cys Phe Asp Gly Leu His Ser Leu Glu Thr Leu Asp Leu Asn Tyr Asn
    210                 215                 220
Asn Leu Asp Glu Phe Pro Thr Ala Ile Arg Thr Leu Ser Asn Leu Lys
225                 230                 235                 240
Glu Leu Gly Phe His Ser Asn Asn Ile Arg Ser Ile Pro Glu Lys Ala
                245                 250                 255
Phe Val Gly Asn Pro Ser Leu Ile Thr Ile His Phe Tyr Asp Asn Pro
            260                 265                 270
Ile Gln Phe Val Gly Arg Ser Ala Phe Gln His Leu Pro Glu Leu Arg
        275                 280                 285
Thr Leu Thr Leu Asn Gly Ala Ser Gln Ile Thr Glu Phe Pro Asp Leu
    290                 295                 300
Thr Gly Thr Ala Asn Leu Glu Ser Leu Thr Leu Thr Gly Ala Gln Ile
305                 310                 315                 320
Ser Ser Leu Pro Gln Thr Val Cys Asn Gln Leu Pro Asn Leu Gln Val
                325                 330                 335
Leu Asp Leu Ser Tyr Asn Leu Leu Glu Asp Leu Pro Ser Phe Ser Val
            340                 345                 350
Cys Gln Lys Leu Gln Lys Ile Asp Leu Arg His Asn Glu Ile Tyr Glu
        355                 360                 365
Ile Lys Val Asp Thr Phe Gln Gln Leu Leu Ser Leu Arg Ser Leu Asn
    370                 375                 380
Leu Ala Trp Asn Lys Ile Ala Ile Ile His Pro Asn Ala Phe Ser Thr
385                 390                 395                 400
Leu Pro Ser Leu Ile Lys Leu Asp Leu Ser Asn Leu Leu Ser Ser
                405                 410                 415
Phe Pro Ile Thr Gly Leu His Gly Leu Thr His Leu Lys Leu Thr Gly
            420                 425                 430
Asn His Ala Leu Gln Ser Leu Ile Ser Ser Glu Asn Phe Pro Glu Leu
        435                 440                 445
Lys Val Ile Glu Met Pro Tyr Ala Tyr Gln Cys Cys Ala Phe Gly Val
    450                 455                 460
Cys Glu Asn Ala Tyr Lys Ile Ser Asn Gln Trp Asn Lys Gly Asp Asn
465                 470                 475                 480
Ser Ser Met Asp Asp Leu His Lys Lys Asp Ala Gly Met Phe Gln Ala
                485                 490                 495
Gln Asp Glu Arg Asp Leu Glu Asp Phe Leu Leu Asp Phe Glu Glu Asp
            500                 505                 510
Leu Lys Ala Leu His Ser Val Gln Cys Ser Pro Ser Pro Gly Pro Phe
        515                 520                 525
Lys Pro Cys Glu His Leu Leu Asp Gly Trp Leu Ile Arg
```

-continued

```
           530             535             540
```

<210> SEQ ID NO 277
<211> LENGTH: 85
<212> TYPE: PRT
<213> ORGANISM: Artificial Sequence
<220> FEATURE:
<223> OTHER INFORMATION: GPA33 Sequence Containing the TM Region

<400> SEQUENCE: 277

```
Val Ala Leu Tyr Val Gly Ile Ala Val Gly Val Ala Ala Leu Ile
1               5                   10                  15

Ile Ile Gly Ile Ile Ile Tyr Cys Cys Cys Cys Arg Gly Lys Asp Asp
            20                  25                  30

Asn Thr Glu Asp Lys Glu Asp Ala Arg Pro Asn Arg Glu Ala Tyr Glu
        35                  40                  45

Glu Pro Pro Glu Gln Leu Arg Glu Leu Ser Arg Glu Arg Glu Glu Glu
    50                  55                  60

Asp Tyr Arg Gln Glu Gln Arg Ser Thr Gly Arg Glu Ser Pro
65                  70                  75                  80

Asp His Leu Asp Gln
            85
```

<210> SEQ ID NO 278
<211> LENGTH: 21
<212> TYPE: PRT
<213> ORGANISM: Artificial Sequence
<220> FEATURE:
<223> OTHER INFORMATION: Signal Peptide

<400> SEQUENCE: 278

```
Met Asp Thr Ser Cys Val His Met Leu Leu Ser Leu Leu Ala Leu Leu
1               5                   10                  15

Gln Leu Val Ala Ala
            20
```

<210> SEQ ID NO 279
<211> LENGTH: 886
<212> TYPE: PRT
<213> ORGANISM: Artificial Sequence
<220> FEATURE:
<223> OTHER INFORMATION: mLGR5 (FL)

<400> SEQUENCE: 279

```
Gly Ser Ser Pro Gly Pro Asp Ala Ile Pro Arg Gly Cys Pro Ser His
1               5                   10                  15

Cys His Cys Glu Leu Asp Gly Arg Met Leu Leu Arg Val Asp Cys Ser
            20                  25                  30

Asp Leu Gly Leu Ser Glu Leu Pro Ser Asn Leu Ser Val Phe Thr Ser
        35                  40                  45

Tyr Leu Asp Leu Ser Met Asn Asn Ile Ser Gln Leu Pro Ala Ser Leu
    50                  55                  60

Leu His Arg Leu Cys Phe Leu Glu Glu Leu Arg Leu Ala Gly Asn Ala
65                  70                  75                  80

Leu Thr His Ile Pro Lys Gly Ala Phe Thr Gly Leu His Ser Leu Lys
            85                  90                  95

Val Leu Met Leu Gln Asn Asn Gln Leu Arg Gln Val Pro Glu Glu Ala
            100                 105                 110

Leu Gln Asn Leu Arg Ser Leu Gln Ser Leu Arg Leu Asp Ala Asn His
        115                 120                 125
```

```
Ile Ser Tyr Val Pro Pro Ser Cys Phe Ser Gly Leu His Ser Leu Arg
    130                 135                 140

His Leu Trp Leu Asp Asp Asn Ala Leu Thr Asp Val Pro Val Gln Ala
145                 150                 155                 160

Phe Arg Ser Leu Ser Ala Leu Gln Ala Met Thr Leu Ala Leu Asn Lys
                165                 170                 175

Ile His His Ile Ala Asp Tyr Ala Phe Gly Asn Leu Ser Ser Leu Val
                180                 185                 190

Val Leu His Leu His Asn Asn Arg Ile His Ser Leu Gly Lys Lys Cys
            195                 200                 205

Phe Asp Gly Leu His Ser Leu Glu Thr Leu Asp Leu Asn Tyr Asn Asn
210                 215                 220

Leu Asp Glu Phe Pro Thr Ala Ile Lys Thr Leu Ser Asn Leu Lys Glu
225                 230                 235                 240

Leu Gly Phe His Ser Asn Asn Ile Arg Ser Ile Pro Glu Arg Ala Phe
                245                 250                 255

Val Gly Asn Pro Ser Leu Ile Thr Ile His Phe Tyr Asp Asn Pro Ile
                260                 265                 270

Gln Phe Val Gly Val Ser Ala Phe Gln His Leu Pro Glu Leu Arg Thr
            275                 280                 285

Leu Thr Leu Asn Gly Ala Ser His Ile Thr Glu Phe Pro His Leu Thr
        290                 295                 300

Gly Thr Ala Thr Leu Glu Ser Leu Thr Leu Thr Gly Ala Lys Ile Ser
305                 310                 315                 320

Ser Leu Pro Gln Ala Val Cys Asp Gln Leu Pro Asn Leu Gln Val Leu
                325                 330                 335

Asp Leu Ser Tyr Asn Leu Leu Glu Asp Leu Pro Ser Leu Ser Gly Cys
                340                 345                 350

Gln Lys Leu Gln Lys Ile Asp Leu Arg His Asn Glu Ile Tyr Glu Ile
            355                 360                 365

Lys Gly Ser Thr Phe Gln Gln Leu Phe Asn Leu Arg Ser Leu Asn Leu
        370                 375                 380

Ala Trp Asn Lys Ile Ala Ile Ile His Pro Asn Ala Phe Ser Thr Leu
385                 390                 395                 400

Pro Ser Leu Ile Lys Leu Asp Leu Ser Ser Asn Leu Leu Ser Ser Phe
                405                 410                 415

Pro Val Thr Gly Leu His Gly Leu Thr His Leu Lys Leu Thr Gly Asn
                420                 425                 430

Arg Ala Leu Gln Ser Leu Ile Pro Ser Ala Asn Phe Pro Glu Leu Lys
            435                 440                 445

Ile Ile Glu Met Pro Ser Ala Tyr Gln Cys Cys Ala Phe Gly Gly Cys
        450                 455                 460

Glu Asn Val Tyr Lys Ile Ser Asn Gln Trp Asn Lys Asp Asp Gly Asn
465                 470                 475                 480

Ser Val Asp Asp Leu His Lys Lys Asp Ala Gly Leu Phe Gln Val Gln
                485                 490                 495

Asp Glu Arg Asp Leu Glu Asp Phe Leu Leu Asp Phe Glu Glu Asp Leu
                500                 505                 510

Lys Ala Leu His Ser Val Gln Cys Ser Pro Ser Pro Gly Pro Phe Lys
            515                 520                 525

Pro Cys Glu His Leu Phe Gly Ser Trp Leu Ile Arg Ile Gly Val Trp
530                 535                 540
```

```
Thr Thr Ala Val Leu Ala Leu Ser Cys Asn Ala Leu Val Ala Leu Thr
545                 550                 555                 560

Val Phe Arg Thr Pro Leu Tyr Ile Ser Ser Ile Lys Leu Leu Ile Gly
                565                 570                 575

Val Ile Ala Val Val Asp Ile Leu Met Gly Val Ser Ser Ala Val Leu
            580                 585                 590

Ala Ala Val Asp Ala Phe Thr Phe Gly Arg Phe Ala Gln His Gly Ala
        595                 600                 605

Trp Trp Glu Asp Gly Ile Gly Cys Gln Ile Val Gly Phe Leu Ser Ile
    610                 615                 620

Phe Ala Ser Glu Ser Ser Ile Phe Leu Leu Thr Leu Ala Ala Leu Glu
625                 630                 635                 640

Arg Gly Phe Ser Val Lys Cys Ser Ser Lys Phe Glu Val Lys Ala Pro
                645                 650                 655

Leu Phe Ser Leu Arg Ala Ile Val Leu Leu Cys Val Leu Leu Ala Leu
            660                 665                 670

Thr Ile Ala Thr Ile Pro Leu Leu Gly Gly Ser Lys Tyr Asn Ala Ser
        675                 680                 685

Pro Leu Cys Leu Pro Leu Pro Phe Gly Glu Pro Ser Thr Thr Gly Tyr
    690                 695                 700

Met Val Ala Leu Val Leu Leu Asn Ser Leu Cys Phe Leu Ile Met Thr
705                 710                 715                 720

Ile Ala Tyr Thr Lys Leu Tyr Cys Ser Leu Glu Lys Gly Glu Leu Glu
                725                 730                 735

Asn Leu Trp Asp Cys Ser Met Val Lys His Ile Ala Leu Leu Leu Phe
            740                 745                 750

Ala Asn Cys Ile Leu Tyr Cys Pro Val Ala Phe Leu Ser Phe Ser Ser
        755                 760                 765

Leu Leu Asn Leu Thr Phe Ile Ser Pro Asp Val Ile Lys Phe Ile Leu
    770                 775                 780

Leu Val Ile Val Pro Leu Pro Ser Cys Leu Asn Pro Leu Leu Tyr Ile
785                 790                 795                 800

Val Phe Asn Pro His Phe Lys Glu Asp Met Gly Ser Leu Gly Lys His
                805                 810                 815

Thr Arg Phe Trp Met Arg Ser Lys His Ala Ser Leu Leu Ser Ile Asn
            820                 825                 830

Ser Asp Asp Val Glu Lys Arg Ser Cys Glu Ser Thr Gln Ala Leu Val
        835                 840                 845

Ser Phe Thr His Ala Ser Ile Ala Tyr Asp Leu Pro Ser Thr Ser Gly
    850                 855                 860

Ala Ser Pro Ala Tyr Pro Met Thr Glu Ser Cys His Leu Ser Ser Val
865                 870                 875                 880

Ala Phe Val Pro Cys Leu
                885

<210> SEQ ID NO 280
<211> LENGTH: 8
<212> TYPE: PRT
<213> ORGANISM: Artificial Sequence
<220> FEATURE:
<223> OTHER INFORMATION: Linker

<400> SEQUENCE: 280

Ala Ala Ala Arg Gly His Pro Phe
1               5
```

<210> SEQ ID NO 281
<211> LENGTH: 10
<212> TYPE: PRT
<213> ORGANISM: Artificial Sequence
<220> FEATURE:
<223> OTHER INFORMATION: cMyc-Derived Epitope Tag

<400> SEQUENCE: 281

Glu Gln Lys Leu Ile Ser Glu Glu Asp Leu
1               5                   10

<210> SEQ ID NO 282
<211> LENGTH: 5
<212> TYPE: PRT
<213> ORGANISM: Artificial Sequence
<220> FEATURE:
<223> OTHER INFORMATION: Linker

<400> SEQUENCE: 282

Asn Met His Thr Gly
1               5

<210> SEQ ID NO 283
<211> LENGTH: 6
<212> TYPE: PRT
<213> ORGANISM: Artificial Sequence
<220> FEATURE:
<223> OTHER INFORMATION: Hexa His tag

<400> SEQUENCE: 283

His His His His His His
1               5

<210> SEQ ID NO 284
<211> LENGTH: 55
<212> TYPE: PRT
<213> ORGANISM: Artificial Sequence
<220> FEATURE:
<223> OTHER INFORMATION: Signal Peptide

<400> SEQUENCE: 284

Met Arg Pro Arg Ser Gly Gly Arg Pro Gly Ala Thr Gly Arg Arg
1               5                   10                  15

Arg Arg Leu Arg Arg Arg Pro Arg Gly Leu Arg Cys Ser Arg Leu Pro
            20                  25                  30

Pro Pro Pro Pro Leu Pro Leu Leu Leu Gly Leu Leu Leu Ala Ala Ala
        35                  40                  45

Gly Pro Gly Ala Ala Arg Ala
        50                  55

<210> SEQ ID NO 285
<211> LENGTH: 163
<212> TYPE: PRT
<213> ORGANISM: Artificial Sequence
<220> FEATURE:
<223> OTHER INFORMATION: ECD of human ZNRF3 VD

<400> SEQUENCE: 285

Lys Glu Thr Ala Phe Val Glu Val Val Leu Phe Glu Ser Ser Pro Ser
1               5                   10                  15

Gly Asp Tyr Thr Thr Tyr Thr Thr Gly Leu Thr Gly Arg Phe Ser Arg
            20                  25                  30

Ala Gly Ala Thr Leu Ser Ala Gly Gly Glu Ile Val Gln Met His Pro
        35                  40                  45

```
Leu Gly Leu Cys Asn Asn Asn Asp Glu Glu Asp Leu Tyr Glu Tyr Gly
            50                  55                  60

Trp Val Gly Val Val Lys Leu Glu Gln Pro Glu Leu Asp Pro Lys Pro
 65                  70                  75                  80

Cys Leu Thr Val Leu Gly Lys Ala Lys Arg Ala Val Gln Arg Gly Ala
                 85                  90                  95

Thr Ala Val Ile Phe Asp Val Ser Glu Asn Pro Glu Ala Ile Asp Gln
            100                 105                 110

Leu Asn Gln Gly Ser Glu Asp Pro Leu Lys Arg Pro Val Val Tyr Val
            115                 120                 125

Lys Gly Ala Asp Ala Ile Lys Leu Met Asn Ile Val Asn Lys Gln Lys
            130                 135                 140

Val Ala Arg Ala Arg Ile Gln His Arg Pro Pro Arg Gln Pro Thr Glu
145                 150                 155                 160

Tyr Phe Asp

<210> SEQ ID NO 286
<211> LENGTH: 886
<212> TYPE: PRT
<213> ORGANISM: Artificial Sequence
<220> FEATURE:
<223> OTHER INFORMATION: Cynomolgus LGR5

<400> SEQUENCE: 286

Ser Ser Ser Pro Arg Ser Gly Ala Leu Leu Arg Gly Cys Pro Thr His
1               5                   10                  15

Cys His Cys Glu Pro Asp Gly Arg Met Leu Leu Arg Val Asp Cys Ser
                20                  25                  30

Asp Leu Gly Leu Ser Glu Leu Pro Ser Asn Leu Ser Val Phe Thr Ser
            35                  40                  45

Tyr Leu Asp Leu Ser Met Asn Asn Ile Ser Gln Leu Leu Pro Asn Pro
        50                  55                  60

Leu Pro Ser Leu Arg Phe Leu Glu Glu Leu Arg Leu Ala Gly Asn Ala
 65                 70                  75                  80

Leu Thr Tyr Ile Pro Lys Gly Ala Phe Thr Gly Leu Tyr Ser Leu Lys
                85                  90                  95

Val Leu Met Leu Gln Asn Asn Gln Leu Arg Gln Val Pro Thr Glu Ala
            100                 105                 110

Leu Gln Asn Leu Arg Ser Leu Gln Ser Leu Arg Leu Asp Ala Asn His
            115                 120                 125

Ile Ser Tyr Val Pro Pro Ser Cys Phe Ser Gly Leu His Ser Leu Arg
            130                 135                 140

His Leu Trp Leu Asp Asp Asn Ala Leu Thr Glu Ile Pro Val Gln Ala
145                 150                 155                 160

Phe Arg Ser Leu Ser Ala Leu Gln Ala Met Thr Leu Ala Leu Asn Lys
                165                 170                 175

Ile His His Ile Pro Asp Tyr Ala Phe Gly Asn Leu Ser Ser Leu Val
            180                 185                 190

Val Leu His Leu His Asn Asn Arg Ile His Ser Leu Gly Lys Lys Cys
            195                 200                 205

Phe Asp Gly Leu His Ser Leu Glu Thr Leu Asp Leu Asn Tyr Asn Asn
            210                 215                 220

Leu Asp Glu Phe Pro Thr Ala Ile Arg Thr Leu Ser Asn Leu Lys Glu
225                 230                 235                 240
```

-continued

Leu Gly Phe His Ser Asn Asn Ile Arg Ser Ile Pro Glu Lys Ala Phe
            245                 250                 255

Val Gly Asn Pro Ser Leu Ile Thr Ile His Phe Tyr Asp Asn Pro Ile
        260                 265                 270

Gln Phe Val Gly Arg Ser Ala Phe Gln His Leu Pro Glu Leu Arg Thr
    275                 280                 285

Leu Thr Leu Asn Gly Ala Ser Gln Ile Thr Glu Phe Pro Asp Leu Thr
290                 295                 300

Gly Thr Ala Asn Leu Glu Ser Leu Thr Leu Thr Gly Ala Gln Ile Ser
305                 310                 315                 320

Ser Leu Pro Gln Thr Val Cys Asn Gln Leu Pro Asn Leu Gln Val Leu
                325                 330                 335

Asp Leu Ser Tyr Asn Leu Leu Glu Asp Leu Pro Ser Phe Ser Val Cys
            340                 345                 350

Gln Lys Leu Gln Lys Ile Asp Leu Arg His Asn Glu Ile Tyr Glu Ile
        355                 360                 365

Lys Val Asp Thr Phe Gln Gln Leu Leu Ser Leu Arg Ser Leu Asn Leu
    370                 375                 380

Ala Trp Asn Lys Ile Ala Ile Ile His Pro Asn Ala Phe Ser Thr Leu
385                 390                 395                 400

Pro Ser Leu Ile Lys Leu Asp Leu Ser Ser Asn Leu Leu Ser Ser Phe
                405                 410                 415

Pro Val Thr Gly Leu His Gly Leu Thr His Leu Lys Leu Thr Gly Asn
            420                 425                 430

His Ala Leu Gln Ser Leu Ile Ser Ser Glu Asn Phe Pro Glu Leu Lys
        435                 440                 445

Ile Ile Glu Met Pro Tyr Ala Tyr Gln Cys Cys Ala Phe Gly Val Cys
    450                 455                 460

Glu Asn Ala Tyr Lys Ile Ser Asn Gln Trp Asn Lys Gly Asp Asn Ser
465                 470                 475                 480

Ser Met Asp Asp Leu His Lys Lys Asp Ala Gly Met Phe Gln Val Gln
                485                 490                 495

Asp Glu Arg Asp Leu Glu Asp Phe Leu Leu Asp Phe Glu Glu Asp Leu
            500                 505                 510

Lys Ala Leu His Ser Val Gln Cys Ser Pro Ser Pro Gly Pro Phe Lys
        515                 520                 525

Pro Cys Glu His Leu Leu Asp Gly Trp Leu Ile Arg Ile Gly Val Trp
    530                 535                 540

Thr Ile Ala Val Leu Ala Leu Thr Cys Asn Ala Leu Val Thr Ser Thr
545                 550                 555                 560

Val Phe Arg Ser Pro Leu Tyr Ile Ser Pro Ile Lys Leu Leu Ile Gly
                565                 570                 575

Val Ile Ala Val Val Asn Met Leu Thr Gly Val Ser Ser Ala Val Leu
            580                 585                 590

Ala Gly Val Asp Ala Phe Thr Phe Gly Ser Phe Ala Arg His Gly Ala
        595                 600                 605

Trp Trp Glu Asn Gly Val Gly Cys Gln Val Ile Gly Phe Leu Ser Ile
    610                 615                 620

Phe Ala Ser Glu Ser Ser Val Phe Leu Leu Thr Leu Ala Ala Leu Glu
625                 630                 635                 640

Arg Gly Phe Ser Val Lys Cys Ser Ala Lys Phe Glu Thr Lys Ala Pro
                645                 650                 655

Phe Ser Ser Leu Lys Val Ile Ile Leu Leu Cys Ala Leu Leu Ala Leu

```
                   660                 665                 670
Thr Met Ala Ala Val Pro Leu Leu Gly Gly Ser Glu Tyr Gly Ala Ser
                675                 680                 685

Pro Leu Cys Leu Pro Leu Pro Phe Gly Glu Pro Ser Thr Thr Gly Tyr
            690                 695                 700

Met Val Ala Leu Ile Leu Leu Asn Ser Leu Cys Phe Leu Met Met Thr
705                 710                 715                 720

Ile Ala Tyr Thr Lys Leu Tyr Cys Asn Leu Asp Lys Gly Asp Leu Glu
                725                 730                 735

Asn Ile Trp Asp Cys Ser Met Val Lys His Ile Ala Leu Leu Leu Phe
            740                 745                 750

Thr Asn Cys Ile Leu Tyr Cys Pro Val Ala Phe Leu Ser Phe Ser Ser
        755                 760                 765

Leu Leu Asn Leu Thr Phe Ile Ser Pro Glu Val Ile Lys Phe Ile Leu
            770                 775                 780

Leu Val Ile Val Pro Leu Pro Ala Cys Leu Asn Pro Leu Leu Tyr Ile
785                 790                 795                 800

Leu Phe Asn Pro His Phe Lys Glu Asp Leu Val Ser Leu Gly Lys Gln
                805                 810                 815

Thr Tyr Phe Trp Thr Arg Ser Lys His Pro Ser Leu Met Ser Ile Asn
            820                 825                 830

Ser Asp Asp Val Glu Lys Gln Ser Cys Asp Ser Thr Gln Ala Leu Val
        835                 840                 845

Thr Phe Thr Ser Ser Ser Ile Ala Tyr Asp Leu Pro Pro Ser Ser Val
        850                 855                 860

Pro Ser Pro Ala Tyr Pro Val Thr Glu Ser Cys His Leu Ser Ser Val
865                 870                 875                 880

Ala Phe Val Pro Cys Leu
                885

<210> SEQ ID NO 287
<211> LENGTH: 50
<212> TYPE: PRT
<213> ORGANISM: Artificial Sequence
<220> FEATURE:
<223> OTHER INFORMATION: PDGFR sequence containing the TM region

<400> SEQUENCE: 287

Asn Ala Val Gly Gln Asp Thr Gln Glu Val Ile Val Pro His Ser
1               5                   10                  15

Leu Pro Phe Lys Val Val Val Ile Ser Ala Ile Leu Ala Leu Val Val
                20                  25                  30

Leu Thr Ile Ile Ser Leu Ile Ile Leu Ile Met Leu Trp Gln Lys Lys
            35                  40                  45

Pro Arg
    50

<210> SEQ ID NO 288
<211> LENGTH: 163
<212> TYPE: PRT
<213> ORGANISM: Artificial Sequence
<220> FEATURE:
<223> OTHER INFORMATION: ECD of human ZNRF3

<400> SEQUENCE: 288

Lys Glu Thr Ala Phe Val Glu Val Val Leu Phe Glu Ser Ser Pro Ser
1               5                   10                  15
```

-continued

```
Gly Asp Tyr Thr Thr Tyr Thr Thr Gly Leu Thr Gly Arg Phe Ser Arg
            20                  25                  30

Ala Gly Ala Thr Leu Ser Ala Glu Gly Glu Ile Val Gln Met His Pro
        35                  40                  45

Leu Gly Leu Cys Asn Asn Asn Asp Glu Glu Asp Leu Tyr Glu Tyr Gly
    50                  55                  60

Trp Val Gly Val Val Lys Leu Glu Gln Pro Glu Leu Asp Pro Lys Pro
65                  70                  75                  80

Cys Leu Thr Val Leu Gly Lys Ala Lys Arg Ala Val Gln Arg Gly Ala
                85                  90                  95

Thr Ala Val Ile Phe Asp Val Ser Glu Asn Pro Glu Ala Ile Asp Gln
            100                 105                 110

Leu Asn Gln Gly Ser Glu Asp Pro Leu Lys Arg Pro Val Val Tyr Val
        115                 120                 125

Lys Gly Ala Asp Ala Ile Lys Leu Met Asn Ile Val Asn Lys Gln Lys
    130                 135                 140

Val Ala Arg Ala Arg Ile Gln His Arg Pro Pro Arg Gln Pro Thr Glu
145                 150                 155                 160

Tyr Phe Asp

<210> SEQ ID NO 289
<211> LENGTH: 14
<212> TYPE: PRT
<213> ORGANISM: Artificial Sequence
<220> FEATURE:
<223> OTHER INFORMATION: Predicted TM region

<400> SEQUENCE: 289

Met Gly Ile Phe Leu Ala Phe Phe Val Val Val Ser Leu Val
1               5                   10

<210> SEQ ID NO 290
<211> LENGTH: 24
<212> TYPE: PRT
<213> ORGANISM: Artificial Sequence
<220> FEATURE:
<223> OTHER INFORMATION: Intra-cellular tail

<400> SEQUENCE: 290

Cys Leu Ile Leu Leu Val Lys Ile Lys Leu Lys Gln Arg Arg Ser Gln
1               5                   10                  15

Asn Ser Met Asn Arg Pro Ala Val
            20

<210> SEQ ID NO 291
<211> LENGTH: 153
<212> TYPE: PRT
<213> ORGANISM: Artificial Sequence
<220> FEATURE:
<223> OTHER INFORMATION: ECD of mouse ZNRF3

<400> SEQUENCE: 291

Lys Glu Thr Ala Phe Val Glu Val Val Leu Phe Glu Ser Ser Pro Ser
1               5                   10                  15

Gly Asp Tyr Thr Thr His Thr Thr Gly Leu Thr Gly Arg Phe Ser Arg
            20                  25                  30

Ala Gly Ala Met Leu Ser Ala Glu Gly Glu Ile Val Gln Met His Pro
        35                  40                  45

Leu Gly Leu Cys Asn Asn Asn Asp Glu Glu Asp Leu Tyr Glu Tyr Gly
    50                  55                  60
```

Trp Val Gly Val Val Lys Leu Glu Gln Pro Glu Leu Asp Pro Lys Pro
65                  70                  75                  80

Cys Leu Thr Val Leu Gly Lys Ala Lys Arg Ala Val Gln Arg Gly Ala
                85                  90                  95

Thr Ala Val Ile Phe Asp Val Ser Glu Asn Pro Glu Ala Ile Asp Gln
            100                 105                 110

Leu Asn Gln Gly Ser Glu Asp Pro Leu Lys Arg Pro Val Val Tyr Val
        115                 120                 125

Lys Gly Ala Asp Ala Ile Lys Leu Met Asn Ile Val Asn Lys Gln Lys
    130                 135                 140

Val Ala Arg Ala Arg Ile Gln His Leu
145                 150

<210> SEQ ID NO 292
<211> LENGTH: 52
<212> TYPE: PRT
<213> ORGANISM: Artificial Sequence
<220> FEATURE:
<223> OTHER INFORMATION: Signal Peptide

<400> SEQUENCE: 292

Met Arg Pro Arg Ser Gly Gly Arg Pro Gly Ala Pro Gly Arg Arg Arg
1               5                   10                  15

Arg Arg Leu Arg Arg Gly Pro Arg Gly Arg Arg Leu Pro Pro Pro Pro
            20                  25                  30

Pro Leu Pro Leu Leu Leu Gly Leu Leu Ala Ala Ala Gly Pro Gly
        35                  40                  45

Ala Ala Arg Ala
    50

<210> SEQ ID NO 293
<211> LENGTH: 164
<212> TYPE: PRT
<213> ORGANISM: Artificial Sequence
<220> FEATURE:
<223> OTHER INFORMATION: ECD mZNRF3

<400> SEQUENCE: 293

Lys Glu Thr Ala Phe Val Glu Val Val Leu Phe Glu Ser Ser Pro Ser
1               5                   10                  15

Gly Asp Tyr Thr Thr His Thr Thr Gly Leu Thr Gly Arg Phe Ser Arg
            20                  25                  30

Ala Gly Ala Met Leu Ser Ala Glu Gly Glu Ile Val Gln Met His Pro
        35                  40                  45

Leu Gly Leu Cys Asn Asn Asn Asp Glu Glu Asp Leu Tyr Glu Tyr Gly
    50                  55                  60

Trp Val Gly Val Val Lys Leu Glu Gln Pro Glu Leu Asp Pro Lys Pro
65                  70                  75                  80

Cys Leu Thr Val Leu Gly Lys Ala Lys Arg Ala Val Gln Arg Gly Ala
                85                  90                  95

Thr Ala Val Ile Phe Asp Val Ser Glu Asn Pro Glu Ala Ile Asp Gln
            100                 105                 110

Leu Asn Gln Gly Ser Glu Asp Pro Leu Lys Arg Pro Val Val Tyr Val
        115                 120                 125

Lys Gly Ala Asp Ala Ile Lys Leu Met Asn Ile Val Asn Lys Gln Lys
    130                 135                 140

Val Ala Arg Ala Arg Ile Gln His Leu Pro Pro Arg Gln Pro Thr Glu

```
145                 150                 155                 160

Tyr Phe Asp Met

<210> SEQ ID NO 294
<211> LENGTH: 42
<212> TYPE: PRT
<213> ORGANISM: Artificial Sequence
<220> FEATURE:
<223> OTHER INFORMATION: Signal Peptide

<400> SEQUENCE: 294

Met Ser Gly Gly His Gln Leu Gln Leu Ala Leu Trp Pro Trp Leu
1               5                   10                  15

Leu Met Ala Thr Leu Gln Ala Gly Phe Gly Arg Thr Gly Leu Val Leu
            20                  25                  30

Ala Ala Ala Val Glu Ser Glu Arg Ser Ala
            35                  40

<210> SEQ ID NO 295
<211> LENGTH: 157
<212> TYPE: PRT
<213> ORGANISM: Artificial Sequence
<220> FEATURE:
<223> OTHER INFORMATION: ECD of human RNF43

<400> SEQUENCE: 295

Glu Gln Lys Ala Ile Ile Arg Val Ile Pro Leu Lys Met Asp Pro Thr
1               5                   10                  15

Gly Lys Leu Asn Leu Thr Leu Glu Gly Val Phe Ala Gly Val Ala Glu
            20                  25                  30

Ile Thr Pro Ala Glu Gly Lys Leu Met Gln Ser His Pro Leu Tyr Leu
            35                  40                  45

Cys Asn Ala Ser Asp Asp Asn Leu Glu Pro Gly Phe Ile Ser Ile
        50                  55                  60

Val Lys Leu Glu Ser Pro Arg Arg Ala Pro Arg Pro Cys Leu Ser Leu
65                  70                  75                  80

Ala Ser Lys Ala Arg Met Ala Gly Glu Arg Gly Ala Ser Ala Val Leu
                85                  90                  95

Phe Asp Ile Thr Glu Asp Arg Ala Ala Ala Glu Gln Leu Gln Gln Pro
            100                 105                 110

Leu Gly Leu Thr Trp Pro Val Val Leu Ile Trp Gly Asn Asp Ala Glu
            115                 120                 125

Lys Leu Met Glu Phe Val Tyr Lys Asn Gln Lys Ala His Val Arg Ile
130                 135                 140

Glu Leu Lys Glu Pro Pro Ala Trp Pro Asp Tyr Asp Val
145                 150                 155

<210> SEQ ID NO 296
<211> LENGTH: 42
<212> TYPE: PRT
<213> ORGANISM: Artificial Sequence
<220> FEATURE:
<223> OTHER INFORMATION: Signal Peptide

<400> SEQUENCE: 296

Met Ser Gly Gly His Gln Leu Gln Leu Ala Val Leu Trp Pro Trp Leu
1               5                   10                  15

Leu Met Ala Thr Leu His Ala Gly Phe Gly His Thr Gly Arg Val Leu
            20                  25                  30
```

-continued

```
Ala Ala Ala Val Glu Ser Glu Arg Ser Ala
        35                  40

<210> SEQ ID NO 297
<211> LENGTH: 157
<212> TYPE: PRT
<213> ORGANISM: Artificial Sequence
<220> FEATURE:
<223> OTHER INFORMATION: ECD of mouse RNF43

<400> SEQUENCE: 297

Glu Gln Lys Ala Val Ile Arg Val Ile Pro Leu Lys Met Asp Pro Thr
1               5                   10                  15

Gly Lys Leu Asn Leu Thr Leu Glu Gly Val Phe Ala Gly Val Ala Glu
            20                  25                  30

Val Thr Pro Ala Glu Gly Lys Leu Met Gln Ser His Pro Leu Tyr Leu
        35                  40                  45

Cys Asn Ala Ser Asp Asp Asn Leu Glu Pro Gly Phe Ile Ser Ile
    50                  55                  60

Val Lys Leu Glu Ser Pro Arg Arg Ala Pro Arg Pro Cys Leu Ser Leu
65                  70                  75                  80

Ala Ser Lys Ala Arg Met Ala Gly Glu Arg Gly Ala Asn Ala Val Leu
                85                  90                  95

Phe Asp Ile Thr Glu Asp Arg Ser Ala Ala Glu Gln Leu Gln Gln Pro
            100                 105                 110

Leu Gly Leu Thr Lys Pro Val Val Leu Ile Trp Gly Ser Asp Ala Ala
        115                 120                 125

Lys Leu Met Glu Phe Val Tyr Lys Asn Arg Lys Ala Tyr Val Trp Ile
    130                 135                 140

Glu Leu Lys Glu Pro Pro Ala Gly Ala Asn Tyr Asp Val
145                 150                 155

<210> SEQ ID NO 298
<211> LENGTH: 21
<212> TYPE: PRT
<213> ORGANISM: Artificial Sequence
<220> FEATURE:
<223> OTHER INFORMATION: Signal Peptide

<400> SEQUENCE: 298

Met Asp Thr Ser Arg Leu Gly Val Leu Leu Ser Leu Pro Val Leu Leu
1               5                   10                  15

Gln Leu Ala Ala Gly
            20

<210> SEQ ID NO 299
<211> LENGTH: 6
<212> TYPE: PRT
<213> ORGANISM: Artificial Sequence
<220> FEATURE:
<223> OTHER INFORMATION: CDR 1

<400> SEQUENCE: 299

Gln Ser Ile Ser Ser Tyr
1               5

<210> SEQ ID NO 300
<211> LENGTH: 9
<212> TYPE: PRT
<213> ORGANISM: Artificial Sequence
<220> FEATURE:
<223> OTHER INFORMATION: CDR3
```

<400> SEQUENCE: 300

Gln Gln Ser Tyr Ser Thr Pro Pro Thr
1               5